United States Patent
Zamboni et al.

(10) Patent No.: US 10,787,443 B2
(45) Date of Patent: Sep. 29, 2020

(54) RAF-DEGRADING CONJUGATE COMPOUNDS

(71) Applicant: ZAMBONI CHEM SOLUTIONS INC., Beaconsfield, CA (US)

(72) Inventors: Robert Zamboni, Beaconsfield (CA); Ryan Henning, San Francisco, CA (US); Xian Alan Ji, Menlo Park, CA (US); Tyler Smith, Pittsburg, CA (US); Bradley Heller, San Francisco, CA (US); Thumkunta Jagadeeswar Reddy, Beaconsfield (CA); Sylvain Rocheleau, Beaconsfield (CA); Marc Andre Beaulieu, Beaconsfield (CA)

(73) Assignee: ZAMBONI CHEM SOLUTIONS INC., Beaconsfiel, Quebec (CA)

( * ) Notice: Subject to any disclaimer, the term of this patent is extended or adjusted under 35 U.S.C. 154(b) by 0 days.

(21) Appl. No.: 15/965,506

(22) Filed: Apr. 27, 2018

(65) Prior Publication Data
US 2018/0346457 A1    Dec. 6, 2018

Related U.S. Application Data

(60) Provisional application No. 62/491,925, filed on Apr. 28, 2017, provisional application No. 62/581,464, filed on Nov. 3, 2017.

(51) Int. Cl.
*C07D 413/14* (2006.01)
*A61P 35/00* (2006.01)
*C07D 417/14* (2006.01)

(52) U.S. Cl.
CPC ............ *C07D 413/14* (2013.01); *A61P 35/00* (2018.01); *C07D 417/14* (2013.01)

(58) Field of Classification Search
CPC .............................. C07D 413/14; A61P 35/00
See application file for complete search history.

(56) References Cited

U.S. PATENT DOCUMENTS

| | | | |
|---|---|---|---|
| 7,041,298 B2 | 5/2006 | Deshaies et al. |
| 7,208,157 B2 | 4/2007 | Deshaies et al. |
| 9,694,084 B2 | 7/2017 | Bradner et al. |
| 9,750,816 B2 | 9/2017 | Bradner et al. |
| 9,770,512 B2 | 9/2017 | Bradner et al. |
| 9,821,068 B2 | 11/2017 | Bradner et al. |
| 2002/0068063 A1 | 6/2002 | Deshaies et al. |
| 2004/0038358 A1 | 2/2004 | Deshaies et al. |
| 2005/0153371 A1 | 7/2005 | Grotzfeld et al. |
| 2014/0256680 A1 | 9/2014 | Proia et al. |
| 2014/0356322 A1 | 12/2014 | Crews et al. |
| 2015/0119435 A1 | 4/2015 | Crews et al. |
| 2015/0291562 A1 | 10/2015 | Crews et al. |
| 2015/0374678 A1 | 12/2015 | Chamberlain et al. |
| 2016/0022642 A1 | 1/2016 | Crews et al. |
| 2016/0045607 A1 | 2/2016 | Crews et al. |
| 2016/0058872 A1 | 3/2016 | Crews et al. |
| 2016/0176916 A1 | 6/2016 | Bradner et al. |
| 2016/0214972 A1 | 7/2016 | Jin et al. |
| 2016/0235730 A1 | 8/2016 | Bradner et al. |
| 2016/0235731 A1 | 8/2016 | Bradner et al. |
| 2016/0243247 A1 | 8/2016 | Bradner et al. |
| 2016/0272639 A1 | 9/2016 | Crews et al. |
| 2017/0008904 A1 | 1/2017 | Crews et al. |
| 2017/0037004 A1 | 2/2017 | Crews et al. |
| 2017/0065719 A1 | 3/2017 | Qian et al. |
| 2018/0009779 A1 | 1/2018 | Bradner et al. |
| 2018/0085465 A1 | 3/2018 | Bradner et al. |
| 2018/0134684 A1 | 5/2018 | Bradner et al. |
| 2018/0147202 A1 | 5/2018 | Crews et al. |

FOREIGN PATENT DOCUMENTS

| | | |
|---|---|---|
| WO | WO-02/020740 A2 | 3/2002 |
| WO | WO-02/020740 A3 | 3/2002 |
| WO | WO-2013/106643 A2 | 7/2013 |
| WO | WO-2013/106643 A3 | 7/2013 |
| WO | WO-2013/106646 A2 | 7/2013 |
| WO | WO-2013/106646 A3 | 7/2013 |
| WO | WO-2013/170147 A1 | 11/2013 |
| WO | WO-2015/160845 A2 | 10/2015 |
| WO | WO-2015/160845 A3 | 10/2015 |
| WO | WO-2016/105518 A1 | 6/2016 |
| WO | WO-2016/118666 A1 | 7/2016 |
| WO | WO-2016/149668 A1 | 9/2016 |
| WO | WO-2016/197032 A1 | 12/2016 |
| WO | WO-2016/197114 A1 | 12/2016 |
| WO | WO-2017/007612 A1 | 1/2017 |
| WO | WO-2017/011371 A1 | 1/2017 |
| WO | WO-2017/011590 A1 | 1/2017 |
| WO | WO-2017/030814 A1 | 2/2017 |

OTHER PUBLICATIONS

International Search Report dated Sep. 21, 2018, for PCT Application No. PCT/US2018/29837, filed Apr. 27, 2018, 5 pages.
Written Opinion dated Sep. 21, 2018, for PCT Application No. PCT/US2018/29837, filed Apr. 27, 2018, 9 pages.

*Primary Examiner* — Golam M Shameem
(74) *Attorney, Agent, or Firm* — Mintz, Levin, Cohn, Ferris, Glovsky and Popeo, P.C.

(57) ABSTRACT

The present disclosure provides, inter alia, RAF-Degrading Conjugate Compounds that are useful in the treatment of cancer and other RAF related diseases. Also provided are, pharmaceutical compositions, methods of treatment, and kits comprising a RAF-Degrading Conjugate Compound.

27 Claims, 7 Drawing Sheets

RAF-DEGRADING CONJUGATE COMPOUNDS

CROSS-REFERENCES TO RELATED APPLICATIONS

This application claims the benefit of priority under 35 U.S.C § 119(e) to U.S. Provisional Application Ser. No. 62/491,925 filed Apr. 28, 2017 and U.S. Provisional Application Ser. No. 62/581,464 filed Nov. 3, 2017, the disclosure of each are incorporated herein by reference in their entirety.

STATEMENT AS TO RIGHTS TO INVENTIONS MADE UNDER FEDERALLY SPONSORED RESEARCH AND DEVELOPMENT

Not Applicable

REFERENCE TO A "SEQUENCE LISTING," A TABLE, OR A COMPUTER PROGRAM LISTING APPENDIX SUBMITTED ON A COMPACT DISK

Not Applicable

BACKGROUND OF THE INVENTION

KRAS is a key component of the canonical MAPK signaling pathway and is the most frequently mutated oncogene across all human cancers. There are no approved therapies that directly target KRAS and treatment for these cancers remains a great unmet medical need. KRAS is difficult to drug due to a lack of known binding pockets suitable for small molecule binding and pM affinity for its natural substrate, GTP. In addition, mutations often arise in other components of the MAPK pathway that lead to cancer and other RAS-associated diseases known as RASopathies.

The RAF family of kinases, including ARAF, BRAF, and CRAF, are the immediate downstream KRAS effectors that propagate downstream tumorigenic signals in cancer cells. Attempts were made to develop RAF inhibitors for KRAS-driven tumors, yet the compounds were discovered to cause paradoxical activation of RAF kinases due to allosteric activation of RAF homo- and hetero-dimers. Therefore, development of non-activating RAF inhibitors is an attractive strategy to block aberrant MAPK signaling.

Despite interest in this target, there remains a need in the art for a potent and specific inhibitor of RAF that effectively inactivates or eliminates MAPK signaling. The present disclosure addresses this need and provides related advantages as well.

BRIEF SUMMARY OF THE INVENTION

Provided herein are RAF-Degrading Conjugate Compounds comprising a Ligand for RAF covalently attached via a Linker Component to a Degradation Recognition Agent.

In still other aspects, provided herein as pharmaceutical compositions, methods for treating diseases, and kits using the RAF-Degrading Conjugate Compounds described.

DETAILED DESCRIPTION OF THE INVENTION

I. Introduction

Figure 1:
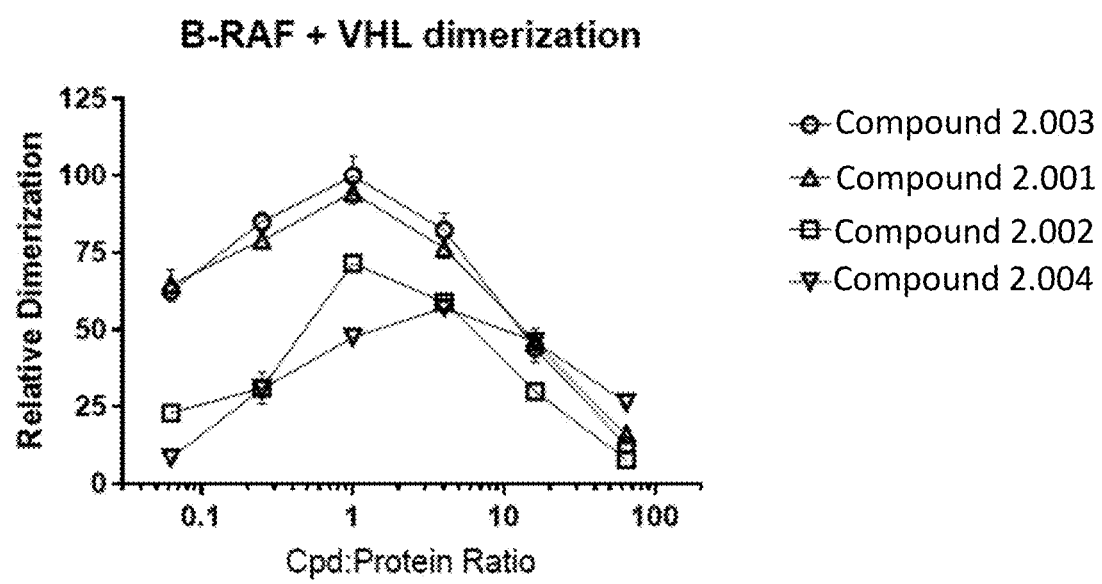
FIG. 1 shows the relative BRAF+VHL dimerization measured for Compound 2.003 (open circles), Compound 2.001 (open triangles), Compound 2.002 (open squares), and Compound 2.004 (open inverted triangles) at varying compound to protein ratios.

The present disclosure provides, inter alia, RAF-Degrading Conjugate Compounds that are useful in the treatment of cancer and other RAF related diseases. Without being bound to any particular theory, it is believed that the currently described conjugates are useful in treating cancer and other RAF related diseases by lowering the relative amount of RAF protein in a cell.

In some embodiments, the conjugate compounds of the present disclosure target RAF for destruction via recruitment of E3 ubiquitin ligases resulting in ubiquitination and proteasomal degradation.

Definitions

Unless specifically indicated otherwise, all technical and scientific terms used herein have the same meaning as commonly understood by those of ordinary skill in the art to which this invention belongs. In addition, any method or material similar or equivalent to a method or material described herein can be used in the practice of the present invention. For purposes of the present invention, the following terms are defined.

The term "alkyl", by itself or as part of another substituent, means, unless otherwise stated, a straight or branched chain hydrocarbon radical, having the number of carbon atoms designated (i.e. $C_{1-8}$ means one to eight carbons). Examples of alkyl groups include methyl, ethyl, n-propyl, isopropyl, n-butyl, t-butyl, isobutyl, sec-butyl, n-pentyl, n-hexyl, n-heptyl, n-octyl, and the like.

The terms "a," "an," or "the" as used herein not only include aspects with one member, but also include aspects with more than one member. For instance, the singular forms "a," "an," and "the" include plural referents unless the context clearly dictates otherwise. Thus, for example, reference to "a cell" includes a plurality of such cells and reference to "the agent" includes reference to one or more agents known to those skilled in the art, and so forth.

The terms "subject", "patient" or "individual" are used herein interchangeably to include a human or animal. For example, the animal subject may be a mammal, a primate (e.g., a monkey), a livestock animal (e.g., a horse, a cow, a sheep, a pig, or a goat), a companion animal (e.g., a dog, a cat), a laboratory test animal (e.g., a mouse, a rat, a guinea pig, a bird), an animal of veterinary significance, or an animal of economic significance.

The term "selective CRAF inhibitor" as used herein describes a CRAF inhibitor that preferentially binds to CRAF over other members of the RAF family including ARAF and BRAF. A selective CRAF inhibitor has at least a 5-fold, 10-fold, 20-fold, 50-fold, or 100-fold lower $IC_{50}$ value when binding CRAF as compared to binding to ARAF or BRAF. The fold difference described herein is for the inhibitor compounds when not covalently linked to a linking component or when part of a RAF-Degrading Conjugate Compound.

II. Description of the Embodiments

A. RAF-Degrading Conjugate Compounds

In certain aspects, the present disclosure provides a RAF-Degrading Conjugate Compound comprising a Ligand for RAF covalently attached via a Linker Component to a Degradation Signaling Agent.

1. Ligands for RAF

A Ligand for RAF is any compound that effectively binds to a RAF protein. Accordingly, Ligands for RAF include, but are not limited to, modified versions of sorafenib, Hah 10d, PF-04880594, LY3009120, PLX4720, RAF709, Vemurafenib, MLN 2480, and LHX254. Select positions of the compounds shown in Table 1 may be modified to accommodate covalent linkage with the Linker Component, yet not obstruct target binding of the Ligand for RAF. When covalently attached to the linker component, the Ligand for RAF maintains sufficient affinity for its target.

TABLE 1

Ligands for RAF

Sorafenib

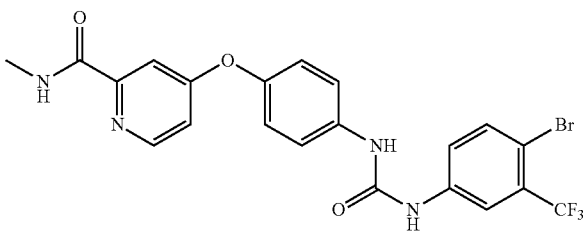

TABLE 1-continued
Ligands for RAF
Hab et al. 10d
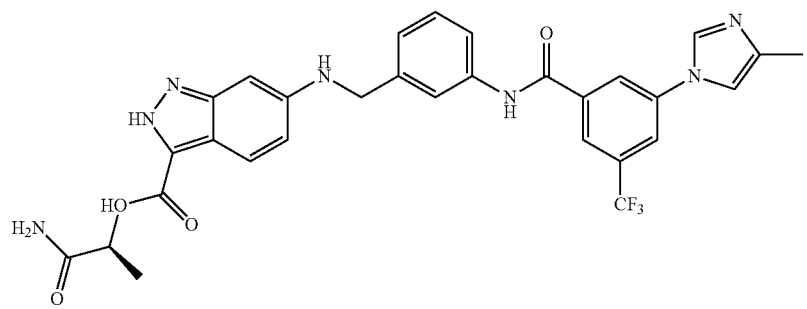
PF-04880594
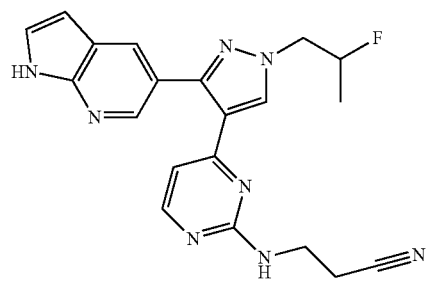
LY3009120
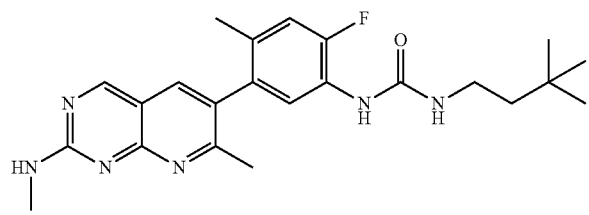
PLX4720
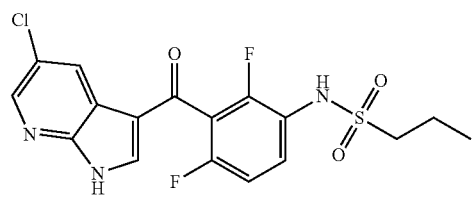

TABLE 1-continued

Ligands for RAF

RAF709

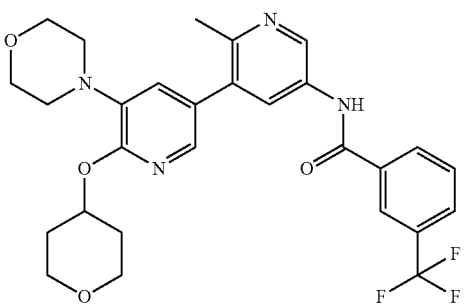

Vemurafenib

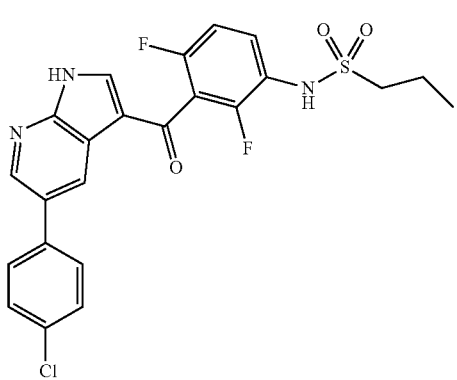

MLN2480

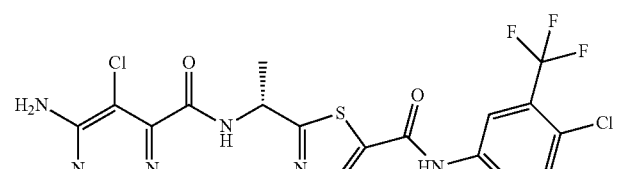

LXH254

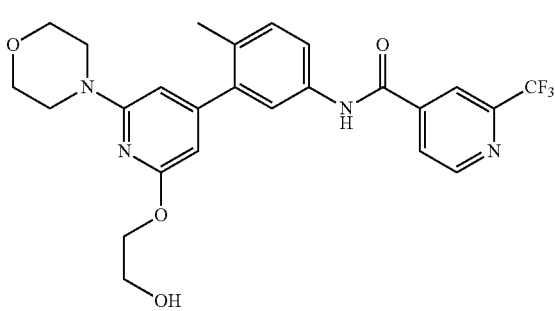

In some embodiments, the Ligand for RAF is a selective CRAF inhibitor. Selective CRAF inhibitors, include sorafenib and Hah et al. 10d.

In some embodiments, a selective CRAF inhibitor is an compound that has an CRAF $IC_{50}$ value that is at least 5-fold, 10-fold, 20-fold, 50-fold, or 100-fold lower than a BRAF $IC_{50}$ value, when measured under the same conditions. In some embodiments, a selective CRAF inhibitor is an compound that has an CRAF $IC_{50}$ value that is at least 5-fold, 10-fold, 20-fold, 50-fold, or 100-fold lower than a ARAF IC$_{50}$ value, when measured under the same conditions. In some embodiments, a selective CRAF inhibitor is a compound that has an CRAF IC$_{50}$ value that is at least 10-fold lower than a BRAF IC$_{50}$ value, when measured under the same conditions. In some embodiments, a selective CRAF inhibitor is a compound that has an CRAF IC$_{50}$ value that is at least 10-fold lower than a ARAF IC$_{50}$ value, when measured under the same conditions.

In some embodiments, the Ligand for RAF is a selective B/C RAF inhibitor. Selective B/C RAF inhibitors include RAF709. In some embodiments, the selective B/C RAF inhibitor has the formula shown below

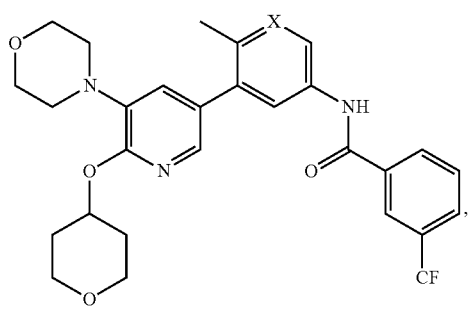

wherein X is N or CH. As described above, select positions of the formula shown above may be modified to accommodate covalent linkage with the Linker Component, yet not obstruct target binding of the Ligand for RAF. For example, in some embodiments, the B/C RAF inhibitor is modified to accommodate covalent linkage with the Linker Component as shown below

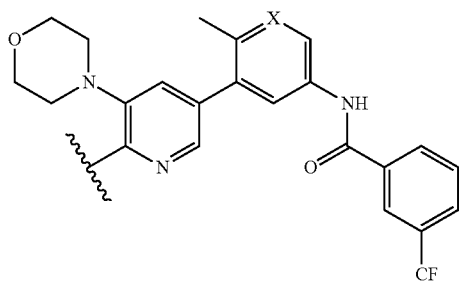

where X is N or CH and the wavy line indicates the site of attachment of the Linker Component.

In some embodiments, RAF709 is modified to accommodate covalent linkage with the Linker Component as shown below

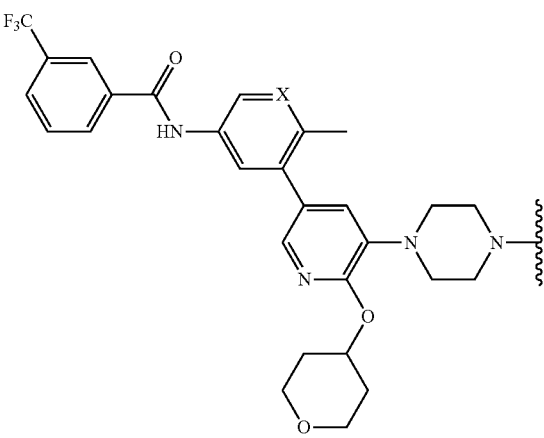

where X is N or CH and the wavy line indicates the site of attachment of the Linker Component.

In some embodiments, LXH254 is modified to accommodate covalent linkage with the Linker Component as shown below

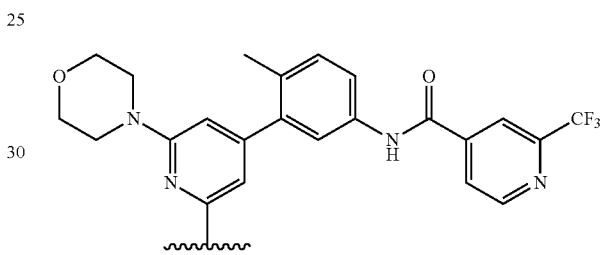

where the wavy line indicates the site of attachment of the Linker Component.

In some embodiments, sorafenib is modified to accommodate covalent linkage with the Linker Component as shown below

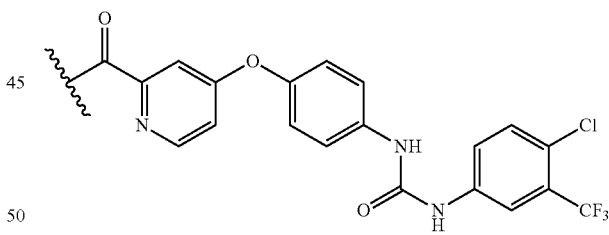

where the wavy line indicates the site of attachment of the Linker Component.

In some embodiments, LY3009120 is modified to accommodate covalent linkage with the Linker Component as shown below

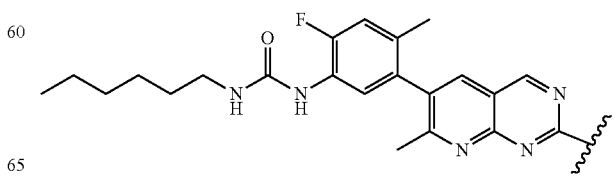

where the wavy line indicates the site of attachment of the Linker Component.

In some embodiments, LY3009120 is modified to accommodate covalent linkage with the Linker Component as shown below

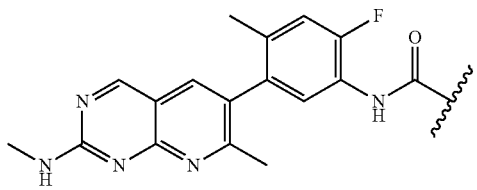 [SMILES: *C(=O)Nc1cc(-c2cc3cnc(NC)nc3nc2C)c(C)cc1F]

where the wavy line indicates the site of attachment of the Linker Component.

In some embodiments, MLN2480 is modified to accommodate covalent linkage with the Linker Component as shown below

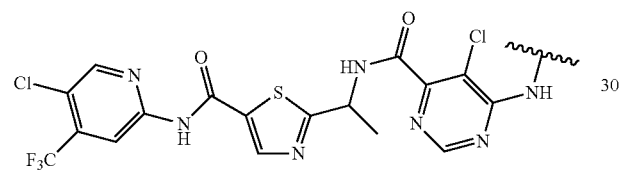

where the wavy line indicates the site of attachment of the Linker Component.

In some embodiments, PF-04880594 is modified to accommodate covalent linkage with the Linker Component as shown below

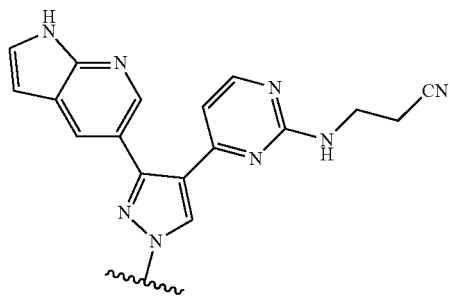 [SMILES: *n1cc(-c2ccnc(NCCC#N)n2)c(-c2cnc3[nH]ccc3c2)n1]

where the wavy line indicates the site of attachment of the Linker Component.

In some embodiments, PF-04880594 is modified to accommodate covalent linkage with the Linker Component as shown below

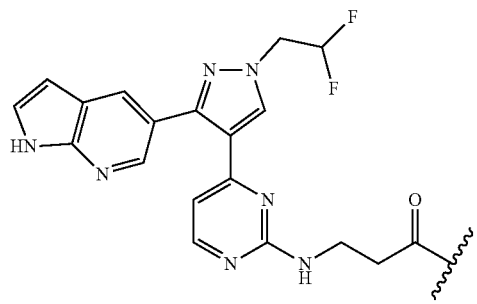 [SMILES: *C(=O)CCNc1nccc(-c2cn(CC(F)F)nc2-c2cnc3[nH]ccc3c2)n1]

where the wavy line indicates the site of attachment of the Linker Component.

In some embodiments, PF-04880594 is modified to accommodate covalent linkage with the Linker Component as shown below

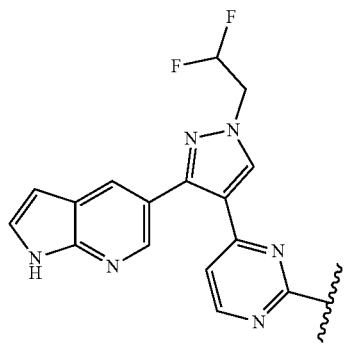 [SMILES: *c1nccc(-c2cn(CC(F)F)nc2-c2cnc3[nH]ccc3c2)n1]

where the wavy line indicates the site of attachment of the Linker Component.

Preparing RAF-Degrading Conjugate Compounds

When preparing RAF-Degrading Conjugate Compounds, the Ligands for RAF may be modified to provide appropriate linker chemistry between the Ligand for RAF and the Linker Component. Appropriate linker chemistry includes, but is not limited to, nucleophilic substitution, amide formation, and click chemistry. Accordingly, in some embodiments, the Ligand for RAF is modified to include a functional group that facilitates linkage between the Linker Component and the Ligand for RAF. Functional groups that facilitate linkage include, but are not limited to a halogen, amine, hydroxyl, carboxylic acid, ester, alkyne, and azide. It is understood that functional group included in the modified Ligand for RAF will depend on the identity of the reactive group of the Linker Component with which it will be reacted. Based on the disclosure provided herein, a person of skill in the art can appropriately choose desirable functional groups.

In some embodiments, generating the Ligand for RAF includes using a synthetic precursor of an existing ligand. For example, a synthetic precursor of sorafenib includes a terminal carboxylic acid moiety at the 2-position of the pyridine (sorafenib acid). Sorafenib has a terminal N-methyl at this position. In some embodiments, the synthetic precursor of sorafenib, sorafenib acid, provides appropriate linker chemistry with the Linker Component. As a non-limiting example, the synthetic precursor of sorafenib (sorafenib acid) can be reacted with a reactive group of the Linker Compound such as an amine or hydroxyl to form the RAF-Degrading Conjugate Compound of the present disclosure. Synthetic precursors used in RAF-Degrading Conjugate Compounds of the present disclosure maintain sufficient affinity for the target of interest. Based on the disclosure provided herein, a person of skill in the art could readily prepare synthetic precursors of the above mentioned Ligands for RAF that facilitate covalent attachment with the Linker Component, yet maintain sufficient affinity for its target.

In some embodiments, generating the Ligand of RAF includes adding a functional group to the Ligand of RAF. In some embodiments, the functional group is added to an aromatic ring of the Ligand for RAF. In some embodiments the functional group is added to an alkyl portion of the Ligand for RAF. When a functional group is added to a Ligand for RAF, the Ligand for RAF maintains sufficient affinity for its target.

In some embodiments, sorafenib is modified as shown below to accommodate appropriate linker chemistry with the Linker Component, where Z is the remainder of Linker Component.

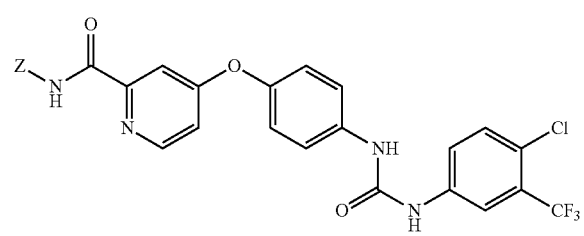

(Exemplary Linkage of Sorafenib to Linker Component)

In some embodiments, Hah et al. 10d is modified as shown below to accommodate appropriate linker chemistry with the Linker Component, where Z is the remainder of Linker Component.

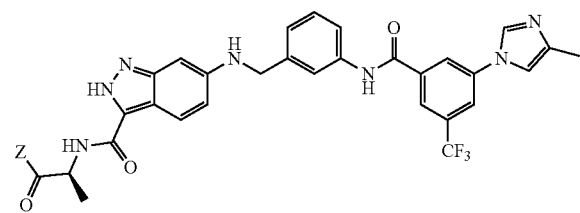

(Exemplary Linkage of Hah et al 10d to Linker Component)

In some embodiments, RAF709 is modified as shown below to accommodate appropriate linker chemistry with the Link Component, where Z is the remainder of the Linker Component

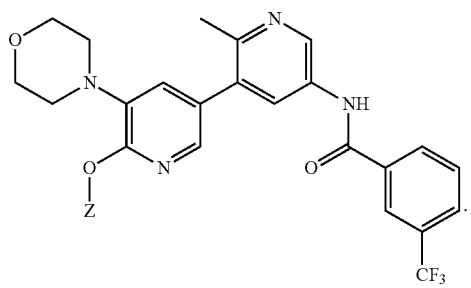

In some embodiments, a selective B/C RAF inhibitor of the formula shown below is modified to accommodate appropriate linker chemistry with the Link Component, where Z is the remainder of the Linker Component and X is N or CH

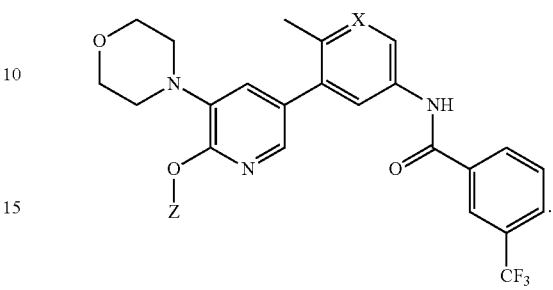

2. Degradation Signaling Agents

Degradation Signaling Agents of the present disclosure include compounds or peptides that induce degradation of the targeted RAF protein. Generally, Degradation Signaling Agents degrade RAF by binding to or recruiting one or more degradation proteins. The degradation proteins are usually associated with the proteasome, the ubiquitin-proteasome pathway, or lysosomal proteolysis. Accordingly, Degradation Signaling Agents include, but are not limited to E3 ligase recognition agents, hydrophobic tagging agents, proteasome recognition agents, and lysosomal recognition peptides.

In some embodiments, the Degradation Signaling Agents binds to a degradation protein or a component of a degradation protein complex. In some embodiments, the bound Degradation Signaling Agent activates the degradation protein or degradation protein complex. In some embodiments, the bound Degradation Signaling Agent does not significantly alter the activity of the degradation protein or degradation protein complex.

In some embodiments, the degradation protein or degradation protein complex is an E3 ubiquitin ligase or an E3 ubiquitin ligase complex. In some embodiments, the E3 ubiquitin ligase or component of the E3 ubiquitin ligase complex targeted is MDM2, cIAP1, VHL protein, CBRN, or $SCF^{\beta-TRCP}$.

In some embodiments, the Degradation Signaling Agents recruits a degradation protein or degradation protein complex by binding to or associating with the RAF protein causing misfolding of the RAF protein. In some embodiments, the Degradation Signaling Agents recruits a degradation protein or degradation protein complex without misfolding the RAF protein.

In some embodiments, the degradation protein or degradation protein complex is the proteasome. In some embodiments, the degradation protein or degradation protein complex is a chaperone protein. In some embodiments, the chaperone protein is hsc70.

i) E3 Ligase Recognition Agents

The E3 ligase recognition agent is any compound or peptide that effectively binds to an E3 ubiquitin ligase or an E3 ubiquitin ligase complex. In some embodiments, the E3 ligase recognition agent is an E3 ubiquitin ligase ligand. In some embodiments, the E3 ubiquitin ligase ligand is a modified version of Pomalidomide, Nutlin-3, VHL Ligand, methyl bestatin, a VHL binding peptide, or a $SCF^{\beta-TRCP}$ targeting peptide. In some embodiments, the VHL binding peptide is HIF-1α-VHL binding peptide or hydroxy proline-HIF-1α-VHL binding peptide.

Select positions of the compounds shown in Table 2 may be modified to accommodate covalent linkage with the Linker Component and do not obstruct target binding of the E3 Ligase Recognition Agent. When covalently attached to the linker component, the E3 Ligase Recognition Agent maintains sufficient affinity for its target.

Without being bound to any particular theory, it is believed that bringing the RAF protein and the E3 ubiquitin ligase or an E3 ubiquitin ligase complex in close proximity increases the rate of RAF degradation.

TABLE 2

E3 Ubiquitin Ligase Ligands

Pomalidomide

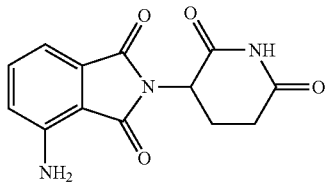

VHL Ligand

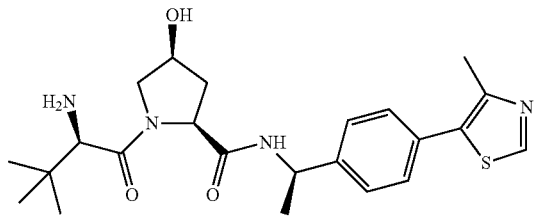

Nutlin-3

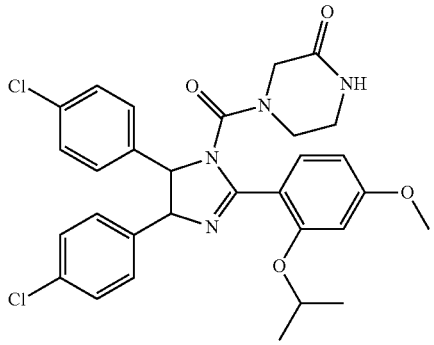

TABLE 2-continued

E3 Ubiquitin Ligase Ligands

Methyl bestatin

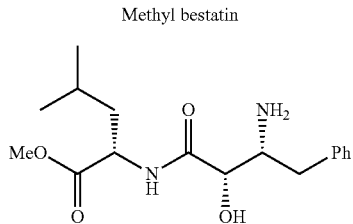 [SMILES: COC(=O)[C@H](CC(C)C)NC(=O)[C@@H](O)[C@H](N)Cc1ccccc1]

HIF-1α - VHL binding peptide

H₂N-ALAPYIPOH

Hydroxy proline-HIF-1α - VHL binding peptide

H₂N-ALAP*YIPOH

P* - hydroxyproline

SCF^{β-TRCP} targeting peptide

H₂N-GGGGGGDRHDS*GLDS*MOH

S* - phosphoserine

The letters of the final three entries (the peptide sequences) represent amino acids.

In some embodiments, pomalidomide is modified to accommodate covalent linkage with the Linker Component as shown below

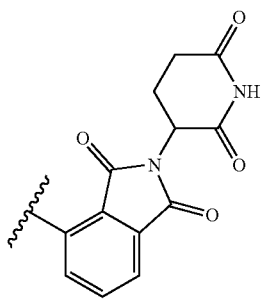 [SMILES: *c1cccc2c1C(=O)N(C1CCC(=O)NC1=O)C2=O]

where the wavy line indicates the site of attachment of the Linker Component.

In some embodiments, pomalidomide is modified to accommodate covalent linkage with the Linker Component as shown below

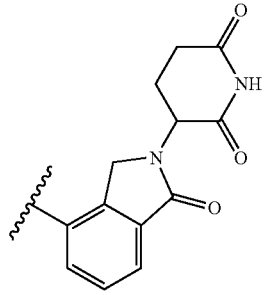 [SMILES: *c1cccc2c1CN(C1CCC(=O)NC1=O)C2=O]

where the wavy line indicates the site of attachment of the Linker Component.

In some embodiments, VHL Ligand is modified to accommodate covalent linkage with the Linker Component as shown below

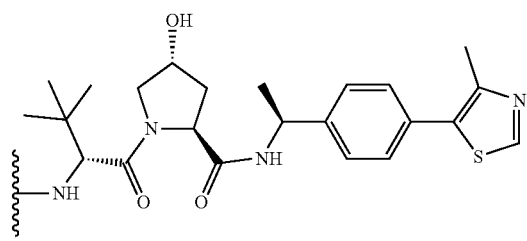 [SMILES: *N[C@@H](C(=O)N1C[C@H](O)C[C@H]1C(=O)N[C@@H](C)c1ccc(-c2scnc2C)cc1)C(C)(C)C]

where the wavy line indicates the site of attachment of the Linker Component.

In some embodiments, VHL Ligand is modified to accommodate covalent linkage with the Linker Component as shown below

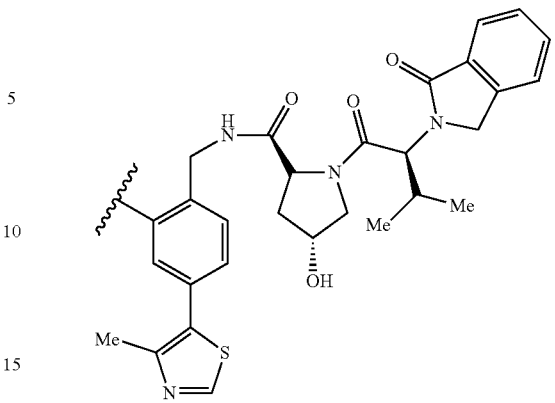

where the wavy line indicates the site of attachment of the Linker Component.

ii) Hydrophobic Tagging Agents

Hydrophobic tagging is a process for manipulating the folding of a protein to cause misfolding by contacting a hydrophobic tagging agent with a protein. Misfolded proteins are recognized by the cell and selectively targeted for degradation. When hydrophobic tagging agents are incorporated into the RAF-Degrading Conjugate Compounds of the present disclosure, the Ligands for RAF bring the hydrophobic tagging agent in close proximity to the targeted RAF, increasing the RAF-hydrophobic tagging agent relative concentration. Without being bound to any particular theory, it is believed that the misfolded protein-hydrophobic tagging agent complex is recognized by molecular chaperones which target the protein for degradation.

In some embodiments, hydrophobic tagging agents are generally small molecules that associate with the hydrophobic surfaces of proteins. Generally, hydrophobic tagging agents include one or more alkyl portions and/or one or more polyethylene glycol units, an amide group, and an optional terminal adamantane group. In some embodiments, hydrophobic tagging agents are HyT36 or HyT13, the structures of which are shown in Table 3, below. Select positions of the compounds shown in Table 3 may be modified to accommodate covalent linkage with the Linker Component and do not obstruct target binding of the hydrophobic tagging agent. When covalently attached to the linker component, the hydrophobic tagging agent maintains sufficient affinity for its target.

TABLE 3

Hydrophobic Tagging Agents

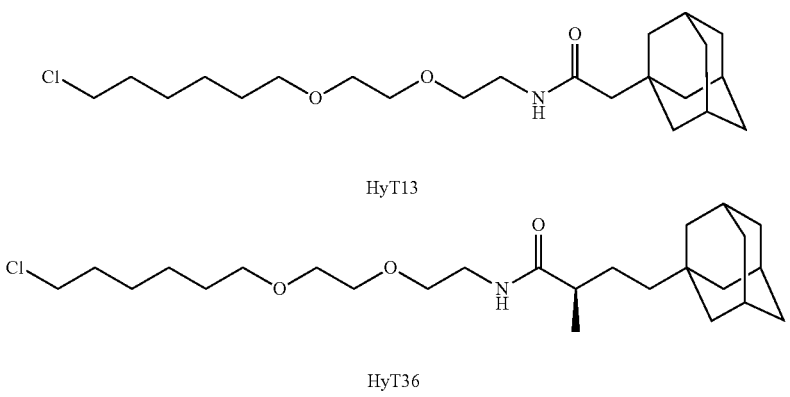

HyT13

HyT36

Suitable hydrophobic Tagging Agents include those described in US 2014/0302523, the contents of which are herein incorporated by reference for all purposes.

iii) Proteasome Recognition Agents

In some embodiments, the Degradation Signaling Agent is a proteasome recognition agent. Proteasome recognition agents are compounds that bind to or recruit the proteasome. When proteasome recognition agents are included in the RAF-Degrading Conjugate Compounds of the present disclosure, they localize target proteins to proteasome. Without being bound to any particular theory, it is believed that proteasome recognition agents induce target protein degradation via direct proteasome recruitment and do not include ubiquitination steps.

In some embodiments, the proteasome recognition agent is Boc$_3$Arginine

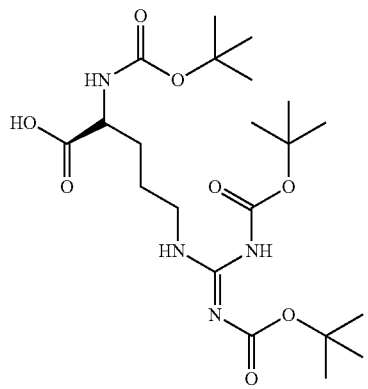

(Boc$_3$Arginine).

iv) Lysosomal Recognition Peptides

Lysosomal recognition peptides are peptides that include a signaling motif for targeted lysosomal degradation. Without being bound to any particular theory, it is believed that the lysosomal recognition peptide, when incorporated into an RAF-Degrading Conjugate Compound of the present disclosure, will mark the targeted RAF protein for degradation via Chaperone-mediated autophagy.

In some embodiments, the lysosomal recognition peptide includes the amino acid motif KFERQ, where each letter is an amino acid. In some embodiments, the lysosomal recognition peptide is the sequence shown in Table 4.

TABLE 4

| Lysosomal recognition peptide |
|---|
|  | v) Preparing RAF-Degrading Conjugate Compounds

When preparing RAF-Degrading Conjugate Compounds, the Degradation Signaling Agents may be modified to provide appropriate linker chemistry between the Degradation Signaling Agent and the Linker Component. As discussed above in Section A, Appropriate linker chemistry includes, but is not limited to, nucleophilic substitution, amide formation, and click chemistry. Accordingly, in some embodiments, the Degradation Signaling Agents is modified to include a functional group that facilitates linkage between the Linker Component and the Degradation Signaling Agents. Functional groups that facilitate linkage include, but are not limited to a halogen, amine, hydroxyl, carboxylic acid, ester, alkyne, and azide. It is understood that functional group included in the modified Degradation Signaling Agents will depend on the identity of the reactive group of the Linker Component with which it will be reacted. Based on the disclosure provided herein, a person of skill in the art can appropriately choose desirable functional groups.

In some embodiments, generating the Degradation Signaling Agents includes using a synthetic precursor. For example, a synthetic precursor of pomalidomide include a fluoro substituent at the 4-position of the isoindoline ring (fluoro pomalidomide). Pomalidomide has an amine group at this position. In some embodiments, the synthetic precursor of pomalidomide, fluoro pomalidomide, provides appropriate linker chemistry with the Linker Component. As a non-limiting example, the synthetic precursor of pomalidomide (fluoro pomalidomide) can be reacted with a reactive group of the Linker Compound such as an amine or hydroxyl to form the RAF-Degrading Conjugate Compound of the present disclosure. Synthetic precursors used in RAF-Degrading Conjugate Compounds of the present disclosure substantially maintain their affinity for binding the target of interest. Based on the disclosure provided herein, a person of skill in the art could readily devise synthetic schemes to prepare synthetic precursors of the above mentioned Degradation Signaling Agents that readily facilitate covalent attachment with the Linker Component and maintain sufficient affinity for its target.

In some embodiments, generating the Degradation Signaling Agents includes adding a functional group to the Degradation Signaling Agents. In some embodiments, the functional group is added to an aromatic ring of the Degradation Signaling Agents. In some embodiments, the functional group is added to an alkyl portion of the Degradation Signaling Agents. When a functional group is added to a Degradation Signaling Agent and the Degradation Signaling Agent is subsequently covalently linked to the Linker Component or the RAF-Degrading Conjugate Compound, the Degradation Signaling Agent maintains sufficient affinity for its target.

In some embodiments, when the Degradation Signaling Agent is a peptide, the Degradation Signaling Agent is covalently linked to the Linker Component by amide formation at the N- or C-terminus of the peptide sequence. For example, the HIF-1α-VHL binding peptide may be linked to the Linger Component, as shown below, where Z is the remainder of Linker Component.

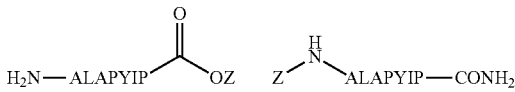

(Exemplary Linkages of HIF-1α-VHL Binding Peptide to Linker Component)

In some embodiments, when the Degradation Signaling Agent is a peptide, the Degradation Signaling Agent is covalently linked to the Liner Component at a side-chain.

In some embodiments, nutlin-3 is modified as shown below to accommodate appropriate linker chemistry with the Linker Component, where Z is the remainder of Linker Component.

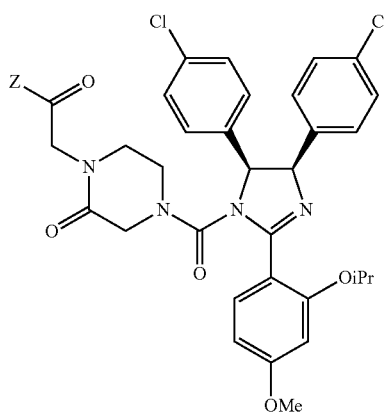

(Exemplary Linkage of Nutlin-3 to Linker Component)

In some embodiments, methylbestatin is modified as shown below to accommodate appropriate linker chemistry with the Linker Component, where Z is the remainder of the linker component.

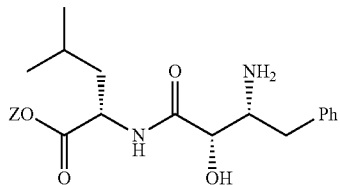

(Exemplary Linkage of Methylbestatin to Linker Component)

In some embodiments, the chloro substituent in HyT13 or HyT36 is used in a nucleophilic substitution reaction to covalently link the Linker Component and the Degradation Signaling Agent as shown below, where Z is the remainder of the linker component.

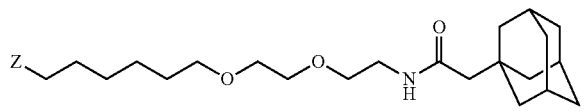

(Exemplary Linkage of HyT13 to Linker Component)

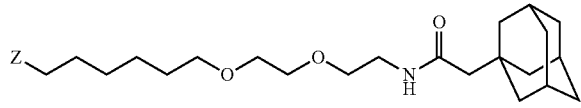

(Exemplary Linkage of HyT36 to Linker Component)

In some embodiments, the appropriate linker chemistry between the Degradation Signaling Agent and the Linker Component is already present and the Degradation Signaling Agent is not modified.

In some embodiments, the carboxylic acid of Boc$_3$Arginine is used to form a covalent linkage with the Linker Component, where Z is the remainder of the linker component.

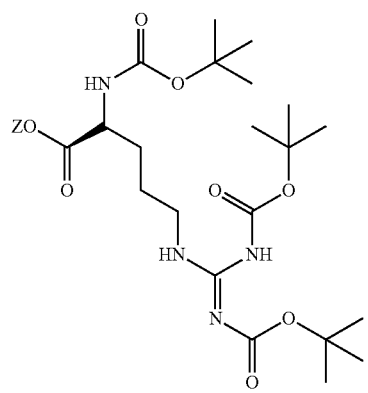

(Exemplary Linkage of Boc$_3$Arginine to Linker Component)

3. Linker Components

The Linker Component of the present disclosure comprise the following features: (1) a first reactive group which facilitates covalent attachment of the Ligand for RAF to the Linker Component; (2) a second reactive group which facilitates covalent attachment of the Degradation Signaling Agent to the Linker Component; and (3) a linking unit which connects the first reactive group and the second reactive group.

The methods of making RAF-Degrading Conjugate Compounds with linker components are discussed below, but a person of skill in the art will readily recognize that a variety of synthetic schemes can be used. For example, in some embodiments, Linker Components are single pre-synthesized molecular entities that are covalently attached to a Ligand for RAF and a Degradation Signaling Agent (either simultaneously or in an order of most synthetic convenience). In some embodiments, Linker Components are made from separate molecules entities (segments of a linker component) which are covalently attached to a Ligand for RAF or a Degradation Signaling Agent. After each segment of the linker component is covalently attached to a respective Ligand for RAF and Degradation Signaling Agent, an additional reaction is performed to covalently link the two segments of the Linker Component to form a RAF-Degrading Conjugate Compound. It is understood that when segments of the Linker Component are covalently attached after pre-attachment to a respective Ligand for RAF or Degradation Signaling Agent, each segment of the Linker component will have an additional reactive group that facilitates covalent attachment between the two segments of the Linker Component.

Reactive groups that facilitate covalent attachment to the Ligand for RAF and the Degradation Signaling Agent depend on the specific Ligand for RAF and Degradation Signaling Agent used, but as discussed above, suitable covalent linking chemistries include, but are not limited to, nucleophilic substitution, amide formation, and click chemistry. Exemplary linker chemistries are shown in Table 5, below. In the table below, $R^1$ is the Ligand for RAF or the Degradation Signaling Agent, and $R^2$ is the remainder of the Linker Component. A person of skill in the art will recognize that the functional groups of $R^1$ and $R^2$ may switch without departing from the scope of the present disclosure.

TABLE 5

Exemplary Linker Chemistry

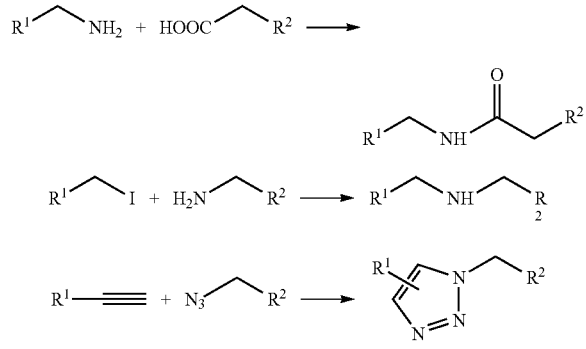

In some embodiments, the first and second reactive group are different functional groups. In some embodiments, the first and second reactive groups are the same functional group.

Although Table 5 shows a nucleophilic substitution reaction with an amine and iodine, it is understood that additional nucleophiles and leaving groups may be used in the nucleophilic substitution reaction. Suitable nucleophiles include, but are not limited to, hydroxyl and thiol groups. Suitable leaving groups include, but are not limited to Cl, Br, and OTs.

In some embodiments, the Ligand for RAF or Degradation Signaling Agent contain a reactive group that readily facilitates covalent attachment to the Linker Component. In some embodiments, the Ligand for RAF and/or Degradation Signaling Agent is modified to include a suitable functional group that readily facilitates covalent attachment. As discussed above, in some embodiments, a sorafenib component (sorafenib acid) is covalently attached to the Linker Component via amide formation. This is achieved by reacting sorafenib acid (comprising a carboxylic acid at the 2-position of the pyridine ring) with an amine group from the Linker Component. In the RAF-Degrading Conjugate Compounds of the present disclosure, after attachment of the Linker Component to the Ligand for RAF and the Degradation Signaling Agent, both the Ligand for RAF and the Degradation Signaling Agent maintain sufficient affinity for their targets to carry out the desired effect.

As discussed above, in some embodiments, Linker Components are made from separate molecular entities which are first covalently attached to a Ligand for RAF or a Degradation Signaling Agent. In such embodiments, the two segments of the Linker Component are covalently attached after each entity has been pre-attached to a respective Ligand for RAF or Degradation Signaling Agent. Suitable functional groups that facilitate covalent attachment of the molecular entities include the exemplary linker chemistry shown in Table 5 and the groups discussed supra. In some embodiments, the two segments of the linker component are covalently attached using azide-alkyne cycloaddition. In, some embodiments, the two segments of the linker component are covalently attached using amid formation chemistry.

Linking units of the Linker Component are generally non-reactive moieties such as alkyl groups. In some embodiments, the alkyl groups include one or more ether linkages. In some embodiments, the alkyl groups are linear. In some embodiments, the alkyl groups are branched. In some embodiments, the first reactive group is an amine group and the second reactive group is a carboxylic acid group. In some embodiments, the Linker Component includes a triazine.

In some embodiments, the Linker Component comprises polyethylene glycol.

In some embodiments, the Linker Component has a formula selected from the group consisting of

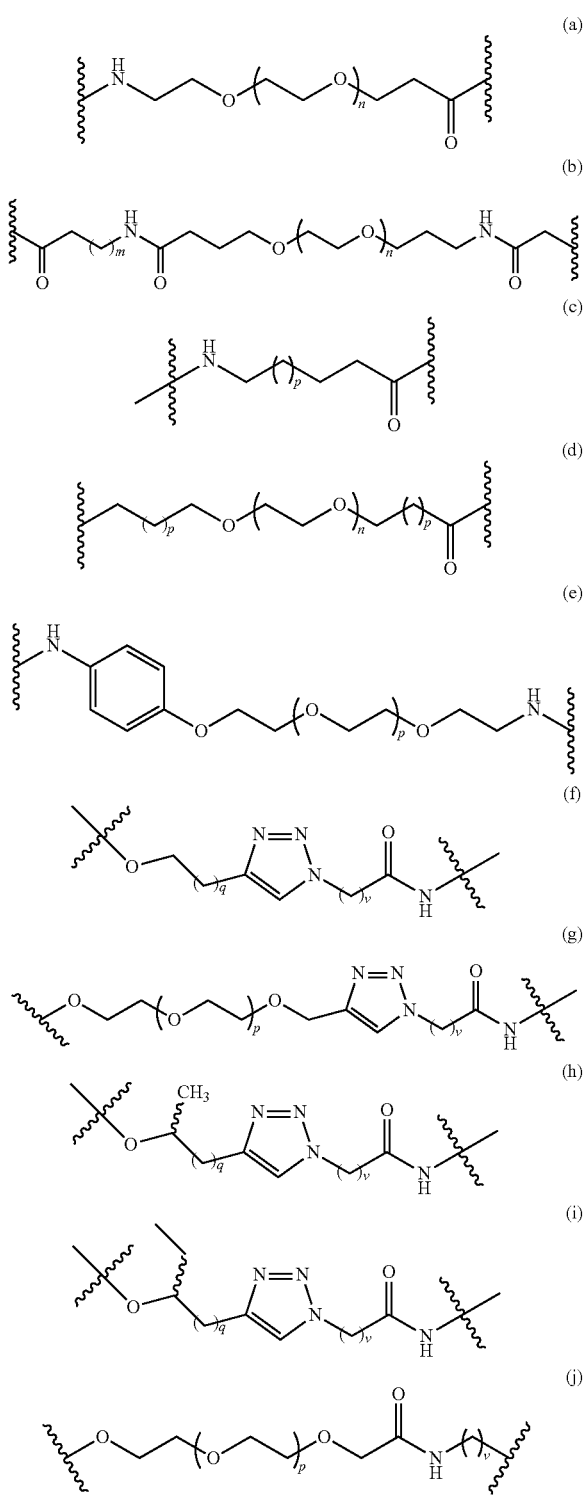

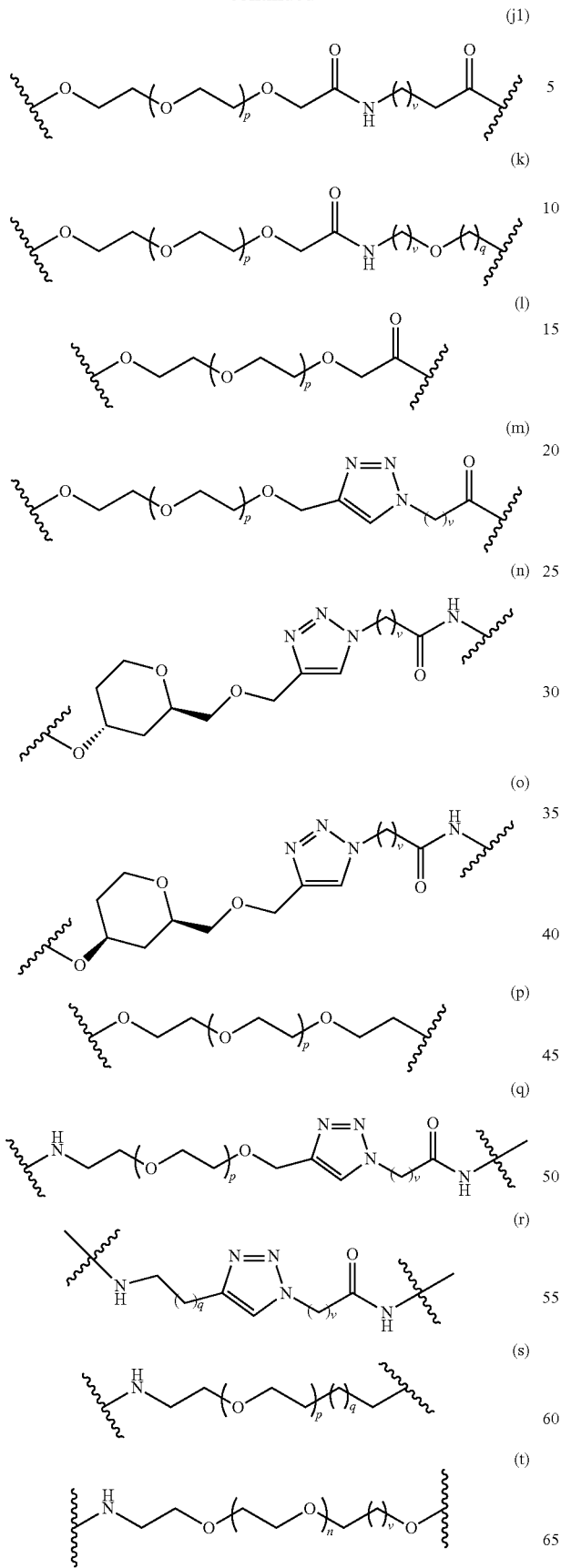

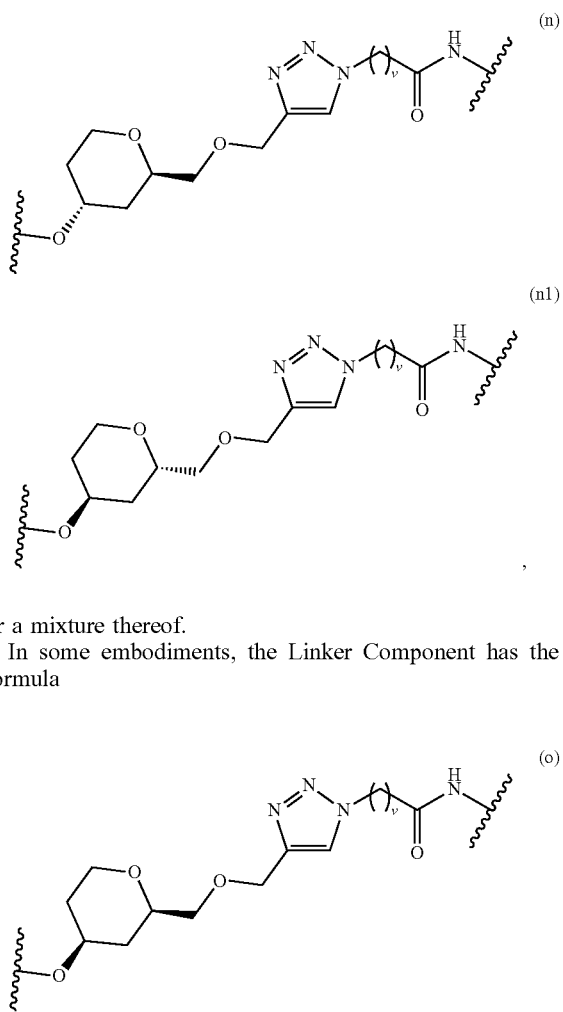

wherein the subscript m is an integer from 1 to 24, the subscript n is an integer from 1 to 14, each subscript p is independently an integer from 0 to 6, the subscript q is an integer from 0 to 8, and subscript v is an integer from 1 to 10 and the wavy lines indicate sites of attachment of the Ligand for RAF and the Degradation Signaling Agent.

In some embodiments, the Linker Component has the formula or a mixture thereof.

In some embodiments, the Linker Component has the formula

-continued

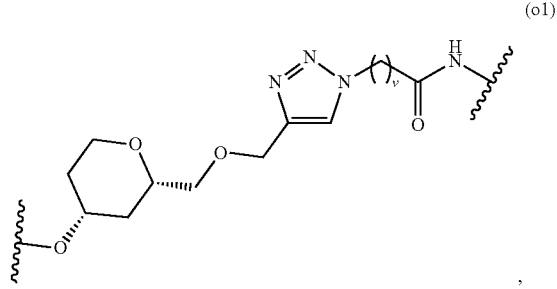

(o1)

or a mixture thereof.

In some embodiments, the Linker Component has a formula selected from the group consisting of

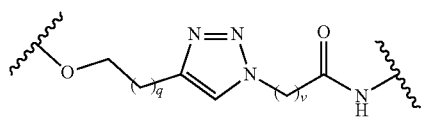

(f)

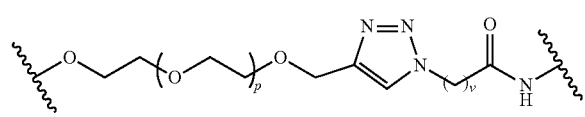

(g)

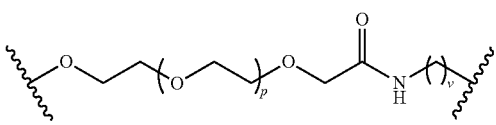

(j)

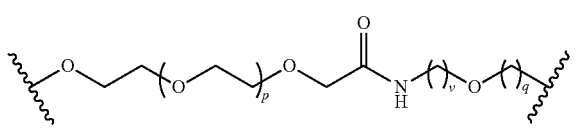

(k)

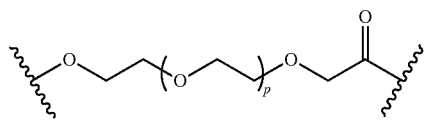

(l)

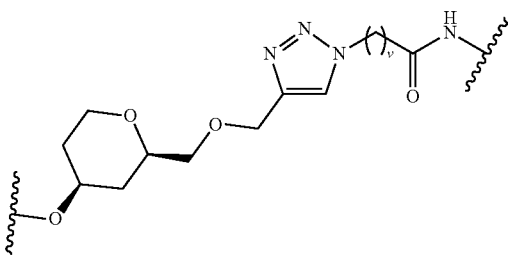

(o)

wherein each subscript p is independently an integer from 0 to 6, the subscript q is an integer from 0 to 8, and subscript v is an integer from 1 to 10 and the wavy lines indicate sites of attachment of the Ligand for RAF and the Degradation Signaling Agent.

In the Linker Component structures above, terminal heteroatoms, when present, may be part of the original Ligand for RAF or the Degradation Signaling Agent structure, or the heteroatom may be added to an alkyl portion of the Ligand for RAF or the Degradation Signaling Agent. A person of skill in the art will recognize that two subsequent heteroatoms such as an oxygen covalently bonded to an oxygen will not be particularly stable compounds. Thus, in instances where there is a terminal heteroatom in the Linker Component and the point of covalent attachment to the Ligand for RAF or the Degradation Signaling Agent is a heteroatom, it is understood that only a single heteroatom is intended. For example, when the Degradation signaling agent has the structure

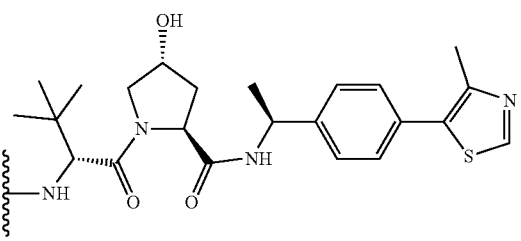 [SMILES: *N[C@@H](C(=O)N1C[C@H](O)C[C@H]1C(=O)N[C@@H](C)c1ccc(-c2scnc2C)cc1)C(C)(C)C]

where the wavy line indicates the point of attachment to the Linker Component, and the Linker Component has the structure

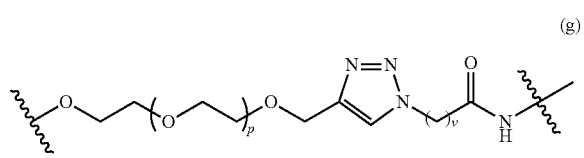

(g)

where the wavy line on the right hand site of the structure indicates the point of attachment to the Degradation Signaling Agent, a person of skill in the art would recognize that an amide linkage is intended rather than an acylhydrazine linkage.

Additionally, the Linker Component structures shown above illustrate terminal secondary amines (i.e. amine groups that are covalently attached to the Ligand for RAF or the Degradation Signaling Agent and the remainder of the Linker Component). In some embodiments, the terminal amine may be a tertiary amine, depending on the amine group from the Ligand for RAF or the Degradation Signaling Agent. For example, the amine group in the pyrazole ring of the modified PF-04880594 or the amine in the piperazine ring of the modified RAF709 (shown below) can be the terminal amine group shown in the Linker Component structure.

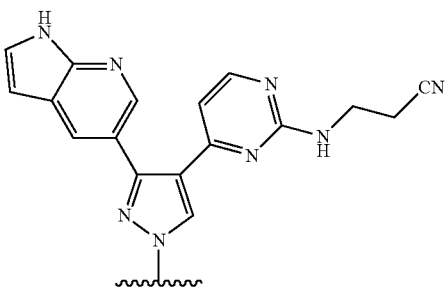

-continued

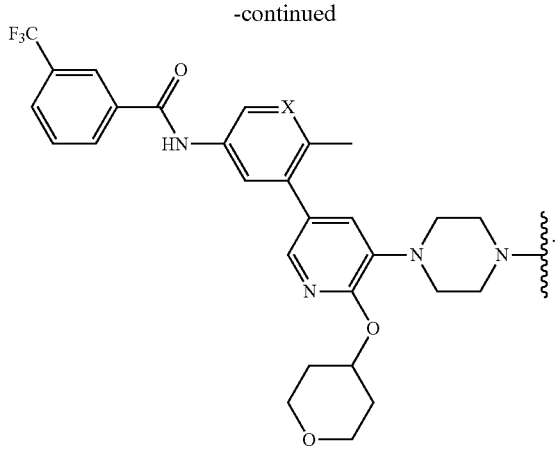

In some embodiments, the subscript m is an integer from 1 to 6, 1 to 8, 1 to 10, 1 to 12, 1 to 14, 1 to 16, 1 to 18, 1 to 20, or 1 to 24. In some embodiments, the subscript m is 1 to 6. In some embodiments, the subscript m is 1 to 12.

In some embodiments, the subscript n is an integer from 1 to 4, 1 to 6, 1 to 8, 1 to 10, or 1 to 12. In some embodiments, the subscript n is 1 to 6. In some embodiments, the subscript n is 1 to 10.

In some embodiments, the subscript p is an integer from 0 to 2, 0 to 3, 0 to 4, or 0 to 5. In some embodiments, the subscript p is 1. In some embodiments, the subscript p is 0 to 4.

In some embodiments, the subscript q is an integer from 0 to 2, 0 to 4, 0 to 6, 0 to 8, 0 to 10, or 0 to 12. In some embodiments, the subscript q is 0 to 6. In some embodiments, the subscript q is 1 to 10.

In some embodiments, the subscript v is an integer from 1 to 2, 1 to 4, 1 to 6, 1 to 8, 1 to 10, or 1 to 12. In some embodiments, the subscript v is 1 to 6. In some embodiments, the subscript v is 1 to 10. In some embodiments, the subscript v is 5.

4. Particular Embodiments of the Present Disclosure

Provided below are specifically contemplated embodiments. The provided disclosure is intended exemplify contemplated embodiments and is not intended to be a comprehensive or limiting list. The RAF-Degrading Conjugate Compounds are generated by covalently linking a Ligand for RAF, a Degradation Signaling Agent, and a Linker Component. Covalent linkages between each component may be achieved using the linker chemistry and the modifications for the Ligands for RAF and the Degradation Signaling Agents described in the preceding sections. The covalently linked Ligands for RAF and the Degradation Signaling Agents maintain sufficient binding affinity for their targets to carry out the desired effect.

In some embodiments, the RAF-Degrading Conjugate Compound comprises a Ligand for RAF that is sorafenib, a Degradation Signaling Agents that is pomalidomide or a small molecule VHL ligand, and a Linker Component of formula (a).

In some embodiments, the RAF-Degrading Conjugate Compound comprises a Ligand for RAF that is sorafenib, a Degradation Signaling Agents that is pomalidomide or a small molecule VHL ligand, and a Linker Component of formula (b).

In some embodiments, the RAF-Degrading Conjugate Compound comprises a Ligand for RAF that is sorafenib, a Degradation Signaling Agents that is pomalidomide or a small molecule VHL ligand, and the Linker Component of formula (c).

In some embodiments, the RAF-Degrading Conjugate Compound comprises a Ligand for RAF that is sorafenib, a Degradation Signaling Agents that is pomalidomide or a small molecule VHL ligand, and the Linker Component of formula (d).

In some embodiments, the RAF-Degrading Conjugate Compound comprises a Ligand for RAF that is Hah 10d, a Degradation Signaling Agents that is pomalidomide or a small molecule VHL ligand, and the Linker Component of formula (a).

In some embodiments, the RAF-Degrading Conjugate Compound comprises a Ligand for RAF that is Hah 10d, a Degradation Signaling Agents that is pomalidomide or a small molecule VHL ligand, and the Linker Component of formula (b).

In some embodiments, the RAF-Degrading Conjugate Compound comprises a Ligand for RAF that is Hah 10d, a Degradation Signaling Agents that is pomalidomide or a small molecule VHL ligand, and the Linker Component of formula (c).

In some embodiments, the RAF-Degrading Conjugate Compound comprises a Ligand for RAF that is Hah 10d, a Degradation Signaling Agents that is pomalidomide or a small molecule VHL ligand, and the Linker Component of formula (d).

In some embodiments, the RAF-Degrading Conjugate Compound comprises a Ligand for RAF that is PF-04880594, a Degradation Signaling Agents that is pomalidomide or a small molecule VHL ligand, and the Linker Component of formula (a).

In some embodiments, the RAF-Degrading Conjugate Compound comprises a Ligand for RAF that is PF-04880594, a Degradation Signaling Agents that is pomalidomide or a small molecule VHL ligand, and the Linker Component of formula (b).

In some embodiments, the RAF-Degrading Conjugate Compound comprises a Ligand for RAF that is PF-04880594, a Degradation Signaling Agents that is pomalidomide or a small molecule VHL ligand, and the Linker Component of formula (c).

In some embodiments, the RAF-Degrading Conjugate Compound comprises a Ligand for RAF that is PF-04880594, a Degradation Signaling Agents that is pomalidomide or a small molecule VHL ligand, and the Linker Component of formula (d).

In some embodiments, the RAF-Degrading Conjugate Compound comprises a Ligand for RAF that is LY3009120, a Degradation Signaling Agents is pomalidomide or a small molecule VHL ligand, and the Linker Component of formula (a).

In some embodiments, the RAF-Degrading Conjugate Compound comprises a Ligand for RAF that is LY3009120, a Degradation Signaling Agents is pomalidomide or a small molecule VHL ligand, and the Linker Component of formula (b).

In some embodiments, the RAF-Degrading Conjugate Compound comprises a Ligand for RAF that is LY3009120, a Degradation Signaling Agents is pomalidomide or a small molecule VHL ligand, and the Linker Component of formula (c).

In some embodiments, the RAF-Degrading Conjugate Compound comprises a Ligand for RAF that is LY3009120, a Degradation Signaling Agents is pomalidomide or a small molecule VHL ligand, and the Linker Component of formula (d).

In some embodiments, the RAF-Degrading Conjugate Compound comprises a Ligand for RAF that is PLX4720, a Degradation Signaling Agents that is pomalidomide or a small molecule VHL ligand, and the Linker Component of formula (a).

In some embodiments, the RAF-Degrading Conjugate Compound comprises a Ligand for RAF that is PLX4720, a Degradation Signaling Agents that is pomalidomide or a small molecule VHL ligand, and the Linker Component of formula (b).

In some embodiments, the RAF-Degrading Conjugate Compound comprises a Ligand for RAF that is PLX4720, a Degradation Signaling Agents that is pomalidomide or a small molecule VHL ligand, and the Linker Component of formula (c).

In some embodiments, the RAF-Degrading Conjugate Compound comprises a Ligand for RAF that is PLX4720, a Degradation Signaling Agents that is pomalidomide or a small molecule VHL ligand, and the Linker Component of formula (d).

In some embodiments, the RAF-Degrading Conjugate Compound includes a Ligand for RAF that is RAF709, and a Degradation Signaling Agent that is pomalidomide.

In some embodiments, the RAF-Degrading Conjugate Compound includes a Ligand for RAF that is RAF709, and a Degradation Signaling Agent that is VHL Ligand.

In some embodiments, the RAF-Degrading Conjugate Compound includes a Ligand for RAF that is sorafenib, and a Degradation Signaling Agent that is is pomalidomide.

In some embodiments, the RAF-Degrading Conjugate Compound includes a Ligand for RAF that is sorafenib, and a Degradation Signaling Agent that is VHL Ligand.

In some embodiments, the RAF-Degrading Conjugate Compound includes a Ligand for RAF that is LY3009120, and a Degradation Signaling Agent that is pomalidomide.

In some embodiments, the RAF-Degrading Conjugate Compound includes a Ligand for RAF that is LY3009120, and a Degradation Signaling Agent that is VHL Ligand.

In some embodiments, the RAF-Degrading Conjugate Compound includes a Ligand for RAF that is MLN2480, and a Degradation Signaling Agent that is pomalidomide.

In some embodiments, the RAF-Degrading Conjugate Compound includes a Ligand for RAF that is MLN24800, and a Degradation Signaling Agent that is VHL Ligand.

In some embodiments, the RAF-Degrading Conjugate Compound includes a Ligand for RAF that is PF-04880594, and a Degradation Signaling Agent that is pomalidomide.

In some embodiments, the RAF-Degrading Conjugate Compound includes a Ligand for RAF that is PF-04880594, and a Degradation Signaling Agent that is VHL Ligand.

In some embodiments, the RAF-Degrading Conjugate Compound includes a Ligand for RAF that is LXH254, and a Degradation Signaling Agent that is pomalidomide.

In some embodiments, the RAF-Degrading Conjugate Compound includes a Ligand for RAF that is LXH254, and a Degradation Signaling Agent that is VHL Ligand.

In some embodiments, RAF709 has a structure selected from the group consisting of

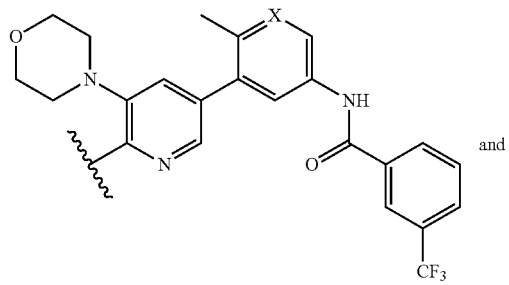

and

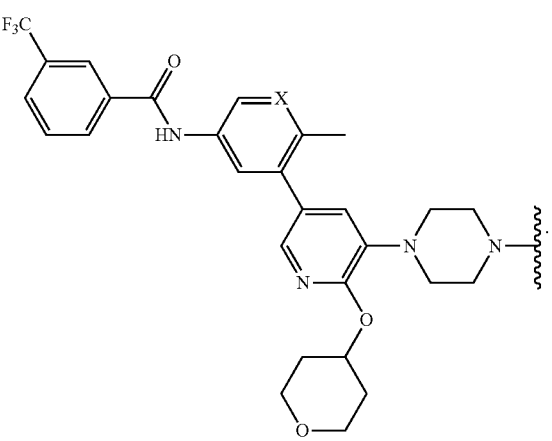

where each X is N or CH and the wavy line indicates the site of attachment of the Linker Component.

In some embodiments, sorafenib has a structure

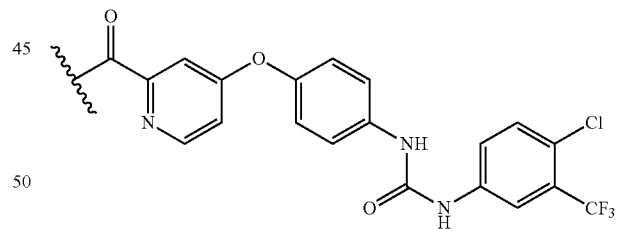

wherein the wavy line indicates the site of attachment of the Linker Component.

In some embodiments, LY3009120 has a structure selected from the group consisting of

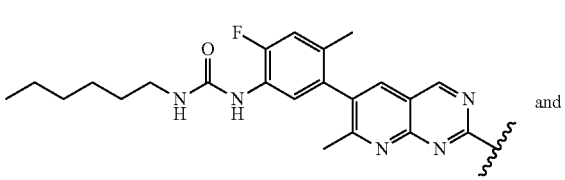

and

-continued

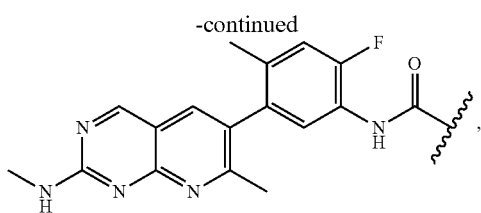

wherein the wavy line indicates the site of attachment of the Linker Component.

In some embodiments, MLN24800 has the structure

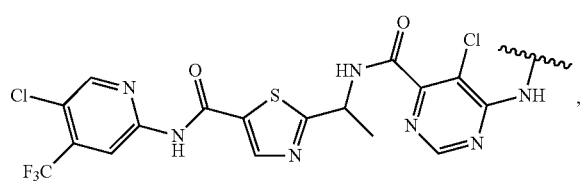 [SMILES: *Nc1ncnc(C(=O)NC(C)c2ncc(C(=O)Nc3cc(C(F)(F)F)c(Cl)cn3)s2)c1Cl]

wherein the wavy line indicates the site of attachment of the Linker Component.

In some embodiments, PF-04880594 has a structure selected from the group consisting of

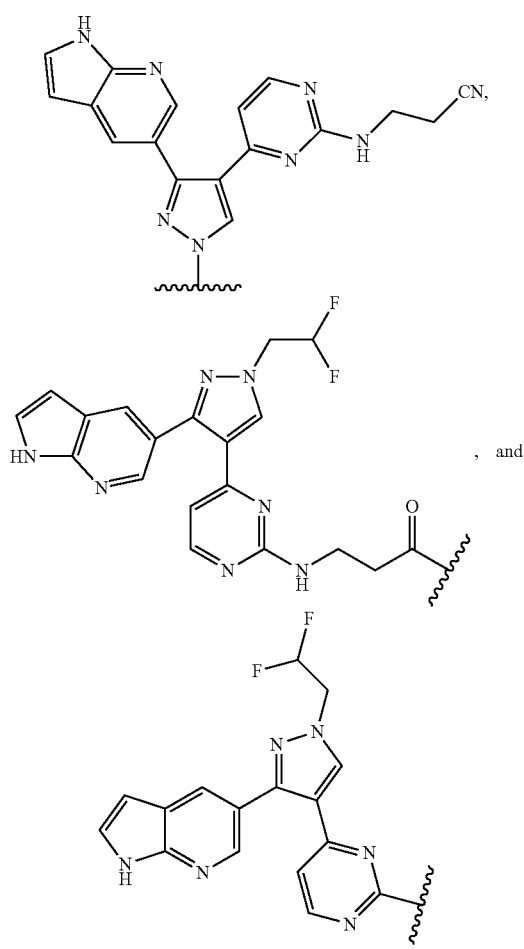

wherein the wavy line indicates the site of attachment of the Linker Component.

In some embodiments, LXH254 has a structure

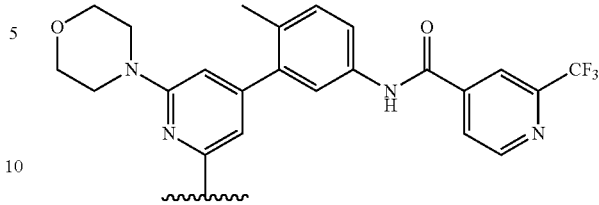

wherein the wavy line indicates the site of attachment of the Linker Component.

In some embodiments, pomalidomide has a structure selected from the group consisting of

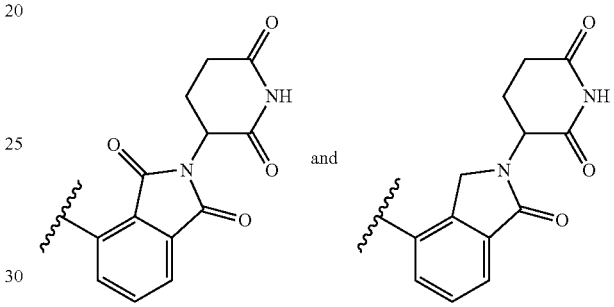

wherein the wavy line indicates the site of attachment of the Linker Component.

In some embodiments, VHL Ligand has a structure selected from the group consisting of

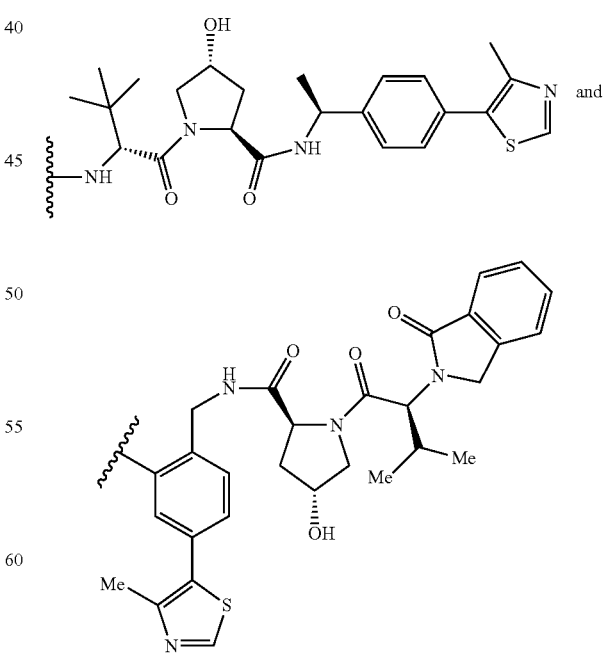

wherein the wavy line indicates the site of attachment of the Linker Component.

In some embodiments, the Linker Component has a formula selected from the group consisting of

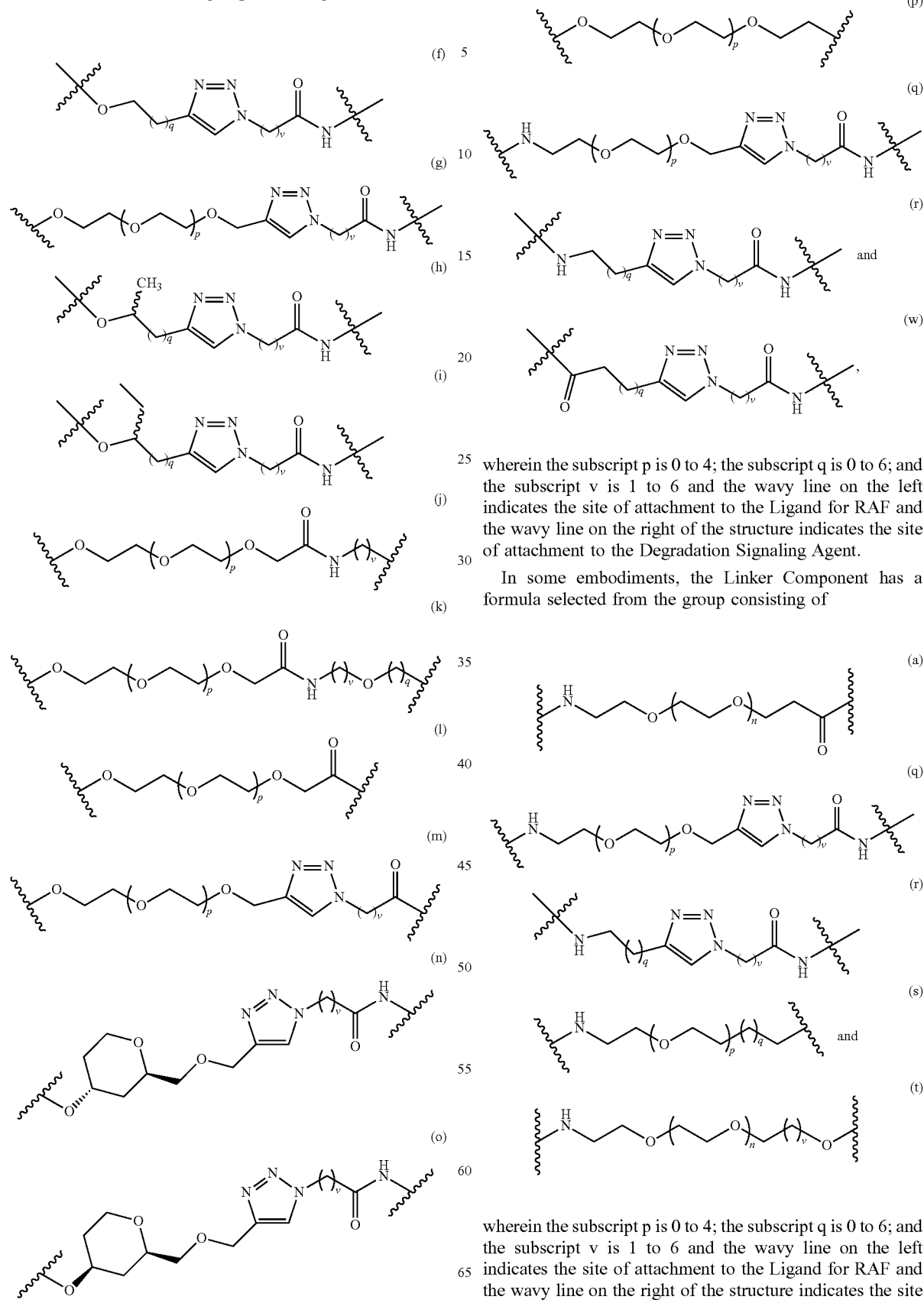

wherein the subscript p is 0 to 4; the subscript q is 0 to 6; and the subscript v is 1 to 6 and the wavy line on the left indicates the site of attachment to the Ligand for RAF and the wavy line on the right of the structure indicates the site of attachment to the Degradation Signaling Agent.

In some embodiments, the Linker Component has a formula selected from the group consisting of wherein the subscript p is 0 to 4; the subscript q is 0 to 6; and the subscript v is 1 to 6 and the wavy line on the left indicates the site of attachment to the Ligand for RAF and the wavy line on the right of the structure indicates the site of attachment to the Degradation Signaling Agent.

In some embodiments, Linker Component has a formula selected from the group consisting of (r)
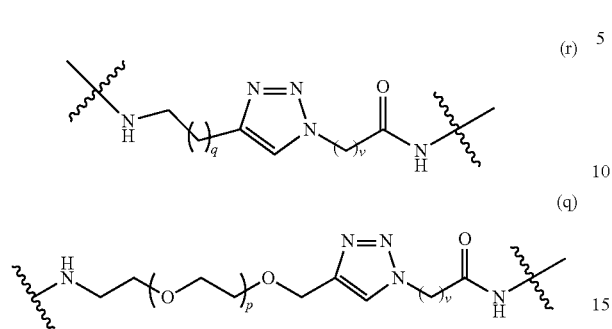
(q)

wherein the subscript p is 0 to 4; the subscript q is 0 to 6; and the subscript v is 1 to 6. and the wavy line on the left indicates the site of attachment to the Ligand for RAF and the wavy line on the right of the structure indicates the site of attachment to the Degradation Signaling Agent In some embodiments, the Linker Component has a formula selected from the group consisting of (r)
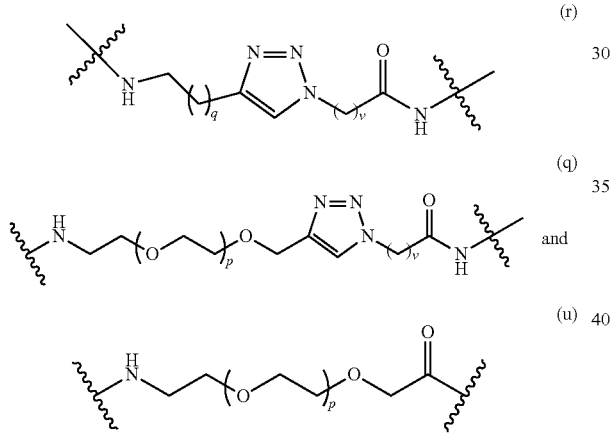
(q)

(u)

wherein the subscript p is 0 to 4; the subscript q is 0 to 6; and the subscript v is 1 to 6 and the wavy line on the left indicates the site of attachment to the Ligand for RAF and the wavy line on the right of the structure indicates the site of attachment to the Degradation Signaling Agent.

In some embodiments, the Linker Component has a formula selected from the group consisting of (l)
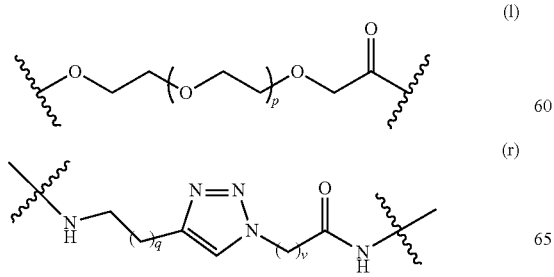
(r)

-continued
(q)
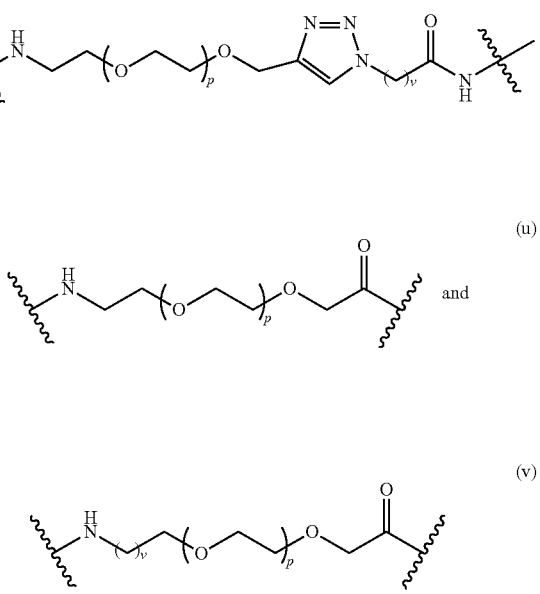
(u)

and (v)

wherein the subscript p is 0 to 4; the subscript q is 0 to 6; and the subscript v is 1 to 6 and the wavy line on the left indicates the site of attachment to the Ligand for RAF and the wavy line on the right of the structure indicates the site of attachment to the Degradation Signaling Agent.

In some embodiments, the RAF-Degrading Conjugate Compound includes a Ligand for RAF has the structure

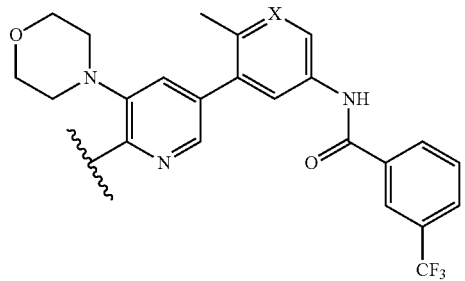

wherein X is N or CH and the wavy line indicates the site of attachment of the Linker Component;

the Degradation Signaling Agent is selected from the group consisting of

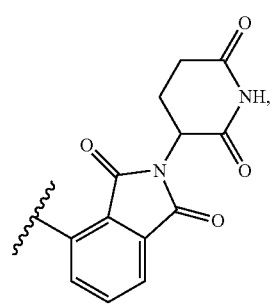

-continued

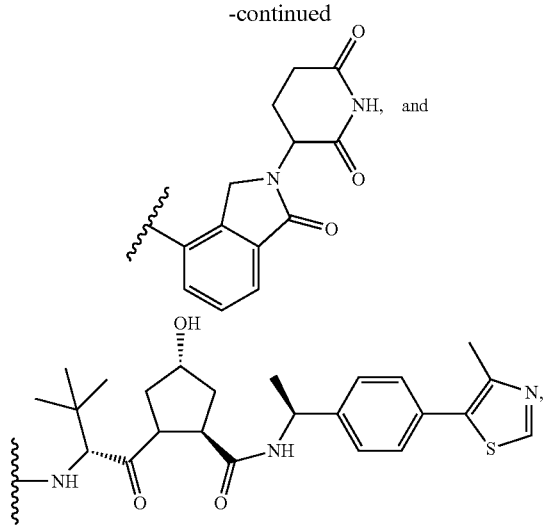

wherein the wavy line indicates the site of attachment of the Linker Component; and the linker component is selected from the group consisting of

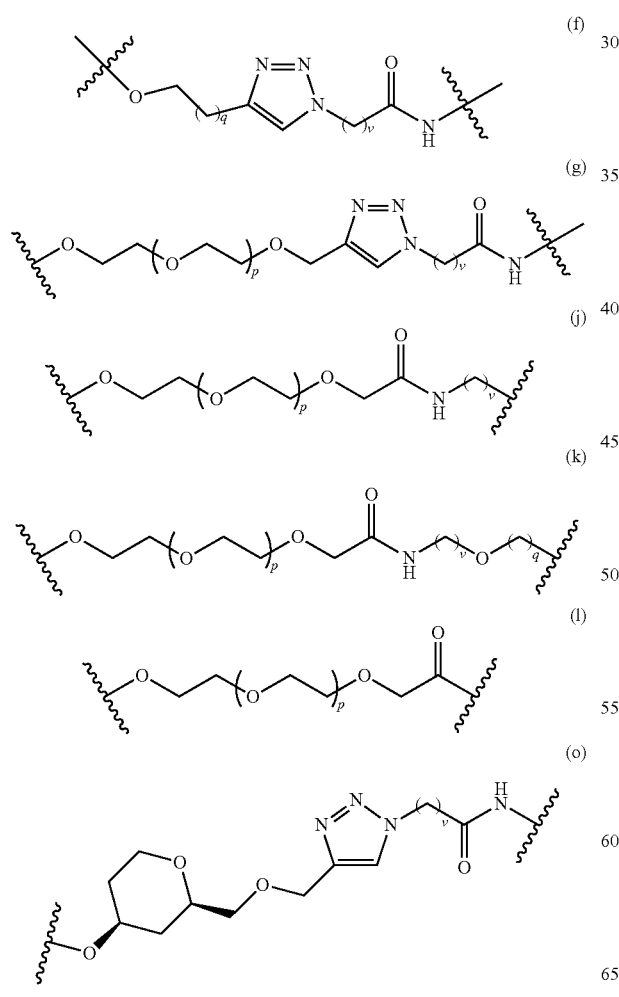

wherein each subscript p is independently an integer from 0 to 6, the subscript q is an integer from 0 to 8, and subscript v is an integer from 1 to 10 and the wavy line on the left indicates the site of attachment to the Ligand for RAF and the wavy line on the right of the structure indicates the site of attachment to the Degradation Signaling Agent.

In some embodiments, the RAF-Degrading Conjugate Compound includes a Ligand for RAF has the structure

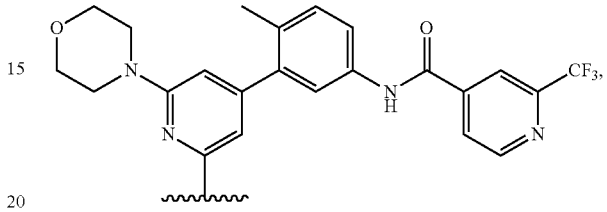

wherein the wavy line indicates the site of attachment of the Linker Component;

the Degradation Signaling Agent is selected from the group consisting of

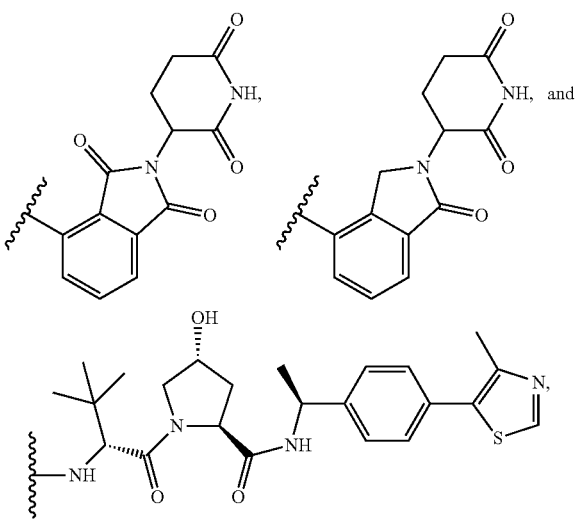

wherein the wavy line indicates the site of attachment of the Linker Component; and the linker component is selected from the group consisting of

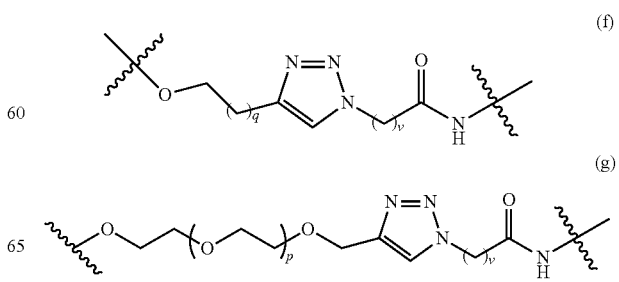

-continued

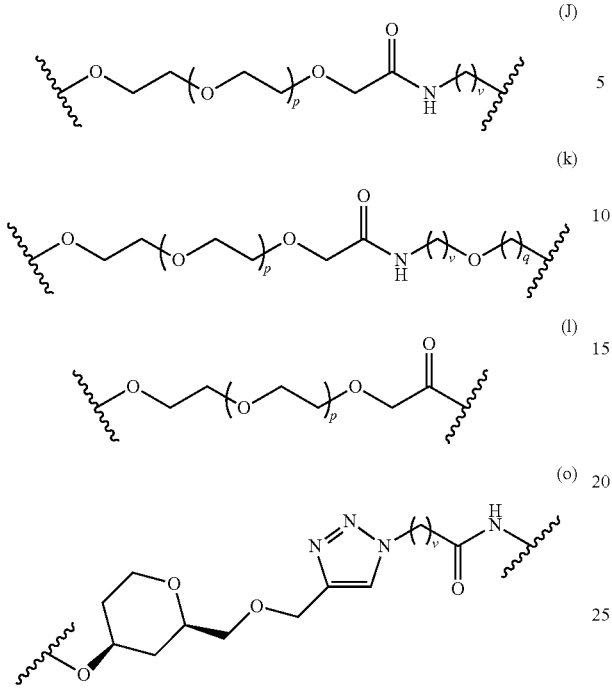

wherein each subscript p is independently an integer from 0 to 6, the subscript q is an integer from 0 to 8, and subscript v is an integer from 1 to 10 and the wavy line on the left indicates the site of attachment to the Ligand for RAF and the wavy line on the right of the structure indicates the site of attachment to the Degradation Signaling Agent.

In some embodiments, each subscript p is independently an integer from 0 to 5, the subscript q is an integer from 0 to 3, and subscript v is an integer from 1 to 7 and the wavy line on the left indicates the site of attachment to the Ligand for RAF and the wavy line on the right of the structure indicates the site of attachment to the Degradation Signaling Agent.

In some embodiments, the Degradation Signaling Agent is

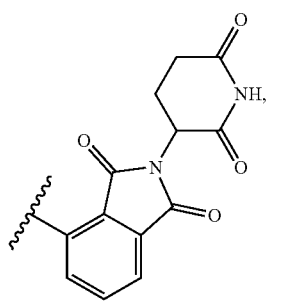 [SMILES: *c1cccc2c1C(=O)N(C1CCC(=O)NC1=O)C2=O]

wherein the wavy line indicates the site of attachment of the Linker Component; and the linker component is selected from the group consisting of

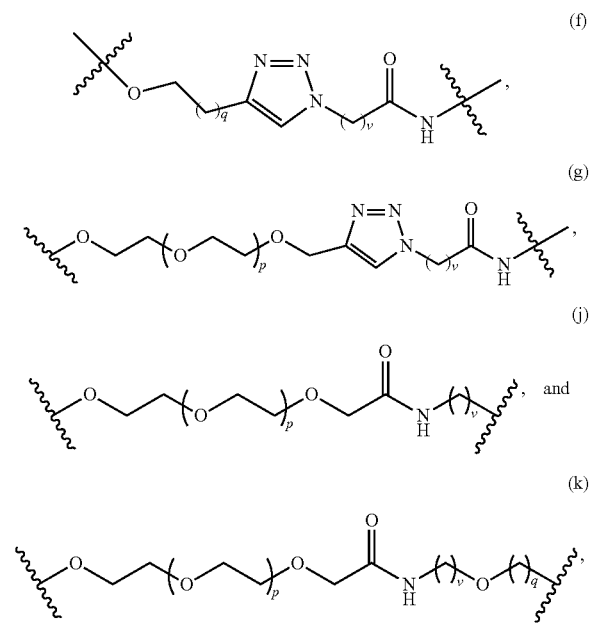

wherein each subscript p is independently an integer from 0 to 3, the subscript q is an integer from 0 to 3, and subscript v is an integer from 1 to 7 and the wavy line on the left indicates the site of attachment to the Ligand for RAF and the wavy line on the right of the structure indicates the site of attachment to the Degradation Signaling Agent.

In some embodiments, the Degradation Signaling Agent is

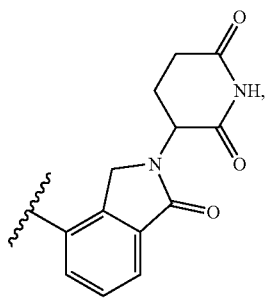 [SMILES: *c1cccc2c1CN(C1CCC(=O)NC1=O)C2=O]

wherein the wavy line indicates the site of attachment of the Linker Component; and the linker component is selected from the group consisting of

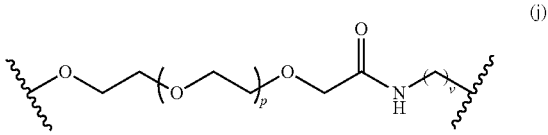

-continued

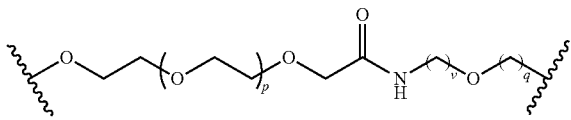
(k)

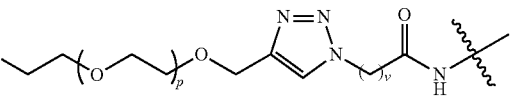
(g)

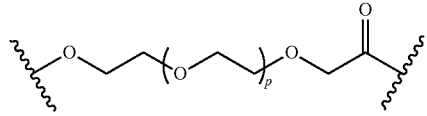
(l)

wherein each subscript p is independently an integer from 0 to 3, the subscript q is an integer from 0 to 3, and subscript v is an integer from 1 to 7 and the wavy line on the left indicates the site of attachment to the Ligand for RAF and the wavy line on the right of the structure indicates the site of attachment to the Degradation Signaling Agent.

In some embodiments, the Degradation Signaling Agent is

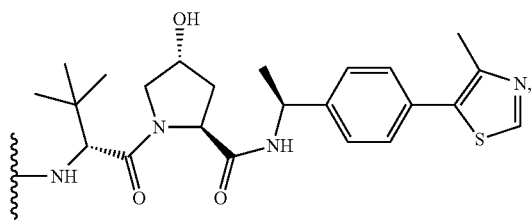 [SMILES: *N[C@@H](C(=O)N1C[C@H](O)C[C@H]1C(=O)N[C@@H](C)c1ccc(-c2scnc2C)cc1)C(C)(C)C]

wherein the wavy line indicates the site of attachment of the Linker Component; and the linker component is selected from the group consisting of

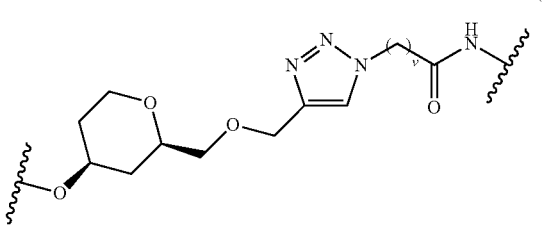
(o)

wherein each subscript p is independently an integer from 0 to 5, and subscript v is an integer from 1 to 7, and the wavy line on the left indicates the site of attachment to the Ligand for RAF and the wavy line on the right of the structure indicates the site of attachment to the Degradation Signaling Agent.

In some embodiments, the RAF-Degrading Conjugate Compound is a compound in Table 6, Table 6A, Table 7, Table 8, Table 8A, Table 9, Table 10, Table 11, Table 12, Table 13, or Table 14.

TABLE 6

Particular RAF-Degrading Conjugate Compounds

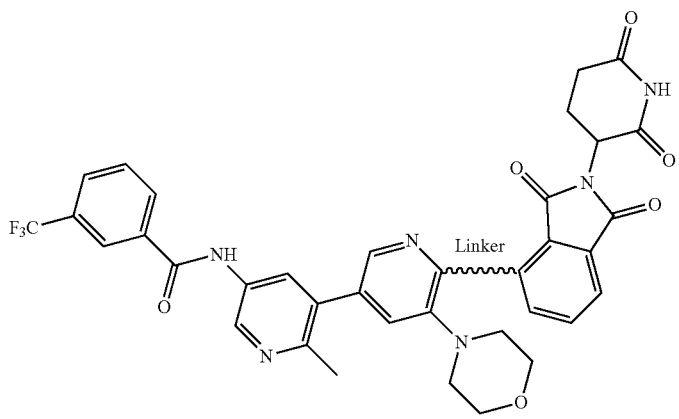 [SMILES: Cc1ncc(NC(=O)c2cccc(C(F)(F)F)c2)cc1-c1cnc(-c2cccc3c2C(=O)N(C2CCC(=O)NC2=O)C3=O)c(N2CCOCC2)c1]

| Compound | Linker |
|---|---|
| 1.001 | |
| 1.002 | |

TABLE 6-continued
Particular RAF-Degrading Conjugate Compounds
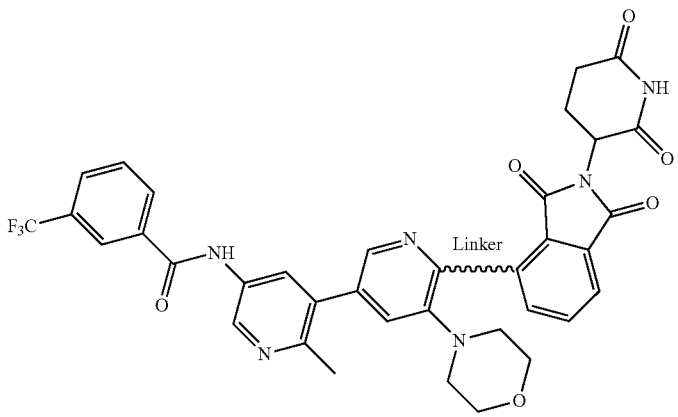
| Compound | Linker |
|---|---|
| 1.003 | 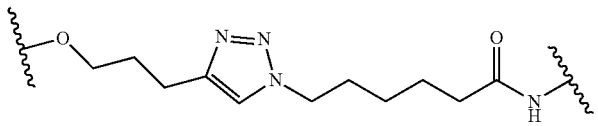 [SMILES: *NC(=O)CCCCCn1cc(CCCO*)nn1] |
| 1.004 | 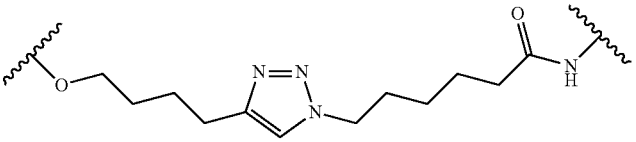 [SMILES: *NC(=O)CCCCCn1cc(CCCCO*)nn1] |
| 1.005 | 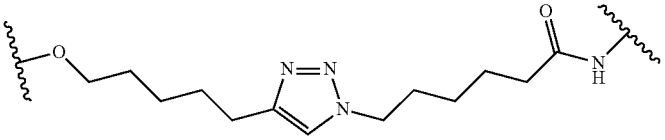 [SMILES: *NC(=O)CCCCCn1cc(CCCCCO*)nn1] |
| 1.006 | 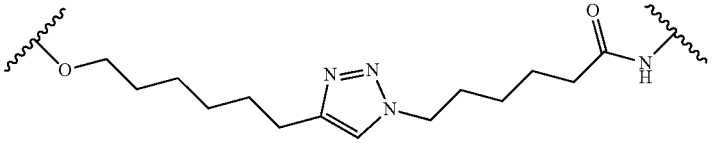 [SMILES: *NC(=O)CCCCCn1cc(CCCCCCO*)nn1] |
| 1.007 | 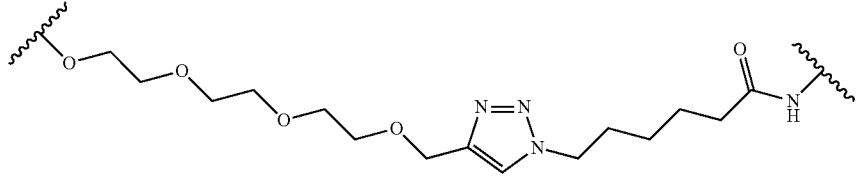 [SMILES: *NC(=O)CCCCCn1cc(COCCOCCOCCO*)nn1] |
| 1.008 | 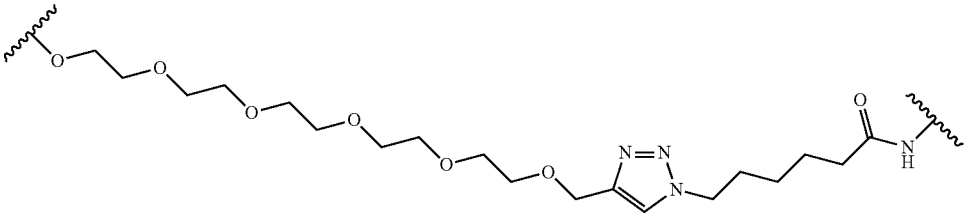 [SMILES: *NC(=O)CCCCCn1cc(COCCOCCOCCOCCOCCO*)nn1] |
| 2.021 | 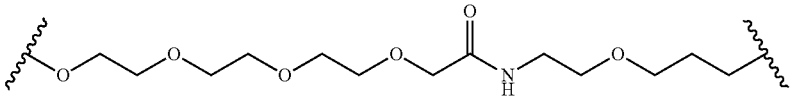 [SMILES: *CCCOCCNC(=O)COCCOCCOCCO*] |

TABLE 6-continued
Particular RAF-Degrading Conjugate Compounds
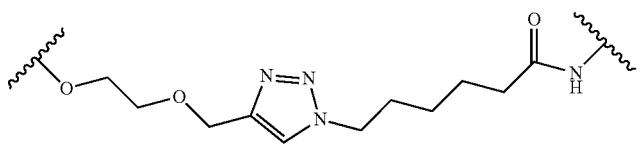 [SMILES: *NC(=O)CCCCCn1cc(COCCO*)nn1]
| Compound | Linker |
|---|---|
| 2.022 | 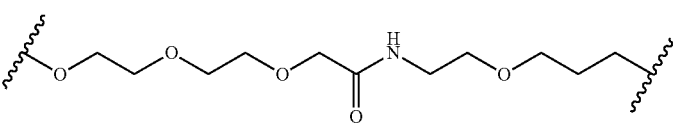 [SMILES: *CCCOCCNC(=O)COCCOCCO*] |
| 2.023 | 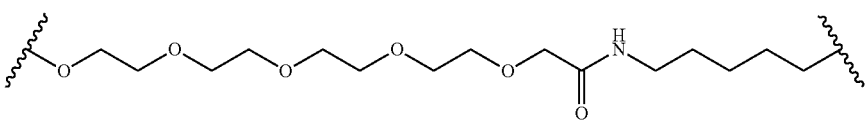 |
TABLE 6A
Particular RAF-Degrading Conjugate Compounds
| Compound | Linker |
|---|---|
| 2.014 | |

TABLE 6A-continued
Particular RAF-Degrading Conjugate Compounds
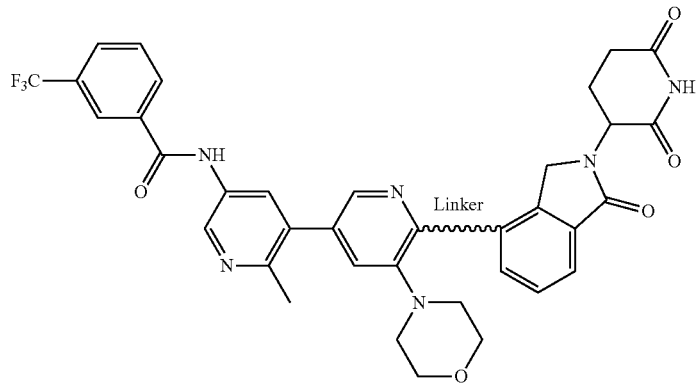 [SMILES: Cc1ncc(NC(=O)c2cccc(C(F)(F)F)c2)cc1-c1cnc(-c2cccc3c2CN(C2CCC(=O)NC2=O)C3=O)c(N2CCOCC2)c1]
| Compound | Linker |
|---|---|
| 2.015 | 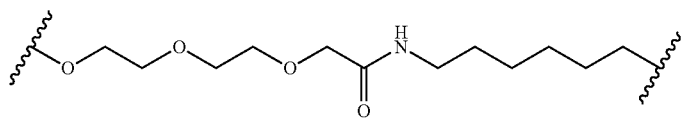 [SMILES: *CCCCCCNC(=O)COCCOCCO*] |
| 2.016 | 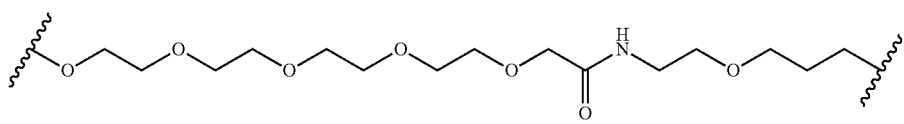 [SMILES: *CCCOCCNC(=O)COCCOCCOCCOCCO*] |
| 2.017 | 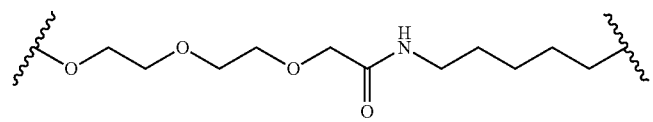 [SMILES: *CCCCCNC(=O)COCCOCCO*] |
| 2.018 | 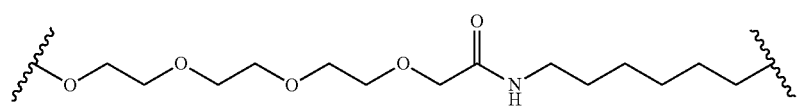 [SMILES: *CCCCCCNC(=O)COCCOCCOCCO*] |
| 2.019 | 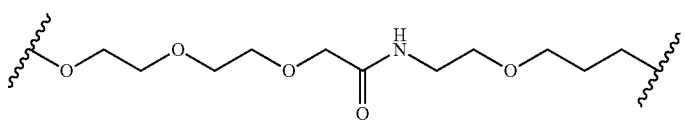 [SMILES: *CCCOCCNC(=O)COCCOCCO*] |
| 2.020 | 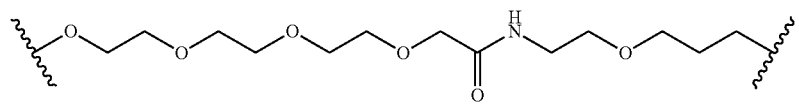 [SMILES: *CCCOCCNC(=O)COCCOCCOCCO*] |

TABLE 7

Particular RAF-Degrading Conjugate Compounds

| Compound | Linker | X |
|---|---|---|
| 1.009 | [triazole linker: -O-CH2CH2-triazole-(CH2)5-C(O)-NH-] | CH |
| 1.010 | [triazole linker: -O-CH(CH3)-CH2-triazole-(CH2)5-C(O)-NH-] | N |
| 1.011 | [triazole linker: -O-CH(CH3)-CH2-triazole-(CH2)5-C(O)-NH-] | CH |
| 1.012 | [triazole linker: -O-CH(CH3)-CH2-triazole-(CH2)5-C(O)-NH-] | N |
| 2.012 | [triazole linker: -O-CH2CH2-O-CH2-triazole-(CH2)4-C(O)-NH-] | CH |
| 2.013 | [triazole linker: -O-(CH2)3-triazole-(CH2)4-C(O)-NH-] | CH |

TABLE 8

Particular RAF-Degrading Conjugate Compounds

| Compound | Linker |
|---|---|
| 1.013 | PEG-type linker: ~O-CH₂CH₂-O-CH₂CH₂-O-CH₂CH₂-O-CH₂-C(=O)~ |
| 2.001 | ~O-(CH₂CH₂O)₅-CH₂-C(=O)~ |
| 2.002 | ~O-(CH₂CH₂O)₄-CH₂-C(=O)~ |
| 2.003 | ~O-CH₂CH₂-O-CH₂CH₂-O-CH₂CH₂-O-CH₂-(1,2,3-triazole)-(CH₂)₄-C(=O)~ |
| 2.004 | tetrahydropyran-O linker with triazole-(CH₂)₄-C(=O)~ (and methoxy-tetrahydropyran variant) *A mixture of the two diasteromers are present |
| 2.005 | tetrahydropyran-O-CH₂-(triazole)-(CH₂)₄-C(=O)~ (two diastereomer variants) **A mixture of the two diasteromers are present |

TABLE 8-continued

Particular RAF-Degrading Conjugate Compounds

| Compound | Linker |
|---|---|
| 2.006 | |
| 2.007 | |
| 2.008 | |
| 2.009 | |
| 2.010 | |

***Inactive isomer of 2.003, see, Example 100

TABLE 8A

Particular RAF-Degrading Conjugate Compounds

TABLE 8A-continued

| Compound | Linker | X |
|---|---|---|
| 2.011 | [PEG4-triazole-pentanoyl linker structure] | CH |

10

TABLE 9

Particular RAF-Degrading Conjugate Compounds

[Core structure: 4-chloro-3-(trifluoromethyl)phenyl urea linked to phenyl-O-pyridine-carbonyl, attached via linker to phthalimide-glutarimide (thalidomide-type) moiety with X substituent]

| Compound | Linker | X |
|---|---|---|
| 2.024 | [-NH-CH2-triazole-(CH2)4-C(O)NH- linker] | O |
| 2.025 | [-NH-CH2CH2-triazole-(CH2)5-C(O)NH- linker] | O |
| 2.026 | [-NH-(CH2)3-triazole-(CH2)4-C(O)NH- linker] | O |
| 2.027 | [-NH-CH2CH2-O-CH2CH2-O-CH2CH2-O-CH2-triazole-(CH2)5-C(O)NH- linker] | O |
| 2.028 | [-NH-CH2CH2-(O-CH2CH2)4-O-CH2-triazole-(CH2)4-C(O)NH- linker] | O |
| 2.029 | [-NH-CH2CH2-O-(CH2)3- linker] | O |

TABLE 9-continued
Particular RAF-Degrading Conjugate Compounds
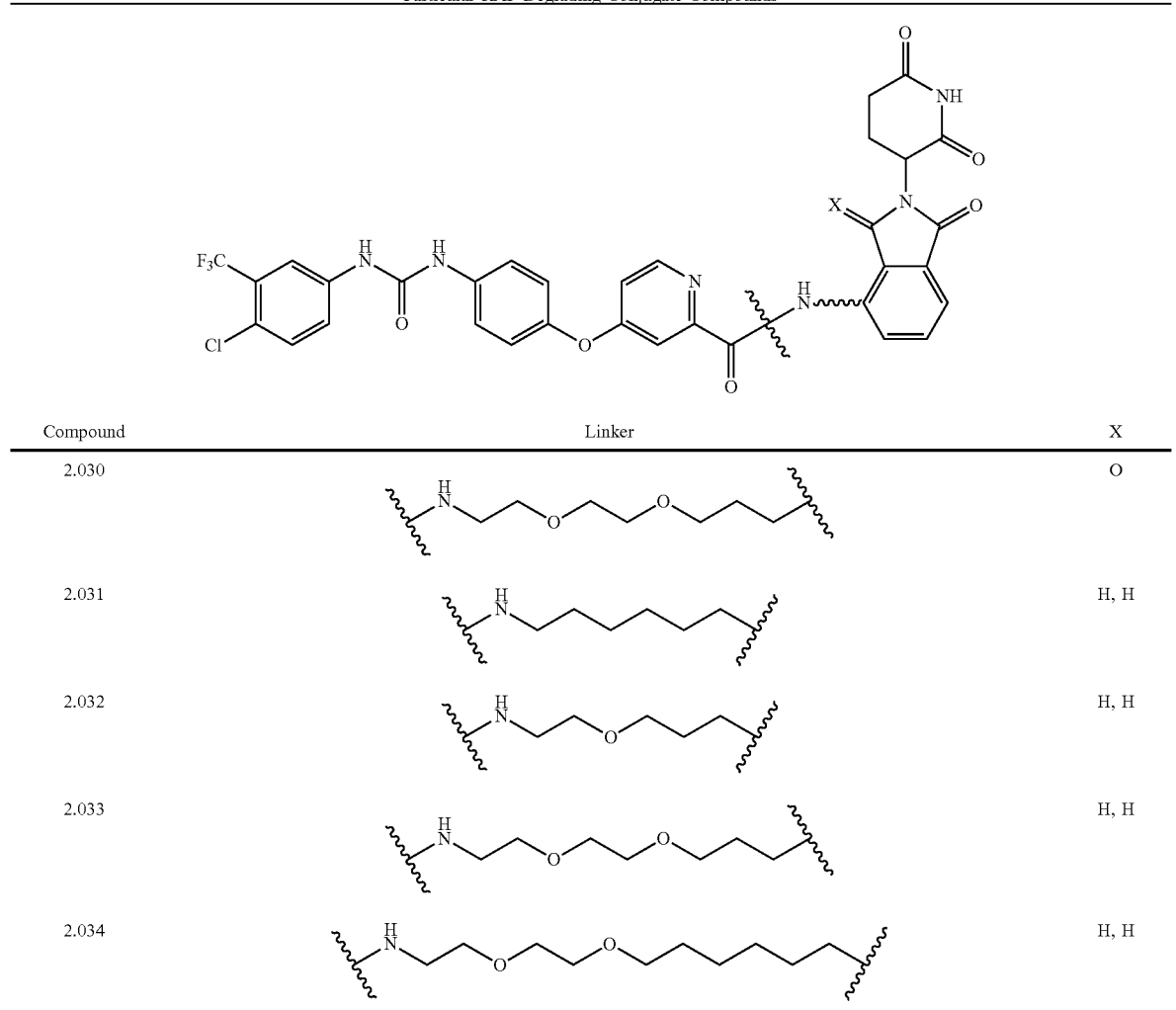
| Compound | Linker | X |
|---|---|---|
| 2.030 | | O |
| 2.031 | | H, H |
| 2.032 | | H, H |
| 2.033 | | H, H |
| 2.034 | | H, H |
TABLE 10
Particular RAF-Degrading Conjugate Compounds
| Compound | Structure |
|---|---|
| 2.035 | 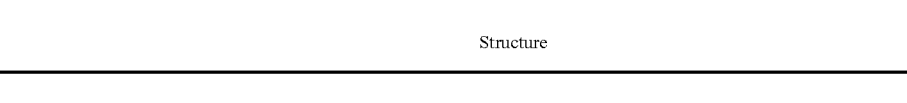 |

TABLE 10-continued
Particular RAF-Degrading Conjugate Compounds
| Compound | Structure |
|---|---|
| 1.014 | 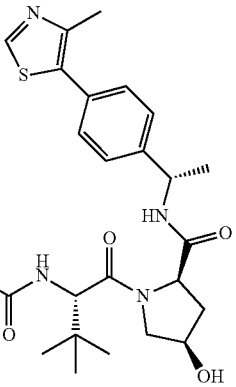 |
| 1.015 | 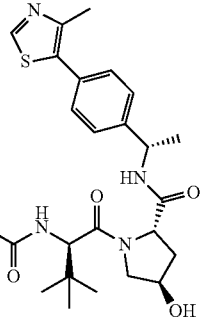 |
| 1.016 | 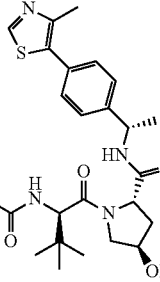 |
| 2.036 | 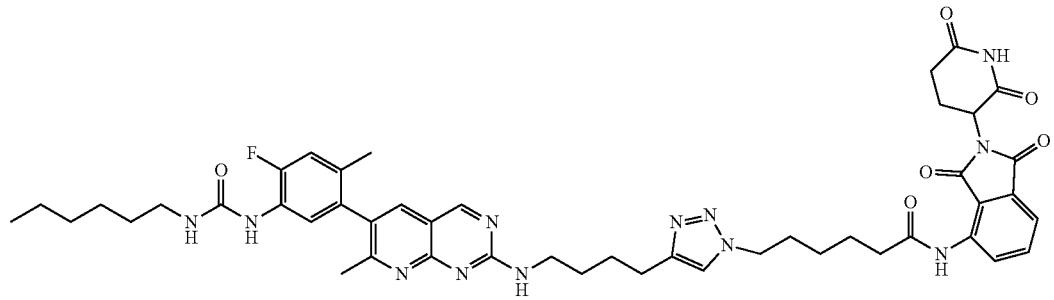 [SMILES: CCCCCCNC(=O)Nc1cc(-c2cc3cnc(NCCCCc4cn(CCCCCC(=O)Nc5cccc6c5C(=O)N(C5CCC(=O)NC5=O)C6=O)nn4)nc3nc2C)c(C)cc1F] |

TABLE 11
Particular RAF-Degrading Conjugate Compounds
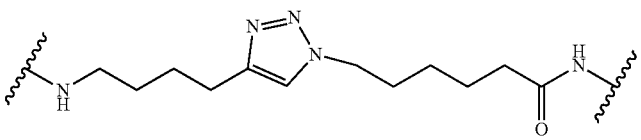 [SMILES: *NCCCCc1cn(CCCCCC(=O)N*)nn1]
| Compound | Linker |
|---|---|
| 2.037 | 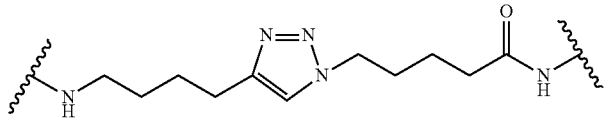 [SMILES: *NCCCCc1cn(CCCCC(=O)N*)nn1] |
| 2.038 | 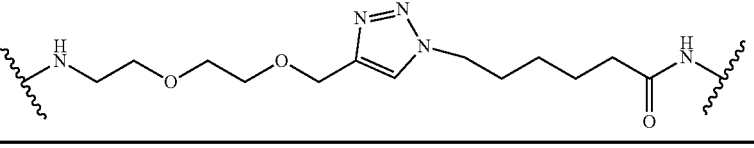 |
| 2.039 | 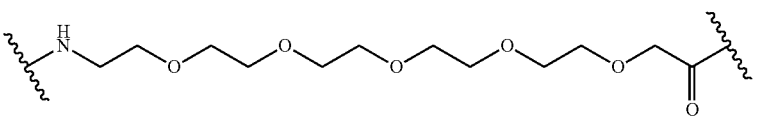 [SMILES: *NCCOCCOCCOCCOCCOCC(*)=O] |
TABLE 12
Particular RAF-Degrading Conjugate Compounds
| Compound | Linker |
|---|---|
| 2.040 | |

TABLE 12-continued
Particular RAF-Degrading Conjugate Compounds
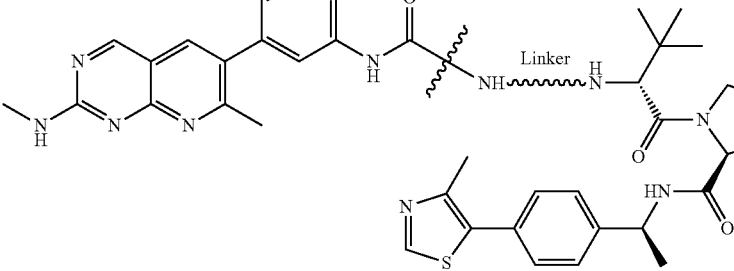
| Compound | Linker |
|---|---|
| 2.041 | 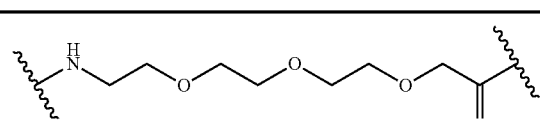 |
| 2.042 | 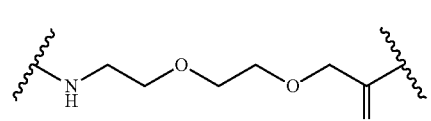 |
| 2.043 | 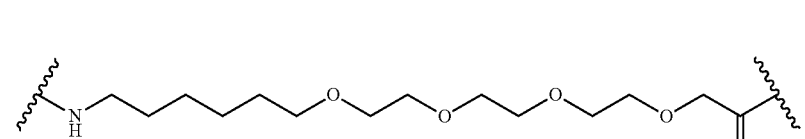 |
TABLE 13
Particular RAF-Degrading Conjugate Compounds
| Compound | Structure |
|---|---|
| 2.044 | 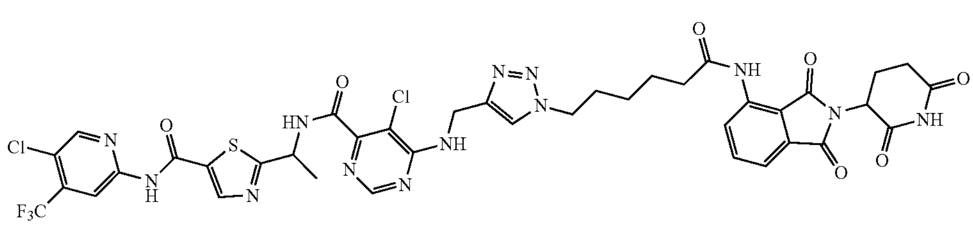 [SMILES: CC(NC(=O)c1ncnc(NCc2cn(CCCCCC(=O)Nc3cccc4c3C(=O)N(C3CCC(=O)NC3=O)C4=O)nn2)c1Cl)c1ncc(C(=O)Nc2cc(C(F)(F)F)c(Cl)cn2)s1] |

TABLE 13-continued

Particular RAF-Degrading Conjugate Compounds

| Compound | Structure |
| --- | --- |
| 2.045 | 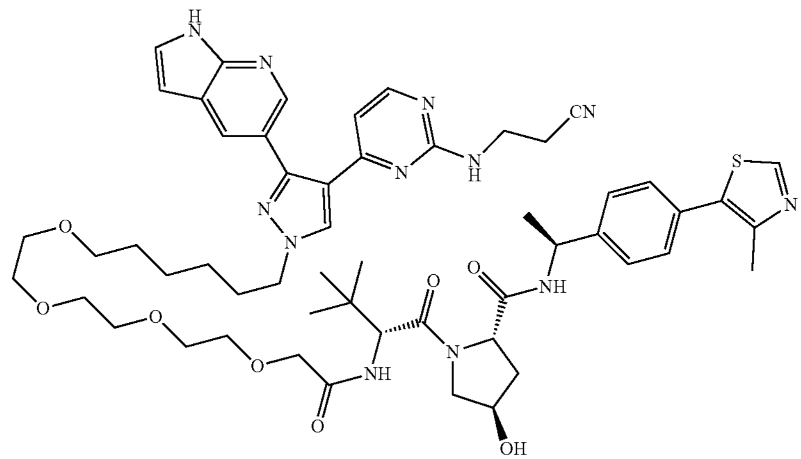 [SMILES: Cc1ncsc1-c1ccc([C@H](C)NC(=O)[C@@H]2C[C@@H](O)CN2C(=O)[C@H](NC(=O)COCCOCCOCCOCCCCCCn2cc(-c3ccnc(NCCC#N)n3)c(-c3cnc4[nH]ccc4c3)n2)C(C)(C)C)cc1] |
| 2.046 | 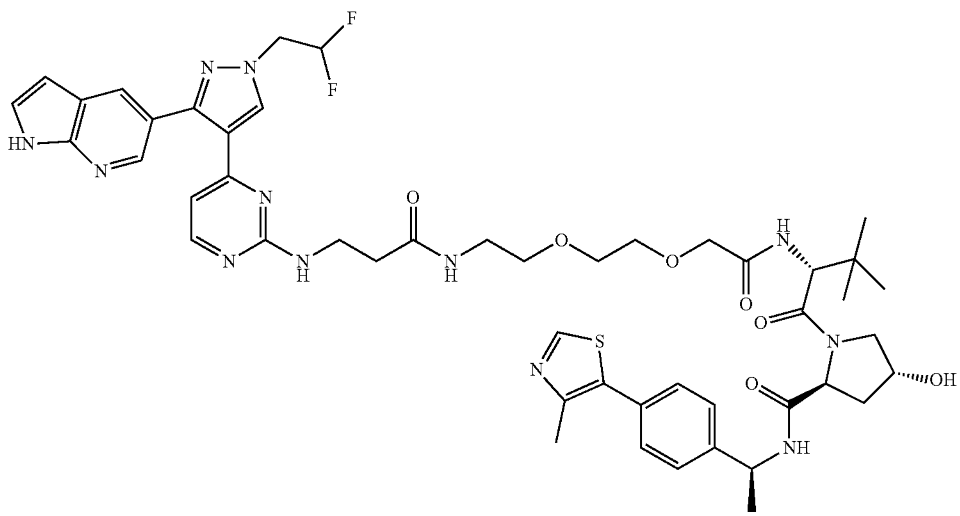 [SMILES: Cc1ncsc1-c1ccc([C@H](C)NC(=O)[C@@H]2C[C@@H](O)CN2C(=O)[C@H](NC(=O)COCCOCCNC(=O)CCNc2nccc(-c3cn(CC(F)F)nc3-c3cnc4[nH]ccc4c3)n2)C(C)(C)C)cc1] |
| 2.047 | 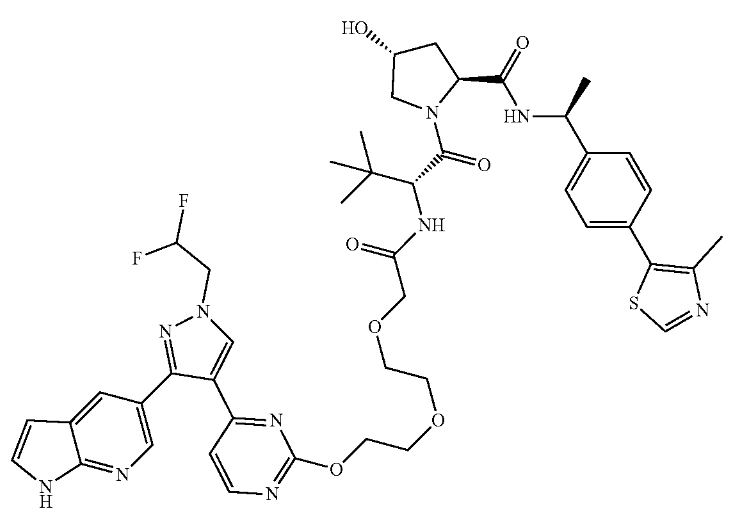 [SMILES: Cc1ncsc1-c1ccc([C@H](C)NC(=O)[C@@H]2C[C@@H](O)CN2C(=O)[C@H](NC(=O)COCCOCCOc2nccc(-c3cn(CC(F)F)nc3-c3cnc4[nH]ccc4c3)n2)C(C)(C)C)cc1] |

TABLE 14

Particular RAF-Degrading Conjugate Compounds

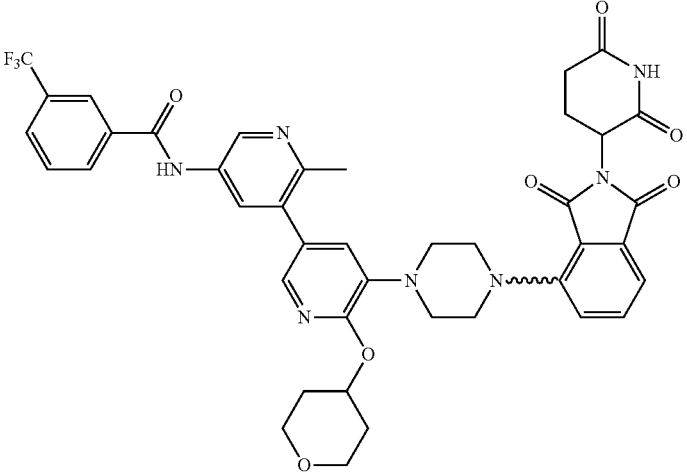 [SMILES: Cc1ncc(NC(=O)c2cccc(C(F)(F)F)c2)cc1-c1cnc(OC2CCOCC2)c(N2CCN(c3cccc4c3C(=O)N(C3CCC(=O)NC3=O)C4=O)CC2)c1]

| Compound | Linker |
|---|---|
| 2.048 | 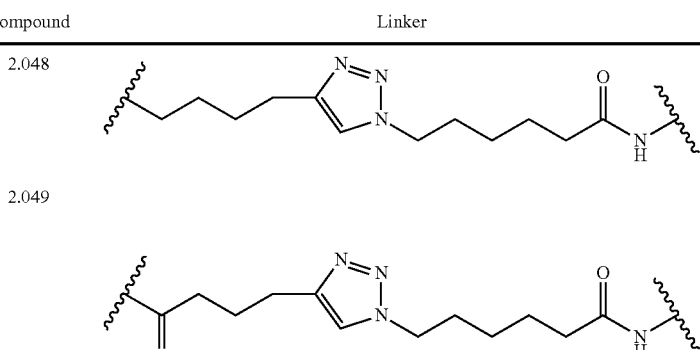 |
| 2.049 | |

B. Pharmaceutical Compositions

In addition the conjugate compounds provided above, the compositions for degrading RAF in humans and animals will typically contain a pharmaceutical carrier or diluent.

The term "composition" as used herein is intended to encompass a product comprising the specified ingredients in the specified amounts, as well as any product which results, directly or indirectly, from combination of the specified ingredients in the specified amounts. By "pharmaceutically acceptable" it is meant the carrier, diluent or excipient must be compatible with the other ingredients of the formulation and not deleterious to the recipient thereof.

The pharmaceutical compositions for the administration of the compounds of this invention may conveniently be presented in unit dosage form and may be prepared by any of the methods well known in the art of pharmacy and drug delivery. All methods include the step of bringing the active ingredient into association with the carrier which constitutes one or more accessory ingredients. In general, the pharmaceutical compositions are prepared by uniformly and intimately bringing the active ingredient into association with a liquid carrier or a finely divided solid carrier or both, and then, if necessary, shaping the product into the desired formulation. In the pharmaceutical composition the active object compound is included in an amount sufficient to produce the desired effect upon the process or condition of diseases.

The pharmaceutical compositions containing the active ingredient may be in a form suitable for oral use, for example, as tablets, troches, lozenges, aqueous or oily suspensions, dispersible powders or granules, emulsions and self emulsifications as described in U.S. Pat. No. 6,451,339, hard or soft capsules, syrups, elixirs, solutions, buccal patch, oral gel, chewing gum, chewable tablets, effervescent powder and effervescent tablets. Compositions intended for oral use may be prepared according to any method known to the art for the manufacture of pharmaceutical compositions and such compositions may contain one or more agents selected from the group consisting of sweetening agents, flavoring agents, coloring agents, antioxidants and preserving agents in order to provide pharmaceutically elegant and palatable preparations. Tablets contain the active ingredient in admixture with non-toxic pharmaceutically acceptable excipients which are suitable for the manufacture of tablets. These excipients may be for example, inert diluents, such as cellulose, silicon dioxide, aluminum oxide, calcium carbonate, sodium carbonate, glucose, mannitol, sorbitol, lactose, calcium phosphate or sodium phosphate; granulating and disintegrating agents, for example, corn starch, or alginic acid; binding agents, for example PVP, cellulose, PEG, starch, gelatin or acacia, and lubricating agents, for example magnesium stearate, stearic acid or talc. The tablets may be uncoated or they may be coated, enterically or otherwise, by known techniques to delay disintegration and absorption in the gastrointestinal tract and thereby provide a sustained action over a longer period. For example, a time delay material such as glyceryl monostearate or glyceryl distearate may be employed. They may also be coated by the techniques described in the U.S. Pat. Nos. 4,256,108; 4,166,452; and 4,265,874 to form osmotic therapeutic tablets for control release.

Formulations for oral use may also be presented as hard gelatin capsules wherein the active ingredient is mixed with an inert solid diluent, for example, calcium carbonate, calcium phosphate or kaolin, or as soft gelatin capsules wherein the active ingredient is mixed with water or an oil medium, for example peanut oil, liquid paraffin, or olive oil. Additionally, emulsions can be prepared with a non-water miscible ingredient such as oils and stabilized with surfactants such as mono-diglycerides, PEG esters and the like.

Aqueous suspensions contain the active materials in admixture with excipients suitable for the manufacture of aqueous suspensions. Such excipients are suspending agents, for example sodium carboxymethylcellulose, methylcellulose, hydroxy-propylmethylcellulose, sodium alginate, polyvinyl-pyrrolidone, gum tragacanth and gum acacia; dispersing or wetting agents may be a naturally-occurring phosphatide, for example lecithin, or condensation products of an alkylene oxide with fatty acids, for example polyoxy-ethylene stearate, or condensation products of ethylene oxide with long chain aliphatic alcohols, for example heptadecaethyleneoxycetanol, or condensation products of ethylene oxide with partial esters derived from fatty acids and a hexitol such as polyoxyethylene sorbitol monooleate, or condensation products of ethylene oxide with partial esters derived from fatty acids and hexitol anhydrides, for example polyethylene sorbitan monooleate. The aqueous suspensions may also contain one or more preservatives, for example ethyl, or n-propyl, p-hydroxybenzoate, one or more coloring agents, one or more flavoring agents, and one or more sweetening agents, such as sucrose or saccharin.

Oily suspensions may be formulated by suspending the active ingredient in a vegetable oil, for example arachis oil, olive oil, sesame oil or coconut oil, or in a mineral oil such as liquid paraffin. The oily suspensions may contain a thickening agent, for example beeswax, hard paraffin or cetyl alcohol. Sweetening agents such as those set forth above, and flavoring agents may be added to provide a palatable oral preparation. These compositions may be preserved by the addition of an anti-oxidant such as ascorbic acid.

Dispersible powders and granules suitable for preparation of an aqueous suspension by the addition of water provide the active ingredient in admixture with a dispersing or wetting agent, suspending agent and one or more preservatives. Suitable dispersing or wetting agents and suspending agents are exemplified by those already mentioned above. Additional excipients, for example sweetening, flavoring and coloring agents, may also be present.

The pharmaceutical compositions of the invention may also be in the form of oil-in-water emulsions. The oily phase may be a vegetable oil, for example olive oil or arachis oil, or a mineral oil, for example liquid paraffin or mixtures of these. Suitable emulsifying agents may be naturally-occurring gums, for example gum acacia or gum tragacanth, naturally-occurring phosphatides, for example soy bean, lecithin, and esters or partial esters derived from fatty acids and hexitol anhydrides, for example sorbitan monooleate, and condensation products of the said partial esters with ethylene oxide, for example polyoxyethylene sorbitan monooleate. The emulsions may also contain sweetening and flavoring agents.

Syrups and elixirs may be formulated with sweetening agents, for example glycerol, propylene glycol, sorbitol or sucrose. Such formulations may also contain a demulcent, a preservative and flavoring and coloring agents. Oral solutions can be prepared in combination with, for example, cyclodextrin, PEG and surfactants.

The pharmaceutical compositions may be in the form of a sterile injectable aqueous or oleagenous suspension. This suspension may be formulated according to the known art using those suitable dispersing or wetting agents and suspending agents which have been mentioned above. The sterile injectable preparation may also be a sterile injectable solution or suspension in a non-toxic parenterally-acceptable diluent or solvent, for example as a solution in 1,3-butane diol. Among the acceptable vehicles and solvents that may be employed are water, Ringer's solution and isotonic sodium chloride solution. In addition, sterile, fixed oils are conventionally employed as a solvent or suspending medium. For this purpose any bland fixed oil may be employed including synthetic mono- or diglycerides. In addition, fatty acids such as oleic acid find use in the preparation of injectables.

The compounds of the present invention may also be administered in the form of suppositories for rectal administration of the drug. These compositions can be prepared by mixing the drug with a suitable non-irritating excipient which is solid at ordinary temperatures but liquid at the rectal temperature and will therefore melt in the rectum to release the drug. Such materials include cocoa butter and polyethylene glycols. Additionally, the compounds can be administered via ocular delivery by means of solutions or ointments. Still further, transdermal delivery of the subject compounds can be accomplished by means of iontophoretic patches and the like. For topical use, creams, ointments, jellies, solutions or suspensions, etc., containing the compounds of the present invention are employed. As used herein, topical application is also meant to include the use of mouth washes and gargles.

The compounds of the invention may be formulated for depositing into a medical device, which may include any of variety of conventional grafts, stents, including stent grafts, catheters, balloons, baskets or other device that can be deployed or permanently implanted within a body lumen. As a particular example, it would be desirable to have devices and methods which can deliver compounds of the invention to the region of a body which has been treated by interventional technique.

In exemplary embodiment, the presently disclosed RAF-Degrading Conjugate Compound may be deposited within a medical device, such as a stent, and delivered to the treatment site for treatment of a portion of the body.

Stents have been used as delivery vehicles for therapeutic agents (i.e., drugs). Intravascular stents are generally permanently implanted in coronary or peripheral vessels. Stent designs include those of U.S. Pat. No. 4,733,655 (Palmaz), U.S. Pat. No. 4,800,882 (Gianturco), or U.S. Pat. No. 4,886,062 (Wiktor). Such designs include both metal and polymeric stents, as well as self-expanding and balloon-expandable stents. Stents may also used to deliver a drug at the site of contact with the vasculature, as disclosed in U.S. Pat. No. 5,102,417 (Palmaz) and in International Patent Application Nos. WO 91/12779 (Medtronic, Inc.) and WO 90/13332 (Cedars-Sanai Medical Center), U.S. Pat. No. 5,419,760 (Narciso, Jr.) and U.S. Pat. No. 5,429,634 (Narciso, Jr.), for example. Stents have also been used to deliver viruses to the wall of a lumen for gene delivery, as disclosed in U.S. Pat. No. 5,833,651 (Donovan et al.).

The term "deposited" means that the RAF-Degrading Conjugate Compound is coated, adsorbed, placed, or otherwise incorporated into the device by methods known in the art. For example, the conjugate may be embedded and released from within ("matrix type") or surrounded by and released through ("reservoir type") polymer materials that coat or span the medical device. In the later example, the conjugate may be entrapped within the polymer materials or coupled to the polymer materials using one or more the techniques for generating such materials known in the art. In other formulations, the conjugate may be linked to the surface of the medical device without the need for a coating by means of detachable bonds and release with time, can be removed by active mechanical or chemical processes, or are in a permanently immobilized form that presents the conjugate at the implantation site.

In one embodiment, the RAF-Degrading Conjugate Compound may be incorporated with polymer compositions during the formation of biocompatible coatings for medical devices, such as stents. The coatings produced from these components are typically homogeneous and are useful for coating a number of devices designed for implantation.

The polymer may be either a biostable or a bioabsorbable polymer depending on the desired rate of release or the desired degree of polymer stability, but a bioabsorbable polymer is preferred for this embodiment since, unlike a biostable polymer, it will not be present long after implantation to cause any adverse, chronic local response. Bioabsorbable polymers that could be used include, but are not limited to, poly(L-lactic acid), polycaprolactone, polyglycolide (PGA), poly(lactide-co-glycolide) (PLLA/PGA), poly(hydroxybutyrate), poly(hydroxybutyrate-co-valerate), polydioxanone, polyorthoester, polyanhydride, poly(glycolic acid), poly(D-lactic acid), poly(L-lactic acid), poly(D, L-lactic acid), poly(D,L-lactide) (PLA), poly (L-lactide) (PLLA), poly(glycolic acid-co-trimethylene carbonate) (PGA/PTMC), polyethylene oxide (PEO), polydioxanone (PDS), polyphosphoester, polyphosphoester urethane, poly (amino acids), cyanoacrylates, poly(trimethylene carbonate), poly(iminocarbonate), copoly(ether-esters) (e.g., PEO/PLA), polyalkylene oxalates, polyphosphazenes and biomolecules such as fibrin, fibrinogen, cellulose, starch, collagen and hyaluronic acid, polyepsilon caprolactone, polyhydroxy butyric acid, polyorthoesters, polyacetals, polydihydropyrans, polycyanoacrylates, cross linked or amphipathic block copolymers of hydrogels, and other suitable bioabsorbable poplymers known in the art. Also, biostable polymers with a relatively low chronic tissue response such as polyurethanes, silicones, and polyesters could be used and other polymers could also be used if they can be dissolved and cured or polymerized on the medical device such as polyolefins, polyisobutylene and ethylene-alphaolefin copolymers; acrylic polymers and copolymers, vinyl halide polymers and copolymers, such as polyvinyl chloride; polyvinylpyrrolidone; polyvinyl ethers, such as polyvinyl methyl ether; polyvinylidene halides, such as polyvinylidene fluoride and polyvinylidene chloride; polyacrylonitrile, polyvinyl ketones; polyvinyl aromatics, such as polystyrene, polyvinyl esters, such as polyvinyl acetate; copolymers of vinyl monomers with each other and olefins, such as ethylene-methyl methacrylate copolymers, acrylonitrile-styrene copolymers, ABS resins, and ethylene-vinyl acetate copolymers; pyran copolymer; polyhydroxy-propyl-methacrylamide-phenol; polyhydroxyethyl-aspartamide-phenol; polyethyleneoxide-polylysine substituted with palmitoyl residues; polyamides, such as Nylon 66 and polycaprolactam; alkyd resins, polycarbonates; polyoxymethylenes; polyimides; polyethers; epoxy resins, polyurethanes; rayon; rayon-triacetate; cellulose, cellulose acetate, cellulose butyrate; cellulose acetate butyrate; cellophane; cellulose nitrate; cellulose propionate; cellulose ethers; and carboxymethyl cellulose.

Polymers and semipermeable polymer matrices may be formed into shaped articles, such as valves, stents, tubing, prostheses and the like.

In one embodiment of the invention, the RAF-Degrading Conjugate Compound is coupled to a polymer or semipermeable polymer matrix that is formed as a stent or stent-graft device.

Typically, polymers are applied to the surface of an implantable device by spin coating, dipping or spraying. Additional methods known in the art can also be utilized for this purpose. Methods of spraying include traditional methods as well as microdeposition techniques with an inkjet type of dispenser. Additionally, a polymer can be deposited on an implantable device using photo-patterning to place the polymer on only specific portions of the device. This coating of the device provides a uniform layer around the device which allows for improved diffusion of various analytes through the device coating.

In preferred embodiments, the RAF-Degrading Conjugate Compound is formulated for release from the polymer coating into the environment in which the medical device is placed. Preferably, the conjugate is released in a controlled manner over an extended time frame (e.g., months) using at least one of several well-known techniques involving polymer carriers or layers to control elution. Some of these techniques were previously described in U.S. Patent Application 20040243225A1.

Moreover, as described for example in U.S. Pat. No. 6,770,729, the reagents and reaction conditions of the polymer compositions can be manipulated so that the release of the RAF-Degrading Conjugate Compound from the polymer coating can be controlled. For example, the diffusion coefficient of the one or more polymer coatings can be modulated to control the release of the conjugate from the polymer coating. In a variation on this theme, the diffusion coefficient of the one or more polymer coatings can be controlled to modulate the ability of an analyte that is present in the environment in which the medical device is placed (e.g. an analyte that facilitates the breakdown or hydrolysis of some portion of the polymer) to access one or more components within the polymer composition (and for example, thereby modulate the release of the conjugate from the polymer coating). Yet another embodiment of the invention includes a device having a plurality of polymer coatings, each having a plurality of diffusion coefficients. In such embodiments of the invention, the release of the conjugate from the polymer coating can be modulated by the plurality of polymer coatings.

In yet another embodiment, the release of the RAF-Degrading Conjugate Compound from the polymer coating is controlled by modulating one or more of the properties of the polymer composition, such as the presence of one or more endogenous or exogenous compounds, or alternatively, the pH of the polymer composition. For example, certain polymer compositions can be designed to release a conjugate in response to a decrease in the pH of the polymer composition. Alternatively, certain polymer compositions can be designed to release the conjugate in response to the presence of hydrogen peroxide.

C. Methods of Treatment

The presently disclosed RAF-Degrading Conjugate Compounds are useful in treating or preventing many disease or conditions including, but not limited to, cancer and RASopathies.

In some embodiments the diseases or conditions are mediated, at least in part, by RAF.

1. Cancer

In certain aspects, cancer can be treated or prevented by administering one or more RAF-Degrading Conjugate Compounds. Cancer generally includes any of various malignant neoplasms characterized by the proliferation of anaplastic cells that tend to invade surrounding tissue and metastasize to new body sites. Non-limiting examples of different types of cancer suitable for treatment using the compositions of the present invention include ovarian cancer, breast cancer, lung cancer (such as non-small-cell lung carcinoma), bladder cancer, thyroid cancer, liver cancer, pleural cancer, pancreatic cancer, cervical cancer, prostate cancer, testicular cancer, colon cancer, anal cancer, colorectal cancer, bile duct cancer, gastrointestinal carcinoid tumors, esophageal cancer, gall bladder cancer, rectal cancer, appendix cancer, small intestine cancer, stomach (gastric) cancer, renal cancer (i.e., renal cell carcinoma), cancer of the central nervous system, skin cancer, choriocarcinomas, head and neck cancers, bone cancer, osteogenic sarcomas, fibrosarcoma, neuroblastoma, glioma, melanoma, leukemia (e.g., acute lymphocytic leukemia, chronic lymphocytic leukemia, acute myelogenous leukemia, chronic myelogenous leukemia, or hairy cell leukemia), lymphoma (e.g., non-Hodgkin's lymphoma, Hodgkin's lymphoma, B-cell lymphoma, or Burkitt's lymphoma), and multiple myeloma.

In some embodiments, the cancer is melanoma, an epithelial cancer (e.g., prostate cancer, ovarian cancer, breast cancer), or a blood cancer (e.g., leukemia, lymphoma, multiple myeloma).

In some embodiments, the cancer is melanoma or colorectal cancer.

In some embodiments, the RAF-Degrading Conjugate Compounds of the present disclosure are useful in treating genetically defined cancers, irrespective or of tissue origin. Genetically defined cancers include, but are not limited to, those mediated, at least in part by mutant KRAS, HRAS, or NRAS proteins. In some embodiments, the mutations in these proteins include, but are not limited to, codons 12, 13, and 61, including misssense mutations to any of the 20 naturally occurring amino acids. In some embodiments, KRAS mutations include, but are not limited to, G12D, G12V, G13D, and G13C; HRAS mutations include, but are not limited to, G12V, Q61R, Q61L, and G13R; and NRAS mutations include, but are not limited to Q61R, Q61K, G12D, and G13D. Genetically defined cancers also include, but are not limited to, cancers mediated, at least in part, by mutant RAF proteins. In some embodiments the mutated RAF protein is BRAF. In some embodiments, the BRAF mutation is V600E.

2. RASopathies

In certain other aspects, RASopathies can be treated or prevented by administering one or more RAF-Degrading Conjugate Compounds. RASopathies are developmental syndromes involving dysregulation of the RAS/MPAK pathway. Non-limiting examples of RASopathies include neurofibromatosis type 1, capillary malformation-arteriovenous malformation syndrome, autoimmune lymphoproliferative syndrome, cardio-facio-cutaneous syndrome, hereditary gingival fibromatosis, neurofibromatosis type 1, Noonan syndrome, Costello syndrome, Legius syndrome, LEOPARD syndrome.

In some embodiments, the RASopathy is Noonan syndrome, Costello syndrome, Legius syndrome, LEOPARD syndrome.

In some embodiments, the RASopathy is Noonan syndrome or LEOPARD syndrome.

D. Combination Therapy

The presently disclosed RAF-Degrading Conjugate Compounds can be used in combination with other cancer treatment agents to treat various types of cancer. Accordingly, in some aspects, the present disclosure includes a method of treating cancer comprising administering to a subject in need thereof a therapeutically effective amount of the RAF-Degrading Conjugate Compound and an additional cancer therapeutic agent. Cancer therapeutic agents include, but are not limited to, chemotherapeutic agents, radiotherapeutic agents, and endocrine therapies.

It is contemplated that any of the above listed cancers can be used in the combination therapy described herein.

In embodiments where combination therapy is employed, the RAF-Degrading Conjugate Compound and the additional cancer therapeutic agent are administered simultaneously or sequentially. In some embodiments the RAF-Degrading Conjugate Compound and the additional cancer therapeutic agent are administered simultaneously. In some embodiments the RAF-Degrading Conjugate Compound and the additional cancer therapeutic agent are administered sequentially. In some embodiments, the RAF-Degrading Conjugate Compounds and the additional therapeutic agent, when administered simultaneously, are formulated in a single pharmaceutical composition. In some embodiments, the RAF-Degrading Conjugate Compounds and the additional therapeutic agent, when administered simultaneously, are two separate compositions.

1. Chemotherapeutic Agents

Chemotherapeutic agents (e.g., anti-cancer agents) are well known in the art and include, but are not limited to, anthracenediones (anthraquinones) such as anthracyclines (e.g., daunorubicin (daunomycin; rubidomycin), doxorubicin, epirubicin, idarubicin, and valrubicin), mitoxantrone, and pixantrone; platinum-based agents (e.g., cisplatin, carboplatin, oxaliplatin, satraplatin, picoplatin, nedaplatin, triplatin, and lipoplatin); tamoxifen and metabolites thereof such as 4-hydroxytamoxifen (afimoxifene) and N-desmethyl-4-hydroxytamoxifen (endoxifen); taxanes such as paclitaxel (taxol) and docetaxel; alkylating agents (e.g., nitrogen mustards such as mechlorethamine (HN2), cyclophosphamide, ifosfamide, melphalan (L-sarcolysin), and chlorambucil); ethylenimines and methylmelamines (e.g., hexamethylmelamine, thiotepa, alkyl sulphonates such as busulfan, nitrosoureas such as carmustine (BCNU), lomustine (CCNLJ), semustine (methyl-CCN-U), and streptozoein (streptozotocin), and triazenes such as decarbazine (DTIC; dimethyltriazenoimidazolecarboxamide)); antimetabolites (e.g., folic acid analogues such as methotrexate (amethopterin), pyrimidine analogues such as fluorouracil (5-fluorouracil; 5-FU), floxuridine (fluorodeoxyuridine; FUdR), and cytarabine (cytosine arabinoside), and purine analogues and related inhibitors such as mercaptopurine (6-mercaptopurine; 6-MP), thioguanine (6-thioguanine; 6-TG), and pentostatin (2'-deoxycofonnycin)); natural products (e.g., vinca alkaloids such as vinblastine (VLB) and vincristine, epipodophyllotoxins such as etoposide and teniposide, and antibiotics such as dactinomycin (actinomycin D), bleomycin, plicamycin (mithramycin), and mitomycin (mitomycin Q); enzymes such as L-asparaginase; biological response modifiers such as interferon alpha); substituted ureas such as hydroxyurea; methyl hydrazine derivatives such as procarbazine (N-methylhydrazine; MIH); adrenocortical suppressants such as mitotane (o,p'-DDD) and aminoglutethimide; analogs thereof; derivatives thereof; and combinations thereof.

In some embodiments, the chemotherapeutic agent is an MEK inhibitor. MEK inhibitors are small molecules or biologics that bind to and inhibit or decrease the normal function of MEK proteins. MEK inhibition is particularly useful in melanoma as well as RAS and RAF mediated cancers. Any known MEK inhibitor can be used in combination with the RAF-Degrading Conjugate Compounds of the present disclosure.

In some embodiments, the MEK inhibitor targets MEK1, MEK2, or both MEK1 and 2. In some embodiments, the MEK inhibitors is a small molecule.

In some embodiments, the MEK inhibitor is trametinib, pimasertib, selumertinib, PD-0325901, Refametinib, TAK733, MEK162, RO5126766, WX-554, RO4987655, CD-0931, or AZD8330.

2. Radiotherapeutic Agents

Radiotherapeutic agents are well known in the art and can comprise external-beam radiation therapy and/or internal radiation therapy. External beam radiation therapy delivers radioactive beams of high energy X-rays and/or gamma rays to a patient's tumor, whereas internal radiation therapy delivers radioactive atoms to a patient's tumor. Both external beam radiation therapy and internal radiation therapy are used to suppress tumor growth or kill cancer cells by delivering a sufficient quantity of radioactivity to the target site. In some embodiments, the radiotherapeutic agent comprises a radioactive atom and is complexed with a biologic or synthetic agent to increase delivery to the target site. Such biologic or synthetic agents are known in the art. Suitable radioactive atoms for use with the RAF-Degrading Conjugate Compounds of the present disclosure include any of the radionuclides described herein, or any other isotope which emits enough energy to destroy a targeted tissue or cell. In some embodiments, radiotherapeutic agents may be coupled to targeting moieties, such as antibodies, to improve the localization of radiotherapeutic agents to cancerous or infected cells.

The term "radionuclide" is intended to include any nuclide that exhibits radioactivity. A "nuclide" refers to a type of atom specified by its atomic number, atomic mass, and energy state, such as carbon 14 ($^{14}C$). "Radioactivity" refers to the radiation, including alpha particles, beta particles, nucleons, electrons, positrons, neutrinos, and gamma rays, emitted by a radioactive substance. Examples of radionuclides suitable for use in the present invention include, but are not limited to, fluorine 18 ($^{18}F$), fluorine 19 ($^{19}F$), phosphorus 32 ($^{32}P$), scandium 47 ($^{47}Sc$), cobalt 55 ($^{55}Co$), copper 60 ($^{60}Cu$), copper 61 ($^{61}Cu$), copper 62 ($^{62}Cu$), copper 64 ($^{64}Cu$), gallium 66 ($^{66}Ga$), copper 67 ($^{67}Cu$), gallium 67 ($^{67}Ga$), gallium 68 ($^{68}Ga$), rubidium 82 ($^{82}Rb$), yttrium 86 ($^{86}Y$), yttrium 87 ($^{87}Y$), strontium 89 ($^{89}Sr$), yttrium 90 ($^{90}Y$), rhodium 105 ($^{105}Rh$), silver 111 ($^{111}Ag$), indium 111 ($^{111}In$), iodine 124 ($^{124}I$), iodine 125 ($^{125}I$), iodine 131 ($^{131}I$), tin 117m ($^{117m}Sn$), technetium 99m ($^{99m}Tc$), promethium 149 ($^{149}Pm$), samarium 153 ($^{153}Sm$), holmium 166 ($^{166}Ho$), lutetium 177 ($^{177}Lu$), rhenium 186 ($^{186}Re$), rhenium 188 ($^{188}Re$), thallium 201 ($^{201}Tl$), astatine 211 ($^{211}At$), and bismuth 212 ($^{212}Bi$). As used herein, the "m" in $^{117m}Sn$ and $^{99m}Tc$ stands for the meta state. Additionally, naturally-occurring radioactive elements such as uranium, radium, and thorium, which typically represent mixtures of radioisotopes, are suitable examples of radionuclides. $^{67}Cu$, $^{131}I$, $^{177}Lu$, and $^{186}Re$ are beta- and gamma-emitting radionuclides. $^{212}Bi$ is an alpha- and beta-emitting radionuclide. $^{211}At$ is an alpha-emitting radionuclide. $^{32}P$, $^{47}Sc$, $^{89}Sr$, $^{90}Y$, $^{105}Rh$, $^{111}Ag$, $^{117m}Sn$, $^{149}Pm$, $^{153}Sm$, $^{166}Ho$, and $^{188}Re$ are examples of beta-emitting radionuclides. $^{67}Ga$, $^{111}In$, $^{99m}Tc$, and $^{201}Tl$ are examples of gamma-emitting radionuclides. $^{55}Co$, $^{60}Cu$, $^{61}Cu$, $^{62}Cu$, $^{66}Ga$, $^{68}Ga$, $^{82}Rb$, and $^{86}Y$ are examples of positron-emitting radionuclides. $^{64}Cu$ is a beta- and positron-emitting radionuclide.

3. Endocrine Therapies

Endocrine therapy is the manipulation of the endocrine system through the administration of specific hormones or drugs which inhibit or decrease the production or activity of targeted hormones or alter the gene expression pattern of targeted cells. Endocrine therapy is particularly useful in certain types of cancer, including breast cancer. Any known hormone antagonist or modulator may be used in combination with the RAF-Degrading Conjugate Compounds of the present disclosure. Useful Endocrine therapies include, but are not limited to, aromatase inhibitors (e.g. letrozole), megestrol acetate, flutamide, tamoxifen, raloxifene, lasofoxifene, bazedoxifene, bazedoxifene/conjugated estrogens, and combinations thereof.

E. Kits, Containers, Devices, and Systems

A wide variety of kits and systems can be prepared according to the present invention, depending upon the intended user of the kit and system and the particular needs of the user. In some aspects, the present disclosure provides a kit that includes one or more RAF-Degrading Conjugate Compounds. In other aspects, the present disclosure provides a kit that includes one or more RAF-Degrading Conjugate Compounds and one or more therapeutic agents selected from a chemotherapeutic agent, a radiotherapeutic agent, an endocrine therapy.

Some of the kits described herein include a label describing a method of administering one or more RAF-Degrading Conjugate Compounds and/or one or more additional cancer therapeutic agents described herein. Some of the kits described herein include a label describing a method of treating a disease or disorder described herein.

The compositions of the present invention, including but not limited to, compositions comprising one or more RAF-Degrading Conjugate Compounds and one or more additional cancer therapeutic agents described herein may, if desired, be presented in a bottle, jar, vial, ampoule, tube, or other container-closure system approved by the Food and Drug Administration (FDA) or other regulatory body, which may provide one or more dosages containing the compounds. The package or dispenser may also be accompanied by a notice associated with the container in a form prescribed by a governmental agency regulating the manufacture, use, or sale of pharmaceuticals, the notice indicating approval by the agency. In certain aspects, the kit may include a formulation or composition as described herein, a container closure system including the formulation or a dosage unit form including the formulation, and a notice or instructions describing a method of use as described herein.

In some embodiments, the kit includes a container which is compartmentalized for holding the various elements of a formulation (e.g., the dry ingredients and the liquid ingredients) or composition, instructions for making the formulation or composition, and instructions for administering the formulation or composition in a subject.

In certain embodiments, the kit may include the pharmaceutical preparation in dehydrated or dry form, with instructions for its rehydration (or reconstitution) and administration.

Kits with unit doses of the compounds described herein, e.g. in oral, rectal, transdermal, or injectable doses (e.g., for intramuscular, intravenous, or subcutaneous injection), are provided.

In such kits, an informational package insert describing the use and attendant benefits of the composition may be included in addition to the containers containing the unit doses.

Some embodiments of the present invention include packages that include one or more RAF-Degrading Conjugate Compounds and one or more additional cancer therapeutic agents described herein.

III. Examples

The following examples are offered to illustrate, but not to limit the claimed invention.
Experimental Details
The following abbreviations are used in the examples below:
aq aqueous
$CH_3CN$ acetonitrile
$CD_3OD$ methanol-D4
$CDCl_3$ chloroform-D
conc concentrate
$CuSO_4$ copper(II) sulfate
CV column volume
DCM methylene chloride or dichloromethane
DIPEA diisopropylethyl amine
DMF dimethylformamide
DMSO dimethylsulfoxide
Eq. equivalent
EtOAc ethyl acetate
HATU O-(7-azabenzotriazol-1-yl),N,N,N'',N''-tetramethyluroniumhexafluorophosphate
h hour(s)
Hex hexanes
HPLC high performance liquid chromatography
LRMS low resolution mass spec
M molar
MeOH methanol
min minute(s)
NaCl sodium chloride
NaN3 sodium azide
$Na_2SO_4$ sodium sulfate
rt room temperature
$t_R$ retention time
$SiO_2$ silica gel
THF tetrahydrofuran
TLC thin layer chromatography The compounds of this invention may be prepared in light of the specification using steps generally known to those of ordinary skill in the art. Those compounds may be analyzed by known methods, including but not limited to LC-MS (liquid chromatography mass spectrometry), HPLC (high performance liquid chromatography) and NMR (nuclear magnetic resonance). It should be understood that the specific conditions shown below are only examples, and are not meant to limit the scope of the conditions that can be used for making compounds of this invention. Instead, this invention also includes conditions that would be apparent to those skilled in that art in light of this specification for making the compounds of this invention. Unless otherwise indicated, all variables in the following Examples are as defined herein.

LRMS values were recorded on Waters micromass ZQ using direct injection of the samples in either methanol or acetonitrile. Analytical HPLC was carried out on Waters alliance using Agilent, Zorbax-SB-CN, 3.5 μm, 4.6×150 mm, mobile phase, acetonitrile in water (0 to 100%) contains ammonium acetate buffer; flow rate, 1.5 mL/min, run time, 20 min].

HPLC Method A: Column, Agilent, Zorbax Eclipse XDB-C8, 5 μm, 4.6×150 mm, mobile phase, acetonitrile in water (0 to 100%) contains ammonium acetate buffer; flow rate, 1.5 mL/min, run time, 20 min.

HPLC Method B: Column, Agilent, Zorbax-SB-CN, 3.5 μm, 4.6×150 mm, mobile phase, acetonitrile in water (0 to 100%) contains ammonium acetate buffer; flow rate, 0.1 mL/min, run time, 20 min.

All reactions were carried out under inert atmosphere either $N_2$ or Ar

HPLC Prep method: Column, Phenomenex, Synergi, 4μ, Max-RP 80A, AX; 250×21.2 mm, mobile phase, acetonitrile in water (10-100%, 25 min, water contains 0.2% $HCO_2H$ buffer); flow rate, 15 mL/min.

Example 1—Synthesis of Sorafenib and Acid Precursor

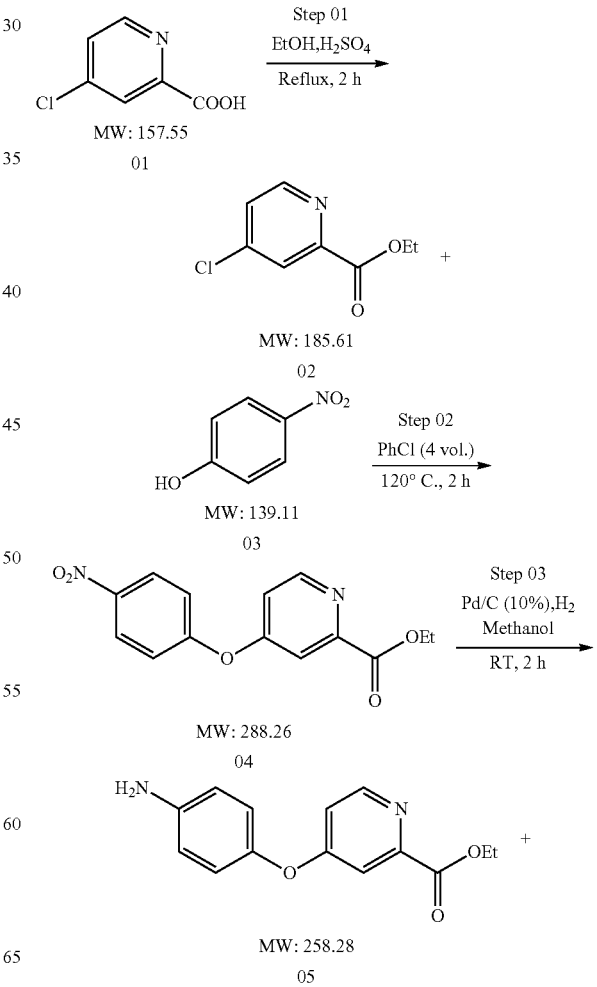

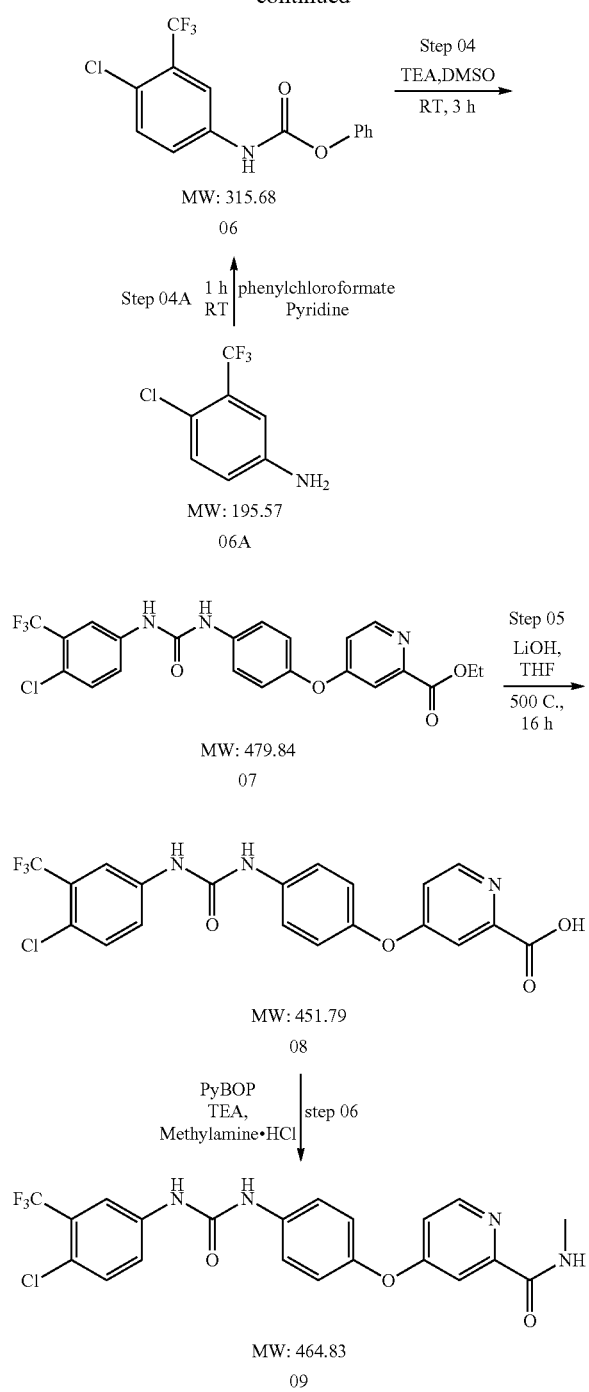

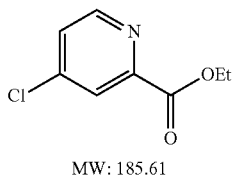

Step 02: Synthesis of ethyl 4-(4-nitrophenoxy)picolinate (04)

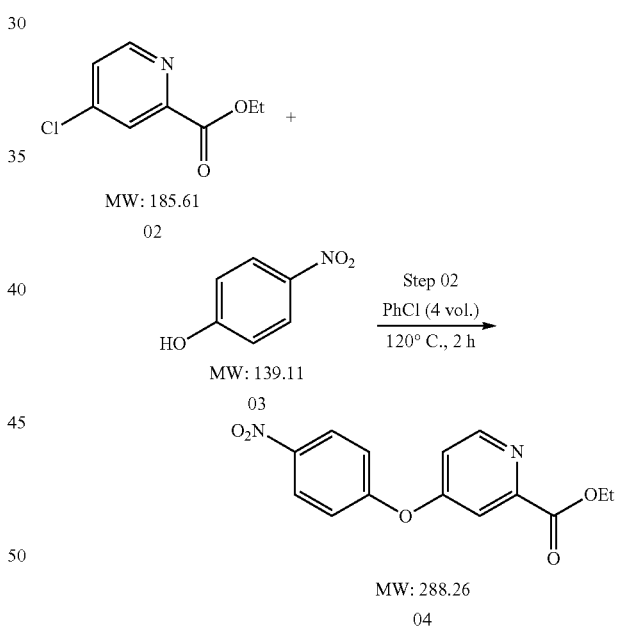

To a stirred solution of 4-chloropicolinic acid (15.0 g, 95.20 mmol, 1.0 equiv) in ethanol (225.0 mL, 15.0 vol. equiv) was added sulfuric acid (34.4 mL, 619 mmol, 6.5 equiv). The resulting mixture was stirred for 2 h at reflux. The completion of reaction was monitored by TLC. The solvent was removed under reduced pressure. The residue was treated with DM water (500.0 mL) and extracted with EtOAc (2×500 mL). The combined organic extract was washed with brine (200.0 mL), saturated solution of sodium bicarbonate (500.0 mL), dried over $Na_2SO_4$ and concentrated under vacuum to afford titled compound (9.84 g, 55.7%) as a light brown oily mass. $^1$H NMR (300 MHz, DMSO-$d_6$) δ 8.70-8.69 (d, 1H), 8.08-8.07 (d, 1H), 7.83-7.81 (m, 1H), 4.39-4.31 (m, 2H), 1.35-1.29 (m, 3H). MS (ES+): 186.0 (M+1).

To a stirred solution of 4-nitrophenol (03) (7.37 g, 53.0 mmol, 1.0 equiv) in chlorobenzene (98.3 mL, 10.0 vol. equiv) was added ethyl 4-chloropicolinate (02) (9.83 g, 53.0 mmol, 1.0 equiv). The resulting mixture was stirred for 65 h at 120° C. The completion of reaction was monitored by TLC. The reaction mixture was quenched with DM water (500.0 mL) and extracted with EtOAc (2×500 mL). The combined organic extract was washed with brine (200.0 mL), saturated solution of sodium bicarbonate (500.0 mL), dried over $Na_2SO_4$ and concentrated under vacuum and the crude was purified through column chromatography eluted with ethyl acetate in n-hexane (20-40%) to afford titled compound (3.35 g, 21.9%) as a yellow solid. $^1$H NMR (300

Step 01: Synthesis of ethyl 4-chloropicolinate (02)

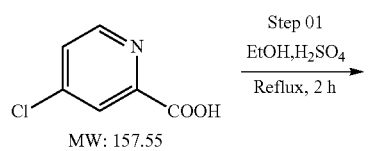

MHz, DMSO-$d_6$) δ 8.70-8.68 (t, 1H), 8.36-8.33 (m, 2H), 7.66-7.65 (d, 1H), 7.47-7.44 (m, 2H), 7.40-7.37 (m, 1H), 4.37-4.30 (m, 2H), 1.33-1.29 (t, 3H). MS (ES+): 289.0 (M+1).

Step 03: Synthesis of ethyl 4-(4-aminophenoxy)picolinate (05)

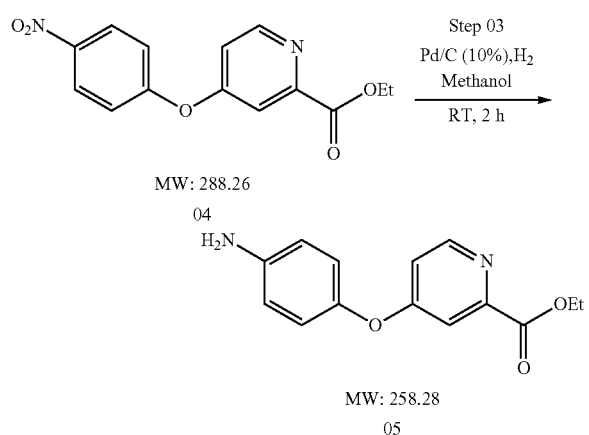

Ethyl 4-(4-nitrophenoxy)picolinate (04) (3.35 g, 11.60 mmol, 1.0 equiv) was dissolved in MeOH (83.80 mL) and hydrogenated in the presence of a catalytic amount of Pd/C (618.0 mg, 0.58 mmol, 0.05 equiv) using balloon for 2.5 h. TLC was monitored to check the completion of the reaction. Pd/C was removed by filtration through celite bed and the filtrate was evaporated to dryness under reduced pressure to afford desired compound (05) (2.97 g, 98.9%) as a brown stick mass. MS (ES+): 259.0 (M+1).

Step 04A: Synthesis of phenyl (4-chloro-3-(trifluoromethyl)phenyl)carbamate (06)

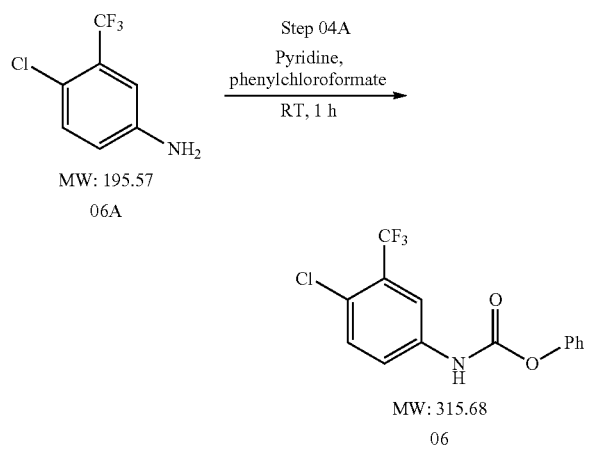

To a stirred solution of 4-chloro-3-(trifluoromethyl)aniline (06A) (5.0 g, 25.6 mmol, 1.00 equiv) in acetonitrile (50.0 mL, 10.0 vol. equiv) were added pyridine (2.02 g, 25.60 mmol, 1.00 equiv) and phenyl chloroformate (4.0 g, 25.60 mmol, 1.00 equiv). The reaction mixture was stirred for 2 h at RT. TLC was checked to check the progress of reaction. The reaction mixture was quenched with water (300.0 mL) to get a white precipitate. The precipitate was filtered and washed with water (50.0 mL), followed by n-hexane (50.0 mL) and precipitate was dried to get desired product (06) (7.5 g, 92.90%) as a white solid. $^1$H NMR (300 MHz, DMSO-$d_6$) δ 10.72 (s, 1H), 8.06-8.05 (d, 1H), 7.78-7.74 (m, 2H), 7.70-7.42 (m, 2H), 7.31-7.24 (m, 3H). MS (ES−): 314.0 (M−1).

Step 04: Synthesis of phenyl (4-chloro-3-(trifluoromethyl)phenyl)carbamate (07)

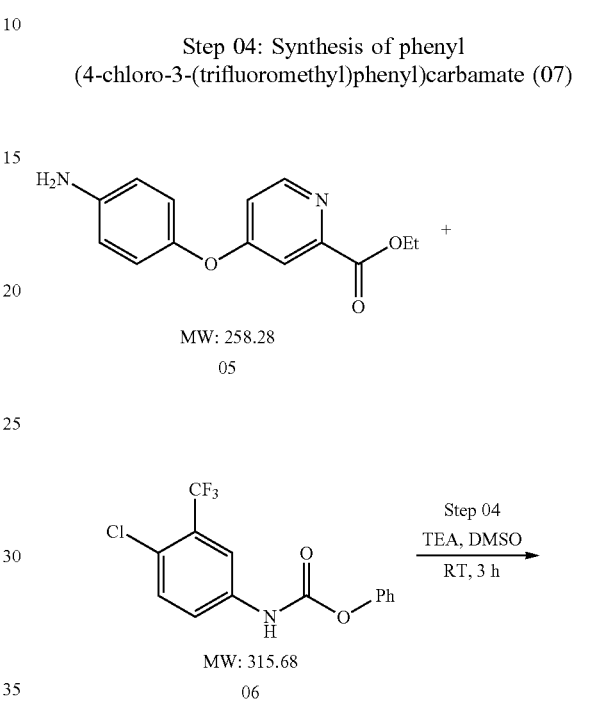

To a stirred solution of ethyl 4-(4-aminophenoxy)picolinate (05) (2.95 g, 11.4 mmol, 1.0 equiv) in DMSO (29.5 mL, 10.0 vol. equiv) were added phenyl (4-chloro-3-(trifluoromethyl)phenyl)carbamate (3.61 g, 11.4 mmol, 1.0 equiv), triethylamine (1.73 g, 17.10 mmol, 1.5 equiv) at RT. The reaction mixture was stirred for 12 h at RT. The completion of reaction was monitored by TLC. The reaction mixture was quenched with DMW (100.0 mL) and extracted with EtOAc (3×350 mL). The combined organic extract was washed with brine (350.0 mL), dried over Na$_2$SO$_4$ and concentrated under vacuum to afford titled compound (5.40 g, 98.5%) as a light brown solid. $^1$H NMR (300 MHz, DMSO-$d_6$) δ 9.23 (s, 1H), 9.02 (s, 1H), 8.56 (s, 1H), 8.15 (s, 1H), 7.64-7.57 (m, 4H), 7.44-7.43 (d, 1H), 7.19-7.16 (m, 3H), 4.32-4.30 (d, 2H), 1.31-1.27 (t, 3H). MS (ES+): 480.0 (M+1); MS (ES−): 478.0 (M−1).

Step 05: Synthesis of 4-(4-(3-(4-chloro-3-(trifluoromethyl)phenyl)ureido) phenoxy)picolinic Acid (08)

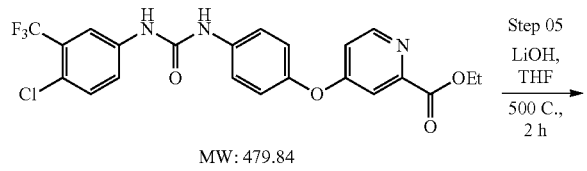

Step 06: Synthesis of 4-(4-(3-(4-chloro-3-(trifluoromethyl)phenyl)ureido)phenoxy)-N-methylpicolinamide (09)

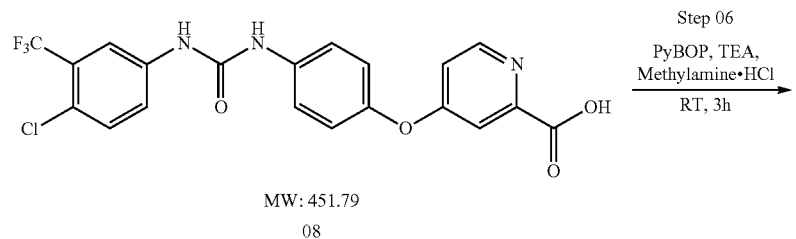

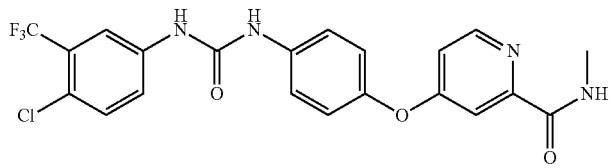

-continued

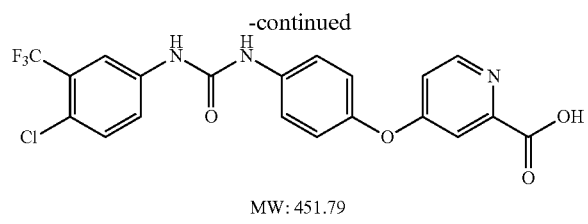

To a mixture of phenyl (4-chloro-3-(trifluoromethyl)phenyl)carbamate (07) (5.40 g, 11.30 mmol, 1.0 equiv), water (54.00 mL, 10 vol. equiv), tetrahydrofuran (43.20 mL, 8.0 vol. equiv) and methanol (81 mL, 15 vol. equiv) was added lithium hydroxide monohydrate (1.42 g, 33.80 mmol, 3.0 equiv) portion wise. The reaction mixture was stirred at ambient temperature for 72 h. The completion of reaction was monitored by TLC. The solvent was evaporated to dryness and 1 M sodium hydroxide solution (15.0 mL) was added to the residue (pH=14). The aqueous phase was extracted with diethyl ether (2×100.0 mL), then aqueous layer was acidified with 1M hydrochloric acid until pH=4. The solid so obtained was filtered and dried in ordinary oven at 50° C. to afford titled compound (08) (4.50 g, 88.50%) as an off-white solid. $^1$H NMR (300 MHz, DMSO-d$_6$) δ 10.58 (s, 1H), 10.35 (s, 1H), 8.49-8.47 (d, 1H), 8.23-8.22 (d, 1H), 7.74-7.71 (d, 1H), 7.60-7.56 (m, 3H), 7.39-7.38 (d, 1H), 7.18-7.11 (m, 3H). MS (ES+): 452.0 (M+1); MS (ES−): 450.0 (M−1).

To a stirred suspension of 4-(4-(3-(4-chloro-3-(trifluoromethyl)phenyl)ureido)-phenoxy)picolinic acid (08) (200.0 mg, 0.44 mmol, 1.0 equiv) in DMF (4.0 mL, 20.0 vol. equiv) were added methylamine hydrochloride (149.0 mg, 2.21 mmol, 5.0 equiv), PyBOP (230.0 mg, 0.44 mmol, 1.0 equiv) and triethylamine (448.0 mg, 2.21 mmol, 10.0 equiv). The reaction mixture was stirred for 3 h at RT. The completion of reaction was monitored by TLC. The reaction mixture was quenched with DMW (100.0 mL) and extracted with EtOAc (3×100.0 mL). The combined organic extracts was washed with brine (100.0 mL), dried over Na$_2$SO$_4$ and concentrated under vacuum to get crude. The crude was purified through column chromatography eluted with ethyl acetate in n-hexane (40-60%) to afford titled compound (09) (130.0 mg, 63.20%) as an off-white solid. $^1$H NMR (300 MHz, DMSO-d$_6$) δ 9.22 (s, 1H), 9.01 (s, 1H), 8.79-8.77 (d, 1H), 8.51-8.49 (d, 1H), 8.13-8.12 (d, 1H), 7.65-7.57 (m, 4H), 7.38-7.37 (d, 1H), 7.19-7.13 (m, 3H). MS (ES+): 465.0 (M+1); MS (ES−): 463.0 (M−1). HPLC: 97.99%.

Example 2—Synthesis of 4-(4-(3-(4-chloro-3-(trifluoromethyl)phenyl)ureido)phenoxy)-N-(2-(2-(3-(((R)-1-((2S,4R)-4-hydroxy-2-(((S)-1-(4-(4-methylthiazol-5-yl)phenyl)ethyl)carbamoyl)pyrrolidin-1-yl)-3,3-dimethyl-1-oxobutan-2-yl)amino)-3-oxopropoxy)ethoxy)ethyl)picolinamide (Compound 1.014)
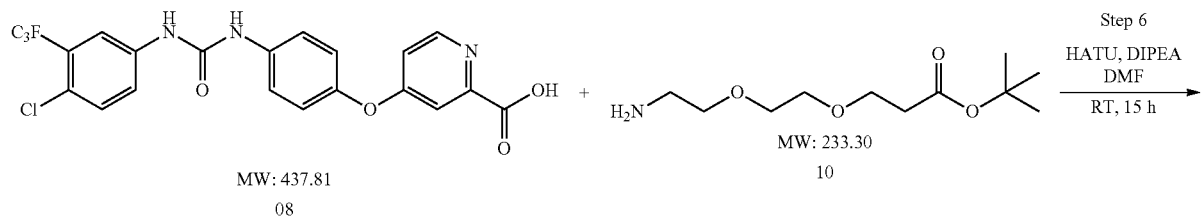
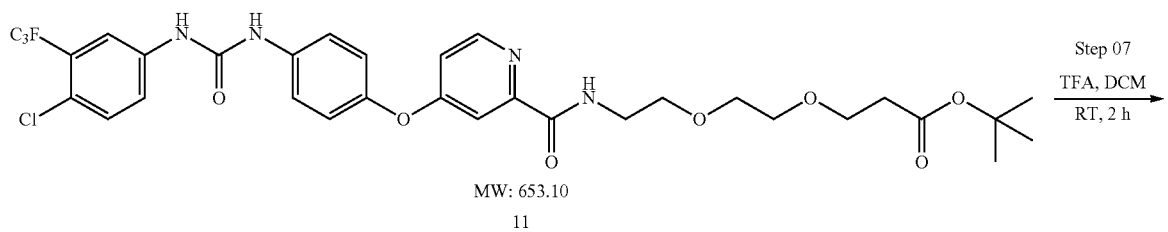
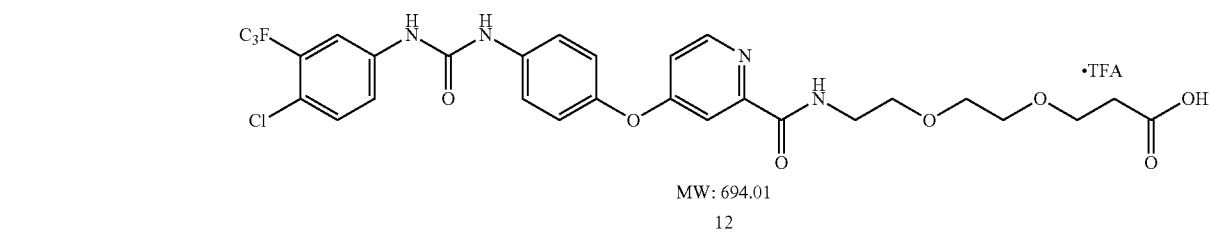
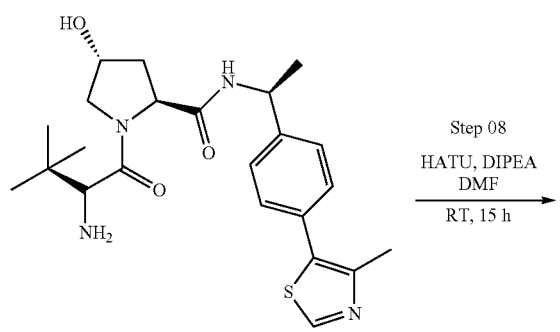

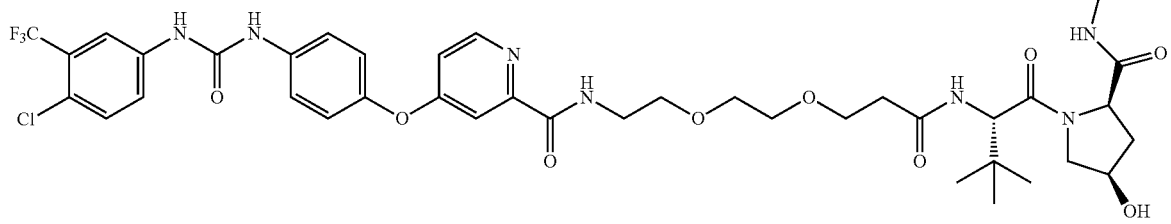

MW: 1037.54

14

Step 06: Synthesis of tert-butyl 3-(2-(2-(4-(4-(3-(4-chloro-3-(trifluoromethyl)phenyl)ureido)phenoxy)picolinamido)ethoxy)ethoxy)propanoate (11)

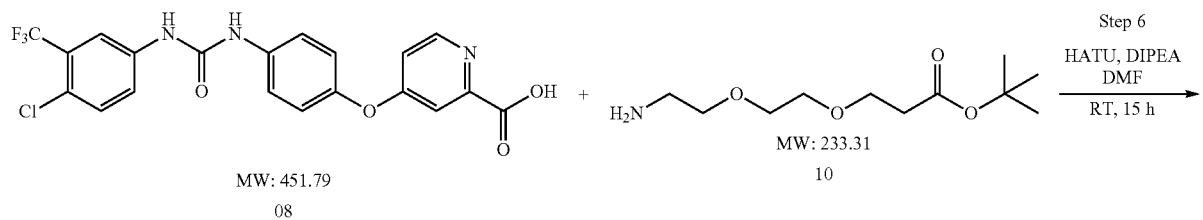

To a stirred solution of 4-(4-(3-(4-chlorom-ethyl)phenyl)ureido-)phenoxy)picolinic acid (08) (200 mg, 0.44 mmol, 1.0 equiv) in DMF (5.0 mL, 25.0 vol. equiv.) were added tert-butyl 3-(2-(2-aminoethoxy)ethoxy)propanoate (10) (124 mg, 0.53 mmol, 1.2 equiv), HATU (505 mg, 1.33 mmol, 3.0 equiv) and DIPEA (68.5 mg, 0.53 mmol, 1.20 equiv). The reaction mixture was stirred for 12 h at RT. Completion of reaction was monitored by TLC. The Reaction mixture was quenched with DMW (100 mL) and extracted with EtOAc (100 mL×3). The combined organic extract was washed with brine (100 mL), dried over $Na_2SO_4$ and concentrated under vacuum to afford the desired compound (11) (290 mg, 98.20%) as a brown gum. $^1$H NMR (300 MHz, DMSO-$d_6$) δ 9.22 (s, 1H), 9.00 (s, 1H), 8.69 (s, 1H), 8.52-8.51 (d, 1H), 8.13-8.12 (d, 1H), 7.65-7.64 (d, 2H), 7.63 (s, 1H), 7.61-7.60 (d, 1H), 7.58 (s, 1H), 7.39-7.38 (d, 1H), 7.19-7.16 (m, 3H), 3.59-3.41 (m, 16H), 2.89 (s, 2H), 2.41-2.39 (d, 2H) 1.40-1.37 (t, 9H). MS (ES+): 755.0 (M+1); MS (ES−): 753.2 (M−1).

Step 07: Synthesis of 3-(2-(2-(4-(4-(3-(4-chloro-3-(trifluoromethyl)phenyl)ureido)phenoxy)-picolinamido)ethoxy)ethoxy)propanoic Acid (12)

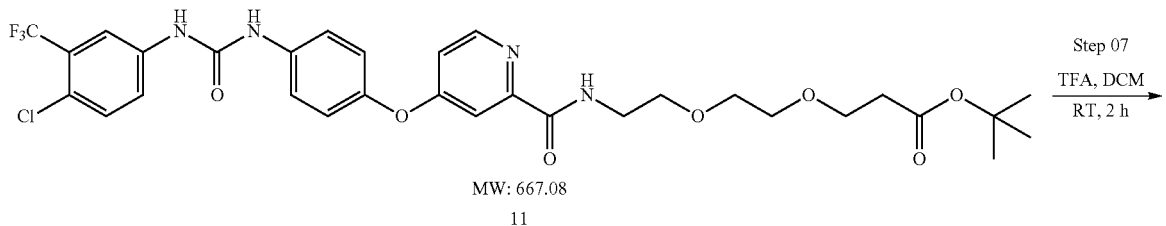

MW: 667.08
11

Step 07
TFA, DCM
RT, 2 h

MW: 610.97
12

To a stirred solution of tert-butyl 2-(3-(2-(4-(4-(3-(4-chloro-3-(trifluoromethyl)phenyl)-ureido)phenoxy)pico-linamido)ethoxy)propoxy)acetate (11) (290 mg, 0.43 mmol, 1.0 equiv) in DCM (5.80 mL, 20.0 vol. equiv.) and pour in cooled trifluoroacetic acid (5.80 mL, 20 vol. equiv.). The reaction mixture was stirred for 2 h at RT. Completion of the reaction was monitored by TLC. The Reaction mixture was taken and concentrated under vacuum to afford titled compound (12) (220 mg, 82.8%) as a brown gum. $^1$H NMR (300 MHz, DMSO-$d_6$) δ 9.29 (s, 1H), 9.00 (s, 1H), 8.69 (s, 1H), 8.52-8.51 (d, 1H), 8.13-8.12 (d, 1H), 7.65-7.64 (d, 2H), 7.63 (s, 1H), 7.61-7.60 (d, 1H), 7.58 (s, 1H), 7.39-7.38 (d, 1H), 7.19-7.16 (m, 3H), 3.59-3.55 (t, 3H), 3.52-3.49 (m, 7H), 3.45-3.41 (m, 2H). MS (ES−): 609.2 (M−1).

Step 08: Synthesis of 4-(4-(3-(4-chloro-3-(trifluoromethyl)phenyl)ureido)phenoxy)-N-(2-(2-(3-(((R)-1-((2S,4R)-4-hydroxy-2-(((S)-1-(4-(4-methylthiazol-5-yl)phenyl)ethyl)carbamoyl)pyrrolidin-1-yl)-3,3-dimethyl-1-oxobutan-2-yl)amino)-3-oxopropoxy)ethoxy)ethyl)picolinamide (14)

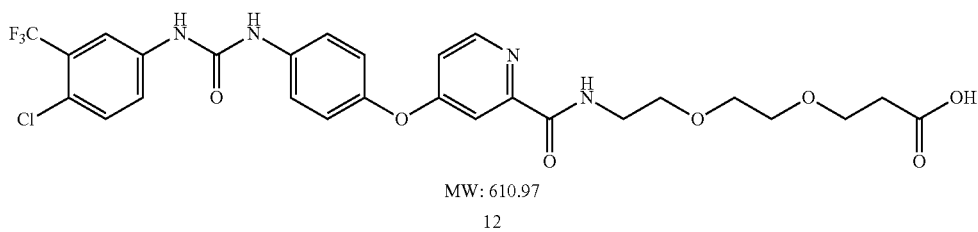

MW: 610.97
12

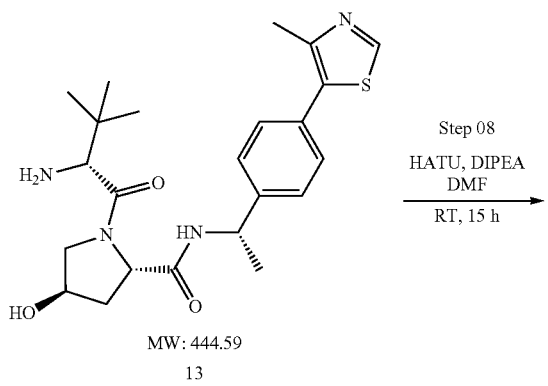

MW: 444.59
13

Step 08
HATU, DIPEA
DMF
RT, 15 h

-continued

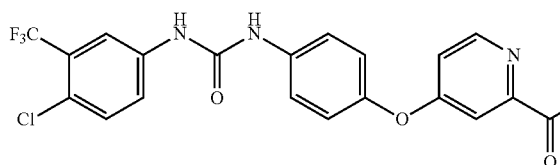

MW: 1037.55
14

To a stirred solution of 3-(2-(2-(4-(4-(3-(4-chloro-3-(trifluoromethyl)phenyl)ureido)-phenoxy)picolinamido)ethoxy)ethoxy)propanoic acid (12) (70 mg, 0.1 mmol, 1.0 equiv) in DMF (2.80 mL, 40.0 vol. equiv.) were added (2S,4R)-1-((R)-2-amino-3,3-dimethylbutanoyl)-4-hydroxy-N—((S)-1-(4-(4-methylthiazol-5-yl)phenyl)ethyl)pyrrolidine-2-carboxamide (13) (50.9 mg, 0.11 mmol, 1.0 equiv), HATU (131 mg, 0.34 mmol, 3.0 equiv) and DIPEA (317 mg, 1.15 mmol, 10.0 equiv). The reaction mixture was stirred for 12 h at RT. Completion of the reaction was monitored by TLC. The Reaction mixture was quenched with DMW (100 mL) and extracted with EtOAc (50 mL×3). Reaction extract was washed with brine (50 mL), dried over $Na_2SO_4$ and concentrated under vacuum to get crude. The crude was purified through column chromatography eluted with methanol in DCM (0-5%) to afford the titled compound (14) (30 mg, 25.20%) as a brown solid. $^1$H NMR (300 MHz, DMSO-$d_6$) δ 9.31 (s, 1H), 9.08 (s, 1H), 8.98 (s, 1H), 8.70 (s, 1H), 8.52-8.50 (d, 1H), 8.39 (s, 1H), 8.12 (s, 1H), 7.87-7.84 (d, 1H), 7.62-7.57 (t, 4H), 7.41-7.38 (d, 5H), 7.18-7.16 (d, 3H), 5.10 (s, 1H), 4.53-4.50 (d, 1H), 4.41 (s, 2H), 4.27 (s, 1H), 3.58-3.50 (m, 12H), 2.44 (s, 2H), 2.0 (s, 1H), 1.85 (s, 1H), 1.37-1.35 (s, 3H), 1.10-1.06 (s, 3H), 0.92 (s, 9H). MS (ES+): 1037 (M+1); MS (ES−): 1035.2 (M−1). HPLC: 93.47%.

Increased Scale: Synthesis of 4-(4-(3-(4-chloro-3-(trifluoromethyl)phenyl)ureido)phenoxy)-N-(2-(2-(3-(((R)-1-((2S,4R)-4-hydroxy-2-(((S)-1-(4-(4-methylthiazol-5-yl)phenyl)ethyl)carbamoyl)pyrrolidin-1-yl)-3,3-dimethyl-1-oxobutan-2-yl)amino)-3-oxopropoxy)ethoxy)ethyl)picolinamide (14)

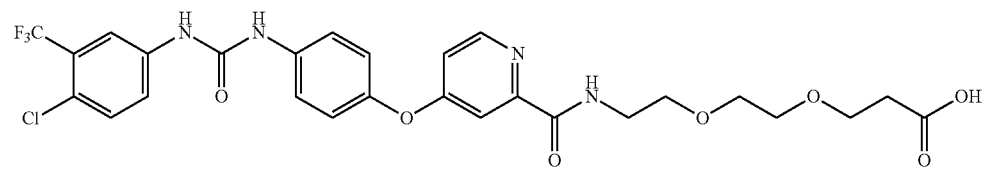

MW: 610.97
12

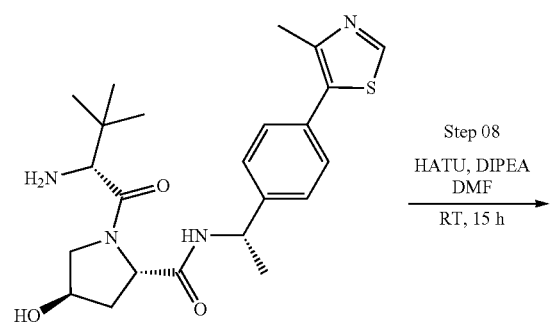

MW: 444.59
13

Step 08
HATU, DIPEA
DMF
RT, 15 h

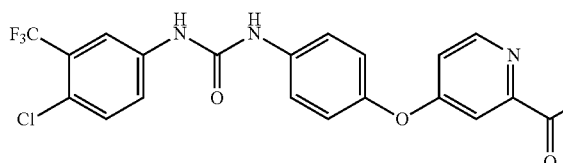
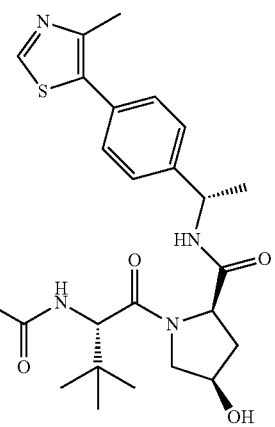

MW: 1037.55

14

To a stirred solution of 3-(2-(2-(4-(4-(3-(4-chloro-3-(trifluoromethyl)phenyl)ureido)-phenoxy)picolinamido)ethoxy)ethoxy)propanoic acid (12) (500 mg, 0.818 mmol, 1.0 equiv) in DMF (20 mL, 40.0 vol. equiv.) were added (2S,4R)-1-((R)-2-amino-3,3-dimethylbutanoyl)-4-hydroxy-N—((S)-1-(4-(4-methylthiazol-5-yl)phenyl)ethyl)pyrrolidine-2-carboxamide (364 mg, 0.818 mmol, 1.0 equiv), $T_3P$ (1.30 g, 4.09 mmol, 5.0 equiv) and DIPEA (1.06 g, 8.18 mmol, 10.0 equiv). The reaction mixture was stirred for 12 h at RT. Completion of reaction was monitored by TLC. The reaction mixture was taken and added DMW (100 mL) and extracted with EtOAc (50 mL×3). Reaction extract was washed with brine (50 mL), dried over $Na_2SO_4$ and concentrated under vacuum to get crude. The crude was purified through column chromatography eluted with methanol in DCM (0-5%) to afford the titled compound (14) (510 mg, 60.10%) as an off white solid. $^1$H NMR (300 MHz, DMSO-$d_6$) $^1$H NMR (300 MHz, DMSO-$d_6$) δ 9.31 (s, 1H), 9.08 (s, 1H), 8.98 (s, 1H), 8.70 (s, 1H), 8.52-8.50 (d, 1H), 8.39 (s, 1H), 8.12 (s, 1H), 7.87-7.84 (d, 1H), 7.62-7.57 (t, 4H), 7.41-7.38 (d, 5H), 7.18-7.16 (d, 3H), 5.10 (s, 1H), 4.53-4.50 (d, 1H), 4.41 (s, 2H), 4.27 (s, 1H), 3.58-3.50 (m, 12H), 2.44 (s, 2H), 2.0 (s, 1H), 1.85 (s, 1H), 1.37-1.35 (s, 3H), 1.10-1.06 (s, 3H), 0.92 (s, 9H). MS (ES+): 1037.9 (M+1); MS (ES−): 1035.1 (M−1). HPLC: 93.32%.

Example 3—Synthesis of 4-(4-(3-(4-chloro-3-(trifluoromethyl)phenyl)ureido)phenoxy)-N-(2-(2-(3-(((R)-1-((2R,4S)-4-hydroxy-2-(((S)-1-(4-(4-methylthiazol-5-yl)phenyl)ethyl)carbamoyl)pyrrolidin-1-yl)-3,3-dimethyl-1-oxobutan-2-yl)amino)-3-oxopropoxy)ethoxy)ethyl)picolinamide

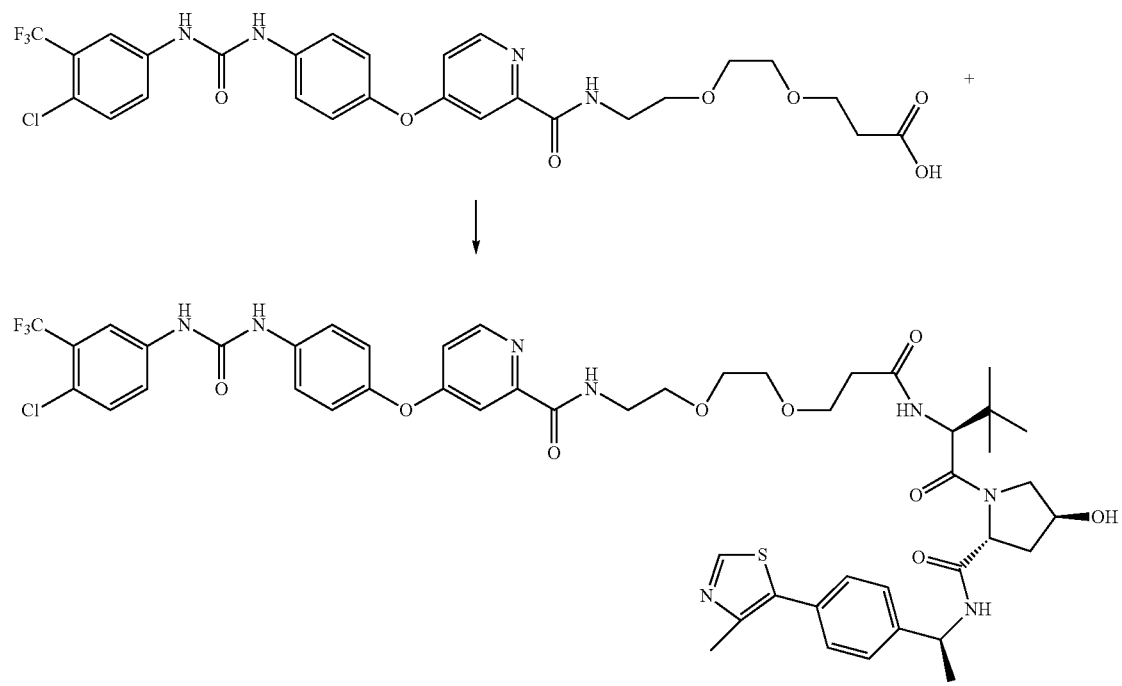

-continued

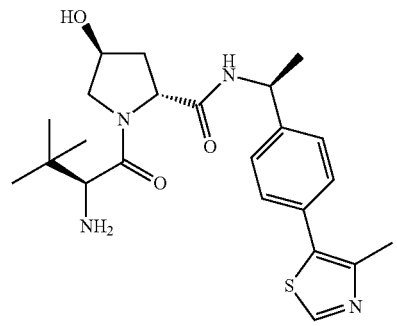

15

To a stirred solution of 3-(2-(2-(4-(4-(3-(4-chloro-3-(trifluoromethyl)phenyl)ureido)-phenoxy)picolinamido) ethoxy)ethoxy)propanoic acid (140 mg, 0.23 mmol, 1.0 equiv) in DMF (5.60 mL, 40.0 vol. equiv) were added (2R,4S)-1-((R)-2-amino-3,3-dimethylbutanoyl)-4-hydroxy-N—((S)-1-(4-(4-methylthiazol-5-yl)phenyl)ethyl)pyrrolidine-2-carboxamide (153 mg, 0.34 mmol, 1.0 equiv), TBTU (221 mg, 0.68 mmol, 3.0 equiv) and DIPEA (296 mg, 2.29 mmol, 10.0 equiv). The reaction mixture was stirred for 12 h at RT. Completion of reaction was monitored by TLC. The Reaction mixture was quenched with DMW (150 mL) and extracted with EtOAc (150 mL×3). The combined organic extract was washed with brine (150 mL), dried over Na$_2$SO$_4$ and concentrated under vacuum to get crude. The crude was purified by column chromatography using 0-5% MeOH in DCM to get the titled compound (65 mg, 28.7%) as a light grey solid. $^1$H NMR (300 MHz, DMSO-d$_6$ $^1$H NMR (300 MHz, DMSO-d$_6$) δ 9.40 (s, 1H), 9.19 (s, 1H), 8.98 (s, 1H), 8.70 (s, 1H), 8.52-8.50 (d, 1H), 8.39 (s, 1H), 8.12 (s, 1H), 7.87-7.84 (d, 1H), 7.62-7.57 (t, 4H), 7.41-7.38 (d, 5H), 7.18-7.16 (d, 3H), 5.10 (s, 1H), 4.53-4.50 (d, 1H), 4.41 (s, 2H), 4.27 (s, 1H), 3.58-3.50 (m, 12H), 2.44 (s, 2H), 2.0 (s, 1H), 1.85 (s, 1H), 1.37-1.35 (s, 3H), 1.10-1.06 (s, 3H), 0.92 (s, 9H). MS (ES+): 1037.2 (M+1); MS (ES−): 1035.1 (M−1). HPLC: 94.65%.

Example 4—Synthesis of 4-(4-(3-(4-chloro-3-(trifluoromethyl)phenyl)ureido)phenoxy)-N-(17-((2S, 4R)-4-hydroxy-2-(((S)-1-(4-(4-methylthiazol-5-yl) phenyl)ethyl)carbamoyl)pyrrolidine-1-carbonyl)-18, 18-dimethyl-15-oxo-3,6,9,12-tetraoxa-16-azanonadecyl)picolinamide (Compound 1.015)

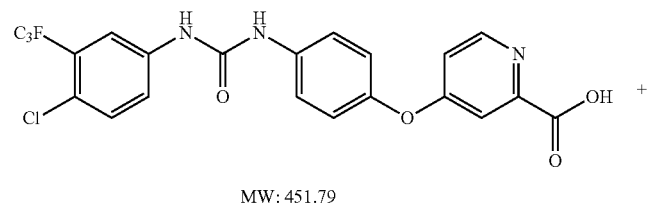

MW: 451.79
08

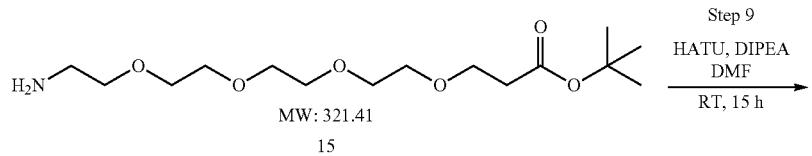

MW: 321.41
15

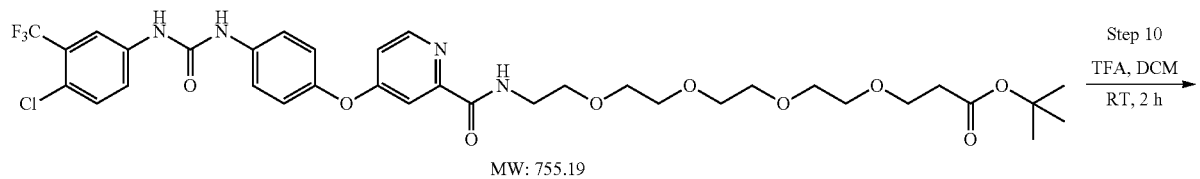

MW: 755.19
16

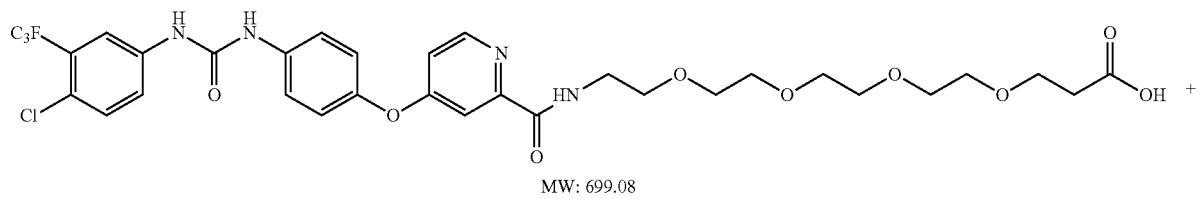

MW: 699.08
17

-continued

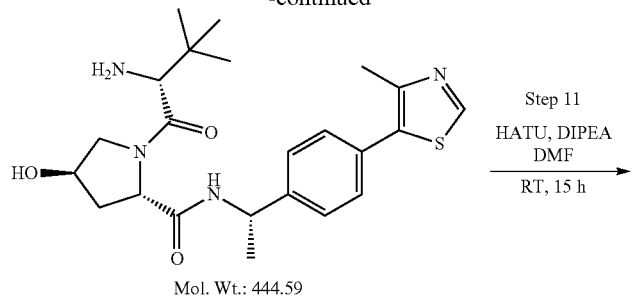

Mol. Wt.: 444.59
13

Step 11
HATU, DIPEA
DMF
RT, 15 h

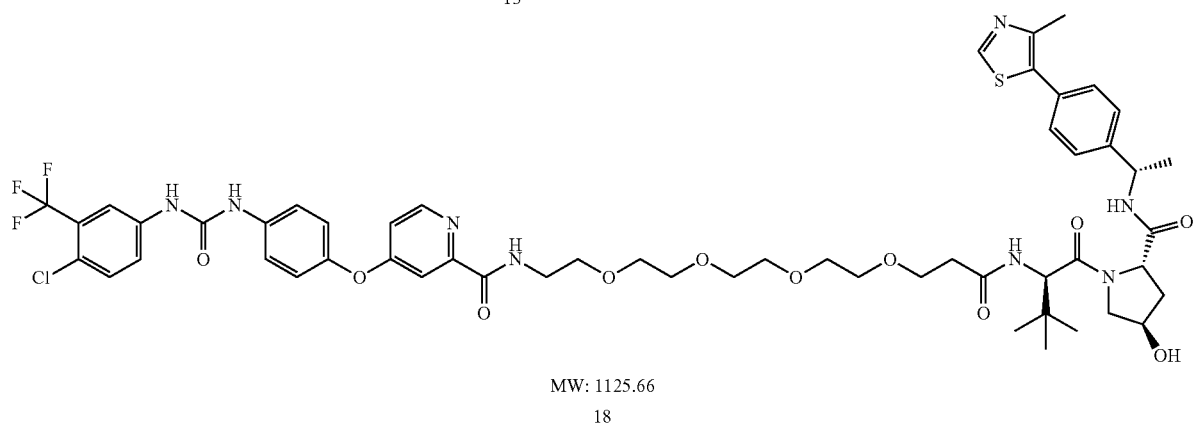

MW: 1125.66
18

Step 09: Synthesis of tert-butyl 1-(4-(4-(3-(4-chloro-3-(trifluoromethyl)phenyl)ureido)-phenoxy)pyridin-2-yl)-1-oxo-5,8,11,14-tetraoxa-2-azaheptadecan-17-oate (16)

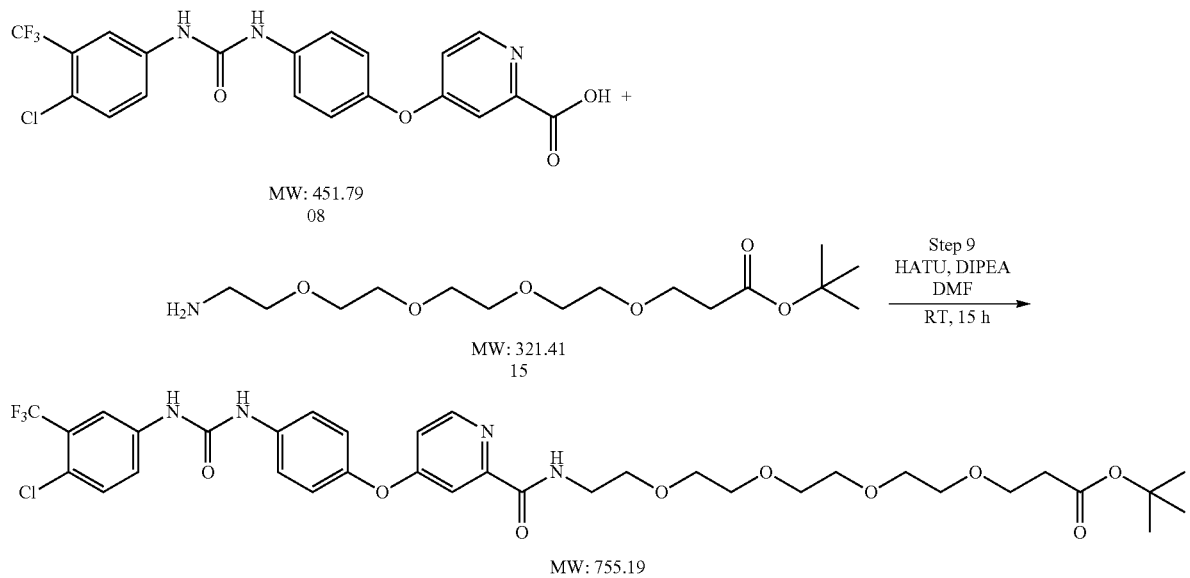

To a stirred solution of 4-(4-(3-(4-chloro-3-(trifluoromethyl)phenyl)ureido)phenoxy)-picolinic acid (08) (200 mg, 0.44 mmol, 1.0 equiv) in DMF (5.0 mL, 25.0 vol. equiv), were added tert-butyl 1-amino-3,6,9,12-tetraoxapentadecan-15-oate (165 (171.0 mg, 0.53 mmol, 1.2 equiv), HATU (505 mg, 1.33 mmol, 3.0 equiv) and DIPEA (68.50 mg, 0.53 mmol, 1.20 equiv). The reaction mixture was stirred for 12 h at RT. Completion of the reaction was monitored by TLC. The Reaction mixture was quenched with DMW (100 mL) and extracted with EtOAc (100 mL×3). The combined organic extract was washed with brine (100 mL), dried over $Na_2SO_4$ and concentrated under vacuum to afford the titled compound (16) (160 mg, 47.90%) as a brownish gum. $^1$H NMR (300 MHz, DMSO-$d_6$) δ 9.23 (s, 1H), 9.02 (s, 1H), 8.75 (s, 1H), 8.52-8.51 (d, 1H), 8.13-8.12 (d, 1H), 7.64-7.63

(d, 2H), 7.61 (s, 1H), 7.58 (s, 1H), 7.38-7.37 (d, 1H), 7.19-7.16 (m, 3H), 3.58-3.44 (m, 18H), 2.51-2.49 (t, 2H), 1.38 (s, 9H). MS (ES+): 755.0 (M+1); MS (ES-): 753.3 (M-1). HPLC: 97.56%.

Step 10: Synthesis of 1-(4-(4-(3-(4-chloro-3-(trifluoromethyl)phenyl)ureido)phenoxy)-pyridin-2-yl)-1-oxo-5,8,11,14-tetraoxa-2-azaheptadecan-17-oic Acid (17)

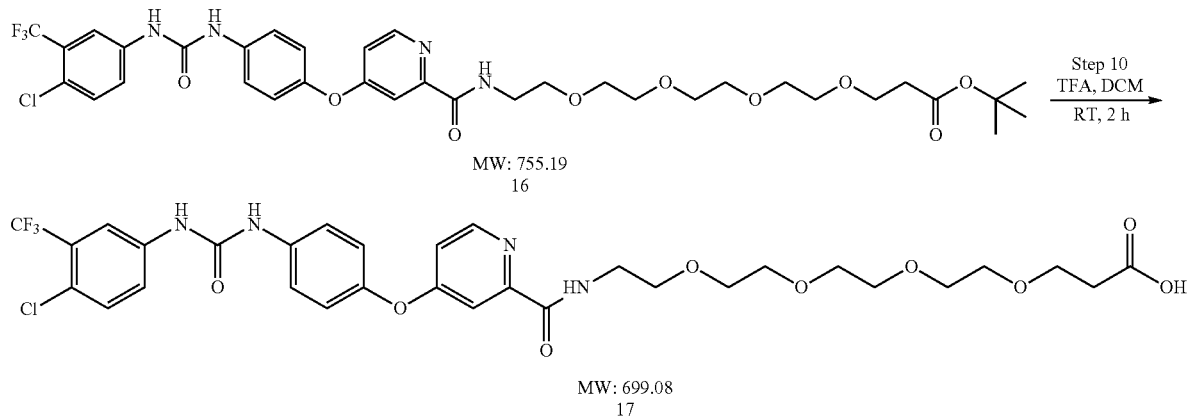

To a stirred solution of tert-butyl 1-(4-(4-(3-(4-chloro-3-(trifluoromethyl)phenyl)-ureido)phenoxy)pyridin-2-yl)-1-oxo-5,8,11,14-tetraoxa-2-azaheptadecan-17-oate (16) (155 mg, 0.205 mmol, 1.0 equiv) in DCM (3.10 mL, 20.0 vol Equiv) and pour in cooled trifluoroacetic acid (3.10 mL, 20 vol. equiv). The reaction mixture was stirred for 2 h at RT. Completion of reaction was monitored by TLC. The reaction mixture was taken and concentrated under vacuum to afford titled compound (17) (260 mg) as a light brown gum. $^1$H NMR (300 MHz, DMSO-d$_6$) 1H NMR (300 MHz, DMSO-d6)? 9.35 (s, 1H), 9.10 (s, 1H), 8.80 (s, 1H), 8.60-8.58 (d, 1H), 8.20 (d, 1H), 7.68-7.58 (m, 4H), 7.41-7.40 (d, 1H), 7.19-7.16 (t, 3H), 3.76-3.71 (t, 2H), 3.60-3.42 (m, 14H), 2.68 (s, 2H) 2.50-2.42 (m, 2H). MS (ES+): 699.0 (M+1); MS (ES-): 697.1 (M-1).

Step 11: Synthesis of 4-(4-(3-(4-chloro-3-(trifluoromethyl)phenyl)ureido)phenoxy)-N-(17-(((2S,4R)-4-hydroxy-2-(((S)-1-(4-(4-methylthiazol-5-yl)phenyl)ethyl)carbamoyl)pyrrolidine-1-carbonyl)-18,18-dimethyl-15-oxo-3,6,9,12-tetraoxa-16-azanonadecyl) picolinamide (18)

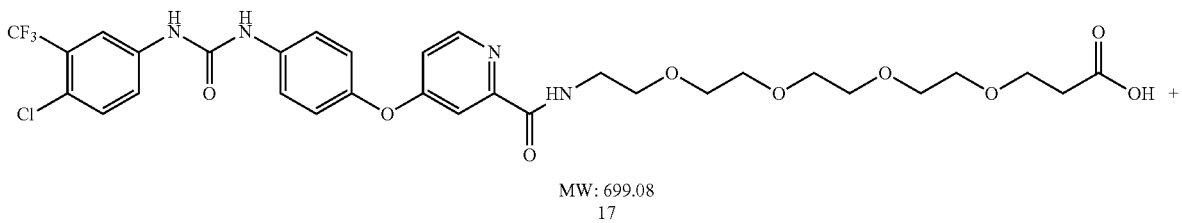

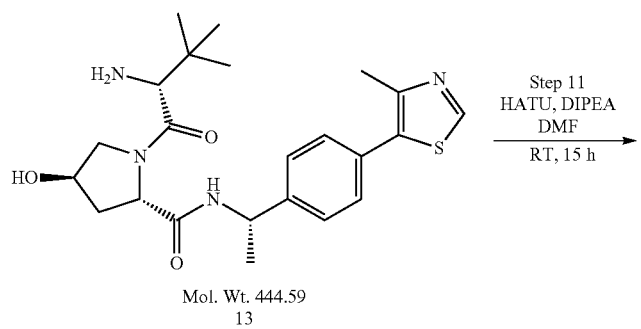

-continued

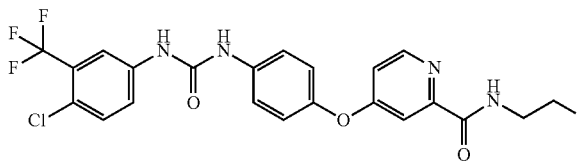

MW: 1125.66
18

To a stirred solution of 1-(4-(4-(3-(4-chloro-3-(trifluoromethyl)phenyl)ureido)-phenoxy)pyridin-2-yl)-1-oxo-5,8,11,14-tetraoxa-2-azaheptadecan-17-oic acid (17) (150 mg, 0.22 mmol, 1.0 equiv) in DMF (10.0 mL, 40.0 vol. equiv) were added (2S,4R)-1-((R)-2-amino-3,3-dimethylbutanoyl)-4-hydroxy-N—((S)-1-(4-(4-methylthiazol-5-yl)phenyl)ethyl)pyrrolidine-2-carboxamide (13) (143 mg, 0.32 mmol, 1.0 equiv), TBTU (207 mg, 0.64 mmol, 3.0 equiv) and DIPEA (277 mg, 2.15 mmol, 10.0 equiv). The reaction mixture was stirred for 12 h at RT. Completion of reaction was monitored by TLC. The Reaction mixture was quenched with DMW (150 mL) and extracted with EtOAc (150 mL×3). Reaction extract was washed with brine (150 mL), dried over $Na_2SO_4$ and concentrated under vacuum to get crude. The crude was purified through column chromatography eluted with methanol in DCM (0-10%) to afford the titled compound (18) (73 mg, 30.20%) as a off white solid. $^1$H NMR (300 MHz, DMSO-$d_6$) δ 9.31 (s, 1H), 9.08 (s, 1H), 8.98 (s, 1H), 8.70 (s, 1H), 8.52-8.50 (d, 1H), 8.39 (s, 1H), 8.12 (s, 1H), 7.87-7.84 (d, 1H), 7.62-7.57 (t, 4H), 7.41-7.38 (d, 5H), 7.18-7.16 (d, 3H), 5.10 (s, 1H), 4.53-4.50 (d, 1H), 4.41 (s, 2H), 4.27 (s, 1H), 3.58-3.50 (m, 20H), 2.44 (s, 2H), 2.0 (s, 1H), 1.85 (s, 1H), 1.37-1.35 (s, 3H), 1.10-1.06 (s, 3H), 0.92 (s, 9H). MS (ES+): 1026.1 (M+1); MS (ES−): 1125.1 (M−1). HPLC: 90.88%.

Example 5—Synthesis of 4-(4-(3-(4-chloro-3-(trifluoromethyl)phenyl)ureido)phenoxy)-N—((R)-23-((2S,4R)-4-hydroxy-2-(((S)-1-(4-(4-methylthiazol-5-yl)phenyl)ethyl)carbamoyl)pyrrolidine-1-carbonyl)-24,24-dimethyl-21-oxo-3,6,9,12,15,18-hexaoxa-22-azapentacosyl)picolinamide (Compound 1.016)

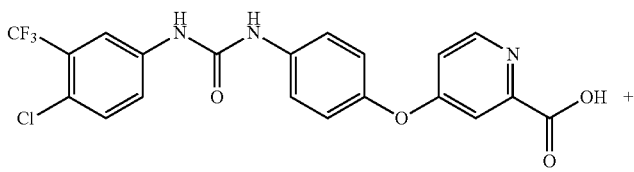

MW: 451.79
08

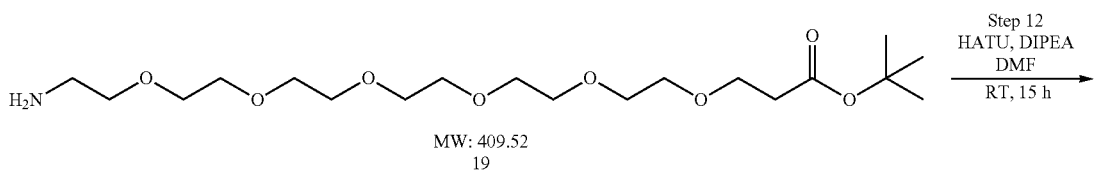

MW: 409.52
19

Step 12
HATU, DIPEA
DMF
RT, 15 h

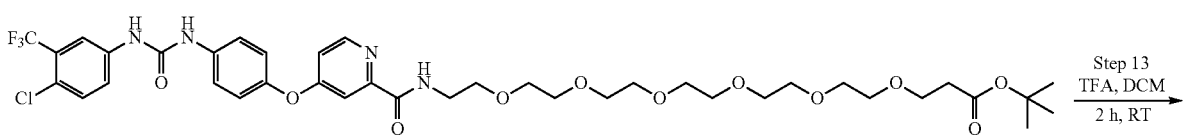

MW: 843.29
20

Step 13
TFA, DCM
2 h, RT

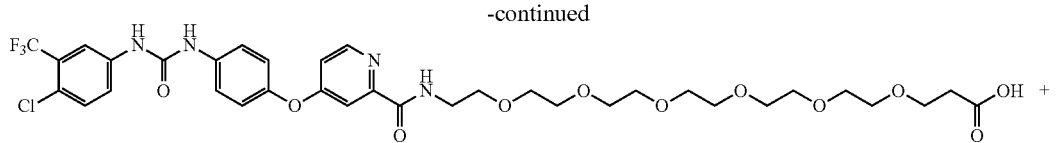
MW: 787.18
21
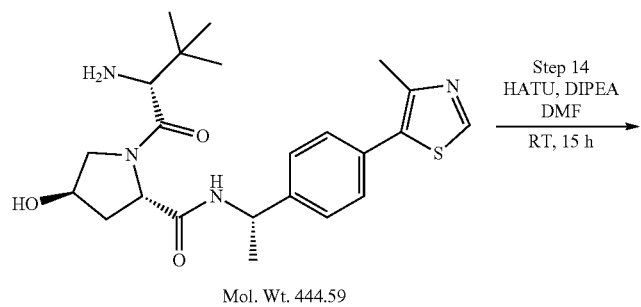
Mol. Wt. 444.59
13
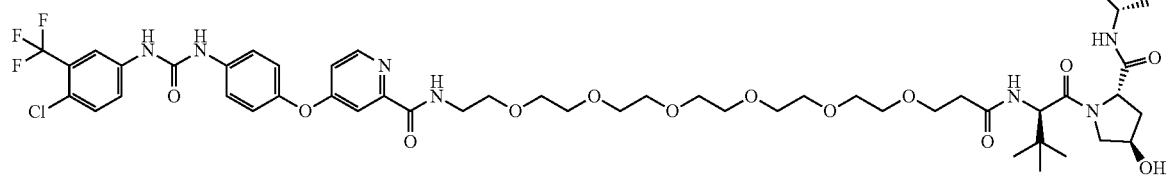
22
Step 12: Synthesis of tert-butyl 1-(4-(4-(3-(4-chloro-3-(trifluoromethyl)phenyl)ureido)phenoxy)pyridin-2-yl)-1-oxo-5,8,11,14,17,20-hexaoxa-2-aza-tricosan-23-oate (20)
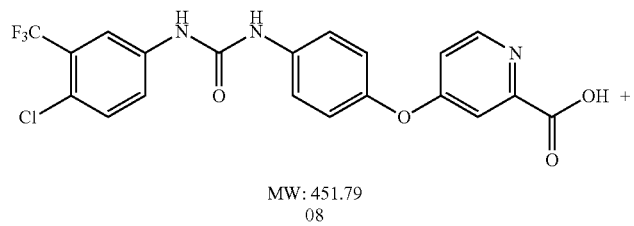
MW: 451.79
08
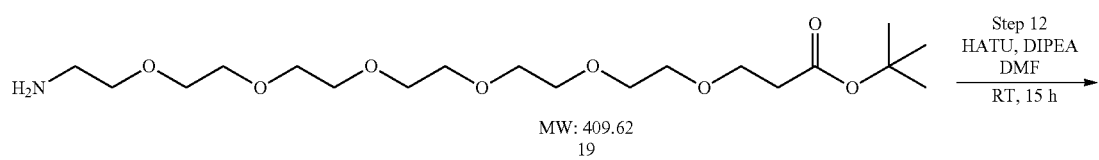
MW: 409.62
19
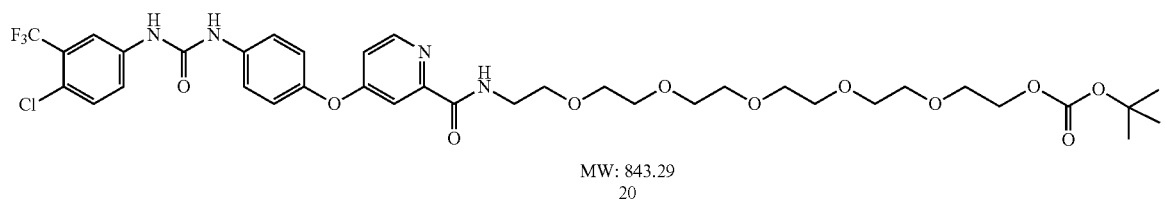
MW: 843.29
20

To a stirred solution of 4-(4-(3-(4-chloro-3-(trifluoromethyl)phenyl)ureido)phenoxy)-picolinic acid (08) (200 mg, 0.44 mmol, 1.0 equiv) in DMF (5.0 mL, 25.0 vol. equiv), were added tert-butyl 2-(3-(2-aminoethoxy)propoxy)acetate (19) (218.0 mg, 0.53 mmol, 1.2 equiv), HATU (505 mg, 1.33 mmol, 3.0 equiv) and DIPEA (68.50 mg, 0.53 mmol, 1.20 equiv). The reaction mixture was stirred for 12 h at RT. Completion of reaction was monitored by TLC. The Reaction mixture was quenched with DMW (100 mL) and extracted with EtOAc (100 mL×3). The combined organic extract was washed with brine (100 mL), dried over $Na_2SO_4$ and concentrated under vacuum to afford titled compound (20) (350 mg, 93.80%) brownish gum. $^1H$ NMR (300 MHz, DMSO-$d_6$) δ 9.30 (s, 1H), 9.10 (s, 1H), 8.70 (s, 1H), 8.60 (d, 1H), 8.13-8.12 (d, 1H), 7.70-7.65 (m, 4H), 7.50 (s, 1H), 7.21-7.18 (m, 3H), 3.58-3.44 (m, 26H), 2.51-2.49 (t, 2H). MS (ES+): 843 (M+1); MS (ES−): 841.2 (M−1).

Step 13: Synthesis of 1-(4-(4-(3-(4-chloro-3-(trifluoromethyl)phenyl)ureido)phenoxy)pyridin-2-yl)-1-oxo-5,8,11,14,17,20-hexaoxa-2-azatricosan-23-oic Acid (21)

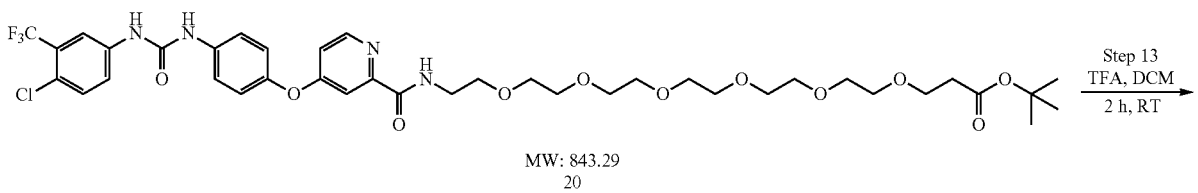

MW: 843.29
20

MW: 787.18
21

To a stirred solution of tert-butyl 1-(4-(4-(3-(4-chloro-3-(trifluoromethyl)phenyl)-ureido)phenoxy)pyridin-2-yl)-1-oxo-5,8,11,14,17,20-hexaoxa-2-azatricosan-23-oate (20) (350 mg, 0.41 mmol, 1.0 equiv) in DCM (7.00 mL, 20.0 vol. equiv) and pour in cooled trifluoroacetic acid (7.00 mL, 20 vol. equiv). The reaction mixture was stirred for 2 h at RT. Completion of reaction was monitored by TLC. The Reaction mixture was taken and concentrated under vacuum to afford titled compound (21) (320 mg, 97.9%) as a brownish gum. $^1H$ NMR (300 MHz, DMSO-$d_6$) 1H NMR (300 MHz, DMSO-d6) 9.40 (s, 1H), 9.20 (s, 1H), 8.80 (s, 1H), 8.60-8.58 (d, 1H), 8.20 (d, 1H), 7.68-7.58 (m, 4H), 7.41-7.40 (d, 1H), 7.19-7.16 (t, 3H), 3.76-3.71 (t, 2H), 3.60-3.42 (m, 22H), 2.68 (s, 2H) 2.50-2.42 (m, 2H). MS (ES+): 787.3.0 (M+1); MS (ES−): 785 (M−1).

Step 14: Synthesis of 4-(4-(3-(4-chloro-3-(trifluoromethyl)phenyl)ureido)phenoxy)-N—((R)-23-((2S,4R)-4-hydroxy-2-(((S)-1-(4-(4-methylthiazol-5-yl)phenyl)ethyl)carbamoyl)pyrrolidine-1-carbonyl)-24,24-dimethyl-21-oxo-3,6,9,12,15,18-hexaoxa-22-azapentacosyl)picolinamide (22)

MW: 787.18
21

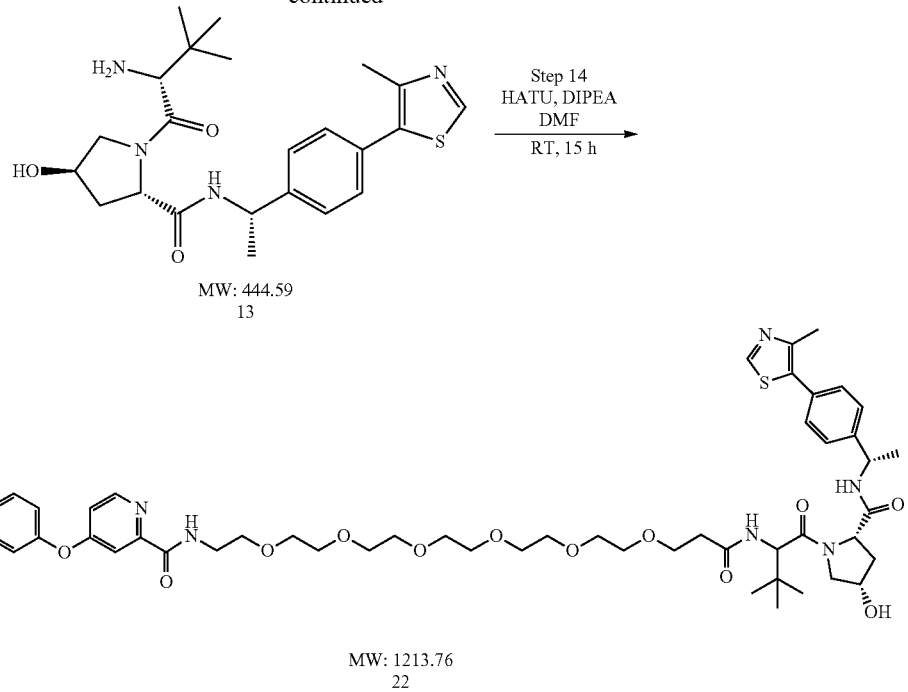

To a stirred solution of 1-(4-(4-(3-(4-chloro-3-(trifluoromethyl)phenyl)ureido)-phenoxy)pyridin-2-yl)-1-oxo-5,8,11,14,17,20-hexaoxa-2-azatricosan-23-oic acid (21) (150 mg, 0.19 mmol, 1.0 equiv) in DMF (12.40 mL, 40.0 vol. equiv.) were added (2S,4R)-1-((R)-2-amino-3,3-dimethylbutanoyl)-4-hydroxy-N—((S)-1-(4-(4-methylthiazol-5-yl)phenyl)ethyl)pyrrolidine-2-carboxamide (13) (127 mg, 0.29 mmol, 1.5 equiv), TBTU (0.18 g, 0.57 mmol, 3.0 equiv) and DIPEA (246 mg, 1.91 mmol, 10.0 equiv). The reaction mixture was stirred for 12 h at RT. Completion of reaction was monitored by TLC. The Reaction mixture was quenched with DMW (100 mL) and extracted with EtOAc (150 mL×3). The combined organic extract was washed with brine (150 mL), dried over $Na_2SO_4$ and concentrated under vacuum to get crude. Crude was purified through column chromatography eluted with methanol in DCM (0-5%) to afford titled the compound (85 mg, 36.8%) as an off white solid. $^1$H NMR (300 MHz, DMSO-$d_6$) δ 9.50 (s, 1H), 9.27 (s, 1H), 8.98 (s, 1H), 8.75 (s, 1H), 8.60 (s, 1H), 8.39 (s, 1H), 8.12 (s, 1H), 7.85 (d, 1H), 7.63-7.58 (t, 4H), 7.41-7.38 (d, 5H), 7.18-7.16 (d, 2H), 5.10 (s, 1H), 4.53-4.50 (d, 1H), 4.41 (s, 2H), 4.27 (s, 1H), 3.58-3.50 (m, 28H), 2.44 (s, 2H), 2.0 (s, 1H), 1.85 (s, 1H), 1.37-1.35 (s, 3H), 1.10-1.06 (s, 3H), 0.92 (s, 9H). MS (ES+): 1213.1 (M+1); MS (ES−): 1211.3 (M−1). HPLC: 78.83%.

Example 6—Synthesis of N-((2S,15R)-15-((2S,4R)-4-hydroxy-2-(((S)-1-(4-(4-methylthiazol-5-yl)phenyl)ethyl)carbamoyl)pyrrolidine-1-carbonyl)-16,16-dimethyl-3,13-dioxo-7,10-dioxa-4,14-diazaheptadecan-2-yl)-6-((3-(3-(5-methyl-1H-imidazol-1-yl)-5-(trifluoromethyl)benzamido)benzyl)amino)-2H-indazole-3-carboxamide

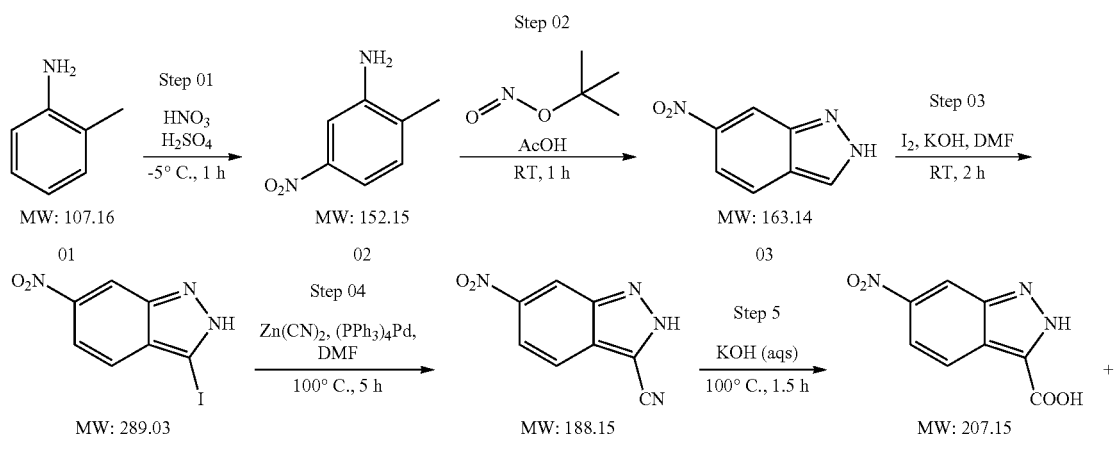

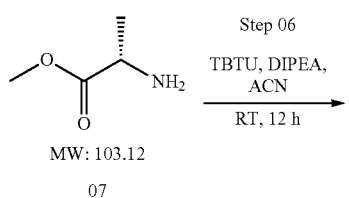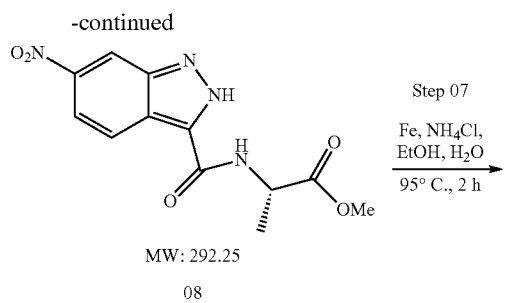
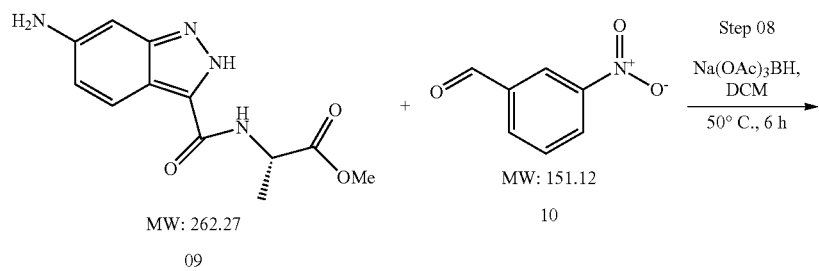
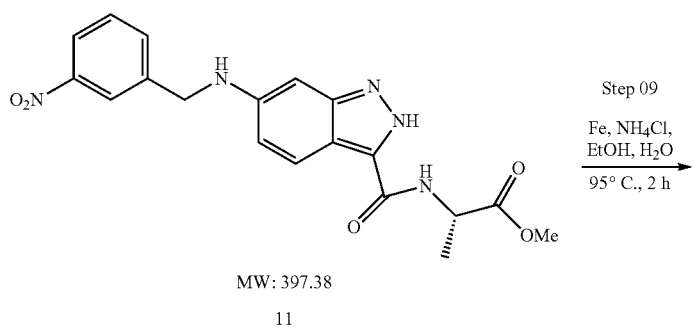
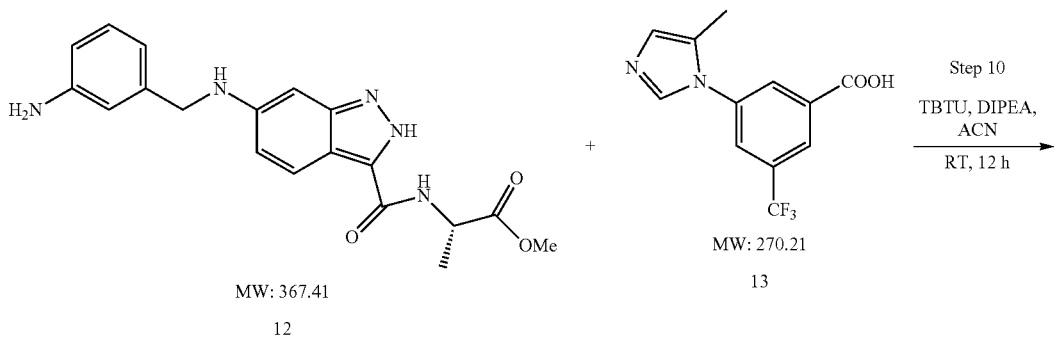
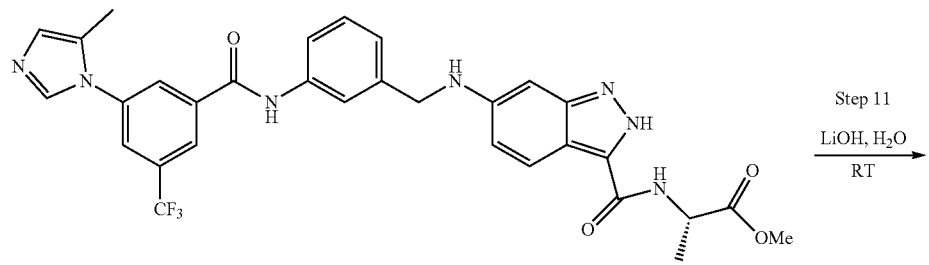

-continued
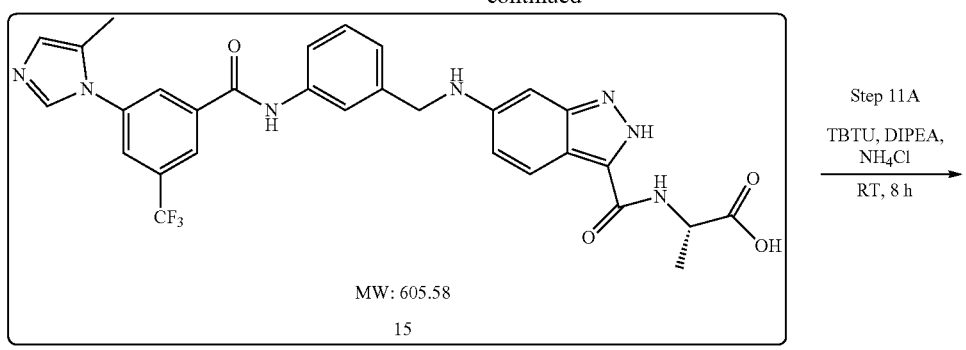
Step 11A
TBTU, DIPEA, NH₄Cl
RT, 8 h
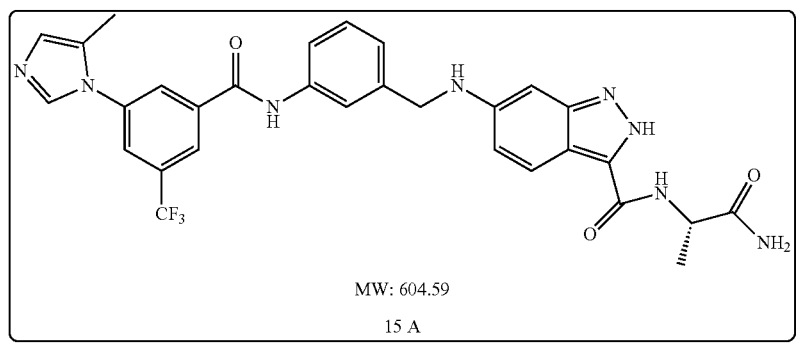
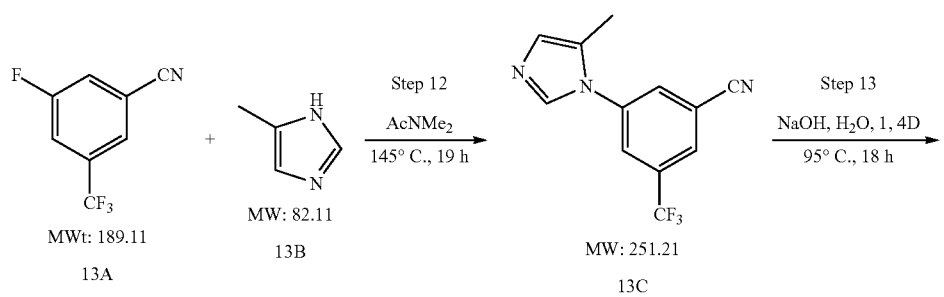
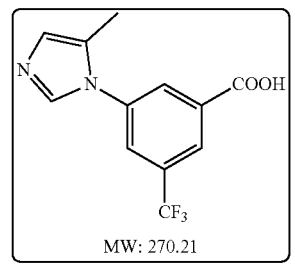
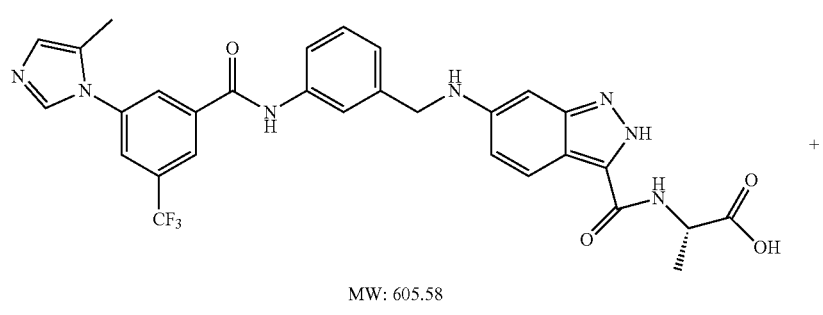

-continued
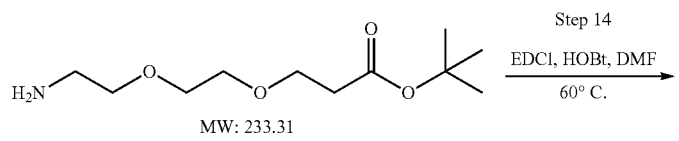
MW: 233.31
16
Step 14
EDCl, HOBt, DMF
60° C.
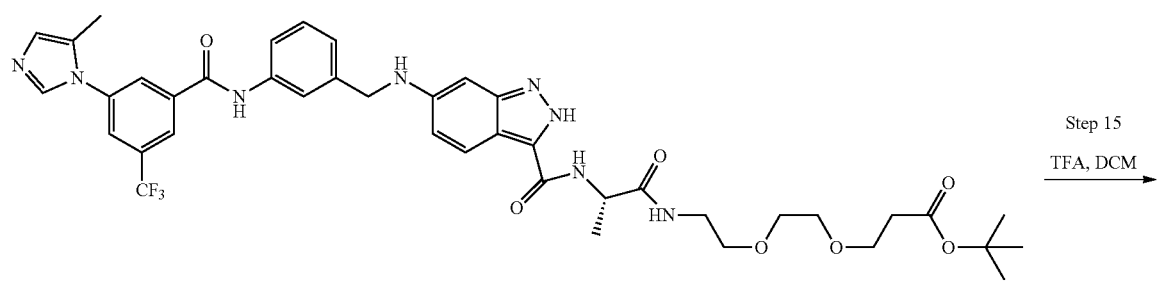
MW: 820.87
17
Step 15
TFA, DCM
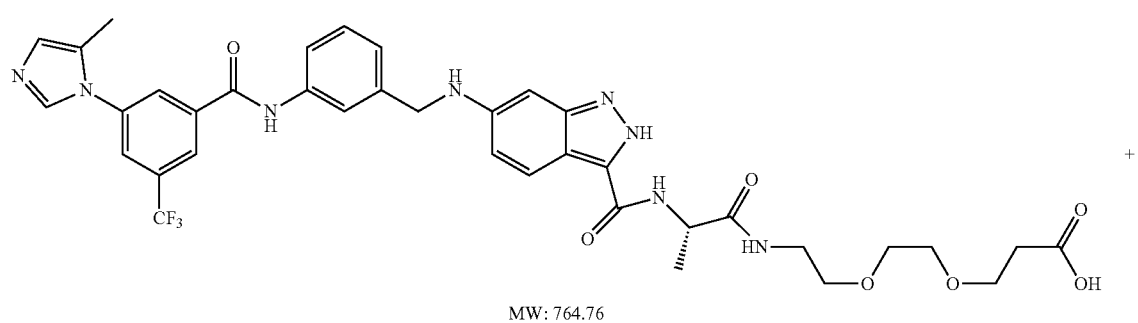
MW: 764.76
18
+
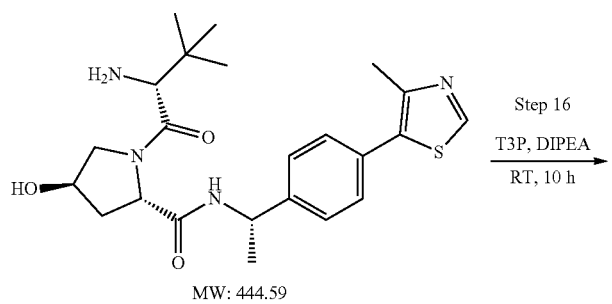
MW: 444.59
19
Step 16
T3P, DIPEA
RT, 10 h -continued

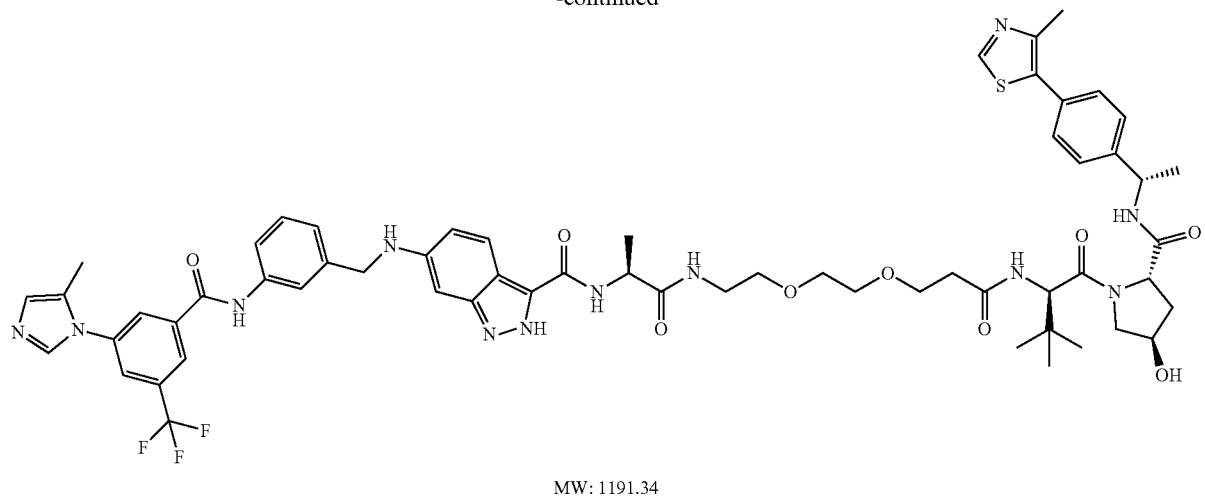

MW: 1191.34
20

Step 01: Synthesis of 2-methyl-5-nitroaniline (02)

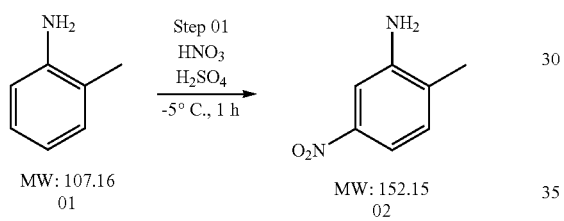

To a stirred solution of sulfuric acid (750.0 mL, 15.0 vol. equiv) was added o-toluidine (01) (50.0 g, 467.0 mmol, 1.0 equiv) at −5° C. Mixed acid (55.6 mL of 65% nitric acid and 250.0 mL of sulfuric acid) was then added drop wise at −5° C. during 2 h. The resulting mixture was stirred for 1 h at 0° C. The completion of reaction was monitored by TLC. Then the mixture was poured onto crushed ice and made alkaline with aqueous sodium hydroxide. The precipitate formed was collected by filtration and dried to get titled compound (02) (55.4 g, 78.0%) as a yellow solid. $^1$H NMR (300 MHz, DMSO-$d_6$) δ 7.45-7.44 (d, 1H), 7.31-7.27 (m, 1H), 7.17-7.14 (d, 1H), 5.55 (s, 2H), 2.14 (s, 3H).

Step 02: Synthesis of 6-nitro-2H-indazol (03)

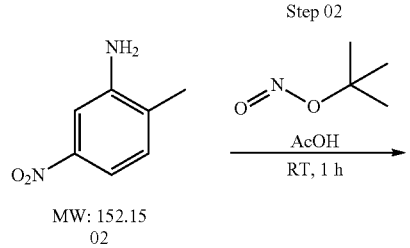

-continued

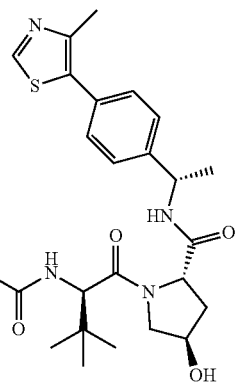

MW: 163.14
03

To a stirred solution of tert-butyl nitrite (02) (20.3 g, 197.0 mmol, 1.50 equiv) in acetic acid (100.0 mL, 5.0 vol. equiv) was added drop wise a solution of 2-methyl-5-nitroaniline (20.0 g, 131.0 mmol, 1.0 equiv) in acetic acid (400 mL, 20.0 vol. equiv) at RT. The resulting mixture was stirred for 1 h at RT. The completion of reaction was monitored by TLC (Mf: 30% EtOAc in n-hexane, Rf; 0.4). The reaction mixture was concentrated under vacuum and residue was dissolved in ethyl acetate (500.0 mL). Then residue were washed with sodium bicarbonate solution (150.0 mL), brine (100.0 mL), dried over $Na_2SO_4$ and concentrated under vacuum to afford titled compound (03) (18.2 g, 84.9%) as a reddish solid. $^1$H NMR (300 MHz, DMSO-$d_6$) δ 13.80 (s, 1H), 8.46 (s, 1H), 8.33 (s, 1H), 8.01 (s, 1H). MS (ES−): 162.20 (M−1).

Step 03: Synthesis of 3-iodo-6-nitro-2H-indazole (04)

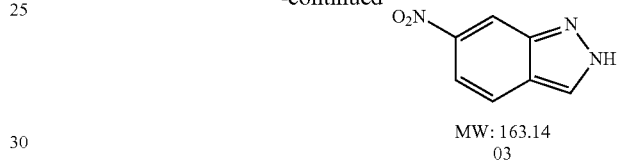

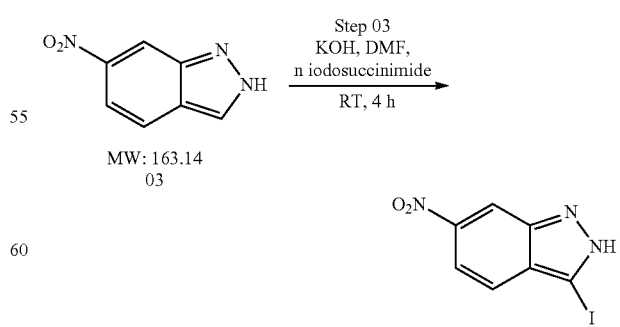

To a stirred solution of 6-nitro-2H-indazole (03) (48.0 g, 294.0 mmol, 1.0 equiv) in DMF (720.0 mL, 15.0 vol. equiv) were added N-iodosuccinimide (99.3 g, 441.0 mmol, 1.50 equiv), potassium carbonate (102.0 g, 736.0 mmol, 2.50 equiv) at RT. The resulting mixture was stirred for 5 h at RT. The completion of reaction was monitored by TLC (Mf: 30% EtOAc in n-hexane, Rf: 0.6). The reaction mixture was quenched with DMW and extracted with EtOAc (4×300.0 mL). The combined organic extract was washed with sodium thiosulphate solution (300.0 mL), brine (300.0 mL), dried over Na$_2$SO$_4$ and concentrated under vacuum to get crude. The crude was purified with column chromatography eluted with EtOAc in n-hexane (0-20%) to get titled compound (04) (32.5 g, 38.2%) as a yellow solid. $^1$H NMR (300 MHz, DMSO-d$_6$) δ 14.2 (s, 1H), 8.48-8.47 (d, 1H), 8.01-7.97 (m, 1H), 7.70-7.68 (d, 1H). MS (ES−): 287.9 (M−1).

Step 04: Synthesis of
6-nitro-2H-indazole-3-carbonitrile (05)

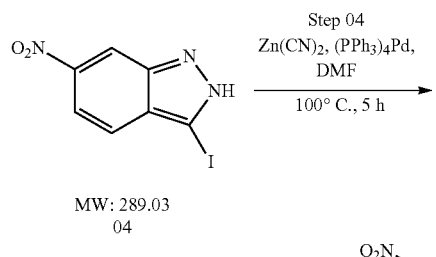

MW: 289.03
04

MW: 188.15
05

To a stirred solution of 3-iodo-6-nitro-2H-indazole (04) (10.0 g, 34.6 mmol, 1.0 equiv) in N, N-dimethylacetamide (100.0 mL, 10.0 vol. equiv) was added zinc cyanide (16.3 g, 138.0 mmol, 4.0 equiv) and tetrakis(triphenylphosphine)palladium (10.0 g, 8.65 mmol, 0.25 equiv) at RT. The resulting mixture was stirred for 4 h at 100° C. The completion of reaction was monitored by TLC (M.Ph.: 30% EtOAc in n-hexane, Rf: 0.5). The reaction mixture was filtered through a celite pad and then filtrate was extracted with ethyl acetate (3×200.0). The combined organic extract was washed with brine (150.0 mL), dried over sodium sulphate and concentrated under vacuum to afford titled compound (05) (3.5 g, 53.8%) as a yellow solid. $^1$H NMR (300 MHz, DMSO-d$_6$) δ 14.30 (s, 1H), 8.65-8.64 (t, 1H), 8.15-8.14 (d, 2H). MS (ES−): 187.40 (M−1).

Step 05: Synthesis of
6-nitro-2H-indazole-3-carboxylic Acid (06)

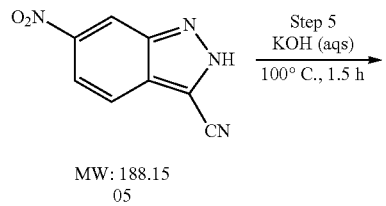

MW: 188.15
05

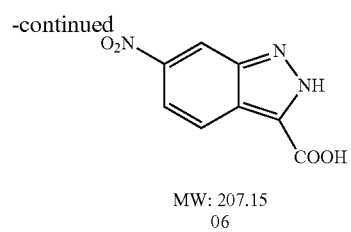

MW: 207.15
06

To a stirred solution of 6-nitro-2H-indazole-3-carbonitrile (05) (2.5 g, 13.3 mmol, 1.0 equiv) in a solution of 10 N potassium hydroxide (45.0 mL, 18.0 vol. equiv) was added water (25.0 mL, 10.0 vol. equiv), potassium hydroxide (2.24 g, 39.9 mmol, 3.0 equiv) at RT. The resulting mixture was stirred for 2 h at 95° C. The completion of reaction was monitored by TLC (Mf: 20% MeOH in DCM, Rf: 0.3). The reaction mixture was concentrated under vacuum and the residue was dissolved in water, adjusts pH acidic with 2N HCl and cooled to 5° C., filtered to get titled compound (06) (2.1 g, 76.3%) as a reddish solid. $^1$H NMR (300 MHz, DMSO-d$_6$) δ 14.51 (s, 1H), 8.55-8.48 (m, 1H), 8.28-8.25 (d, 1H), 8.11-8.01 (m, 1H). MS (ES−): 206.3 (M−1).

Step 06: Synthesis of methyl (6-nitro-2H-indazole-3-carbonyl)-L-alaninate (08)

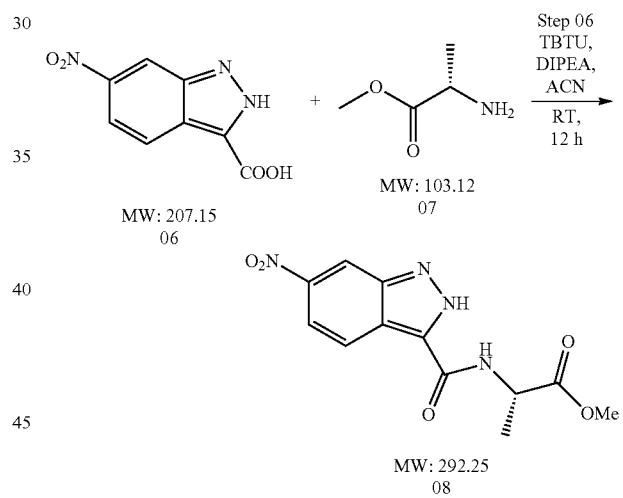

To a stirred solution of 6-nitro-2H-indazole-3-carboxylic acid (06) (1.80 g, 8.69 mmol, 1.0 equiv) in acetonitrile (54.0 mL, 30.0 vol. equiv) was added methyl D-alaninate hydrochloride (1.33 g, 9.56 mmol, 1.10 equiv), TBTU (4.19 g, 13.0 mmol, 1.50 equiv) and DIPEA (4.49 g, 4.83 mmol, 4.0 equiv) at RT. The resulting mixture was stirred for 15 h at RT. The completion of reaction was monitored by TLC (M.Ph.: 20% MeOH in DCM, Rf: 0.7). The reaction mixture was quenched with water and extracted with ethyl acetate (3×100.0 mL). The combined organic was washed with brine (100.0 mL), dried over sodium sulphate and concentrated under vacuum to get crude. The crude was purified with column chromatography eluted with ethyl acetate in n-hexane (0 to 20%) to afford titled compound (1.5 g, 59.1%) as a yellow solid. $^1$H NMR (300 MHz, DMSO-d$_6$) δ 8.90-8.88 (d, 1H), 8.55-8.54 (d, 1H), 8.35-8.32 (d, 1H), 8.09-8.05 (m, 1H), 4.61-4.56 (t, 1H), 3.65 (s, 3H), 1.45-1.43 (d, 3H). MS (ES+): 293.1 (M+1); MS (ES−): 291.0 (M−1).

Step 07: Synthesis of methyl (6-amino-2H-indazole-3-carbonyl)-L-alaninate (09)

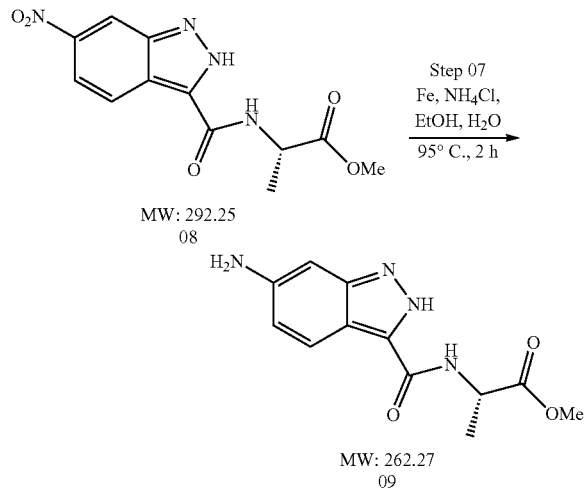

To a stirred solution of methyl (6-nitro-2H-indazole-3-carbonyl)-L-alaninate (08) (1.0 g, 3.42 mmol, 1.0 equiv) in ethanol (50.0 mL, 50.0 vol. equiv) were added ammonium chloride (915.0 mg, 17.1 mmol, 5.0 equiv), iron powder (956.0 mg, 17.1 mmol, 5.0 equiv) and water (30.0 mL, 30.0 vol. equiv) at RT. The resulting mixture was stirred for 2 h under reflux. The completion of reaction was monitored by TLC (Mf: 50% EtOAc in n-hexane, Rf: 0.4). The reaction mixture was filtered through a celite pad and then filtrate was extracted with ethyl acetate (3×100.0), washed with brine (100.0 mL), dried over sodium sulphate and concentrated under vacuum to get crude. The crude was purified with column chromatography eluted with ethyl acetate in n-hexane (0 to 30%) to afford titled compound (09) (680.0 mg, 75.8%) as a brownish solid. $^1$H NMR (300 MHz, DMSO-$d_6$) δ 12.8 (s, 1H), 8.40 (s, 1H), 7.70 (s, 1H), 6.54 (s, 2H), 5.39 (s, 1H), 4.50 (m, 1H), 4.64 (s, 3H), 1.40 (d, 3H). MS (ES+): 263.4 (M+1); MS (ES−): 261.3 (M−1).

Step 08: Synthesis of methyl (6-((3-nitrobenzyl)amino)-2H-indazole-3-carbonyl)-L-alaninate (11)

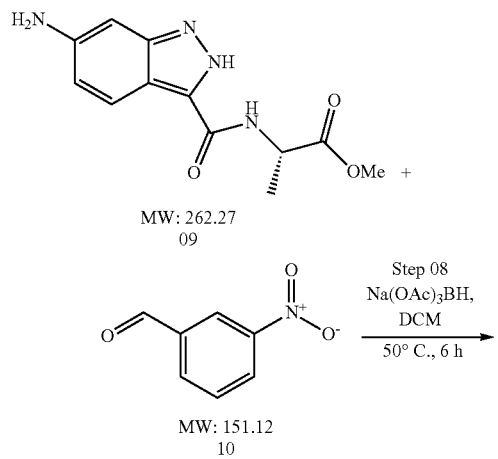

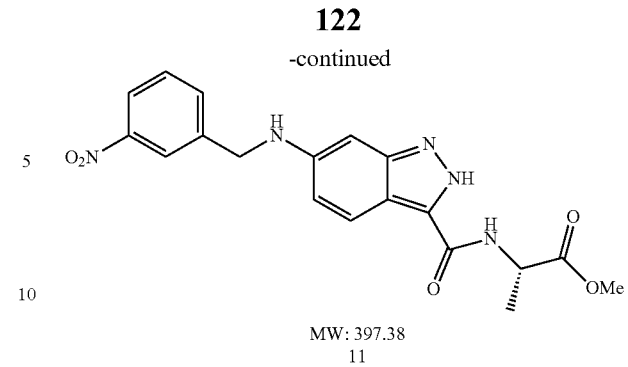

To a stirred solution of methyl (6-amino-2H-indazole-3-carbonyl)-L-alaninate (09) (980.0 mg, 3.74 mmol, 1.0 equiv) in DCM (29.4 mL, 30.0 vol. equiv) was added 3-nitrobenzaldehyde (10) (565.0 mg, 3.74 mmol, 1.0 equiv), sodium triacetoxyborohydride (1.19 g, 5.60 mmol, 1.50 equiv) and acetic acid (224.0 mg, 3.74 mmol, 1.0 equiv) at RT. The resulting mixture was stirred for 12 h at RT. The completion of reaction was monitored by TLC (M.Ph.: 60% EtOAc in n-hexane, Rf: 0.4). The reaction mixture was quenched with water and extracted with ethyl acetate (3×100.0). The combined organic extract was washed with brine (100.0 mL), dried over sodium sulphate and concentrated under vacuum to get crude. The crude was purified with column chromatography eluted with ethyl acetate in n-hexane (0 to 40%) to afford titled compound (11) (800.0 mg, 53.9%) as a yellow solid. $^1$H NMR (300 MHz, DMSO-$d_6$) δ 12.83 (s, 1H), 8.41-8.39 (d, 1H), 8.25 (s, 1H), 7.84 (s, 1H), 7.80-7.77 (d, 1H), 7.67 (s, 1H), 7.64 (s, 1H), 6.87 (s, 2H), 6.30 (d, 1H), 4.51-4.49 (t, 3H), 3.64 (s, 3H), 1.41-1.39 (d, 3H).

MS (ES+): 398.10 (M+1); MS (ES−): 396.4 (M−1).

Step 09: Synthesis of methyl (6-((3-aminobenzyl)amino)-2H-indazole-3-carbonyl)-L-alaninate (12)

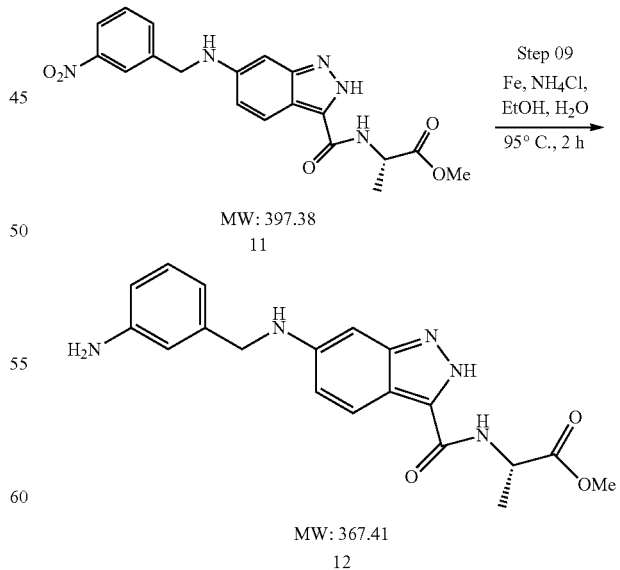

To a stirred solution of methyl (6-((3-nitrobenzyl)amino)-2H-indazole-3-carbonyl)-L-alaninate (11) (780.0 mg, 1.96 mmol, 1.0 equiv) in ethanol (39.0 mL, 50.0 vol. equiv) were added ammonium chloride (525.0 mg, 9.81 mmol, 5.0 equiv), iron powder (548.0 mg, 9.81 mmol, 5.0 equiv) and water (23.4 mL, 30.0 vol. equiv) at RT. The resulting mixture was stirred for 2 h under reflux. The completion of reaction was monitored by TLC (Mf: 10% MeOH in DCM, Rf: 0.5). The reaction mixture was filtered through a celite pad and then filtrate was extracted with ethyl acetate (3×100.0). The combined organic extract was washed with brine (100.0 mL), dried over sodium sulphate and concentrated under vacuum to get crude. The crude was purified with column chromatography eluted with ethyl acetate in n-hexane (0 to 30%) to afford titled compound (650.0 mg, 90.1%) as a brownish solid. $^1$H NMR (300 MHz, DMSO-d$_6$) δ 12.83 (s, 1H), 8.41-8.39 (d, 1H), 8.25 (s, 1H), 7.84 (s, 1H), 7.80-7.77 (d, 1H), 7.67 (s, 1H), 7.64 (s, 1H), 6.87 (s, 2H), 6.30 (d, 1H), 5.05 (s, 2H), 4.51-4.49 (t, 3H), 3.64 (s, 3H), 1.41-1.39 (d, 3H). MS (ES+): 368.4 (M+1); MS (ES−): 366.3 (M−1).

Step 10: Synthesis of methyl (6-((3-(3-(5-methyl-1H-imidazol-1-yl)-5-(trifluoromethyl)benzamido)benzyl)amino)-2H-indazole-3-carbonyl)-L-alaninate (14)

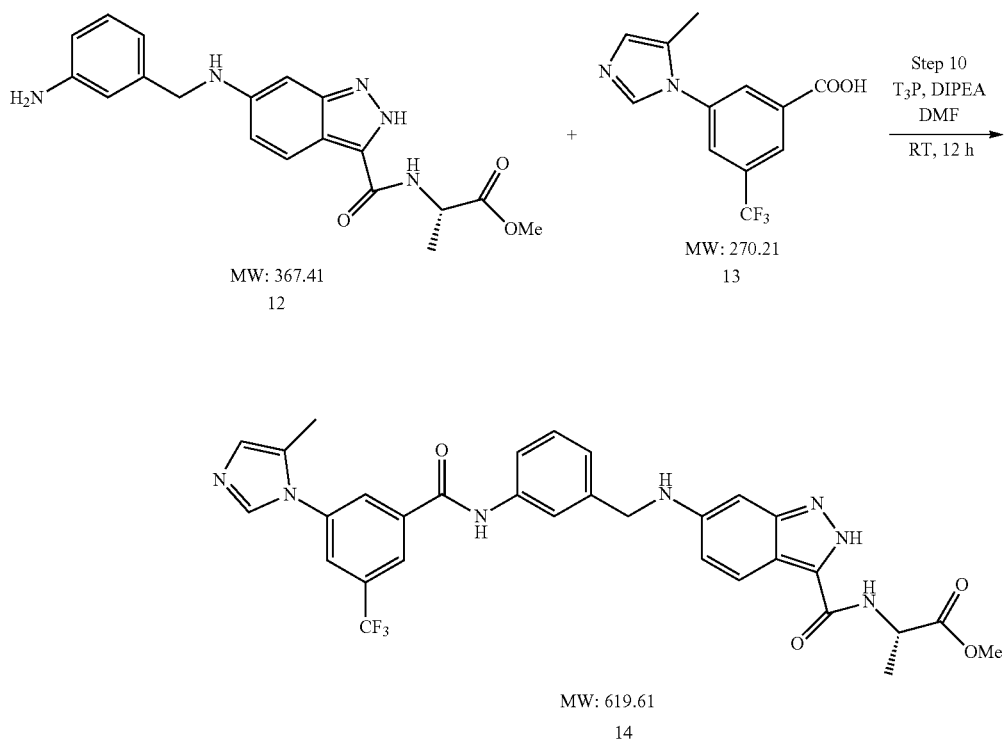

To a stirred solution of 3-(5-methyl-1H-imidazol-1-yl)-5-(trifluoromethyl)benzoic acid (13) (1.02 g, 3.77 mmol, 1.0 equiv) in DMF (45.9 mL, 45.0 vol. equiv) were added methyl (6-((3-aminobenzyl)amino)-2H-indazole-3-carbonyl)-L-alaninate (12) (1.25 g, 3.40 mmol, 0.9 equiv), T$_3$P (6.01 g, 18.9 mmol, 5.0 equiv) and DIPEA (1.95 g, 15.1 mmol, 4.0 equiv) at RT. The resulting mixture was stirred for 12 h at RT. The completion of reaction was monitored by TLC (M.Ph.: 5% MeOH in EtOAC, Rf: 0.6). The reaction mixture was quenched with water and extracted with ethyl acetate (3×100.0 mL). The combined organic extract was washed with brine (100.0 mL), dried over sodium sulphate and concentrated under vacuum to afford titled compound (14) (630.0 mg, 26.9%) as an off white solid. $^1$H NMR (300 MHz, DMSO-d$_6$) δ 12.85-12.84 (d, 1H), 10.52 (s, 1H), 8.42-8.39 (d, 3H), 8.23 (s, 1H), 8.15 (s, 1H), 7.79-7.75 (t, 2H), 7.37 (s, 1H), 7.25-7.19 (m, 2H), 6.76-6.74 (d, 1H), 6.30 (s, 1H), 4.51 (s, 1H), 4.36-4.35 (d, 2H), 3.63 (s, 3H), 2.18 (s, 3H), 1.41-1.39 (d, 3H) MS (ES+): 620.0 (M+1); MS (ES−): 618.30 (M−1).

Step 11: Synthesis of (6-((3-(3-(5-methyl-1H-imidazol-1-yl)-5-(trifluoromethyl)benzamido)benzyl)amino)-2H-indazole-3-carbonyl)-L-alanine (15)

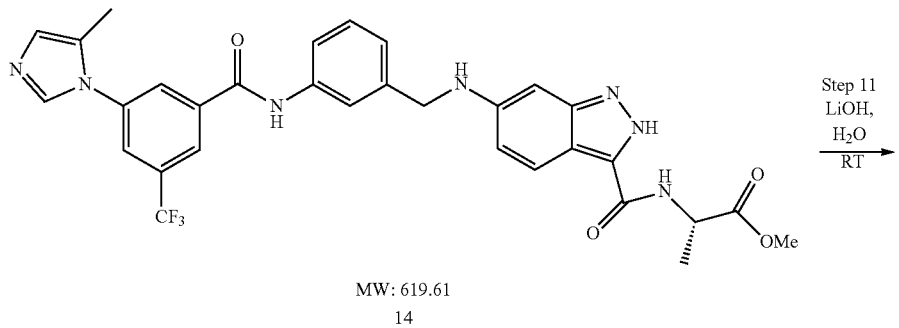

MW: 619.61
14

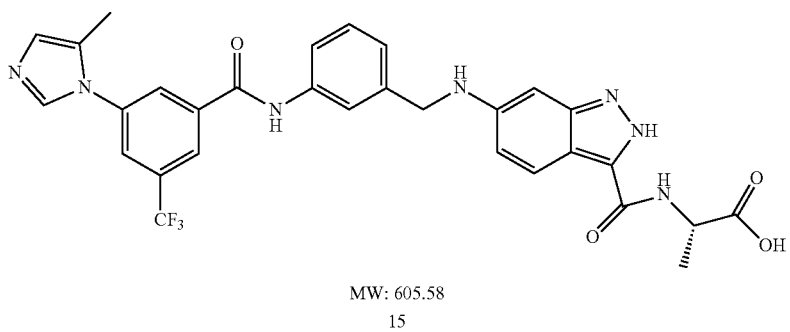

MW: 605.58
15

To a stirred solution of methyl 6-((3-nitrobenzyl)amino)-2H-indazole-3-carboxylate (14) (620.0 mg, 1.0 mmol, 1.0 equiv) in methanol (15.5 mL, 25.0 vol. equiv) were added lithium hydroxide (210.0 mg, 5.0 mmol, 5.0 equiv), water (15.5 mL, 25.0 vol. equiv) at RT. The resulting mixture was stirred for 5 h at 95° C. The completion of reaction was monitored by TLC (M.Ph: 20% MeOH in DCM, Rf: 0.2). The reaction mixture was concentrated under vacuum and the residues was dissolved in water, adjust pH acidic with 2N HCl and cooled to 5° C. then precipitate was filtered to get titled compound (15) (280.0 mg, 46.2%) as a brownish solid. $^1$H NMR (300 MHz, DMSO-$d_6$) δ 12.83 (s, 1H), 10.54 (s, 1H), 8.63 (s, 1H), 8.46 (s, 1H), 8.26-8.13 (m, 3H), 7.79-7.69 (m, 4H), 7.39-7.34 (t, 1H), 7.21-7.19 (d, 1H), 6.76-6.74 (d, 2H), 6.30 (s, 1H), 4.46-4.36 (m, 3H), 2.21 (s, 3H), 1.45-1.38 (t, 3H). MS (ES+): 606 (M+1); MS (ES−): 604.3 (M−1).

Step 11A: Synthesis of (S)—N-(1-amino-1-oxopropan-2-yl)-6-((3-(3-(5-methyl-1H-imidazol-1-yl)-5-(trifluoromethyl)benzamido)benzyl)amino)-2H-indazole-3-carboxamide (15A)

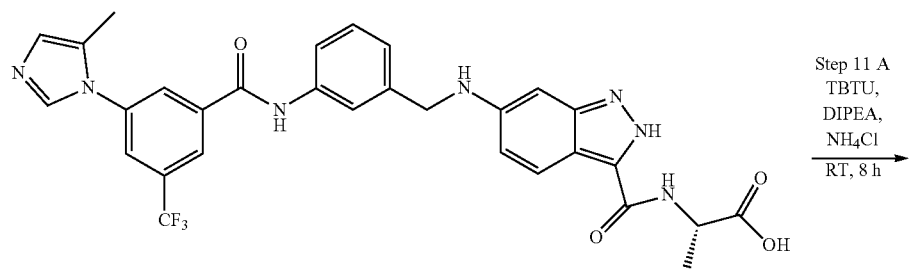

MW: 605.58
15

-continued

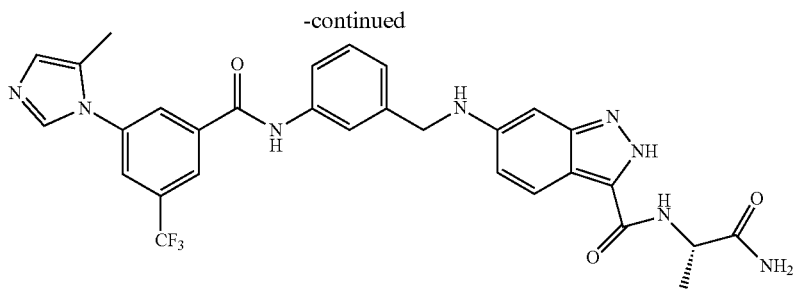

MW: 604.59
15 A

To a stirred solution of (6-((3-(3-(5-methyl-1H-imidazol-1-yl)-5-(trifluoromethyl)-benzamido)benzyl)amino)-2H-indazole-3-carbonyl)-L-alanine (15) (100 mg, 0.16 mmol, 1.0 equiv) in DMF (2.50 mL, 25.0 vol. equiv.) were added ammonium chloride (26.50 mg, 0.49 mmol, 3.0 equiv), TBTU (106 mg, 0.33 mmol, 2.0 equiv) and DIPEA (63.90 mg, 0.49 mmol, 3.0 equiv). The reaction mixture was stirred for 8 h at RT. Completion of reaction was monitored by TLC. The Reaction mixture was quenched with DMW (100 mL) and extracted with EtOAc (100 mL×5). The combine organic extract was washed with brine (200 mL), dried over $Na_2SO_4$ and concentrated under vacuum to get crude of desired compound. The crude was purified with column chromatography eluted with methanol in DCM (0 to 20%) to afford titled compound (15 A) (60 mg, 70.10%) as a light orange solid. $^1$H NMR (300 MHz, DMSO-$d_6$) δ 12.80 (s, 1H), 10.53 (s, 1H), 8.45-8.43 (m, 2H), 8.20 (s, 1H), 8.00-7.90 (m, 2H), 7.80-7.70 (m, 5H), 7.55 (s, 1H), 7.44-7.40 (d, 2H), 7.10 (s, 2H), 6.80 (s, 1H), 4.30 (m, 3H), 2.20 (s, 3H), 1.10 (s, 3H). MS (ES+): 605 (M+1); MS (ES−): 603.2 (M−1).

Step 12: Synthesis of 3-(5-methyl-1H-imidazol-1-yl)-5-(trifluoromethyl)benzonitrile (13C)

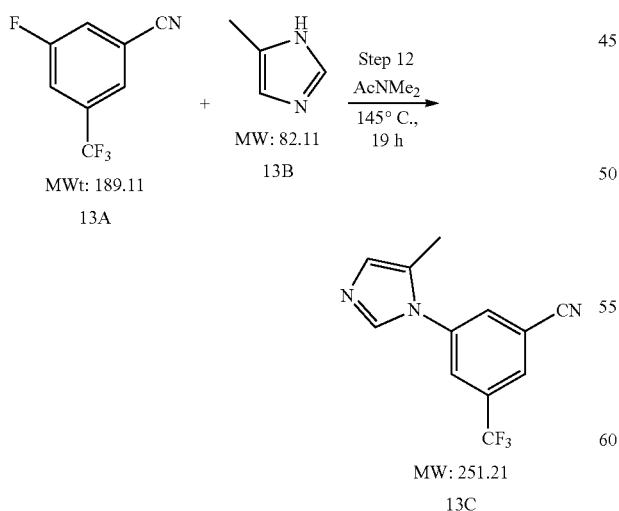

To a stirred solution of 3-fluoro-5-(trifluoromethyl)benzonitrile (13A) (10.0 g, 52.9 mmol, 1.0 equiv) in N,N-dimethylacetamide (50.0 mL, 5.0 vol. equiv) was added 5-methyl-1H-imidazole (13B) (13.5 g, 164.0 mmol, 3.1 equiv) at RT. The resulting mixture was stirred for 3 h at 145° C. The completion of reaction was monitored by TLC. The reaction mixture was quenched with water and extracted with ethyl acetate (3×200.0). The combined organic extract was washed with brine (200.0 mL), dried over sodium sulphate and concentrated under vacuum to get crude. The crude was purified with column chromatography eluted with ethyl acetate in n-hexane (0 to 40%) to afford titled compound (13C) (12.7 g, 95.6%) as an off white solid. $^1$H NMR (300 MHz, DMSO-$d_6$) δ 8.28-8.24 (t, 3H), 8.05-7.99 (d, 2H), 2.49-2.37 (m, 3H). MS (ES+): 252.2 (M+1); MS (ES−): 250.4 (M−1).

Step 13: Synthesis of 3-(5-methyl-1H-imidazol-1-yl)-5-(trifluoromethyl)benzonitrile (13C)

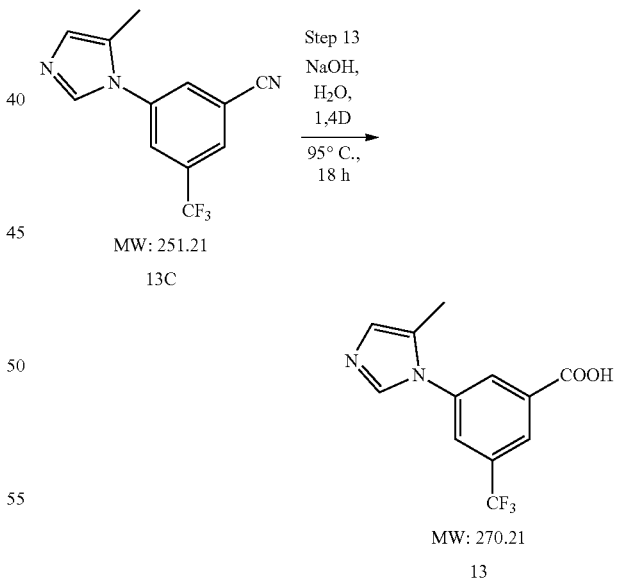

To a stirred solution of 3-(5-methyl-1H-imidazol-1-yl)-5-(trifluoromethyl)benzonitrile (13C) (12.6 g, 50.2 mmol, 1.0 equiv) in 1,4-dioxane (252.0 mL, 20.0 vol. equiv) was added a solution of sodium hydroxide (10.0 g, 251.0 mmol, 5.0 equiv) in water (315.0 mL, 25.0 vol. equiv) at RT. The resulting mixture was stirred for 15 h at 95° C. The completion of reaction was monitored by TLC. The reaction mixture was concentrated under vacuum and the residue was dissolved in water, adjust pH acidic with 2N HCl and extracted with ethyl acetate (3×150.0 mL). The combined organic extract was washed with brine (150.0 mL), dried over sodium sulphate and concentrated under vacuum to afford titled compound (13) (6.45 g, 47.6%) as an off white solid. $^1$H NMR (300 MHz, DMSO-d$_6$) δ 8.28-8.24 (t, 3H), 8.05-7.99 (d, 2H), 7.59 (s, 1H), 2.49-2.37 (m, 3H). MS (ES+): 271 (M+1); MS (ES−): 269.3 (M−1).

Step 14: Synthesis of tert-butyl (S)-3-methyl-1-(6-((3-(3-(5-methyl-1H-imidazol-1-yl)-5-(trifluoromethyl)benzamido)benzyl)amino)-2H-indazol-3-yl)-1,4-dioxo-8,11-dioxa-2,5-diazatetradecan-14-oate (17)

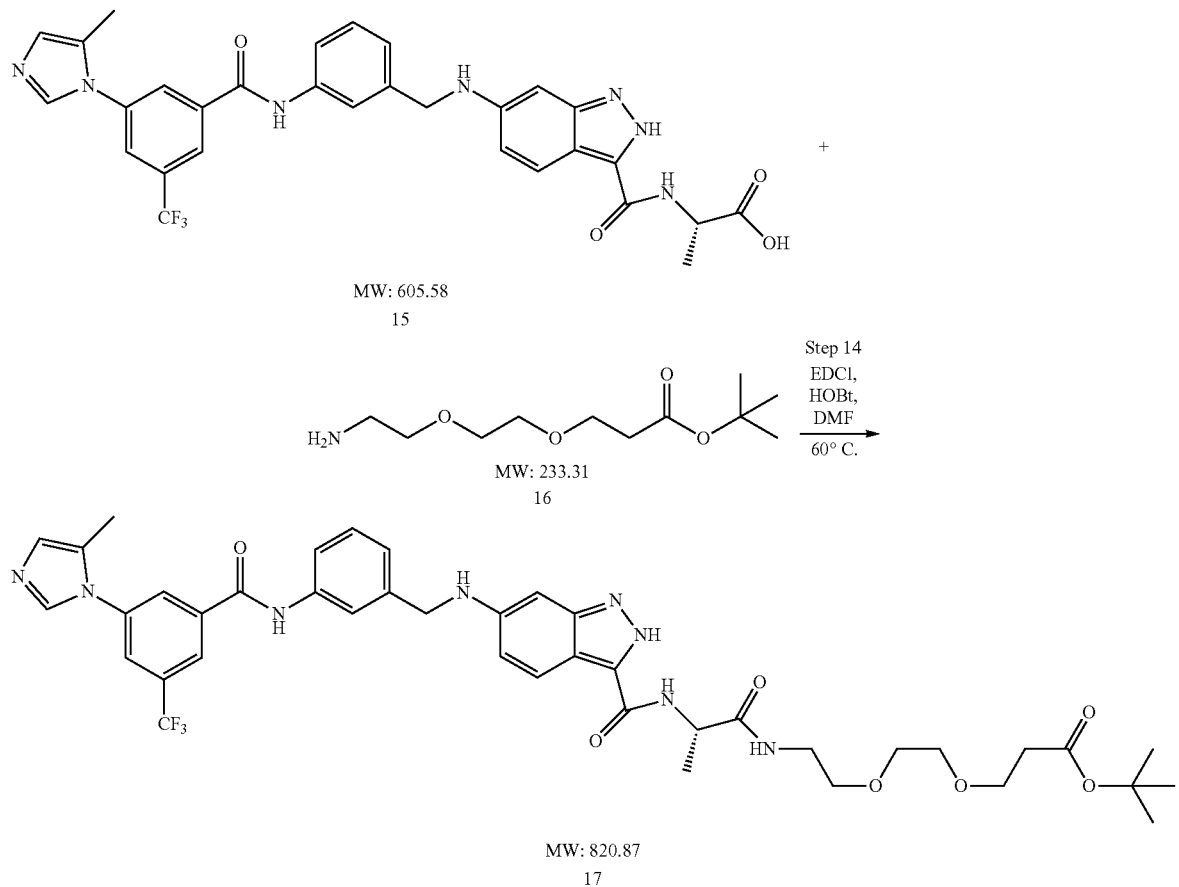

To a stirred solution of (6-((3-(3-(5-methyl-1H-imidazol-1-yl)-5-(trifluoromethyl)benzamido)benzyl)amino)-2H-indazole-3-carbonyl)-L-alanine (16) (170 mg, 0.28 mmol, 1.0 equiv) in DMF (6.8.0 mL, 40.0 vol. equiv) were added tert-butyl 3-(2-(2-aminoethoxy)ethoxy)propanoate (16) (78.60 mg, 0.34 mmol, 1.2 equiv), HATU (320 mg, 0.84 mmol, 3.0 equiv) and DIPEA (43.5 mg, 0.34 mmol, 1.20 equiv). The reaction mixture was stirred for 4 h at RT. The completion of reaction was monitored by TLC. The Reaction mixture was quenched with DMW (100 mL) and extracted with EtOAc (100 mL×3). The combined organic extract was washed with brine (100 mL), dried over Na$_2$SO$_4$ and concentrated under vacuum to get crude of desired compound. The crude was purified with column chromatography eluted with methanol in DCM (0 to 10%) to afford titled compound (17) (220 mg, 95.5%) as a light brown gum. $^1$H NMR (300 MHz, DMSO-d$_6$) δ 12.90 (s, 1H), 10.59 (s, 1H), 8.68 (s, 1H), 8.46 (s, 1H), 8.32-8.16 (m, 4H), 7.79-7.69 (m, 4H), 7.39-7.34 (t, 1H), 7.21-7.19 (d, 1H), 6.76-6.8 (s, 2H), 6.35 (s, 1H), 4.46-4.36 (m, 3H), 4.12-4.00 (t, 2H), 3.63-3.41 (m, 8H), 2.94 (s, 2H) 2.21 (s, 3H), 1.45-1.38 (m, 12H). MS (ES+): 821.3 (M+1); MS (ES−): 819.5 (M−1).

Step 15: Synthesis of S)-3-methyl-1-(6-((3-(3-(5-methyl-1H-imidazol-1-yl)-5-(trifluoromethyl)benzamido)benzyl)amino)-2H-indazol-3-yl)-1,4-dioxo-8,11-dioxa-2,5-diazatetradecan-14-oic acid (18)

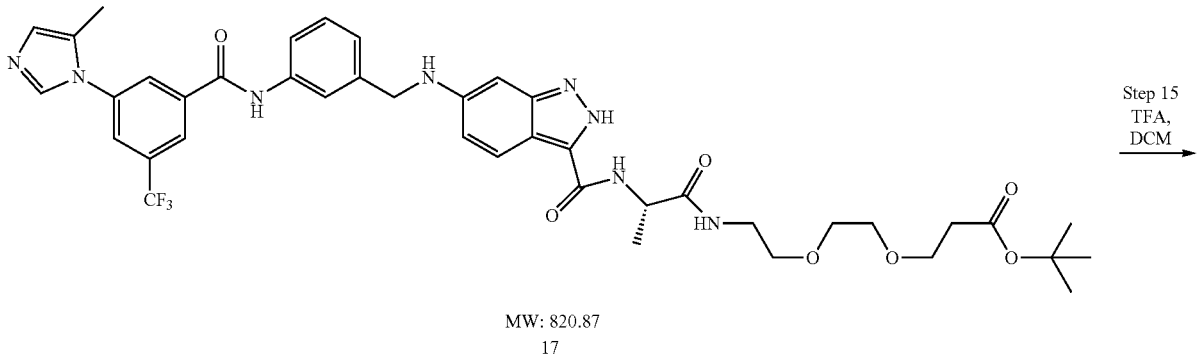

MW: 820.87
17

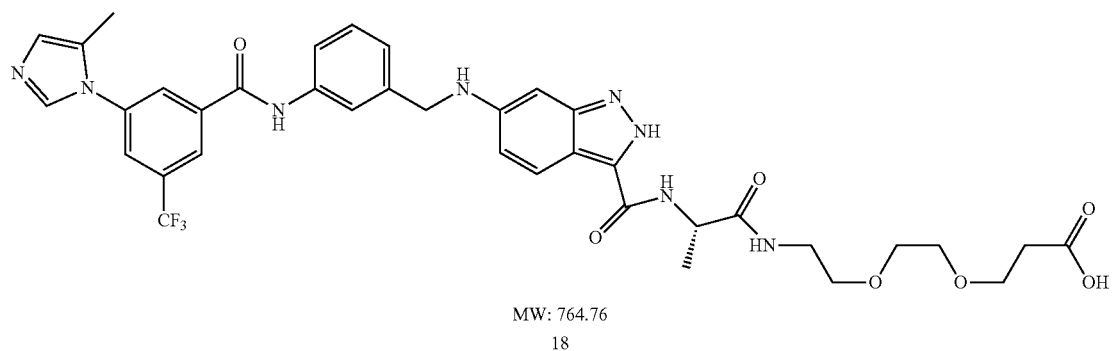

MW: 764.76
18

To a stirred solution of tert-butyl (S)-3-methyl-1-(6-((3-(3-(5-methyl-1H-imidazol-1-yl)-5-(trifluoromethyl)benzamido)benzyl)amino)-2H-indazol-3-yl)-1,4-dioxo-8,12-dioxa-2,5-diazatetradecan-14-oate (17) (220 mg, 0.27 mmol, 1.0 equiv) in DCM (4.40 mL, 20.0 vol. equiv.) and pour in cooled trifluoroacetic acid (4.40 mL, 20 vol. equiv.). The reaction mixture was stirred for 4 h at RT. Completion of reaction was monitored by TLC. The Reaction mixture was taken and concentrated under vacuum to afford titled compound (18) (160 mg, 78.10%) as a brown solid. $^1$H NMR (300 MHz, DMSO-$d_6$) δ 12.80 (s, 1H), 10.55 (s, 1H), 8.62 (s, 1H), 8.43 (s, 1H), 8.29-8.14 (m, 4H), 7.78-7.69 (m, 4H), 7.39-7.34 (t, 1H), 7.21-7.19 (d, 1H), 6.76-6.8 (m, 2H), 6.35 (s, 1H), 4.46-4.36 (m, 3H), 4.12-4.00 (t, 2H), 3.63-3.41 (m, 8H), 2.94 (s, 2H) 2.21 (s, 3H), 1.45-1.38 (t, 3H). MS (ES+): 764.9 (M+1); MS (ES−): 763.2 (M−1).

Step 16: Synthesis of N-((2S,15R)-15-((2S,4R)-4-hydroxy-2-(((S)-1-(4-(4-methylthiazol-5-yl)phenyl)ethyl)carbamoyl)pyrrolidine-1-carbonyl)-16,16-dimethyl-3,13-dioxo-7,10-dioxa-4,14-diazaheptadecan-2-yl)-6-((3-(3-(5-methyl-1H-imidazol-1-yl)-5-(trifluoromethyl)benzamido)benzyl)amino)-2H-indazole-3-carboxamide (20)

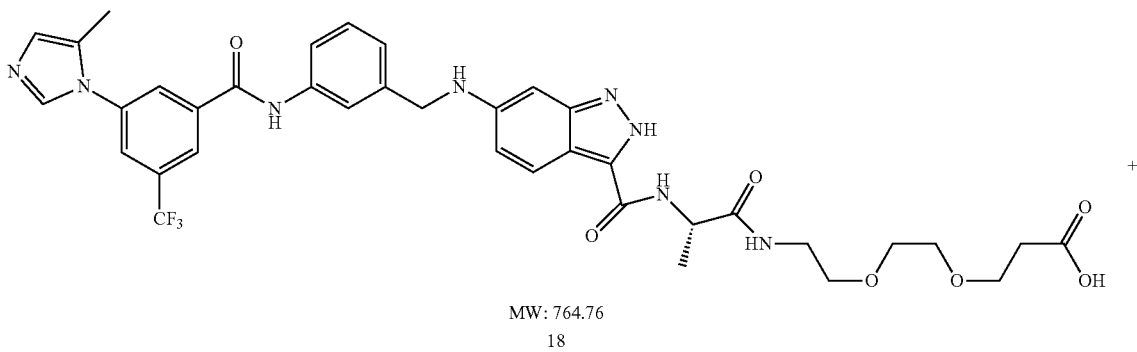

MW: 764.76
18

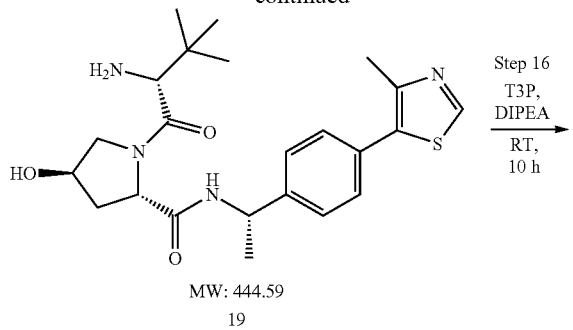

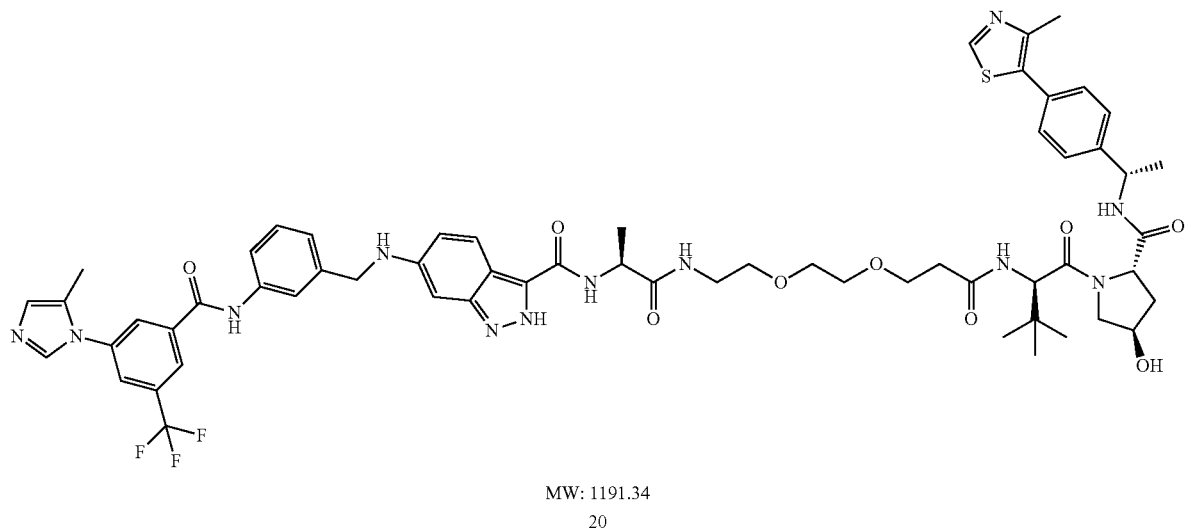

To a stirred solution of (S)-3-methyl-1-(6-((3-(3-(5-methyl-1H-imidazol-1-yl)-5-(trifluoromethyl)benzamido)benzyl)amino)-2H-indazol-3-yl)-1,4-dioxo-8,12-dioxa-2,5-diazatetradecan-14-oic acid (18) (120 mg, 0.03 mmol, 1.0 equiv) in DMF (4.80 mL, 40.0 vol. equiv.) were added (2S,4R)-1-((R)-2-amino-3,3-dimethylbutanoyl)-4-hydroxy-N—((S)-1-(4-(4-methylthiazol-5-yl)phenyl)ethyl)pyrrolidine-2-carboxamide (91.10 mg, 0.119 mmol, 1.20 equiv), T$_3$P (189.0 mg, 0.59 mmol, 3.0 equiv) and DIPEA (128 mg, 0.99 mmol, 10.0 equiv). The reaction mixture was stirred for 12 h at RT. Completion of reaction was monitored by TLC. The reaction mixture was quenched with DMW (50 mL) and extracted with EtOAc (150 mL×3). The combined organic extract was washed with brine (150 mL), dried over Na$_2$SO$_4$ and concentrated under vacuum to get crude. The crude was purified with column chromatography eluted with methanol in DCM (0 to 10%) to afford titled compound (20) (45 mg, 38.10%) as a light orange solid. $^1$H NMR (300 MHz, DMSO-d$_6$) δ 12.84 (s, 1H), 10.56 (s, 1H), 8.98 (s, 1H), 8.44-8.40 (d, 3H), 8.23 (d, 2H), 8.15 (d, 1H), 7.80-7.76 (t, 4H), 7.70 (s, 2H), 7.43-7.35 (m, 5H), 7.20 (s, 1H), 6.76-6.74 (d, 2H), 6.29 (s, 1H), 5.12-5.11 (d, 1H), 4.51 (s, 1H), 4.42 (s, 2H), 4.36-4.34 (d, 4H), 3.59-3.57 (d, 4H), 3.47-3.39 (m, 4H), 3.24-3.15 (m, 3H), 2.85 (d, 2H), 2.78-2.72 (s, 3H), 2.45 (s, 3H), 2.25 (s, 3H), 1.68 (m, 2H), 1.45-1.40 (m, 6H), 1.20-1.15 (s, 3H), 1.10 (d, 3H). MS (ES+): 1191.2 (M+1); MS (ES−): 1189.4 (M−1).

Example 7—Synthesis of N-(4-(2-(2-(2-(2-((2-(2,6-dioxopiperidin-3-yl)-1,3-dioxoisoindolin-4-yl)amino)ethoxy)ethoxy)ethoxy)ethoxy)phenyl)-4-(4-(3-(3-(trifluoromethyl)phenyl)-ureido)phenoxy)picolinamide

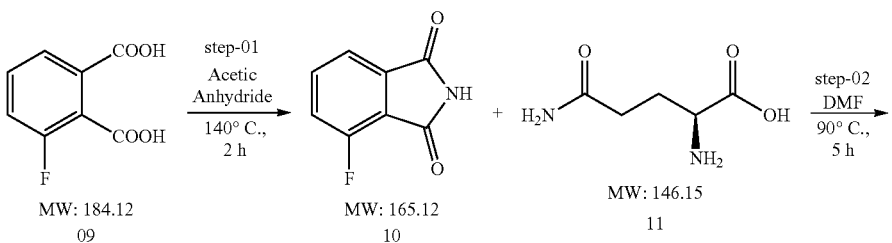

-continued
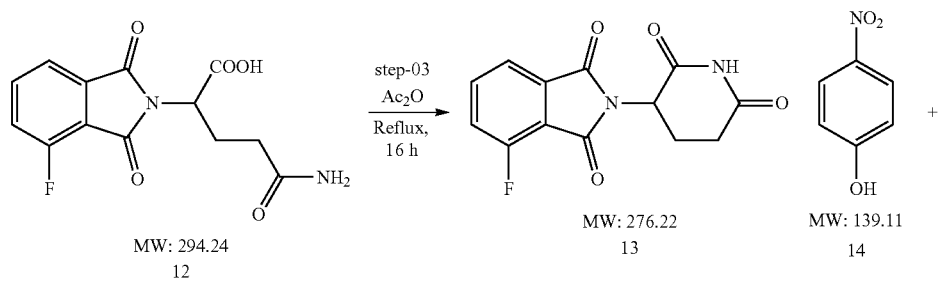
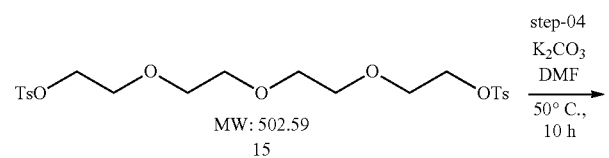
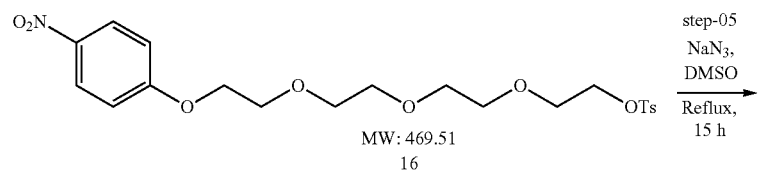
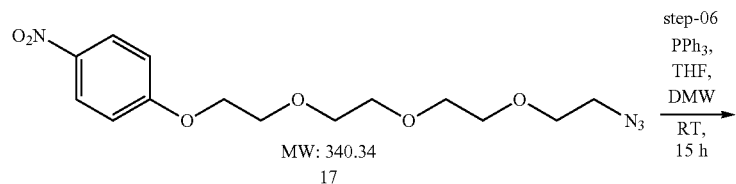
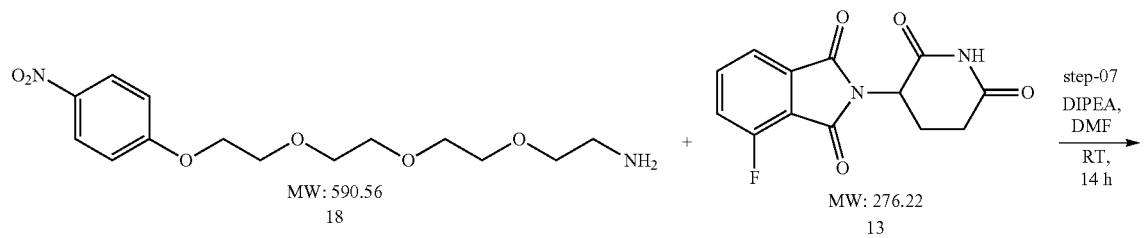
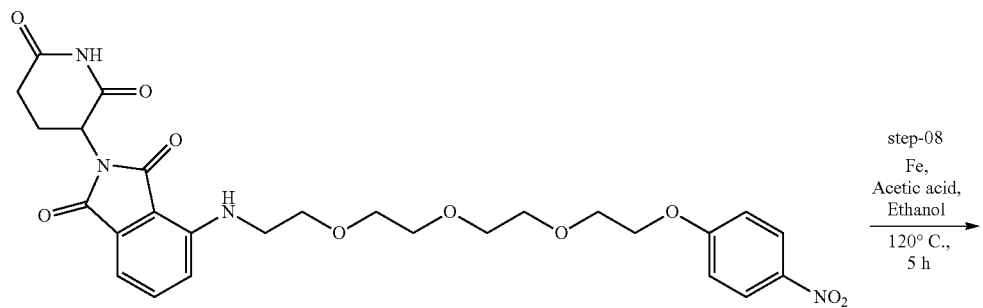

-continued

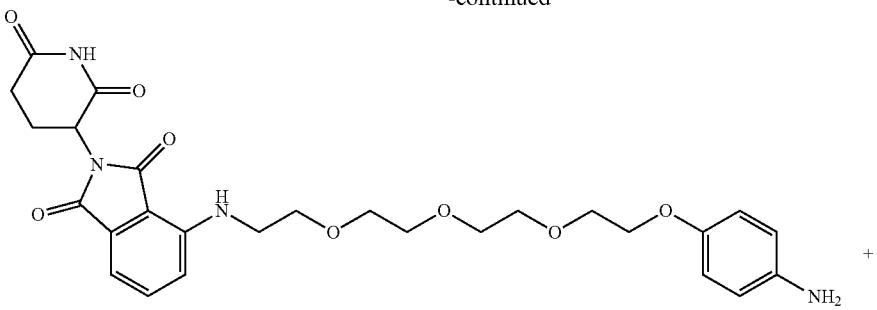

MW: 540.57
20

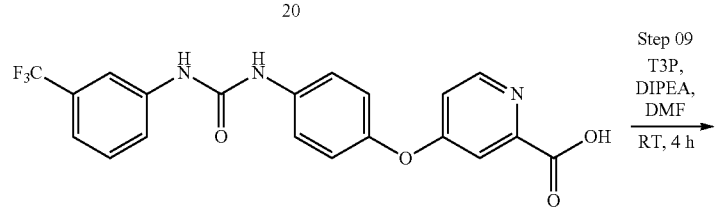

MW: 417.34
08

Step 09
T3P,
DIPEA,
DMF
RT, 4 h

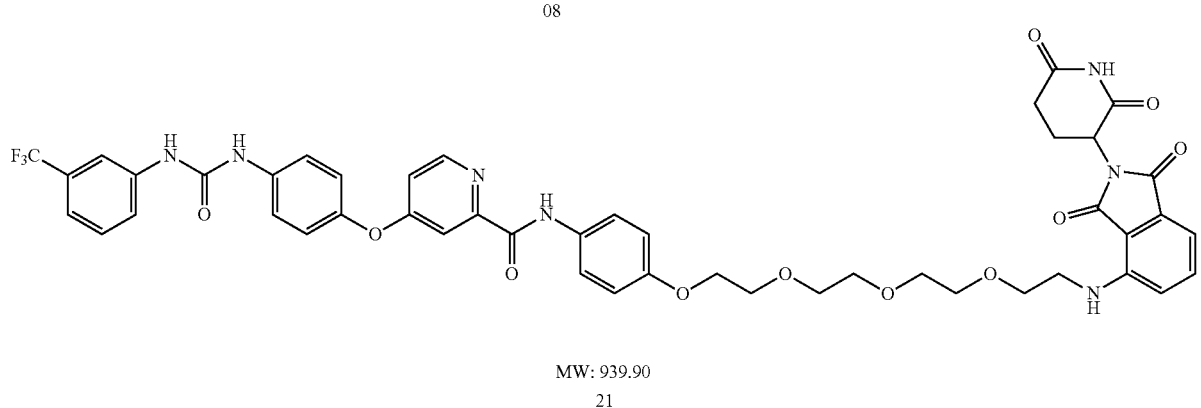

MW: 939.90
21

Step 01: Synthesis of 4-fluoroisoindoline-1,3-dione (10)

Step 02: Synthesis of 5-amino-2-(4-fluoro-1,3-dioxoisoindolin-2-yl)-5-oxopentanoic Acid

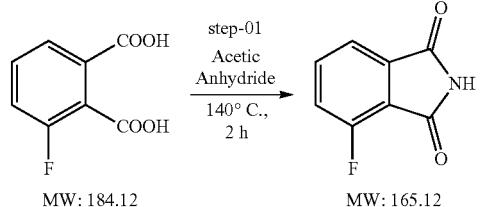 [SMILES: O=C(O)c1cccc(F)c1C(=O)O ; O=C1NC(=O)c2c(F)cccc21]

MW: 184.12   MW: 165.12

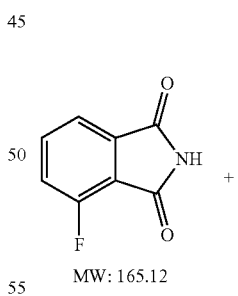

MW: 165.12

To a stirred solution of 3-fluorophthalic acid (10.0 g, 54.3 mmol, 1.0 equiv) in acetic anhydride (40 mL, 4.0 vol. equiv), stirred the resulting mixture for 2 h at 140°. Completion of reaction was monitored by TLC. The volatiles were removed by vacuum, and the residues were crystallized in acetic anhydride to afford titled compound (5.10 g, 56.5%) as an off white solid. $^1$H NMR (300 MHz, DMSO-d$_6$) δ 8.07-8.01 (m, 1H), 7.94-7.88 (t, 1H), 7.85-7.82 (d, 1H), 7.59-7.54 (m, 1H). MS (ES+): 167.10 (M+1); MS (ES−): −(M−1).

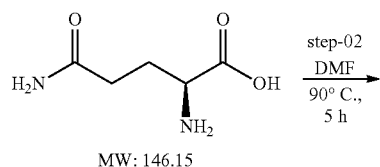

MW: 146.15 step-02
DMF
90° C.,
5 h

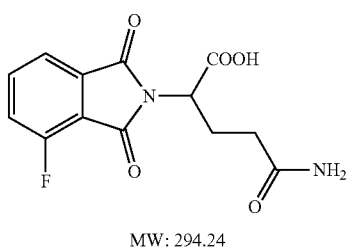

MW: 294.24

To a stirred solution of 4-fluoroisobenzofuran-1,3-dione (5.0 g, 30.10 mmol, 1.0 equiv) in DMF (25.0 mL, 5.0 vol. equiv), added L-glutamine (4.40 g, 30.1 mmol, 1.0 equiv), stirred the resulting mixture for 8 h at 90°. Completion of reaction was monitored by TLC. The solvent was removed under reduced pressure. The residue was re-dissolved in 4N HCl (200 mL) and stirred for additional 8 h. The resulting precipitation was collected by filtration, washed with water, and dried to afford titled compound (5.70 g, 64.40%) as an off white solid. $^1$H NMR (300 MHz, DMSO-$d_6$) δ 7.99-7.90 (s, 1H), 7.8-7.65 (m, 2H), 4.86-4.71 (m, 1H), 2.40-2.25 (m, 4H), 3.40 (br, 3H). MS (ES+): 295.9 (M+1); MS (ES−): 294.1 (M−1).

Step 03: Synthesis of 2-(2,6-dioxopiperidin-3-yl)-4-fluoroisoindoline-1,3-dione (13)

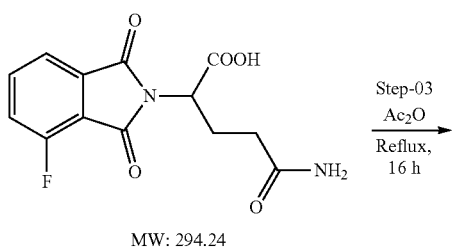

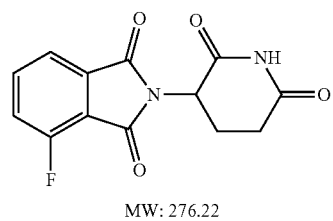

MW: 276.22

To a stirred solution of 5-amino-2-(4-fluoro-1,3-dioxoisoindolin-2-yl)-5-oxopentanoic acid (5.60 g, 19.0 mmol, 1.0 equiv) in acetic anhydride (44.80 mL, 8.0 vol. equiv), stirred the resulting mixture for 4 h at 140°. Completion of reaction was monitored by TLC. The resulting solid was collected by filtration, and washed with acetonitrile (100 mL) to afford the crude product, which was purified by silica gel chromatography using 1-10% of MeOH in DCM as an eluent to afford titled compound (1.65 g, 31.40%) as a light yellow solid. $^1$H NMR (300 MHz, DMSO-$d_6$) δ 11.16 (s, 1H), 7.96-7.91 (m, 1H), 7.80-7.71 (m, 2H), 5.19-5.13 (m, 1H), 2.90-2.70 (m, 1H), 2.63 (s, 1H), 2.57-2.49 (m, 1H), 2.19 (m, 1H). MS (ES+): 276.90 (M+1); MS (ES−): 275.3 (M−1).

Step 04: Synthesis of 2-(2-(2-(2-(4-nitrophenoxy)ethoxy)ethoxy)ethoxy)ethyl 4-methylbenzenesulfonate (16)

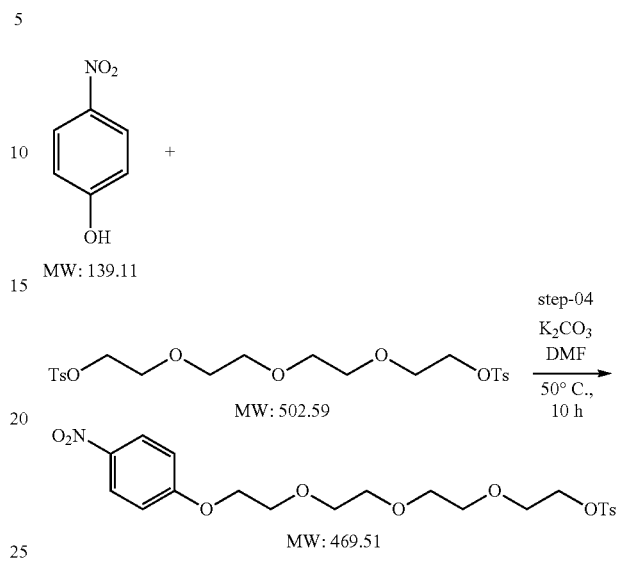

To a stirred solution of ((oxybis(ethane-2,1-diyl))bis(oxy))bis(ethane-2,1-diyl) bis(4-methylbenzenesulfonate) (7.0 g, 13.90 mmol, 1.0 equiv) in DMF (49 mL, 7.0 vol. equiv), 4-nitrophenol (1.94 g, 13.90 mmol, 1.00 equiv) and potassium carbonate (4.81 g, 34.80 mmol, 2.50 equiv), stirred the resulting mixture for 12 h at 50° C. Completion of reaction was monitored by TLC. The mixture was cooled to room temperature and poured into water (100 mL), then extracted with ethyl acetate (100 mL×3). The combined organic phases were washed with water (150 mL) and brine (150 mL), dried over anhydrous sodium sulfate, and concentrated under reduced pressure to afford titled compound (6.45 g, 98.60%) as a light yellow oil. $^1$H NMR (300 MHz, DMSO-$d_6$) δ 8.18-8.16 (t, 2H), 7.79-7.76 (d, 2H), 7.48-7.45 (d, 2H), 7.17-7.12 (m, 2H), 4.26-4.22 (m, 2H), 4.11-4.01 (m, 2H), 3.78-3.75 (t, 2H), 3.59-3.42 (m, 10H), 1.25 (s, 3H).

Step 05: Synthesis of 1-(2-(2-(2-(2-azidoethoxy)ethoxy)ethoxy)ethoxy)-4-nitrobenzene (17)

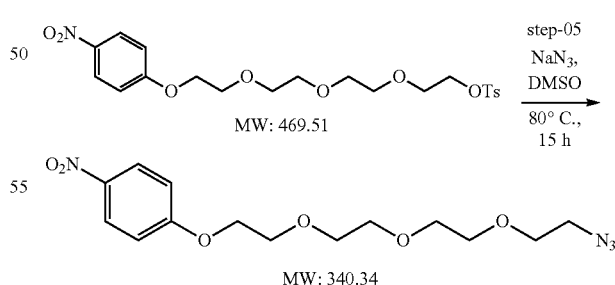

To a stirred solution of 2-(2-(2-(2-(4-nitrophenoxy)ethoxy)ethoxy)ethoxy)ethyl 4-methylbenzenesulfonate (4.50 g, 9.58 mol, 1.0 eqv.) in DMSO (34.0 mL, 7.5 vol.) was added NaN$_3$ (2.18 g, 33.5 mmol, 3.50 eqv.). The resulting mixture was stirred for 4.0 h at 80° C. TLC was checked to ensure the completion of reaction (Elution: 60% EtOAc in n-hexane). The reaction mass was quenched with water (250.0 mL) and extracted with EtOAc (3×150 L). The combined organic extract was washed with water (2×100 mL), brine (200 mL) and dried over sodium sulphate. The solvent was concentrated to dryness to afford desired compound (3.10 g, 95%) as an oily mass. $^1$H NMR (300 MHz, DMSO-$d_6$) δ 8.21-8.16 (m, 2H), 7.17-7.12 (m, 2H), 4.26-4.22 (t, 2H), 3.79-3.75 (m, 2H), 3.61-3.50 (m, 10H), 3.40-3.34 (m, 2H). MS (ES+): 341 (M+1); MS (ES−): 339.4 (M−1).

Step 06: Synthesis of 2-(2-(2-(2-(4-nitrophenoxy)ethoxy)ethoxy)ethoxy)ethan-1-amine (18)

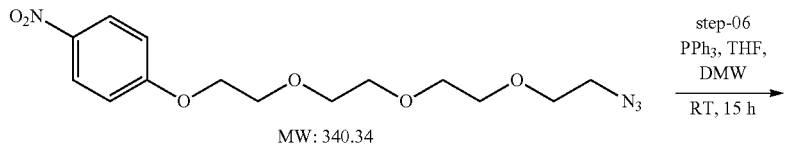

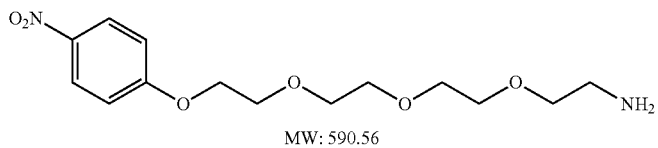

To a stirred solution of 1-(2-(2-(2-(2-azidoethoxy)ethoxy)ethoxy)ethoxy)-4-nitrobenzene (3.10 g, 9.11 mmol, 1.0 equiv) in THF (37.20 mL, 12.0 vol. equiv), were added triphenyl phosphine (4.78 g, 18.20 mmol, 2.00 equiv), DMW (9.30 mL, 3.0 vol. equiv) stirred the resulting mixture for 3.0 h at RT. Completion of reaction was monitored by TLC. The solvent (THF) was removed under vacuum and diluted with water (100.0 mL). The pH was adjusted to 2 by adding 6N HCl (40 mL). The solid (triphenyl phosphine & triphenyl phosphate) was removed by filtration. The filtrated was basified by using 10% NaOH (40 mL) and extracted by EtOAc (2×250 mL). The combined organic extract was washed with brine (150 mL) and dried over sodium sulphate. The solvent was concentrated to dryness to afford desired compound crude. The crude was purified through column chromatography with using elution of solvents: 0-5% MeOH in DCM to afford the titled compound (980 mg, 34.20%) as a light brown gum. $^1$H NMR (300 MHz, DMSO-$d_6$) δ 8.10 (s, 2H), 6.94-6.89 (m, 2H), 4.17-4.14 (t, 2H), 3.84-3.81 (t, 2H), 3.85-3.52 (m, 12H), 1.90 (t, 2H). MS (ES+): 315.1 (M+1).

Step 07: Synthesis of 2-(2,6-dioxopiperidin-3-yl)-4-((2-(2-(2-(2-(4-nitrophenoxy)ethoxy)ethoxy)ethoxy)ethyl)amino)isoindoline-1,3-dione (19)

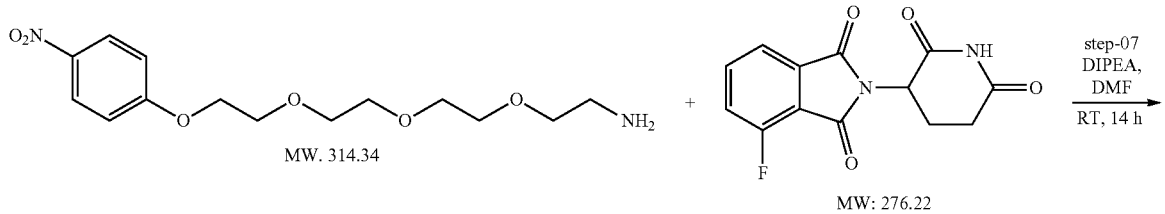

-continued

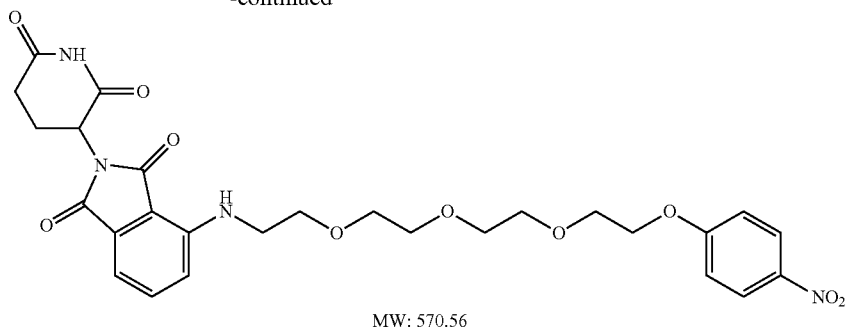

MW: 570.56

To a stirred solution of 2-(2-(2-(2-(4-nitrophenoxy)ethoxy)ethoxy)ethoxy)ethan-1-amine (1.20 g, 4.32 mmol, 1.0 equiv) in DMF (24.0 mL, 20.0 vol. equiv), were added 2-(2,6-dioxopiperidin-3-yl)-4-fluoroisoindoline-1,3-dione (1.05 g, 3.82 mmol, 1.00 equiv), DIPEA (1.23 g, 9.54 mmol, 2.50 equiv), stirred the resulting mixture at 90° C. for 12 h. Completion of reaction was monitored by TLC. Now the reaction mixture cooled at RT then added DMW (100 mL) and extracted by EtOAc (2×250 mL). The organic extract was taken and washed with brine (200 mL) and dried over sodium sulphate. The solvent was concentrated to dryness to afford the desired compound through column chromatography with using elution of 30-100% ethyl acetate in n-hexane (0.83 g, 38.10%) as an oily greenish mass. $^1$H NMR (300 MHz, DMSO-$d_6$) δ NMR was not clear. MS (ES+): 571.1 (M+1); MS (ES−): 569.3 (M−1).

Step 08: Synthesis of 4-((2-(2-(2-(2-(4-aminophenoxy)ethoxy)ethoxy)ethoxy)ethyl)amino)-2-(2,6-dioxopiperidin-3-yl)isoindoline-1,3-dione (20)

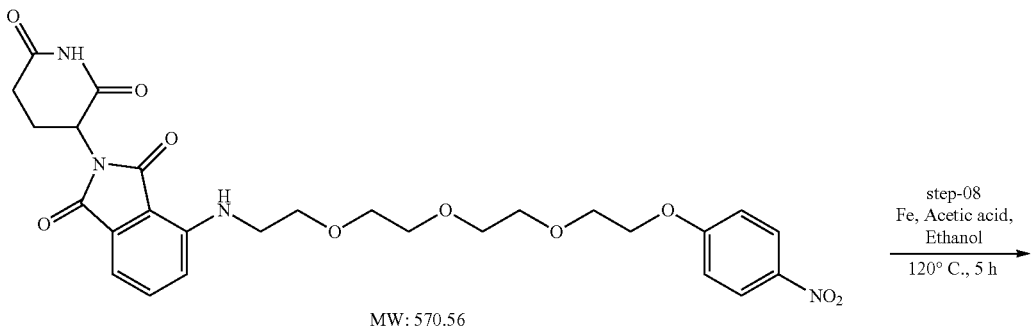

MW: 570.56 step-08
Fe, Acetic acid,
Ethanol
120° C., 5 h

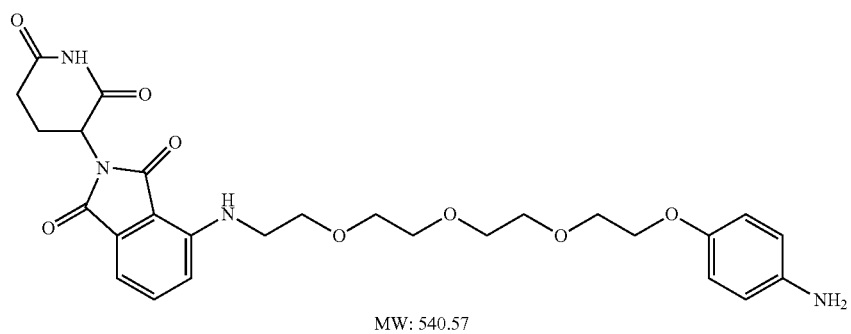

MW: 540.57

To a stirred solution of 2-(2-(2-(2-(4-nitrophenoxy)ethoxy)ethoxy)ethoxy)ethan-1-amine (820 mg, 1.44 mmol, 1.0 equiv) in acetic acid (16.40 mL, 20.0 vol. equiv) were added iron (281 mg, 5.03 mmol, 3.50 equiv), ethanol (16.40 mL, 20.0 volEquiv) and DMW (8.20 mg, 10.0 volEquiv), stirred the resulting mixture at 100° C. for 12 h. Completion of reaction was monitored by TLC. The reaction mixture cooled at RT then added DMW (100 mL) and extracted by EtOAc (3×150 mL). The organic extract was washed with brine (100 mL) and dried over sodium sulphate. The solvent was concentrated to dryness to afford the desired compound (590 mg, 75.90%) as an oily mass. $^1$H NMR (300 MHz, DMSO-$d_6$) δ 11.10 (s, 1H), 7.62-7.55 (m, 3H), 7.14-7.02 (m, 1H), 7.04-7.02 (d, 1H), 6.64-6.61 (d, 2H), 6.49-6.47 (d, 2H), 5.08-5.02 (m, 1H), 4.61 (s, 1H), 4.06-4.00 (m, 2H), 3.90 (s, 1H), 3.64-3.59 (m, 5H), 3.56-3.45 (m, 10H), 2.92 (s, 1H). MS (ES+): 541.3 (M+1); MS (ES−): 539.2 (M−1).

Step 09: Synthesis of N-(4-(2-(2-(2-(2-((2-(2,6-dioxopiperidin-3-yl)-1,3-dioxoisoindolin-4-yl)amino)ethoxy)ethoxy)ethoxy)ethoxy)phenyl)-4-(4-(3-(3-(trifluoromethyl)phenyl)-ureido)phenoxy)picolinamide (21)

ethoxy)ethyl)amino)-2-(2,6-dioxopiperidin-3-yl)isoindoline-1,3-dione (287.0 mg, 0.53 mmol, 1.2 equiv), T$_3$P (423 mg, 1.33 mmol, 3.0 equiv) and DIPEA (68.5 mg, 0.53 mmol, 1.20 equiv). The reaction mixture was stirred for 12 h at RT. Completion of reaction was monitored by TLC. The Reaction mixture was quenched with DMW (100 mL) and extracted with EtOAc (150 mL×3). Reaction extract was washed with brine (150 mL), dried over Na$_2$SO$_4$ and concentrated under vacuum to get crude. The crude was purified through column chromatography with using elution of 0-4% MeOH in DCM to afford the titled compound (180 mg, 41.70%) as a yellow solid. $^1$H NMR (300 MHz, DMSO-$d_6$) δ 11.10 (s, 1H), 10.53 (s, 1H), 9.29 (s, 1H), 9.08 (s, 1H), 8.60-8.58 (d, 1H), 8.13 (s, 1H), 7.78-7.75 (d, 2H), 7.78-7.58 (m, 5H), 7.49-7.45 (d, 1H), 7.22-7.19 (t, 3H), 7.13-7.10 (d, 1H), 7.03-7.01 (d, 1H), 6.92 (s, 2H), 6.61-6.59 (d, 1H) 5.10 (m, 1H), 4.53-4.50 (t, 1H), 4.41 (s, 2H), 3.58-3.50 (m, 12H), 2.88 (s, 2H), 2.72 (s, 2H), 2.59 (s, 1H). MS (ES+): 973.8 (M+1); MS (ES−): 972.1 (M−1). HPLC: 91.27%.

The following examples describe (1) the preparation of Ligands for RAF with a segment of the Linker Component, (2) the preparation of Degradation Signaling Agents with a

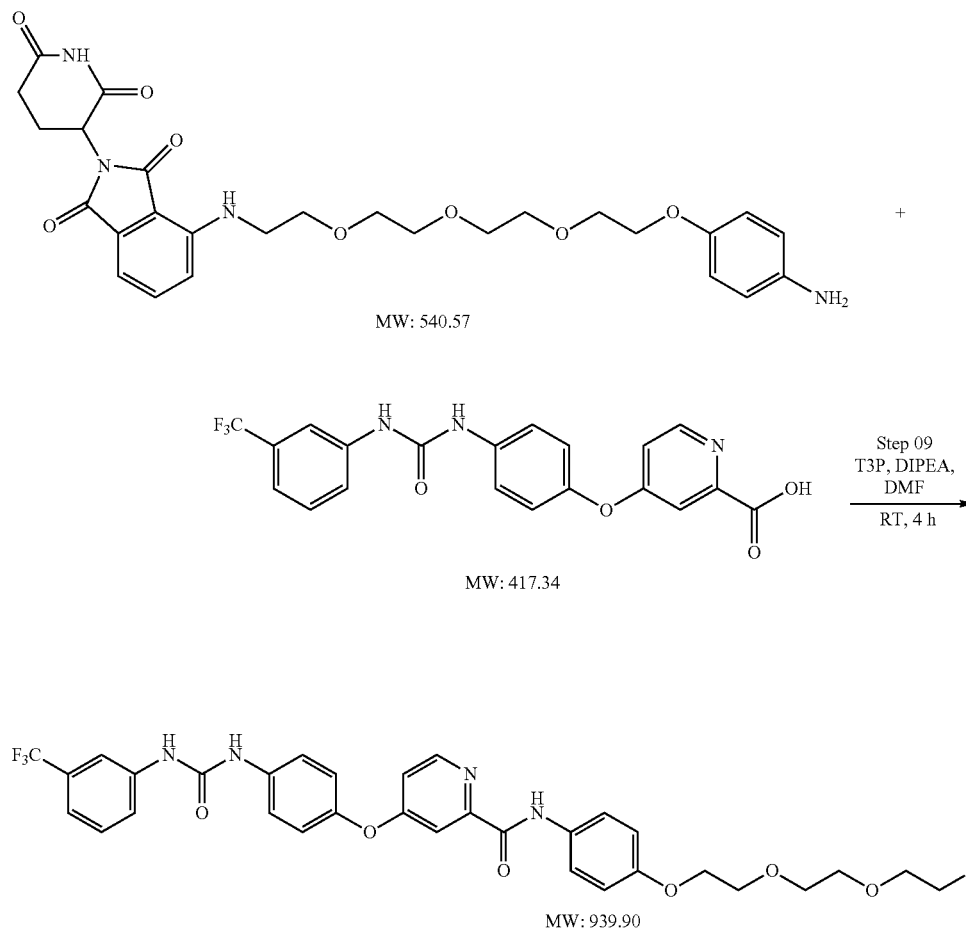

To a stirred solution of 4-(4-(3-(4-chloro-3-(trifluoromethyl)phenyl)ureido)phenoxy)-picolinic acid (200 mg, 0.44 mmol, 1.0 equiv) in DMF (5.0 mL, 25.0 vol. equiv) were added 4-((2-(2-(2-(2-(4-aminophenoxy)ethoxy)ethoxy)

segment of the Linker Component, and (3) the preparation of the RAF-Degrading Conjugate Compounds of the following generic formulae by covalently linking the two segments of the Linker Component.

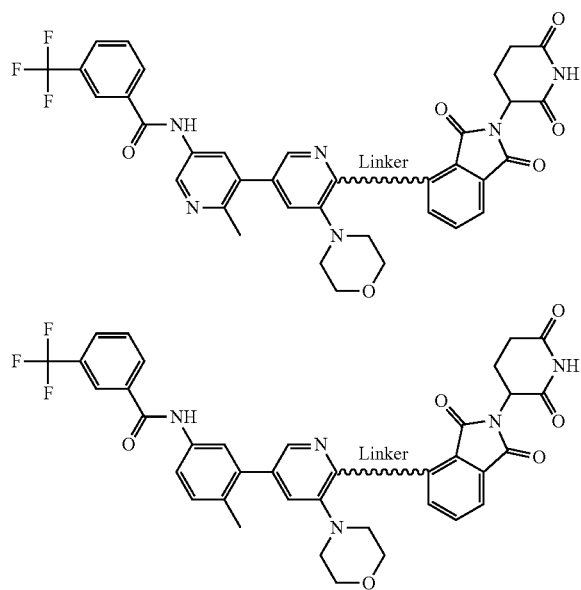

(1) Preparation of Degradation Signaling Agents with a segment of the Linker Component Example 8—Synthesis of 6-azido-N-(2-(2,6-dioxopiperidin-3-yl)-1,3-dioxoisoindolin-4-yl)hexanamide

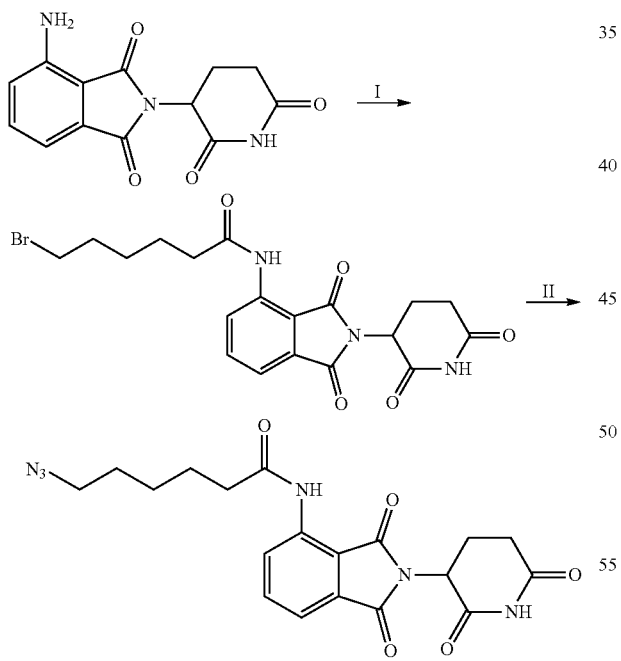

Step 1: Thionyl chloride (40 mL, 0.55 mol) and DMF (2.01 g, 27.40 mmol) were added to a stirred solution of 6-bromohexanoic acid (12.80 g, 65.90 mmol) in THF (300 mL). The resulting reaction mixture was stirred at 70° C. for 2 h. The progress of the reaction was monitored by TLC (30% EtOAc in n-hexane) to ensure completion of the reaction. The solvent was evaporated under reduced pressure. A solution of 4-amino-2-(2,6-dioxopiperidin-3-yl)isoindoline-1,3-dione (15.0 g, 54.90 mmol) in THF (300 mL) was added to the reaction mixture. The reaction mixture was stirred at reflux for 12 h. The progress of the reaction was monitored by TLC (5% MeOH in DCM) to ensure completion of the reaction. The solvent was distilled out under reduced pressure. Water (700 mL) was added to the residue and the product was extracted with EtOAc (2×750 mL). The combined EtOAc extracts were washed with brine (750 mL), dried over $Na_2SO_4$, and concentrated under reduced pressure to afford 6-bromo-N-(2-(2,6-dioxopiperidin-3-yl)-1,3-dioxoisoindolin-4-yl)hexanamide (17.80 g, 72.0%) as an off-white solid. $^1$HNMR (300 MHz, DMSO-$d_6$): δ11.15 (s, 1H), 9.71 (s, 1H), 8.47 (d, 1H), 7.83 (d, 1H), 7.62 (d, 1H), 5.15 (m, 1H), 3.58 (m, 2H), 2.90 (m, 2H), 2.60 (m, 2H), 2.47 (d, 2H), 2.07 (m, 1H), 1.84 (m, 2H), 1.66 (m, 2H), 1.47 (m, 2H) ppm. MS (ESI): Calculated for $C_{19}H_{20}BrN_3O_5$, 449.06, found, 449.80 (M−H)$^-$.

Step 2: Sodium azide (6.15 g, 94.70 mmol) and 18-crown-6 (773.0 mg, 2.58 mmol) were added to a stirred solution of 6-bromo-N-(2-(2,6-dioxopiperidin-3-yl)-1,3-dioxoisoindolin-4-yl)hexanamide (7.75 g, 17.20 mmol) in DMF (233 mL, 30 vol. equiv). The reaction mixture was stirred for 8.0 h at 70° C., cooled to rt, water (800 mL) was added and extracted with EtOAc (3×550 mL). The combined EtOAc extracts were washed with brine (150 mL), dried over $Na_2SO_4$, and concentrated under reduced pressure to provide the crude product. The crude product was purified by column chromatography on silica gel (230-400 mesh size) using a gradient of ethyl acetate in hexanes (40-90%) as eluent to afford title compound (4.50 g, 63.4%) as an off-white solid. $^1$HNMR (300 MHz, DMSO-$d_6$): δ 11.15 (s, 1H), 9.71 (s, 1H), 8.47 (d, J=8.4 Hz, 1H), 7.83 (t, J=7.9 Hz, 1H), 7.62 (d, J=7.3 Hz, 1H), 5.15 (dd, J=12.8, 5.4 Hz, 1H), 3.00-2.81 (m, 1H), 2.7-2.4 (m, 6H), 2.20-2.0 (m, 1H), 1.64-1.30 (m, 6H). MS (ESI): calculated for $C_{19}H_{20}N_6O_5$, 412.15, found, 413.0 (M+H)$^+$, 411 (M−H)$^-$.

(2) Preparation of Ligands for RAF with a Segment of the Linker Component

Example 9—Synthesis of N-(6'-(but-3-yn-1-yloxy)-2-methyl-5'-morpholino-[3,3'-bipyridin]-5-yl)-3-(trifluoromethyl)benzamide (for Compound 1.002)

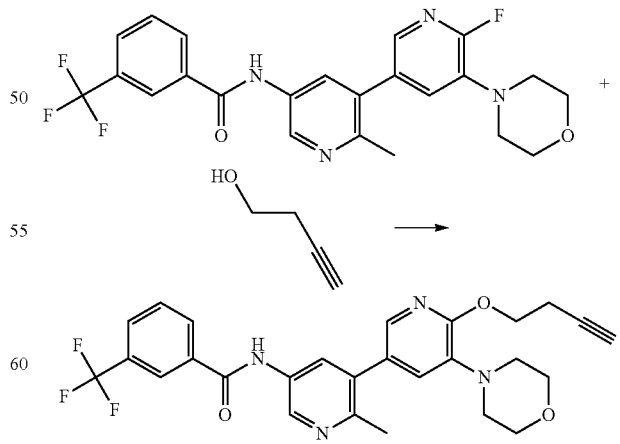

To a stirred solution of but-3-yn-1-ol (114 mg, 1.63 mmol) in 1,4-dioxane (1.5 mL) was added 60% sodium hydride (65.2 mg, 1.63 mmol), after stirred at rt for 30 min, N-(6'-fluoro-2-methyl-5'-morpholino-[3,3'-bipyridin]-5-yl)-3-(trifluoromethyl)benzamide (150 mg, 0.326 mmol) was added in one portion, it was placed on pre-heated oil bath at 80° C. for 30 min, The reaction mixture was cooled to rt, poured into water (10 mL), extracted with ethyl acetate (3×10 mL), combined extracts were dried (Na$_2$SO$_4$), and concentrated. The residue was purified on 25 g SiO$_2$ cartridge using a gradient of ethyl acetate in hexanes (50% to 100%, 3.5 CV; 100%, 12 CV) to afford title compound (60 mg, 54.1%) as white solid. Rf=0.38 (EtOAc). $^1$H NMR (400 MHz, CDCl$_3$) δ 8.55 (d, J=2.5 Hz, 1H), 8.09-8.05 (m, 2H), 8.04-7.99 (m, 2H), 7.77 (d, J=7.9 Hz, 1H), 7.69 (d, J=2.0 Hz, 1H), 7.59 (t, J=7.8 Hz, 1H), 6.99 (d, J=2.0 Hz, 1H), 4.48 (t, J=6.5 Hz, 2H), 3.87-3.80 (m, 4H), 3.15-3.07 (m, 4H), 2.70 (td, J=6.5, 2.6 Hz, 2H), 2.43 (s, 3H), 1.95 (t, J=2.6 Hz, 1H).

Example 10—Synthesis of N-(2-methyl-5'-morpholino-6'-(prop-2-yn-1-yloxy)-[3,3'-bipyridin]-5-yl)-3-(trifluoromethyl)benzamide (for Compound 1.001)

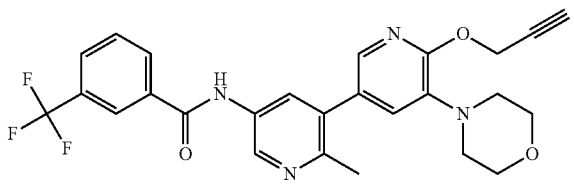 [SMILES: C#CCOc1ncc(-c2cc(NC(=O)c3cccc(C(F)(F)F)c3)cnc2C)cc1N1CCOCC1]

Title compound (13 mg, 12%) was prepared as light yellow solid from N-(6'-fluoro-2-methyl-5'-morpholino-[3,3'-bipyridin]-5-yl)-3-(trifluoromethyl)benzamide (100 mg, 0.217 mmol) and propargyl alcohol (60.9 mg, 1.09 mmol) in DMF as described in Example 9. Rf=0.3 (EtOAc). $^1$H NMR (400 MHz, CDCl$_3$) δ 8.61 (d, J=2.5 Hz, 1H), 8.16-8.13 (m, 2H), 8.09 (d, J=7.9 Hz, 1H), 8.02 (s, 1H), 7.84 (d, J=7.8 Hz, 1H), 7.81 (d, J=2.1 Hz, 1H), 7.66 (t, J=7.8 Hz, 1H), 7.08 (d, J=2.1 Hz, 1H), 5.10 (d, J=2.4 Hz, 2H), 3.93-3.87 (m, 4H), 3.19-3.12 (m, 4H), 2.50 (s, 3H), 2.48 (t, J=2.4 Hz, 1H). LRMS, m/z, calculated for C$_{26}$H$_{23}$F$_3$N$_4$O$_3$, 496.17, found, 497.03 (M+H)$^+$, 519.04 (M+Na)$^+$.

Example 11—Synthesis of N-(2-methyl-5'-morpholino-6'-(pent-4-yn-1-yloxy)-[3,3'-bipyridin]-5-yl)-3-(trifluoromethyl)benzamide (for Compound 1.003)

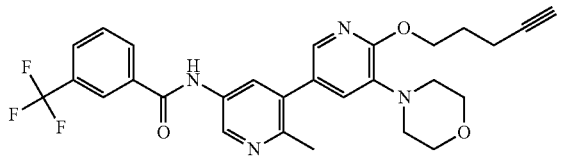 [SMILES: C#CCCCOc1ncc(-c2cc(NC(=O)c3cccc(C(F)(F)F)c3)cnc2C)cc1N1CCOCC1]

Title compound (25 mg, 21.9%) was prepared as a white solid from pent-4-yn-1-ol (76.1 mg, 1.09 mmol) and N-(6'-fluoro-2-methyl-5'-morpholino-[3,3'-bipyridin]-5-yl)-3-(trifluoromethyl)benzamide (100 mg, 0.217 mmol) in DMF (1.5 mL) as described for N-(6'-(but-3-yn-1-yloxy)-2-methyl-5'-morpholino-[3,3'-bipyridin]-5-yl)-3-(trifluoromethyl)ben-zamide. Rf=0.3 (EtOAc). $^1$H NMR (400 MHz, CDCl$_3$) δ 8.62 (d, J=2.5 Hz, 1H), 8.46 (s, 1H), 8.17-8.12 (m, 2H), 8.10 (d, J=7.8 Hz, 1H), 7.81 (d, J=7.8 Hz, 1H), 7.76 (d, J=2.1 Hz, 1H), 7.63 (t, J=7.8 Hz, 1H), 7.04 (d, J=2.1 Hz, 1H), 4.51 (t, J=6.3 Hz, 2H), 3.91-3.84 (m, 4H), 3.16-3.08 (m, 4H), 2.48 (s, 3H), 2.41 (dt, J=7.0, 3.6 Hz, 2H), 2.12-2.04 (m, 2H), 1.99 (t, J=2.6 Hz, 1H). LRMS, m/z, calculated for C$_{28}$H$_{27}$F$_3$N$_4$O$_3$, 524.2; found, 547.14 (M+Na)$^+$.

Example 12—Synthesis of N-(6'-(hex-5-yn-1-yloxy)-2-methyl-5'-morpholino-[3,3'-bipyridin]-5-yl)-3-(trifluoromethyl)benzamide (for Compound 1.004)

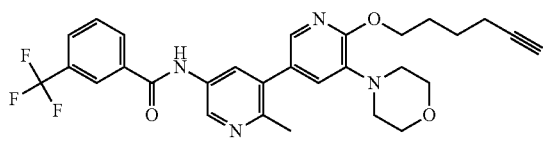 [SMILES: C#CCCCCOc1ncc(-c2cc(NC(=O)c3cccc(C(F)(F)F)c3)cnc2C)cc1N1CCOCC1]

Title compound (118.7 mg, 94.9%) was prepared as a white solid from Hex-5-yn-1-ol (112.2 mg, 1.14 mmol) and N-(6'-fluoro-2-methyl-5'-morpholino-[3,3'-bipyridin]-5-yl)-3-(trifluoromethyl)benzamide (107 mg, 0.232 mmol) in DMF (1.5 mL) as described for N-(6'-(but-3-yn-1-yloxy)-2-methyl-5'-morpholino-[3,3'-bipyridin]-5-yl)-3-(trifluoromethyl)ben-zamide. Rf=0.32 (EtOAc). $^1$H NMR (400 MHz, CDCl$_3$) δ 8.61 (d, J=2.5 Hz, 1H), 8.14 (s, 1H), 8.12 (d, J=2.4 Hz, 1H), 8.09 (d, J=6.7 Hz, 2H), 7.83 (d, J=7.8 Hz, 1H), 7.77 (d, J=2.1 Hz, 1H), 7.65 (t, J=7.8 Hz, 1H), 7.04 (d, J=2.0 Hz, 1H), 4.50 (t, J=6.4 Hz, 2H), 3.92-3.85 (m, 4H), 3.18-3.08 (m, 4H), 2.50 (s, 3H), 2.38-2.32 (m, 1H), 2.08-1.99 (m, 2H), 1.78 (t, J=2.5 Hz, 2H), 1.66 (s, 2H). $^{19}$F NMR (376 MHz, CDCl$_3$) δ −63.16 (s). LRMS, m/z, calculated for C$_{29}$H$_{29}$F$_3$N$_4$O$_3$: 538.22; found, 561.15 (M+Na)$^+$.

Example 13—Synthesis of N-(6'-(hept-6-yn-1-yloxy)-2-methyl-5'-morpholino-[3,3'-bipyridin]-5-yl)-3-(trifluoromethyl)benzamide (for Compound 1.005)

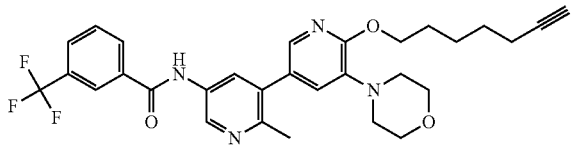 [SMILES: C#CCCCCCOc1ncc(-c2cc(NC(=O)c3cccc(C(F)(F)F)c3)cnc2C)cc1N1CCOCC1]

Title compound (110 mg, 90.7%) was prepared as a white solid from Hept-6-yn-1-ol (161.2 mg, 1.44 mmol) and N-(6'-fluoro-2-methyl-5'-morpholino-[3,3'-bipyridin]-5-yl)-3-(trifluoromethyl)benzamide (101 mg, 0.220 mmol) in DMF (1.5 mL) as described for N-(6'-(but-3-yn-1-yloxy)-2-methyl-5'-morpholino-[3,3'-bipyridin]-5-yl)-3-(trifluoromethyl)ben-zamide. Rf=0.33 (EtOAc). $^1$H NMR (400 MHz, CDCl$_3$) δ 8.62 (d, J=2.4 Hz, 1H), 8.15 (s, 1H), 8.12 (s, 1H), 8.09 (d, J=7.7 Hz, 1H), 7.93 (s, 1H), 7.84 (d, J=7.8 Hz, 1H), 7.78 (d, J=1.9 Hz, 1H), 7.67 (t, J=7.7 Hz, 1H), 7.05 (s, 1H), 4.43 (t, J=6.5 Hz, 2H), 3.90 (s, 4H), 3.15 (s, 4H), 2.51 (s, 3H), 2.25 (s, 2H), 2.12 (s, 1H), 1.97 (d, J=10.7 Hz, 1H), 1.89 (s, 1H), 1.79 (s, 1H), 1.67 (dd, J=20.9, 6.2 Hz, 3H). $^{19}$F NMR (376 MHz, CDCl$_3$) δ −63.17 (s). LRMS, m/z, calculated for C$_{30}$H$_{31}$F$_3$N$_4$O$_3$: 552.23; found, 575.23 (M+Na)$^+$.

Example 14—Synthesis of N-(2-methyl-5'-morpholino-6'-(oct-7-yn-1-yloxy)-[3,3'-bipyridin]-5-yl)-3-(trifluoromethyl)benzamide (for Compound 1.006)

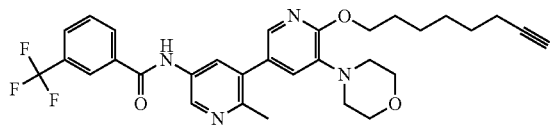 [SMILES: C#CCCCCCCOc1ncc(-c2cc(NC(=O)c3cccc(C(F)(F)F)c3)cnc2C)cc1N1CCOCC1]

Title compound (88.9 mg, 68.7%) was prepared as a white solid from oct-7-yn-1-ol (141.3 mg, 1.12 mmol) and N-(6'-fluoro-2-methyl-5'-morpholino-[3,3'-bipyridin]-5-yl)-3-(trifluoromethyl)benzamide (105 mg, 0.228 mmol) in DMF (1.5 mL) as described for N-(6'-(but-3-yn-1-yloxy)-2-methyl-5'-morpholino-[3,3'-bipyridin]-5-yl)-3-(trifluoromethyl)ben-zamide. Rf=0.28 (EtOAc). $^1$H NMR (400 MHz, CDCl$_3$) δ 8.62 (s, 1H), 8.15 (s, 1H), 8.12 (s, 1H), 8.09 (d, J=7.3 Hz, 1H), 7.86 (d, J=12.7 Hz, 2H), 7.78 (d, J=2.0 Hz, 1H), 7.67 (t, J=7.9 Hz, 1H), 7.04 (s, 1H), 4.42 (s, 2H), 3.90 (s, 4H), 3.15 (s, 4H), 2.51 (s, 3H), 2.25-2.14 (m, 1H), 2.12-2.01 (m, 1H), 1.91-1.83 (m, 2H), 1.79 (t, J=2.5 Hz, 1H), 1.60 (dd, J=6.3, 4.5 Hz, 2H), 1.45-1.40 (m, 1H), 1.26 (dd, J=8.5, 3.8 Hz, 1H), 0.83 (ddd, J=12.7, 10.3, 6.4 Hz, 2H). $^{19}$F NMR (376 MHz, CDCl$_3$) δ −63.17 (s). LRMS, m/z, calculated for C$_{31}$H$_{33}$F$_3$N$_4$O$_3$: 566.25; found, 589.18 (M+Na)$^+$.

Example 15—Synthesis of N-(2-methyl-5'-morpholino-6'-(2-(2-(2-(prop-2-yn-1-yloxy)ethoxy)ethoxy)ethoxy)-[3,3'-bipyridin]-5-yl)-3-(trifluoromethyl)benzamide (for Compound 1.007)

Step 1: In a 500 mL round bottom flask, to a stirred solution of triethylene glycol (14.25 mL, 107 mmol) in dry DMF (40 mL) was added sodium hydride (1.0552 g, 27.54 mmol, 60% in oil) in three portions. The resulting suspension was stirred at 0° C. for 30 min, and propargyl bromide (3 mL, 26.9 mmol, 80% in toluene) was added dropwise. The reaction mixture turned from clear yellow to clear brown and slowly warmed up to rt, stirred over a weekend (70 h). The reaction mixture was poured into water (100 mL) and extracted with ethyl acetate (3×50 mL), washed with water (50 mL), washed with brine (50 mL), dried (Na$_2$SO$_4$), and concentrated under reduced pressure. Most of the compound was remained in the aqueous solution. The aqueous solution was saturated with NaCl, stirred for 16 h, extracted with chloroform (3×50 mL), dried (Na$_2$SO$_4$), and concentrated. The residue was purified on 100 g SiO$_2$ cartridge using a gradient of ethyl acetate in hexanes (50% to 100%, 4CV, 100%) to afford 2-(2-(2-(prop-2-yn-1-yloxy)ethoxy)ethoxy)ethanol (1 g, 9.28%) (the solvents were removed under reduced pressure, purified over asilica gel column to obtain the desired 2-(2-(2-(prop-2-yn-1-yloxy)ethoxy)ethoxy)ethanol (1.00 g, 9.8%) as a pale yellow oil. Rf=0.26 (EtOAc). $^1$H NMR (400 MHz, CDCl$_3$) δ 4.20 (d, J=2.4 Hz, 2H), 3.76-3.71 (m, 3H), 3.68 (tt, J=5.6, 3.0 Hz, 7H), 3.64-3.59 (m, 3H), 2.43 (t, J=2.4 Hz, 1H). Percec, V. et. al. PCT, WO2014/190024 A1 and Ahmed et al., JOC, 2006, 71, pp. 9884-9886.

Step 2: Title compound (80 mg, 68.6%) was prepared as a oil from 2-(2-(2-(prop-2-yn-1-yloxy)ethoxy)ethoxy)ethanol (261.1 mg, 0.645 mmol) and N-(6'-fluoro-2-methyl-5'-morpholino-[3,3'-bipyridin]-5-yl)-3-(trifluoromethyl)benzamide (100.0 mg, 0.217 mmol) in 1,4-dioxane (1.5 mL) as described in Example 9. Rf=0.26 (5% MeOH/DCM). $^1$H NMR (400 MHz, CDCl$_3$) δ 8.63 (d, J=2.5 Hz, 1H), 8.15 (s, 1H), 8.12 (d, J=2.5 Hz, 1H), 8.08 (s, 1H), 7.93 (s, 1H), 7.85 (d, J=7.8 Hz, 1H), 7.76 (d, J=2.0 Hz, 1H), 7.67 (t, J=7.7 Hz,

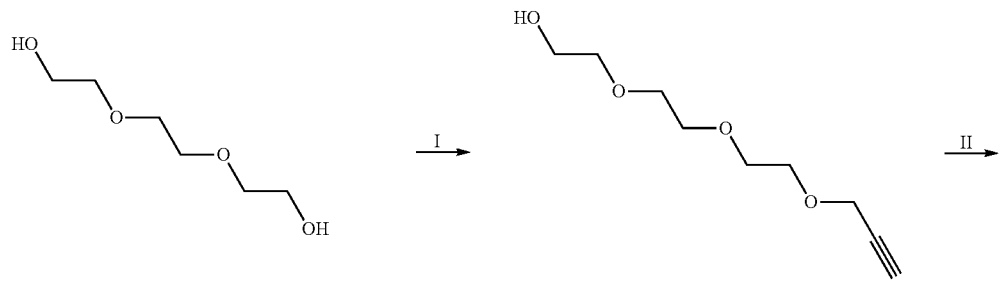

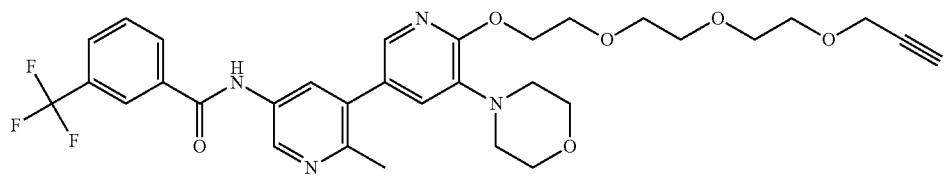

1H), 7.05 (d, J=2.0 Hz, 1H), 4.61-4.56 (m, 2H), 4.20 (d, J=2.4 Hz, 2H), 3.88 (d, J=4.5 Hz, 4H), 3.75-3.65 (m, 10H), 3.18-3.13 (m, 4H), 2.51 (s, 3H), 2.43 (t, J=2.4 Hz, 1H). $^{19}$F NMR (376 MHz, CDCl$_3$) δ −63.11 (s). LRMS, m/z, calculated for C$_{32}$H$_{35}$F$_3$N$_4$O$_6$, 628.25; found, 627.17 (M−H)$^−$.

Example 16—Synthesis of N-(6'-(3,6,9,12,15-pentaoxaoctadec-17-yn-1-yloxy)-2-methyl-5'-morpholino-[3,3'-bipyridin]-5-yl)-3-(trifluoromethyl)benzamide (for Compound 1.008)

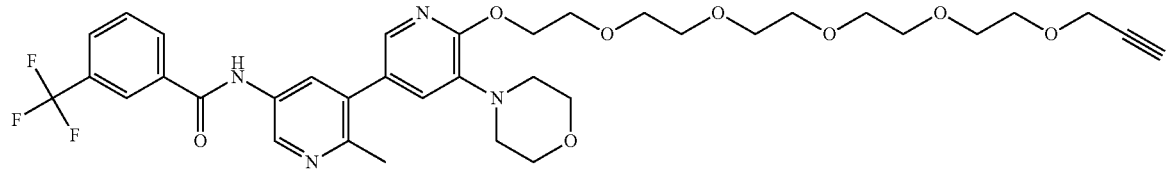 [SMILES: C#CCOCCOCCOCCOCCOCCOc1ncc(-c2cc(NC(=O)c3cccc(C(F)(F)F)c3)cnc2C)cc1N1CCOCC1]

Title compound (170 mg, 53.3%) was prepared as an oil from 3,6,9,12,15-pentaoxaoctadec-17-yn-1-ol (780.0 mg, 1.31 mmol) (Parthi, A. K. et. al. Tetrahedron Letters, 2008, 49, 3395-3399) and N-(6'-fluoro-2-methyl-5'-morpholino-[3,3'-bipyridin]-5-yl)-3-(trifluoromethyl)benzamide (204.9 mg, 0.445 mmol) in 1,4-dioxane (3.0 mL) as described in Example 9). Rf=0.27 (5% MeOH in DCM). $^1$H NMR (400 MHz, CDCl$_3$) δ 8.68 (d, J=2.5 Hz, 1H), 8.23 (s, 1H), 8.19 (s, 1H), 8.12 (t, J=6.0 Hz, 2H), 7.84 (d, J=7.7 Hz, 1H), 7.76 (d, J=2.0 Hz, 1H), 7.66 (t, J=7.8 Hz, 1H), 7.05 (d, J=2.0 Hz, 1H), 4.61-4.56 (m, 2H), 4.19 (d, J=2.4 Hz, 2H), 3.90-3.86 (m, 6H), 3.65 (dd, J=5.8, 3.1 Hz, 16H), 3.54 (dd, J=5.8, 3.5 Hz, 1H), 3.19-3.12 (m, 4H), 2.51 (s, 3H). $^{19}$F NMR (376 MHz, CDCl$_3$) δ −63.11 (s). LRMS, m/z, calculated for C$_{36}$H$_{43}$F$_3$N$_4$O$_8$, 716.30; found, 715.35 (M−H)$^−$.

Example 17—Synthesis of N-(3-(6-(but-3-yn-1-yloxy)-5-morpholinopyridin-3-yl)-4-methylphenyl)-3-(trifluoromethyl)-benzamide (for Compound 1.009)

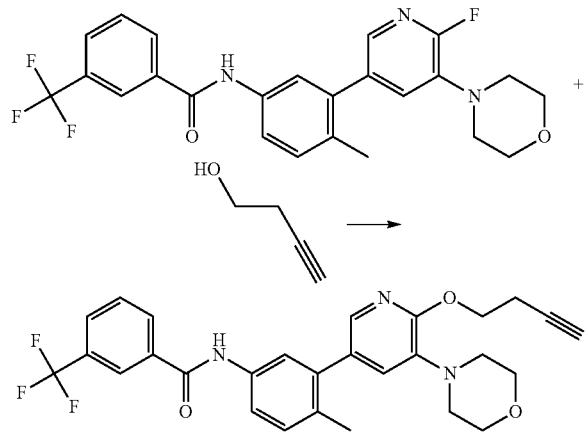

Title compound (52 mg, 46.9%) was prepared as white solid from but-3-yn-1-ol (114 mg, 1.63 mmol) and N-(3-(6-fluoro-5-morpholinopyridin-3-yl)-4-methylphenyl)-3-(trifluoromethyl)benzamide (100 mg, 0.218 mmol) (as described for compound 14, see, Nishiguchi, et. al. JMC 2017, 60, 4869) in 1,4-dioxane (3.0 mL) as described for N-(6'-(but-3-yn-1-yloxy)-2-methyl-5'-morpholino-[3,3'-bipyridin]-5-yl)-3-(trifluorometh-yl)benza-mide. Rf=0.42 (50% EtOAc). $^1$H NMR (400 MHz, CDCl$_3$) δ 8.12 (s, 1H), 8.06 (d, J=7.8 Hz, 1H), 7.84-7.79 (m, 2H), 7.75 (d, J=2.1 Hz, 1H), 7.64 (t, J=7.8 Hz, 1H), 7.58 (dd, J=8.2, 2.3 Hz, 1H), 7.48 (d, J=2.2 Hz, 1H), 7.30 (d, J=8.3 Hz, 1H), 7.06 (d, J=2.0 Hz, 1H), 4.55 (t, J=6.5 Hz, 2H), 3.93-3.85 (m, 4H), 3.20-3.13 (m, 4H), 2.76 (td, J=6.5, 2.6 Hz, 2H), 2.26 (s, 3H), 2.01 (t, J=2.6 Hz, 1H). $^{19}$F NMR (376 MHz, CDCl$_3$) δ −63.15 (s). LRMS, m/z, calculated for C$_{28}$H$_{26}$F$_3$N$_3$O$_3$, 509.19, found, 532.10 (M+Na)$^+$, 508.10 (M−H)$^−$.

Example 18—Synthesis of (±)-N-(2-methyl-5'-morpholino-6'-(pent-4-yn-2-yloxy)-[3,3'-bipyridin]-5-yl)-3-(trifluoromethyl)benzamide (for Compound 1.010)

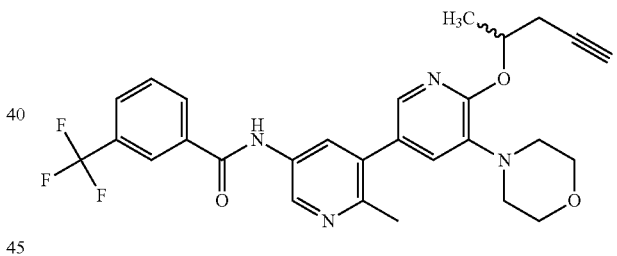

Title compound (86.2 mg, 50.2%) was prepared as white solid from (±)-pent-4-yn-2-ol (0.27 mL, 2.87 mmol) and N-(6'-fluoro-2-methyl-5'-morpholino-[3,3'-bipyridin]-5-yl)-3-(trifluoromethyl)benzamide (150.6 mg, 0.327 mmol) in 1,4-dioxane (2.3 mL) as described for N-(6'-(but-3-yn-1-yloxy)-2-methyl-5'-morpholino-[3,3'-bipyridin]-5-yl)-3-(trifluorometh-yl)benzamide. Rf=0.21 (EtOAc). $^1$H NMR (400 MHz, CDCl$_3$) δ 8.61 (d, J=2.5 Hz, 1H), 8.15 (s, 1H), 8.12 (d, J=2.5 Hz, 1H), 8.09 (d, J=7.9 Hz, 1H), 7.88 (s, 1H), 7.85 (d, J=7.7 Hz, 1H), 7.76 (d, J=2.1 Hz, 1H), 7.67 (t, J=7.8 Hz, 1H), 7.04 (d, J=2.1 Hz, 1H), 5.44 (dd, J=11.0, 6.1 Hz, 1H), 3.89 (t, J=4.6 Hz, 4H), 3.29-3.20 (m, 2H), 3.13-3.05 (m, 2H), 2.72-2.67 (m, 2H), 2.52 (s, 3H), 2.03 (t, J=2.6 Hz, 1H), 1.54 (d, J=6.2 Hz, 3H). $^{19}$F NMR (376 MHz, CDCl$_3$) δ −63.17 (s). LRMS, m/z calculated for C$_{28}$H$_{27}$F$_3$N$_4$O$_3$, 524.2; found, 525.06 (M+H)$^+$ and 547.07 (M+Na)$^+$.

Example 19—Synthesis of (±)-N-(4-methyl-3-(5-morpholino-6-(pent-4-yn-2-yloxy)pyridin-3-yl)phenyl)-3-(trifluoromethyl)benzamide (for Compound 1.011)

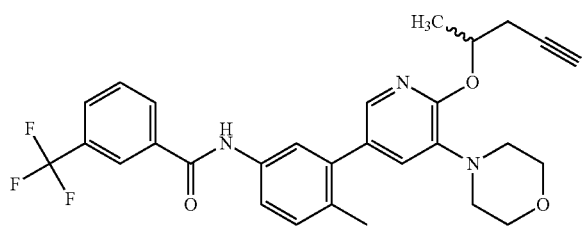 [SMILES: C#CCC(C)Oc1ncc(-c2cc(NC(=O)c3cccc(C(F)(F)F)c3)ccc2C)cc1N1CCOCC1]

Title compound (86.9 mg, 49.7%) was prepared as a pale yellow oil from (±)-pent-4-yn-2-ol (0.27 mL, 2.87 mmol) and N-(3-(6-fluoro-5-morpholinopyridin-3-yl)-4-methylphenyl)-3-(trifluoromethyl)benzamide was added (153.5 mg, 0.334 mmol) in 1,4-dioxane (2.3 mL) as described for N-(6'-(but-3-yn-1-yloxy)-2-methyl-5'-morpholino-[3,3'-bipyridin]-5-yl)-3-(trifluorometh-yl)benzamide. Rf=0.67 (EtOAc). $^1$H NMR (400 MHz, CDCl$_3$) δ 8.12 (s, 1H), 8.07 (d, J=7.8 Hz, 1H), 7.82 (d, J=8.1 Hz, 1H), 7.78 (s, 1H), 7.74 (d, J=2.0 Hz, 1H), 7.65 (t, J=7.8 Hz, 1H), 7.58 (d, J=8.3 Hz, 1H), 7.48 (s, 1H), 7.30 (d, J=8.4 Hz, 1H), 7.03 (d, J=2.0 Hz, 1H), 5.43 (dd, J=11.2, 5.9 Hz, 1H), 3.88 (t, J=4.6 Hz, 4H), 3.23 (d, J=11.7 Hz, 2H), 3.13-3.02 (m, 2H), 2.72-2.67 (m, 2H), 2.27 (s, 3H), 2.02 (t, J=2.6 Hz, 1H), 1.53 (s, 3H). $^{19}$F NMR (376 MHz, CDCl$_3$) δ −63.15 (s). LRMS, m/z calculated for C$_{29}$H$_{28}$F$_3$N$_3$O$_3$, 523.21; found, 524.03 (M+H)$^+$, 545.98 (M+Na)$^+$.

Example 20—Synthesis of (±)-N-(6'-(hex-5-yn-3-yloxy)-2-methyl-5'-morpholino-[3,3'-bipyridin]-5-yl)-3-(trifluoromethyl)benzamide (for Compound 1.012)

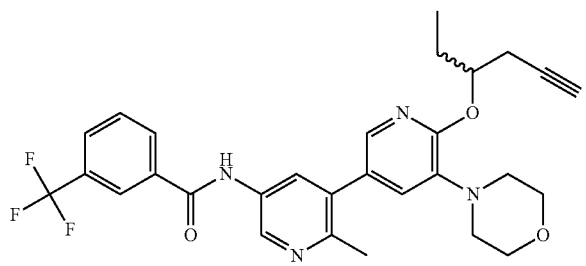 [SMILES: C#CCC(CC)Oc1ncc(-c2cc(NC(=O)c3cccc(C(F)(F)F)c3)cnc2C)cc1N1CCOCC1]

Title compound (73 mg, 40.8%) was prepared as white solid from (±)-hex-5-yn-3-ol (0.31 mL, 2.80 mmol) and N-(6'-fluoro-2-methyl-5'-morpholino-[3,3'-bipyridin]-5-yl)-3-(trifluoromethyl)benzamide (153.1 mg, 0.333 mmol) in 1,4-dioxane (2.3 mL) as described for N-(6'-(but-3-yn-1-yloxy)-2-methyl-5'-morpholino-[3,3'-bipyridin]-5-yl)-3-(trifluorometh-yl)benzamide. Rf=0.23 (EtOAc). $^1$H NMR (400 MHz, CDCl$_3$) δ 8.61 (d, J=2.5 Hz, 1H), 8.15 (s, 1H), 8.12 (d, J=2.4 Hz, 1H), 8.09 (d, J=7.9 Hz, 1H), 7.92 (s, 1H), 7.85 (d, J=7.9 Hz, 1H), 7.74 (d, J=2.1 Hz, 1H), 7.67 (t, J=7.8 Hz, 1H), 7.03 (d, J=2.0 Hz, 1H), 5.33-5.24 (m, 1H), 3.87 (dd, J=10.9, 6.3 Hz, 4H), 3.32-3.19 (m, 2H), 3.12-3.01 (m, 2H), 2.72 (dt, J=4.8, 2.8 Hz, 2H), 2.52 (s, 3H), 2.01-1.93 (m, 2H), 1.04 (t, J=7.5 Hz, 3H). $^{19}$F NMR (376 MHz, CDCl$_3$) δ −63.17 (s). LRMS, m/z calculated for C$_{29}$H$_{29}$F$_3$N$_4$O$_3$, 538.22; found, 539.07 (M+H)$^+$, 561.09 (M+Na)$^+$.

Example 21—Synthesis of N-(3-(6-(hex-5-yn-1-yloxy)-5-morpholinopyridin-3-yl)-4-methylphenyl)-3-(trifluoromethyl) benzamide (for Example 34)

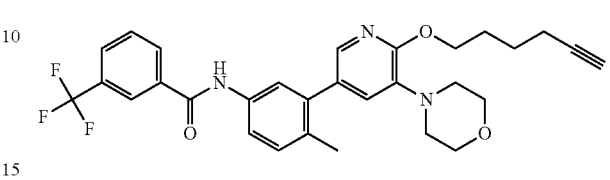

Title compound (169.4 mg, 95.6%) was prepared as a pale yellow oil from hex-5-yn-1-ol (0.18 mL, 1.63 mmol) and N-(3-(6-fluoro-5-morpholinopyridin-3-yl)-4-methylphenyl)-3-(trifluoromethyl)benzamide (151.41 mg, 0.33 mmol) in 1,4-dioxane (2.3 mL) as described for N-(6'-(but-3-yn-1-yloxy)-2-methyl-5'-morpholino-[3,3'-bipyridin]-5-yl)-3-(trifluorometh-yl)benzamide. Rf=0.63 (50% EtOAc in Hexanes). $^1$H NMR (400 MHz, CDCl$_3$) δ 8.12 (s, 1H), 8.06 (d, J=8.1 Hz, 1H), 7.81 (t, J=8.4 Hz, 2H), 7.76 (d, J=2.0 Hz, 1H), 7.64 (t, J=7.8 Hz, 1H), 7.58 (d, J=8.2 Hz, 1H), 7.48 (s, 1H), 7.30 (d, J=8.1 Hz, 1H), 7.05 (d, J=2.0 Hz, 1H), 4.43 (t, J=6.5 Hz, 2H), 3.92-3.86 (m, 4H), 3.72-3.65 (m, 2H), 3.16-3.10 (m, 4H), 2.32 (td, J=7.0, 2.7 Hz, 2H), 2.27 (s, 3H), 2.24 (dd, J=6.7, 2.6 Hz, 2H), 1.97-1.95 (m, 1H). $^{19}$F NMR (376 MHz, CDCl$_3$) δ −63.15 (s). LRMS, m/z, calculated for C$_{30}$H$_{30}$F$_3$N$_3$O$_3$, 537.22; found, 560.11 (M+Na)$^+$.

(3) Preparation of RAF-Degrading Conjugate Compounds

Example 22—Synthesis of N-(6'-(2-(1-(6-((2-(2,6-dioxopiperidin-3-yl)-1,3-dioxoisoindolin-4-yl)amino)-6-oxohexyl)-1H-1,2,3-triazol-4-yl)ethoxy)-2-methyl-5'-morpholino-[3,3'-bipyridin]-5-yl)-3-(trifluoromethyl)benzamide (Compound 1.002)

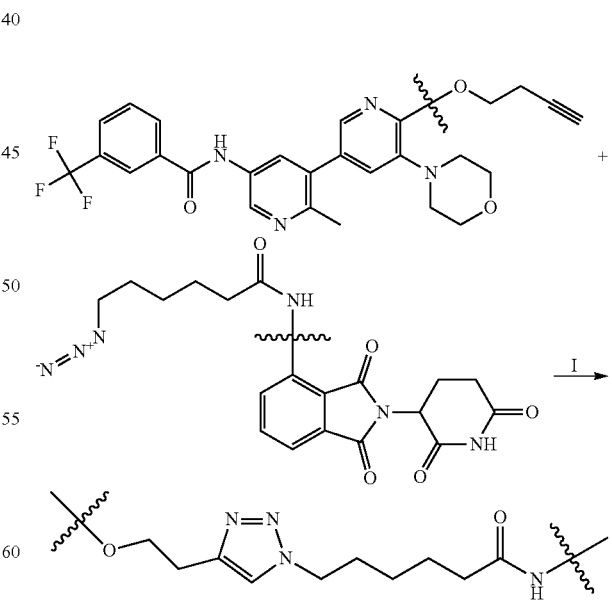

In a RBF, N-(6'-(but-3-yn-1-yloxy)-2-methyl-5'-morpholino-[3,3'-bipyridin]-5-yl)-3-(trifluoromethyl)benzamide (Example 9) (50.0 mg, 0.0979 mmol), 6-azido-N-(2-(2,6-dioxopiperidin-3-yl)-1,3-dioxoisoindolin-4-yl)hexanamide (Example 8) (48.5 mg, 0.051 mmol), copper sulfate pentahydrate (5.38 mg, 0.0105 mmol) and sodium ascorbate (7.76 mg, 0.039 mmol) was added THF (2.0 mL and water (200 µL), purged with nitrogen, stirred at rt over weekend (60 h), copper sulfate was deposited and half of the solvent was evaporated, TLC showed >50% conversion. The reaction mixture was diluted with water (5 mL), extracted with methylene chloride (2×10 mL), combined extracts were concentrated, purified on 25 g SiO$_2$ cartridge using a gradient of methanol in methylene chloride (0 to 15%) to afford N-(6'-(2-(1-(6-((2-(2,6-dioxopiperidin-3-yl)-1,3-dioxoisoindolin-4-yl)amino)-6-oxo-hexyl)-1H-1,2,3-triazol-4-yl)ethoxy)-2-methyl-5'-morpholino-[3,3'-bipyridin]-5-yl)-3-(tri-fluoromethyl)benzamide (80 mg, 88.5%) as white solid. Rf=0.14 (5% MeOH in DCM). $^1$H NMR (400 MHz, CDCl$_3$) δ 9.30 (s, 1H), 8.70 (d, J=8.5 Hz, 1H), 8.58 (d, J=2.2 Hz, 1H), 8.44 (s, 1H), 8.23 (s, 1H), 8.09 (s, 1H), 8.05-8.00 (m, 2H), 7.76 (d, J=7.8 Hz, 1H), 7.69 (d, J=1.7 Hz, 1H), 7.64-7.54 (m, 2H), 7.48-7.43 (m, 2H), 6.98 (d, J=1.8 Hz, 1H), 4.87 (dd, J=12.4, 5.5 Hz, 1H), 4.64 (t, J=6.5 Hz, 2H), 4.29 (t, J=7.0 Hz, 2H), 3.81-3.72 (m, 4H), 3.21 (t, J=6.5 Hz, 2H), 2.99 (s, 4H), 2.86-2.64 (m, 3H), 2.42 (s, 3H), 2.37 (t, J=7.3 Hz, 2H), 2.13-2.04 (m, 1H), 1.95-1.83 (m, 2H), 1.77-1.65 (m, 2H), 1.41-1.28 (m, 2H). LRMS, m/z calculated for C$_{46}$H$_{45}$F$_3$N$_{10}$O$_8$, 922.34; found, 945.42 (M+Na)$^+$. HPLC, t$_R$=10.29 min (purity, 98.74%). HPLC Method: Column, Agilent, Zorbax-SB-CN, 3.5 [m, 4.6×150 mm, mobile phase, acetonitrile in water (0 to 100%) contains ammonium acetate buffer; flow rate, 1.5 mL/min, run time, 20 min].

Example 23—Synthesis of N-(6'-((1-(6-((2-(2,6-dioxopiperidin-3-yl)-1,3-dioxoisoindolin-4-yl)amino)-6-oxohexyl)-1H-1,2,3-triazol-4-yl)methoxy)-2-methyl-5'-morpholino-[3,3'-bipyridin]-5-yl)-3-(trifluoromethyl)benzamide (Compound 1.001)

Title compound (9 mg, 37.8%) was prepared as white solid from N-(2-methyl-5'-morpholino-6'-(prop-2-yn-1-yloxy)-[3,3'-bipyridin]-5-yl)-3-(trifluoromethyl)benzamide (Example 10) (13 mg, 0.026 mmol), and 6-azido-N-(2-(2,6-dioxopiperidin-3-yl)-1,3-dioxoisoindolin-4-yl)hexanamide (Example 8) (11.6 mg, 0.028 mmol) as described in Example 22. Rf=0.14 (5% MeOH in DCM). $^1$H NMR (400 MHz, CDCl$_3$) δ 9.34 (s, 1H), 8.75 (d, J=8.6 Hz, 2H), 8.63 (s, 1H), 8.33 (s, 1H), 8.15 (s, 2H), 8.10 (d, J=8.0 Hz, 1H), 7.84-7.77 (m, 2H), 7.72 (s, 1H), 7.69-7.60 (m, 2H), 7.50 (d, J=7.2 Hz, 1H), 7.05 (s, 1H), 5.62 (s, 2H), 4.95 (s, 1H), 4.39 (t, J=6.8 Hz, 2H), 3.85 (s, 4H), 3.11 (s, 4H), 2.94-2.71 (m, 3H), 2.49 (s, 3H), 2.44 (t, J=7.2 Hz, 2H), 2.20-2.11 (m, 1H), 2.01-1.92 (m, 2H), 1.84-1.73 (m, 2H), 1.47-1.34 (m, 2H). LRMS, m/z, calculated for C$_{45}$H$_{43}$F$_3$N$_{10}$O$_8$, 908.32, found, 931.34 (M+Na)$^+$. HPLC, t$_R$=10.1 min (purity, 98.35%).

Example 24—Synthesis of N-(6'-(3-(1-(6-((2-(2,6-dioxopiperidin-3-yl)-1,3-dioxoisoindolin-4-yl)amino)-6-oxohexyl)-1H-1,2,3-triazol-4-yl)propoxy)-2-methyl-5'-morpholino-[3,3'-bipyridin]-5-yl)-3-(trifluoromethyl)benzamide (Compound 1.003)

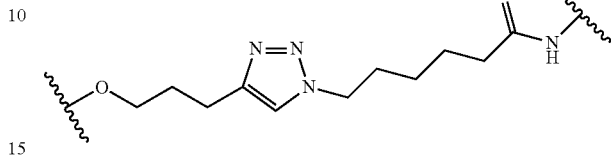

Title compound (20 mg, 44.8%) was prepared as white solid from N-(2-methyl-5'-morpholino-6'-(pent-4-yn-1-yloxy)-[3,3'-bipyridin]-5-yl)-3-(trifluoromethyl)benzamide (Example 11) (25.0 mg, 0.0477 mmol), and 6-azido-N-(2-(2,6-dioxopiperidin-3-yl)-1,3-dioxoisoindolin-4-yl)hexanamide (Example 8) (21 mg, 0.051 mmol) as described in Example 22. Rf=0.14 (5% MeOH in DCM). $^1$H NMR (400 MHz, CDCl$_3$) δ 9.37 (s, 1H), 8.76 (d, J=8.4 Hz, 1H), 8.66 (d, J=2.5 Hz, 1H), 8.54 (s, 1H), 8.30 (s, 1H), 8.15 (s, 1H), 8.12-8.06 (m, 2H), 7.82 (d, J=7.8 Hz, 1H), 7.75 (d, J=2.1 Hz, 1H), 7.71-7.60 (m, 2H), 7.52 (dd, J=7.3, 0.6 Hz, 1H), 7.35 (s, 1H), 7.05 (d, J=2.1 Hz, 1H), 4.93 (dd, J=12.6, 5.3 Hz, 1H), 4.45 (t, J=6.5 Hz, 2H), 4.34 (t, J=7.1 Hz, 2H), 3.94-3.86 (m, 4H), 3.18-3.10 (m, 4H), 2.94-2.87 (m, 3H), 2.83-2.70 (m, 2H), 2.49 (s, 3H), 2.44 (t, J=7.4 Hz, 2H), 2.29-2.11 (m, 2H), 1.99-1.89 (m, 2H), 1.83-1.73 (m, 2H), 1.46-1.35 (m, 2H). LRMS, calculated for C$_{47}$H$_{47}$F$_3$N$_{10}$O$_8$, 936.35, found, 959.43 (M+Na)$^+$. HPLC, t$_R$=10.29 min (purity, 95.9%).

Example 25—Synthesis of N-(6'-(4-(1-(6-((2-(2,6-dioxopiperidin-3-yl)-1,3-dioxoisoindolin-4-yl)amino)-6-oxohexyl)-1H-1,2,3-triazol-4-yl)butoxy)-2-methyl-5'-morpholino-[3,3'-bipyridin]-5-yl)-3-(trifluoromethyl)benzamide (Compound 1.004)

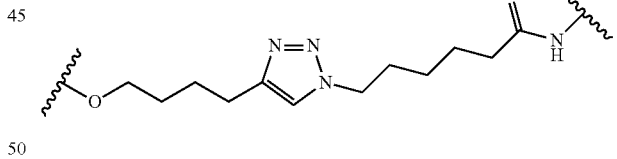

Title compound (18.1 mg, 8.39%) was prepared as white solid from N-(6'-(hex-5-yn-1-yloxy)-2-methyl-5'-morpholino-[3,3'-bipyridin]-5-yl)-3-(trifluoromethyl)benzamide (Example 12) (118.7 mg, 0.220 mmol), and 6-azido-N-(2-(2,6-dioxopiperidin-3-yl)-1,3-dioxoisoindolin-4-yl)hexanamide (Example 8) (102.0 mg, 0.247 mmol) as described in Example 22. Rf=0.11 (5% MeOH in DCM). $^1$H NMR (400 MHz, CDCl$_3$) δ 9.38 (s, 1H), 8.78 (d, J=8.5 Hz, 1H), 8.66 (s, 1H), 8.58 (s, 1H), 8.40 (s, 1H), 8.17 (s, 1H), 8.11 (d, J=7.2 Hz, 2H), 7.82 (d, J=7.9 Hz, 1H), 7.76 (d, J=1.9 Hz, 1H), 7.72-7.67 (m, 1H), 7.64 (t, J=7.8 Hz, 1H), 7.53 (d, J=7.2 Hz, 1H), 7.31 (s, 1H), 7.04 (d, J=1.9 Hz, 1H), 4.95 (dd, J=12.3, 5.3 Hz, 1H), 4.43 (t, J=6.2 Hz, 2H), 4.34 (t, J=7.1 Hz, 2H), 3.91-3.82 (m, 4H), 3.12 (s, 4H), 2.79 (dd, J=15.0, 8.1 Hz, 3H), 2.50 (s, 3H), 2.45 (t, J=7.3 Hz, 2H), 1.93 (ddd, J=21.5, 15.5, 7.0 Hz, 7H), 1.79 (dt, J=15.3, 7.5 Hz, 3H), 1.41 (dt, J=16.7, 8.2 Hz, 3H). $^{19}$F NMR (376 MHz, CDCl$_3$)

δ −63.11 (s). LRMS, m/z: calculated for $C_{48}H_{49}F_3N_{10}O_8$, 950.37; found, 973.32 (M+Na)$^+$. HPLC, $t_R$=10.36 min (purity, >99%).

Example 26—Synthesis of N-(6'-((5-(1-(6-((2-(2,6-dioxopiperidin-3-yl)-1,3-dioxoisoindolin-4-yl)amino)-6-oxohexyl)-1H-1,2,3-triazol-4-yl)pentyl)oxy)-2-methyl-5'-morpholino-[3,3'-bipyridin]-5-yl)-3-(trifluoromethyl)benzamide (Compound 1.005)

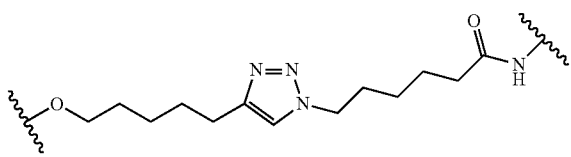 [SMILES: *NC(=O)CCCCCn1cc(CCCCCO*)nn1]

Title compound (34 mg, 17.7%) was prepared as white solid from N-(6'-(hept-6-yn-1-yloxy)-2-methyl-5'-morpholino-[3,3'-bipyridin]-5-yl)-3-(trifluoromethyl)benzamide (Example 13) (50.0 mg, 0.0882 mmol), and 6-azido-N-(2-(2,6-dioxopiperidin-3-yl)-1,3-dioxoisoindolin-4-yl)hexanamide (Example 8) (41.3 mg, 0.100 mmol) as described in Example 22. Rf=0.21 (5% MeOH in DCM). $^1$H NMR (400 MHz, CDCl$_3$) δ 9.37 (s, 1H), 8.77 (d, J=8.5 Hz, 2H), 8.65 (s, 1H), 8.55 (s, 1H), 8.16 (s, 1H), 8.10 (d, J=2.6 Hz, 2H), Title compound (19.4 mg, 10.6%) was prepared as white solid from N-(2-methyl-5'-morpholino-6'-(oct-7-yn-1-yloxy)-[3,3'-bipyridin]-5-yl)-3-(trifluoromethyl)benzamide (Example 14) (108.9 mg, 0.192 mmol), and 6-azido-N-(2-(2,6-dioxopiperidin-3-yl)-1,3-dioxoisoindolin-4-yl)hexanamide (Example 8) (87.6 mg, 0.212 mmol) as described in Example 22. Rf=0.13 (5% MeOH in DCM). $^1$H NMR (400 MHz, CDCl$_3$) δ 9.37 (s, 1H), 8.93 (s, 1H), 8.81 (s, 1H), 8.76 (d, J=8.5 Hz, 1H), 8.67 (s, 1H), 8.17 (s, 1H), 8.12 (d, J=8.7 Hz, 2H), 7.78 (d, J=7.8 Hz, 1H), 7.74 (s, 1H), 7.67 (t, J=7.9 Hz, 1H), 7.60 (t, J=7.8 Hz, 1H), 7.51 (d, J=7.2 Hz, 1H), 7.27 (d, J=4.2 Hz, 1H), 7.03 (s, 1H), 4.95 (s, 1H), 4.38 (t, J=6.6 Hz, 2H), 4.30 (t, J=7.0 Hz, 2H), 3.87 (s, 4H), 3.71 (dd, J=13.8, 6.8 Hz, 1H), 3.11 (s, 4H), 2.68 (t, J=7.5 Hz, 2H), 2.47 (s, 3H), 2.43 (d, J=7.2 Hz, 2H), 1.97-1.88 (m, 2H), 1.87-1.79 (m, 2H), 1.79-1.72 (m, 2H), 1.72-1.61 (m, 2H), 1.42 (dd, J=18.3, 10.3 Hz, 7H), 1.23 (q, J=7.2 Hz, 2H). $^{19}$F NMR (376 MHz, CDCl$_3$) δ −63.09 (s). LRMS, m/z: calculated for $C_{50}H_{53}F_3N_{10}O_8$, 978.4; found 979.39 (M+H)$^+$. HPLC, $t_R$=10.6 min (purity, >99%).

Example 28—Synthesis of N-(6'-(2-(2-(2-((1-(6-((2-(2,6-dioxopiperidin-3-yl)-1,3-dioxoisoindolin-4-yl)amino)-6-oxohexyl)-1H-1,2,3-triazol-4-yl)methoxy)ethoxy)ethoxy)ethoxy)-2-methyl-5'-morpholino-[3,3'-bipyridin]-5-yl)-3-(trifluoromethyl)benzamide (Compound 1.007)

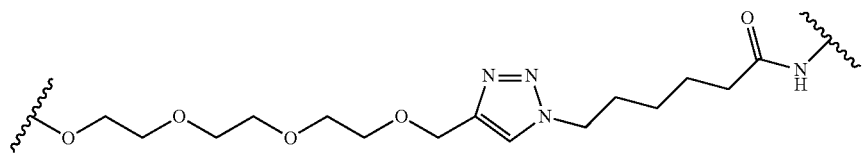

7.80 (d, J=7.9 Hz, 1H), 7.74 (d, J=1.9 Hz, 1H), 7.71-7.65 (m, 1H), 7.62 (t, J=7.9 Hz, 1H), 7.52 (d, J=7.3 Hz, 1H), 7.29 (s, 1H), 7.03 (d, J=1.9 Hz, 1H), 4.94 (dd, J=12.3, 5.3 Hz, 1H), 4.39 (t, J=6.7 Hz, 2H), 4.32 (t, J=7.1 Hz, 2H), 3.92-3.81 (m, 4H), 3.11 (s, 4H), 2.75-2.68 (m, 2H), 2.48 (s, 3H), 2.45 (t, J=7.4 Hz, 2H), 2.16 (d, J=10.1 Hz, 1H), 1.95 (dd, J=15.1, 7.5 Hz, 2H), 1.87 (dd, J=14.6, 7.2 Hz, 2H), 1.83-1.70 (m, 7H), 1.54 (dd, J=15.2, 8.1 Hz, 2H), 1.45-1.34 (m, 2H). $^{19}$F NMR (376 MHz, CDCl$_3$) δ −63.10 (s). LRMS, m/z, calculated for $C_{49}H_{51}F_3N_{10}O_8$: 964.99; found, 987.45 (M+Na)$^+$. HPLC, $t_R$=10.62 min (purity, >99%).

Example 27—Synthesis of N-(6'-((6-(1-(6-((2-(2,6-dioxopiperidin-3-yl)-1,3-dioxoisoindolin-4-yl)amino)-6-oxohexyl)-1H-1,2,3-triazol-4-yl)hexyl)oxy)-2-methyl-5'-morpholino-[3,3'-bipyridin]-5-yl)-3-(trifluoromethyl)benzamide (Compound 1.006)

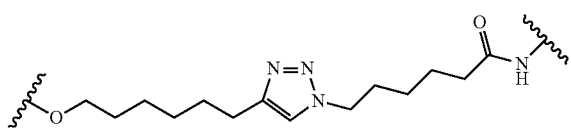 [SMILES: *NC(=O)CCCCCn1cc(CCCCCCO*)nn1]

Title compound (53.9 mg, 40.7%) was prepared as white solid from N-(2-methyl-5'-morpholino-6'-(2-(2-(2-(prop-2-yn-1-yloxy)ethoxy)ethoxy)ethoxy)-[3,3'-bipyridin]-5-yl)-3-(trifluoromethyl)benzamide (Example 15) (80.0 mg, 0.127 mmol), and 6-azido-N-(2-(2,6-dioxopiperidin-3-yl)-1,3-dioxoisoindolin-4-yl)hexanamide (Example 8) (58.5 mg, 0.142 mmol) as described in Example 22. Rf=0.10 (5% MeOH in DCM). $^1$H NMR (400 MHz, CDCl$_3$) δ 9.38 (s, 1H), 8.76 (t, J=6.0 Hz, 2H), 8.62 (s, 1H), 8.43 (s, 1H), 8.17 (s, 1H), 8.12 (d, J=7.7 Hz, 1H), 8.05 (d, J=2.5 Hz, 1H), 7.82 (d, J=8.0 Hz, 1H), 7.74 (d, J=2.1 Hz, 1H), 7.71-7.66 (m, 1H), 7.64 (t, J=7.8 Hz, 1H), 7.59 (s, 1H), 7.53 (d, J=6.9 Hz, 1H), 7.04 (d, J=2.0 Hz, 1H), 4.94 (dd, J=12.5, 5.3 Hz, 1H), 4.61-4.56 (m, 2H), 4.32 (t, J=7.2 Hz, 2H), 3.93-3.84 (m, 6H), 3.75-3.61 (m, 10H), 3.15 (d, J=4.3 Hz, 4H), 2.77 (dd, J=19.8, 8.7 Hz, 2H), 2.50 (s, 3H), 2.44 (t, J=7.3 Hz, 2H), 1.94 (dt, J=15.0, 7.4 Hz, 2H), 1.82-1.72 (m, 2H), 1.64 (s, 4H), 1.45-1.35 (m, 2H). $^{19}$F NMR (376 MHz, CDCl$_3$) δ −63.13 (d, J=16.2 Hz). LRMS, m/z, calculated for $C_{51}H_{55}F_3N_{10}O_{11}$, 1040.4; Found, 1063.37 (M+Na)$^+$. HPLC, TR=9.89 min (purity, >95.9%).

Example 29—Synthesis of N-(6'-((1-(1-(6-((2-(2,6-dioxopiperidin-3-yl)-1,3-dioxoisoindolin-4-yl)amino)-6-oxohexyl)-1H-1,2,3-triazol-4-yl)-2,5,8,11,14-pentaoxahexadecan-16-yl)oxy)-2-methyl-5'-morpholino-[3,3'-bipyridin]-5-yl)-3-(trifluoromethyl)benzamide (for Compound 1.008)

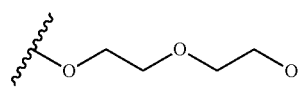

Title compound (59.9 mg, 44.7%) was prepared as white solid from N-(6'-(3,6,9,12,15-pentaoxaoctadec-17-yn-1-yloxy)-2-methyl-5'-morpholino-[3,3'-bipyridin]-5-yl)-3-(trifluoro-methyl)benzamide (Example 16) (85.0 mg, 0.119 mmol), and 6-azido-N-(2-(2,6-dioxopiperidin-3-yl)-1,3-dioxoisoindolin-4-yl)hexanamide (Example 8) (58.2 mg, 0.141 mmol) as described in Example 22. Rf=0.08 (5% MeOH in DCM). $^1$H NMR (400 MHz, CDCl$_3$) δ 9.39 (s, 1H), 8.77 (d, J=8.4 Hz, 1H), 8.75 (s, 1H), 8.62 (s, 1H), 8.51 (s, 1H), 8.18 (s, 1H), 8.13 (d, J=7.9 Hz, 1H), 8.05 (s, 1H), 7.81 (d, J=7.6 Hz, 1H), 7.74 (d, J=1.9 Hz, 1H), 7.73-7.67 (m, 1H), 7.63 (t, J=7.7 Hz, 1H), 7.55 (s, 1H), 7.53 (d, J=7.4 Hz, 1H), 7.05 (d, J=1.9 Hz, 1H), 4.98-4.92 (m, 1H), 4.62 (s, 2H), 4.60-4.55 (m, 2H), 4.32 (t, J=7.2 Hz, 2H), 3.89 (dd, J=9.4, 7.1 Hz, 6H), 3.72-3.59 (m, 16H), 3.15 (d, J=4.3 Hz, 4H), 2.78 (t, J=11.9 Hz, 2H), 2.45 (t, J=7.3 Hz, 2H), 1.94 (dt, J=14.9, 7.3 Hz, 2H), 1.82-1.73 (m, 3H), 1.65 (s, 4H), 1.45-1.35 (m, 2H). $^{19}$F NMR (376 MHz, CDCl$_3$) δ −63.07 (d, J=11.6 Hz). LRMS, m/z, calculated for C$_{55}$H$_{63}$F$_3$N$_{10}$NO$_{13}$, 1128.45; found, 1151.40 (M+Na)$^+$. HPLC, t$_R$=9.86 min (purity, 99%).

Example 30—Synthesis of (±)-N-(6'-((1-(1-(6-((2-(2,6-dioxopiperidin-3-yl)-1,3-dioxoisoindolin-4-yl)amino)-6-oxohexyl)-1H-1,2,3-triazol-5-yl)propan-2-yl)oxy)-2-methyl-5'-morpholino-[3,3'-bipyridin]-5-yl)-3-(trifluoromethyl)benzamide (Compound 1.010)

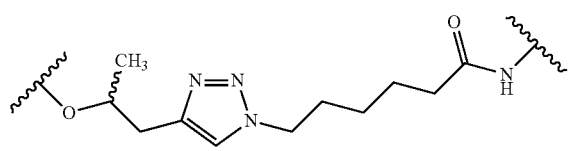 [SMILES: *NC(=O)CCCCCn1cc(CC(C)O*)nn1]

Title compound (103.4 mg, 67.2%) was prepared as pale yellow solid from (±)-N-(2-methyl-5'-morpholino-6'-(pent-4-yn-2-yloxy)-[3,3'-bipyridin]-5-yl)-3-(trifluoromethyl)benzamide (Example 18) (86.2 mg, 0.164 mmol), and 6-azido-N-(2-(2,6-dioxopiperidin-3-yl)-1,3-dioxoisoindolin-4-yl)hexanamide (Example 8) (76.9 mg, 0.186 mmol) as described in Example 22. Rf=0.17 (5% MeOH in DCM). $^1$H NMR (400 MHz, CDCl$_3$, 1:1 mixture of diastereomers) δ 9.31 (s, 1H), 8.71 (dd, J=8.3, 2.1 Hz, 1H), 8.64 (dd, J=4.7, 2.5 Hz, 1H), 8.51 (d, J=14.1 Hz, 1H), 8.38 (d, J=6.5 Hz, 1H), 8.14 (s, 1H), 8.10 (d, J=7.9 Hz, 1H), 8.06 (dd, J=6.5, 2.5 Hz, 1H), 7.81 (d, J=7.8 Hz, 1H), 7.74 (d, J=1.9 Hz, 1H), 7.64 (q, J=7.6 Hz, 2H), 7.55 (d, J=3.0 Hz, 1H), 7.50 (d, J=7.4 Hz, 1H), 7.04 (d, J=1.8 Hz, 1H), 5.59 (dd, J=12.2, 6.2 Hz, 1H), 4.91 (dd, J=12.4, 5.0 Hz, 1H), 4.40-4.26 (m, 2H), 3.86 (t, J=4.5 Hz, 4H), 3.25-3.09 (m, 4H), 3.04 (d, J=15.9 Hz, 2H), 2.91 (d, J=13.3 Hz, 1H), 2.76 (dd, J=19.5, 7.8 Hz, 2H), 2.50 (s, 3H), 2.39 (dd, J=13.6, 7.4 Hz, 2H), 2.16 (d, J=7.9 Hz, 1H), 1.91 (dd, J=15.2, 7.6 Hz, 2H), 1.77-1.68 (m, 2H), 1.46 (d, J=6.2 Hz, 3H), 1.34 (s, 2H). $^{19}$F NMR (376 MHz, CDCl$_3$) δ −63.10 (s). LRMS, m/z, calculated for C$_{47}$H$_{47}$F$_3$N$_{10}$O$_8$, 936.35; found, 959.51 (M+Na)$^+$. HPLC, t$_R$=9.99 min (purity, >99.9%).

Example 31—Synthesis of (±)-N-(6'-((1-(1-(6-((2-(2,6-dioxopiperidin-3-yl)-1,3-dioxoisoindolin-4-yl)amino)-6-oxohexyl)-1H-1,2,3-triazol-5-yl)butan-2-yl)oxy)-2-methyl-5'-morpholino-[3,3'-bipyridin]-5-yl)-3-(trifluoromethyl)benzamide (Compound 1.012)

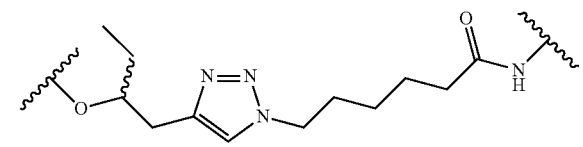 [SMILES: *NC(=O)CCCCCn1cc(CC(CC)O*)nn1]

Title compound (103.4 mg, 80.2%) was prepared as pale yellow solid from (±)-N-(6'-(hex-5-yn-3-yloxy)-2-methyl-5'-morpholino-[3,3'-bipyridin]-5-yl)-3-(trifluoromethyl)ben-zamide (Example 20) (73.0 mg, 0.136 mmol), and 6-azido-N-(2-(2,6-dioxopiperidin-3-yl)-1,3-dioxoisoindolin-4-yl)hexanamide (Example 8) (62.7 mg, 0.152 mmol) as described in Example 22. Rf=0.23 (5% MeOH in DCM). $^1$H NMR (400 MHz, CDCl$_3$, 1:1 mixture of diastereomers) δ 9.29 (s, 1H), 8.70 (dd, J=8.4, 2.5 Hz, 1H), 8.64 (dd, J=6.0, 2.4 Hz, 1H), 8.53 (d, J=7.0 Hz, 1H), 8.42 (d, J=6.6 Hz, 1H), 8.14 (s, 1H), 8.12-8.04 (m, 2H), 7.81 (d, J=7.8 Hz, 1H), 7.73 (d, J=1.3 Hz, 1H), 7.67-7.59 (m, 2H), 7.55 (d, J=2.9 Hz, 1H), 7.50 (d, J=7.3 Hz, 1H), 7.04 (d, J=1.9 Hz, 1H), 5.54-5.45 (m, 1H), 4.91 (dd, J=12.3, 5.0 Hz, 1H), 4.33 (dd, J=8.6, 4.6 Hz, 2H), 3.86 (s, 4H), 3.18 (d, J=6.0 Hz, 2H), 3.14 (s, 2H), 3.05 (d, J=16.0 Hz, 2H), 2.91 (d, J=13.1 Hz, 1H), 2.76 (t, J=11.5 Hz, 2H), 2.50 (s, 3H), 2.38 (dd, J=13.6, 7.3 Hz, 2H), 2.15 (s, 1H), 1.89 (dd, J=14.6, 6.9 Hz, 2H), 1.82 (dd, J=14.7, 7.3 Hz, 2H), 1.71 (dt, J=15.4, 7.6 Hz, 2H), 1.32 (s, 2H), 1.04 (t, J=7.4 Hz, 3H). $^{19}$F NMR (376 MHz, CDCl$_3$) δ −63.09 (s). LRMS, m/z, calculated for C$_{48}$H$_{49}$F$_3$N$_{10}$O$_8$, 950.37; found, 973.32 (M+Na)$^+$. HPLC, t$_R$=10.23 min (purity, >99.9%).

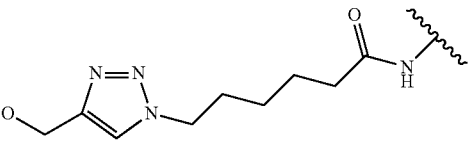

Example 32—Synthesis of N-(3-(6-(2-(1-(6-((2-(2,6-dioxopiperidin-3-yl)-1,3-dioxoisoindolin-4-yl)amino)-6-oxohexyl)-1H-1,2,3-triazol-4-yl)ethoxy)-5-morpholinopyridin-3-yl)-4-methylphenyl)-3-(trifluoromethyl)benzamide (Compound 1.009)

Example 33—Synthesis of (±)-N-(3-(6-((1-(1-(6-((2-(2,6-dioxopiperidin-3-yl)-1,3-dioxoisoindolin-4-yl)amino)-6-oxohexyl)-1H-1,2,3-triazol-5-yl)propan-2-yl)oxy)-5-morpholinopyridin-3-yl)-4-methylphenyl)-3-(trifluoromethyl)benzamide (Compound 1.011)

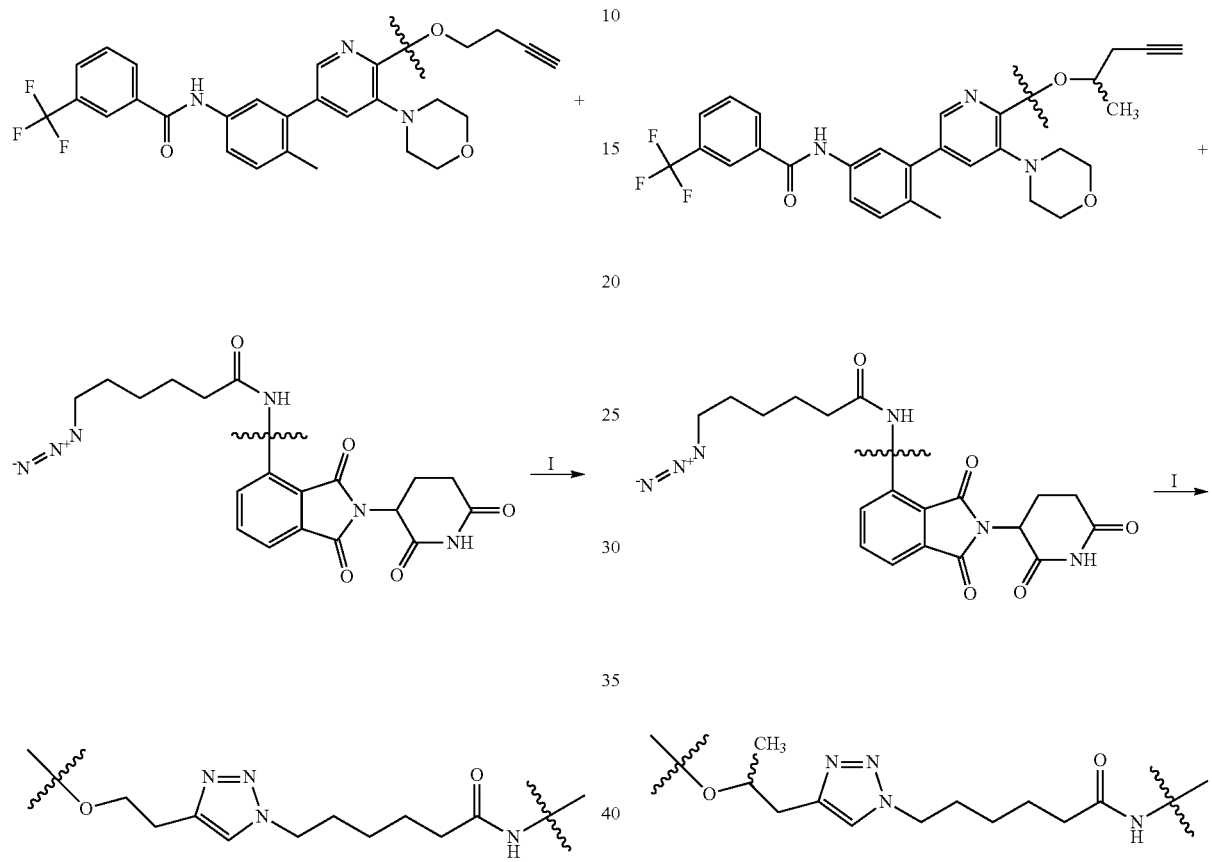

Title compound (34 mg, 36.8%) was prepared as pale yellow solid from N-(3-(6-(but-3-yn-1-yloxy)-5-morpholinopyridin-3-yl)-4-methylphenyl)-3-(trifluoromethyl)benzamide (Example 17) (51 mg, 0.100 mmol), 6-azido-N-(2-(2,6-dioxopiperidin-3-yl)-1,3-dioxoisoindolin-4-yl)hexanamide (Example 8) (49.5 mg, 0.120 mmol) as described in Example 22. Rf=0.25 (5% MeOH in DCM). $^1$H NMR (400 MHz, CDCl$_3$) δ 9.37 (s, 1H), 8.76 (d, J=8.4 Hz, 1H), 8.37 (s, 1H), 8.13 (s, 2H), 8.08 (d, J=8.0 Hz, 1H), 7.80 (d, J=7.8 Hz, 1H), 7.74 (d, J=2.0 Hz, 1H), 7.70-7.56 (m, 3H), 7.54-7.50 (m, 2H), 7.47 (d, J=2.1 Hz, 1H), 7.25 (s, 1H), 7.05 (d, J=2.0 Hz, 1H), 4.93 (dd, J=12.3, 5.4 Hz, 1H), 4.70 (t, J=6.6 Hz, 2H), 4.35 (t, J=7.1 Hz, 2H), 3.86-3.78 (m, 4H), 3.27 (t, J=6.5 Hz, 2H), 3.09-3.01 (m, 4H), 2.92-2.69 (m, 3H), 2.44 (t, J=7.4 Hz, 2H), 2.25 (s, 3H), 2.20-2.11 (m, 1H), 2.00-1.90 (m, 2H), 1.84-1.73 (m, 2H), 1.46-1.34 (m, 2H). $^{19}$F NMR (376 MHz, CDCl$_3$) δ −63.09 (s). LRMS, m/z, calculated for C$_{47}$H$_{46}$F$_3$N$_9$O$_8$, 921.34; found, 920.30 (M−H)$^−$, 944.23 (M+Na)$^+$. HPLC, t$_R$=10.35 min (purity, >99.9%).

Title compound (91.3 mg, 58.8%) was prepared as pale yellow solid from (±)-N-(4-methyl-3-(5-morpholino-6-(pent-4-yn-2-yloxy)pyridin-3-yl)phenyl)-3-(trifluoromethyl)benzamide (Example 19) (86.9 mg, 0.166 mmol) and 6-azido-N-(2-(2,6-dioxopiperidin-3-yl)-1,3-dioxoisoindolin-4-yl)hexanamide (Example 8) (78.5 mg, 0.190 mmol) as described in Example 22. Rf=0.31 (5% MeOH in DCM). $^1$H NMR (400 MHz, CDCl$_3$, 1:1 mixture of diastereomers) δ 9.30 (s, 1H), 8.70 (dd, J=8.4, 3.8 Hz, 1H), 8.22 (d, J=18.6 Hz, 1H), 8.17 (s, 1H), 8.12 (s, 1H), 8.08 (d, J=7.7 Hz, 1H), 7.79 (d, J=7.9 Hz, 1H), 7.74 (d, J=2.0 Hz, 1H), 7.63 (dt, J=15.7, 5.0 Hz, 2H), 7.57-7.44 (m, 4H), 7.21 (d, J=8.2 Hz, 1H), 7.05 (t, J=2.3 Hz, 1H), 5.58 (dd, J=11.1, 5.0 Hz, 1H), 4.95-4.87 (m, 1H), 4.41-4.25 (m, 2H), 3.85 (dd, J=10.7, 6.3 Hz, 4H), 3.25-3.16 (m, 2H), 3.13 (d, J=3.3 Hz, 2H), 3.03 (dd, J=11.2, 4.6 Hz, 2H), 2.90 (d, J=12.8 Hz, 1H), 2.80-2.71 (m, 2H), 2.38 (dt, J=15.2, 5.8 Hz, 2H), 2.26 (s, 3H), 2.15 (d, J=9.3 Hz, 1H), 1.90 (dt, J=14.2, 7.1 Hz, 2H), 1.72 (dt, J=14.9, 7.3 Hz, 2H), 1.46 (d, J=6.2 Hz, 3H), 1.37-1.28 (m, 2H). $^{19}$F NMR (376 MHz, CDCl$_3$) δ −63.08 (s). LRMS, m/z, calculated for C$_{48}$H$_{48}$F$_3$N$_9$O$_8$, 935.36; found, 958.45 (M+Na)$^+$. HPLC, t$_R$=10.4 min (purity, >99.9%).

Example 34—Synthesis of N-(3-(6-(4-(1-(6-((2-(2, 6-dioxopiperidin-3-yl)-1,3-dioxoisoindolin-4-yl) amino)-6-oxohexyl)-1H-1,2,3-triazol-4-yl)butoxy)- 5-morpholinopyridin-3-yl)-4-methylphenyl)-3- (trifluoromethyl)benzamide

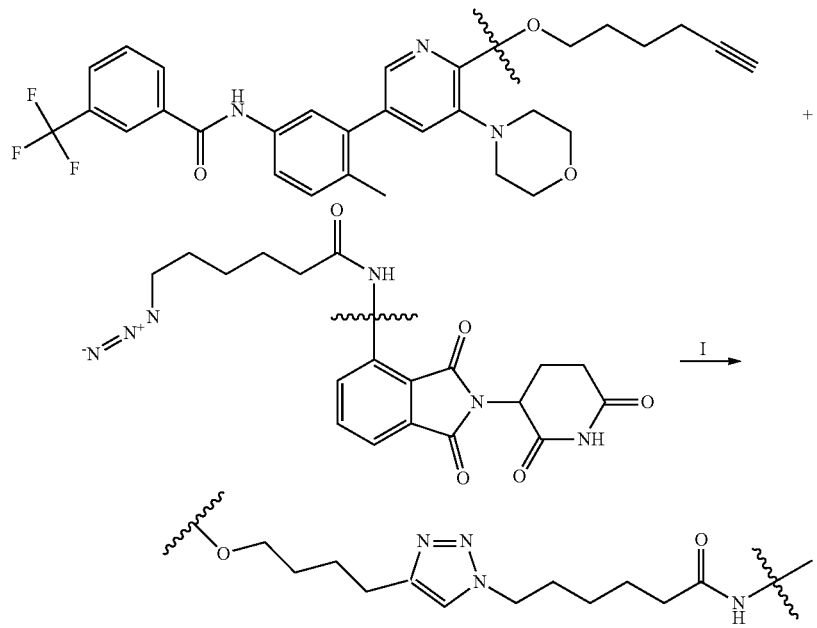

Title compound (57.3 mg, 37.1%) was prepared as pale yellow solid from N-(3-(6-(hex-5-yn-1-yloxy)-5-morpholin-opyridin-3-yl)-4-methylphenyl)-3-(trifluoromethyl)benz-amide (Example 21) (87.4 mg, 0.163 mmol), and 6-azido-N-(2-(2,6-dioxopiperidin-3-yl)-1,3-dioxoisoindolin-4-yl) hexanamide (Example 8) (72.3 mg, 0.175 mmol) as described for as described in Example 22. Rf=0.26 (5% MeOH in DCM). $^1$H NMR (400 MHz, CDCl$_3$) δ 9.38 (s, 1H), 8.78 (d, J=8.6 Hz, 1H), 8.23 (s, 1H), 8.13 (s, 1H), 8.07 (d, J=8.0 Hz, 1H), 7.98 (s, 1H), 7.80 (d, J=7.8 Hz, 1H), 7.74 (d, J=2.0 Hz, 1H), 7.72-7.67 (m, 1H), 7.62 (dd, J=16.9, 9.1 Hz, 2H), 7.53 (d, J=7.3 Hz, 1H), 7.46 (s, 1H), 7.31 (s, 1H), 7.28 (d, J=8.5 Hz, 1H), 7.04 (d, J=2.0 Hz, 1H), 4.94 (dd, J=12.3, 5.4 Hz, 1H), 4.43 (t, J=6.3 Hz, 2H), 4.34 (t, J=7.1 Hz, 2H), 3.90-3.84 (m, 4H), 3.12 (d, J=4.3 Hz, 4H), 2.91 (d, J=15.1 Hz, 1H), 2.81 (dd, J=12.6, 5.7 Hz, 2H), 2.45 (t, J=7.4 Hz, 2H), 2.26 (s, 3H), 2.20-2.13 (m, 1H), 1.94 (dt, J=25.5, 11.0 Hz, 6H), 1.79 (dt, J=14.9, 7.3 Hz, 2H), 1.42 (dd, J=15.7, 8.1 Hz, 2H), 1.26 (t, J=7.2 Hz, 2H). $^{19}$F NMR (376 MHz, CDCl$_3$) δ −63.12 (s). LRMS, m/z, calculated for C$_{49}$H$_{50}$F$_3$N$_9$O$_8$, 949.37; found, 972.45 (M+Na)$^+$. HPLC, t$_R$=10.61 min (purity, >99.9%).

The following examples describe (1) the preparation of Ligands for RAF with a Linker Component and (2) the preparation of RAF-Degrading Conjugate Compounds of the following generic formulae:

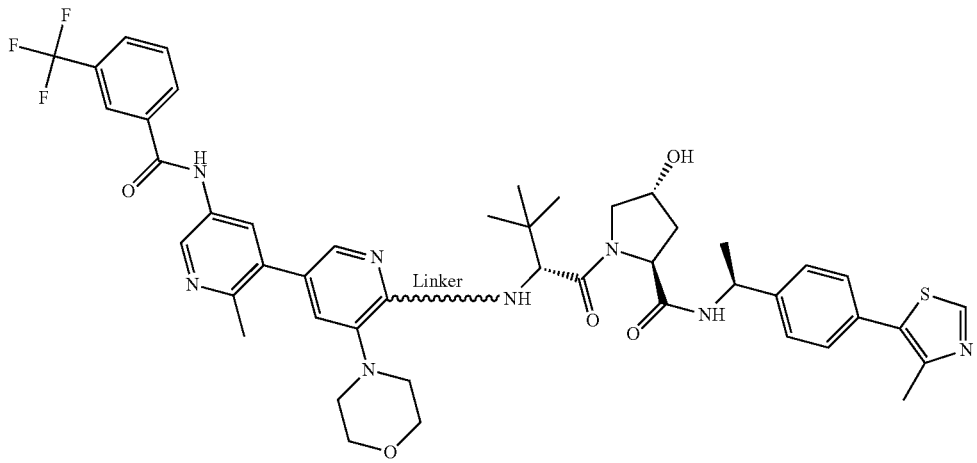 [SMILES: Cc1ncc(NC(=O)c2cccc(C(F)(F)F)c2)cc1-c1cnc(N[C@@H](C(=O)N2C[C@H](O)C[C@H]2C(=O)N[C@@H](C)c2ccc(-c3scnc3C)cc2)C(C)(C)C)c(N2CCOCC2)c1]

(1) Preparation of Ligands for RAF with a Linker Component

Example 35—Synthesis of 2-(2-(2-(2-((2'-methyl-5-morpholino-5'-(3-(trifluoromethyl)benzamido)-[3,3'-bipyridin]-6-yl)oxy)ethoxy)ethoxy)ethoxy)acetic Acid (for Compound 1.013)

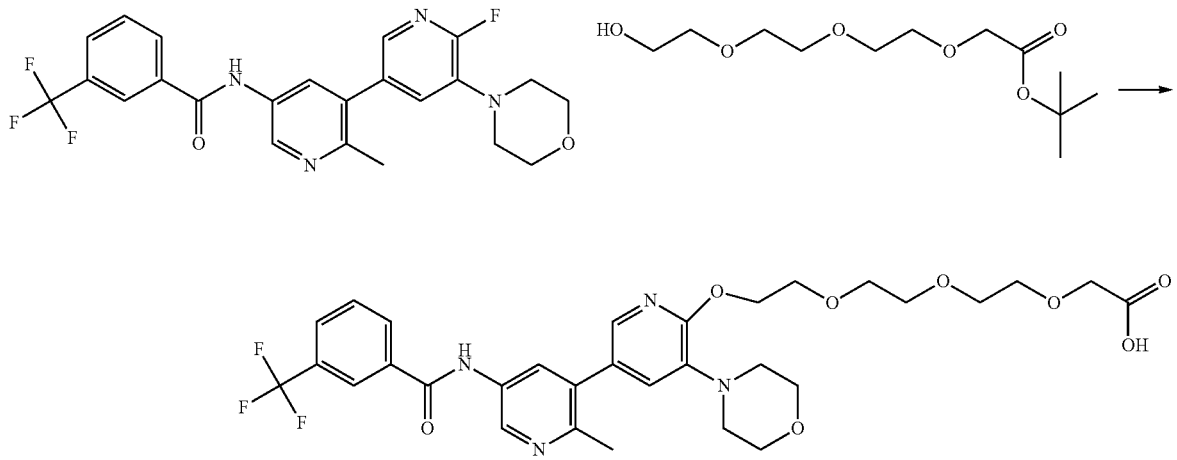

To stirred solution of tert-butyl 2-(2-(2-(2-hydroxyethoxy)ethoxy)ethoxy)acetate (287 mg, 1.09 mmol) in DMF (1.5 mL) was added sodium hydride (43.4 mg, 1.09 mmol, 60% dispersion in oil), after stirred for 30 min, N-(6'-fluoro-2-methyl-5'-morpholino-[3,3'-bipyridin]-5-yl)-3-(trifluoromethyl)benzamide (100 mg, 0.217 mmol) was added, placed it on pre-heated oil bath at 80° C., stirred for 1 h, TLC showed mostly starting material, additional amount of sodium hydride (43.4 mg) was added, heated for 1 h, no more SM, most polar product was formed. Reaction mixture was cooled to rt, it was acidified with aq 1 N HCl, extracted with ethyl acetate (3×10 mL), combined extracts were washed, dried ($Na_2SO_4$), and concentrated. LRMS showed the presence of desired mass. The residue was purified on 12 g $SiO_2$ cartridge using a gradient of MeOH in DCM to afford title compound (28 mg, 19.9%) as beige solid. This product contains small amount of 2-(2-(2-(2-hydroxyethoxy)ethoxy)ethoxy)acetic acid. This material was used as such in the next step without further purification. LRMS, m/z, calculated for $C_{31}H_{35}F_3N_4O_8$, 648.24, found, 647.17 (M−H)⁻.

(2) Preparation of RAF-Degrading Conjugate Compounds

Example 36—Synthesis of (2S,4R)-1-((R)-2-(tert-butyl)-14-((2'-methyl-5-morpholino-5'-(3-(trifluoromethyl)benza-mido)-[3,3'-bipyridin]-6-yl)oxy)-4-oxo-6,9,12-trioxa-3-azatetradecan-1-oyl)-4-hydroxy-N—((S)-1-(4-(4-methylthiazol-5-yl)phenyl)ethyl)pyrrolidine-2-carboxamide (Compound 1.013)

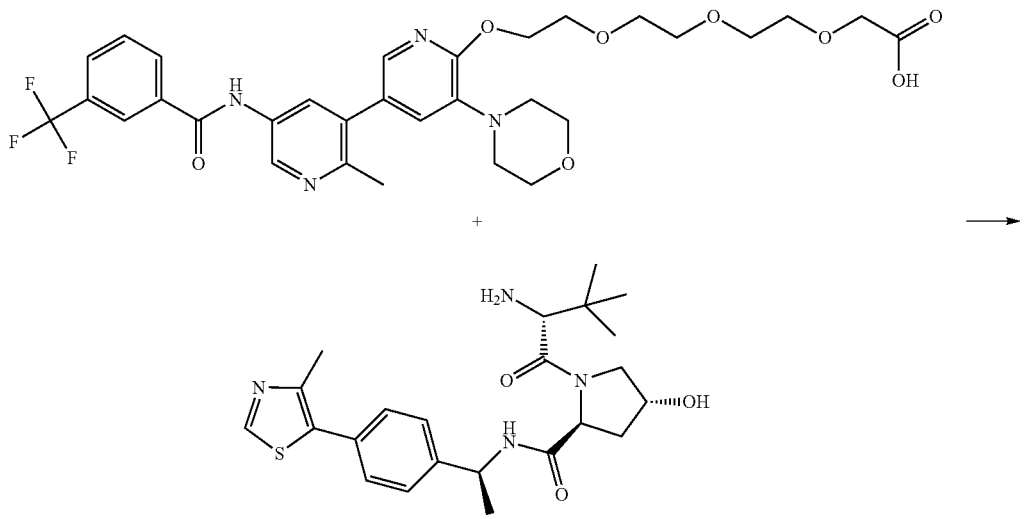

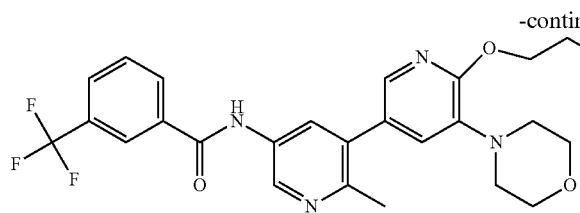
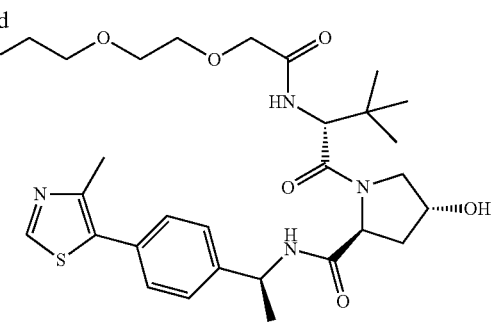

To a cold (0° C.) stirred solution of 2-(2-(2-(2-((2'-methyl-5-morpholino-5'-(3-(trifluoromethyl)benzamido)-[3,3'-bipyridin]-6-yl)oxy)ethoxy)ethoxy)ethoxy)acetic acid (Example 35) (25 mg, 0.0385 mmol) and (2S,4R)-1-((R)-2-amino-3,3-dimethylbutanoyl)-4-hydroxy-N—((S)-1-(4-(4-methylthiazol-5-yl)phenyl)ethyl)pyrrolidine-2-carboxamide (17.1 mg, 0.0385 mmol) and HATU (44 mg, 0.116 mmol) in DMF (0.8 mL) was added neat DIPEA (33.6 µL, 0.193 mmol), slowly warmed up to rt, stirred for over weekend (72 h), diluted with water (3 mL), extracted with ethyl acetate (3×5 mL), combined extracts were washed with satd. bicarbonate solution, brine, dried (Na$_2$SO$_4$), concentrated. The residue was absorbed on 2 g of Celite, purified on 12 g SiO$_2$ cartridge using a gradient of MeOH in DCM (0 to 20%) to afford title compound (18 mg, 43.4%) as white solid.

Rf=0.45 (10% MeOH in DCM). $^1$H NMR (400 MHz, CDCl$_3$) δ 9.10 (s, 1H), 8.81-8.77 (m, 1H), 8.65 (s, 1H), 8.20 (s, 1H), 8.10 (d, J=7.8 Hz, 1H), 8.04 (d, J=2.2 Hz, 1H), 7.78 (d, J=7.8 Hz, 1H), 7.73 (d, J=2.0 Hz, 1H), 7.57 (t, J=7.8 Hz, 1H), 7.43 (d, J=7.5 Hz, 1H), 7.36-7.28 (m, J=8.3 Hz, 5H), 7.09 (d, J=1.9 Hz, 1H), 5.06-4.95 (m, 1H), 4.78-4.65 (m, 2H), 4.62-4.53 (m, 2H), 4.46 (s, 1H), 4.06-3.84 (m, 8H), 3.79-3.51 (m, 10H), 3.21-3.10 (m, 4H), 2.49 (s, 3H), 2.48 (s, 3H), 2.40-2.31 (m, 1H), 2.18-2.05 (m, 1H), 1.44 (d, J=6.9 Hz, 3H), 0.97 (s, 9H). $^{19}$F NMR (376 MHz, CDCl$_3$) δ -63.01 (s). LRMS, m/z, calculated for C$_{54}$H$_{65}$F$_3$N$_8$O$_{10}$S, 1074.45; found, 1073.43 (M–H)$^-$; 1097.42 (M+Na)$^+$. HPLC, t$_R$=10.14 min (purity, 98.69%).

Example 37 to Example 53 describes the synthesis of Compounds 2.001 to 2.009, each of these conjugates are embraced by the following Formula

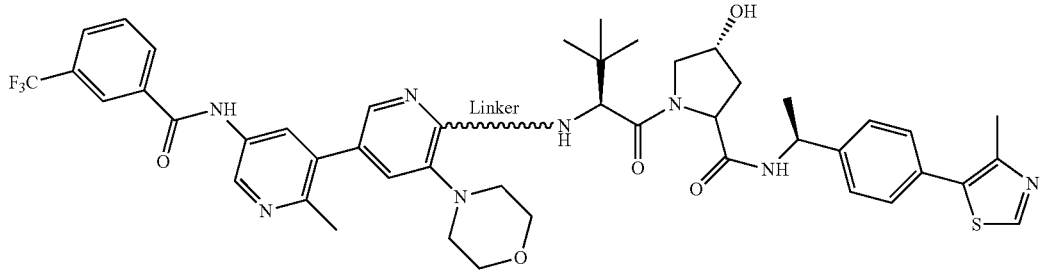 [SMILES: Cc1ncc(NC(=O)c2cccc(C(F)(F)F)c2)cc1-c1cnc(N[C@H](C(=O)N2C[C@H](O)CC2C(=O)N[C@@H](C)c2ccc(-c3scnc3C)cc2)C(C)(C)C)c(N2CCOCC2)c1]

Example 37—Synthesis of 17-((2'-methyl-5-morpholino-5'-(3-(trifluoromethyl)benzamido)-[3,3'-bipyridin]-6-yl)oxy)-3,6,9,12,15-pentaoxaheptadecan-1-oic Acid (for Compound 2.001)

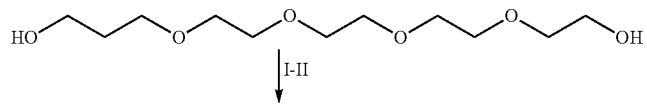

↓ I-II

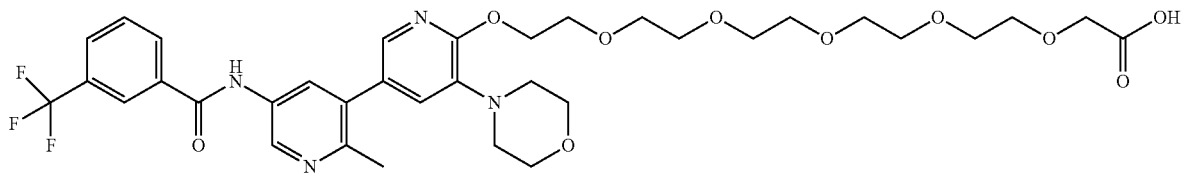

Step I: tert-butyl 17-hydroxy-3,6,9,12,15-pentaoxaheptadecan-1-oate

To a cold (0° C.) stirred solution of tert-butyl 2-bromoacetate (5.4 mL, 36.6 mmol) and 3,6,9,12-tetraoxatetradecane-1,14-diol (27.0 mL, 128 mmol) in DMSO (50.0 mL) was added NaH (1.6033 g, 40.1 mmol, 60% in oil) in 2 portions. The reaction mixture was warmed up to rt, stirred for 20 h, diluted with water (50 mL), and saturated with NaCl (60 g), it was extracted with ether (3×100 mL) [aqueous solution was re-extracted with ethyl acetate (4×50 mL) to afford 7.5 g* which contains PEG, DMSO] organic extracts were dried to afford crude product (8.0 g) [1H NMR contains the presence of PEG, DMSO and oil]. The residue (8.0 g) was dissolved in ether (50 mL), washed with water (5×5 mL), passed through a phase separator, concentrated to afford 1.75 g of the product, $^1$H NMR showed small amount of the oil and it was removed with a pipette to afford the title compound (1.1 g, 8.5%) as oil. The aqueous solution was concentrated to afford the title product (4.85 g, 37.6%). $^1$H NMR showed small of amount of DMSO, PEG. *The residue (7.5 g) was dissolved in DCM (50 mL) and diluted with water (50 mL), passed through a phase separator, pholino-[3,3'-bipyridin]-5-yl)-3-(trifluoromethyl)benzamide (275 mg, 0.597 mmol) in one portion, it was placed it on pre-heated oil bath at 80° C. for 45 min, cooled to rt, water and aq. 1 N HCl was added (adjusted to pH4-5), concentrated, the crude residue was purified in two batches on reverse phase SiO$_2$ cartridge (86 g) using acetonitrile in water (5-100%) to afford the title compound (130 mg, 29.%). $^1$HNMR showed the presence of some PEG acid, this material was used as such in the next step without further purification. Rf=0.3 (30% MeOH in DCM). $^1$H NMR (400 MHz, CDCl$_3$) δ 10.59 (s, 1H), 9.14 (s, 1H), 8.41 (s, 1H), 8.35 (d, J=7.3 Hz, 1H), 8.13 (s, 1H), 7.76-7.68 (m, 2H), 7.56 (t, J=7.8 Hz, 1H), 7.06 (s, 1H), 4.60-4.44 (m, 2H), 3.98-3.53 (m, 24H), 3.18-3.01 (m, 4H), 2.47 (s, 3H). LRMS, m/z, calculated for C$_{35}$H$_{43}$F$_3$N$_4$O$_{10}$, 736.29; found, 735.17 (M−H)$^-$; 759.05 (M+Na)$^+$.

Example 38—Synthesis of (2S,4R)-1-((R)-2-(tert-butyl)-20-((2'-methyl-5-morpholino-5'-(3-(trifluoromethyl)-benzamido)-[3,3'-bipyridin]-6-yl)oxy)-4-oxo-6,9,12,15,18-pentaoxa-3-azaicosan-1-oyl)-4-hydroxy-N—((S)-1-(4-(4-methylthiazol-5-yl)phenyl)ethyl)pyrrolidine-2-carboxamide (Compound 2.001)

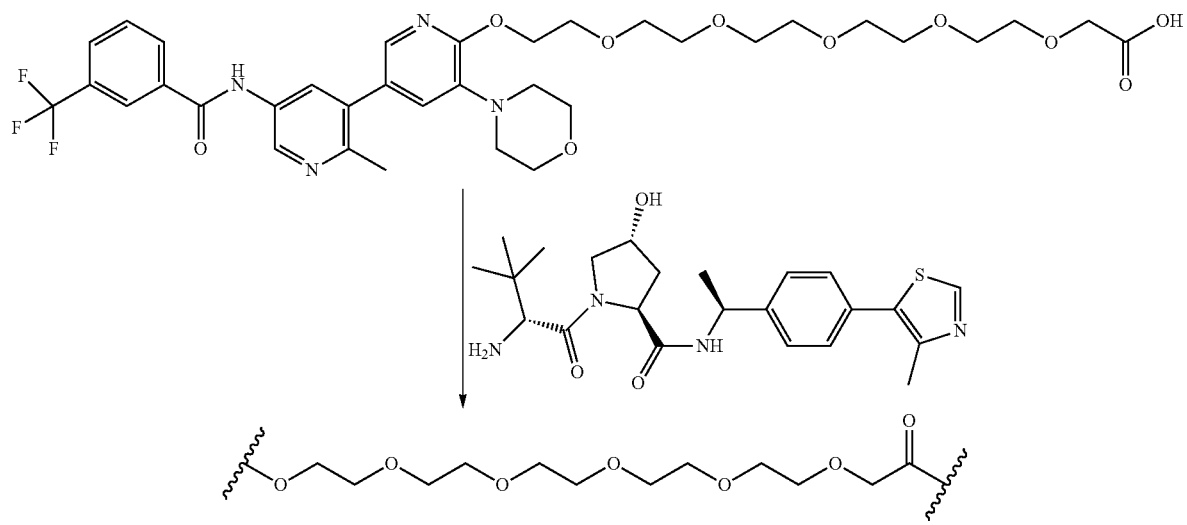

organic solution was diluted with water (20 mL), stirred for 5 min, passed through a phase separator, concentrated to afford the title product (2.7 g, 21%). $^1$H NMR showed small amount of PEG and DMSO. Rf=0.09 (EtOAc). $^1$H NMR (400 MHz, CDCl$_3$) δ 4.02 (s, 2H), 3.75-3.58 (m, 20H), 1.47 (s, 9H). LRMS (ESI) m/z: calculated for C$_{16}$H$_{32}$O$_8$, 352.21; found 374.83 (M+Na)$^+$.

Step II, 17-((2'-methyl-5-morpholino-5'-(3-(trifluoromethyl)benzamido)-[3,3'-bipyridin]-6-yl)oxy)-3,6,9,12,15-pentaoxaheptadecan-1-oic Acid To a stirred solution of tert-butyl 17-hydroxy-3,6,9,12,15-pentaoxaheptadecan-1-oate (1.05 g, 2.99 mmol) in 1,4-dioxane (4.2 mL) was added 60% sodium hydride (251 mg, 6.27 mmol, 60% in oil), after stirred at rt for 30 min, PEG was crashed out and turned into sphere ball, sonicated, did not help, DMF (1 mL) was added, sonicated, to the resultant suspension was added N-(6'-fluoro-2-methyl-5'-mor- To a cold (0° C.) stirred solution of 17-((2'-methyl-5-morpholino-5'-(3-(trifluoro-methyl)benzamido)-[3,3'-bipyridin]-6-yl)oxy)-3,6,9,12,15-pentaoxaheptadecan-1-oic acid (130 mg, 0.176 mmol) and (2S,4R)-1-((R)-2-amino-3,3-dimethylbutanoyl)-4-hydroxy-N—((S)-1-(4-(4-methylthiazol-5-yl)phenyl)ethyl)pyrrolidine-2-carboxamide (17.1 mg, 0.0385 mmol) and HATU (44 mg, 0.116 mmol) in DMF (0.8 mL) was added neat DIPEA (33.6 µL, 0.193 mmol), slowly warmed up to rt, stirred over weekend (72 h), diluted with water (4 mL), extracted with ethyl acetate (3×5 mL), combined extracts were washed with brine, dried (Na$_2$SO$_4$), and concentrated. The residue was purified on 24 g Gold SiO$_2$ cartridge (Isco) using a gradient of methanol in DCM (0 to 20%) to afford the title compound (48 mg, 23.4%) as white solid. Rf=0.36 (10% MeOH in DCM). $^1$H NMR (400 MHz, CDCl$_3$) δ 9.24 (s, 1H), 8.78 (d, J=2.2 Hz, 1H), 8.67 (s, 1H), 8.25 (s, 1H), 8.22-8.14 (m, 2H), 7.80 (d, J=7.9 Hz, 1H), 7.72 (d, J=1.9 Hz, 1H), 7.61 (t, J=7.8 Hz, 1H), 7.45 (d, J=7.8 Hz, 1H), 7.38-7.28 (m, 5H), 7.04 (d, J=1.9 Hz, 1H), 5.08-4.98 (m, 1H), 4.74 (t, J=7.8 Hz, 1H), 4.62-4.54 (m, 3H), 4.49 (s, 1H), 4.05-3.83 (m, 10H), 3.74-3.55 (m, 16H), 3.18-3.10 (m, 4H), 2.50 (s, 6H), 2.47-2.41 (m, 1H), 2.13-2.02 (m, 1H), 1.45 (d, J=6.9 Hz, 3H), 1.03 (s, 9H). $^{19}$F NMR (376 MHz, CDCl$_3$) δ −63.04 (s). LRMS, m/z, calculated for $C_{58}H_{73}F_3N_8O_{12}S$, 1162.5; found, 1161.33 (M−H)$^-$; 1185.2 (M+Na)$^+$; HPLC, $t_R$=9.94 min (purity, 98%).

Example 39—Synthesis of 14-((2'-methyl-5-morpholino-5'-(3-(trifluoromethyl)benzamido)-[3,3'-bipyridin]-6-yl)oxy)-3,6,9,12-tetraoxatetradecan-1-oic Acid (for Compound 2.002)

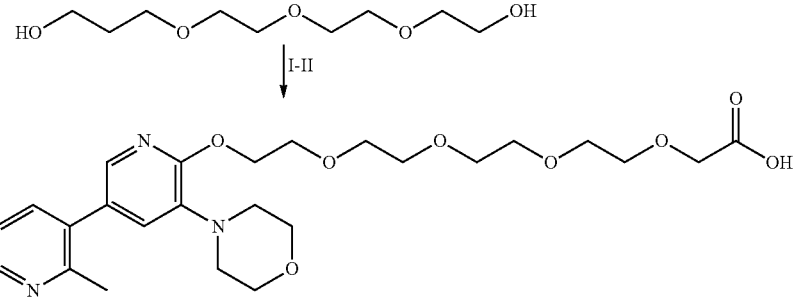

Step I, tert-butyl 14-hydroxy-3,6,9,12-tetraoxatetradecan-1-oate

To a cold (0° C.) stirred solution of tert-butyl 2-bromoacetate (5.4 mL, 36.6 mmol) and 2,2'-((oxybis(ethane-2,1-diyl))bis(oxy))diethanol (35.0 mL, 203 mmol) in DMSO (50 mL) was added NaH (1.6217 g, 40.6 mmol, 60% in oil) in two portions. The reaction mixture was slowly warmed up to rt, stirred for 23 h, diluted with water (50 mL), saturated with NaCl (50 g), stirred for 5 min, extracted with Et$_2$O (3×100 mL), and concentrated. The residue was taken in DCM (50 mL) and water (25 mL), stirred for 5 min. The organic solution was passed through a phase separator, concentrated and purified on a 80 g SiO$_2$ cartridge using a gradient of ethyl acetate in hexanes (50-100%) to afford the title compound (8.2 g, 72.7% yield) as a pale yellow oil. Rf=0.08 (EtOAc). $^1$H NMR (400 MHz, CDCl$_3$) δ 4.02 (d, J=1.0 Hz, 2H), 3.75-3.60 (m, 12H), 1.47 (s, 9H) ppm. LRMS (ESI) m/z: calculated for $C_{14}H_{28}O_7$ 308.3679; found 330.95 (M+Na)$^+$; Found 347.01 (M+K)$^+$.

Step II, 14-((2'-methyl-5-morpholino-5'-(3-(trifluoromethyl)benzamido)-[3,3'-bipyridin]-6-yl)oxy)-3,6,9,12-tetraoxatetradecan-1-oic Acid To a stirred solution of tert-butyl 14-hydroxy-3,6,9,12-tetraoxatetradecan-1-oate (983.6 mg, 3.19 mmol) in dioxane (4.5 mL) was added sodium hydride (280.1 mg, 7.02 mmol, 60% in mineral oil) at rt, stirred for 30 minutes. The reaction mixture was turned from pale colorless to beige, to this was added N-(6'-fluoro-2-methyl-5'-morpholino-[3,3'-bipyridin]-5-yl)-3-(trifluoromethyl)benzamide (300.5 mg, 0.635 mmol), after 15 min, a beige precipitate was formed, turned into lump, DMF (1 mL) was added to break up the lump. The reaction mixture was heated at 80° C. for 1 h and cooled down to rt, acidified with aq. 1 M HCl (~0.1 mL), the resulting mixture was stirred for 5 minutes at rt, and concentrated. The residue was purified on 40 g SiO$_2$ cartridge using a gradient of MeOH in DCM (0 to 10%) to afford the title compound (70 mg, 15.5% yield) as yellow oil. Rf=0.15 (20% MeOH in DCM) $^1$H NMR (400 MHz, CDCl$_3$) δ 10.44 (s, 1H), 9.18 (s, 1H), 8.41 (s, 1H), 8.31 (d, J=7.8 Hz, 1H), 7.95 (s, 1H), 7.75-7.69 (m, 2H), 7.56 (t, J=7.8 Hz, 1H), 7.06 (d, J=1.7 Hz, 1H), 4.54 (s, 2H), 3.84 (m, 6H), 3.75-3.48 (m, 14H), 3.08 (s, 4H), 2.45 (s, 3H) ppm. $^{19}$F NMR (376 MHz, CDCl3) δ −62.95 (s) ppm. LRMS (ESI) m/z: calculated for $C_{33}H_{39}F_3N_4O_9$, 692.27; found 691.07 (M−H)$^-$.

Example 40—Synthesis of N-(6'-(((16R)-16-((2R,4S)-4-hydroxy-2-(((S)-1-(4-(4-methylthiazol-5-yl)phenyl)ethyl)carbamoyl)cyclopentanecarbonyl)-17,17-dimethyl-14-oxo-3,6,9,12-tetraoxa-15-azaoctadecyl)oxy)-2-methyl-5'-morpholino-[3,3'-bipyridin]-5-yl)-3-(trifluoromethyl)benzamide (Compound 2.002)

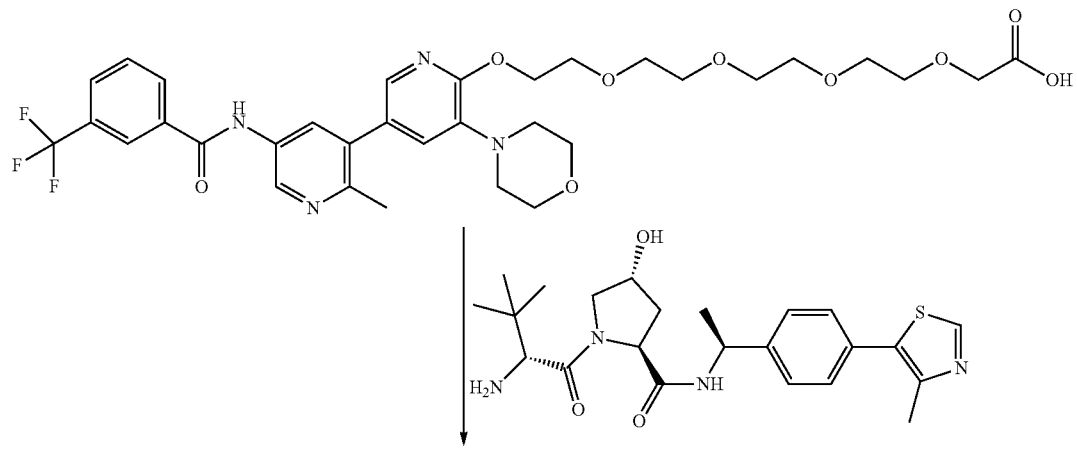

-continued

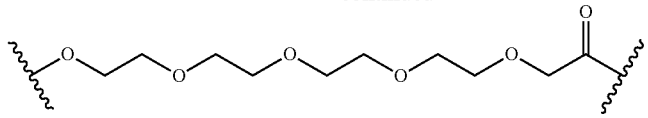

Title compound (19.2 mg, 28.3%) was prepared as an off-white solid from 14-((2'-methyl-5-morpholino-5'-(3-(trifluoromethyl)benzamido)-[3,3'-bipyridin]-6-yl)oxy)-3,6,9,12-tetraoxatetradecan-1-oic acid (42.0 mg, 60.6 μmol) and (2S,4R)-1-((R)-2-amino-3,3-dimethylbutanoyl)-4-hydroxy-N—((S)-1-(4-(4-methylthiazol-5-yl)phenyl)ethyl)pyrrolidine-2-carboxamide (35 mg, 0.0789 mmol) as described in Example 38. Rf=0.25 (5% MeOH in DCM). $^1$H NMR (400 MHz, CDCl$_3$) δ 9.27 (s, 1H), 8.66 (s, 1H), 8.63 (s, 1H), 8.26-8.19 (m, 2H), 8.15 (d, J=7.9 Hz, 1H), 7.80 (d, J=7.9 Hz, 1H), 7.73 (d, J=1.9 Hz, 1H), 7.61 (t, J=7.8 Hz, 1H), 7.43 (t, J=7.6 Hz, 2H), 7.39 (d, J=8.3 Hz, 2H), 7.34 (d, J=8.2 Hz, 2H), 7.04 (d, J=1.8 Hz, 1H), 5.07 (m, 1H), 4.75 (t, J=7.9 Hz, 1H), 4.63 (d, J=8.9 Hz, 1H), 4.59-4.53 (m, 2H), 4.48 (bs, 1H), 4.02-3.85 (m, 10H), 3.74-3.53 (m, 14H), 3.21-3.09 (m, 4H), 2.51 (s, 3H), 2.48 (s, 3H), 2.07 (dd, J=13.4, 8.3 Hz, 1H), 1.47 (d, J=6.9 Hz, 3H), 1.04 (s, 9H) ppm. $^{19}$F NMR (376 MHz, CDCl$_3$) δ −62.97 (s) ppm. LRMS (ESI) m/z: calculated for C$_{57}$H$_{70}$F$_3$N$_7$O$_{11}$S, 1117.48; found 1119.22 (M+H)$^+$; found 1141.15 (M+Na)$^+$; found 1157.15 (M+K)$^+$. HPLC, t$_R$=9.99 min (purity, >99%). HPLC Method: Cartridge, Agilent, Zorbax-SB-CN, 3.5 μm, 4.6×150 mm, mobile phase, acetonitrile in water (0 to 100%) contains ammonium acetate buffer; flow rate, 1.5 mL/min, run time, 20 min.

Example 41—Synthesis of (2S,4R)-1-((R)-2-(6-bromohexanamido)-3,3-dimethylbutanoyl)-4-hydroxy-N—((S)-1-(4-(4-methylthiazol-5-yl)phenyl)ethyl)pyrrolidine-2-carboxamide, Method A (for Compound 2.003)

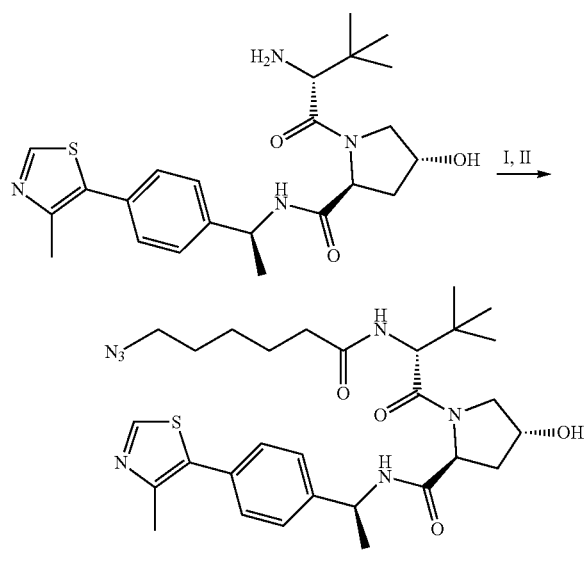

Step I, (2S,4R)-1-((R)-2-(6-bromohexanamido)-3,3-dimethylbutanoyl)-4-hydroxy-N—((S)-1-(4-(3-methylthiophen-2-yl)phenyl)ethyl)pyrrolidine-2-carboxamide To a stirred solution of 6-bromohexanoic acid (400.5 mg, 2.05 mmol) in DMF (8.0 mL) was sequentially added (2S,4R)-1-((R)-2-amino-3,3-dimethylbutanoyl)-4-hydroxy-N—((S)-1-(4-(4-methylthiazol-5-yl)phenyl)ethyl)pyrrolidine-2-carboxamide (912.7 mg, 2.05 mmol) and HATU (859.2 mg, 2.26 mmol) followed by DIPEA (0.72 mL, 4.13 mmol). The reaction mixture was stirred at rt for 53 h, diluted with water (50 mL), extracted with EtOAc (6×20 mL). Combined organic extracts were washed with aq. 1M HCl (20 mL), aq. saturated NaHCO$_3$ solution (20 mL), water (20 mL), brine (20 mL), dried (Na$_2$SO$_4$), and concentrated. The residue was purified on 80 g gold SiO$_2$ cartridge using a gradient of methanol in DCM (0-10%) to afford the title compound (780.0 mg, 61.1%) as a white solid. Rf=0.44 (10% MeOH in DCM). $^1$H NMR (400 MHz, CDCl$_3$) δ 8.68 (s, 1H), 7.45-7.34 (m, 4H), 6.09 (d, J=8.3 Hz, 1H), 5.08 (p, J=7.1 Hz, 1H), 4.74 (t, J=7.8 Hz, 1H), 4.53 (d, J=8.3 Hz, 2H), 4.13 (d, J=11.5 Hz, 1H), 3.60 (dd, J=11.5, 3.4 Hz, 1H), 3.40 (t, J=6.7 Hz, 1H), 2.78 (d, J=3.8 Hz, 1H), 2.63-2.54 (m, 1H), 2.53 (s, 3H), 2.23 (t, J=7.5 Hz, 2H), 2.12-2.01 (m, 1H), 1.90-1.83 (m, 1H), 1.82-1.73 (m, 2H), 1.70-1.59 (m, 2H), 1.47 (d, J=6.9 Hz, 3H), 1.05 (s, 9H). LRMS, m/z, calculated for C$_{29}$H$_{41}$BrN$_4$O$_9$S, 620.20; found, 643.07 (M+Na)$^+$.

Step II, (2S,4R)-1-((R)-2-(6-azidohexanamido)-3,3-dimethylbutanoyl)-4-hydroxy-N—((S)-1-(4-(4-methylthiazol-5-yl)phenyl)ethyl)pyrrolidine-2-carboxamide To a stirred solution of (2S,4R)-1-((R)-2-(6-bromohexanamido)-3,3-dimethylbutanoyl)-4-hydroxy-N—((S)-1-(4-(4-methylthiazol-5-yl)phenyl)ethyl)pyrrolidine-2-carboxamide (780.0 mg, 1.25 mmol) in DMSO (15.0 mL) was sequentially added potassium iodide (212.7 mg, 1.28 mmol) and sodium azide (326.5 mg, 5.02 mmol). The reaction mixture was stirred at rt for 16 h, diluted with water (50 mL), extracted with Et$_2$O (4×20 mL). The combined organic extracts were dried (Na$_2$SO$_4$), and concentrated, The residue was purified on 40 g gold SiO$_2$ cartridge using a gradient of methanol in DCM (0-15%) to afford the title compound (600 mg, 81.9%) as a white solid. Rf=0.51 (10% MeOH in DCM). $^1$H NMR (400 MHz, CDCl$_3$) δ 8.68 (s, 1H), 7.44-7.35 (m, 5H), 6.13 (d, J=8.6 Hz, 1H), 5.08 (p, J=7.0 Hz, 1H), 4.73 (t, J=7.8 Hz, 1H), 4.55 (d, J=8.7 Hz, 1H), 4.10 (d, J=11.4 Hz, 1H), 3.61 (dd, J=11.3, 3.7 Hz, 1H), 3.53 (t, J=6.6 Hz, 1H), 3.26 (t, J=6.8 Hz, 1H), 3.06 (bs, 1H), 2.62 (s, 1H), 2.57 (dd, J=8.0, 5.2 Hz, 1H), 2.54 (s, 3H), 2.22 (t, J=7.4 Hz, 2H), 2.10-2.01 (m, 1H), 1.83 (s, 1H), 1.81-1.72 (m, 1H), 1.69-1.54 (m, 3H), 1.47 (d, J=6.9 Hz, 2H), 1.45-1.35 (m, 2H), 1.05 (s, 9H). LRMS, m/z, calculated (for C$_{29}$H$_{41}$N$_7$O$_4$S), 583.29; Found, 606.14 (M+Na)$^+$; Found, 581.95 (M−H)$^−$.

Example 42—Synthesis of (2S,4R)-1-((R)-3,3-dimethyl-2-(6-(4-((2-(2-(2-((2'-methyl-5-morpholino-5'-(3-(trifluoromethyl)benzamido)-[3,3'-bipyridin]-6-yl)oxy)ethoxy)ethoxy)ethoxy)methyl)-1H-1,2,3-triazol-1-yl)hexanamido)butanoyl)-4-hydroxy-N—((S)-1-(4-(4-methylthiazol-5-yl)phenyl)ethyl)pyrrolidine-2-carboxamide (Compound 2.003)

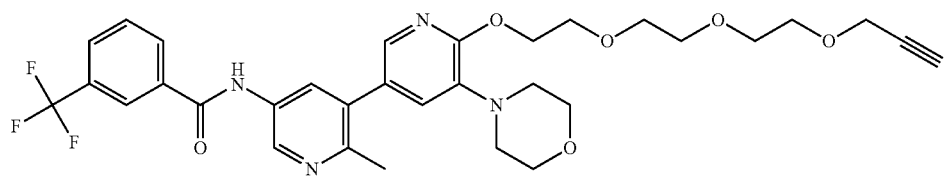

Title compound (34.9 mg, 51.7%) was prepared as pale yellow solid from N-(2-methyl-5'-morpholino-6'-(2-(2-(2-(prop-2-yn-1-yloxy)ethoxy)ethoxy)ethoxy)-[3,3'-bipyridin]-5-yl)-3-(trifluoromethyl)benzamide (35.0 mg, 0.0557 mmol) and (2S,4R)-1-((R)-2-(6-azidohexanamido)-3,3-dimethylbutanoyl)-4-hydroxy-N—((S)-1-(4-(4-methylthiazol-5-yl)phenyl)ethyl)pyrrolidine-2-carboxamide (35.8 mg, 0.0612 mmol) as described in Example 22. Rf=0.17 (5% MeOH in DCM). $^1$H NMR (400 MHz, CDCl$_3$) δ 9.51 (s, 1H), 8.66 (s, 2H), 8.26 (d, J=13.8 Hz, 2H), 8.18 (d, J=7.8 Hz, 1H), 7.79 (d, J=7.6 Hz, 1H), 7.71 (s, 1H), 7.61 (t, J=7.8 Hz, 1H), 7.50 (s, 1H), 7.36 (q, J=8.1 Hz, 5H), 7.02 (s, 1H), 6.33 (d, J=8.9 Hz, 1H), 5.11-5.02 (m, 1H), 4.77-4.64 (m, 3H), 4.63-4.54 (m, 4H), 4.52 (s, 1H), 4.19 (t, J=7.0 Hz, 2H), 3.88 (dd, J=9.4, 4.3 Hz, 6H), 3.69 (d, J=4.7 Hz, 2H), 3.61 (s, 6H), 3.13 (s, 4H), 2.49 (d, J=9.6 Hz, 3H), 2.47 (s, 3H), 2.24-2.06 (m, 4H), 1.73 (dtd, J=21.1, 14.0, 7.1 Hz, 2H), 1.60-1.50 (m, 2H), 1.47 (d, J=6.8 Hz, 3H), 1.21 (dd, J=15.5, 7.9 Hz, 2H), 1.02 (s, 9H) ppm. $^{19}$F NMR (376 MHz, CDCl$_3$) δ −63.01 (s) ppm. LRMS, m/z, calculated for C$_{61}$H$_{76}$F$_3$N$_{11}$O$_9$, 1211.54; found, 1234.25 (M+Na)$^+$. HPLC, t$_R$=9.91 min (purity, >99%).

Example 43—Synthesis of (2S,4R)-1-((R)-2-(6-bromohexanamido)-3,3-dimethylbutanoyl)-4-hydroxy-N—((S)-1-(4-(4-methylthiazol-5-yl)phenyl)ethyl)pyrrolidine-2-carboxamide, Method A (for Compound 2.004)

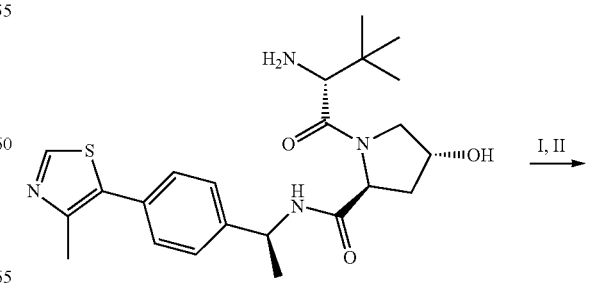

-continued

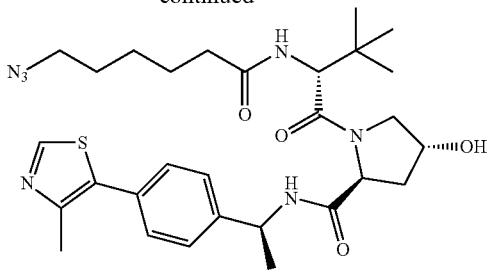

Step I, (2S,4R)-1-((R)-2-(6-bromohexanamido)-3,3-dimethylbutanoyl)-4-hydroxy-N—((S)-1-(4-(3-methylthiophen-2-yl)phenyl)ethyl)pyrrolidine-2-carboxamide To a stirred solution of 6-bromohexanoic acid (400.5 mg, 2.05 mmol) in DMF (8.0 mL) was sequentially added (2S,4R)-1-((R)-2-amino-3,3-dimethylbutanoyl)-4-hydroxy-N—((S)-1-(4-(4-methylthiazol-5-yl)phenyl)ethyl)pyrrolidine-2-carboxamide (912.7 mg, 2.05 mmol) and HATU (859.2 mg, 2.26 mmol) followed by DIPEA (0.72 mL, 4.13 mmol). The reaction mixture was stirred at rt for 53 h, diluted with water (50 mL), extracted with EtOAc (6×20 mL). Combined organic extracts were washed with aq. 1M HCl (20 mL), aq. saturated NaHCO$_3$ solution (20 mL), water (20 mL), brine (20 mL), dried (Na$_2$SO$_4$), and concentrated. The residue was purified on 80 g gold SiO$_2$ cartridge using a gradient of methanol in DCM (0-10%) to afford the title compound (780.0 mg, 61.1%) as a white solid. Rf=0.44 (10% MeOH in DCM). $^1$H NMR (400 MHz, CDCl$_3$) δ 8.68 (s, 1H), 7.45-7.34 (m, 4H), 6.09 (d, J=8.3 Hz, 1H), 5.08 (p, J=7.1 Hz, 1H), 4.74 (t, J=7.8 Hz, 1H), 4.53 (d, J=8.3 Hz, 2H), 4.13 (d, J=11.5 Hz, 1H), 3.60 (dd, J=11.5, 3.4 Hz, 1H), 3.40 (t, J=6.7 Hz, 1H), 2.78 (d, J=3.8 Hz, 1H), 2.63-2.54 (m, 1H), 2.53 (s, 3H), 2.23 (t, J=7.5 Hz, 2H), 2.12-2.01 (m, 1H), 1.90-1.83 (m, 1H), 1.82-1.73 (m, 2H), 1.70-1.59 (m, 2H), 1.47 (d, J=6.9 Hz, 3H), 1.05 (s, 9H). LRMS, m/z, calculated for C$_{29}$H$_{41}$BrN$_4$O$_9$S, 620.20; found, 643.07 (M+Na)$^+$.

Step II, (2S,4R)-1-((R)-2-(6-azidohexanamido)-3,3-dimethylbutanoyl)-4-hydroxy-N—((S)-1-(4-(4-methylthiazol-5-yl)phenyl)ethyl)pyrrolidine-2-carboxamide To a stirred solution of (2S,4R)-1-((R)-2-(6-bromohexanamido)-3,3-dimethylbutanoyl)-4-hydroxy-N—((S)-1-(4-(4-methylthiazol-5-yl)phenyl)ethyl)pyrrolidine-2-carboxamide (780.0 mg, 1.25 mmol) in DMSO (15.0 mL) was sequentially added potassium iodide (212.7 mg, 1.28 mmol) and sodium azide (326.5 mg, 5.02 mmol). The reaction mixture was stirred at rt for 16 h, diluted with water (50 mL), extracted with Et$_2$O (4×20 mL). The combined organic extracts were dried (Na$_2$SO$_4$), and concentrated, The residue was purified on 40 g gold SiO$_2$ cartridge using a gradient of methanol in DCM (0-15%) to afford the title compound (600 mg, 81.9%) as a white solid. Rf=0.51 (10% MeOH in DCM). $^1$H NMR (400 MHz, CDCl$_3$) δ 8.68 (s, 1H), 7.44-7.35 (m, 5H), 6.13 (d, J=8.6 Hz, 1H), 5.08 (p, J=7.0 Hz, 1H), 4.73 (t, J=7.8 Hz, 1H), 4.55 (d, J=8.7 Hz, 1H), 4.10 (d, J=11.4 Hz, 1H), 3.61 (dd, J=11.3, 3.7 Hz, 1H), 3.53 (t, J=6.6 Hz, 1H), 3.26 (t, J=6.8 Hz, 1H), 3.06 (bs, 1H), 2.62 (s, 1H), 2.57 (dd, J=8.0, 5.2 Hz, 1H), 2.54 (s, 3H), 2.22 (t, J=7.4 Hz, 2H), 2.10-2.01 (m, 1H), 1.83 (s, 1H), 1.81-1.72 (m, 1H), 1.69-1.54 (m, 3H), 1.47 (d, J=6.9 Hz, 2H), 1.45-1.35 (m, 2H), 1.05 (s, 9H). LRMS, m/z, calculated (for C$_{29}$H$_{41}$N$_7$O$_4$S), 583.29; Found, 606.14 (M+Na)$^+$; Found, 581.95 (M−H)$^-$.

Example 44—Synthesis of (2R*,4S*)—N-(2-methyl-5'-morpholino-6'-((2-((prop-2-yn-1-yloxy)methyl)tetrahy-dro-2H-pyran-4-yl)oxy)-[3,3'-bipyridin]-5-yl)-3-(trifluoromethyl)-benzamide (for Compound 2.004)

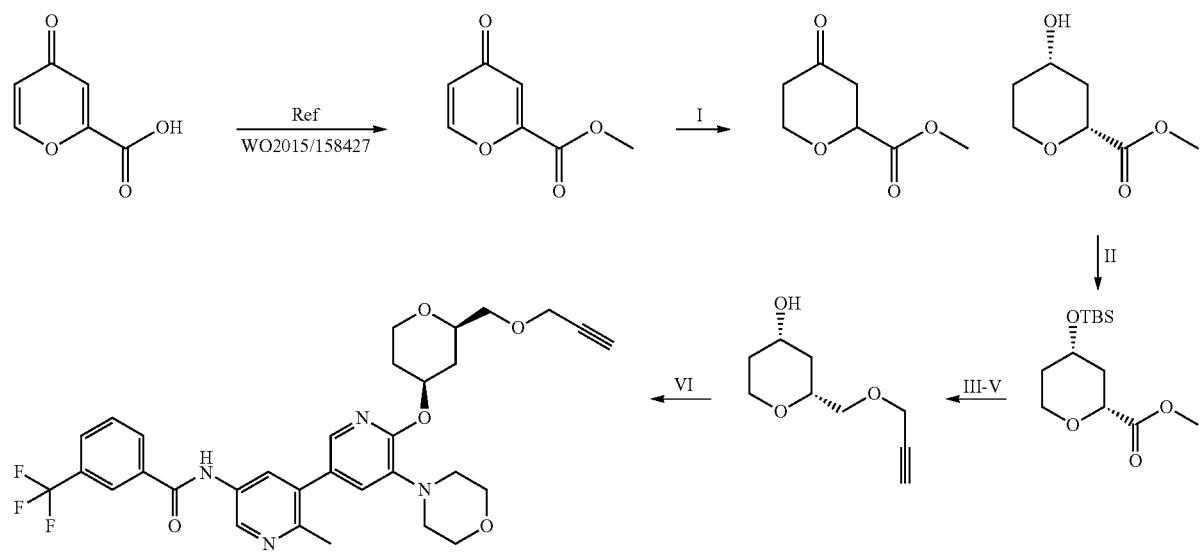

Step I, (2R*,4S*)-Methyl 4-hydroxytetrahydro-2H-pyran-2-carboxylate

Argon gas was bubbled through a solution of crude methyl 4-oxo-4H-pyran-2-carboxylate (5 g, 32.4 mmol) (Ref: WO2015/158427, p-34) in methanol (100 mL) for 5 min, 10% Pd on activated charcoal (1.59 g) was added, stirred under hydrogen atmosphere using balloon (two balloons inserted into each other) for 40 h, filtered off the catalyst, rinsed with methanol (50 mL), the filtrate was concentrated. The residue was purified on 2×100 g SiO$_2$ cartridge using a gradient of ethyl acetate in hexanes (0-100%) to afford methyl 4-oxotetrahydro-2H-pyran-2-carboxylate (1.56 g, 30.4%) and title compound (3.03 g, 58.3%) as colorless oil. Methyl 4-oxotetrahydro-2H-pyran-2-carboxylate. $^1$H NMR (400 MHz, CDCl$_3$) δ 4.41 (ddd, J=11.7, 7.0, 2.5 Hz, 1H), 4.32 (dd, J=10.8, 3.9 Hz, 1H), 3.82 (s, 3H), 3.78 (dd, J=11.6, 3.4 Hz, 1H), 2.77-2.60 (m, 3H), 2.46-2.38 (m, 1H). (2R*,4S*)-methyl 4-hydroxytetrahydro-2H-pyran-2-carboxylate. $^1$H NMR (400 MHz, CDCl$_3$) δ 4.18 (ddd, J=11.9, 4.7, 2.5 Hz, 1H), 4.00 (dd, J=11.3, 2.6 Hz, 1H), 3.94-3.84 (m, 1H), 3.79 (s, 3H), 3.48 (td, J=11.9, 2.4 Hz, 1H), 2.35-2.27 (m, 1H), 1.97-1.87 (m, 1H), 1.73 (d, J=3.9 Hz, 1H), 1.66-1.52 (m, 2H). The relative stereochemistry of the hydroxyl group was tentatively assigned as Cis.

Step II, (2R*,4S*)-methyl 4-((tert-butyldimethylsilyl)oxy)tetrahydro-2H-pyran-2-carboxylate To a stirred solution of (2R*,4S*)-methyl 4-hydroxytetrahydro-2H-pyran-2-carboxylate (3.04 g, 19 mmol) and imidazole (1.94 g, 20.9 mmol) in DCM (32 mL) was added tert-butyldimethylsilyl chloride (3.15 g, 20.9 mmol) at rt, after stirred for 2 h, filtered off the solids, rinsed with ether, combined filtrate was concentrated. The residue was taken in ether (100 mL), washed with water (30 mL), dried (Na$_2$SO$_4$), and concentrated to afford the title compound (5.2 g, 99.8%) as colorless oil. Rf=0.6 (EtOAc). $^1$H NMR (400 MHz, CDCl$_3$) δ 4.14 (ddd, J=11.8, 4.5, 3.0 Hz, 1H), 3.98 (dd, J=11.0, 2.8 Hz, 1H), 3.88-3.78 (m, 1H), 3.76 (s, 3H), 3.44 (td, J=11.7, 2.5 Hz, 1H), 2.18-2.09 (m, 1H), 1.80-1.71 (m, 1H), 1.65-1.53 (m, 2H), 0.87 (s, 9H), 0.06 (s, 6H).

Step III, (2R*,4S*)-4-((tert-butyldimethylsilyl)oxy)tetrahydro-2H-pyran-2-yl)methanol To a cold (0° C.) stirred solution of LiAlH$_4$ in THF (28.4 mL, 56.8 mmol) was added a solution of (2R*,4S*)-methyl 4-((tert-butyldimethylsilyl)oxy)tetrahydro-2H-pyran-2-carboxylate (5.2 g, 18.9 mmol) in THF (4 mL), stirred for 2 h (bath temp reached to 10 C), cooling bath was removed, stirred for 1 h, cooled with ice-bath, water (2.06 mL) and 15% aq. NaOH (2.06 mL) was added dropwise (extreme caution), to the resultant white solid was added water (6.9 mL), stirred for 10 min, diluted with ether (100 mL), filtered off, rinsed with ether (100 mL), combined filtrate was dried, and concentrated. The residue was purified on 40 g SiO$_2$ cartridge using a gradient of ethyl acetate in hexanes (0-100%) to afford the title compound (4.08 g, 87.4%) as colorless oil. Rf=0.42 (60% EtOAc in Hexanes). $^1$H NMR (400 MHz, CDCl$_3$) δ 4.01 (ddd, J=11.7, 4.7, 1.6 Hz, 1H), 3.83-3.73 (m, 1H), 3.63-3.51 (m, 2H), 3.46-3.38 (m, 2H), 1.98 (dd, J=7.7, 4.8 Hz, 1H), 1.80-1.69 (m, 2H), 1.61-1.50 (m, 1H), 1.37-1.25 (m, 1H), 0.88 (s, 9H), 0.06 (s, 6H).

Step IV, (2R*,4S*)-tert-butyldimethyl((2-((prop-2-yn-1-yloxy)methyl)tetrahydro-2H-pyran-4-yl)oxy)silane To a cold (ice) stirred suspension of sodium hydride (312 mg, 7.79 mmol, 60% in oil) in THF (9 mL) was added a solution of (2R*,4S*)-4-((tert-butyldimethylsilyl)oxy)tetrahydro-2H-pyran-2-yl)methanol (960 mg, 3.9 mmol) in THF (3 mL), after stirred for 50 min, TBAI (126 mg, 0.39 mmol) and a solution of propargyl bromide (1.16 mL, 7.79 mmol, 80% solution in toluene) was added, let it warmed up to rt, stirred for 3 h, heated at 50° C. for 3 hours, let it stirred over weekend (conversion is more than >85%), cooled with ice bath, poured into cold sat. ammonium chloride solution, extracted with ethyl acetate (3×30 mL), combined extracts were washed with brine, dried (Na$_2$SO$_4$), and concentrated. The residue was purified on 40 g SiO$_2$ cartridge using a gradient of ethyl acetate in hexanes (0-50% and 100%) to afford the title compound (600 mg, 54.1%) as colorless oil. Rf=0.45 (20% ethyl acetate in hexanes). $^1$H NMR (400 MHz, CDCl$_3$) δ 4.24 (dd, J=15.9, 2.4 Hz, 1H), 4.18 (dd, J=15.9, 2.4 Hz, 1H), 4.05-3.98 (m, 1H), 3.81-3.71 (m, 1H), 3.58-3.48 (m, 3H), 3.41 (td, J=12.3, 2.1 Hz, 1H), 2.43 (t, J=2.4 Hz, 1H), 1.82-1.70 (m, 2H), 1.63-1.46 (m, 1H), 1.40-1.24 (m, 1H), 0.88 (s, 9H), 0.06 (s, 6H).

Step V, (2R*,4S*)-2-((prop-2-yn-1-yloxy)methyl)tetrahydro-2H-pyran-4-ol

A solution of TBAF (3.16 mL, 3.16 mmol) in THF was added to (2R*,4S*)-tert-butyldimethyl((2-((prop-2-yn-1-yloxy)methyl)tetrahydro-2H-pyran-4-yl)oxy)silane (600 mg, 2.11 mmol), heated at 50° C. for 2 h, cooled to rt, concentrated. The residue was purified on 40 g SiO$_2$ cartridge using a gradient of ethyl acetate in hexanes (0-100%) to afford the title compound (355 mg, 99%) as colorless oil. Rf=0.39 (EtOAc). $^1$H NMR (400 MHz, CDCl$_3$) δ 4.24 (dd, J=15.9, 2.4 Hz, 1H), 4.19 (dd, J=15.9, 2.4 Hz, 1H), 4.07 (ddd, J=11.8, 4.8, 1.6 Hz, 1H), 3.87-3.77 (m, 1H), 3.59-3.52 (m, 3H), 3.44 (td, J=12.2, 2.0 Hz, 1H), 2.44 (t, J=2.4 Hz, 1H), 1.98-1.86 (m, 2H), 1.61-1.46 (m, 2H), 1.38-1.23 (m, 1H).

Step VI, (2R*,4S*)—N-(2-methyl-5'-morpholino-6'-((2-((prop-2-yn-1-yloxy)methyl)tetrahy-dro-2H-pyran-4-yl)oxy)-[3,3'-bipyridin]-5-yl)-3-(trifluoromethyl)-benzamide To a stirred solution of (2R*,4S*)-2-((prop-2-yn-1-yloxy)methyl)tetrahydro-2H-pyran-4-ol (121 mg, 0.713 mmol) in 1,4-dioxane (1.2 mL) was added sodium hydride (28.5 mg, 0.713 mmol, 60% in oil), after stirred at rt for 30 min, N-(6'-fluoro-2-methyl-5'-morpholino-[3,3'-bipyridin]-5-yl)-3-(trifluoromethyl)benzamide (73 mg, 0.159 mmol) was added in one portion, it was placed on pre-heated oil bath at 80° C. for 2 h 15 min. The reaction mixture was cooled to rt, poured into water (10 mL), extracted with ethyl acetate (3×10 mL), combined extracts were washed with brine, dried (Na$_2$SO$_4$), and concentrated. The residue was purified on 25 g SiO$_2$ cartridge using a gradient of methanol in methylene chloride (0-15%) to afford the title compound (44 mg, 45.4%) as colorless oil. Rf=0.2 (50% EtOAc). $^1$H NMR (400 MHz, CDCl$_3$) δ 8.67-8.58 (m, 2H), 8.20-8.14 (m, 2H), 8.11 (d, J=7.8 Hz, 1H), 7.86-7.79 (m, 1H), 7.74 (d, J=1.9 Hz, 1H), 7.64 (t, J=7.7 Hz, 1H), 7.04 (d, J=1.8 Hz, 1H), 5.43-5.28 (m, 1H), 4.28-4.02 (m, 3H), 3.92-3.85 (m, 4H), 3.83-3.69 (m, 1H), 3.67-3.50 (m, 3H), 3.18-3.06 (m, 4H), 2.49 (s, 3H), 2.46-2.40 (m, 1H), 2.32-2.17 (m, 2H), 1.96-1.74 (m, 2H), 1.65-1.50 (m, 1H). $^{19}$F NMR (376 MHz, CDCl$_3$) δ −63.10 (s). LRMS, m/z, calculated for C$_{32}$H$_{33}$F$_3$N$_4$O$_5$, 610.24, found, 609.02 (M−H)$^-$.

Example 45—Synthesis of (2S,4R)-1-((R)-3,3-dimethyl-2-(6-(4-((((2R*,4S*)-4-((2'-methyl-5-morpholino-5'-(3-(trifluoromethyl)benzamido)-[3,3'-bipyridin]-6-yl)oxy)tetrahydro-2H-pyran-2-yl)methoxy)methyl)-1H-1,2,3-triazol-1-yl)hexanamido)butanoyl)-4-hydroxy-N—((S)-1-(4-(4-methylthiazol-5-yl)phenyl)ethyl)pyrrolidine-2-carboxamide (Compound 2.004)

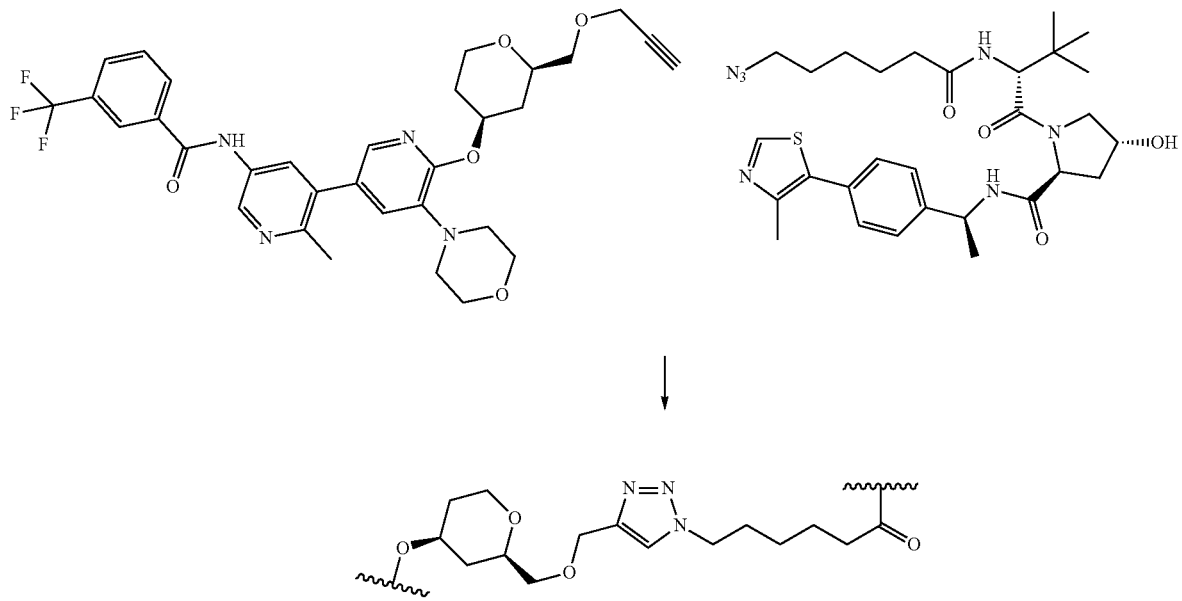 [SMILES: C#CCOC[C@H]1C[C@@H](Oc2ncc(-c3cc(NC(=O)c4cccc(C(F)(F)F)c4)cnc3C)cc2N2CCOCC2)CCO1 ; Cc1ncsc1-c1ccc([C@H](C)NC(=O)[C@@H]2C[C@@H](O)CN2C(=O)[C@H](NC(=O)CCCCCN=[N+]=[N-])C(C)(C)C)cc1 ; *O[C@H]1CCO[C@@H](COCc2cn(CCCCCC(*)=O)nn2)C1]

In RBF, racemic-N-(2-methyl-5'-morpholino-6'-(((2R*,4S*)-2-((prop-2-yn-1-yloxy)methyl)tetrahydro-2H-pyran-4-yl)oxy)-[3,3'-bipyridin]-5-yl)-3-(trifluoromethyl)-benzamide (44 mg, 0.072 mmol), (2S,4R)-1-((R)-2-(6-azidohexanamido)-3,3-dimethylbutanoyl)-4-hydroxy-N—((S)-1-(4-(4-methylthiazol-5-yl)phenyl)ethyl)pyrrolidine-2-carboxamide (50.5 mg, 0.0865 mmol) in THF (1.2 mL) was added a solution of copper sulphate pentahydrate (3.6 mg, 0.0144 mmol) in water (0.3 mL) and sodium ascorbate (2.86 mg, 0.0144 mmol) in water (0.3 mL), purged with argon, stirred for 42 h. The reaction mixture was concentrated, absorbed on the Celite® using 5% MeOH in DCM, purified on 25 g $SiO_2$ cartridge using a gradient of methanol in DCM (0 to 15%) to afford diastereomeric mixture of the title compound (28.5 mg, 33.1%) as light yellow solid. Rf=0.15 (10% methanol in DCM). $^1$H NMR (400 MHz, $CDCl_3$) δ 9.39-9.20 (m, 1H), 8.67 (s, 1H), 8.64-8.59 (m, 1H), 8.29-8.22 (m, 2H), 8.17 (d, J=8.1 Hz, 1H), 7.81 (d, J=7.6 Hz, 1H), 7.70 (s, 1H), 7.62 (t, J=7.8 Hz, 1H), 7.54 (d, J=2.4 Hz, 1H), 7.44-7.32 (m, 5H), 7.06-7.00 (m, 1H), 6.34-6.26 (m, 1H), 5.39-5.31 (m, 1H), 5.13-5.02 (m, 1H), 4.78-4.63 (m, 4H), 4.52 (s, 1H), 4.32-4.24 (m, 2H), 4.16-4.07 (m, 1H), 4.00 (d, J=11.2 Hz, 1H), 3.91-3.82 (m, 4H), 3.77-3.68 (m, 1H), 3.65-3.53 (m, 4H), 3.16-3.04 (m, 4H), 2.55-2.45 (m, 6H), 2.31-2.06 (m, 5H), 1.86-1.73 (m, 3H), 1.64-1.51 (m, 3H), 1.48 (d, J=6.9 Hz, 3H), 1.31-1.22 (m, 3H), 1.03 (s, 9H). $^{19}$F NMR (376 MHz, $CDCl_3$) δ −63.01 (s). LRMS, m/z, calculated for $C_{61}H_{74}F_3N_{11}O_9S$, 1193.53; found, 1194.16 (M+H)+; 1216.91 (M+Na)+; 1192.01 (M−H)−. HPLC, $t_R$=9.997 min (purity, 97%).

Example 46—Synthesis of (±)-N-(2-methyl-5'-morpholino-6'-(((2S*,4S*)-2-((prop-2-yn-1-yloxy)methyl)tetrahydro-2H-pyran-4-yl)oxy)-[3,3'-bipyridin]-5-yl)-3-(trifluoromethyl)benzamide (for Compound 2.005)

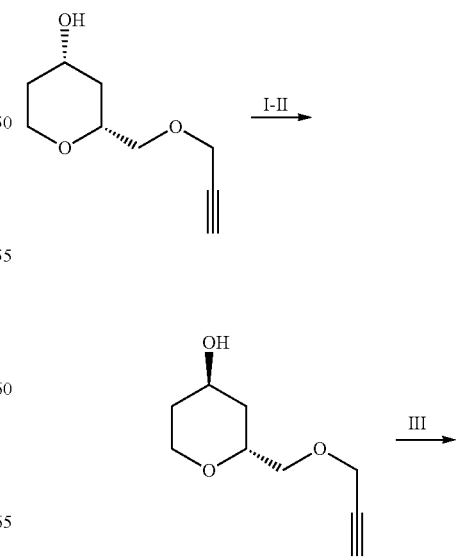

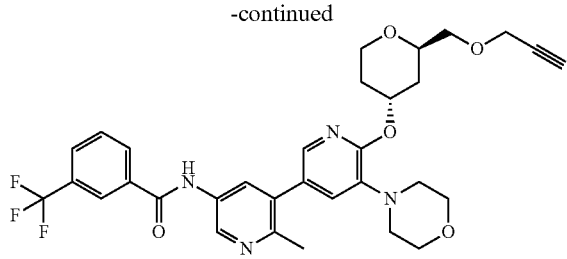

Step I, (±)-(2S*,4S*)-2-((prop-2-yn-1-yloxy)methyl)tetrahydro-2H-pyran-4-yl benzoate To a stirred solution of racemic (2S*,4R*)-2-((prop-2-yn-1-yloxy)methyl)tetrahydro-2H-pyran-4-ol (355 mg, 2.09 mmol) in THF (9 mL) was added sequentially triphenylphosphine (821 mg, 3.13 mmol) and benzoic acid (382 mg, 3.13 mmol). To the resultant solution was added neat diisopropylazodicarboxylate (0.615 uL, 3.13 mmol) [slightly exotherm], stirred at rt for 24 h, solvent was removed and purified on 40 g SiO$_2$ cartridge using a gradient of ethyl acetate in hexanes (0-70%) to afford the title compound (720 mg, quant, 79.5% purity) as colorless oil. Rf=0.28 (50% EtOAc in hexanes). $^1$H NMR (400 MHz, CDCl$_3$) δ 7.61-7.38 (m, 5H), 5.51-5.43 (m, 1H), 4.25 (dd, J=15.9, 2.4 Hz, 1H), 4.20 (dd, J=15.9, 2.4 Hz, 1H), 4.08-4.00 (m, 1H), 4.00-3.90 (m, 2H), 3.62-3.51 (m, 2H), 2.43 (t, J=2.4 Hz, 1H), 2.03-1.73 (m, 4H).

Step II, (±)-(2S*,4S*)-2-((prop-2-yn-1-yloxy)methyl)tetrahydro-2H-pyran-4-ol To a stirred solution of (±)-(2S*,4S*)-2-((prop-2-yn-1-yloxy)methyl)tetrahydro-2H-pyran-4-yl benzoate (720 mg, 2.09 mmol, 79.5% purity) in methanol (7 mL) was added aq. LiOH solution (4.2 mL, 4.2 mmol) at rt, reaction mixture was stirred at rt for 16 h, methanol was evaporated, diluted with water (5 mL), extracted with DCM (3×10 mL), combined extracts were washed with brine, dried (Na$_2$SO$_4$), and concentrated. The residue was purified on 25 g SiO$_2$ cartridge using a gradient of ethyl acetate in hexanes (0-100%) to afford the title compound (290 mg, 81.7% overall yield for two steps) as colorless oil. Rf=0.4 (EtOAc). $^1$H NMR (400 MHz, CDCl$_3$) δ 4.31-4.26 (m, 1H), 4.21 (t, J=2.1 Hz, 2H), 4.05-3.97 (m, 1H), 3.96-3.88 (m, 1H), 3.84 (dd, J=11.6, 4.2 Hz, 1H), 3.55 (dd, J=10.2, 3.5 Hz, 1H), 3.51 (dd, J=10.2, 6.2 Hz, 1H), 2.43 (t, J=2.4 Hz, 1H), 1.88 (dddd, J=14.0, 12.7, 5.5, 2.8 Hz, 1H), 1.73-1.54 (m, 3H), 1.41 (brs, 1H). LRMS, m/z, calculated for C$_9$H$_{14}$O$_3$, 170.09; found, 192.93 (M+Na)$^+$.

Step III, (±)-N-(2-methyl-5'-morpholino-6'-(((2S*,4S*)-2-((prop-2-yn-1-yloxy)methyl)tetrahydro-2H-pyran-4-yl)oxy)-[3,3'-bipyridin]-5-yl)-3-(trifluoromethyl)benzamide To a stirred solution of (±)-(2S*,4S*)-2-((prop-2-yn-1-yloxy)methyl)tetrahydro-2H-pyran-4-ol (286 mg, 1.68 mmol) in 1,4-dioxane (1.2 mL) was added sodium hydride (28.5 mg, 0.713 mmol, 60% in oil), after stirred at rt for 30 min, N-(6'-fluoro-2-methyl-5'-morpholino-[3,3'-bipyridin]-5-yl)-3-(trifluoromethyl)benzamide (155 mg, 0.337 mmol) was added in one portion, it was placed on pre-heated oil bath at 80° C. for 2 h 15 min. The reaction mixture was cooled to rt, poured into water (10 mL), extracted with ethyl acetate (3×10 mL), combined extracts were washed with brine, dried (Na$_2$SO$_4$), concentrated. The residue was purified on 25 g SiO$_2$ cartridge using a gradient of methanol in methylene chloride (0-15%) to afford the title compound (80 mg, 38.9%) as colorless oil. Rf=0.2 (50% EtOAc in hexanes). $^1$H NMR (400 MHz, CDCl$_3$) δ 8.60 (s, 1H), 8.32 (s, 1H), 8.20-8.12 (m, 2H), 8.10 (d, J=7.8 Hz, 1H), 7.83 (d, J=7.8 Hz, 1H), 7.76 (d, J=2.0 Hz, 1H), 7.65 (t, J=7.8 Hz, 1H), 7.06 (s, 1H), 5.68-5.62 (m, 1H), 5.47-5.39 (m, 1H), 4.27-4.18 (m, 1H), 4.07-3.92 (m, 2H), 3.92-3.84 (m, 4H), 3.64-3.49 (m, 2H), 3.23-3.12 (m, 4H), 2.51 (s, 3H), 2.43 (t, J=2.3 Hz, 1H), 2.09-1.94 (m, 3H), 1.85-1.73 (m, 1H). LRMS, m/z, calculated for C$_{32}$H$_{33}$F$_3$N$_4$O$_5$, 610.24, found, 633.09 (M+Na)$^+$; 608.96 (M–H)$^-$.

Example 47—Synthesis of (2S,4R)-1-((R)-3,3-dimethyl-2-(6-(4-((((2R,4R)-4-((2'-methyl-5-morpholino-5'-(3-(trifluoromethyl)benzamido)-[3,3'-bipyridin]-6-yl)oxy)tetrahydro-2H-pyran-2-yl)methoxy)methyl)-1H-1,2,3-triazol-1-yl)hexanamido)butanoyl)-4-hydroxy-N—((S)-1-(4-(4-methylthiazol-5-yl)phenyl)ethyl)pyrrolidine-2-carboxamide and (2S,4R)-1-((R)-3,3-dimethyl-2-(6-(4-((((2S,4S)-4-((2'-methyl-5-morpholino-5'-(3-(trifluoromethyl)benzamido)-[3,3'-bipyridin]-6-yl)oxy)tetrahydro-2H-pyran-2-yl)methoxy)methyl)-1H-1,2,3-triazol-1-yl)hexanamido)butanoyl)-4-hydroxy-N—((S)-1-(4-(4-methylthiazol-5-yl)phenyl)ethyl)pyrrolidine-2-carboxamide (Compound 2.005)

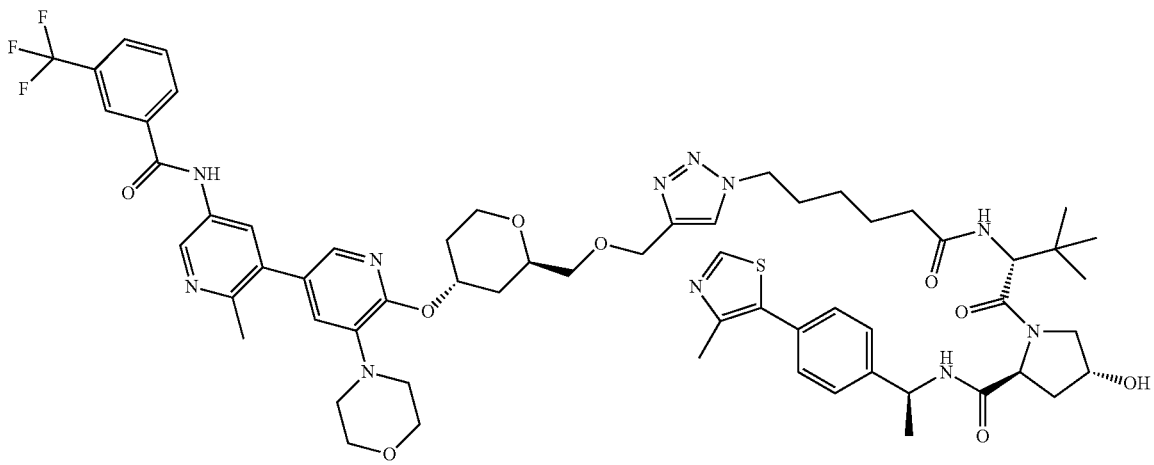 [SMILES: Cc1ncc(NC(=O)c2cccc(C(F)(F)F)c2)cc1-c1cnc(O[C@@H]2CCO[C@@H](COCc3cn(CCCCCC(=O)N[C@@H](C(=O)N4C[C@H](O)C[C@H]4C(=O)N[C@@H](C)c4ccc(-c5scnc5C)cc4)C(C)(C)C)nn3)C2)c(N2CCOCC2)c1]

Diasteromeric mixture of the title compounds (28 mg, 17.9%) were prepared as light yellow solid from N-(2-methyl-5'-morpholino-6'-(((2R,4R)-2-((prop-2-yn-1-yloxy)methyl)tetrahydro-2H-pyran-4-yl)oxy)-[3,3'-bipyridin]-5-yl)-3-(trifluoromethyl)benzamide and N-(2-methyl-5'-morpholino-6'-(((2S,4S)-2-((prop-2-yn-1-yloxy)methyl)tetrahydro-2H-pyran-4-yl)oxy)-[3,3'-bipyridin]-5-yl)-3-(trifluoromethyl)benzamide (80 mg, 0.131 mmol) and (2S,4R)-1-((R)-2-(6-azidohexanamido)-3,3-dimethylbutanoyl)-4-hydroxy-N—((S)-1-(4-(4-methylthiazol-5-yl)phenyl)ethyl)pyrrolidine-2-carboxamide (91.8 mg, 0.157 mmol) as described in 2.004. $^1$H NMR (400 MHz, CDCl$_3$; ~1:1 diastereoisomeric mixture) δ 9.40-9.31 (m, 1H), 8.67 (s, 1H), 8.61 (s, 1H), 8.30-8.23 (m, 2H), 8.17 (d, J=7.7 Hz, 1H), 7.80 (d, J=7.8 Hz, 1H), 7.74-7.70 (m, 1H), 7.62 (t, J=7.8 Hz, 1H), 7.52 (d, J=6.0 Hz, 1H), 7.44-7.32 (m, 5H), 7.07-7.01 (m, 1H), 6.31 (d, J=8.7 Hz, 1H), 5.60 (brs, 1H), 5.12-5.02 (m, 1H), 4.77-4.70 (m, 1H), 4.69-4.65 (m, 3H), 4.52 (brs, 1H), 4.32-4.19 (m, 2H), 4.03-3.91 (m, 3H), 3.88-3.82 (m, 4H), 3.68-3.45 (m, 4H), 3.20-3.08 (m, 3H), 2.51 (s, 3H), 2.50 (s, 3H), 2.26-1.90 (m, 6H), 1.85-1.67 (m, 3H), 1.64-1.50 (m, 3H), 1.48 (d, J=6.8 Hz, 3H), 1.30-1.21 (m, 2H), 1.03 (s, 9H). $^{19}$F NMR (376 MHz, CDCl$_3$) δ -63.01 (s). LRMS, m/z, calculated for C$_{61}$H$_{74}$F$_3$N$_{11}$O$_9$S, 1193.53; found, 1217.1 (M+Na)$^+$; 1192.23 (M−H)$^-$. HPLC, t$_R$=10.04 min (purity, 98.7%).

Example 48—Synthesis of N-(6'-(2-(2-(2-(2-hydroxyethoxy)ethoxy)ethoxy)ethoxy)-2-methyl-5'-morpholino-[3,3'-bipyridin]-5-yl)-3-(trifluoromethyl) benzamide (for 2.006)

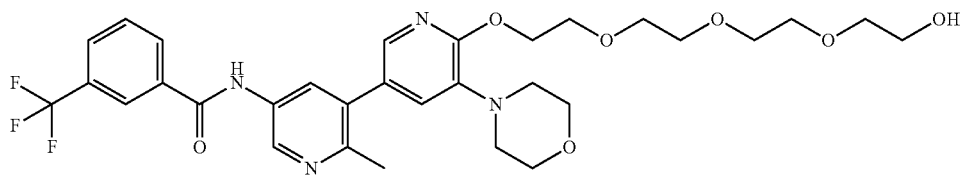 [SMILES: Cc1ncc(NC(=O)c2cccc(C(F)(F)F)c2)cc1-c1cnc(OCCOCCOCCOCCO)c(N2CCOCC2)c1]

Title compound (115 mg, 33.4%) was prepared as gum from 2,2'-((oxybis(ethane-2,1-diyl))bis(oxy))diethanol (1.05 g, 5.43 mmol), sodium hydride (5.43 mmol), and N-(6'-fluoro-2-methyl-5'-morpholino-[3,3'-bipyridin]-5-yl)-3-(trifluoromethyl)benzamide (250 mg, 0.543 mmol) as described in Example 9. Rf=0.3 (10% MeOH in DCM). $^1$H NMR (400 MHz, CDCl$_3$) δ 8.77 (s, 1H), 8.67 (d, J=2.4 Hz, 1H), 8.21 (s, 1H), 8.13 (d, J=7.8 Hz, 1H), 8.09 (d, J=2.4 Hz, 1H), 7.81 (d, J=7.8 Hz, 1H), 7.70 (d, J=2.0 Hz, 1H), 7.63 (t, J=7.8 Hz, 1H), 7.02 (d, J=2.0 Hz, 1H), 4.58-4.50 (m, 2H), 3.92-3.87 (m, 2H), 3.87-3.81 (m, 4H), 3.74-3.68 (m, 4H), 3.68-3.61 (m, 6H), 3.58-3.53 (m, 2H), 3.16-3.08 (m, 4H), 2.47 (s, 3H). $^{19}$F NMR (376 MHz, CDCl3) δ -63.05 (s). $^{19}$F NMR (376 MHz, CDCl$_3$). LRMS, m/z, calculated for C$_{31}$H$_{37}$F$_3$N$_4$O$_7$, 634.26, found, 657 (M+Na)$^+$, 633 (M−H)$^-$.

Example 49—Synthesis of (R)-1-((2S,4R)-4-hydroxy-2-(((S)-1-(4-(4-methylthiazol-5-yl)phenyl)ethyl)carbamoyl)-pyrrolidin-1-yl)-3,3-dimethyl-N-(2-(2-(2-(2-((2'-methyl-5-morpholino-5'-(3-(trifluoro-methyl)benzamido)-[3,3'-bipyridin]-6-yl)oxy)ethoxy)ethoxy)ethoxy)ethyl)-1-oxobutan-2-aminium formate (Compound 2.006)

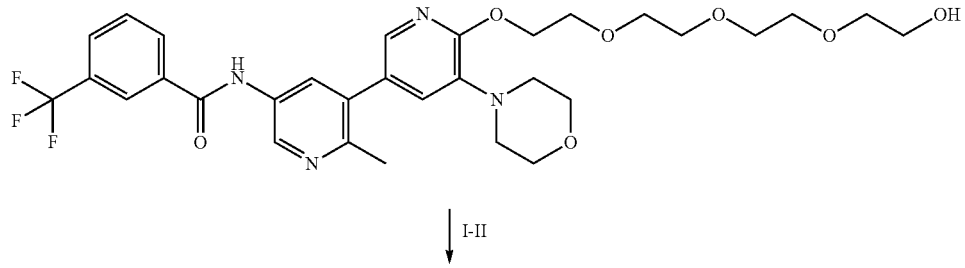

I-II

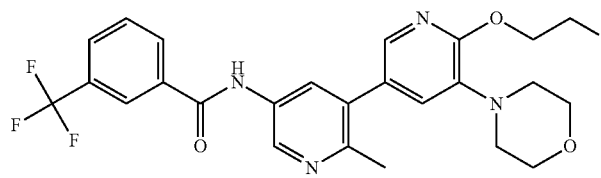
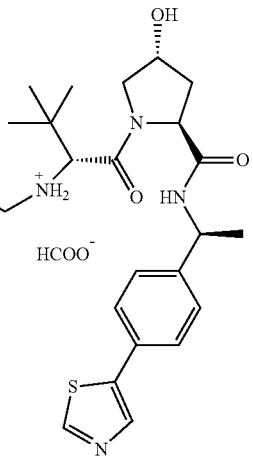

Step I, N-(2-methyl-5'-morpholino-6'-(2-(2-(2-(2-oxoethoxy)ethoxy)ethoxy)ethoxy)-[3,3'-bipyridin]-5-yl)-3-(trifluoromethyl)benzamide To a cold (−70° C.) stirred solution of oxalyl chloride (21 µL, 0.245 mmol) in DCM (2 mL) was added a solution of DMSO (37 µL, 0.521 mmol) in DCM (1 mL), after stirred for 30 min, a solution of N-(6'-(2-(2-(2-(2-hydroxyethoxy)ethoxy)ethoxy)ethoxy)-2-methyl-5'-morpholino-[3,3'-bipyridin]-5-yl)-3-(trifluoromethyl)benzamide (115 mg, 0.181 mmol) in DCM (2 mL) was added, after stirred at the same temp for 30 min, triethyl amine (78 µL, 0.556 mmol) was added, stirred for 1 h, quenched with water (1 mL). The reaction mixture was extracted with ethyl acetate (3×10 mL), combined extracts we rewashed with brine, dried ($Na_2SO_4$), concentrated to afford N-(2-methyl-5'-morpholino-6'-(2-(2-(2-(2-oxoethoxy)ethoxy)ethoxy)ethoxy)-[3,3'-bipyridin]-5-yl)-3-(trifluoromethyl)benzamide (120 mg) as colorless oil along with SM. This material was used as such in the next step without further purification. LRMS m/z, calculated for $C_{31}H_{35}F_3N_4O_7$, 632.25; found, 656.96 $(M+Na)^+$.

Step II, (R)-1-((2S,4R)-4-hydroxy-2-(((S)-1-(4-(4-methylthiazol-5-yl)phenyl)ethyl)carba-moyl)pyrrolidin-1-yl)-3,3-dimethyl-N-(2-(2-(2-(2-((2'-methyl-5-morpholino-5'-(3-(trifluoromethyl)benzamido)-[3,3'-bipyridin]-6-yl)oxy)ethoxy)-ethoxy)ethoxy)ethyl)-1-oxobutan-2-aminium formate To a stirred mixture of N-(2-methyl-5'-morpholino-6'-(2-(2-(2-(2-oxoethoxy)ethoxy)ethoxy)ethoxy)-[3,3'-bipyridin]-5-yl)-3-(trifluoromethyl)benzamide (120 mg, 0.182 mmol), from step I, and (2S,4R)-1-((R)-2-amino-3,3-dimethylbutanoyl)-4-hydroxy-N—((S)-1-(4-(4-methylthiazol-5-yl)phenyl)ethyl)pyrrolidine-2-carboxamide (81 mg, 0.182 mmol) in DCE (3 mL) was added sodium triacetoxyborohydride (77 mg, 0.364 mmol), reaction mixture was stirred at rt for 16 h, diluted with water (5 mL), extracted with ethyl acetate (3×10 mL), combined extracts were washed with brine, dried ($Na_2SO_4$), and concentrated. The residue was absorbed on the Celite®, purified on 25 g $SiO_2$ Cartridge using a gradient of methanol in DCM (0-30%) to afford (2S,4R)-1-((R)-2-(tert-butyl)-14-((2'-methyl-5-morpholino-5'-(3-(trifluoromethyl)benzamido)-[3,3'-bipyridin]-6-yl)oxy)-6,9,12-trioxa-3-azatetradecan-1-oyl)-4-hydroxy-N—((S)-1-(4-(4-methylthiazol-5-yl)phenyl)ethyl)pyrrolidine-2-carboxamide (25 mg, 12.9%) as gum. The purity of this compound is ~85% which was repurified by reverse phase prep HPLC to afford the title compound (20 mg, 9.92%) as white solid. Rf=0.15 (10% MeOH in DCM). $^1$H NMR (400 MHz, $CDCl_3$) δ 9.33 (s, 1H), 8.97 (s, 1H), 8.69 (s, 1H), 8.25 (s, 2H), 8.16 (d, J=7.8 Hz, 1H), 8.05 (s, 1H), 7.88-7.76 (m, 4H), 7.72 (s, 1H), 7.60 (t, J=7.8 Hz, 1H), 7.33 (d, J=8.0 Hz, 2H), 7.27 (d, J=6.8 Hz, 2H), 7.03 (s, 1H), 5.00-4.90 (m, 1H), 4.84 (t, J=8.0 Hz, 1H), 4.59 (brs, 2H), 4.39 (s, 1H), 3.99 (d, J=11.1 Hz, 1H), 3.95-3.83 (m, 6H), 3.76-3.55 (m, 10H), 3.38 (d, J=9.3 Hz, 1H), 3.19-3.08 (m, 4H), 3.03-2.91 (m, 1H), 2.87-2.73 (m, 1H), 2.63 (s, 2H), 2.49 (s, 6H), 2.44-2.33 (m, 1H), 2.08-1.97 (m, 1H), 1.41 (d, J=6.8 Hz, 3H), 1.05 (s, 9H). It is a formic acid salt. LRMS, m/z, calculated for parent $C_{54}H_{67}F_3N_8O_9S$, 1060.47, found, 1059.09 $(M-H)^-$; 1061.1 $(M+H)^+$; 1083.03 $(M+Na)^+$. HPLC, $t_R$=9.77 min (purity, >95%). HPLC Prep method: Column, Phenomenex, Synergi, 4µ, Max-RP 80A, AX; 250×21.2 mm, mobile phase, acetonitrile in water (10% to 100%, 25 min) using 0.2% formic acid buffer in water; flow rate, 15 mL/min. HPLC Method: Column, Agilent, Zorbax Eclipse XDB-C8, 5 µm, 4.6×150 mm, mobile phase, acetonitrile in water (5 to 100%) contains ammonium acetate buffer (0.5 g/L); flow rate, 1.5 mL/min, run time, 20 min.

Example 50—Synthesis of (2S,4R)-1-((R)-2-(6-aminohexanamido)-3,3-dimethylbutanoyl)-4-hydroxy-N—((S)-1-(4-(4-methylthiazol-5-yl)phenyl)ethyl)pyrrolidine-2-carboxamide (for Compound 2.007)

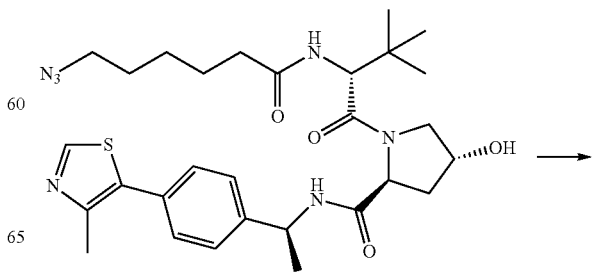

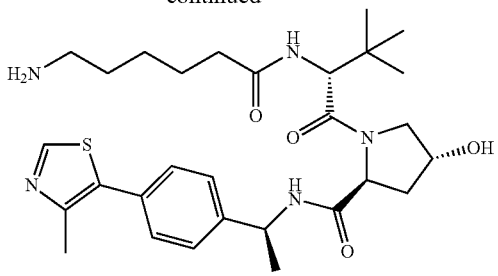

To a degassed stirred solution of (2S,4R)-1-((R)-2-(6-azidohexanamido)-3,3-dimethylbutanoyl)-4-hydroxy-N—((S)-1-(4-(4-methylthiazol-5-yl)phenyl)ethyl)pyrrolidine-2-carboxamide (115 mg, 0.197 mmol) in ethyl acetate (3 mL) and methanol (0.5 mL) was added 10% Pd on Carbon (21 mg), purged with hydrogen gas, stirred under hydrogen atmosphere using a balloon for 16 h, filtered through a pad of Celite®, rinsed with methanol-ethyl acetate (1:1, 50 mL), filtrate was concentrated to afford the title compound (85 mg, 77.4%) as white solid. This crude material was used as such in the next step without further purification. LRMS, m/z, calculated for $C_{29}H_{43}N_5O_4S$, 557.30; found, 580.09 $(M+Na)^+$, 555.9 $(M-H)^-$.

Example 51—Synthesis of (2S,4R)-1-((R)-20-(tert-butyl)-1-((2'-methyl-5-morpholino-5'-(3-(trifluoromethyl)benza-mido)-[3,3'-bipyridin]-6-yl)oxy)-11,18-dioxo-3,6,9-trioxa-12,19-diazahenicosan-21-oyl)-4-hydroxy-N—((S)-1-(4-(4-methylthiazol-5-yl)phenyl)ethyl)pyrrolidine-2-carboxamide (Compound 2.007)

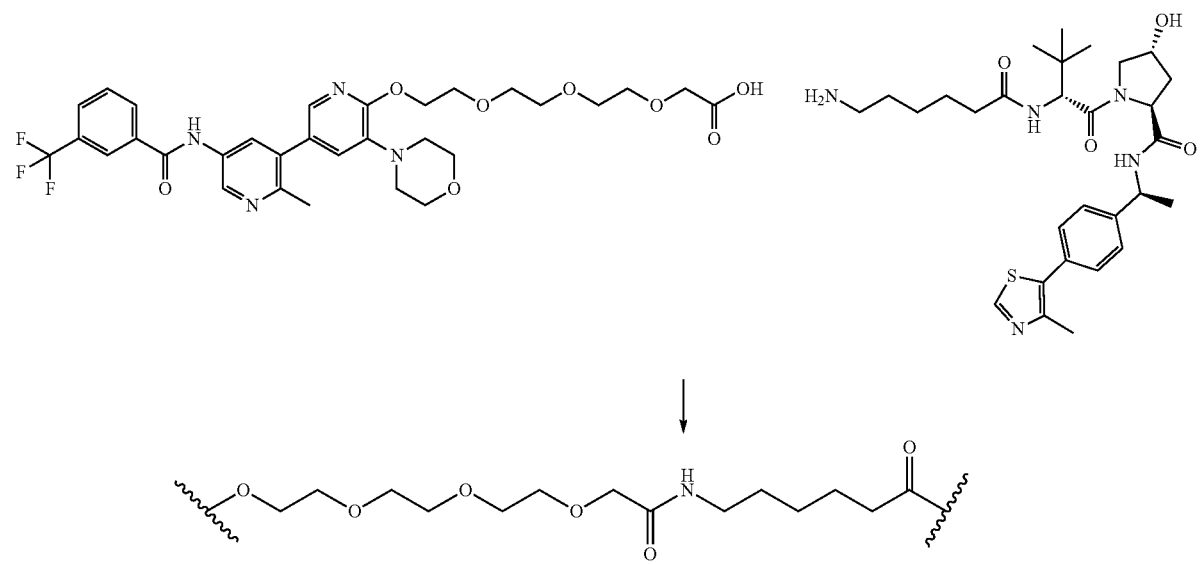

Title compound (12.1 mg, 13.2%) was prepared as light yellow solid from 2-(2-(2-(2-((2'-methyl-5-morpholino-5'-(3-(trifluoromethyl)benzamido)-[3,3'-bipyridin]-6-yl)oxy)ethoxy)ethoxy)ethoxy)acetic acid (50 mg, 0.077 mmol) and (2S,4R)-1-((R)-2-(6-aminohexanamido)-3,3-dimethylbutanoyl)-4-hydroxy-N—((S)-1-(4-(4-methylthiazol-5-yl)phenyl)ethyl)pyrrolidine-2-carboxamide (43 mg, 0.077 mmol) in DMF (1 mL) as described in Example 36. Rf=0.25 (10% MeOH in DCM). $^1$H NMR (400 MHz, CDCl$_3$) δ 9.31 (s, 1H), 8.79 (d, J=2.3 Hz, 1H), 8.66 (s, 1H), 8.29 (s, 1H), 8.20 (d, J=8.0 Hz, 1H), 8.06 (d, J=2.2 Hz, 1H), 7.80 (d, J=7.9 Hz, 1H), 7.75 (d, J=2.0 Hz, 1H), 7.62 (t, J=7.8 Hz, 1H), 7.42-7.31 (m, 5H), 7.07 (d, J=2.0 Hz, 1H), 6.89-6.83 (m, 1H), 6.33 (d, J=8.5 Hz, 1H), 5.09-5.01 (m, 1H), 4.71 (t, J=8.2 Hz, 1H), 4.64-4.55 (m, 3H), 4.48 (brs, 1H), 4.00 (d, J=11.2 Hz, 1H), 3.96-3.83 (m, 7H), 3.77-3.54 (m, 11H), 3.17-3.07 (m, 5H), 2.51 (s, 3H), 2.48 (s, 3H), 2.44-2.34 (m, 1H), 2.21-2.06 (m, 3H), 1.88-1.75 (m, 2H), 1.46 (d, J=7.0 Hz, 3H), 1.5-1.1 (m, 4H), 1.00 (s, 9H). $^{19}$F NMR (376 MHz, CDCl$_3$) δ -63.02 (s). LRMS, m/z, calculated for $C_{60}H_{76}F_3N_9O_{11}S$, 1187.53; found, 1210.16 $(M+Na)^+$. HPLC, $t_R$=9.35 min (purity, 94% @254 nM; 95.5% @ 234 nM). HPLC Method: Column, Agilent, Zorbax Eclipse XDB-C8, 5 μm, 4.6×150 mm, mobile phase, acetonitrile in water (5 to 100%) contains ammonium acetate buffer (0.5 g/L); flow rate, 1.5 mL/min, run time, 20 min.

Example 52—Synthesis of (2S,4R)-1-((R)-3,3-dimethyl-2-(6-(4-(16-((2'-methyl-5-morpholino-5'-(3-(trifluoromethyl)benzamido)-[3,3'-bipyridin]-6-yl)oxy)-2,5,8,11,14-pentaoxahexadecyl)-H-1,2,3-triazol-1-yl)hexanamido)butanoyl)-4-hydroxy-N—((S)-1-(4-(4-methylthiazol-5-yl)phenyl)ethyl)pyrrolidine-2-carboxamide (Compound 2.008)

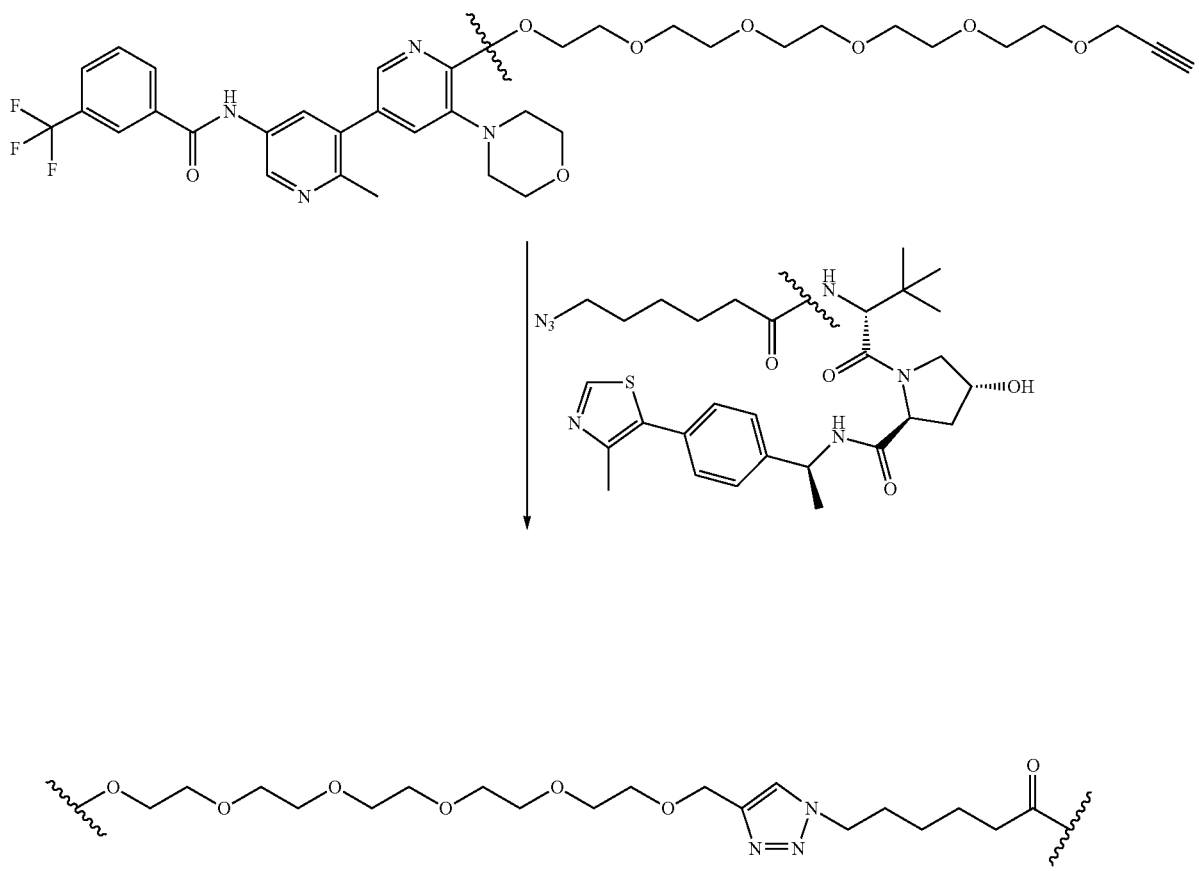

Title compound (29.9 mg, 16.5%) was prepared as a white solid from N-(6'-(3,6,9,12,15-pentaoxaoctadec-17-yn-1-yloxy)-2-methyl-5'-morpholino-[3,3'-bipyridin]-5-yl)-3-(trifluoromethyl)benzamide (99.6 mg, 0.139 mmol) and (2S,4R)-1-((R)-2-(6-azidohexanamido)-3,3-dimethylbutanoyl)-4-hydroxy-N—((S)-1-(4-(4-methylthiazol-5-yl)phenyl)ethyl)pyrrolidine-2-carboxamide (90.0 mg, 0.154 mmol) as described in Example 22. Rf=0.25 (10% MeOH/DCM). $^1$H NMR (400 MHz, CDCl$_3$) δ 9.73 (s, 1H), 8.67 (s, 1H), 8.62 (d, J=2.4 Hz, 1H), 8.33 (t, J=8.2 Hz, 1H), 8.30 (s, 1H), 8.20 (d, J=7.9 Hz, 1H), 7.79 (d, J=7.8 Hz, 1H), 7.74 (d, J=2.0 Hz, 1H), 7.61 (t, J=7.8 Hz, 1H), 7.49 (s, 1H), 7.38 (m, 5H), 7.05 (d, J=2.0 Hz, 1H), 6.40 (d, J=9.0 Hz, 1H), 5.10 (dd, J=14.3, 7.1 Hz, 1H), 4.74 (t, J=8.4 Hz, 2H), 4.62 (d, J=2.4 Hz, 2H), 4.60-4.57 (m, 2H), 4.54 (s, 1H), 4.21 (t, J=7.1 Hz, 2H), 3.98 (d, J=11.4 Hz, 1H), 3.89 (t, J=8.4 Hz, 6H), 3.70 (dd, J=5.7, 3.1 Hz, 2H), 3.66-3.57 (m, 16H), 3.16 (d, J=4.2 Hz, 4H), 2.52 (s, 3H), 2.49 (s, 3H), 2.25-2.08 (m, 4H), 1.80-1.67 (m, 2H), 1.60-1.51 (m, 2H), 1.49 (d, J=6.9 Hz, 3H), 1.27-1.16 (m, 2H), 1.04 (s, 9H) ppm. $^{19}$F NMR (376 MHz, CDCl$_3$) δ −62.97 (s) ppm. LRMS (ESI) m/z: calculated for $C_{65}H_{84}F_3N_{11}O_{12}S$, 1299.60; found 1322.09 (M+Na)$^+$; found 1298.06 (MH)$^-$. HPLC, t$_R$=9.76 min (purity, >99%). HPLC Method: Cartridge, Agilent, Zorbax-SB-CN, 3.5 μm, 4.6×150 mm, mobile phase, acetonitrile in water (0-100%) contains ammonium acetate buffer; flow rate, 0.1 mL/min, run time, 20 min.

Example 53—Synthesis of (2S,4R)-1-((R)-3,3-dimethyl-2-(5-(4-((2-(2-(2-((2'-methyl-5-morpholino-5'-(3-(trifluoromethyl)benzamido)-[3,3'-bipyridin]-6-yl)oxy)ethoxy)ethoxy)ethoxy)methyl)-1H-1,2,3-triazol-1-yl)pentanamido)butanoyl)-4-hydroxy-N—((S)-1-(4-(4-methylthiazol-5-yl)phenyl)ethyl)pyrrolidine-2-carboxamide (Compound 2.009)

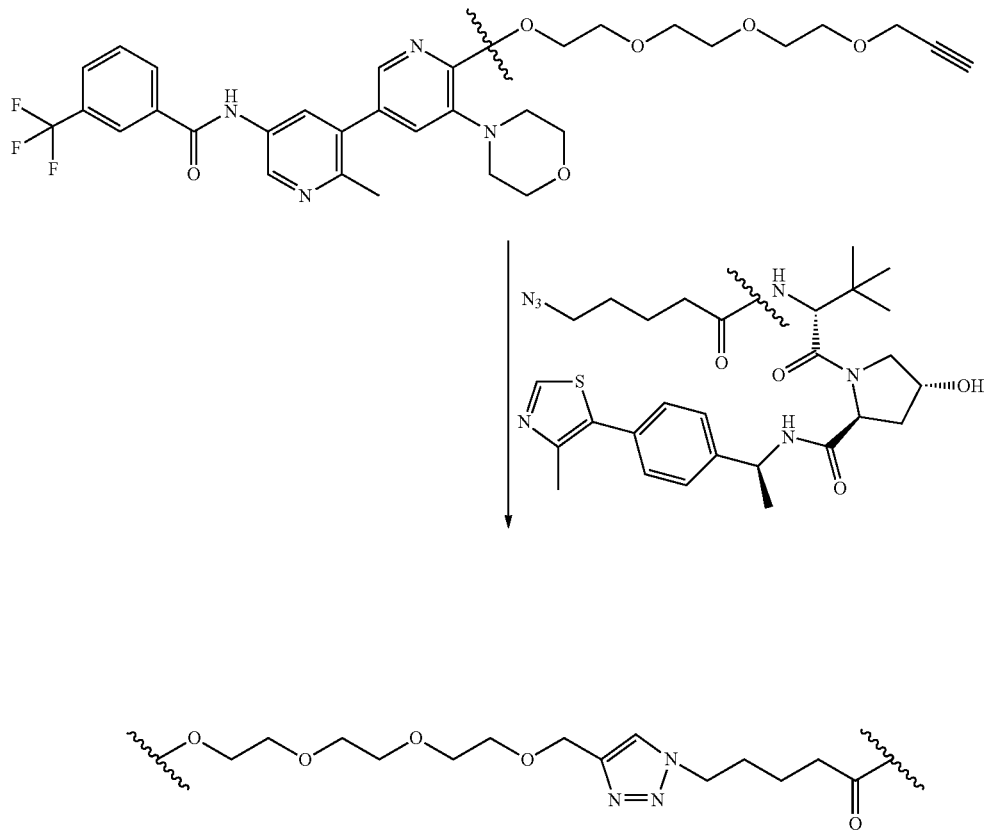

Title compound (32.8 mg, 33.6% yield) was prepared as a white solid from N-(2-methyl-5'-morpholino-6'-(2-(2-(2-(prop-2-yn-1-yloxy)ethoxy)ethoxy)ethoxy)-[3,3'-bipyridin]-5-yl)-3-(trifluoromethyl)benzamide (51.2 mg, 0.0814 mmol), and (2S,4R)-1-((R)-2-(5-azidopentanamido)-3,3-dimethylbutanoyl)-4-hydroxy-N—((S)-1-(4-(4-methylthiazol-5-yl)phenyl)ethyl)pyrrolidine-2-carboxamide (84.9 mg, 0.149 mmol) as described in Example 22. Rf=0.31 (10% MeOH in DCM). $^1$H NMR (400 MHz, CDCl$_3$) δ 9.25 (s, 1H), 8.71 (d, J=2.4 Hz, 1H), 8.67 (s, 1H), 8.25 (s, 1H), 8.18-8.16 (m k, 2H), 7.81 (d, J=7.9 Hz, 1H), 7.73 (d, J=2.0 Hz, 1H), 7.62 (t, J=7.8 Hz, 1H), 7.51 (s, 1H), 7.40-7.38 (m, 2H), 7.35 (s, 2H), 7.34 (d, J=1.8 Hz, 1H), 7.04 (d, J=2.0 Hz, 1H), 6.32 (d, J=8.9 Hz, 1H), 5.30 (s, 1H), 5.10-5.01 (m, 1H), 4.70 (t, J=8.1 Hz, 1H), 4.65 (d, J=9.0 Hz, 1H), 4.62-4.57 (m, 4H), 4.50 (bs, 1H), 4.31 (bs, 1H), 4.21 (td, J=7.0, 2.3 Hz, 2H), 3.99 (d, J=11.3 Hz, 1H), 3.92-3.83 (m, 6H), 3.71-3.69 (m, 2H), 3.64-3.61 (m, 2H), 3.60 (s, 3H), 3.17-3.10 (m, 4H), 2.51 (s, 3H), 2.49 (s, 3H), 2.21 (ddd, J=23.7, 14.9, 7.4 Hz, 2H), 2.10 (dd, J=13.8, 8.5 Hz, 1H), 1.88 (s, 1H), 1.88-1.78 (m, 2H), 1.59-1.50 (m, 2H), 1.47 (d, J=6.9 Hz, 3H), 1.02 (s, 9H) ppm. $^{19}$F NMR (376 MHz, CDCl$_3$) δ −63.01 (s) ppm. LRMS (ESI) m/z: calculated for C$_{60}$H$_{74}$F$_3$N$_{11}$O$_{10}$S, 1197.53; found 1220.03 (M+H)$^+$; found 1196.91 (M−H)$^-$. HPLC purity (>99% @ 254 nm; >99% @ 234 nm; 9.719 min). HPLC Method: Cartridge, Agilent, Zorbax-SB-CN, 3.5 μm, 4.6×150 mm, mobile phase, acetonitrile in water (0 to 100%) contains ammonium acetate buffer; flow rate, 0.1 mL/min, run time, 20 min.

Example 54 and Example 55 describes the synthesis of Compound 2.011, this conjugate is embraced by the following Formula

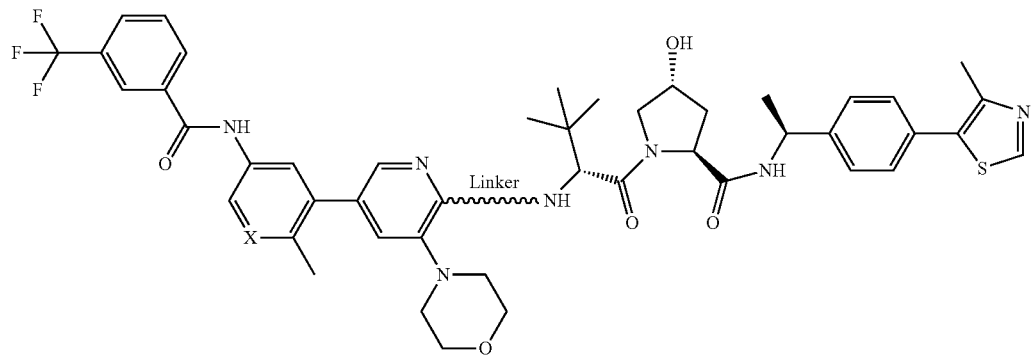

X = CH

Example 54—Synthesis of N-(3-(6-(but-3-yn-1-yloxy)-5-morpholinopyridin-3-yl)-4-methylphenyl)-3-(trifluoromethyl)benzamide (for Compound 2.011)

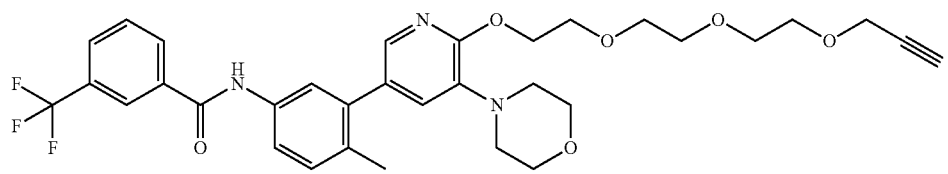 [SMILES: C#CCOCCOCCOCCOc1ncc(-c2cc(NC(=O)c3cccc(C(F)(F)F)c3)ccc2C)cc1N1CCOCC1]

Title compound (140 mg, 44.6%) was prepared as colorless oil from 2-(2-(2-(prop-2-yn-1-yloxy)ethoxy)ethoxy)ethanol (471 mg, 2.5 mmol) and N-(3-(6-fluoro-5-morpholinopyridin-3-yl)-4-methylphenyl)-3-(trifluoromethyl)benzamide (230 mg, 0.501 mmol) as described in Example 9. Rf=0.5 (EtOAc). $^1$H NMR (400 MHz, CDCl$_3$) δ 8.13 (s, 1H), 8.09 (s, 1H), 8.06 (d, J=7.9 Hz, 1H), 7.79 (d, J=7.8 Hz, 1H), 7.72 (d, J=1.9 Hz, 1H), 7.64-7.56 (m, 2H), 7.48 (brs, 1H), 7.29-7.24 (m, 1H), 7.03 (d, J=1.8 Hz, 1H), 4.59-4.52 (m, 2H), 4.19 (d, J=2.4 Hz, 2H), 3.94-3.84 (m, 6H), 3.75-3.64 (m, 8H), 3.14 (d, J=4.1 Hz, 4H), 2.42 (t, J=2.3 Hz, 1H), 2.25 (s, 3H). $^{19}$F NMR (376 MHz, CDCl$_3$) δ −63.09 (s).

LRMS, m/z, calculated for $C_{33}H_{36}F_3N_3O_6$, 627.26, found, 649.987 (M+H)$^+$, 626.11 (M−H)$^−$.

Example 55—Synthesis of (2S,4R)-1-((R)-3,3-dimethyl-2-(6-(4-((2-(2-(2-((5-(2-methyl-5-(3-(trifluoromethyl)benza-mido)phenyl)-3-morpholinopyridin-2-yl)oxy)ethoxy)ethoxy)ethoxy)methyl)-1H-1,2,3-triazol-1-yl)hexanamido)butanoyl)-4-hydroxy-N—((S)-1-(4-(4-methylthiazol-5-yl)phenyl)-ethyl)pyrrolidine-2-carboxamide (Compound 2.011)

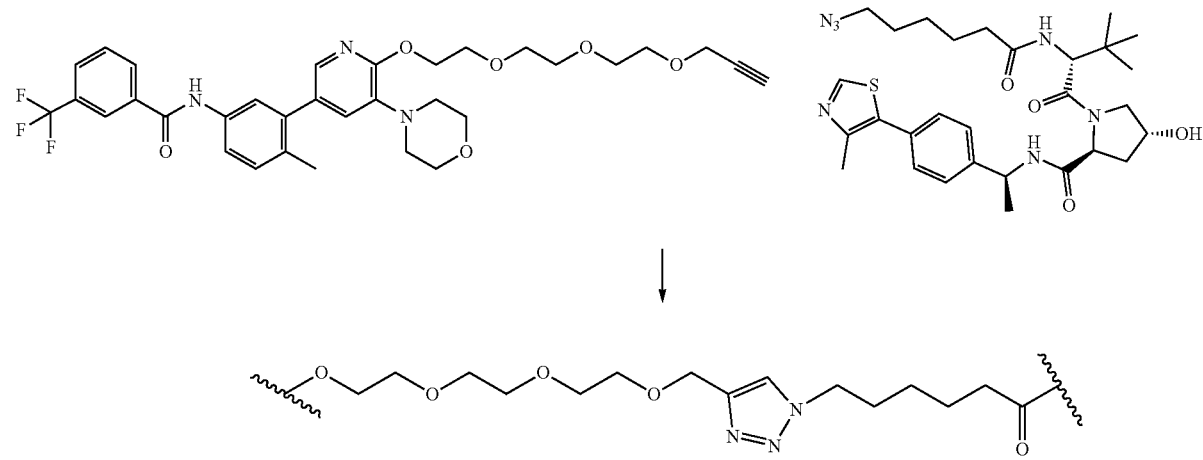 [SMILES: C#CCOCCOCCOCCOc1ncc(-c2cc(NC(=O)c3cccc(C(F)(F)F)c3)ccc2C)cc1N1CCOCC1 ; Cc1ncsc1-c1ccc([C@H](C)NC(=O)[C@@H]2C[C@@H](O)CN2C(=O)[C@H](NC(=O)CCCCCN=[N+]=[N-])C(C)(C)C)cc1 ; *OCCOCCOCCOCc1cn(CCCCCC(*)=O)nn1]

Title compound (30 mg, 34.5%) as white solid from N-(4-methyl-3-(5-morpholino-6-(2-(2-(2-(prop-2-yn-1-yloxy)ethoxy)ethoxy)-ethoxy)pyridin-3-yl)phenyl)-3-(trifluoromethyl)benzamide (45 mg, 0.0717 mmol), (2S,4R)-1-((R)-2-(6-azidohexanamido)-3,3-dimethylbutanoyl)-4-hydroxy-N—((S)-1-(4-(4-methylthiazol-5-yl)phenyl)ethyl) pyrrolidine-2-carboxamide (50.2 mg, 0.086 mmol) as described in 2.004 followed by reverse phase prep HPLC using a gradient of acetonitrile in water (10-100%, using 0.2% formic acid buffer). Rf=0.45 (10% methanol in DCM). $^1$H NMR (400 MHz, CDCl$_3$) δ 8.67 (s, 1H), 8.55 (s, 1H), 8.18 (s, 1H), 8.11 (d, J=7.8 Hz, 1H), 7.78 (d, J=7.8 Hz, 1H), 7.74-7.69 (m, 2H), 7.63-7.58 (m, 1H), 7.57 (s, 1H), 7.42 (d, J=7.8 Hz, 1H), 7.40-7.36 (m, 3H), 7.34 (d, J=8.3 Hz, 2H), 7.28 (d, J=9.2 Hz, 1H), 7.03 (d, J=2.0 Hz, 1H), 6.21 (d, J=8.7 Hz, 1H), 5.05 (p, J=7.0 Hz, 1H), 4.69 (t, J=7.9 Hz, 1H), 4.65 (d, J=2.7 Hz, 2H), 4.58-4.51 (m, 3H), 4.47 (brs, 1H), 4.28 (t, J=7.0 Hz, 2H), 3.99 (d, J=11.3 Hz, 1H), 3.92-3.84 (m, 6H), 3.73-3.68 (m, 2H), 3.66-3.61 (m, 6H), 3.57 (dd, J=11.2, 3.7 Hz, 1H), 3.17-3.08 (m, 4H), 2.51 (s, 3H), 2.49-2.41 (m, 1H), 2.25 (s, 3H), 2.23-2.10 (m, 2H), 2.10-2.01 (m, 1H), 1.90-1.77 (m, 2H), 1.69-1.55 (m, 2H), 1.46 (d, J=6.9 Hz, 3H), 1.33-1.22 (m, 2H), 1.00 (s, 9H). $^{19}$F NMR (376 MHz, CDCl$_3$) δ -63.05 (s). LRMS, m/z, calculated for C$_{62}$H$_{77}$F$_3$N$_{10}$O$_{10}$S, 1210.55; found, 1211.23 (M+H)$^+$; 1210.22 (M−H)$^−$. HPLC, t$_R$=10.47 min (purity, >99.5% @254 and 234 nM). HPLC Method: Column, Agilent, Zorbax Eclipse XDB-C8, 5 μm, 4.6×150 mm, mobile phase, acetonitrile in water (5-100%) contains ammonium acetate buffer; flow rate, 1.5 mL/min, run time, 20 min. HPLC Prep method: Column, Phenomenex, Synergi, 4μ, Max-RP 80A, AX; 250×21.2 mm, mobile phase, acetonitrile in water (10% to 100%, 25 min) using 0.2% formic acid buffer in water; flow rate, 15 mL/min.

Example 56 to Example 59 describes the synthesis of Compounds 2.012 & 2.013, each of these conjugates are embraced by the following Formula

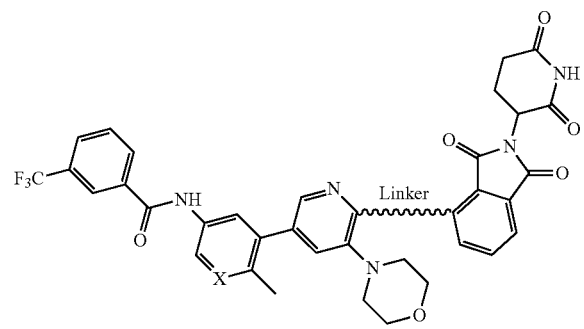

Example 56—Synthesis of N-(4-methyl-3-(5-morpholino-6-(2-(prop-2-yn-1-yloxy)ethoxy)pyridin-3-yl)phenyl)-3-(trifluoromethyl)benzamide (for Compound 2.012)

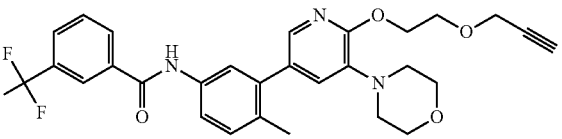

Title compound (100 mg, 82.1%) was prepared as a pale yellow oil from 2-(prop-2-yn 1-yloxy)ethanol (110.5 mg, 1.10 mmol), Aeschi et al., *Eur. J. Org. Chem,* 2017, pp. 4091-4103, and N-(3-(6-fluoro-5-morpholinopyridin-3-yl)-4-methylphenyl)-3-(trifluoromethyl)benzamide (103.7 mg, 0.226 mmol) in 1,4-dioxane (1.5 mL) as described in Example 9. Rf=0.64 (EtOAc). $^1$H NMR (400 MHz, CDCl$_3$) δ 8.12 (s, 1H), 8.06 (d, J=7.9 Hz, 1H), 7.81 (d, J=3.6 Hz, 2H), 7.74 (d, J=2.0 Hz, 1H), 7.64 (t, J=7.8 Hz, 1H), 7.59 (dd, J=8.2, 2.2 Hz, 1H), 7.48 (d, J=2.0 Hz, 1H), 7.30 (d, J=8.2 Hz, 1H), 7.05 (d, J=2.0 Hz, 1H), 4.62-4.57 (m, 2H), 4.27 (d, J=2.4 Hz, 2H), 3.99-3.94 (m, 2H), 3.93-3.86 (m, 4H), 3.19-3.09 (m, 4H), 2.45 (t, J=2.4 Hz, 1H), 2.26 (s, 3H) ppm. $^{19}$F NMR (376 MHz, CDCl$_3$) δ -63.15 (s) ppm. LRMS, m/z, calculated for C$_{29}$H$_{28}$F$_3$N$_3$O$_4$, 539.20; found, 537.98 (M−H)$^−$.

Example 57—Synthesis of N-(3-(6-(2-((1-(6-((2-(2,6-dioxopiperidin-3-yl)-1,3-dioxoisoindolin-4-yl)amino)-6-oxohexyl)-1H-1,2,3-triazol-4-yl)methoxy)ethoxy)-5-morpholinopyridin-3-yl)-4-methylphenyl)-3-(trifluoromethyl)benzamide (Compound 2.012)

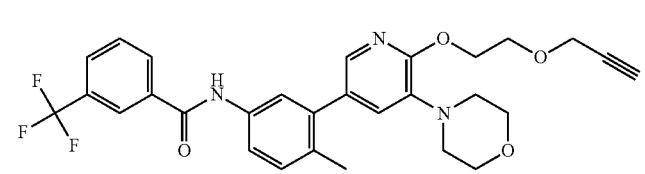 [SMILES: C#CCOCCOc1ncc(-c2cc(NC(=O)c3cccc(C(F)(F)F)c3)ccc2C)cc1N1CCOCC1]

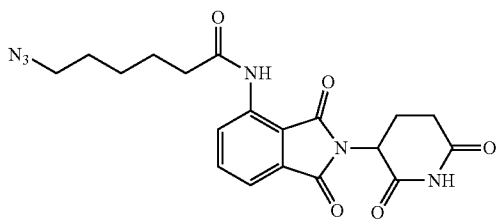

-continued

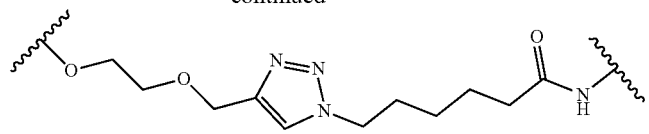

Title compound (27.3 mg, 30.9%) was prepared as pale orange solid from N-(4-methyl-3-(5-morpholino-6-(2-(prop-2-yn-1-yloxy)ethoxy)pyridin-3-yl)phenyl)-3-(trifluoromethyl)-benzamide (50.0 mg, 0.0927 mmol) and 6-azido-N-(2-(2,6-dioxopiperidin-3-yl)-1,3-dioxoisoindolin-4-yl)hexanamide (43.2 mg, 0.105 mmol) as described in Example 22. Rf=0.25 (5% MeOH in DCM). $^1$H NMR (400 MHz, CDCl$_3$) δ 9.39 (s, 1H), 8.78 (d, J=8.5 Hz, 1H), 8.28 (s, 1H), 8.13 (s, 1H), 8.08 (d, J=7.7 Hz, 1H), 7.97 (s, 1H), 7.81 (d, J=7.3 Hz, 1H), 7.74 (d, J=1.6 Hz, 1H), 7.72-7.67 (m, 1H), 7.67-7.61 (m, 1H), 7.59 (s, 1H), 7.53 (d, J=6.5 Hz, 2H), 7.46 (s, 1H), 7.28 (d, J=6.3 Hz, 1H), 7.05 (s, 1H), 4.93 (dd, J=12.1, 5.4 Hz, 1H), 4.75 (s, 2H), 4.63-4.56 (m, 2H), 4.37 (t, J=7.1 Hz, 2H), 3.99-3.93 (m, 2H), 3.88-3.82 (m, 4H), 3.13 (s, 4H), 2.91 (d, J=14.3 Hz, 1H), 2.77 (dd, J=17.0, 12.9 Hz, 2H), 2.45 (t, J=7.3 Hz, 2H), 2.25 (s, 3H), 2.15 (s, 1H), 2.01-1.92 (m, 2H), 1.83-1.73 (m, 2H), 1.42 (s, 2H) ppm. $^{19}$F NMR (376 MHz, CDCl$_3$) δ −63.11 (s) ppm. LRMS, m/z, calculated for C$_{48}$H$_{48}$F$_3$N$_9$O$_9$, 951.35; found, 974.32 (M+Na)$^+$. HPLC, t$_R$=10.22 min (purity, >99.9%).

Example 58—Synthesis of N-(3-(6-(hex-5-yn-1-yloxy)-5-morpholinopyridin-3-yl)-4-methylphenyl)-3-(trifluoromethyl) benzamide (for Compound SR-2.013)

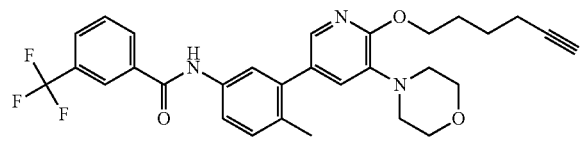 [SMILES: C#CCCCCOc1ncc(-c2cc(NC(=O)c3cccc(C(F)(F)F)c3)ccc2C)cc1N1CCOCC1]

Title compound (169.4 mg, 95.6%) was prepared as a pale yellow oil from hex-5-yn-1-ol (0.18 mL, 1.63 mmol) and N-(3-(6-fluoro-5-morpholinopyridin-3-yl)-4-methylphenyl)-3-(trifluoromethyl)benzamide (151.41 mg, 0.33 mmol) in 1,4-dioxane (2.3 mL) as described in Example 9. Rf=0.63 (50% EtOAc in Hexanes). $^1$H NMR (400 MHz, CDCl$_3$) δ 8.12 (s, 1H), 8.06 (d, J=8.1 Hz, 1H), 7.81 (t, J=8.4 Hz, 2H), 7.76 (d, J=2.0 Hz, 1H), 7.64 (t, J=7.8 Hz, 1H), 7.58 (d, J=8.2 Hz, 1H), 7.48 (s, 1H), 7.30 (d, J=8.1 Hz, 1H), 7.05 (d, J=2.0 Hz, 1H), 4.43 (t, J=6.5 Hz, 2H), 3.92-3.86 (m, 4H), 3.72-3.65 (m, 2H), 3.16-3.10 (m, 4H), 2.32 (td, J=7.0, 2.7 Hz, 2H), 2.27 (s, 3H), 2.24 (dd, J=6.7, 2.6 Hz, 2H), 1.97-1.95 (m, 1H). $^{19}$F NMR (376 MHz, CDCl$_3$) δ −63.15 (s). LRMS, m/z, calculated for C$_{30}$H$_{30}$F$_3$N$_3$O$_3$, 537.22; found, 560.11 (M+Na)$^+$.

Example 59—Synthesis of N-(3-(6-(4-(1-(6-((2-(2,6-dioxopiperidin-3-yl)-1,3-dioxoisoindolin-4-yl)amino)-6-oxohexyl)-1H-1,2,3-triazol-4-yl)butoxy)-5-morpholinopyridin-3-yl)-4-methylphenyl)-3-(trifluoromethyl)benzamide (Compound 2.013)

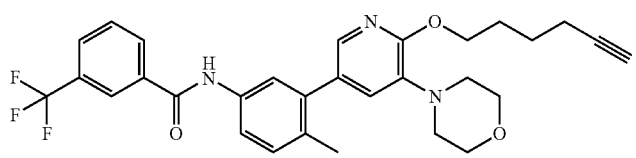

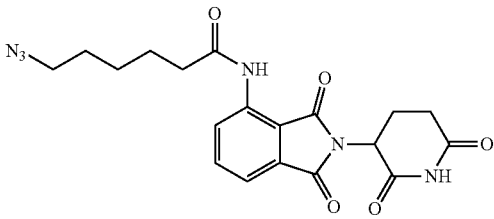

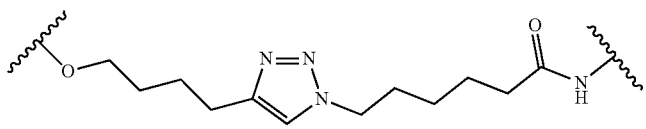

Title compound (57.3 mg, 37.1%) was prepared as pale yellow solid from N-(3-(6-(hex-5-yn-1-yloxy)-5-morpholinopyridin-3-yl)-4-methylphenyl)-3-(trifluoromethyl)benzamide (87.4 mg, 0.163 mmol), and 6-azido-N-(2-(2,6-dioxopiperidin-3-yl)-1,3-dioxoisoindolin-4-yl)hexanamide (72.3 mg, 0.175 mmol) as described in Example 22. Rf=0.26 (5% MeOH in DCM). $^1$H NMR (400 MHz, CDCl$_3$) δ 9.38 (s, 1H), 8.78 (d, J=8.6 Hz, 1H), 8.23 (s, 1H), 8.13 (s, 1H), 8.07 (d, J=8.0 Hz, 1H), 7.98 (s, 1H), 7.80 (d, J=7.8 Hz, 1H), 7.74 (d, J=2.0 Hz, 1H), 7.72-7.67 (m, 1H), 7.62 (dd, J=16.9, 9.1 Hz, 2H), 7.53 (d, J=7.3 Hz, 1H), 7.46 (s, 1H), 7.31 (s, 1H), 7.28 (d, J=8.5 Hz, 1H), 7.04 (d, J=2.0 Hz, 1H), 4.94 (dd, J=12.3, 5.4 Hz, 1H), 4.43 (t, J=6.3 Hz, 2H), 4.34 (t, J=7.1 Hz, 2H), 3.90-3.84 (m, 4H), 3.12 (d, J=4.3 Hz, 4H), 2.91 (d, J=15.1 Hz, 1H), 2.81 (dd, J=12.6, 5.7 Hz, 2H), 2.45 (t, J=7.4 Hz, 2H), 2.26 (s, 3H), 2.20-2.13 (m, 1H), 1.94 (dt, J=25.5, 11.0 Hz, 6H), 1.79 (dt, J=14.9, 7.3 Hz, 2H), 1.42 (dd, J=15.7, 8.1 Hz, 2H), 1.26 (t, J=7.2 Hz, 2H) ppm. $^{19}$F NMR (376 MHz, CDCl$_3$) δ −63.12 (s) ppm. LRMS, m/z, calculated for C$_{49}$H$_{50}$F$_3$N$_9$O$_8$, 949.37; found, 972.45 (M+Na)$^+$. HPLC, t$_R$=10.61 min (purity, >99.9%).

Example 60 to Example 68 describes the synthesis of Compounds 2.014-2.020, each of these conjugates are embraced by the following Formula

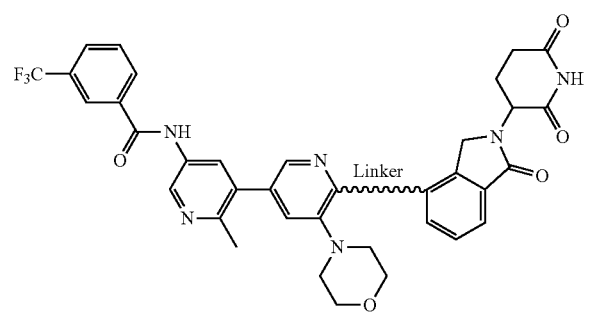 [SMILES: Cc1ncc(NC(=O)c2cccc(C(F)(F)F)c2)cc1-c1cnc(-c2cccc3c2CN(C2CCC(=O)NC2=O)C3=O)c(N2CCOCC2)c1]

Example 60—Synthesis of 14-((2'-methyl-5-morpholino-5'-(3-(trifluoromethyl)benzamido)-[3,3'-bipyridin]-6-yl)oxy)-3,6,9,12-tetraoxatetradecan-1-oic Acid (for Compound 2.014)

Step I, tert-butyl 14-hydroxy-3,6,9,12-tetraoxatetradecan-1-oate

To a cold (0° C.) stirred solution of tert-butyl 2-bromoacetate (5.4 mL, 36.6 mmol) and 2,2'-((oxybis(ethane-2,1-diyl))bis(oxy))diethanol (35.0 mL, 203 mmol) in DMSO (50 mL) was added NaH (1.6217 g, 40.6 mmol, 60% in oil) in two portions. The reaction mixture was slowly warmed up to rt, stirred for 23 h, diluted with water (50 mL), saturated with NaCl (50 g), stirred for 5 min, extracted with Et$_2$O (3×100 mL), and concentrated. The residue was taken in DCM (50 mL) and water (25 mL), stirred for 5 min. The organic solution was passed through a phase separator, concentrated and purified on a 80 g SiO$_2$ cartridge using a gradient of ethyl acetate in hexanes (50-100%) to afford the title compound (8.2 g, 72.7% yield) as a pale yellow oil. Rf=0.08 (EtOAc). $^1$H NMR (400 MHz, CDCl$_3$) δ 4.02 (d, J=1.0 Hz, 2H), 3.75-3.60 (m, 12H), 1.47 (s, 9H) ppm. LRMS (ESI) m/z: calculated for C$_{14}$H$_{28}$O$_7$ 308.3679; found 330.95 (M+Na)$^+$; Found 347.01 (M+K)$^+$.

Step II, 14-((2'-methyl-5-morpholino-5'-(3-(trifluoromethyl)benzamido)-[3,3'-bipyridin]-6-yl)oxy)-3,6,9,12-tetraoxatetradecan-1-oic Acid To a stirred solution of tert-butyl 14-hydroxy-3,6,9,12-tetraoxatetradecan-1-oate (983.6 mg, 3.19 mmol) in dioxane (4.5 mL) was added sodium hydride (280.1 mg, 7.02 mmol, 60% in mineral oil) at rt, stirred for 30 minutes. The reaction mixture was turned from pale colorless to beige, to this was added N-(6'-fluoro-2-methyl-5'-morpholino-[3,3'-bipyridin]-5-yl)-3-(trifluoromethyl)benzamide (300.5 mg, 0.635 mmol), after 15 min, a beige precipitate was formed, turned into lump, DMF (1 mL) was added to break up the lump. The reaction mixture was heated at 80° C. for 1 h and cooled down to rt, acidified with aq. 1 M HCl (~0.1 mL), the resulting mixture was stirred for 5 minutes at rt, and concentrated. The residue was purified on 40 g SiO$_2$ cartridge using a gradient of MeOH in DCM (0 to 10%) to afford the title compound (70 mg, 15.5% yield) as yellow oil. Rf=0.15 (20% MeOH in DCM) $^1$H NMR (400 MHz, CDCl$_3$) δ 10.44 (s, 1H), 9.18 (s, 1H), 8.41 (s, 1H), 8.31 (d, J=7.8 Hz, 1H), 7.95 (s, 1H), 7.75-7.69 (m, 2H), 7.56 (t, J=7.8 Hz, 1H), 7.06 (d, J=1.7 Hz, 1H), 4.54 (s, 2H), 3.84 (m, 6H), 3.75-3.48 (m,

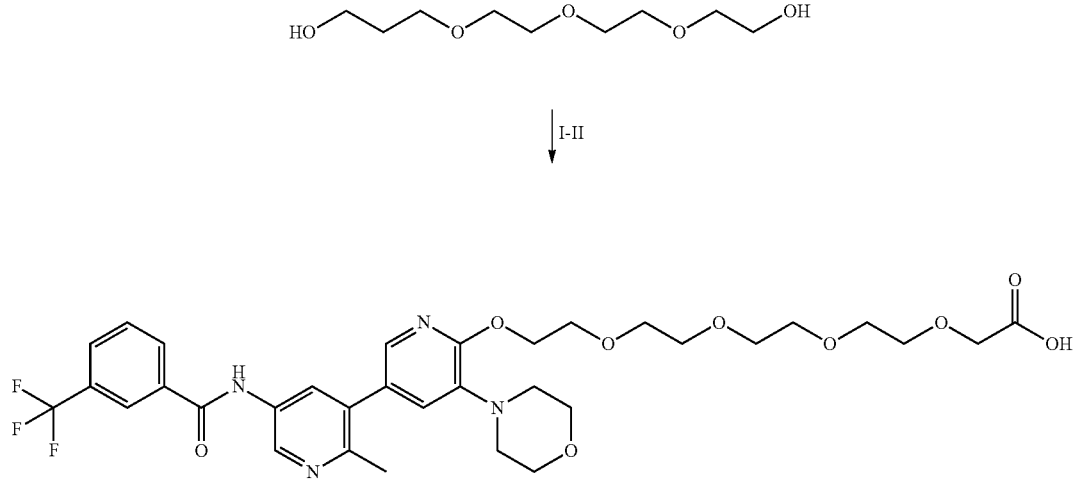

14H), 3.08 (s, 4H), 2.45 (s, 3H) ppm. $^{19}$F NMR (376 MHz, CDCl3) δ −62.95 (s) ppm. LRMS (ESI) m/z: calculated for $C_{33}H_{39}F_3N_4O_9$, 692.27; found 691.07 (M−H)$^-$.

Example 61—Synthesis of N-(5-(2-(2,6-dioxopiperidin-3-yl)-1-oxoisoindolin-4-yl)pentyl)-14-((2'-methyl-5-morpholino-5'-(3-(trifluoromethyl)benzamido)-[3,3'-bipyridin]-6-yl)oxy)-3,6,9,12-tetraoxatetradecan-1-amide (Compound 2.014)

5.19 (dd, J=13.3, 5.1 Hz, 1H), 4.56 (m, 2H), 4.41 (d, J=16.1 Hz, 1H), 4.29 (d, J=15.9 Hz, 1H), 3.93-3.82 (m, 9H), 3.72-3.57 (m, 12H), 3.22 (d, J=6.3 Hz, 2H), 3.13 (s, 4H), 2.95-2.85 (m, 1H), 2.84-2.72 (m, 1H), 2.59 (t, J=7.7 Hz, 2H), 2.49 (s, 3H), 2.40 (ddd, J=17.8, 13.3, 5.2 Hz, 1H), 2.24-2.14 (m, 1H), 1.81 (bs, 1H), 1.63 (dt, J=15.1, 7.7 Hz, 2H), 1.53 (dt, J=14.6, 7.3 Hz, 2H), 1.39-1.29 (m, 2H). $^{19}$F NMR (376 MHz, CDCl$_3$) δ −63.01 (s) ppm. LRMS (ESI) m/z: calculated for $C_{51}H_{60}F_3N_7O_{11}$, 1003.43; found 1026.06 (M+Na)$^+$; found 1002.19 (M−H)$^-$. HPLC, t$_R$=9.35 min (purity, 95%). HPLC Method: Cartridge, Agilent, Zor-

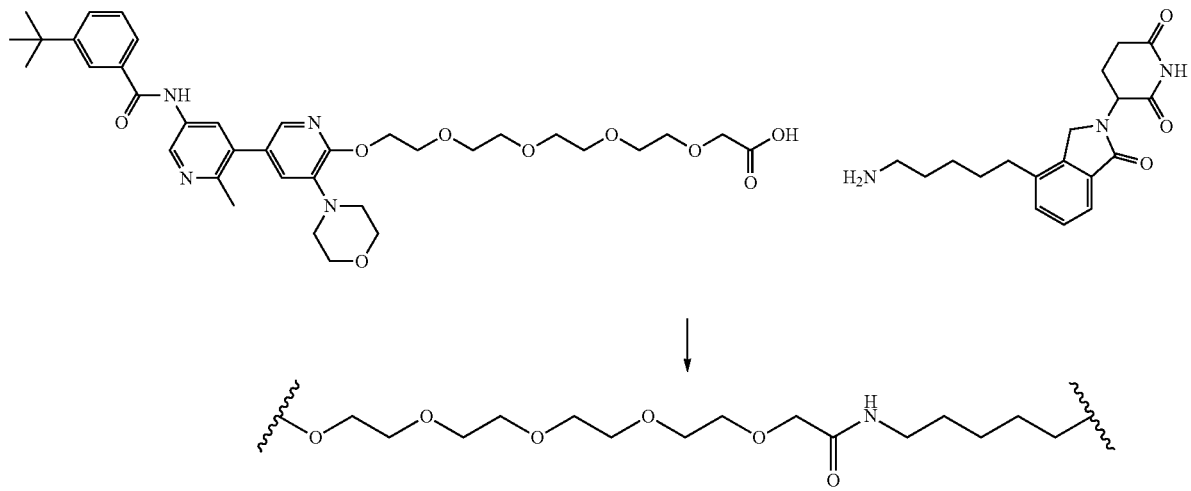

Title compound (7.9 mg, 9%) was prepared as a white solid from 2-(2-(2-(2-((2'-methyl-5-morpholino-5'-(3-(trifluoromethyl)benzamido)-[3,3'-bipyridin]-6-yl)oxy)ethoxy)ethoxy)ethoxy)acetic acid (60.6 mg, 0.0875 mmol) and 3-(4-(5-aminopentyl)-1-oxoisoindolin-2-yl)piperidine-2,6-dione (32.1 mg, 0.0974 mmol) (Zhou et. al. J. Med. Chem. 2018, 61 (2), 462-481) as described in Example 36. Rf=0.41 (10% MeOH in DCM). $^1$H NMR (400 MHz, CDCl$_3$) δ 9.04 (s, 1H), 8.89 (s, 1H), 8.71 (bs, 1H), 8.27 (s, 1H), 8.19 (d, J=8.0 Hz, 1H), 7.97 (s, 1H), 7.79 (d, J=7.9 Hz, 1H), 7.70 (s, 1H), 7.62 (m, 2H), 7.36 (m, 2H), 7.05 (m, 1H), 7.03 (s, 1H), bax-SB-CN, 3.5 μm, 4.6×150 mm, mobile phase, acetonitrile in water (0 to 100%) contains ammonium acetate buffer; flow rate, 0.1 mL/min, run time, 20 min.

Example 62—Synthesis of 2-(2-(2-((2'-methyl-5-morpholino-5'-(3-(trifluoromethyl)benzamido)-[3,3'-bipyridin]-6-yl)oxy)ethoxy)ethoxy)acetic acid (for Compound 2.015)

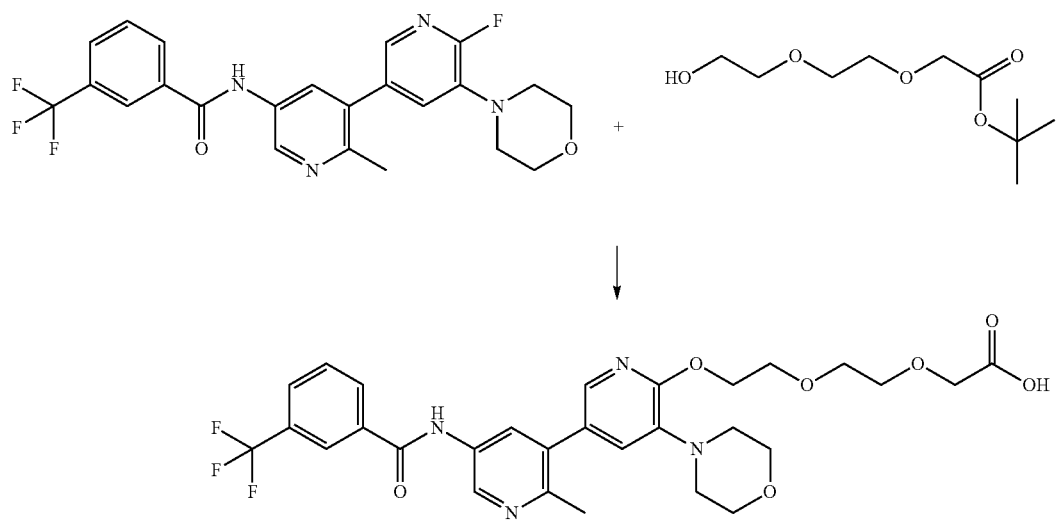

To a stirred solution of tert-butyl 2-(2-(2-hydroxyethoxy)ethoxy)acetate (350 mg, 0.76 mmol) in dioxane (5.0 mL) was added sodium hydride (334 mg, 7.98 mmol, 60% in oil), after stirred for 30 min, N-(6'-fluoro-2-methyl-5'-morpholino-[3,3'-bipyridin]-5-yl)-3-(trifluoromethyl)benzamide (350 mg, 0.76 mmol) was added, placed it on pre-heated oil bath at 80° C. for 5 min, DMF (3 mL) was added, heated for 3 h. Reaction mixture was cooled to rt, diluted with water (15 mL), it was acidified with aq. 1 N HCl, extracted with ethyl acetate (4×10 mL), combined organic extracts were washed, dried ($Na_2SO_4$), and concentrated. The residue was purified on 40 g $SiO_2$ cartridge using a gradient of MeOH in DCM (0 to 20%) to afford the title compound (180 mg, 39.2%) as brown solid. Rf=0.3 (30% MeOH in DCM). $^1$H NMR (400 MHz, $CD_3OD$) δ 8.83 (s, 1H), 8.47 (s, 1H), 8.30 (s, 1H), 8.24 (d, J=7.5 Hz, 1H), 8.10 (s, 1H), 7.91 (d, J=7.4 Hz, 1H), 7.81-7.69 (m, 2H), 7.25 (s, 1H), 4.62-4.52 (m, 2H), 4.03-3.63 (m, 10H), 3.21-3.09 (m, 4H), 2.48 (s, 3H). $^{19}$F NMR (376 MHz, $CD_3OD$) δ −60.66 (d, J=19.9 Hz). LRMS, m/z, calculated for $C_{29}H_{31}F_3N_4O_7$, 604.21; found, 602.94 (M−H)$^-$.

Example 63—Synthesis of N-(6'-(2-(2-(2-((6-(2-(2, 6-dioxopiperidin-3-yl)-1-oxoisoindolin-4-yl)hexyl) amino)-2-oxoethoxy)ethoxy)ethoxy)-2-methyl-5'-morpholino-[3,3'-bipyridin]-5-yl)-3-(trifluoromethyl) benzamide (Compound 2.015)

Med. Chem. 2018, 61 (2), 462-481) in DMF was sequentially added 50% DMF solution of propylphosphonic anhydride (123 μL, 0.269 mmol) and DIPEA (94 μL, 0.538 mmol), stirred for 20 h, diluted with water (5 mL), extracted with ethyl acetate (4×10 mL), combined extracts were washed with bicarbonate solution, brine, dried ($Na_2SO_4$), concentrated. The residue was absorbed on 3 g Celite® using DCM and purified on 24 g Gold $SiO_2$ cartridge (Isco) using a gradient of methanol in DCM (Oto 20%) to afford 28 mg of the product (90%). This product was repurified on reverse phase prep column (three injections) using a gradient of acetonitrile in water (10-100% for 25 min, no buffer) to afford the title compound (24 mg, 31.2%) as a white solid. Rf=0.45 (10% MeOH-DCM). $^1$H NMR (400 MHz, $CDCl_3$) δ 8.82 (s, 1H), 8.77 (d, J=2.5 Hz, 1H), 8.66 (s, 1H), 8.23 (s, 1H), 8.14 (d, J=7.8 Hz, 1H), 8.03 (d, J=2.4 Hz, 1H), 7.80 (d, J=7.9 Hz, 1H), 7.68 (d, J=2.0 Hz, 1H), 7.62 (t, J=7.8 Hz, 1H), 7.57 (dd, J=6.5, 2.0 Hz, 1H), 7.37-7.29 (m, 2H), 7.06-7.00 (m, 2H), 5.18 (dd, J=13.3, 5.1 Hz, 1H), 4.62-4.54 (m, 2H), 4.37 (d, J=16.0 Hz, 1H), 4.25 (d, J=16.0 Hz, 1H), 3.96 (s, 2H), 3.94-3.90 (m, 2H), 3.88-3.81 (m, 4H), 3.76-3.70 (m, 2H), 3.70-3.64 (m, 2H), 3.25-3.15 (m, 2H), 3.15-3.08 (m, 4H), 2.94-2.84 (m, 1H), 2.83-2.72 (m, 1H), 2.59-2.52 (m, 2H), 2.49 (s, 3H), 2.44-2.31 (m, 1H), 2.24-2.13 (m, 1H), 1.64-1.55 (m, 2H), 1.49-1.39 (m, 2H), 1.35-1.23 (m, 4H). $^{19}$F NMR (376 MHz, $CDCl_3$) δ −63.06 (s). LRMS, m/z, calculated for $C_{48}H_{54}F_3N_7O_9$, 929.39; found, 928.09

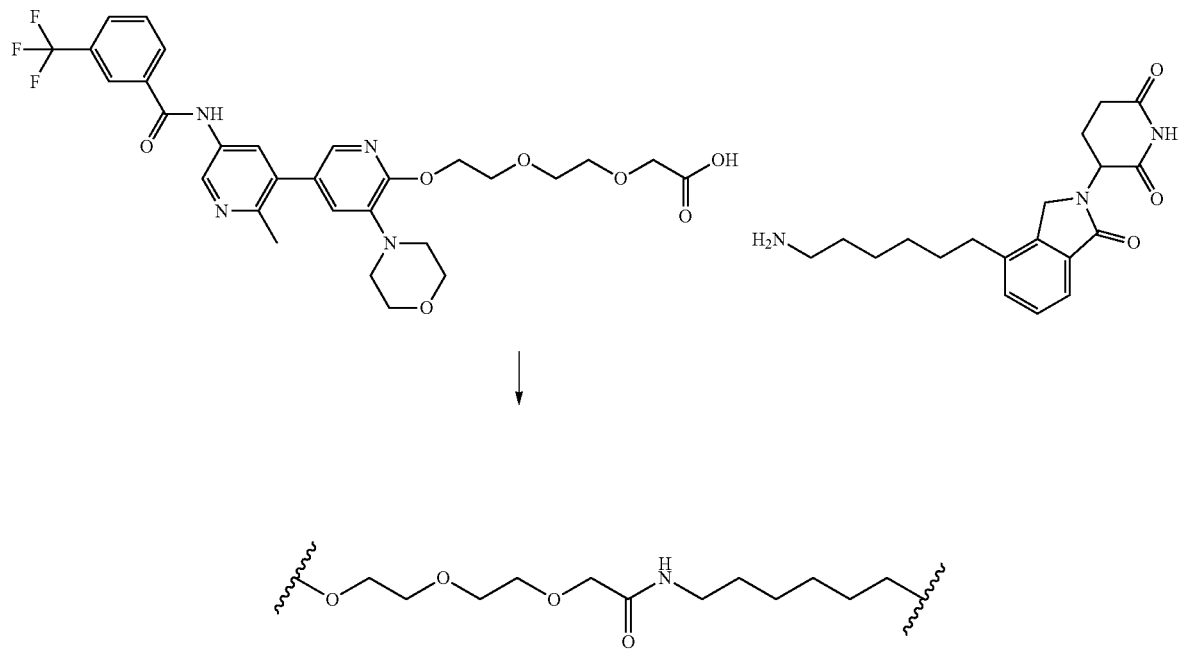

To a cold (0° C.) stirred solution of 2-(2-(2-((2'-methyl-5-morpholino-5'-(3-(trifluoromethyl)benzamido)-[3,3'-bipyridin]-6-yl)oxy)ethoxy)ethoxy)acetic acid (65 mg, 0.108 mmol) and 3-(4-(6-aminohexyl)-1-oxoisoindolin-2-yl)piperidine-2,6-dione (37.1 mg, 0.108 mmol) (Zhou et. al. J.

(M−H)$^-$; 930.27 (M+H)$^+$; 952.24 (M+Na)$^+$. HPLC, $t_R$=9.56 min (purity, >99.5%). HPLC Prep method: Column, Phenomenex, Synergi, 4μ, Max-RP 80A, AX; 250×21.2 mm, mobile phase, acetonitrile in water (10% to 100%, 25 min); flow rate, 15 mL/min.

Example 64—Synthesis of N-(2-(3-(2-(2,6-dioxopiperidin-3-yl)-1-oxoisoindolin-4-yl)propoxy)ethyl)-14-((2'-methyl-5-morpholino-5'-(3-(trifluoromethyl)benzamido)-[3,3'-bipyridin]-6-yl)oxy)-3,6,9,12-tetraoxatetradecan-1-amide (Compound 2.016)

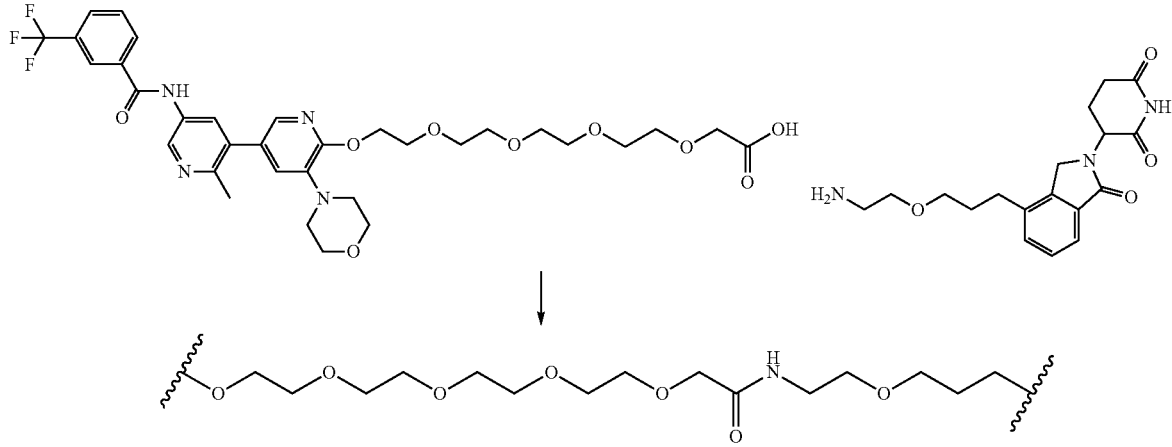

Title compound (4.4 mg, 4.6%) was prepared as solid starting from 14-((2'-methyl-5-morpholino-5'-(3-(trifluoromethyl)benzamido)-[3,3'-bipyridin]-6-yl)oxy)-3,6,9,12-tetraoxatetradecan-1-oic acid (prepared as described in Example 39) (65 mg, 0.938 mmol) and 3-(4-(3-(2-aminoethoxy)propyl)-1-oxoisoindolin-2-yl)piperidine-2,6-dione (32.4 mg, 0.938 mmol) (Zhou et. al. *J. Med. Chem.* 2018, 61 (2), 462-481) as described in Example 62. Rf=0.45 (10% MeOH in DCM). $^1$H NMR (400 MHz, CDCl$_3$) δ 8.92 (s, 1H), 8.82 (s, 1H), 8.67 (s, 1H), 8.26 (s, 1H), 8.19 (d, J=7.8 Hz, 1H), 7.94 (s, 1H), 7.81 (d, J=7.8 Hz, 1H), 7.71 (d, J=2.0 Hz, 1H), 7.65-7.60 (m, 2H), 7.42-7.33 (m, 2H), 7.18 (brs, 1H), 7.03 (d, J=2.0 Hz, 1H), 5.20 (dd, J=13.4, 5.1 Hz, 1H), 4.62-4.54 (m, 2H), 4.43 (d, J=16.1 Hz, 1H), 4.29 (d, J=16.1 Hz, 1H), 3.94 (s, 2H), 3.92-3.83 (m, 6H), 3.73-3.67 (m, 2H), 3.67-3.58 (m, 10H), 3.50-3.35 (m, 6H), 3.17-3.09 (m, 4H), 2.94-2.84 (m, 1H), 2.84-2.74 (m, 1H), 2.69 (t, J=7.5 Hz, 2H), 2.50 (s, 3H), 2.45-2.32 (m, 1H), 2.23-2.14 (m, 1H), 1.96-1.82 (m, 2H). $^{19}$F NMR (376 MHz, CDCl$_3$) δ −63.04 (s). LRMS, m/z, calculated for C$_{51}$H$_{60}$F$_3$N$_7$O$_{12}$, 1019.43; found, 1018.25 (M−H)$^-$; 1042.19 (M+Na)$^+$. HPLC, RT=9.1 min (purity, 97%). HPLC Prep method: Column, Phenomenex, Synergi, 4μ, Max-RP 80A, AX; 250×21.2 mm, mobile phase, acetonitrile in water (10% to 100%, 25 min); flow rate, 15 mL/min.

Example 65—Synthesis of N-(6'-(2-(2-(2-((5-(2-(2,6-dioxopiperidin-3-yl)-1-oxoisoindolin-4-yl)pentyl)amino)-2-oxoethoxy)ethoxy)ethoxy)-2-methyl-5'-morpholino-[3,3'-bipyridin]-5-yl)-3-(trifluoromethyl)benzamide (Compound 2.017)

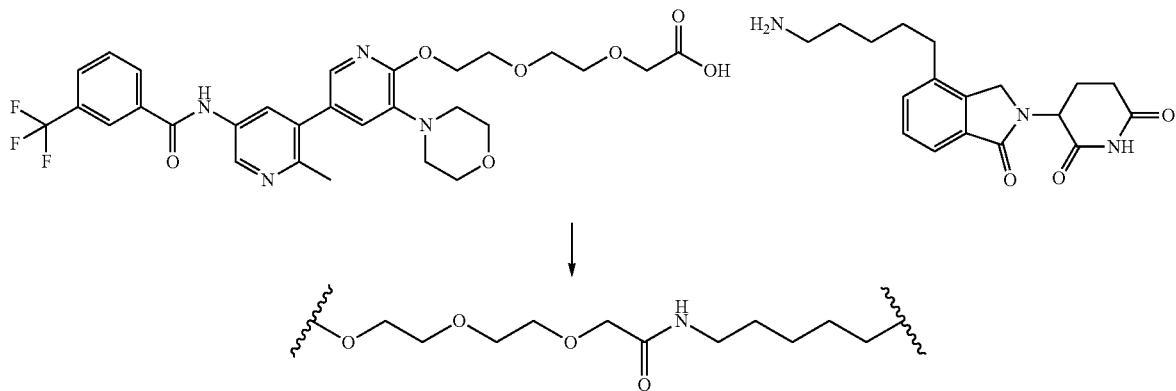

Title compound (6 mg, 6.09%) was prepared as light yellow solid from 2-(2-(2-((2'-methyl-5-morpholino-5'-(3-(trifluoromethyl)benzamido)-[3,3'-bipyridin]-6-yl)oxy)ethoxy)ethoxy)acetic acid (65 mg, 0.108 mmol) and 3-(4-(5-aminopentyl)-1-oxoisoindolin-2-yl)piperidine-2,6-dione (35.4 mg, 0.108 mmol) as described in 2.015 followed by reverse phase prep HPLC using a gradient of acetonitrile in water (10-100%, 25 min, 0.2% formic acid buffer in water). Rf=0.44 (10% MeOH-DCM). $^1$H NMR (400 MHz, CDCl$_3$) δ 8.78 (d, J=2.2 Hz, 1H), 8.68 (brs, 1H), 8.41 (brs, 1H), 8.25 (s, 1H), 8.16 (d, J=7.8 Hz, 1H), 7.95 (s, 1H), 7.82 (d, J=7.9 Hz, 1H), 7.68-7.55 (m, 3H), 7.37-7.31 (m, 2H), 7.10-7.04 (m, 1H), 7.03 (d, J=2.0 Hz, 1H), 5.17 (dd, J=13.2, 5.1 Hz, 1H), 4.62-4.56 (m, 2H), 4.37 (d, J=16.0 Hz, 1H), 4.26 (d, J=16.0 Hz, 1H), 3.96 (s, 2H), 3.92 (t, J=4.8 Hz, 2H), 3.89-3.81 (m, 4H), 3.76-3.70 (m, 2H), 3.69-3.64 (m, 2H), 3.26-3.16 (m, 2H), 3.16-3.09 (m, 4H), 2.93-2.85 (m, 1H), 2.84-2.71 (m, 1H), 2.59-2.53 (m, 2H), 2.48 (s, 3H), 2.43-2.31 (m, 1H), 2.25-2.13 (m, 1H), 1.66-1.55 (m, 3H), 1.54-1.45 (m, 2H), 1.37-1.23 (m, 2H). $^{19}$F NMR (376 MHz, CDCl$_3$) δ −63.05 (s). LRMS, m/z, calculated for $C_{47}H_{52}F_3N_7O_9$, 915.38; found, 913.77 (M−H)$^-$; 916.14 (M+Na). HPLC, $t_R$=9.29 min (purity, >95%). HPLC Prep method: Column, Phenomenex, Synergi, 4μ, Max-RP 80A, AX; 250×21.2 mm, mobile phase, acetonitrile in water (10% to 100%, 25 min) using 0.2% formic acid buffer in water; flow rate, 15 mL/min.

Example 66—Synthesis of N-(6'-((18-(2-(2,6-dioxopiperidin-3-yl)-1-oxoisoindolin-4-yl)-11-oxo-3,6,9-trioxa-12-azaoctadecyl)oxy)-2-methyl-5'-morpholino-[3,3'-bipyridin]-5-yl)-3-(trifluoromethyl)benzamide (Compound 2.018)

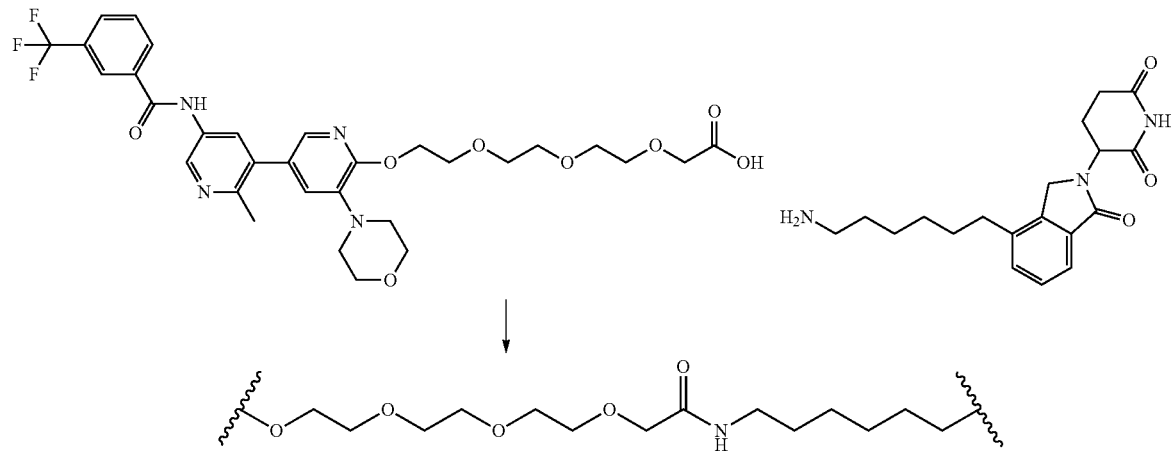

Title compound (15.2 mg, 16.4%) was prepared as a white solid from 2-(2-(2-(2-((2'-methyl-5-morpholino-5'-(3-(trifluoromethyl)benzamido)-[3,3'-bipyridin]-6-yl)oxy)ethoxy)ethoxy)ethoxy)acetic acid (82.0 mg, 0.420 mmol) and 3-(4-(6-aminohexyl)-1-oxoisoindolin-2-yl)piperidine-2,6-dione (202.1 mg, 0.455 mmol) as described in 2.016. Rf=0.39 (10% MeOH in DCM). $^1$H NMR (400 MHz, CDCl$_3$) δ 9.18 (s, 1H), 8.93 (bs, 1H), 8.82 (d, J=2.4 Hz, 1H), 8.26 (s, 1H), 8.17 (d, J=7.8 Hz, 1H), 8.03 (d, J=2.3 Hz, 1H), 7.78 (d, J=7.7 Hz, 1H), 7.69 (d, J=1.9 Hz, 1H), 7.60 (m, 2H), 7.36 (m, 2H), 7.03 (d, J=1.9 Hz, 1H), 6.98 (t, J=5.8 Hz, 1H), 5.19 (dd, J=13.3, 5.1 Hz, 1H), 4.61-4.54 (m, 2H), 4.40 (d, J=16.0 Hz, 1H), 4.27 (d, J=16.0 Hz, 1H), 3.93 (s, 2H), 3.91-3.88 (m, 2H), 3.88-3.84 (m, 4H), 3.72 (m, 2H), 3.68-3.61 (m, 6H), 3.23 (dd, J=13.8, 6.6 Hz, 2H), 3.13 (m, 4H), 2.91-2.83 (m, 1H), 2.84-2.72 (m, 1H), 2.59 (m, 2H), 2.48 (s, 3H), 2.38 (ddd, J=26.4, 13.3, 5.0 Hz, 1H), 2.23-2.13 (m, 1H), 1.60 (m, 2H), 1.53-1.44 (m, 2H), 1.33 (m, 4H) ppm. $^{19}$F NMR (376 MHz, CDCl$_3$) δ −63.02 (s) ppm. LRMS (ESI) m/z: Calculated for $C_{50}H_{58}F_3N_7O_{10}$, 973.42; found 996.19 (M+Na)$^+$; found 972.14 (M−H)−. HPLC, $t_R$=9.60 min (purity, >99%). HPLC Method: Cartridge, Agilent, Zorbax-SB-CN, 3.5 μm, 4.6×150 mm, mobile phase, acetonitrile in water (0 to 100%) contains ammonium acetate buffer; flow rate, 0.1 mL/min, run time, 20 min.

Example 67—Synthesis of N-(6'-((15-(2-(2,6-dioxopiperidin-3-yl)-1-oxoisoindolin-4-yl)-8-oxo-3,6,12-trioxa-9-azapentadecyl)oxy)-2-methyl-5'-morpholino-[3,3'-bipyridin]-5-yl)-3-(trifluoromethyl)benzamide (Compound 2.019)

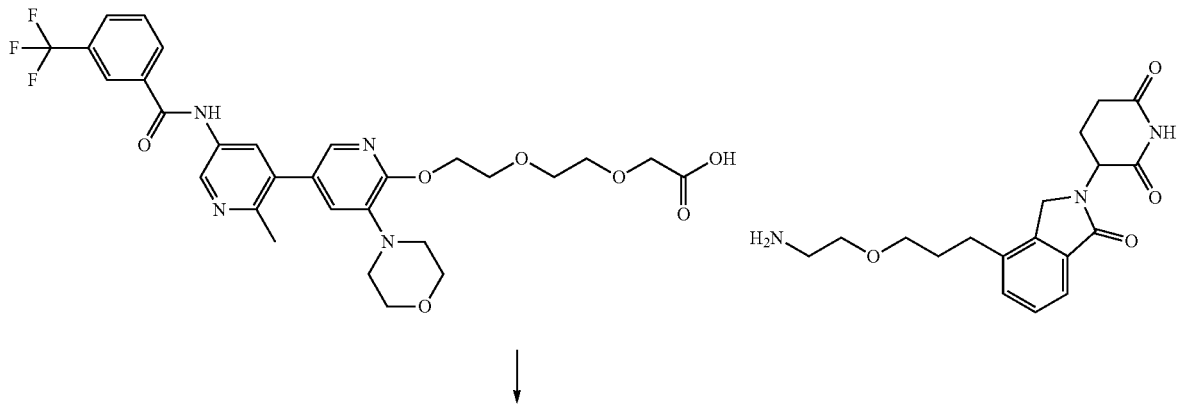

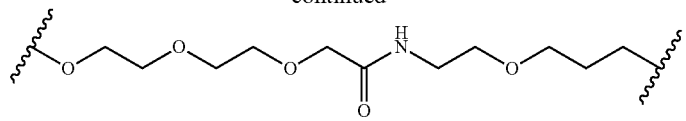

Title compound (33.8 mg, 33.7%) was prepared as a white solid from 2-(2-(2-(2-((2'-methyl-5-morpholino-5'-(3-(trifluoromethyl)benza-mido)-[3,3'-bipyridin]-6-yl)oxy)ethoxy)ethoxy)acetic acid (65 mg, 0.108 mmol) and 3-(4-(3-(2-aminoethoxy)propyl)-1-oxoisoindolin-2-yl)piperidine-2,6-dione (37.1 mg, 0.108 mmol) as described in 2.015. Rf=0.44 (10% MeOH in DCM). $^1$H NMR (400 MHz, CDCl$_3$) δ 8.93 (s, 1H), 8.86 (d, J=2.4 Hz, 1H), 8.78 (s, 1H), 8.27 (s, 1H), 8.19 (d, J=7.8 Hz, 1H), 7.94 (d, J=2.4 Hz, 1H), 7.81 (d, J=7.5 Hz, 1H), 7.66-7.56 (m, 3H), 7.35 (d, J=4.0 Hz, 2H), 7.21-7.13 (m, 1H), 7.02 (d, J=2.0 Hz, 1H), 5.16 (dd, J=13.4, 5.1 Hz, 1H), 4.63-4.53 (m, 2H), 4.41 (d, J=16.1 Hz, 1H), 4.28 (d, J=16.1 Hz, 1H), 3.99 (s, 2H), 3.93-3.87 (m, 2H), 3.88-3.81 (m, 4H), 3.76-3.65 (m, 4H), 3.52-3.33 (m, 6H), 3.15-3.07 (m, 4H), 2.92-2.73 (m, 2H), 2.69 (t, J=7.6 Hz, 2H), 2.48 (s, 3H), 2.44-2.29 (m, 1H), 2.20-2.09 (m, 1H), 1.96-1.82 (m, 2H). $^{19}$F NMR (376 MHz, CDCl$_3$) δ −63.04 (s). LRMS, m/z, calculated for C$_{47}$H$_{52}$F$_3$N$_7$O$_{10}$, 931.37; found, 930.19 (M−H)$^-$; 954.18 (M+Na)$^+$. HPLC, t$_R$=9.07 min (purity, 96.4%).

Example 68—Synthesis of N-(6'-((18-(2-(2,6-dioxopiperidin-3-yl)-1-oxoisoindolin-4-yl)-11-oxo-3,6,9,15-tetraoxa-12-azaoctadecyl)oxy)-2-methyl-5'-morpholino-[3,3'-bipyridin]-5-yl)-3-(trifluoromethyl)-benzamide (Compound 2.020)

Title compound (16 mg, 17.7%) was prepared as light yellow solid from 2-(2-(2-(2-(2-((2'-methyl-5-morpholino-5'-(3-(trifluoromethyl)benzamido)-[3,3'-bipyridin]-6-yl)oxy)ethoxy)ethoxy)ethoxy)acetic acid (60 mg) and 3-(4-(3-(2-aminoethoxy)propyl)-1-oxoisoindolin-2-yl)piperidine-2,6-dione (38.3 mg, 0.111 mmol) as described in 2.015. Rf=0.36 (10% MeOH in DCM). $^1$H NMR (400 MHz, CDCl$_3$) δ 9.03 (s, 1H), 8.92-8.84 (m, 2H), 8.27 (s, 1H), 8.19 (d, J=7.8 Hz, 1H), 7.96 (d, J=2.4 Hz, 1H), 7.80 (d, J=7.8 Hz, 1H), 7.68 (d, J=2.0 Hz, 1H), 7.65-7.58 (m, 2H), 7.37-7.33 (m, 2H), 7.19-7.12 (m, 1H), 7.02 (d, J=2.0 Hz, 1H), 5.18 (dd, J=13.3, 5.1 Hz, 1H), 4.62-4.54 (m, 2H), 4.43 (d, J=16.2 Hz, 1H), 4.29 (d, J=16.1 Hz, 1H), 3.96 (s, 2H), 3.93-3.81 (m, 6H), 3.74-3.68 (m, 2H), 3.67-3.61 (m, 5H), 3.51-3.36 (m, 7H), 3.17-3.07 (m, 4H), 2.93-2.65 (m, 4H), 2.48 (s, 3H), 2.45-2.30 (m, 1H), 2.24-2.13 (m, 1H), 1.96-1.85 (m, 2H). $^{19}$F NMR (376 MHz, CDCl$_3$) δ −63.04 (s). LRMS, m/z, calculated for C$_{49}$H$_{56}$F$_3$N$_7$O$_{11}$, 975.4; found, 974.07 (M−H)$^-$; 998.26 (M+Na)$^+$. HPLC, t$_R$=9.1 min (purity, 95%).

Example 69 and Example 100 describes the synthesis of Compounds 2.021 to 2.023, each of these conjugates are embraced by the following Formula

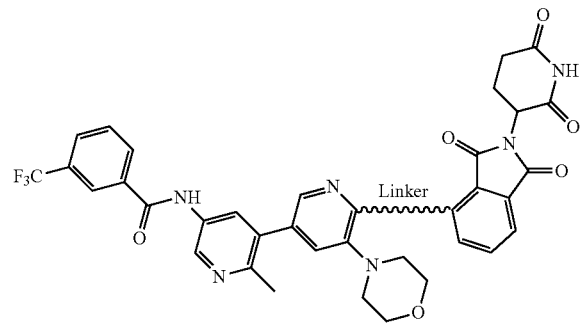 [SMILES: Cc1ncc(NC(=O)c2cccc(C(F)(F)F)c2)cc1-c1cnc(-c2cccc3c2C(=O)N(C2CCC(=O)NC2=O)C3=O)c(N2CCOCC2)c1]

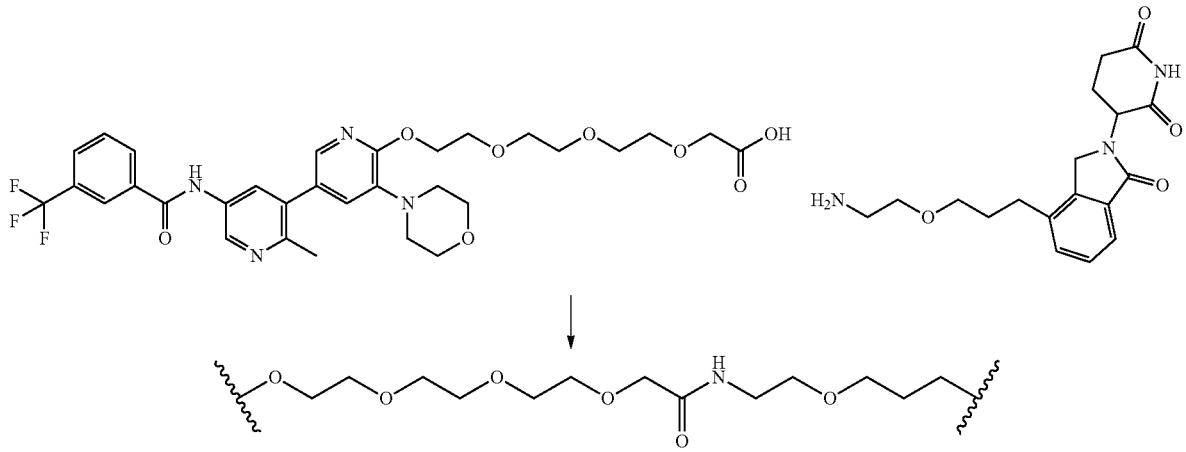

Example 69—Synthesis of tert-butyl 2-(2-(2-(2-hydroxyethoxy)ethoxy)ethoxy)acetate (for Compound 2.021)

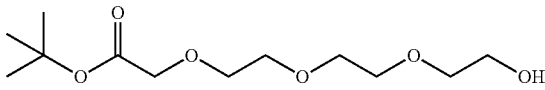 [SMILES: CC(C)(C)OC(=O)COCCOCCOCCO]

To a cold (0° C.) stirred solution of tert-butyl 2-bromo-acetate (5.4 mL, 36.6 mmol) and 2,2'-(ethane-1,2-diylbis (oxy))diethanol (22.0 mL, 164 mmol) in DMSO (50.0 mL) was added 60% NaH (1.6033 g, 40.1 mmol) in 2 portions. The reaction mixture was slowly warmed up to rt, stirred for 24 h, diluted with water (100 mL) and extracted with EtOAc (3×100 mL). The combined organic extracts were dried, and concentrated. The residue was purified on a 80 g $SiO_2$ cartridge using a gradient of ethyl acetate in hexanes (50-100%) to afford the title compound (3.35 g, 34.7% yield) as a colorless oil. Rf=0.18 (EtOAc). $^1$H NMR (400 MHz, $CDCl_3$) δ 4.02 (s, 2H), 3.71 (qd, J=4.9, 2.9 Hz, 6H), 3.68-3.66 (m, 4H), 3.63-3.59 (m, 2H), 1.47 (s, 9H) ppm. LRMS (ESI) m/z: calculated for $C_{12}H_{24}O_6$ 264.16; found 287.02 (M+Na)$^+$.

Example 70—Synthesis of N-(6'-((18-(2-(2,6-diox-opiperidin-3-yl)-1,3-dioxoisoindolin-4-yl)-11-oxo-3,6,9,15-tetraoxa-12-azaoctadecyl)oxy)-2-methyl-5'-morpholino-[3,3'-bipyridin]-5-yl)-3-(trifluoromethyl)-benzamide (Compound 2.021)

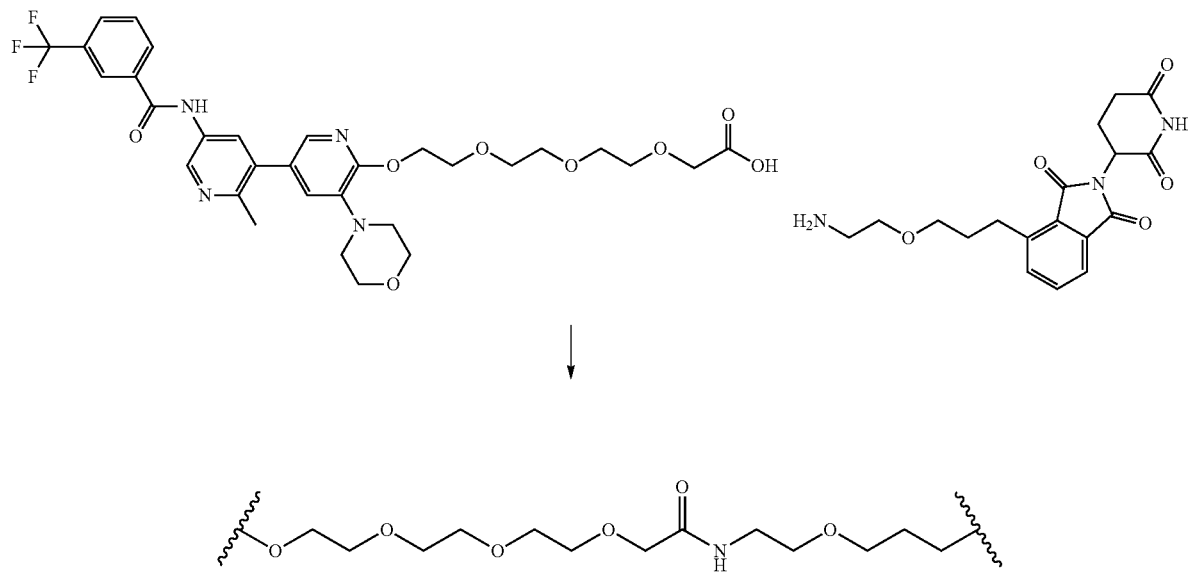

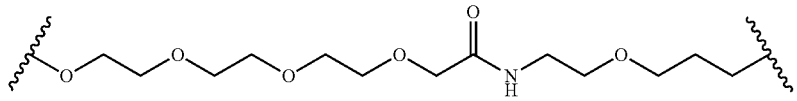

Title compound (22.4 mg, 23.9%) was prepared as a white solid from 2-(2-(2-(2-(((2'-methyl-5-morpholino-5'-(3-(trifluoromethyl)benzamido)-[3,3'-bipyridin]-6-yl)oxy)ethoxy)ethoxy)ethoxy)acetic acid (61.3 mg, 0.0945 mmol) and 4-(3-(2-aminoethoxy)propyl)-2-(2,6-dioxopiperidin-3-yl) isoindoline-1,3-dione (149.6 mg, 0.416 mmol) (Zhou et. al. J. Med. Chem. 2018, 61 (2), 462-481) as described in Example 36. Rf=0.45 (10% MeOH in DCM). $^1$H NMR (400 MHz, $CDCl_3$) δ 8.79 (d, J=2.5 Hz, 1H), 8.76-8.68 (bs, 1H), 8.61 (s, 1H), 8.21 (s, 1H), 8.14 (d, J=7.8 Hz, 1H), 8.01 (d, J=2.4 Hz, 1H), 7.82 (d, J=7.8 Hz, 1H), 7.74 (d, J=2.0 Hz, 1H), 7.69 (d, J=6.7 Hz, 1H), 7.65 (d, J=8.2 Hz, 1H), 7.61 (d, J=7.4 Hz, 1H), 7.52 (d, J=7.4 Hz, 1H), 7.18 (s, 1H), 7.05 (d, J=2.0 Hz, 1H), 4.95 (dd, J=12.2, 5.3 Hz, 1H), 4.62-4.55 (m, 2H), 3.96 (s, 2H), 3.93-3.83 (m, 6H), 3.75-3.68 (m, 2H), 3.68-3.59 (m, 6H), 3.45 (t, J=5.3 Hz, 5H), 3.18-3.09 (m, 6H), 2.88 (dd, J=13.8, 3.7 Hz, 1H), 2.80 (dd, J=12.5, 3.7 Hz, 1H), 2.77-2.70 (m, 1H), 2.50 (s, 3H), 2.13 (dd, J=11.4, 6.1 Hz, 1H), 1.96-1.87 (m, 2H) ppm. $^{19}$F NMR (376 MHz, $CDCl_3$) δ -63.07 (s) ppm. LRMS (ESI) m/z: calculated for $C_{49}H_{54}F_3N_7O_{12}$, 989.38; found 990.26 (M+H)$^+$; found 1011.94 (M+Na)$^+$; found 988.38 (M–H)$^-$. HPLC, $t_R$=9.60 min (purity, >99%). HPLC Method: Cartridge, Agilent, Zorbax-SB-CN, 3.5 μm, 4.6×150 mm, mobile phase, acetonitrile in water (0 to 100%) contains ammonium acetate buffer; flow rate, 0.1 mL/min, run time, 20 min.

Example 71—Synthesis of N-(2-methyl-5'-morpholino-6'-(2-(prop-2-yn-1-yloxy)ethoxy)-[3,3'-bipyridin]-5-yl)-3-(trifluoromethyl)benzamide (for Compound 2.022)

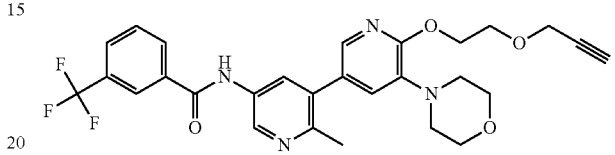

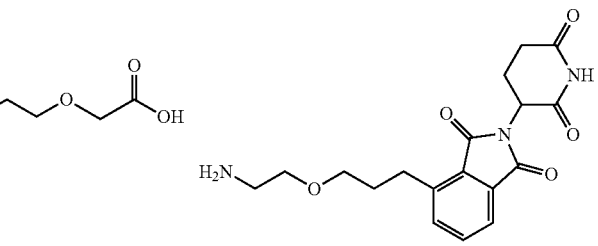

Title compound (81.9 mg, 67%) was prepared as a white solid from 2-(prop-2-yn-1-yloxy)ethanol (109.6 mg, 1.10 mmol) and N-(6'-fluoro-2-methyl-5'-morpholino-[3,3'-bipyridin]-5-yl)-3-(trifluoromethyl)benzamide (104.2 mg, 0.226 mmol) in 1,4-dioxane (1.5 mL) as described in Example 9. Rf=0.18 (EtOAc). $^1$H NMR (400 MHz, $CDCl_3$) δ 8.62 (d, J=2.5 Hz, 1H), 8.15 (s, 1H), 8.13 (d, J=2.5 Hz, 1H), 8.09 (d, J=7.6 Hz, 1H), 7.90-7.82 (m, 2H), 7.77 (d, J=2.0 Hz, 1H), 7.67 (t, J=7.8 Hz, 1H), 7.06 (d, J=2.0 Hz, 1H), 4.63-4.58 (m, 2H), 4.27 (d, J=2.4 Hz, 2H), 3.99-3.95 (m, 2H), 3.93-3.87 (m, 4H), 3.20-3.13 (m, 4H), 2.51 (s, 3H), 2.46 (t, J=2.4 Hz, 1H) ppm. $^{19}$F NMR (376 MHz, $CDCl_3$) δ -63.16 (s) ppm. LRMS, m/z, calculated for $C_{28}H_{27}F_3N_4O_4$, 540.2; found, 539.01 (M–H)$^-$.

Example 72—Synthesis of N-(6'-(2-((1-(6-((2-(2,6-dioxopiperidin-3-yl)-1,3-dioxoisoindolin-4-yl)amino)-6-oxohexyl)-1H-1,2,3-triazol-4-yl)methoxy)ethoxy)-2-methyl-5'-morpholino-[3,3'-bipyridin]-5-yl)-3-(trifluoromethyl)benzamide (Compound 2.022)

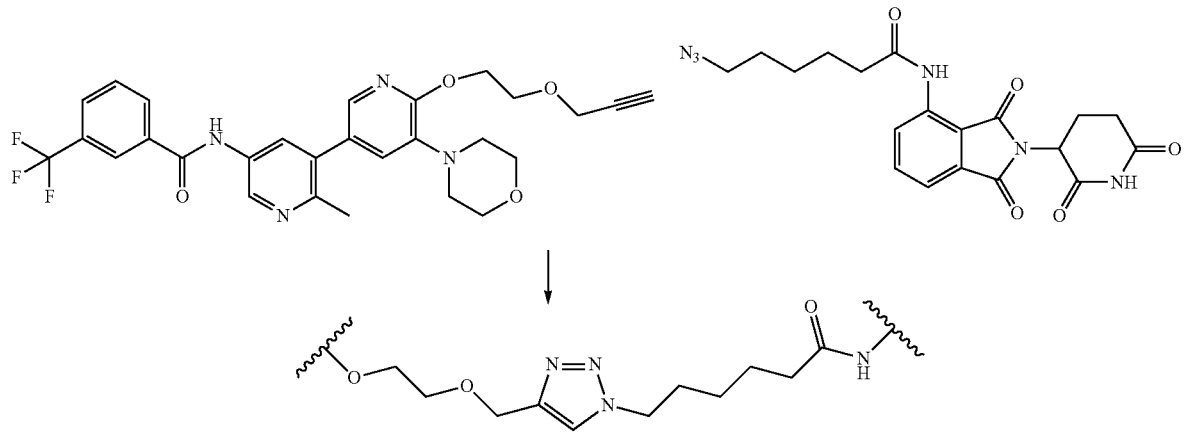

Title compound (45.5 mg, 51.6%) was prepared as pale yellow solid from N-(2-methyl-5'-morpholino-6'-(2-(prop-2-yn-1-yloxy)ethoxy)-[3,3'-bipyridin]-5-yl)-3-(trifluoromethyl) benzamide (50.0 mg, 0.0925 mmol) as described in Example 22. Rf=0.14 (5% MeOH in DCM). $^1$H NMR (400 MHz, CDCl$_3$) δ 9.38 (s, 1H), 8.77 (d, J=8.4 Hz, 1H), 8.66 (s, 1H), 8.57 (s, 1H), 8.25 (s, 1H), 8.16 (s, 1H), 8.10 (d, J=2.9 Hz, 2H), 7.83 (d, J=7.8 Hz, 1H), 7.74 (d, J=1.9 Hz, 1H), 7.72-7.67 (m, 1H), 7.65 (t, J=7.8 Hz, 1H), 7.53 (d, J=8.1 Hz, 2H), 7.04 (d, J=1.8 Hz, 1H), 4.94 (dd, J=12.3, 5.5 Hz, 1H), 4.74 (s, 2H), 4.63-4.55 (m, 2H), 4.36 (t, J=7.1 Hz, 2H), 3.98-3.93 (m, 2H), 3.87-3.82 (m, 4H), 3.13 (s, 4H), 2.94-2.82 (m, 1H), 2.86-2.72 (m, 2H), 2.50 (d, J=4.5 Hz, 3H), 2.45 (t, J=7.3 Hz, 2H), 2.16 (d, J=10.8 Hz, 1H), 1.95 (dd, J=15.1, 7.3 Hz, 2H), 1.78 (dt, J=15.0, 7.4 Hz, 2H), 1.43 (dd, J=15.6, 8.3 Hz, 2H) ppm. $^{19}$F NMR (376 MHz, CDCl$_3$) δ −63.11 (s) ppm. LRMS, m/z, calculated for C$_{47}$H$_{47}$F$_3$N$_{10}$O$_9$, 952.35; found, 975.32 (M+Na)$^+$. HPLC, t$_R$=9.83 min (purity, 95.3%).

Example 73—Synthesis of N-(6'-((15-(2-(2,6-dioxopiperidin-3-yl)-1,3-dioxoisoindolin-4-yl)-8-oxo-3,6,12-trioxa-9-azapentadecyl)oxy)-2-methyl-5'-morpholino-[3,3'-bipyridin]-5-yl)-3-(trifluoromethyl)ben-zamide (Compound 2.023)

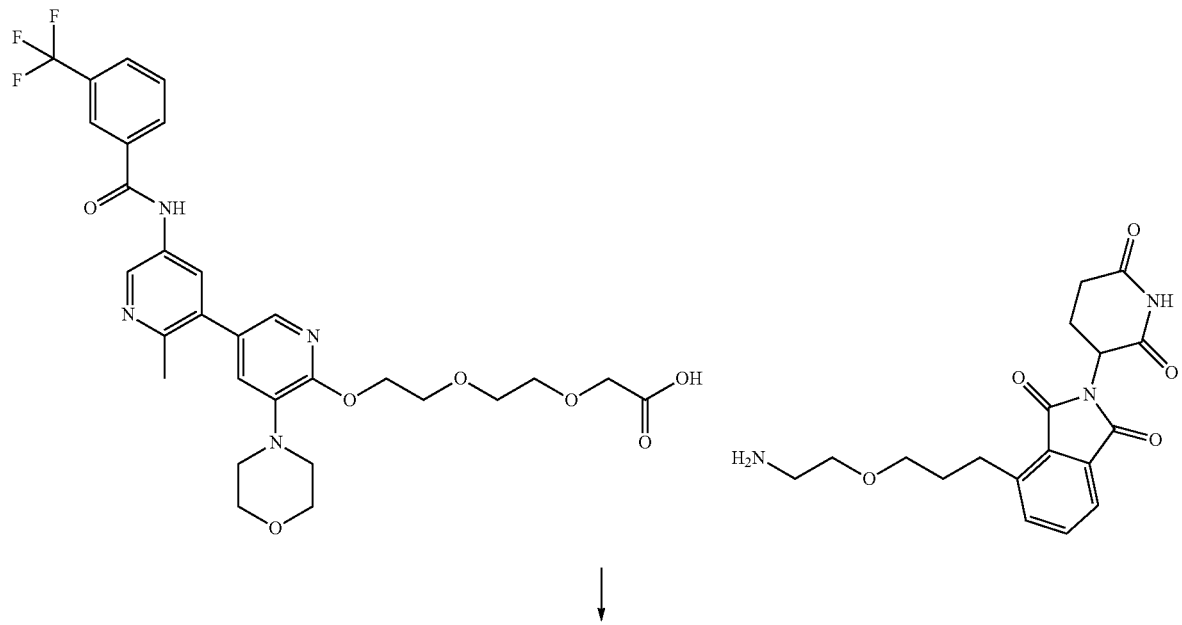

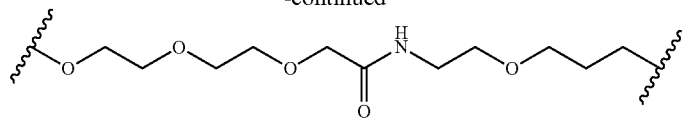

Title compound (16 mg, 15.7%) was prepared as a white solid from 2-(2-(2-((2'-methyl-5-morpholino-5'-(3-(trifluoromethyl)benzamido)-[3,3'-bipyridin]-6-yl)oxy)ethoxy)ethoxy)acetic acid (65 mg, 0.108 mmol) and 4-(3-(2-aminoethoxy)propyl)-2-(2,6-dioxopiperidin-3-yl)isoindoline-1,3-dione (38.6 mg, 0.108 mmol) as described in TJ-183. Rf=0.45 (10% Methanol in DCM). $^1$H NMR (400 MHz, CDCl$_3$) δ 8.71 (d, J=2.2 Hz, 2H), 8.46 (s, 1H), 8.17 (s, 1H), 8.11 (d, J=8.0 Hz, 1H), 8.04 (d, J=2.4 Hz, 1H), 7.82 (d, J=7.8 Hz, 1H), 7.74 (d, J=2.0 Hz, 1H), 7.67-7.63 (m, 2H), 7.60 (t, J=7.5 Hz, 1H), 7.51 (d, J=7.6 Hz, 1H), 7.19 (brs, 1H), 7.06 (d, J=2.0 Hz, 1H), 4.93 (dd, J=12.1, 5.3 Hz, 1H), 4.63-4.57 (m, 2H), 3.99 (s, 2H), 3.95-3.89 (m, 2H), 3.89-3.83 (m, 4H), 3.75-3.70 (m, 2H), 3.70-3.65 (m, 2H), 3.49-3.40 (m, 6H), 3.18-3.05 (m, 6H), 2.91-2.69 (m, 3H), 2.50 (s, 3H), 2.17-2.08 (m, 1H), 1.94-1.85 (m, 2H). $^{19}$F NMR (376 MHz, CDCl3) δ −63.08 (s). LRMS, m/z, calculated for C$_{47}$H$_{50}$F$_3$N$_7$O$_{11}$, 945.35; found, 943.89 (M−H)$^−$; 968.07 (M+Na)$^+$. HPLC, $t_R$=9.6 min (>99.5%). HPLC Prep method: Column, Phenomenex, Synergi, 4μ, Max-RP 80A, AX; 250×21.2 mm, mobile phase, acetonitrile in water (10% to 100%, 25 min); flow rate, 15 mL/min.

Example 74 to Example 84 describes the synthesis of Compounds 2.024 to 2.034, each of these conjugates are embraced by the following Formula

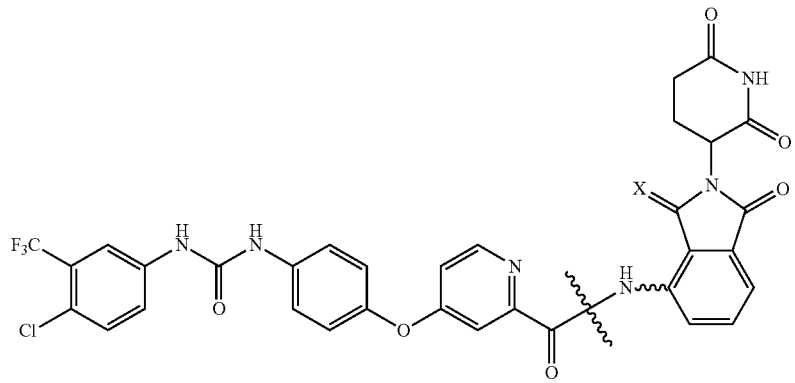

Example 74—Synthesis of 4-(4-(3-(4-chloro-3-(trifluoromethyl)phenyl)ureido)phenoxy)-N-((1-(6-((2-(2,6-dioxopiperidin-3-yl)-1,3-dioxoisoindolin-4-yl)amino)-6-oxohexyl)-1H-1,2,3-triazol-4-yl)methyl)picolinamide (Compound 2.024)

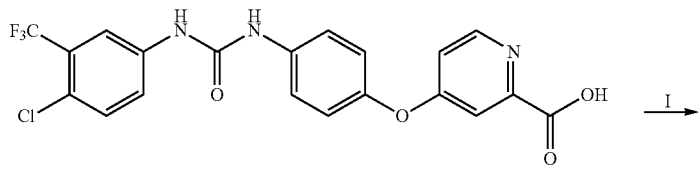

I

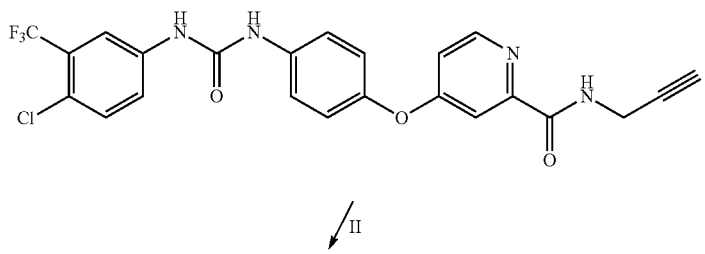

II

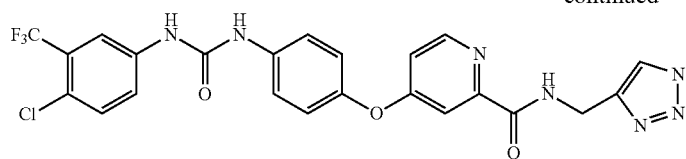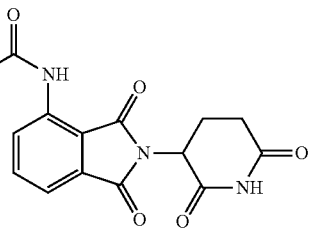

Step I, Synthesis of 4-(4-(3-(4-chloro-3-(trifluoromethyl)phenyl)ureido)phenoxy)-N-(prop-2-yn-1-yl)picolinamide To a stirred solution of 4-(4-(3-(4-chloro-3-(trifluoromethyl)phenyl)ureido)phenoxy)picolinic acid (132 mg, 0.292 mmol) in DMF (2.0 mL) were added propargylamine (20 uL, 0.313 mmol), HATU (167 mg, 0.438 mmol) and DIPEA (403 μL, 2.34 mmol). The reaction mixture was stirred overnight at rt. The mixture was diluted with EtOAc and water. The phases were separated and the aqueous layer was then extracted twice with EtOAc. The combined organic layers were washed with brine, dried over $Na_2SO_4$, filtered and concentrated to dryness under reduced pressure. The residue was purified by flash chromatography on silica gel using a gradient of EtOAc acetate in hexanes (0-100%) to afford the title compound (101 mg, 71%). $^1$H NMR (600 MHz, $CDCl_3$) δ 8.53-8.44 (m, 2H), 7.79 (s, 1H), 7.72 (s, 1H), 7.70 (s, 1H), 7.64 (d, J=8.6 Hz, 1H), 7.56 (s, 1H), 7.39 (d, J=8.7 Hz, 1H), 7.34 (d, J=8.5 Hz, 2H), 7.16 (d, J=5.4 Hz, 1H), 6.99 (d, J=8.4 Hz, 2H), 4.23 (d, J=5.2 Hz, 2H), 2.26 (s, 1H). LRMS (m/z) calculated, 488.09; found, 490.7 (M+H)$^+$.

Step II, Synthesis of 4-(4-(3-(4-chloro-3-(trifluoromethyl)phenyl)ureido)phenoxy)-N-((1-(6-((2-(2,6-dioxopiperidin-3-yl)-1,3-dioxoisoindolin-4-yl)amino)-6-oxohexyl)-1H-1,2,3-triazol-4-yl)methyl)picolinamide To a mixture of 4-(4-(3-(4-chloro-3-(trifluoromethyl)phenyl)ureido)phenoxy)-N-(prop-2-yn-1-yl)picolinamide (35 mg, 0.072 mmol), sodium ascorbate (2.8 mg, 0.014 mmol), copper(II) sulfate pentahydrate (3.5 mg, 0.014 mmol) and 6-azido-N-(2-(2,6-dioxopiperidin-3-yl)-1,3-dioxoisoindolin-4-yl)hexanamide (31 mg, 0.075 mmol) (Example 8) was added THF (1.0 mL) and water (20 uL). The head space of the flask was purged briefly with argon and stirred at rt for 18 h. The mixture was diluted with EtOAc and water. The phases were separated and the aqueous layer was extracted twice with EtOAc. The combined organic layers were washed with brine, dried ($Na_2SO_4$), filtered and concentrated. The crude product was purified by flash chromatography on silica gel using a gradient of MeOH in DCM to afford the product. The product was dissolved in DMSO and purified by reverse phase chromatography using a gradient of acetonitrile in water followed by lyophilisation to afford the title compound (22 mg, 32%) as a white solid. $^1$H NMR (600 MHz, DMSO) δ 11.14 (s, 1H), 9.68 (s, 1H), 9.28-9.13 (m, 2H), 9.00 (s, 1H), 8.51 (d, J=5.4 Hz, 1H), 8.44 (d, J=8.3 Hz, 1H), 8.11 (s, 1H), 7.93 (s, 1H), 7.81 (t, J=7.8 Hz, 1H), 7.69-7.55 (m, 5H), 7.40 (s, 1H), 7.17 (d, J=6.9 Hz, 3H), 5.14 (dd, J=12.7, 5.0 Hz, 1H), 4.50 (d, J=4.8 Hz, 2H), 4.31 (t, J=6.9 Hz, 2H), 2.88 (dd, J=22.0, 9.0 Hz, 1H), 2.65-2.53 (m, 2H), 2.45 (t, J=7.2 Hz, 2H), 2.10-2.01 (m, 1H), 1.86-1.77 (m, 2H), 1.69-1.57 (m, 2H), 1.33-1.26 (m, 2H). LRMS (m/z) calculated, 900.236; found, 924.736 (M+Na)$^+$. HPLC, $t_R$=11.82 min (purity: 94%).

Example 75—Synthesis of 4-(4-(3-(4-chloro-3-(trifluoromethyl)phenyl)ureido)phenoxy)-N-(2-(1-(6-((2-(2,6-dioxopiperidin-3-yl)-1,3-dioxoisoindolin-4-yl)amino)-6-oxohexyl)-1H-1,2,3-triazol-4-yl)ethyl)picolinamide (Compound 2.025)

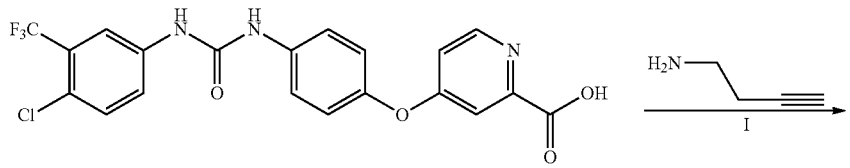

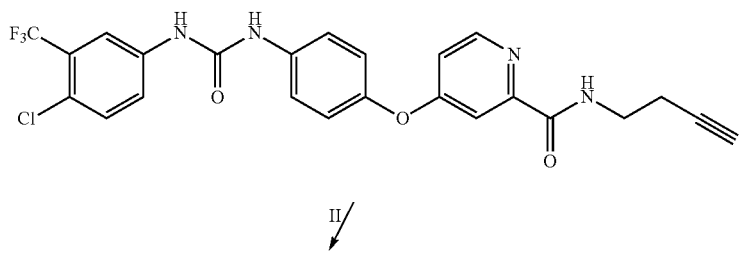

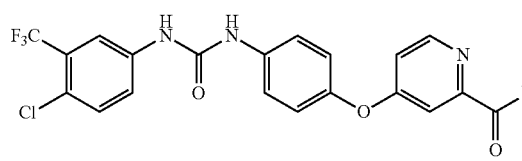

Step I, Synthesis of N-(but-3-yn-1-yl)-4-(4-(3-(4-chloro-3-(trifluoromethyl)phenyl)ureido)-phenoxy)picolinamide To a stirred solution of 4-(4-(3-(4-chloro-3-(trifluoromethyl)phenyl)ureido)-phenoxy)picolinic acid (175 mg, 0.387 mmol) in DMF (2.0 mL) were added 1-amino-3-butyne (34 uL, 0.414 mmol), HATU (221 mg, 0.581 mmol) and DIPEA (534 uL, 3.10 mmol). The reaction mixture was stirred overnight at rt. The mixture was diluted with EtOAc and water. The phases were separated and the aqueous layer was then extracted twice with EtOAc. The combined organic layers were washed with brine, dried over $Na_2SO_4$, filtered and concentrated to dryness under reduced pressure. The residue was purified by flash chromatography on silica gel using a gradient of EtOAc in hexanes (0-100%) to afford the title compound (157 mg, 81%) as a white solid. $^1$H NMR (600 MHz, CDCl$_3$) δ 8.63 (t, J=6.2 Hz, 1H), 8.48 (d, J=5.6 Hz, 1H), 8.09 (s, 1H), 7.92 (s, 1H), 7.69 (d, J=2.4 Hz, 1H), 7.62 (dd, J=8.7, 2.4 Hz, 1H), 7.54 (d, J=2.3 Hz, 1H), 7.37 (d, J=8.7 Hz, 1H), 7.32 (d, J=8.8 Hz, 2H), 7.16 (dd, J=5.6, 2.5 Hz, 1H), 6.97 (d, J=8.9 Hz, 2H), 3.63 (q, J=6.5 Hz, 2H), 2.52 (td, J=6.6, 2.6 Hz, 2H), 2.03 (t, J=2.6 Hz, 1H). LRMS (m/z) calculated, 502.1; found, 504.9 (M+H)$^+$.

Step II, Synthesis of 4-(4-(3-(4-chloro-3-(trifluoromethyl)phenyl)ureido)phenoxy)-N-(2-(1-(6-((2-(2,6-dioxopiperidin-3-yl)-1,3-dioxoisoindolin-4-yl)amino)-6-oxohexyl)-1H-1,2,3-triazol-4-yl)ethyl)picolinamide To a mixture of N-(but-3-yn-1-yl)-4-(4-(3-(4-chloro-3-(trifluoromethyl)phenyl)-ureido)phenoxy)picolinamide (155 mg, 0.308 mmol), sodium ascorbate (12 mg, 0.060 mmol), copper(II) sulfate pentahydrate (15 mg, 0.060 mmol) and 6-azido-N-(2-(2,6-dioxopiperidin-3-yl)-1,3-dioxoisoindolin-4-yl)hexanamide (136 mg, 0.330 mmol) were added THF (3.0 mL) and water (300 uL). The head space of the flask was purged briefly with argon and the mixture was stirred at rt for 7 h before being diluted with THF and water. The phases were separated and the aqueous layer was extracted twice with THF. The combined organic layers were washed with brine, dried over $Na_2SO_4$, filtered and concentrated. The crude product was stored in the freezer over the weekend. The crude product absorbed on the Celite® using methanol in DCM and purified by flash chromatography on silica gel using a gradient of EtOAc in DCM (0-100%) followed by MeOH in DCM (0-15%) to afford the title compound (120 mg, 41% yield) as a white solid. $^1$H NMR (600 MHz, DMSO) δ 11.14 (s, 1H), 9.67 (s, 1H), 9.21 (s, 1H), 8.99 (s, 1H), 8.95-8.86 (m, 1H), 8.50 (d, J=5.4 Hz, 1H), 8.45 (d, J=8.3 Hz, 1H), 8.11 (s, 1H), 7.89 (s, 1H), 7.81 (t, J=7.8 Hz, 1H), 7.69-7.50 (m, 5H), 7.38 (s, 1H), 7.16 (d, J=8.9 Hz, 3H), 5.14 (dd, J=12.7, 5.1 Hz, 1H), 4.30 (t, J=6.6 Hz, 2H), 3.54 (d, J=6.4 Hz, 2H), 2.96-2.78 (m, 3H), 2.66-2.53 (m, 2H), 2.43 (t, J=7.1 Hz, 2H), 2.12-1.97 (m, 1H), 1.91-1.72 (m, 2H), 1.68-1.55 (m, 2H), 1.33-1.16 (m, 2H). LRMS (m/z) calculated, 914.251; found, 939.275 (M+Na)$^+$. HPLC, $t_R$=11.7 min (purity: 97%).

Example 76—Synthesis of 4-(4-(3-(4-chloro-3-(trifluoromethyl)phenyl)ureido)phenoxy)-N-(4-(1-(6-((2-(2,6-dioxopiperidin-3-yl)-1,3-dioxoisoindolin-4-yl)amino)-6-oxohexyl)-1H-1,2,3-triazol-4-yl)butyl)picolinamide (Compound 2.026)

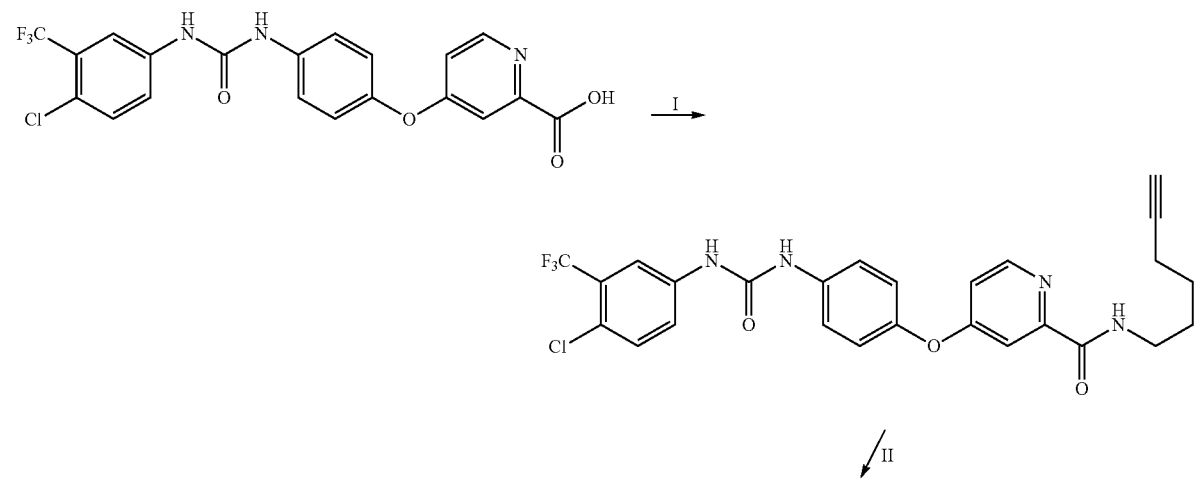

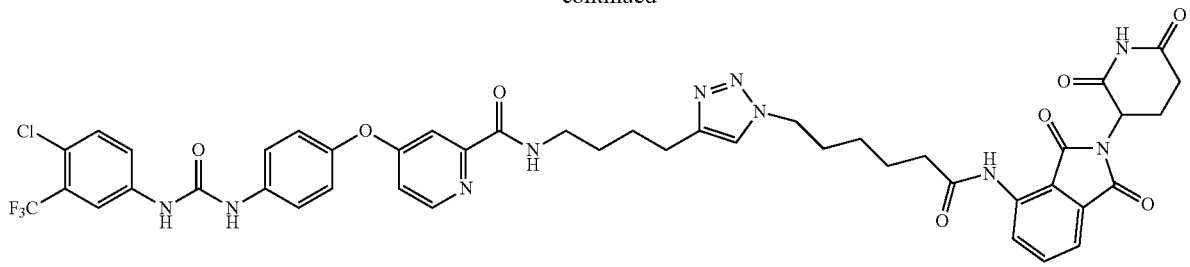

As described in Compound 2.025, Step I, Synthesis of 4-(4-(3-(4-chloro-3-(trifluoromethyl)phenyl)ureido)phenoxy)-N-(hex-5-yn-1-yl)picolinamide (147 mg, 72%). $^1$H NMR (600 MHz, CDCl$_3$) δ 8.47-8.36 (m, 3H), 8.15 (s, 1H), 7.65 (d, J=2.4 Hz, 1H), 7.60 (dd, J=8.7, 2.2 Hz, 1H), 7.53 (d, J=2.4 Hz, 1H), 7.34 (d, J=8.7 Hz, 1H), 7.30 (d, J=8.8 Hz, 2H), 7.11 (dd, J=5.6, 2.5 Hz, 1H), 6.93 (d, J=8.8 Hz, 2H), 3.47 (dd, J=13.4, 6.8 Hz, 2H), 2.20 (td, J=6.9, 2.6 Hz, 2H), 1.92 (t, J=2.5 Hz, 1H), 1.80-1.70 (m, 2H), 1.61-1.50 (m, 2H). LRMS (m/z) calculated, 530.13; found, 533.0 (M+H)$^+$.

Step II, Synthesis of 4-(4-(3-(4-chloro-3-(trifluoromethyl)phenyl)ureido)phenoxy)-N-(4-(1-(6-((2-(2,6-dioxopiperidin-3-yl)-1,3-dioxoisoindolin-4-yl)amino)-6-oxohexyl)-1H-1,2,3-triazol-4-yl)butyl)picolinamide (180 mg, 62%). $^1$H NMR (600 MHz, CDCl$_3$) δ 9.36 (s, 1H), 8.82-8.69 (m, 2H), 8.42 (s, 1H), 8.37 (d, J=5.6 Hz, 1H), 8.29 (t, J=6.1 Hz, 1H), 8.20 (s, 1H), 7.72-7.61 (m, 3H), 7.55-7.47 (m, 2H), 7.41-7.30 (m, 3H), 7.28 (s, 1H), 7.03 (dd, J=5.5, 2.3 Hz, 1H), 6.95 (d, J=8.7 Hz, 2H), 5.02-4.90 (m, 1H), 4.30 (t, J=7.1 Hz, 2H), 3.45 (q, J=6.3 Hz, 2H), 2.94-2.83 (m, 1H), 2.82-2.74 (m, 2H), 2.71 (t, J=7.2 Hz, 2H), 2.43 (t, J=7.3 Hz, 2H), 2.18-2.13 (m, 1H), 1.97-1.88 (m, 2H), 1.81-1.69 (m, 6H), 1.45-1.34 (m, 2H). LRMS (m/z) calculated, 942.282; found, 944.602 (M+H)$^+$. HPLC, $t_R$=12.1 min (purity: 98%).

Example 77—Synthesis of 4-(4-(3-(4-chloro-3-(trifluoromethyl)phenyl)ureido)phenoxy)-N-(2-(2-(2-((1-(6-((2-(2,6-dioxopiperidin-3-yl)-1,3-dioxoisoindolin-4-yl)amino)-6-oxohexyl)-1H-1,2,3-triazol-4-yl)methoxy)ethoxy)ethoxy)ethyl)picolinamide (Compound 2.027)

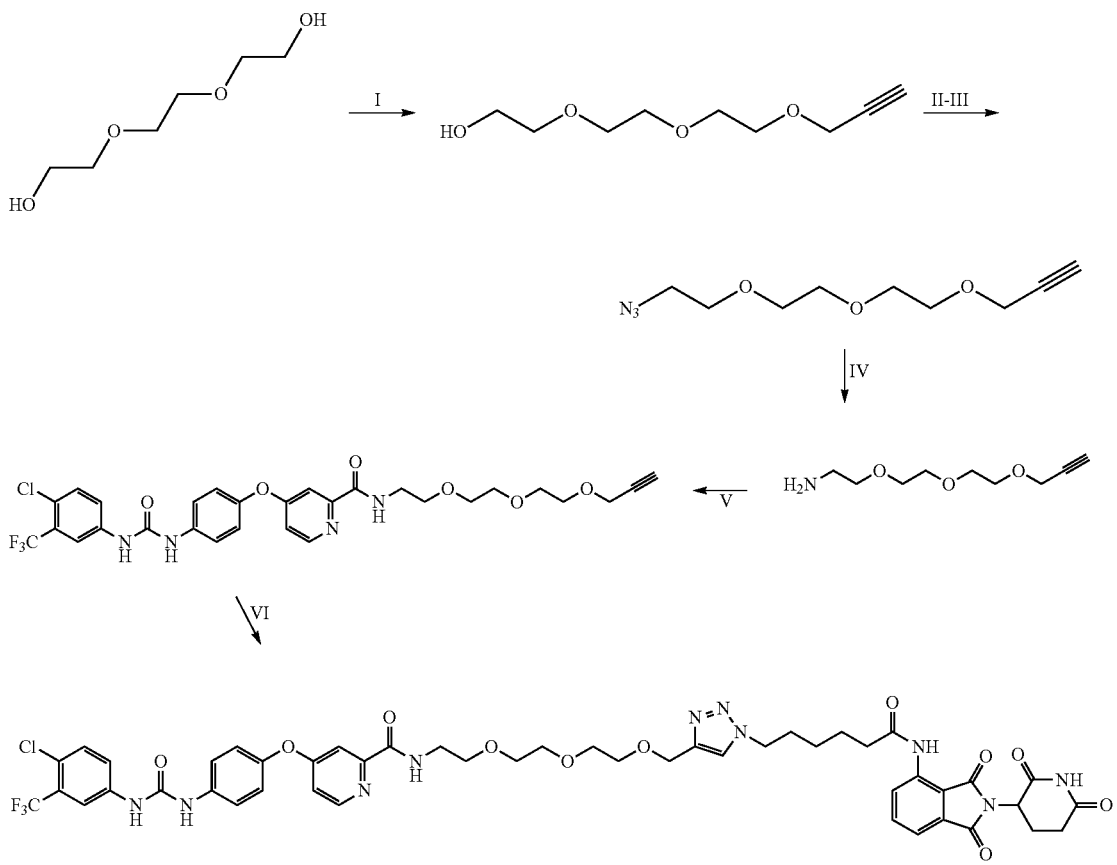

Step I, Synthesis of 2-(2-(2-(prop-2-yn-1-yloxy)ethoxy)ethoxy)ethanol

To a cold (0° C.) stirred suspension of ᵗBuOK (747 mg, 6.66 mmol) in dry THF (30 mL) was added triethyleneglycol (1.78 mL, 13.3 mmol). The reaction mixture was allowed to stir at rt for 30 min then propargyl bromide (742 uL, 6.66 mmol, 80% wt. in toluene) was added dropwise. The resulting mixture was allowed to stir at rt for 21 h. The mixture was filtered under reduced pressure using a glass frit. The filtrate was concentrated and the residue was purified by flash column chromatography on silica gel using a gradient of EtOAc in hexanes (0-100%) to afford the title compound (823 mg, 33%) as a yellow oil. $^1$H NMR (600 MHz, CDCl$_3$) δ 4.21 (d, J=2.4 Hz, 2H), 3.78-3.64 (m, 10H), 3.63-3.59 (m, 2H), 2.43 (t, J=2.4 Hz, 1H). LRMS (m/z) calculated, 188.10; found, 188.3 (M+H)$^+$.

Step II, Synthesis of 2-(2-(2-(prop-2-yn-1-yloxy)ethoxy)ethoxy)ethyl 4-methylbenzenesulfonate To a stirred solution of 2-(2-(2-(prop-2-yn-1-yloxy)ethoxy)ethoxy)ethanol (823 mg, 4.37 mmol) in DCM (10 mL) was added pyridine (1.06 mL, 13.1 mmol) and tosyl chloride (1.25 g, 6.56 mmol). The mixture was stirred at rt for 18 h (completion was not observed by TLC), additional amount of pyridine (1.06 mL, 13.1 mmol) and tosyl chloride (1.25 g, 6.56 mmol) were added. After 18 h, the reaction mixture was diluted with DCM and poured into water. The phases were separated and the aqueous layer was extracted twice with DCM. The combined organic layers were washed with brine, dried over Na$_2$SO$_4$, filtered and concentrated. The residue was purified by flash chromatography on silica gel using a gradient of EtOAc in hexanes (0-100%) to afford the title compound (1.17 g, 78%) as a colorless oil. $^1$H NMR (600 MHz, CDCl$_3$) δ 7.80 (d, J=8.3 Hz, 2H), 7.34 (d, J=8.0 Hz, 2H), 4.19 (d, J=2.4 Hz, 2H), 4.18-4.15 (m, 2H), 3.71-3.66 (m, 4H), 3.66-3.62 (m, 2H), 3.59 (s, 4H), 2.45 (s, 3H), 2.42 (t, J=2.4 Hz, 1H). LRMS (m/z) calculated, 342.113; found, 343.3 (M+H)$^+$.

Step III, Synthesis of 3-(2-(2-(2-azidoethoxy)ethoxy)ethoxy)prop-1-yne 2-(2-(2-(prop-2-yn-1-yloxy)ethoxy)ethoxy)ethyl 4-methylbenzenesulfonate (1.17 g, 3.42 mmol) was dissolved in DMF (10 mL) and sodium azide (889 mg, 13.7 mmol) was added, followed by tetrabutyl ammonium iodide (TBAI) (126 mg, 0.342 mmol). The mixture was then stirred vigorously at 45° C. overnight. The resulting mixture was diluted with EtOAc and water. The phases were separated and the aqueous layer was extracted twice with EtOAc. The combined organic layers were washed with brine, dried over Na$_2$SO$_4$, filtered and concentrated. The residue was purified by flash chromatography on silica gel using a gradient of EtOAc in hexanes (0-100%) to afford the title compound (619 mg, 85%) as a colorless oil. $^1$H NMR (600 MHz, CDCl$_3$) δ 4.20 (d, J=2.4 Hz, 2H), 3.71-3.65 (m, 10H), 3.39 (t, J=5.1 Hz, 2H), 2.42 (t, J=2.4 Hz, 1H).

Step IV, Synthesis of 2-(2-(2-(prop-2-yn-1-yloxy)ethoxy)ethoxy)ethanamine

Triphenylphosphine (777 mg, 2.96 mmol) was added to a stirred solution of 3-(2-(2-(2-azidoethoxy)ethoxy)ethoxy)prop-1-yne (619 mg, 2.90 mmol) in THF (20 mL) and water (200 uL) at rt. The mixture was stirred for 24 h (complete consumption of the SM was observed by TLC) and was diluted with DCM (5 mL) and concentrated to dryness under reduced pressure. The crude product was purified by flash chromatography on silica gel using a gradient of MeOH in DCM (0-30%) to afford the title compound (45 mg, 8.3%) as a beige gum. $^1$H NMR (600 MHz, CDCl$_3$) δ 4.27 (d, J=2.3 Hz, 2H), 3.75-3.65 (m, 10H), 3.13-3.09 (m, 2H), 2.49 (t, J=2.3 Hz, 1H).

Step V, Synthesis of 4-(4-(3-(4-chloro-3-(trifluoromethyl)phenyl)ureido)phenoxy)-N-(2-(2-(2-(prop-2-yn-1-yloxy)ethoxy)ethoxy)ethyl)picolinamide To a stirred solution of 4-(4-(3-(4-chloro-3-(trifluoromethyl)phenyl)ureido)phenoxy)picolinic acid (90.0 mg, 0.199 mmol) and 2-(2-(2-(prop-2-yn-1-yloxy)ethoxy)ethoxy)ethanamine (44.8 mg, 0.239 mmol) in DMF (1.0 mL) was added HATU (114 mg, 0.299 mmol) and DIPEA (275 uL, 1.59 mmol). The mixture was stirred at rt for 2 h (complete consumption of SM was observed by TLC). The mixture was diluted with EtOAc, then water and a bit of brine were added. The phases were separated and the aqueous layer were then extracted twice with EtOAc. The combined organic layer were washed with brine, dried over Na$_2$SO$_4$, filtered and concentrated. The residue was purified by flash chromatography on silica gel using a gradient of MeOH-EtOAc mixture (20% v/v of MeOH in EtOAc) in DCM (0 to 50%) to afford the title compound (104 mg, 84%) as a pale yellow residue. $^1$H NMR (600 MHz, CDCl3) δ 8.63-8.53 (m, 1H), 8.48-8.40 (m, 1H), 8.30-8.16 (m, 1H), 7.72-7.65 (m, 2H), 7.55 (d, J=2.3 Hz, 1H), 7.41-7.33 (m, 3H), 7.13-7.07 (m, 1H), 7.02-6.94 (m, 2H), 4.18 (d, J=2.3 Hz, 1H), 3.74-3.61 (m, 12H), 2.85-2.81 (m, 2H), 2.41 (t, J=2.3 Hz, 1H). LRMS (m/z) calculated, 620.165; found, 623.3 (M+H)$^+$.

Step VI, Synthesis of 4-(4-(3-(4-chloro-3-(trifluoromethyl)phenyl)ureido)phenoxy)-N-(2-(2-(2-((1-(6-((2-(2,6-dioxopiperidin-3-yl)-1,3-dioxoisoindolin-4-yl)amino)-6-oxohexyl)-1H-1,2,3-triazol-4-yl)methoxy)ethoxy)ethoxy)ethyl)picolinamide (Compound 2.027)

Under argon atmosphere, THF (2.0 mL) and water (200 uL) were added to 4-(4-(3-(4-chloro-3-(trifluoromethyl)phenyl)ureido)phenoxy)-N-(2-(2-(2-(prop-2-yn-1-yloxy)ethoxy)ethoxy)ethyl)picolinamide (104 mg, 0.167 mmol). Then, 6-azido-N-(2-(2,6-dioxopiperidin-3-yl)-1,3-dioxoisoindolin-4-yl)hexanamide (73.9 mg, 0.179 mmol) was added, followed by sodium ascorbate (6.6 mg, 0.033 mmol) and copper(II) sulfate pentahydrate (8.3 mg, 0.033 mmol). The resultant mixture was sonicated for about 15 seconds and the mixture was stirred at rt for 2 h (completion observed by TLC). Then, EtOAc, water and brine were added. The phases were separated and the aqueous layer was extracted twice with EtOAc. Since the solubility of the product in EtOAc was very bad, the product crashed/oiled out of the organic phase as a greenish solid which sticked onto the glassware of the separatory funnel. After the extractions were done, this green solid (which was the desired product according to TLC analysis) was collected from the separatory funnel using a mixture of solvents including DCM, MeOH, acetonitrile and a bit of acetone. This finally allowed the residual solid to go into solution, which was then combined with the original EtOAc extracts. The latter was directly dried over Na$_2$SO$_4$, filtered and concentrated. The residue was absorbed on the Celite® and purified by flash chromatography on silica gel using a gradient of EtOAc in DCM (0-100%) and MeOH in DCM (0-10%), followed by lyophilisation in acetonitrile and water to afford the title compound (106 mg, 59%) as a white solid. $^1$H NMR (600 MHz, CDCl$_3$) δ 9.36 (s, J=23.9 Hz, 1H), 8.85 (s, 1H), 8.74 (d, J=8.5 Hz, 1H), 8.65-8.00 (m, 4H), 7.73 (s, J=15.6 Hz, 1H), 7.69-7.60 (m, 2H), 7.60-7.45 (m, 3H), 7.44-7.28 (m, 3H), 7.12-6.74 (m, 3H), 4.95 (dd, J=12.2, 5.4 Hz, 1H), 4.65 (s, J=26.5 Hz, 2H), 4.32 (t, J=7.1 Hz, 2H), 3.74-3.53 (m, 12H), 2.94-2.82 (m, 1H), 2.82-2.68 (m, 2H), 2.42 (t, J=7.3 Hz, 2H), 2.19-2.11 (m, 1H), 1.92 (dt, J=14.8, 7.3 Hz, 2H), 1.76 (dt, J=15.1, 7.4 Hz, 2H), 1.46-1.32 (m, 2H). LRMS (m/z) calculated, 1032.314; found, 1058.541 (M+Na)$^+$. HPLC, t$_R$=11.7 min (purity: 97%).

Example 78—Synthesis of 4-(4-(3-(4-chloro-3-(trifluoromethyl)phenyl)ureido)phenoxy)-N-(1-(1-(6-((2-(2,6-dioxopiperidin-3-yl)-1,3-dioxoisoindolin-4-yl)amino)-6-oxohexyl)-1H-1,2,3-triazol-4-yl)-2,5,8,11,14-pentaoxahexadecan-16-yl)picolinamide (Compound 2.028)

Step III, Synthesis of 1-azido-3,6,9,12,15-pentaoxaoctadec-17-yne (82% yield). $^1$H NMR (600 MHz, CDCl$_3$) δ 4.20 (d, J=2.4 Hz, 2H), 3.71-3.65 (m, 18H), 3.39 (t, J=5.1 Hz, 2H), 2.42 (t, J=2.4 Hz, 1H).

Step IV, Synthesis of 3,6,9,12,15-pentaoxaoctadec-17-yn-1-amine (8.4% yield). $^1$H NMR (600 MHz, CDCl$_3$) δ 4.27 (d, J=2.4 Hz, 2H), 3.96-3.93 (m, 2H), 3.80-3.76 (m, 2H), 3.75-3.65 (m, 14H), 3.19-3.12 (m, 2H), 2.48 (t, J=2.4 Hz, 1H).

Step V, Synthesis of 4-(4-(3-(4-chloro-3-(trifluoromethyl)phenyl)ureido)phenoxy)-N-(3,6,9,12,15-pentaoxaoctadec-17-yn-1-yl)picolinamide (84% yield). $^1$H NMR (600 MHz, CDCl$_3$) δ 8.52-8.46 (m, 1H), 8.40 (d, J=5.6 Hz, 1H), 8.28 (s, 1H), 8.07 (s, 1H), 7.72 (d, J=2.2 Hz, 1H), 7.67 (dd, J=8.7, 2.1 Hz, 1H), 7.56 (d, J=2.2 Hz, 1H), 7.43-7.35 (m, 3H), 7.04 (dd, J=5.5, 2.4 Hz, 1H), 6.97 (d, J=8.7 Hz, 2H), 4.16 (d, J=2.3 Hz, 2H), 3.70-3.60 (m, 18H), 2.83 (s, 2H), 2.41 (t, J=1.9 Hz, 1H). LRMS (m/z) calculated, 708.217; found, 712.3 (M+H)$^+$.

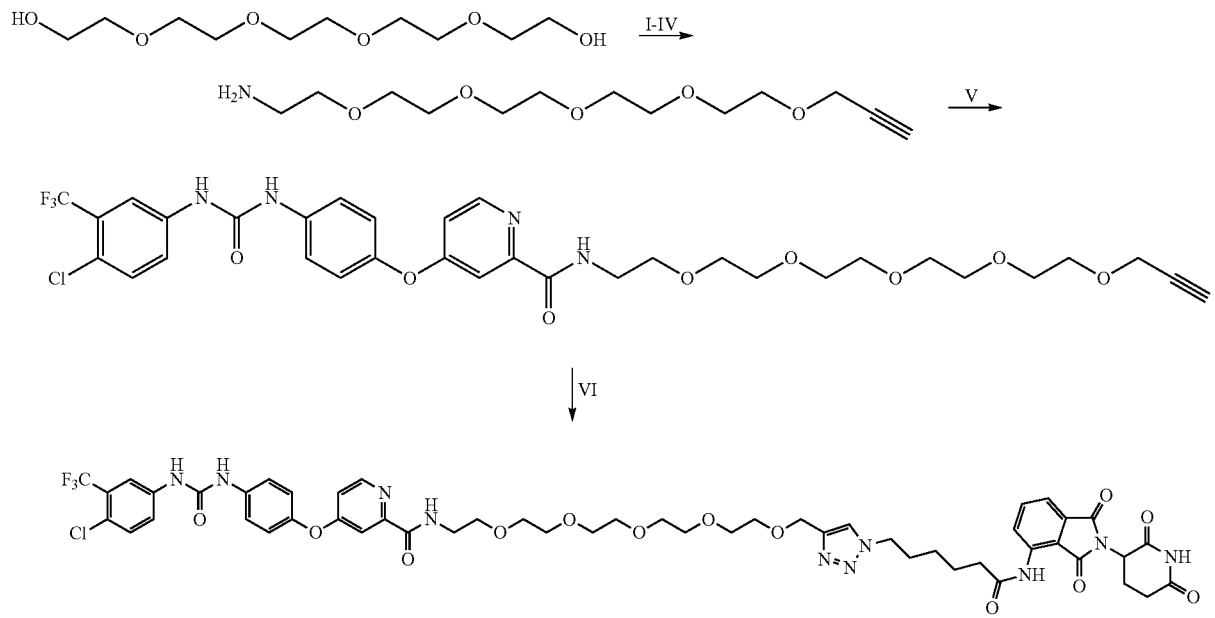

The title compound was prepared using the same reaction sequence from 3,6,9,12,15-pentaoxaoctadec-17-yn-1-ol as described in Compound 2.027

Step I, Synthesis of 3,6,9,12,15-pentaoxaoctadec-17-yn-1-ol (30% yield). $^1$H NMR (600 MHz, CDCl$_3$) δ 4.20 (d, J=2.4 Hz, 2H), 3.72-3.66 (m, 18H), 3.62-3.60 (m, 2H), 2.69 (s, 1H), 2.42 (t, J=2.4 Hz, 1H). LRMS (m/z) calculated, 276.16; found, 277.1 (M+H)$^+$.

Step II, Synthesis of 3,6,9,12,15-pentaoxaoctadec-17-yn-1-yl 4-methylbenzenesulfonate (78% yield). $^1$H NMR (600 MHz, CDCl$_3$) δ 7.80 (d, J=8.3 Hz, 2H), 7.34 (d, J=8.1 Hz, 2H), 4.20 (d, J=2.4 Hz, 2H), 4.17-4.15 (m, 2H), 3.70-3.61 (m, 14H), 3.58 (s, 4H), 2.45 (s, 3H), 2.42 (t, J=2.4 Hz, 1H). LRMS (m/z) calculated, 430.166; found, 455.6 (M+Na)$^+$.

Step VI, Synthesis of 4-(4-(3-(4-chloro-3-(trifluoromethyl)phenyl)ureido)phenoxy)-N-(1-(1-(6-((2-(2,6-dioxopiperidin-3-yl)-1,3-dioxoisoindolin-4-yl)amino)-6-oxohexyl)-1H-1,2,3-triazol-4-yl)-2,5,8,11,14-pentaoxahexadecan-16-yl)picolinamide (60% yield). $^1$H NMR (600 MHz, CDCl$_3$) δ 9.37 (s, 1H), 8.76 (d, J=8.5 Hz, 1H), 8.66 (s, 1H), 8.38 (s, 4H), 7.77 (s, 1H), 7.71-7.65 (m, 2H), 7.58 (s, J=28.0 Hz, 2H), 7.52 (d, J=7.2 Hz, 1H), 7.46 (s, 2H), 7.35 (d, J=8.5 Hz, 1H), 6.97 (d, J=6.9 Hz, 3H), 5.01-4.89 (m, 1H), 4.65 (s, 2H), 4.34 (t, J=7.0 Hz, 2H), 3.69-3.55 (m, 20H), 2.93-2.84 (m, 1H), 2.81-2.71 (m, 2H), 2.44 (t, J=7.2 Hz, 2H), 2.19-2.13 (m, 1H), 1.99-1.89 (m, 2H), 1.78-1.77 (m, 2H), 1.47-1.35 (m, 2H). LRMS (m/z) calculated, 1120.366; found, 1145.417 (M+Na)$^+$. HPLC, t$_R$=11.7 min (purity: 96%).

Example 79—Synthesis of 4-(4-(3-(4-chloro-3-(trifluoromethyl)phenyl)ureido)phenoxy)-N-(2-(3-(2-(2,6-dioxopiperidin-3-yl)-1,3-dioxoisoindolin-4-yl)propoxy)ethyl)picolinamide (Compound 2.029)

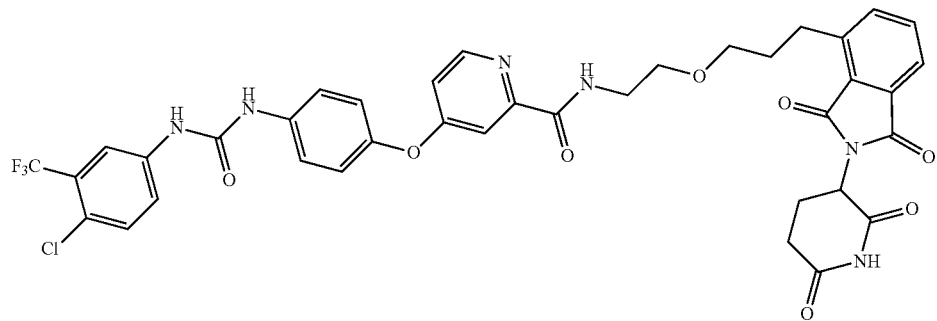 [SMILES: O=C1CCC(N2C(=O)c3cccc(CCCOCCNC(=O)c4cc(Oc5ccc(NC(=O)Nc6ccc(Cl)c(C(F)(F)F)c6)cc5)ccn4)c3C2=O)C(=O)N1]

Prepared from 4-(4-(3-(4-chloro-3-(trifluoromethyl)phenyl)ureido)phenoxy)-picolinic acid and 4-(3-(2-aminoethoxy)propyl)-2-(2,6-dioxopiperidin-3-yl)isoindoline-1,3-dione (Zhou et. al. *J. Med. Chem.* 2018, 61 (2), 462-481) using HATU as described in Example 2. $^1$H NMR (600 MHz, CDCl$_3$) δ 8.62 (t, J=5.5 Hz, 1H), 8.45 (d, J=5.6 Hz, 1H), 8.34 (s, 1H), 8.14 (s, 1H), 7.95 (s, 1H), 7.72-7.67 (m, 2H), 7.65 (d, J=8.7 Hz, 1H), 7.59 (t, J=7.6 Hz, 1H), 7.53 (d, J=1.9 Hz, 1H), 7.50 (d, J=7.7 Hz, 1H), 7.37 (d, J=8.6 Hz, 1H), 7.31 (d, J=8.7 Hz, 2H), 7.14 (dd, J=5.4, 2.2 Hz, 1H), 6.95 (d, J=8.7 Hz, 2H), 4.95 (dd, J=12.4, 5.3 Hz, 1H), 3.69-3.61 (m, 2H), 3.59 (t, J=4.9 Hz, 2H), 3.53-3.44 (m, 2H), 3.21-3.13 (m, 1H), 3.12-3.05 (m, 1H), 2.88 (d, J=16.3 Hz, 1H), 2.85-2.67 (m, 2H), 2.16-2.10 (m, 1H), 1.96-1.87 (m, 2H). LRMS (m/z) calculated, 792.192; found, 793.987 (M+H)$^+$. HPLC, $t_R$=12.5 min (purity: 99%).

Example 80—Synthesis of 4-(4-(3-(4-chloro-3-(trifluoromethyl)phenyl)ureido)phenoxy)-N-(2-(2-(3-(2-(2,6-dioxopiperidin-3-yl)-1,3-dioxoisoindolin-4-yl)propoxy)ethoxy)ethyl)picolinamide (Compound 2.030)

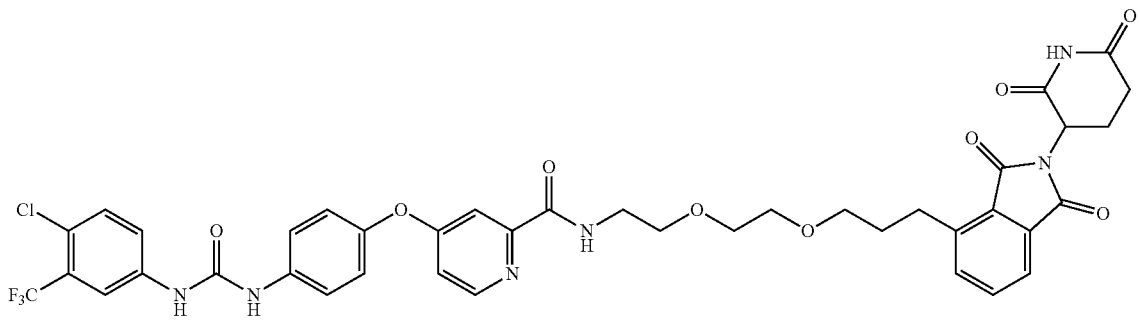 [SMILES: O=C1CCC(N2C(=O)c3cccc(CCCOCCOCCNC(=O)c4cc(Oc5ccc(NC(=O)Nc6ccc(Cl)c(C(F)(F)F)c6)cc5)ccn4)c3C2=O)C(=O)N1]

Prepared from 4-(4-(3-(4-chloro-3-(trifluoromethyl)phenyl)ureido)phenoxy)-picolinic acid and 4-(3-(2-(2-aminoethoxy)ethoxy)propyl)-2-(2,6-dioxopiperidin-3-yl)isoindoline-1,3-dione using HATU as described in Example 2. $^1$H NMR (600 MHz, CDCl$_3$) δ 8.58 (t, J=5.7 Hz, 1H), 8.48 (s, 1H), 8.39 (d, J=5.6 Hz, 1H), 8.01 (s, 1H), 7.81 (s, 1H), 7.71-7.66 (m, 2H), 7.64-7.57 (m, 2H), 7.53-7.49 (m, 2H), 7.36 (d, J=8.7 Hz, 1H), 7.32 (d, J=8.8 Hz, 2H), 7.08 (dd, J=5.5, 2.5 Hz, 1H), 6.95 (d, J=8.8 Hz, 2H), 4.96 (dd, J=12.4, 5.4 Hz, 1H), 3.75-3.40 (m, 10H), 3.15-3.03 (m, 2H), 2.91-2.85 (m, 1H), 2.84-2.69 (m, 2H), 2.16-2.09 (m, 1H), 1.94-1.86 (m, 2H). LRMS (m/z) calculated, 836.218; found, 860.527 (M+Na)$^+$. HPLC, $t_R$=12.4 min (purity: 98%).

Example 81—Synthesis of 4-(4-(3-(4-chloro-3-(trifluoromethyl)phenyl)ureido)phenoxy)-N-(6-(2-(2,6-dioxopiperidin-3-yl)-1-oxoisoindolin-4-yl)hexyl)picolinamide (Compound 2.031)

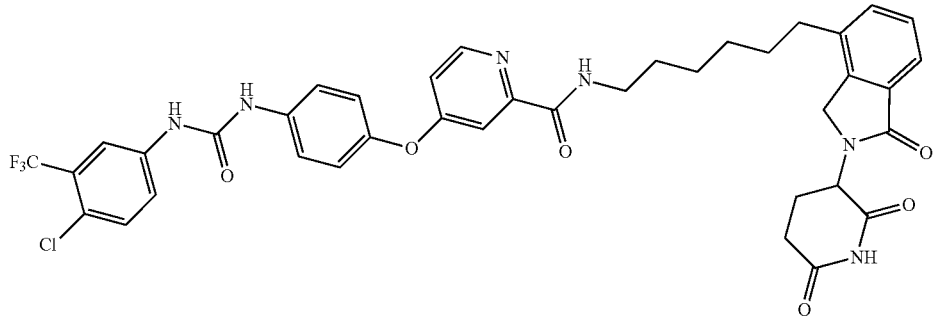 [SMILES: O=C1CCC(N2Cc3c(CCCCCCNC(=O)c4cc(Oc5ccc(NC(=O)Nc6ccc(Cl)c(C(F)(F)F)c6)cc5)ccn4)cccc3C2=O)C(=O)N1]

Prepared from 4-(4-(3-(4-chloro-3-(trifluoromethyl)phenyl)ureido)phenoxy)-picolinic acid and 3-(4-(6-aminohexyl)-1-oxoisoindolin-2-yl)piperidine-2,6-dione (Zhou et. al. *J. Med. Chem.* 2018, 61 (2), 462-481) using HATU as described in Example 2. $^1$H NMR (600 MHz, CDCl$_3$) δ 8.52-8.40 (m, 2H), 8.33 (t, J=5.5 Hz, 1H), 8.24 (s, 1H), 7.99 (s, 1H), 7.76-7.68 (m, 2H), 7.65 (d, J=8.7 Hz, 1H), 7.50 (d, J=1.4 Hz, 1H), 7.43-7.32 (m, 5H), 7.15 (dd, J=5.5, 2.0 Hz, 1H), 6.95 (d, J=8.6 Hz, 2H), 5.23 (dd, J=13.3, 4.9 Hz, 1H), 4.41 (d, J=15.9 Hz, 1H), 4.30 (d, J=15.9 Hz, 1H), 3.51-3.34 (m, 2H), 2.92-2.74 (m, 2H), 2.56 (t, J=7.6 Hz, 2H), 2.46-2.35 (m, 1H), 2.24-2.15 (m, 1H), 1.63-1.55 (m, 4H), 1.35 (s, 4H). LRMS (m/z) calculated, 776.233; found, 800.495 (M+Na)$^+$. HPLC, t$_R$=12.7 min (purity: 83%).

Example 82—Synthesis of 4-(4-(3-(4-chloro-3-(trifluoromethyl)phenyl)ureido)phenoxy)-N-(2-(3-(2-(2,6-dioxopiperidin-3-yl)-1-oxoisoindolin-4-yl)propoxy)ethyl)picolinamide (Compound 2.032)

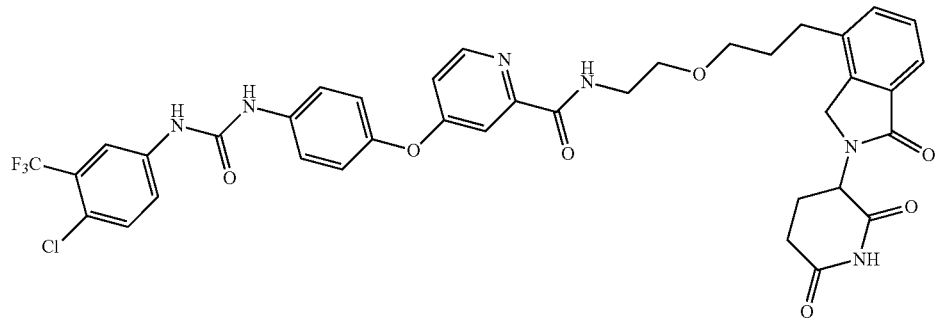 [SMILES: O=C1CCC(N2Cc3c(CCCOCCNC(=O)c4cc(Oc5ccc(NC(=O)Nc6ccc(Cl)c(C(F)(F)F)c6)cc5)ccn4)cccc3C2=O)C(=O)N1]

Prepared from 4-(4-(3-(4-chloro-3-(trifluoromethyl)phenyl)ureido)phenoxy)-picolinic acid and 3-(4-(3-(2-aminoethoxy)propyl)-1-oxoisoindolin-2-yl)piperidine-2,6-dione (Zhou et. al. *J. Med. Chem.* 2018, 61 (2), 462-481) using HATU as described in Example 2. $^1$H NMR (600 MHz, CDCl$_3$) δ 8.69 (s, 1H), 8.47-8.39 (m, 2H), 8.08 (s, 1H), 7.83 (s, 1H), 7.75 (d, J=2.3 Hz, 1H), 7.69 (d, J=7.3 Hz, 1H), 7.65 (d, J=8.7 Hz, 1H), 7.49 (d, J=2.3 Hz, 1H), 7.42 (dd, J=12.6, 5.1 Hz, 1H), 7.37 (d, J=8.3 Hz, 2H), 7.32 (d, J=8.8 Hz, 2H), 7.12-7.06 (m, 1H), 6.95 (d, J=8.8 Hz, 2H), 5.12 (dd, J=13.4, 5.0 Hz, 1H), 4.43 (d, J=16.3 Hz, 1H), 4.33 (d, J=16.2 Hz, 1H), 3.73-3.64 (m, 1H), 3.62-3.52 (m, 3H), 3.48-3.37 (m, 2H), 2.83-2.65 (m, 4H), 2.38-2.27 (m, 1H), 2.14-2.07 (m, 1H), 1.94-1.82 (m, 2H). LRMS (m/z) calculated, 778.213; found, 779.573 (M+H)$^+$. HPLC, t$_R$=11.9 min (purity: 98%).

Example 83—Synthesis of 4-(4-(3-(4-chloro-3-(trifluoromethyl)phenyl)ureido)phenoxy)-N-(2-(2-(3-(2-(2,6-dioxopiperidin-3-yl)-1-oxoisoindolin-4-yl)propoxy)ethoxy)ethyl)picolinamide (Compound 2.033)

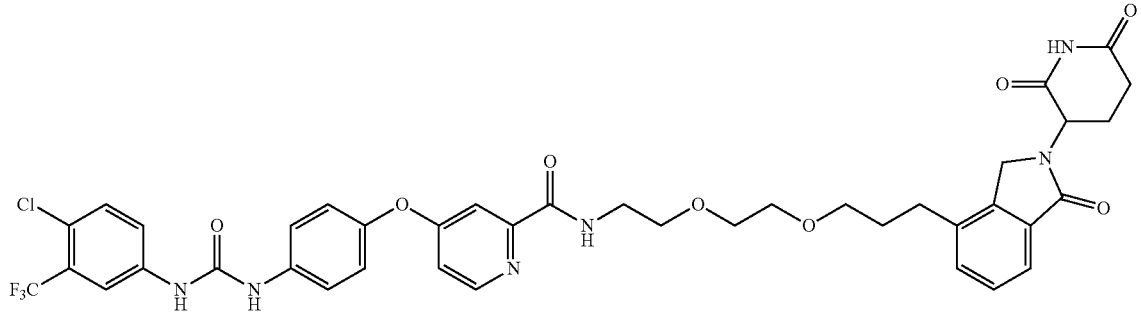 [SMILES: O=C1CCC(N2Cc3c(CCCOCCOCCNC(=O)c4cc(Oc5ccc(NC(=O)Nc6ccc(Cl)c(C(F)(F)F)c6)cc5)ccn4)cccc3C2=O)C(=O)N1]

Prepared from 4-(4-(3-(4-chloro-3-(trifluoromethyl)phenyl)ureido)phenoxy)-picolinic acid and 3-(4-(3-(2-(2-aminoethoxy)ethoxy)propyl)-1-oxoisoindolin-2-yl)piperidine-2,6-dione using HATU as described in Example 2. $^1$H NMR (600 MHz, CDCl$_3$) δ 8.82 (s, 1H), 8.52 (s, 1H), 8.38 (d, J=5.7 Hz, 1H), 8.07 (s, 1H), 7.87 (s, 1H), 7.78 (d, J=1.6 Hz, 1H), 7.69 (d, J=7.3 Hz, 1H), 7.61 (d, J=8.5 Hz, 1H), 7.50 (d, J=1.9 Hz, 1H), 7.44-7.40 (m, 1H), 7.39-7.36 (m, 2H), 7.32 (d, J=8.6 Hz, 2H), 7.07 (dd, J=5.6, 2.3 Hz, 1H), 6.90 (d, J=8.6 Hz, 2H), 5.20 (dd, J=13.2, 5.1 Hz, 1H), 4.42 (d, J=16.3 Hz, 1H), 4.30 (d, J=16.3 Hz, 1H), 3.69-3.34 (m, 12H), 2.90-2.77 (m, 2H), 2.67 (t, J=7.6 Hz, 2H), 2.45-2.36 (m, 1H), 2.22-2.15 (m, 1H). LRMS (m/z) calculated, 822.239; found, 846.556 (M+Na)$^+$. HPLC, t$_R$=11.8 min (purity: 97%).

Example 84—Synthesis of 4-(4-(3-(4-chloro-3-(trifluoromethyl)phenyl)ureido)phenoxy)-N-(2-(2-((6-(2-(2,6-dioxopiperidin-3-yl)-1-oxoisoindolin-4-yl)hexyl)oxy)ethoxy)ethyl)picolinamide (Compound 2.034)

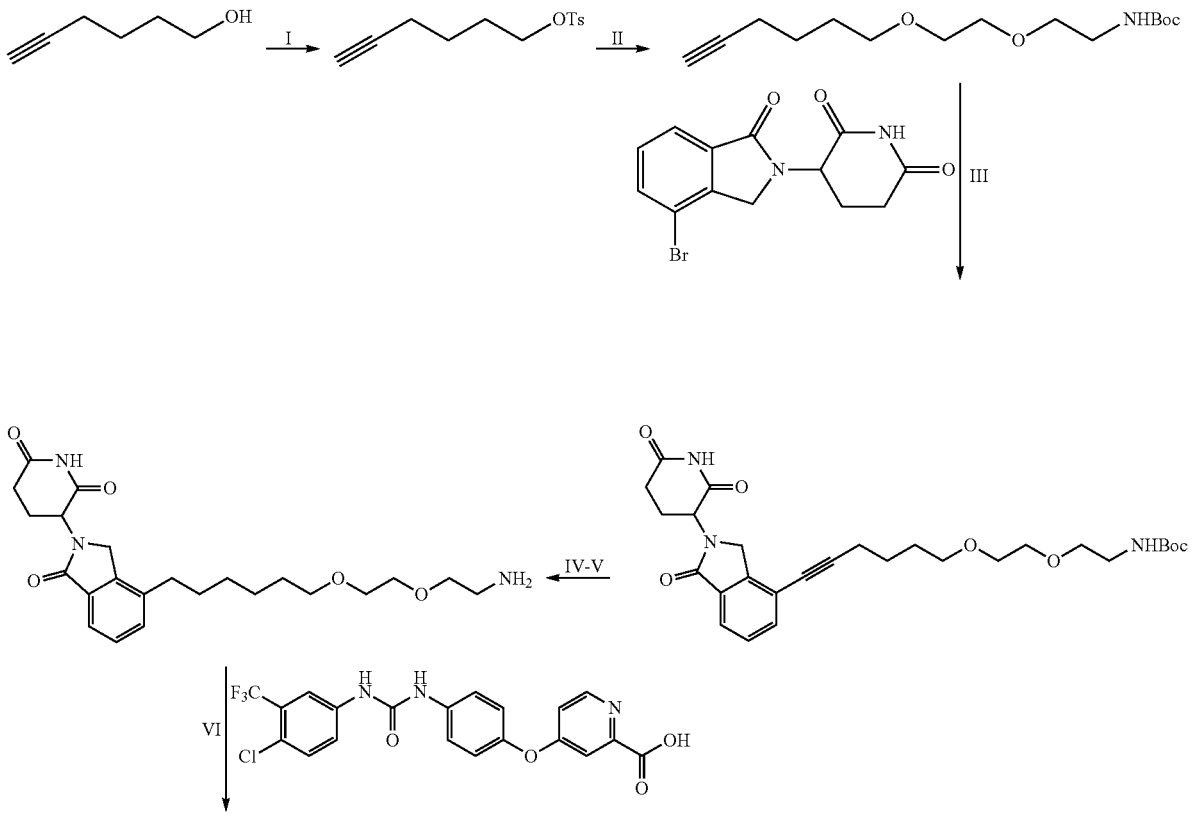

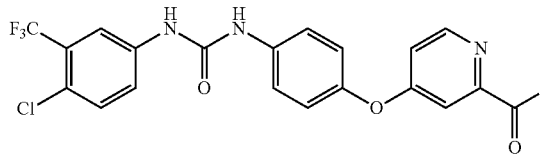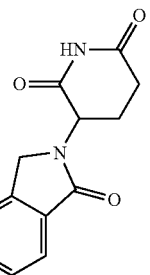

Step I, Synthesis of hex-5-yn-1-yl 4-methylbenzenesulfonate

Triethylamine (21.30 mL, 153.0 mmol, 3.0 equiv) was added to a stirred solution of hex-5-yn-1-ol (5.0 g, 50.90 mmol, 1.0 equiv.) in DCM (150.0 mL, 30.0 vol. equiv.) at rt followed by the addition of TsCl (11.7 g, 61.1 mmol, 1.2 equiv.). The reaction mixture was stirred at rt for 15 h. The progress of the reaction was monitored by TLC (20% EtOAc in n-hexane) to ensure the completion of the reaction, water (100.0 mL) was added and the aqueous layer was extracted with DCM (3×200 mL). The combined organic extracts were dried over $Na_2SO_4$, concentrated. The residue was purified by column chromatography on silica gel (230-400 mesh size) using a gradient of EtOAc in hexanes (5-30% EtOAc in n-hexane) to afford the title compound (11.2 g, 87.1%) as a colorless oil. $^1H$ NMR (300 MHz, $CDCl_3$): δ 7.79 (dd, J=8.7, 2.1 Hz, 2H), 7.40-7.25 (m, 2H), 4.19-4.00 (m, 2H), 2.45 (s, 3H), 2.16 (td, J=6.9, 2.7 Hz, 2H), 1.94 (q, J=3.7, 2.6 Hz, 1H), 1.86-1.70 (m, 2H), 1.64-1.47 (m, 2H), 1.12 (t, J=7.1 Hz, 1H).

Step II, Synthesis of tert-butyl (2-(2-(hex-5-yn-1-yloxy)ethoxy)ethyl)carbamate

Sodium hydride (0.096 g, 2.4 mmol, 1.0 equiv, 60% in oil) was added to a stirred solution of tert-butyl (2-(2-hydroxyethoxy)ethyl)carbamate (0.50 g, 2.4 mmol, 1.0 equiv) in DMF (10.0 mL, 20.0 vol. equiv.) at 0° C. The reaction mixture was stirred for 30 min at rt. Hex-5-yn-1-yl 4-methylbenzenesulfonate (0.62 g, 2.4 mmol, 1.0 equiv) was added to the reaction mixture at 0° C. The reaction mixture was stirred for 20 h at rt, diluted with water (50.0 mL) and extracted with EtOAc (3×75.0 mL). The combined organic extracts were washed with brine, dried over $Na_2SO_4$, filtered, and concentrated. The residue was purified by column chromatography on silica gel (230-400 mesh size) using a gradient of EtOAc in hexanes (10-60%) to afford the title compound (270.0 mg, 38.8%) as a colorless oil. $^1H$ NMR (300 MHz, $CDCl_3$): δ 4.95 (s, 1H), 3.68-3.38 (m, 8H), 3.25 (q, J=5.4 Hz, 2H), 2.16 (td, J=6.9, 2.6 Hz, 2H), 1.88 (t, J=2.6 Hz, 1H), 1.73-1.47 (m, 5H), 1.38 (s, 9H).

Step III, Synthesis of tert-butyl (2-(2-((6-(2-(2,6-dioxopiperidin-3-yl)-1-oxoisoindolin-4-yl)hex-5-yn-1-yl)oxy)ethoxy)ethyl)carbamate tert-Butyl (2-(2-(hex-5-yn-1-yloxy)ethoxy)ethyl)carbamate (0.26 g, 0.92 mmol, 1.0 equiv), CuI (35.0 mg, 0.18 mmol, 0.20 equiv.) and $PdCl_2(PPh_3)_2$ (64.50 mg, 0.09 mmol, 0.10 equiv) were added to a stirred solution of 3-(4-bromo-1-oxoisoindolin-2-yl)piperidine-2,6-dione (0.30 g, 0.92 mmol, 1.0 equiv.) in DMF (6.0 mL, 20.0 vol. equiv.). The solution was purged and refilled with nitrogen three times then diisopropylethylamine (4.01 mL, 23.0 mmol) was added and the solution was degassed again two times with alternating vacuum and nitrogen. The reaction mixture was heated at 70° C. for 13 h. The progress of the reaction was monitored by TLC (80% EtOAc in n-hexane) to ensure the completion of the reaction. The reaction mixture was cooled to rt, diluted with water (100.0 mL), and extracted with ethyl acetate (2×200.0 mL). The combined organic extracts were washed with brine, dried over $Na_2SO_4$, filtered and concentrated under reduced pressure. The residue was purified by column chromatography on silica gel (230-400 mesh size) using a gradient of EtOAc in hexanes (40 to 90%) to afford the title compound (200.0 mg, 41.20%) as a light brown solid. $^1H$ NMR (300 MHz, $CDCl_3$): δ 7.67-7.55 (m, 2H), 7.54-7.45 (m, 2H), 7.45-7.33 (m, 3H), 5.27-5.11 (m, 1H), 4.91 (d, J=40.2 Hz, 1H), 4.50-4.19 (m, 2H), 3.61-3.36 (m, 6H), 3.25 (d, J=5.9 Hz, 2H), 2.93-2.69 (m, 2H), 2.48-2.23 (m, 2H), 2.23-2.05 (m, 1H), 1.67 (ddp, J=21.0, 11.8, 4.2 Hz, 3H), 1.37 (s, 8H), 1.26-1.14 (m, 2H); LRMS (m/z) calculated, 527.26; found, 526.1 (M–H)⁻.

Step IV: Synthesis of tert-butyl (2-(2-((6-(2-(2,6-dioxopiperidin-3-yl)-1-oxoisoindolin-4-yl)hexyl)oxy)ethoxy)ethyl)carbamate 10% Pd/C (50% wet, 37.90 mg, 0.017 mmol, 0.048 equiv.) was added to a stirred solution of tert-butyl (2-(2-((6-(2-(2,6-dioxopiperidin-3-yl)-1-oxoisoindolin-4-yl)hex-5-yn-1-yl)oxy)ethoxy)ethyl)carbamate (190.0 mg, 0.36 mmol, 1.0 equiv) in ethanol (3.80 mL, 20.0 vol. equiv.). The solution was degassed with alternated vacuum and hydrogen three times then the resulting reaction mixture was stirred for 2.5 h at rt under the hydrogen atmosphere. The progress of the reaction was monitored by TLC (80% ethylacetate in n-hexane) to ensure the completion of the reaction. The reaction mixture was filtered through Hyflo pad (similar to Celite®). Filterate was concentrated to afford the title compound (185.0 mg, 97.60%) as a light brown gum. This product was used as such in the next step.

Step V, Synthesis of 3-(4-(6-(2-(2-aminoethoxy)ethoxy)hexyl)-1-oxoisoindolin-2-yl)piperidine-2,6-dione A mixture of tert-butyl (2-(2-((6-(2-(2,6-dioxopiperidin-3-yl)-1-oxoisoindolin-4-yl)hexyl)oxy)ethoxy)ethyl)carbamate (180 mg, 0.34 mmol, 1.0 equiv) in 4M HCl in 1,4-dioxane (3.60 mL) was stirred for 12 h at rt. The progress of the reaction was monitored by TLC (5% MeOH in DCM) to ensure the completion of the reaction. The reaction mixture was concentrated, diluted with water and neutralized with saturated solution of $NaHCO_3$. Product was extracted with EtOAc (2×100 mL), dried over Na$_2$SO$_4$ and concentrated to afford the title compound (130 mg, 89.2%) as a light brown gum. $^1$H NMR (300 MHz, DMSO-d$_6$) δ 11.02 (s, 1H), 7.96 (s, 3H), 7.74 (d, J=7.6 Hz, 0H), 7.64 (d, J=7.6 Hz, 2H), 7.65-7.42 (m, 6H), 5.14 (dd, J=13.6, 4.9 Hz, 1H), 4.47 (d, J=17.1 Hz, 1H), 4.32 (dd, J=17.4, 10.0 Hz, 1H), 3.65-3.46 (m, 6H), 3.01-2.85 (m, 3H), 2.63 (d, J=7.1 Hz, 2H), 2.42 (s, 1H), 2.01 (d, J=11.8 Hz, 1H), 1.91 (s, 0H), 1.60 (s, 2H), 1.48 (d, J=8.3 Hz, 2H), 1.39-1.20 (m, 6H) ppm. LRMS (m/z) calculated, 431.24, found, 432 (M+H)$^+$.

Step VI: Synthesis of 4-(4-(3-(4-chloro-3-(trifluoromethyl)phenyl)ureido)phenoxy)-N-(2-(2-((6-(2-(2,6-dioxopiperidin-3-yl)-1-oxoisoindolin-4-yl)hexyl)oxy)ethoxy)ethyl)-picolinamide Prepared from 4-(4-(3-(4-chloro-3-(trifluoromethyl)phenyl)ureido)phenoxy)-picolinic acid and 3-(4-(6-(2-(2-aminoethoxy)ethoxy)hexyl)-1-oxoisoindolin-2-yl)piperidine-2,6-dione using HATU as described in Example 2. $^1$H NMR (600 MHz, CDCl$_3$) δ 8.86 (s, 1H), 8.61 (s, 1H), 8.43 (d, J=5.9 Hz, 1H), 8.19 (s, 1H), 7.99 (s, 1H), 7.83 (d, J=2.3 Hz, 1H), 7.70 (d, J=7.3 Hz, 1H), 7.62 (d, J=8.6 Hz, 1H), 7.54 (d, J=2.2 Hz, 1H), 7.43 (t, J=7.5 Hz, 1H), 7.39 (t, J=7.4 Hz, 2H), 7.35 (d, J=8.8 Hz, 2H), 7.13 (dd, J=5.9, 2.5 Hz, 1H), 6.92 (d, J=8.8 Hz, 2H), 5.22 (dd, J=13.4, 5.1 Hz, 1H), 4.42 (d, J=16.2 Hz, 1H), 4.32 (d, J=16.2 Hz, 1H), 3.67-3.51 (m, 9H), 3.47-3.37 (m, 2H), 2.95-2.74 (m, 2H), 2.58 (dd, J=8.3, 5.3 Hz, 2H), 2.24-2.21 (m, 1H), 1.62-1.55 (m, 2H), 1.54-1.48 (m, 2H), 1.34-1.29 (m, 4H). LRMS (m/z) calculated, 864.286; found, 888.663 (M+Na)$^+$. HPLC, t$_R$=12.8 min (purity: 95%).

Example 85—Synthesis of 4-(4-(3-(4-chloro-3-(trifluoromethyl)phenyl)ureido)phenoxy)-N-(2-(2-(3-(2-(((2S,4R)-4-hydroxy-1-((S)-3-methyl-2-(I-oxoisoindolin-2-yl)butanoyl)pyrrolidine-2-carboxamido)-methyl)-5-(4-methylthiazol-5-yl)phenoxy)propoxy)ethoxy)ethyl)picolinamide (Compound 2.035)

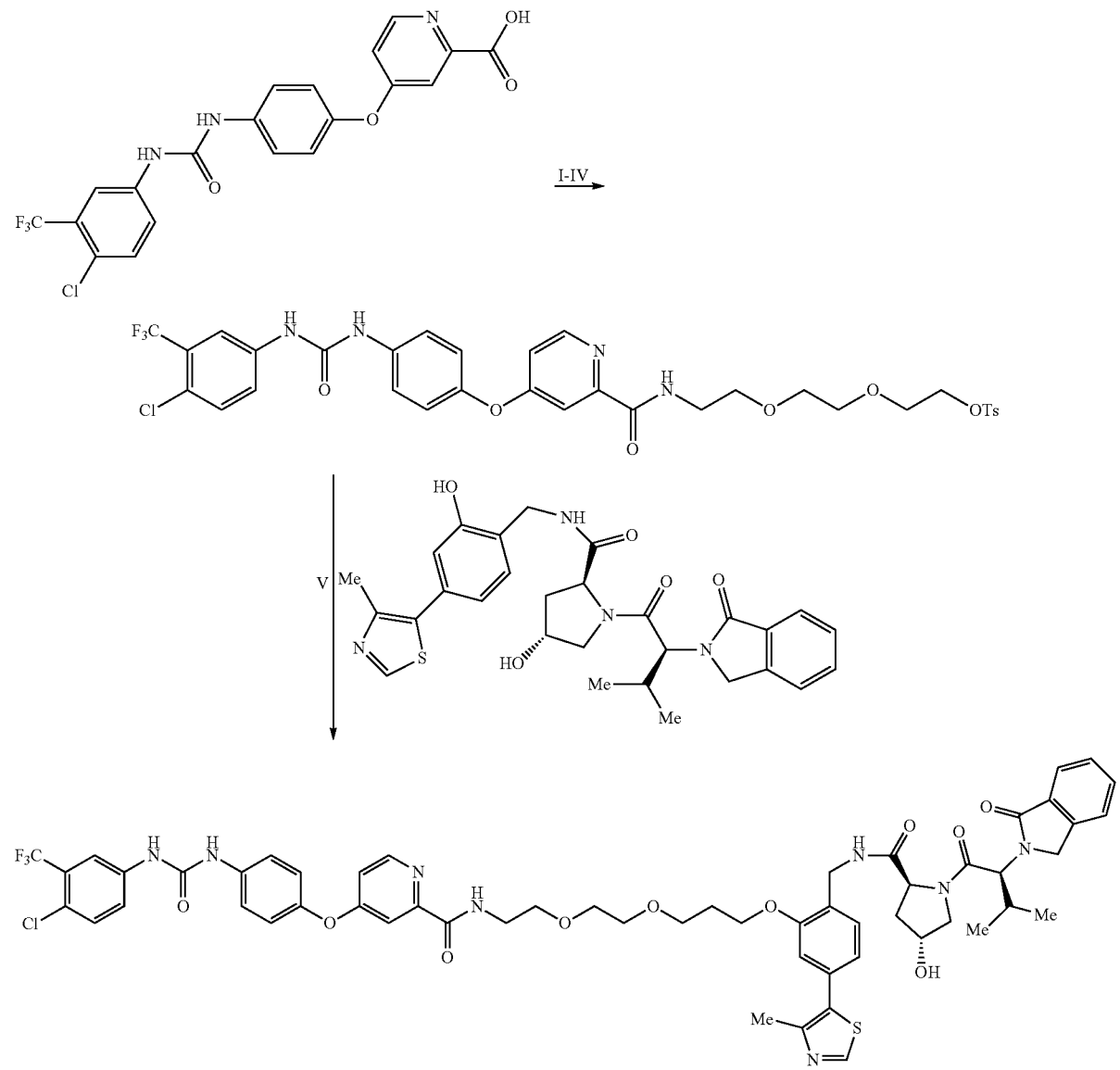

Step I, Synthesis of tert-butyl 3-(2-(2-(4-(4-(3-(4-chloro-3-(trifluoromethyl)phenyl)-ureido)phenoxy)picolinamido)ethoxy)ethoxy)propanoate To a stirred solution of 4-(4-(3-(4-chloro-3-(trifluoromethyl)phenyl)ureido)-phenoxy)picolinic acid (1.0 g, 2.21 mmol, 1.0 equiv) in DMF (40.0 mL, 40.0 vol. equiv.) was added tert-butyl 3-(2-(2-aminoethoxy)ethoxy)propanoate (0.568 g, 2.43 mmol, 1.10 equiv), HATU (1.26 g, 3.32 mmol, 1.50 equiv) and DIPEA (2.31 mL, 13.3 mmol, 6.0 equiv). The reaction mixture was stirred for 16 h at rt, quenched with water (200 mL) and the aqueous layer was extracted with EtOAc (3×300 mL). Combined organic extracts were washed with brine (200 mL), dried over Na$_2$SO$_4$, and concentrated. The residue was purified by column chromatography using a gradient of EtOAc in n-hexane (50-100%) to afford the title compound (1.34 g, 90.8%) as a light yellow gum. LRMS (m/z) calculated, 666.21; found, 667.3 (M+H)$^+$.

Step II, Synthesis of 3-(2-(2-(4-(4-(3-(4-chloro-3-(trifluoromethyl)phenyl)ureido)-phenoxy)picolinamido)ethoxy)ethoxy)propanoic Acid A solution of tert-butyl 3-(2-(2-(4-(4-(3-(4-chloro-3-(trifluoromethyl)phenyl)ureido)-phenoxy)picolinamido)ethoxy)ethoxy)propanoate (1.34 g, 2.01 mmol, 1.0 equiv) in DCM (26.8 mL) was added trifluoroacetic acid (13.4 mL). The reaction mixture was stirred at rt for 2 h, concentrated to afford the title compound (830 mg, 67.6%) as an off-white solid. LRMS (m/z) calculated, 610.14; found, 609.2 (M−H)$^−$.

Step III, Synthesis of 4-(4-(3-(4-chloro-3-(trifluoromethyl)phenyl)ureido)phenoxy)-N-(2-(2-(3-hydroxypropoxy)ethoxy)ethyl)picolinamide To a stirred solution of 3-(2-(2-(4-(4-(3-(4-chloro-3-(trifluoromethyl)phenyl)-ureido)phenoxy)picolinamido)ethoxy)ethoxy)propanoic acid (0.600 g, 0.982 mmol, 1.0 equiv) in THF (12.0 mL) was added N-methyl morpholine (109 mg, 1.08 mmol) followed by the addition of isobutyl chloroformate (148 mg, 1.08 mmol) at −10° C. The reaction mixture was stirred for 10 min at the same temperature. The reaction mixture was filtered through Hyflo bed (similar to Celite® bed) and rinsed twice with THF. The filtrate was cooled to 0° C. followed by the addition of NaBH$_4$ solution (55.7 mg, 1.47 mmol) in water (0.78 mL). The reaction mixture was stirred for 1 h at rt, quenched with water (100 mL) and the aqueous layer was extract with ethyl acetate (3×50 mL). The combined organic extracts were washed with brine (200 mL), dried over Na$_2$SO$_4$, and concentrated. The residue was purified by column chromatography using a gradient of MeOH in DCM (0-5%) to afford the title compound (0.5 g, 85.3%) as an off-white sticky solid. LRMS (m/z) calculated, 596.16; found, 596.8 (M+H)$^+$, 595.0 (M−H)$^−$.

Step IV, Synthesis of 3-(2-(2-(4-(4-(3-(4-chloro-3-(trifluoromethyl)phenyl)ureido)-phenoxy)picolinamido)ethoxy)ethoxy)propyl 4-methylbenzenesulfonate To a solution of 4-(4-(3-(4-chloro-3-(trifluoromethyl)phenyl)ureido)phenoxy)-N-(2-(2-(3-hydroxypropoxy)ethoxy)ethyl)picolinamide (0.500 g, 0.838 mmol) in DCM (25.0 mL) were added triethylamine (339 mg, 3.35 mmol) and TsCl (192 mg, 1.01 mmol) at 0° C. The reaction was stirred at rt for 2 h, quenched with water and the aqueous layer was extracted with ethyl acetate. The organic extracts were dried over Na$_2$SO$_4$ and the solvent was removed under vacuum to afford the title compound (260 mg, 41.3%) as an off white sticky solid. LRMS (m/z) calculated, 750.17; found, 749 (M−H)$^−$.

Step V, Synthesis of 4-(4-(3-(4-chloro-3-(trifluoromethyl)phenyl)ureido)phenoxy)-N-(2-(2-(3-(2-(((2S,4R)-4-hydroxy-1-((S)-3-methyl-2-(1-oxoisoindolin-2-yl)butanoyl)pyrro-lidine-2-carboxamido)methyl)-5-(4-methylthiazol-5-yl)phenoxy)propoxy)ethoxy)ethyl)-picolinamide To a stirred solution of 3-(2-(2-(4-(4-(3-(4-chloro-3-(trifluoromethyl)phenyl)-ureido)phenoxy)picolinamido)ethoxy)ethoxy)propyl 4-methylbenzenesulfonate (0.160 g, 0.213 mmol) in DMF (8.0 mL) was added (2S,4R)-4-hydroxy-N-(2-hydroxy-4-(4-methylthiazol-5-yl)benzyl)-1-((S)-3-methyl-2-(1-oxoisoindolin-2-yl)butanoyl)pyrrolidine-2-carboxamide (105.0 mg, 0.19 mmol) and K$_2$CO$_3$ (147.0 mg, 1.06 mmol) (WO2017/30813, 2017). The reaction mixture was stirred at 80° C. for 20 h, cooled to rt, quenched with water (200 mL) and the aqueous layer was extracted with EtOAc (4×100 mL). The combined organic extracts were washed with brine (2×100 mL), dried over Na$_2$SO$_4$, and concentrated. The residue was purified by column chromatography using a gradient of MeOH in DCM (0-5%) to afford the title compound (60 mg, 25.0%) as an off-white solid. $^1$H NMR (300 MHz, DMSO-d$_6$) δ 9.44 (s, 1H), 9.21 (s, 1H), 8.98 (s, 1H), 8.69 (m, 1H), 8.48 (d, J=5.6 Hz, 1H), 8.40 (m, 1H), 8.13 (s, 1H), 7.78-7.3 (m, 10H), 7.2-7.1 (m, 3H), 7.05-6.95 (m, 2H), 5.11 (d, J=3.8 Hz, 1H), 4.71 (d, J=11.1 Hz, 1H), 4.60-3.5 (m, 20H), 2.45 (s, 3H), 2.4-1.7 (m, 5H), 0.96 (d, J=6.4 Hz, 3H), 0.73 (d, J=6.6 Hz, 3H). LRMS (m/z) calculated, 1126.36; found, 1127.10 (M+H)$^+$, 1125.0 (M−H)$^−$. HPLC, t$_R$=11.1 min (purity: 94.5%).

Example 86—Synthesis of N-(2-(2,6-dioxopiperidin-3-yl)-1,3-dioxoisoindolin-4-yl)-6-(4-(4-((6-(4-fluoro-5-(3-hexylureido)-2-methylphenyl)-7-methyl-pyrido[2,3-d]pyrimidin-2-yl)amino)butyl)-1H-1,2,3-triazol-1-yl)hexanamide (Compound 2.036)

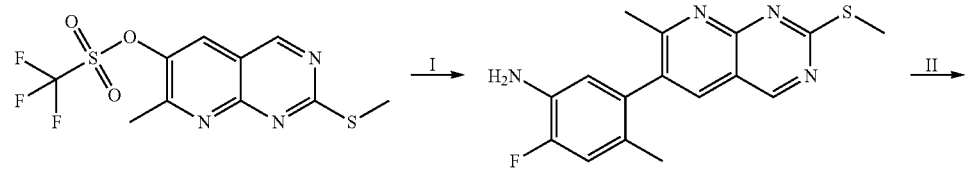

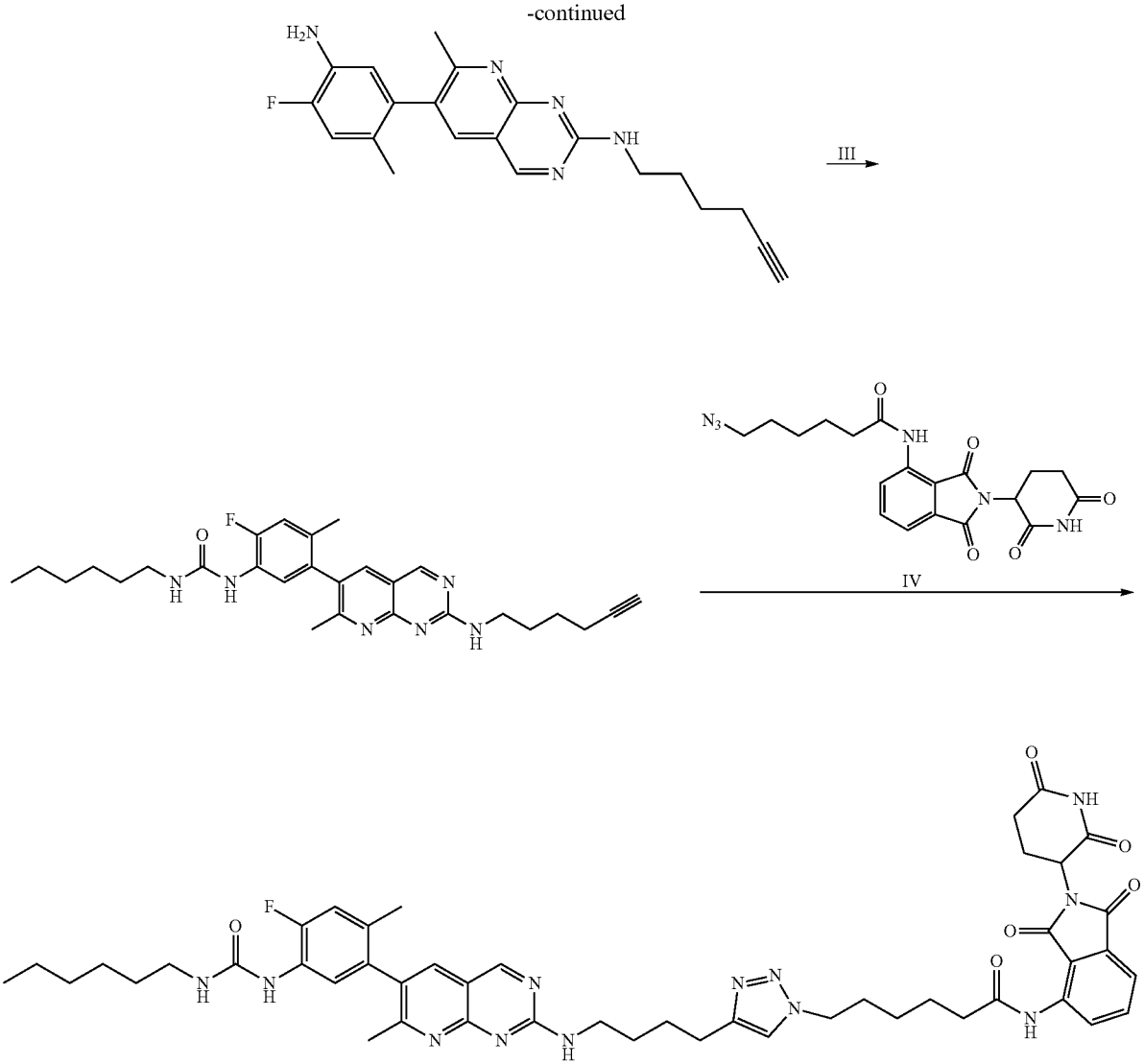

Step I, 2-Fluoro-4-methyl-5-(7-methyl-2-(methylthio)pyrido[2,3-d]pyrimidin-6-yl)aniline To a stirred solution of 7-methyl-2-(methylthio)pyrido[2,3-d]pyrimidin-6-yl trifluoromethane sulfonate (1.0 g, 2.95 mmol, 1.0 equiv.) (Henry et. al. *J. Med. Chem.* 2015, 58 (10), 4165-4179) in THF (25 mL, 25 vol. equiv.) was added 2-fluoro-4-methyl-5-(4,4,5,5-tetramethyl-1,3,2-dioxaborolan-2-yl)aniline (888 mg, 3.54 mmol, 1.0 equiv.) (Henry et. al. *J. Med. Chem.* 2015, 58 (10), 4165-4179), potassium carbonate (1.22 g, 8.84 mmol, 3.0 equiv.), water (2 mL, 2 vol. equiv.) and PdCl$_2$(dppf). DCM adduct (241 mg, 0.295 mmol, 0.1 equiv.). The reaction mixture was degassed three times with alternating vacuum and nitrogen. The resulting reaction mixture was heated at 70° C. for 2.0 h. The progress of the reaction was monitored by TLC (70% EtOAc in n-hexane) to ensure completion of the reaction. The reaction mixture was washed with water and brine (60 mL), dried (Na$_2$SO$_4$), and concentrated. The residue was purified on SiO$_2$ cartridge (80 g) using a gradient of EtOAc in hexanes (10-70%) to afford the title compound (563 mg, 60.8%) as a yellow solid. The product was triturated with ether (10 mL) and hexanes (25 mL) to afford the title compound. Rf=0.48 (70% EtOAc in hexanes). $^1$H NMR (400 MHz, CDCl$_3$) δ 9.11 (s, 1H), 7.86 (s, 1H), 6.96 (d, J=11.7 Hz, 1H), 6.58 (d, J=8.9 Hz, 1H), 3.71 (s, 2H), 2.77 (s, 3H), 2.55 (s, 3H), 1.94 (s, 3H). $^{19}$F NMR (376 MHz, CDCl$_3$) δ −135.85 (dd, J=11.7, 9.0 Hz). LRMS (m/z) calculated for C$_{16}$H$_{15}$FN$_4$S, 314.10; found 336.90 (M+Na)$^+$, 314.96 (M+H)$^+$.

Step II, 6-(5-Amino-4-fluoro-2-methylphenyl)-N-(hex-5-yn-1-yl)-7-methylpyrido[2,3-d]pyrimidin-2-amine 3-Chloroperoxybenzoic acid (652 mg, 3.78 mmol, 2.0 equiv.) was added to a cold (ice+salt, <0° C.) stirred solution of 2-fluoro-4-methyl-5-(7-methyl-2-(methylthio)pyrido[2,3-d]pyrimidin-6-yl)aniline (594 mg, 31.89 mmol, 1.0 equiv.) in DCM (12 mL, 20.8 vol. equiv.). The reaction mixture was stirred for 2.0 h at 0° C. The progress of the reaction was monitored by TLC (30% EtOAc in n-hexane) to ensure completion of the reaction. Then, hex-5-yn-1-amine (459 mg, 3.78 mmol) was added, stirred at the same temperature for 2 h [progress of the reaction was monitored by TLC]. The reaction mixture was diluted with water (5 mL), and the product was extracted with DCM (2×100 mL). The combined DCM extracts were dried over sodium sulfate and concentrated under reduced pressure. The residue was purified on SiO$_2$ cartridge (24 g) using a gradient of methanol in DCM (0 to 5%) to afford the title compound (89 mg, 13%) as an off-white solid. Rf=0.48 (5% MeOH in DCM), 0.3 (70% EtOAc in hexanes). $^1$H NMR (400 MHz, CDCl$_3$) δ 8.89 (s, 1H), 7.65 (s, 1H), 6.93 (d, J=11.8 Hz, 1H), 6.57 (d, J=9.0 Hz, 1H), 5.50 (t, J=5.9 Hz, 1H), 3.73-3.61 (m, 4H), 2.45 (s, 3H), 2.31-2.24 (m, 2H), 1.99-1.95 (m, 1H), 1.94 (s, 3H), 1.88-1.77 (m, 2H), 1.73-1.64 (m, 2H). $^{19}$F NMR (376 MHz, CDCl$_3$) δ −136.52 (dd, J=11.7, 9.1 Hz). LRMS (m/z) calculated for C$_{21}$H$_{22}$FN$_5$, 363.186, found 364.03 (M+H)$^+$.

Step III, 1-(2-Fluoro-5-(2-(hex-5-yn-1-ylamino)-7-methylpyrido[2,3-d]pyrimidin-6-yl)-4-methylphenyl)-3-hexylurea Pyridine (0.0205 mL, 0.253 mmol, 1.0 equiv.) and phenyl chloroformate (0.031 mL, 0.235 mmol, 1.0 equiv.) were added to a stirred solution of 6-(5-amino-4-fluoro-2-methylphenyl)-N-(hex-5-yn-1-yl)-7-methylpyrido[2,3-d]pyrimidin-2-amine (92 mg, 0.253 mmol, 1.0 equiv.) in acetonitrile (20 mL, 20 vol. equiv.). The resulting reaction mixture was stirred at rt for 2.5 h. The progress of the reaction was monitored by TLC (5% MeOH in DCM) to ensure completion of the reaction. The reaction mixture was concentrated to afford crude product (phenyl (2-fluoro-5-(2-(hex-5-yn-1-ylamino)-7-methylpyrido[2,3-d]pyrimidin-6-yl)-4-methylphenyl)carbamate) which was used for the next step. Rf=0.5 (70% EtOAc/Hexanes); LRMS (m/z) calculated for C$_{28}$H$_{26}$FN$_5$O$_2$, 483.21; found 438.98 (M+H)$^+$. To a stirred solution of phenyl (2-fluoro-5-(2-(hex-5-yn-1-ylamino)-7-methylpyrido[2,3-d]pyrimidin-6-yl)-4-methylphenyl)carbamate (122 mg, 0.252 mmol) in DMF (2.8 ml) was added DMAP (123 mg, 1.01 mmol) and n-hexylamine (0.0667 mL, 0.505 mmol) at rt. The reaction mixture was stirred over weekend at rt. The reaction mixture was poured into ice-cold water containing aq. HCl. (0.25 M, 20 mL), filtered off the precipitate, dried to afford the product and purified on SiO$_2$ cartridge (25 g) using a gradient of EtOAc in hexanes (10 to 100%) followed by MeOH in DCM (0 to 10%) to afford the title compound (35 mg, 28%). Rf=0.2 (5% MeOH in DCM) and Rf=0.3 (70% EtOAc in hexanes). $^1$H NMR (400 MHz, CDCl$_3$) δ 8.88 (s, 1H), 7.95 (d, J=8.3 Hz, 1H), 7.70 (s, 1H), 6.99 (s, 1H), 6.94 (d, J=11.9 Hz, 1H), 5.59 (t, J=5.1 Hz, 1H), 5.40 (s, 1H), 3.74-3.59 (m, 2H), 3.23 (dd, J=12.9, 6.7 Hz, 2H), 2.43 (s, 3H), 2.25 (m, 2H), 2.02-1.93 (m, 4H), 1.88-1.75 (m, 2H), 1.73-1.60 (m, 2H), 1.55-1.44 (m, 2H), 1.37-1.23 (m, 6H), 0.85 (t, J=6.3 Hz, 3H). $^{19}$F NMR (376 MHz, CDCl$_3$) δ −133.15 (s). LRMS (m/z) calculated, 490.258; found, 490.95 (M+H)$^+$, 489.04 (M−H)$^−$; HPLC, t$_R$=11.4 min (purity: 96.03%). HPLC method A.

Step IV, N-(2-(2,6-dioxopiperidin-3-yl)-1,3-dioxoisoindolin-4-yl)-6-(4-(4-((6-(4-fluoro-5-(3-hexylureido)-2-methylphenyl)-7-methylpyrido[2,3-d]pyrimidin-2-yl)amino)butyl)-1H-1,2,3-triazol-1-yl)hexanamide To a stirred solution of 1-(2-fluoro-5-(2-(hex-5-yn-1-ylamino)-7-methylpyrido[2,3-d]pyrimidin-6-yl)-4-methylphenyl)-3-hexylurea (28 mg, 0.057 mmol) and 6-azido-N-(2-(2,6-dioxopiperidin-3-yl)-1,3-dioxoisoindolin-4-yl)hexanamide (28.2 mg, 0.068 mmol) in THF (1 mL) were added a solution of CuSO$_4$.5H$_2$O (2.85 mg, 0.011 mmol) in water (0.25 mL) and a solution of sodium ascorbate (2.26 mg, 0.011 mmol) in water (0.25 mL). Reaction mixture was stirred at rt for 24 h, Na$_2$SO$_4$ was added to absorb water in the reaction mixture, filtered off the solids, and rinsed with EtOAc. The filtrate was concentrated and the crude product was purified on SiO$_2$ gold cartridge (24 g, Isco) using a gradient of methanol in DCM (0 to 20%) to afford the title compound (15 mg, 29%). Rf=0.48 (10% MeOH in DCM); $^1$H NMR (400 MHz, CDCl$_3$) δ 9.74 (s, 1H), 9.42 (s, 1H), 8.90 (s, 1H), 8.79 (d, J=8.5 Hz, 1H), 7.94 (d, J=8.3 Hz, 1H), 7.72 (d, J=7.9 Hz, 1H), 7.69 (s, 1H), 7.55 (d, J=7.3 Hz, 1H), 7.33 (s, 1H), 6.95 (d, J=11.9 Hz, 1H), 6.85 (s, 1H), 6.10 (s, 1H), 5.23 (t, J=5.3 Hz, 1H), 5.04-4.92 (m, 1H), 4.33 (t, J=6.9 Hz, 2H), 3.71-3.57 (m, 2H), 3.27-3.16 (m, 2H), 3.00-2.85 (m, 1H), 2.86-2.70 (m, 3H), 2.52-2.37 (m, 4H), 2.23-2.13 (m, 1H), 1.97 (s, 3H), 1.96-1.89 (m, 1H), 1.85-1.72 (m, 5H), 1.56-1.46 (m, 2H), 1.45-1.35 (m, 2H), 1.36-1.16 (m, 10H), 0.85 (t, J=6.6 Hz, 3H). $^{19}$F NMR (376 MHz, CDCl$_3$) δ −133.31 (br s). LRMS (m/z) calculated, 902.44; found, 901.21 (M−H)$^−$, 925.15 (M+Na)$^+$; HPLC, t$_R$=10.5 min (purity: 97.6%).

Example 87 to Example 89 describes the synthesis of Compounds 2.024 to 2.034, each of these conjugates are embraced by the following Formula

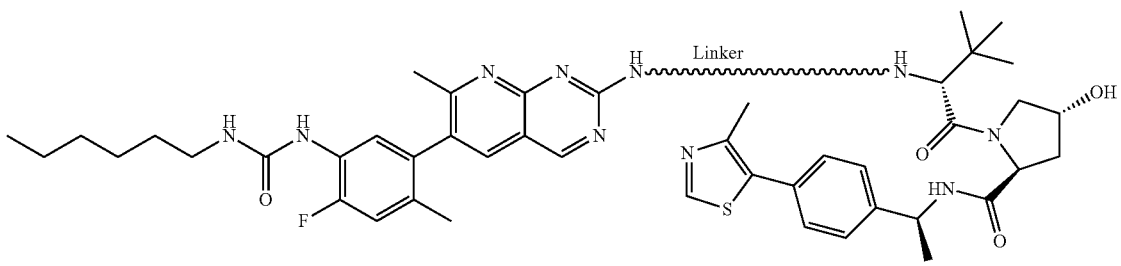 [SMILES: CCCCCCNC(=O)Nc1cc(-c2cc3cnc(NN[C@@H](C(=O)N4C[C@H](O)C[C@H]4C(=O)N[C@@H](C)c4ccc(-c5scnc5C)cc4)C(C)(C)C)nc3nc2C)c(C)cc1F]

Example 87—Synthesis of (2S,4R)-1-((R)-2-(6-(4-(4-((6-(4-fluoro-5-(3-hexylureido)-2-methylphenyl)-7-methylpyrido[2,3-d]pyrimidin-2-yl)amino)butyl)-1H-1,2,3-triazol-1-yl)hexanamido)-3,3-dimethylbutanoyl)-4-hydroxy-N—((S)-1-(4-(4-methylthiazol-5-yl)phenyl)ethyl)pyrrolidine-2-carboxamide (Compound 2.037)

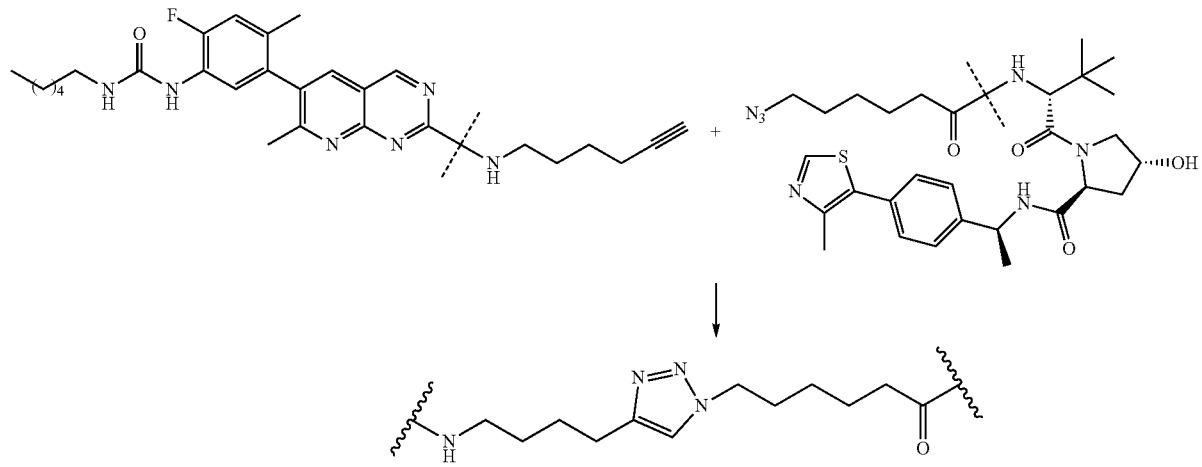

Title compound (9.1 mg, 18%) was prepared as a pale yellow solid from 1-(2-fluoro-5-(2-(hex-5-yn-1-ylamino)-7-methylpyrido[2,3-d]pyrimidin-6-yl)-4-methylphenyl)-3-hexylurea (22.5 mg, 45.9 mmol) and (2S,4R)-1-((R)-2-(6-azidohexanamido)-3,3-dimethylbutanoyl)-4-hydroxy-N—((S)-1-(4-(4-methylthiazol-5-yl)phenyl)ethyl)pyrrolidine-2-carboxamide (33 mg, 1.23 mmol) as described in Compound 2.036. Rf=0.24 (10% MeOH-DCM). $^1$H NMR (400 MHz, CDCl$_3$) δ 8.84 (s, 1H), 8.67 (s, 1H), 7.95 (d, J=8.2 Hz, 1H), 7.66 (s, 1H), 7.63-7.57 (m, 1H), 7.47-7.32 (m, 4H), 7.15-6.97 (m, 1H), 6.94 (d, J=11.8 Hz, 1H), 6.74-6.61 (m, 1H), 6.21 (s, 1H), 6.03 (bs, 1H), 5.56-5.33 (m, 1H), 5.30 (s, 1H), 5.18-5.01 (m, 1H), 4.75 (t, J=7.8 Hz, 1H), 4.61 (d, J=8.9 Hz, 1H), 4.54 (bs, 1H), 4.37-4.20 (m, 2H), 4.07 (d, J=10.8 Hz, 1H), 3.71-3.51 (m, 3H), 3.48 (q, J=7.0 Hz, 1H), 3.21 (dd, J=13.0, 6.7 Hz, 2H), 2.75 (t, J=6.0 Hz, 2H), 2.51 (s, 3H), 2.48-2.36 (m, 3H), 2.30-2.07 (m, 3H), 1.97 (s, 3H), 1.88-1.68 (m, 6H), 1.68-1.54 (m, 2H), 1.49 (d, J=7.0 Hz, 4H), 1.22 (dd, J=16.8, 9.8 Hz, 9H), 1.03 (s, 9H), 0.84 (t, J=6.6 Hz, 3H). $^{19}$F NMR (376 MHz, CDCl$_3$) δ −133.17 (s). LRMs (m/z) calculated, 1073.580; found, 1074.37 (M+H)$^+$, 1072.42 (M−H)$^−$. HPLC, $t_R$=10.5 min (purity >99.9%). HPLC method B.

Example 88—Synthesis of (2S,4R)-1-((R)-2-(5-(4-(4-((6-(4-fluoro-5-(3-hexylureido)-2-methylphenyl)-7-methylpyrido[2,3-d]pyrimidin-2-yl)amino)butyl)-1H-1,2,3-triazol-1-yl)pentanamido)-3,3-dimethylbutanoyl)-4-hydroxy-N—((S)-1-(4-(4-methylthiazol-5-yl)phenyl)ethyl)pyrrolidine-2-carboxamide (Compound 2.028)

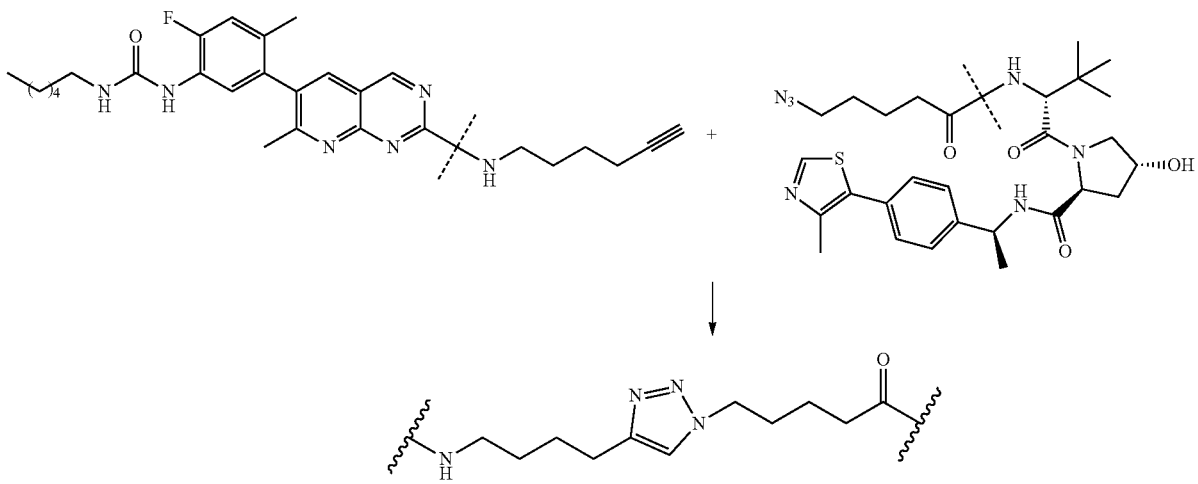

Title compound (10.9 mg, 21.9%) was prepared as an off-white solid from 1-(2-fluoro-5-(2-(hex-5-yn-1-ylamino)-7-methylpyrido[2,3-d]pyrimidin-6-yl)-4-methylphenyl)-3-hexylurea (23.0 mg, 0.0469 mmol) and (2S,4R)-1-((R)-2-(5-azidopentanamido)-3,3-dimethylbutanoyl)-4-hydroxy-N—((S)-1-(4-(4-methylthiazol-5-yl)phenyl)ethyl) pyrrolidine-2-carboxamide (27.8 mg, 0.0488 mmol) as described in Compound 2.036. Rf=0.24 (10% MeOH/DCM). $^1$H NMR (400 MHz, CDCl$_3$) δ 8.82 (bs, 1H), 8.67 (s, 1H), 8.49 (bs, 1H), 8.12 (bs, 1H), 7.97 (t, J=9.2 Hz, 1H), 7.64 (m, 2H), 7.43-7.33 (m, 5H), 7.12 (m, 1H), 6.92 (dd, J=11.8, 7.1 Hz, 2H), 6.47 (bs, 1H), 5.74 (bs, 1H), 5.56 (bs, 1H), 5.17-5.06 (m, 1H), 4.77-4.62 (m, 2H), 4.56 (bs, 1H), 4.37-4.20 (m, 2H), 4.12-4.03 (bs, 1H), 3.66 (m, 4H), 3.21 (dd, J=12.7, 6.3 Hz, 4H), 2.75 (bs, 2H), 2.63 (s, 3H), 2.52 (s, 3H), 2.41 (bs, 2H), 1.94 (d, J=14.1 Hz, 3H), 1.80 (m, 6H), 1.61-1.53 (m, 2H), 1.52-1.48 (m, 4H), 1.29-1.22 (m, 6H), 1.06 (s, 9H), 0.84 (t, J=6.5 Hz, 3H) ppm. $^{19}$F NMR (376 MHz, CDCl$_3$) δ −133.15 (s) ppm. LRMS (m/z) calculated for C$_{56}$H$_{74}$FN$_{13}$O$_5$S, 1059.56; found 1082.29 (M+Na)$^+$; found 1058.19 (M−H)$^-$. HPLC, t$_R$=10.3 min (purity: >95%). HPLC method B.

Example 89—Synthesis of (2S,4R)-1-((R)-2-(6-(4-((2-(2-((6-(4-fluoro-5-(3-hexylureido)-2-methylphenyl)-7-methylpyrido[2,3-d]pyrimidin-2-yl)amino)ethoxy)ethoxy)methyl)-1H-1,2,3-triazol-1-yl)hexanamido)-3,3-dimethylbutanoyl)-4-hydroxy-N—((S)-1-(4-(4-methylthiazol-5-yl)phenyl)ethyl)pyrrolidine-2-carboxamide (Compound 2.039)

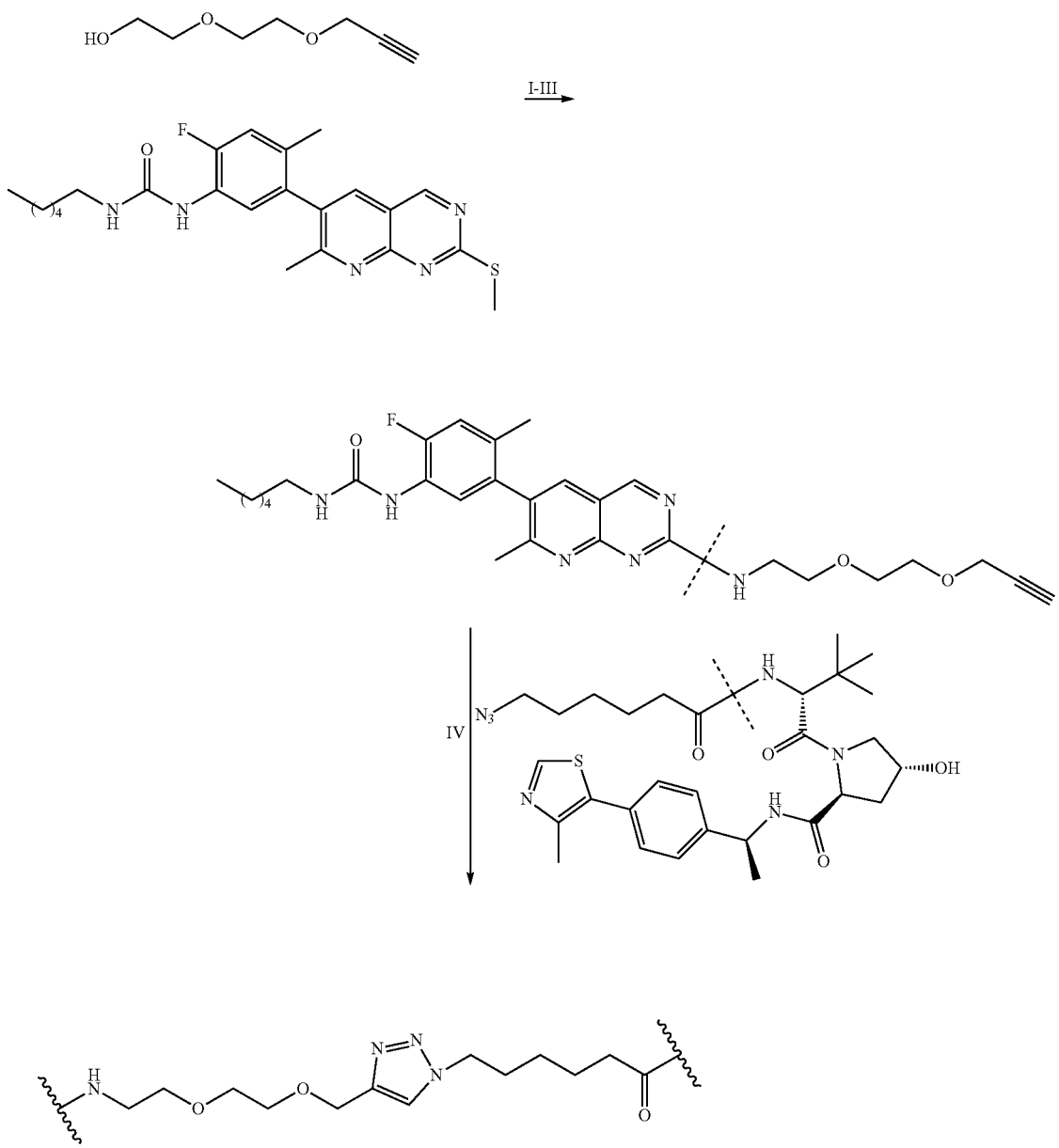

Step I, 2-(2-(2-(prop-2-yn-1-yloxy)ethoxy)ethyl) isoindoline-1,3-dione

To a cold (0° C.) stirred solution of phthalimide (1.073 g, 7.29 mmol) and triphenylphosphine (1.92 g, 7.30 mmol) in THF (9.0 mL) was added a solution of 2-(2-(prop-2-yn-1-yloxy)ethoxy)ethanol (706 mg, 4.90 mmol) and diisopropylazodicarboxylate (1.8 mL, 9.15 mmol) in THF (9.0 mL). The reaction mixture was slowly warmed up to rt, stirred for 4 days, concentrated. The residue was diluted with water (10 mL) and extracted with EtOAc (3×10 mL). The combined organic extracts were combined, dried ($Na_2SO_4$), concentrated and purified on a 80 g $SiO_2$ cartridge using a gradient of ethyl acetate in hexanes (10 to 30%) to afford the title compound (1.08 g @87.2% purity, 70.4%) as a white solid. Rf=0.16 (20% EtOAc in Hexanes). $^1$H NMR (400 MHz, $CDCl_3$) δ 7.87-7.83 (m, 2H), 7.75-7.68 (m, 2H), 4.13 (d, J=2.3 Hz, 2H), 3.91 (t, J=5.8 Hz, 2H), 3.75 (t, J=5.8 Hz, 2H), 3.70-3.62 (m, 4H), 2.38 (t, J=2.3 Hz, 1H). LRMS (m/z) calculated, 273.10; found 295.91 (M+Na)$^+$.

Step II, 2-(2-(prop-2-yn-1-yloxy)ethoxy)ethanamine

To a stirred solution of 2-(2-(2-(prop-2-yn-1-yloxy)ethoxy)ethyl)isoindoline-1,3-dione (1.08 g @ 87.2% purity, 3.45 mmol) THF (71.0 mL) was added hydrazine hydrate (3.1 mL, 63.7 mmol). The reaction mixture was refluxed for 1 h. The reaction mixture cooled to rt and filtered, filtrate was concentrated to afford the title compound (251.3 mg, 50.9%). Rf=0.12 (10% MeOH in DCM). $^1$H NMR (400 MHz, $CDCl_3$) δ 4.21 (d, J=2.3 Hz, 2H), 3.72-3.70 (m, 2H), 3.66-3.64 (m, 2H), 3.53 (t, J=5.2 Hz, 2H), 2.89 (t, J=5.1 Hz, 2H), 2.44 (t, J=2.4 Hz, 1H), 1.87 (m, 2H), 1.84 (bs, 1H) ppm. LRMS (m/z) calculated, 143.09; found 143.95 (M+H)$^+$.

Step III, 1-(2-fluoro-4-methyl-5-(7-methyl-2-((2-(2-(prop-2-yn-1-yloxy)ethoxy)ethyl)-amino)pyrido[2,3-d]pyrimidin-6-yl)phenyl)-3-hexylurea To a cold (0° C.) stirred solution of 1-(2-fluoro-4-methyl-5-(7-methyl-2-(methylthio)pyrido[2,3-d]pyrimidin-6-yl)phenyl)-3-hexylurea (203.0 mg, 0.460 mmol) in DCM (4.0 mL) was added m-CPBA (226.6 mg @ 77% purity, 1.31 mmol), stirred for 2 h. 2-(Prop-2-yn-1-yloxy)ethanamine (51.5 mg, 0.520 mmol) was added, slowly warmed up to rt, stirred for 15 h. The reaction mixture was diluted with water (5 mL), extracted with EtOAc (3×10 mL). Combined organic extracts were dried ($Na_2SO_4$), concentrated. The residue was purified on 25 g $SiO_2$ cartridge using a gradient of methanol in DCM (0 to 10%) to afford 1-(2-fluoro-4-methyl-5-(7-methyl-2-(methylsulfonyl)pyrido[2,3-d]pyrimidin-6-yl)phenyl)-3-hexylurea (100 mg, 45.9%). Rf=0.20 (70% MeOH in DCM). $^1$H NMR (400 MHz, $CDCl_3$) δ 9.61 (s, 1H), 8.24 (s, 1H), 8.04 (d, J=8.2 Hz, 1H), 7.05 (bs, 1H), 6.96 (d, J=11.8 Hz, 1H), 5.42 (m, 1H), 3.57 (s, 3H), 3.22 (dd, J=12.8, 7.0 Hz, 2H), 2.63 (s, 3H), 1.97 (s, 3H), 1.54-1.44 (m, 2H), 1.33-1.22 (m, 6H), 0.85 (t, J=6.8 Hz, 3H). $^{19}$F NMR (376 MHz, $CDCl_3$) δ -131.92 (t, J=9.3 Hz). LRMS (m/z) calculated, 473.19; found, 473.84 (M+H)$^+$. To a stirred solution of 1-(2-fluoro-4-methyl-5-(7-methyl-2-(methylsulfonyl)pyrido[2,3-d]pyrimidin-6-yl)phenyl)-3-hexylurea (100 mg, 0.211 mmol) in DCM (2.0 mL) was added 2-(2-(prop-2-yn-1-yloxy)ethoxy)ethanamine (34.7 mg, 0.242 mmol), stirred for 16 h at rt, a second portion of 2-(2-(prop-2-yn-1-yloxy)ethoxy)ethanamine (30.3 mg, 0.212 mmol) was added. The reaction mixture was stirred at rt for 19 h, poured into water (5 mL) and extracted with EtOAc (3×10 mL). The combined organic extracts were dried ($Na_2SO_4$), and concentrated. The residue was purified on 25 g $SiO_2$ cartridge using a gradient of methanol in DCM (0 to 15%) to afford the title compound (58.4 mg, 51.5%) as a yellow solid. Rf=0.24 (5% MeOH in DCM). $^1$H NMR (400 MHz, $CDCl_3$) δ 8.90 (s, 1H), 7.93 (d, J=8.3 Hz, 1H), 7.70 (s, 1H), 6.99 (d, J=11.9 Hz, 1H), 6.51 (d, J=2.8 Hz, 1H), 5.96 (bs, 1H), 4.82 (t, J=5.6 Hz, 1H), 4.23 (d, J=2.4 Hz, 2H), 3.88-3.85 (m, 2H), 3.78-3.74 (m, 2H), 3.74-3.66 (m, 4H), 3.24 (dd, J=12.9, 7.1 Hz, 2H), 2.46-2.43 (m, 4H), 2.00 (s, 3H), 1.57-1.47 (m, 2H), 1.36-1.25 (m, 6H), 0.87 (t, J=6.9 Hz, 3H) ppm. $^{19}$F NMR (376 MHz, $CDCl_3$) δ -133.57 (s) ppm. LRMS (m/z) calculated, 536.29; found 537.02 (M+H)$^+$.

Step IV, (2S,4R)-1-((R)-2-(6-(4-((2-(2-((6-(4-fluoro-5-(3-hexylureido)-2-methylphenyl)-7-methylpyrido[2,3-d]pyrimidin-2-yl)amino)ethoxy)ethoxy)methyl)-1H-1,2,3-triazol-1-yl)hexanamido)-3,3-dimethylbutanoyl)-4-hydroxy-N—((S)-1-(4-(4-methylthiazol-5-yl)phenyl)ethyl)pyrrolidine-2-carboxamide Title compound (13.2 mg, 10.8%) was prepared as pale orange solid from 1-(2-fluoro-4-methyl-5-(7-methyl-2-((2-(2-(prop-2-yn-1-yloxy)ethoxy)ethyl)amino)pyrido[2,3-d]pyrimidin-6-yl)phenyl)-3-hexylurea (58.4 mg, 0.109 mmol) and (2S,4R)-1-((R)-2-(6-azidohexanamido)-3,3-dimethylbutanoyl)-4-hydroxy-N—((S)-1-(4-(4-methylthiazol-5-yl)phenyl)ethyl)pyrrolidine-2-carboxamide (72.6 mg, 0.124 mmol) as described in Compound 2.036. Rf=0.16 (10% MeOH in DCM). $^1$H NMR (400 MHz, $CDCl_3$) δ 8.90 (bs, 1H), 8.67 (s, 1H), 7.90 (d, J=8.4 Hz, 1H), 7.71 (d, J=2.7 Hz, 1H), 7.66 (bs, 1H), 7.45 (d, J=7.9 Hz, 1H), 7.41 (m, 2H), 7.37 (m, 2H), 7.00 (d, J=11.8 Hz, 1H), 6.52 (bs, 1H), 6.28 (bs, 1H), 6.16 (bs, 1H), 5.14-5.04 (m, 1H), 4.83 (bs, 1H), 4.71 (d, J=2.9 Hz, 2H), 4.57 (d, J=8.9 Hz, 1H), 4.54 (bs, 1H), 4.32 (t, J=6.8 Hz, 2H), 4.10-4.04 (m, 1H), 3.83 (bs, 2H), 3.76-3.65 (m, 6H), 3.62 (dd, J=11.2, 3.7 Hz, 1H), 3.48 (bs, 1H), 3.23 (dd, J=13.0, 7.1 Hz, 2H), 2.57-2.50 (m, 1H), 2.53 (s, 3H), 2.44 (s, 3H), 2.27-2.21 (m, 1H), 2.20-2.13 (m, 1H), 2.00 (s, 3H), 1.86 (m, 2H), 1.61 (s, 3H), 1.52 (m, 2H), 1.48 (d, J=6.9 Hz, 3H), 1.27 (m, 8H), 1.03 (s, 9H), 0.87 (t, J=6.8 Hz, 3H) ppm. $^{19}$F NMR (376 MHz, $CDCl_3$) δ -133.15 (s) ppm. LRMS (m/z) calculated, 1119.59; found 1142.27 (M+Na)$^+$; 1118.29 (M–H)$^-$. HPLC, $t_R$=10.1 min (purity: >99%). HPLC method B.

Example 90 to Example 93 describes the synthesis of Compounds 2.024 to 2.034, each of these conjugates are embraced by the following Formula 253 254
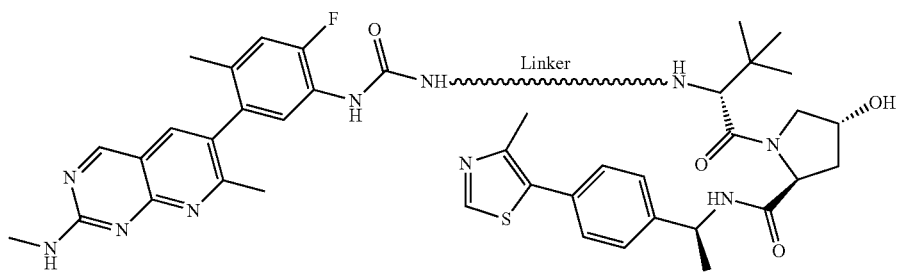 [SMILES: CNc1ncc2cc(-c3cc(NC(=O)NN[C@@H](C(=O)N4C[C@H](O)C[C@H]4C(=O)N[C@@H](C)c4ccc(-c5scnc5C)cc4)C(C)(C)C)c(F)cc3C)c(C)nc2n1]
Example 90—Synthesis of (2S,4R)-1-((R)-21-(tert-butyl)-1-((2-fluoro-4-methyl-5-(7-methyl-2-(methylamino)pyrido[2,3-d]pyrimidin-6-yl)phenyl)amino)-1,19-dioxo-5,8,11,14,17-pentaoxa-2,20-diazadocosan-22-oyl)-4-hydroxy-N—((S)-1-(4-(4-methylthiazol-5-yl)phenyl)ethyl)pyrrolidine-2-carboxamide (Compound 2.040)
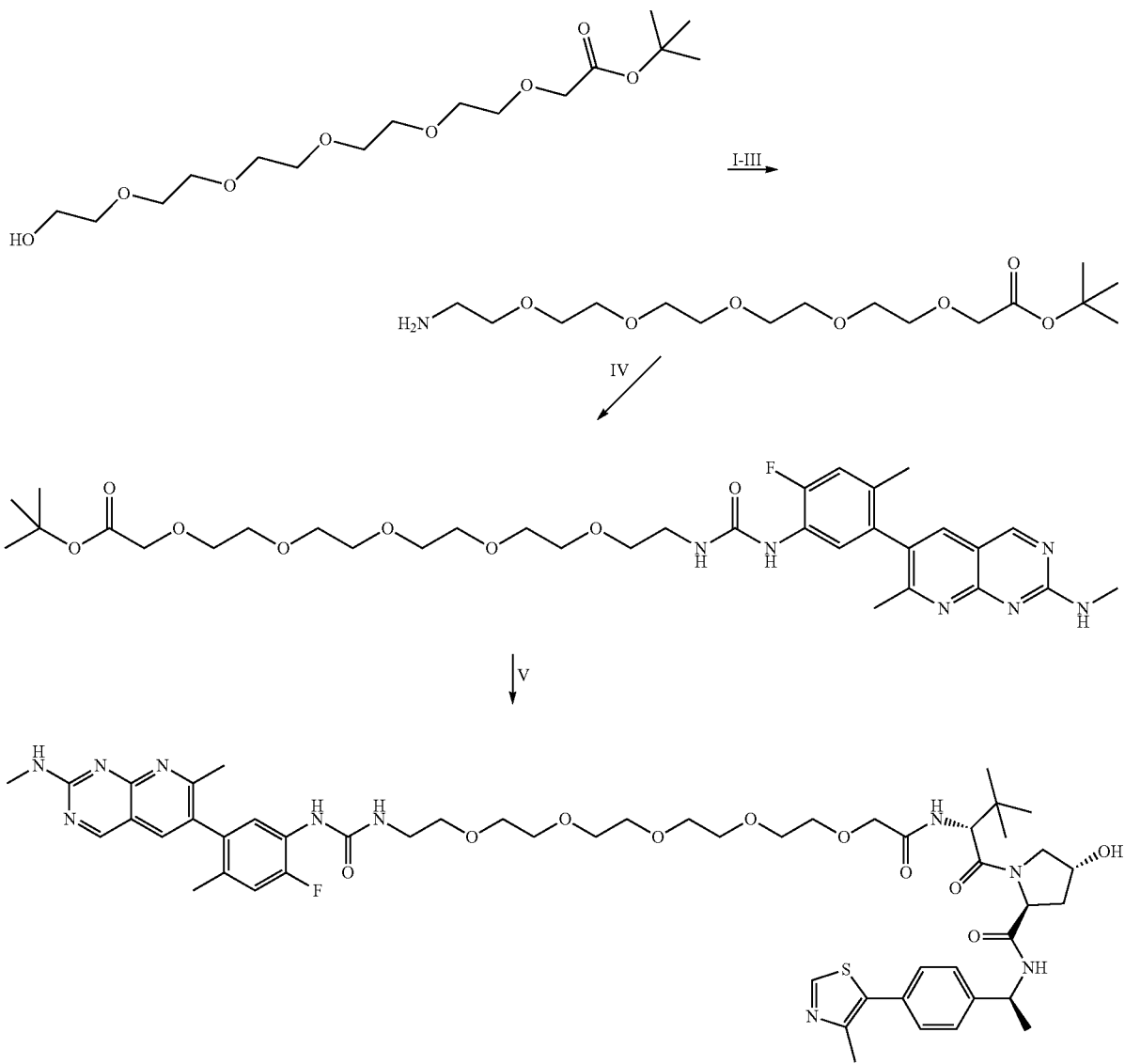

Step I, Synthesis of tert-butyl 17-(tosyloxy)-3,6,9,12,15-pentaoxaheptadecan-1-oate To a stirred solution of tert-butyl 17-hydroxy-3,6,9,12,15-pentaoxaheptadecan-1-oate (827 mg, 2.35 mmol) in DCM (10 mL) was added pyridine (569 uL, 7.04 mmol) followed by tosyl chloride (671 mg, 3.52 mmol). The mixture was stirred at rt for 18 h, diluted with DCM and water. The phases were separated and the aqueous layer was extracted twice with DCM. The combined organic layers were dried over $Na_2SO_4$, filtered and concentrated. The residue was purified by flash chromatography on silica gel using a gradient of EtOAc in hexanes (0-100%) to afford the title compound (870 mg, 73%). $^1$H NMR (600 MHz, CDCl$_3$) δ 7.80 (d, J=8.3 Hz, 2H), 7.34 (d, J=8.0 Hz, 2H), 4.18-4.14 (m, 2H), 4.01 (d, J=2.6 Hz, 2H), 3.72-3.60 (m, 14H), 3.58 (s, 4H), 2.45 (s, 3H), 1.47 (s, 9H).

Step II, Synthesis of tert-butyl 17-azido-3,6,9,12,15-pentaoxaheptadecan-1-oate To a stirred solution of tert-butyl 17-(tosyloxy)-3,6,9,12,15-pentaoxaheptadecan-1-oate (870 mg, 1.72 mmol) in DMF (7.0 mL) was added sodium azide (435 mg, 6.69 mmol) at rt. The mixture was stirred for 18 h, diluted with water and EtOAc. The phases were separated and the aqueous layer was extracted twice with EtOAc. The combined organic layers were washed with brine, dried over $Na_2SO_4$, filtered and concentrated. The crude product was purified by flash chromatography on silica gel using a gradient of EtOAc in hexanes (0-100%) to afford the title compound (520 mg, 80%) as a colorless oil. $^1$H NMR (600 MHz, CDCl$_3$) δ 4.01 (s, 2H), 3.71-3.62 (m, 18H), 3.38 (t, J=4.9 Hz, 2H), 1.47 (s, 9H).

Step III, Synthesis of tert-butyl 17-amino-3,6,9,12,15-pentaoxaheptadecan-1-oate To a stirred solution of tert-butyl 17-azido-3,6,9,12,15-pentaoxaheptadecan-1-oate (520 mg, 1.38 mmol) in THF (5.0 mL) was added 10% palladium on carbon (60 mg, 0.56 mmol). The argon atmosphere was replaced by hydrogen (bubbled into solution for at least 2 min) and the mixture was stirred at rt under hydrogen atmosphere for 20 h before the hydrogen was replaced with argon. Then the mixture was filtered on a Celite® plug. The Celite® plug was rinsed twice with EtOAc. The filtrate was concentrated to dryness to afford the title compound (490 mg, 96% yield, about 95% w/w purity) as brown oil. $^1$H NMR (600 MHz, CDCl$_3$) δ 4.02 (s, 2H), 3.73-3.59 (m, 17H), 3.53 (t, J=4.8 Hz, 2H), 2.88 (t, J=4.7 Hz, 1H), 1.48 (d, J=12.7 Hz, 9H). LRMS (m/z) calculated, 351.23; found, 352.4 (M+H)$^+$.

Step IV, Synthesis of tert-butyl 1-((2-fluoro-4-methyl-5-(7-methyl-2-(methylamino)pyrido[2,3-d]pyrimidin-6-yl)phenyl)amino)-1-oxo-5,8,11,14,17-pentaoxa-2-azanonadecan-19-oate A solution of tert-butyl 17-amino-3,6,9,12,15-pentaoxaheptadecan-1-oate (489 mg, 1.39 mmol) in DMSO (2.0 mL) was added to a stirred solution of phenyl (2-fluoro-4-methyl-5-(7-methyl-2-(methylamino)pyrido[2,3-d]pyrimidin-6-yl)phenyl)carbamate (235 mg, 0.563 mmol) in DMSO (2.0 mL). The mixture was stirred at rt for 18 h, poured into water. DCM was added and the phases were separated. The aqueous layer was extracted twice with DCM. The combined organic layers were dried over $Na_2SO_4$, and concentrated. The residue was purified by flash chromatography on silica gel using a gradient of MeOH in DCM (0-20%) to afford the title compound (380 mg, 70% yield, 70% w/w purity calc.) as a yellow oil. LRMS (m/z) calculated, 674.34; found, 678.1 (M+H)$^+$.

Step V, Synthesis of (2S,4R)-1-((R)-21-(tert-butyl)-1-((2-fluoro-4-methyl-5-(7-methyl-2-(methylamino)pyrido[2,3-d]pyrimidin-6-yl)phenyl)amino)-1,19-dioxo-5,8,11,14,17-pentaoxa-2,20-diazadocosan-22-oyl)-4-hydroxy-N—((S)-1-(4-(4-methylthiazol-5-yl)phenyl)ethyl)pyrrolidine-2-carboxamide TFA (400 uL, 5.39 mmol) was added to a cold (0° C.) stirred solution of tert-butyl 1-((2-fluoro-4-methyl-5-(7-methyl-2-(methylamino)pyrido[2,3-d]pyrimidin-6-yl)phenyl)amino)-1-oxo-5,8,11,14,17-pentaoxa-2-azanonadecan-19-oate (258 mg, 0.382 mmol) in DCM (3.0 mL), after 5 min, ice-bath was removed, stirred for 5 h. The mixture was poured into a mixture of ice-cold water (10 mL) and aq. saturated NaHCO$_3$ (3.0 mL, pH~5). The mixture was freeze dried over 18 h. The resultant yellow solid was suspended in acetone and decanted the solution. The solution was concentrated, absorbed on the Celite® using DCM and acetone, purified by flash chromatography on silica gel using a gradient of MeOH in DCM (0-100%) to afford the 1-((2-fluoro-4-methyl-5-(7-methyl-2-(methylamino)pyrido[2,3-d]pyrimidin-6-yl)phenyl)amino)-1-oxo-5,8,11,14,17-pentaoxa-2-azanonadecan-19-oic acid (145 mg, 46% yield, 75% purity). To a stirred solution of the carboxylic acid (145 mg, 0.176 mmol, 75% w/w purity) in DMF (1.5 mL) were added (2S,4R)-1-((R)-2-amino-3,3-dimethylbutanoyl)-4-hydroxy-N—((S)-1-(4-(4-methylthiazol-5-yl)phenyl)ethyl)pyrrolidine-2-carboxamide (93.8 mg, 0.211 mmol), HATU (100 mg, 0.264 mmol) and DIPEA (242 uL, 1.41 mmol). The reaction mixture was stirred overnight at rt. The mixture was diluted with EtOAc and water. The phases were separated and the aqueous layer was extracted twice with EtOAc. The aqueous layer was then extracted 3 times with DCM and the organic extracts (EtOAc and DCM) were combined, dried over $Na_2SO_4$, filtered and concentrated. The residue was purified by flash chromatography on silica gel using a gradient of MeOH in DCM (0-20%) to afford the gummy solid which was dissolved in acetonitrile in water, and lyophilized to afford the title compound (94 mg, 50%) as a pale yellow fluffy solid. $^1$H NMR showed ~10% of the isomeric mixture. $^1$H NMR (600 MHz, CDCl$_3$) δ 8.88 (s, 1H), 8.67 (s, 1H), 8.03 (d, J=7.7 Hz, 1H), 7.81-7.58 (m, 2H), 7.38 (d, J=14.2 Hz, 5H), 6.95 (d, J=11.3 Hz, 1H), 6.28 (s, 1H), 5.51 (s, 1H), 5.08 (s, 1H), 4.81-4.65 (m, 1H), 4.60 (s, 1H), 4.50 (s, 1H), 4.12-3.90 (m, 3H), 3.73-3.55 (m, 20H), 3.48-3.33 (m, 3H), 3.18 (s, 3H), 2.59-2.39 (m, 7H), 2.14-2.04 (m, 1H), 1.98 (s, 3H), 1.48 (s, 3H), 1.05 (s, 9H). LRMS (m/z) calculated, 1044.49; found, 1069.626 (M+Na)$^+$. HPLC, $t_R$=8.3 min (purity: 98%).

Example 91—Synthesis of (2S,4R)-1-((R)-15-(tert-butyl)-1-((2-fluoro-4-methyl-5-(7-methyl-2-(methylamino)pyrido[2,3-d]pyrimidin-6-yl)phenyl)amino)-1,13-dioxo-5,8,11-trioxa-2,14-diazahexadecan-16-oyl)-4-hydroxy-N—((S)-1-(4-(4-methylthiazol-5-yl)phenyl)ethyl)pyrrolidine-2-carboxamide (Compound 2.041)

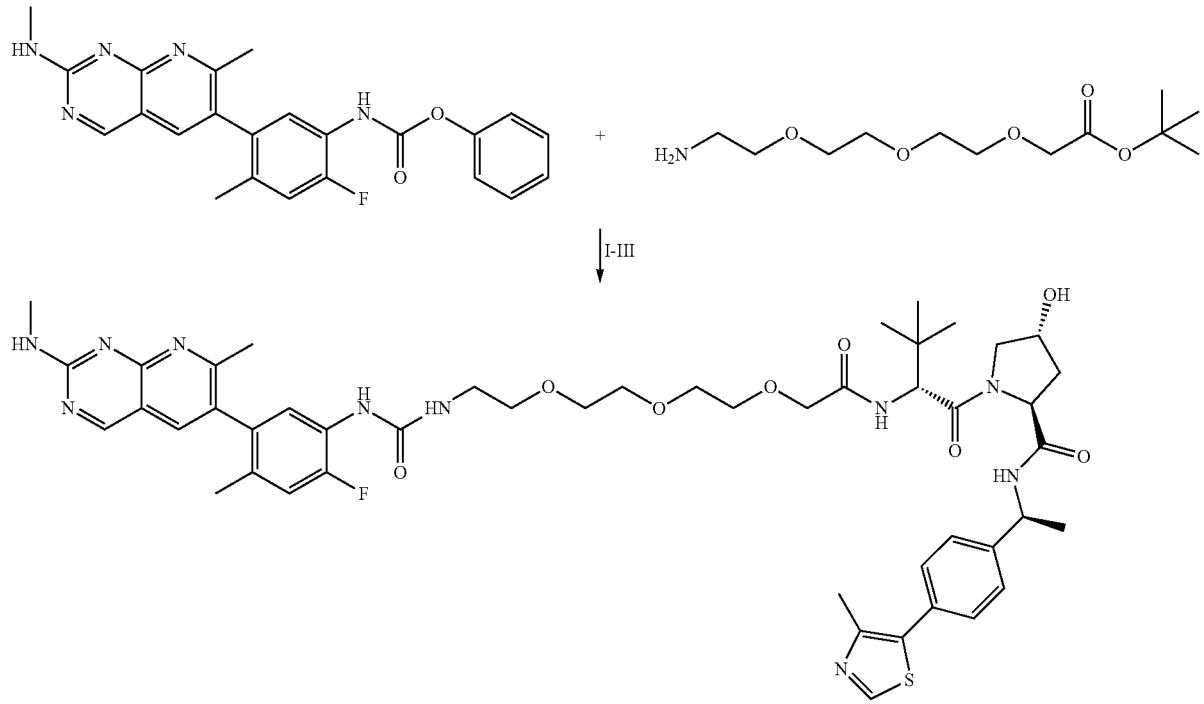

Step I, tert-butyl 1-((2-fluoro-4-methyl-5-(7-methyl-2-(methylamino)pyrido[2,3-d]pyrimidin-6-yl)phenyl)amino)-1-oxo-5,8,11-trioxa-2-azatridecan-13-oate To a stirred solution of the tert-butyl 2-(2-(2-(2-aminoethoxy)ethoxy)ethoxy)acetate (106 mg, 0.403 mmol) in DMSO was added phenyl (2-fluoro-4-methyl-5-(7-methyl-2-(methylamino)pyrido[2,3-d]pyrimidin-6-yl)phenyl)carbamate (86 mg, 0.206 mmol), stirred for 16 h, diluted with ethyl acetate (10 mL), washed with 10 mL of water, aqueous solution was extracted with ethyl acetate (2×10 mL), combined extracts were dried over Na₂SO₄, and concentrated. The residue was purified on 24 g Silica gel cartridge using a gradient of methanol in DCM (5 to 15%, 15CV, 15%, 10 CV) as eluant to afford the title compound (26 mg). $^1$H NMR (400 MHz, CDCl₃) δ 8.87 (s, 1H), 8.04 (d, J=8.4 Hz, 1H), 7.71 (s, 1H), 7.55 (s, 1H), 6.94 (d, J=12.0 Hz, 1H), 6.21 (s, 1H), 5.55 (s, 1H), 4.09 (s, 2H), 3.79-3.69 (m, 4H), 3.68-3.57 (m, 6H), 3.48-3.38 (m, 2H), 3.19 (d, J=5.1 Hz, 3H), 2.45 (s, 3H), 1.98 (s, 3H), 1.48 (s, 9H).

Step II, 1-((2-fluoro-4-methyl-5-(7-methyl-2-(methylamino)pyrido[2,3-d]pyrimidin-6-yl)phenyl)amino)-1-oxo-5,8,11-trioxa-2-azatridecan-13-oic Acid To a stirred solution of tert-butyl 1-((2-fluoro-4-methyl-5-(7-methyl-2-(methylamino)pyrido[2,3-d]pyrimidin-6-yl)phenyl)amino)-1-oxo-5,8,11-trioxa-2-azatridecan-13-oate (36 mg, 0.0614 mmol) in DCM (0.75 mL) was added TFA (0.25 mL), after stirred for 5 h, it was concentrated, excess TFA was co-evaporated with toluene on rotavap in five cycles (make sure TFA is removed completely) to afford the crude acid (32 mg, quant.). This material was used as such in the next step.

Step III, (2S,4R)-1-((R)-15-(tert-butyl)-1-((2-fluoro-4-methyl-5-(7-methyl-2-(methylamino)pyrido[2,3-d]pyrimidin-6-yl)phenyl)amino)-1,13-dioxo-5,8,11-trioxa-2,14-diazahexadecan-16-oyl)-4-hydroxy-N—((S)-1-(4-(4-methylthiazol-5-yl)phenyl)ethyl)pyrrolidine-2-carboxamide To a cold (ice) stirred solution of the 1-((2-fluoro-4-methyl-5-(7-methyl-2-(methylamino)pyrido[2,3-d]pyrimidin-6-yl)phenyl)amino)-1-oxo-5,8,11-trioxa-2-azatridecan-13-oic acid (32.4 mg, 0.061 mmol), (2S,4R)-1-((R)-2-amino-3,3-dimethylbutanoyl)-4-hydroxy-N—((S)-1-(4-(4-methylthiazol-5-yl)phenyl)ethyl)pyrrolidine-2-carboxamide (27.1 mg, 0.061 mmol) and HATU (69.6 mg, 0.183 mmol) in DMF (1 mL) was added neat DIPEA (0.106 mmol, 0.610 mmol), reaction mixture was slowly warmed up to rt during 16 h, it was diluted with ethyl acetate (10 mL) and water (5 mL), stirred for 10 min, the orange product was crashed out of the organic solution, aqueous solution was separated, organic solution was washed with water (2×5 mL), combined aqueous solution was extracted with 5% MeOH in Ethyl acetate, combined organic solution was diluted with methanol, concentrated, re-dissolved in methanol in methylene chloride, absorbed on the Celite®, and purified on 24 g Silica gel cartridge using a gradient of methanol in methylene chloride (0 to 20%) as eluant to afford the title compound (17 mg, 29.1%) as a white solid. Rf=0.45 (10% MeOH in DCM). ¹H NMR (400 MHz, CDCl₃) δ 8.83 (bs, 1H), 8.63 (s, 1H), 7.89 (d, J=8.3 Hz, 1H), 7.67 (s, 1H), 7.54-7.47 (m, 1H), 7.44 (d, J=9.0 Hz, 1H), 7.31 (q, J=8.5 Hz, 4H), 6.93 (d, J=11.9 Hz, 1H), 6.43-6.34 (m, 1H), 5.05-4.94 (m, 1H), 4.64-4.52 (m, 2H), 4.42 (brs, 1H), 4.16-3.97 (m, 2H), 3.88 (d, J=11.2 Hz, 1H), 3.70-3.31 (m, 13H), 3.10 (s, 3H), 2.46 (s, 3H), 2.38 (s, 3H), 2.21-2.02 (m, 2H), 1.93 (s, 3H), 1.43 (d, J=6.9 Hz, 3H), 1.00 (s, 9H). LRMS (m/z) calculated, 957.14; found, 958.62 (M+H)⁺; 980.73 (M+Na)⁺. HPLC, $t_R$=11.2 min.

Example 92—Synthesis of (2S,4R)-1-((R)-12-(tert-butyl)-1-((2-fluoro-4-methyl-5-(7-methyl-2-(methylamino)pyrido[2,3-d]pyrimidin-6-yl)phenyl)amino)-1,10-dioxo-5,8-dioxa-2,11-diazatridecan-13-oyl)-4-hydroxy-N—((S)-1-(4-(4-methylthiazol-5-yl)phenyl)ethyl)pyrrolidine-2-carboxamide (Compound 2.042)

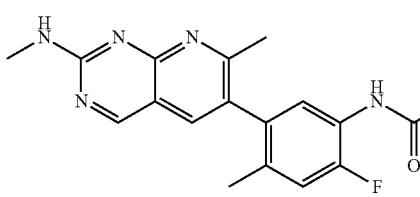
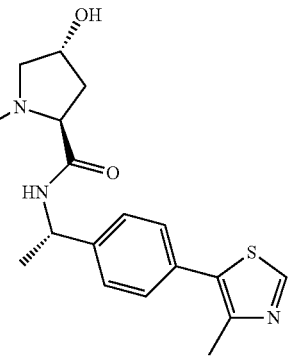

The title compound (10.9) was prepared from phenyl (2-fluoro-4-methyl-5-(7-methyl-2-(methylamino)pyrido[2,3-d]pyrimidin-6-yl)phenyl)carbamate and tert-butyl 2-(2-(2-aminoethoxy)ethoxy)acetate as described in Step I-III of Compound 2.041. ¹H NMR (600 MHz, MeOD) δ 9.16-8.92 (m, 1H), 8.87 (s, 1H), 8.51 (d, J=7.2 Hz, 1H), 7.95-7.88 (m, 1H), 7.84-7.70 (m, 2H), 7.60 (d, J=9.5 Hz, 1H), 7.46-7.33 (m, 4H), 7.17-7.05 (m, 1H), 6.98-6.92 (m, 1H), 6.89-6.80 (m, 1H), 5.06-4.91 (m, 1H), 4.76 (d, J=9.6 Hz, 1H), 4.66-4.54 (m, 1H), 4.48-4.35 (m, 1H), 4.12-4.00 (m, 2H), 3.88-3.82 (m, 1H), 3.80-3.56 (m, 8H), 3.56-3.38 (m, 2H), 3.12-3.04 (m, 3H), 2.51-2.44 (m, 3H), 2.41 (d, J=3.9 Hz, 3H), 2.25-2.18 (m, 1H), 2.07-2.01 (m, 3H), 1.97 (t, J=11.2 Hz, 1H), 1.59-1.42 (m, 3H), 1.06 (s, 9H). LRMS (m/z) calculated, 912.411; found, 917.9 (M+H)⁺.

Example 93—Synthesis of (2S,4R)-1-((R)-22-(tert-butyl)-1-((2-fluoro-4-methyl-5-(7-methyl-2-(methylamino)pyrido[2,3-d]pyrimidin-6-yl)phenyl)amino)-1,20-dioxo-9,12,15,18-tetraoxa-2,21-diazatricosan-23-oyl)-4-hydroxy-N—((S)-1-(4-(4-methylthiazol-5-yl)phenyl)ethyl)pyrrolidine-2-carboxamide (Compound 2.043)

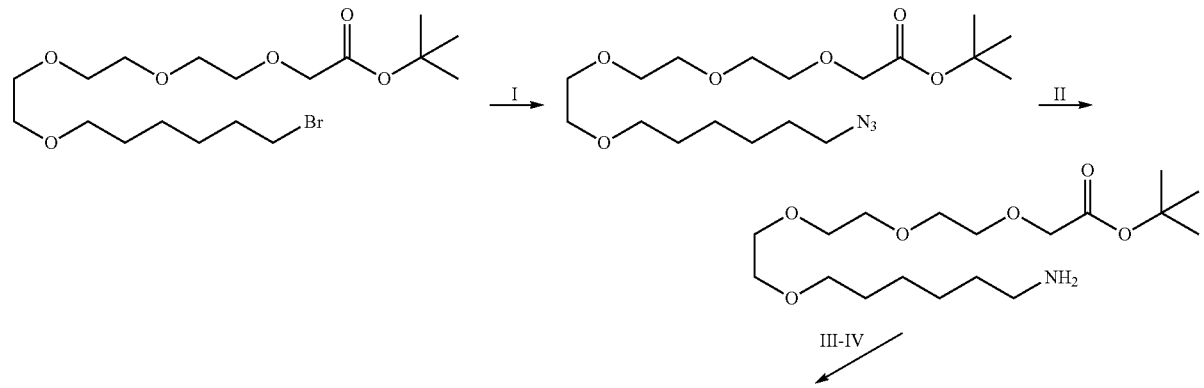

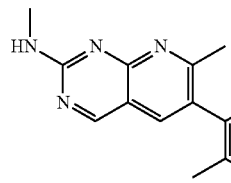
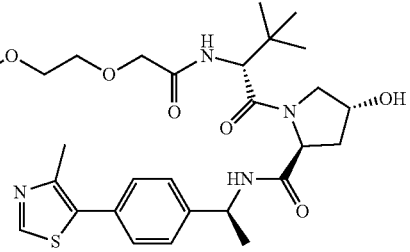

Step I, of tert-butyl 18-azido-3,6,9,12-tetraoxaoctadecan-1-oate

To a cold (0° C.) stirred solution of tert-butyl 18-bromo-3,6,9,12-tetraoxaoctadecan-1-oate (305 mg, 0.713 mmol) in DMF (3.0 mL) was added sodium azide (97.1 mg, 1.49 mmol) and potassium iodide (122 mg, 0.735 mmol). The reaction mixture was allowed to warm up to rt and stirred for 4 h. The reaction mixture was diluted with water (15 mL) and extracted with Et$_2$O (3×15 mL). The combined organic layers were dried over Na$_2$SO$_4$, filtered, and concentrated. The residue was purified on 25 g SiO$_2$ cartridge using a gradient of EtOAc in hexanes (0 to 100%) as eluant to afford the title compound (181.6. mg, 65.4%) as a colorless oil. Rf=0.42 (50% EtOAc in hexanes). $^1$H NMR (400 MHz, acetone) δ 3.99 (s, 2H), 3.67-3.60 (m, 4H), 3.58 (s, 4H), 3.57-3.50 (m, 4H), 3.44 (t, J=6.4 Hz, 2H), 3.33 (t, J=6.9 Hz, 2H), 1.63-1.53 (m, 4H), 1.46 (s, 9H), 1.42-1.37 (m, 4H).

Step II, tert-butyl 18-amino-3,6,9,12-tetraoxaoctadecan-1-oate

To a solution of tert-butyl 18-azido-3,6,9,12-tetraoxaoctadecan-1-oate (181.6 mg, 0.466 mmol) in EtOH (4.5 mL) and small amount of EtOAc was added 10% palladium on charcoal (208 mg) under argon atmosphere. The resulting suspension was stirred at rt for 6 h under hydrogen atmosphere. The reaction mixture was purged with argon then filtered on a pad of Celite. The filtrate was concentrated and purified on 25 g SiO$_2$ cartridge using a gradient of EtOAc in hexanes (0 to 20%) as eluant to afford the title compound (149.5 mg, 88.2% yield) as a pale yellow oil. Rf=0.69 (15% EtOAc in hexanes). $^1$H NMR (400 MHz, DMSO) δ 3.98 (s, 2H), 3.58-3.55 (m, 2H), 3.54-3.52 (m, 2H), 3.50-3.34 (m, 8H), 1.57-1.46 (m, 4H), 1.42 (s, 9H), 1.40-1.30 (m, 2H), 1.28-1.22 (m, 4H), 1.05 (t, J=7.0 Hz, 2H).

Step III, tert-butyl 1-((2-fluoro-4-methyl-5-(7-methyl-2-(methylamino)pyrido[2,3-d]pyrimidin-6-yl)phenyl)amino)-1-oxo-9,12,15,18-tetraoxa-2-azaicosan-20-oate The title compound (50 mg, 21%) was prepared as described in Step I of Compound 2.041. Rf=0.13 (5% MeOH in DCM). $^1$H NMR (400 MHz, Acetone-D6) d 9.05 (s, 1H), 8.16 (d, J=8.5 Hz, 1H), 7.87 (s, 1H), 7.74 (s, 1H), 7.09 (d, J=12.4 Hz, 1H), 6.76 (bs, 1H), 6.20 (t, J=6.0 Hz, 1H), 3.98 (s, 2H), 3.76 (s, 3H), 3.66-3.58 (m, 4H), 3.57 (s, 3H), 3.56-3.48 (m, 4H), 3.42 (t, J=6.5 Hz, 2H), 3.23-3.15 (m, 2H), 3.08 (d, J=4.6 Hz, 2H), 2.38 (s, 3H), 1.55-1.49 (m, 4H), 1.45 (s, 9H), 1.38-1.35 (m, 4H), 1.29 (s, 2H). LRMS (m/z) calculated, 687.39; found, 687.50 (M+H)$^+$.

Step IV, (2S,4R)-1-((R)-22-(tert-butyl)-1-((2-fluoro-4-methyl-5-(7-methyl-2-(methylamino)pyrido[2,3-d]pyrimidin-6-yl)phenyl)amino)-1,20-dioxo-9,12,15,18-tetraoxa-2,21-diazatricosan-23-oyl)-4-hydroxy-N—((S)-1-(4-(4-methylthiazol-5-yl)phenyl)ethyl) pyrrolidine-2-carboxamide The title compound (8.5 mg, 23.5%) was prepared from tert-butyl 1-((2-fluoro-4-methyl-5-(7-methyl-2-(methylamino)pyrido[2,3-d]pyrimidin-6-yl)phenyl)amino)-1-oxo-9,12,15,18-tetraoxa-2-azaicosan-20-oate as described in Step II-III of Compound 2.041. Rf=0.29 (10% MeOH in DCM). $^1$H NMR (400 MHz, CD$_3$OD) δ 9.01 (bs, 1H), 8.86 (s, 1H), 8.60-8.55 (m, 1H), 7.89 (d, J=5.6 Hz, 1H), 7.81 (d, J=8.2 Hz, 1H), 7.44-7.34 (m, 5H), 7.08 (d, J=12.4 Hz, 1H), 6.52-6.44 (m, 1H), 4.99 (d, J=6.9 Hz, 1H), 4.59-4.51 (m, 1H), 4.03 (d, J=4.0 Hz, 2H), 3.68 (s, 3H), 3.64 (s, 4H), 3.62-3.59 (m, 2H), 3.56 (d, J=5.5 Hz, 2H), 3.46 (t, J=6.5 Hz, 2H), 3.17 (t, J=6.9 Hz, 2H), 3.06 (s, 3H), 2.46 (s, 3H), 2.39 (s, 3H), 2.22-2.16 (m, 1H), 2.01 (s, 3H), 1.97-1.91 (m, 2H), 1.61-1.53 (m, 4H), 1.49 (d, J=7.0 Hz, 3H), 1.39-1.35 (m, 5H), 1.33-1.26 (m, 6H), 1.03 (s, 9H), 0.91-0.84 (m, 2H). LRMS (m/z) calculated, 1056.53; found, 1057.65 (M+H)$^+$. HPLC, $t_R$=12.0 min (purity: 99%).

Example 94—Synthesis of N-(5-chloro-4-(trifluoromethyl)pyridin-2-yl)-2-(1-(5-chloro-6-(((1-(6-((2-(2,6-dioxopiperidin-3-yl)-1,3-dioxoisoindolin-4-yl)amino)-6-oxohexyl)-H-1,2,3-triazol-4-yl)methyl)amino)pyrimidine-4-carboxamido)ethyl)thiazole-5-carboxamide (Compound 2.044)

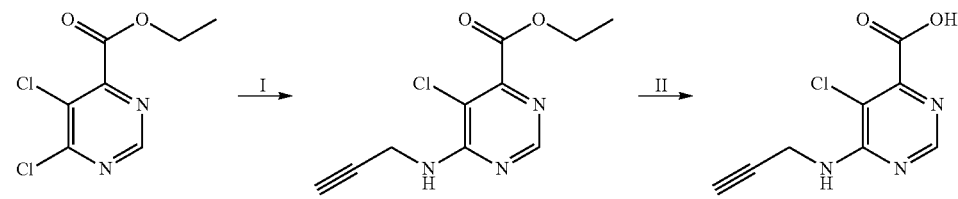

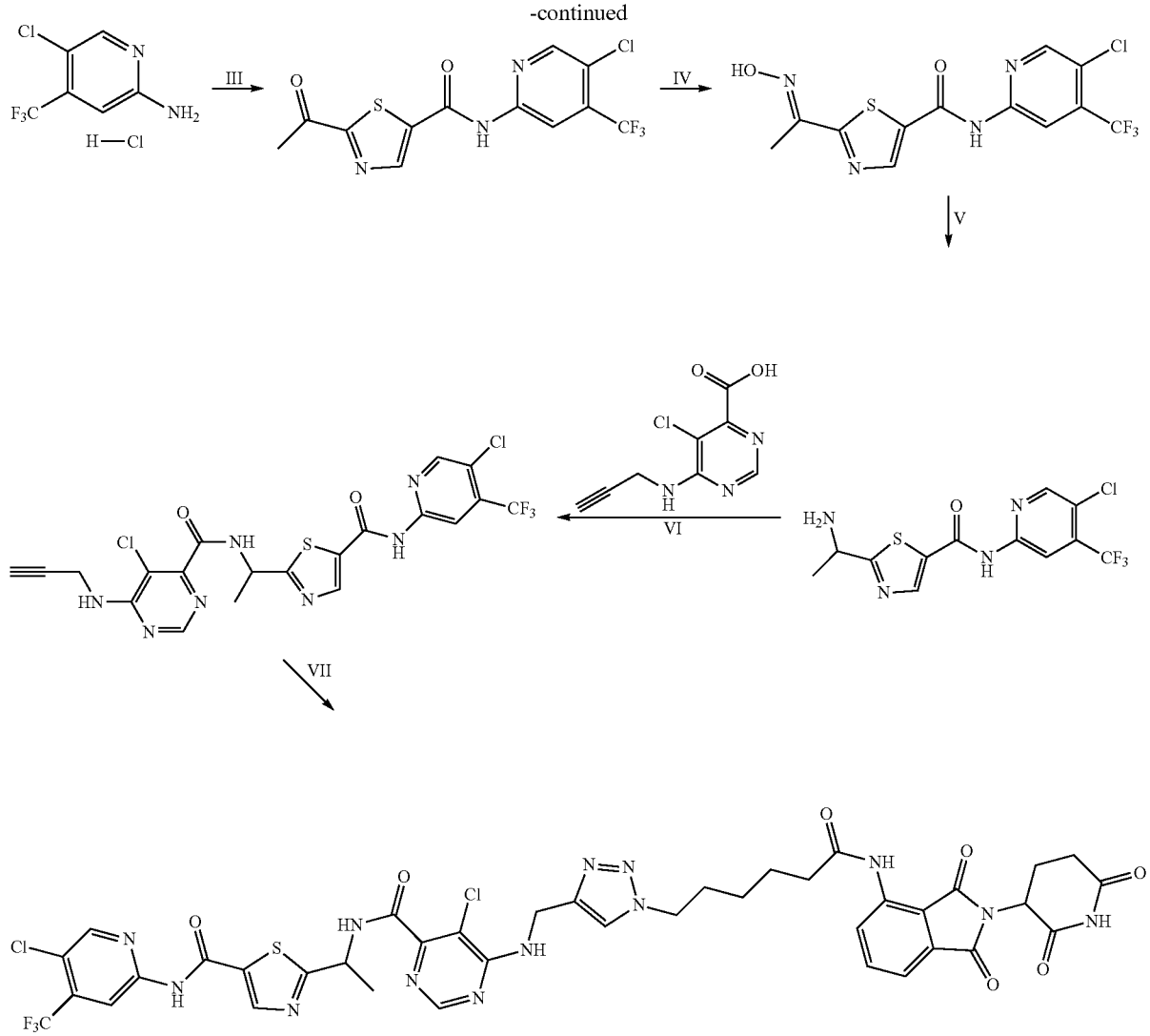

Step I, Synthesis of ethyl 5-chloro-6-(prop-2-yn-1-ylamino)pyrimidine-4-carboxylate To a stirred solution of ethyl 5,6-dichloropyrimidine-4-carboxylate (150 mg, 0.645 mmol, 95% w/w purity) in DCM (900 uL) was added propargylamine (40 uL, 0.62 mmol) and DIPEA (220 uL, 1.28 mmol). The resulting mixture was stirred at rt for 18 h. The reaction mixture was diluted with DCM and was washed twice with aq. 1N HCl, brine. The organic layer was dried over $MgSO_4$, and concentrated. The residue was taken up in a bit of DCM and was purified by flash chromatography on silica gel using a gradient of ethyl acetate in hexanes (0-50%) to afford the title compound (124 mg, 80%). $^1$H NMR (600 MHz, $CDCl_3$) δ 8.56 (s, 1H), 5.92 (s, 1H), 4.44 (q, J=7.1 Hz, 2H), 4.33 (dd, J=5.1, 2.3 Hz, 2H), 2.28 (t, J=2.1 Hz, 1H), 1.40 (t, J=7.1 Hz, 3H). LRMS (m/z) calculated, 239.046; found, 239.6 (M+H)$^+$.

Step II, Synthesis of 5-chloro-6-(prop-2-yn-1-ylamino)pyrimidine-4-carboxylic Acid An aqueous solution of 1N NaOH (1.0 mL, 1.0 mmol) was added to a stirred solution of ethyl 5-chloro-6-(prop-2-yn-1-ylamino)pyrimidine-4-carboxylate (124 mg, 0.517 mmol) in THF (2.5 mL). The mixture was stirred at rt for 18 h before being cooled to 0° C. with ice-water bath. The mixture was acidified with aq. 1N HCl (1.0 mL) and was stirred for 10 min at 0° C. The mixture was diluted with EtOAc and water. The phases were separated and the aqueous layer was extracted 5 times with EtOAc. The combined organic extracts were dried over sodium sulfate, and concentrated to afford the desired product (96 mg, 88%) as a solid. $^1$H NMR (600 MHz, Acetone-D6) δ 8.85 (s, 1H), 8.52 (s, 1H), 7.50 (s, 1H), 4.37 (dd, J=5.6, 2.2 Hz, 2H), 2.64 (t, J=2.2 Hz, 1H). LRMS (m/z) calculated, 211.015; found, 211.5 (M+H)$^+$.

Step III, Synthesis of 2-acetyl-N-(5-chloro-4-(trifluoromethyl)pyridin-2-yl)thiazole-5-carboxamide To a stirred mixture of 2-acetylthiazole-5-carboxylic acid (1.64 g, 9.10 mmols) in DME (3.0 mL) was added catalytic amount of DMF (3.2 uL, 0.041 mmol, one drop) under argon atmosphere. To this was added oxalyl chloride (759 uL, 8.84 mmol) in dropwise at rt over a period of 15 min, and stirred for 3 h. The resultant acid chloride was added over 10 min to a cold (5° C.) stirred mixture of 5-chloro-4-(trifluoromethyl)pyridin-2-amine hydrochloride (2.00 g, 8.58 mmol) in acetonitrile (6.0 mL) and pyridine (2.08 mL, 25.7 mmol), slowly warmed up to rt, stirred for 20 h. Water and EtOAc were added and the phases were separated. The aqueous layer was extracted twice with EtOAc. The combined organic extracts were washed with brine, dried over sodium sulfate, and concentrated. The residue was absorbed on the Celite® using 5:1 mixture of DCM:MeOH, purified by flash chromatography on silica gel cartridge using a gradient of EtOAc in DCM (0-100%) to afford white solid, which was washed with water (3×50 mL), and dried under vacuum to afford the title compound. (2.44 g, 73%, 90% estimated purity) as a white solid. $^1$H NMR (600 MHz, MeOD) δ 8.77 (s, 1H), 8.69 (s, 1H), 8.65 (s, 1H), 2.77 (s, 3H). LRMS (m/z) calculated, 348.99; found 350.5 (M+H)$^+$.

Step IV, Synthesis of (E)-N-(5-chloro-4-(trifluoromethyl)pyridin-2-yl)-2-(1-(hydroxyimino)ethyl)thiazole-5-carboxamide A mixture of 2-acetyl-N-(5-chloro-4-(trifluoromethyl)pyridin-2-yl)thiazole-5-carboxamide (700 mg, 1.80 mmol, 90% w/w purity) in DME (4.0 mL), acetonitrile (8.0 mL) and water (1.0 mL) was heated at 60° C. for 20 min, hydroxylamine hydrochloride (400 mg, 5.76 mmol) was added. The resultant mixture was heated at 60° C. for 5 h, cooled to rt, and the solvent was evaporated. The resulting slurry was suspended in mixture of water and ACN (3:1, 10 mL), and filtered off the solids. The solids were rinsed with ACN (3:1, 10 mL), 10 mL of water, and dried under vacuum to afford the title compound (688 mg, 99%) as a beige solid. $^1$H NMR (600 MHz, DMSO) δ 12.20 (s, 1H), 11.78 (s, 1H), 8.85 (s, 1H), 8.78 (s, 1H), 8.58 (s, 1H), 2.25 (s, 3H). LRMS (m/z) calculated, 364.001; found 365.6 (M+H)$^+$.

Step V, Synthesis of 2-(1-aminoethyl)-N-(5-chloro-4-(trifluoromethyl)pyridin-2-yl)thiazole-5-carboxamide A mixture of (E)-N-(5-chloro-4-(trifluoromethyl)pyridin-2-yl)-2-(1-(hydroxyimino)ethyl)thiazole-5-carboxamide (269 mg, 0.738 mmol), Zinc dust (75.3 mg, 1.15 mmol) in water (700 uL) and n-BuOH (1.0 mL) was stirred vigorously, cooled to 0-5° C. To the cold mixture was added acetic acid (177 uL, 3.10 mmol) dropwise at the same temperature, and then slowly warmed up to rt, stirred for 3 h. The mixture was cooled to ~5° C. and aq. NH$_4$OH solution (177 uL, 2.71 mmol, 29% NH$_3$ basis) was added dropwise while maintaining the reaction below 5° C. The mixture was warmed up to rt, water and EtOAc were added and the phases were separated (emulsions observed). A bit of brine was added to facilitate the separation. The aqueous layer was removed and the organic phase was washed with brine, concentrated on rotavap until the solids were crashed out at the bottom of the flask (so not to dryness). The resultant solids were filtered, and dried under vacuum overnight to afford the title compound (350 mg, 95% yield, about 70% w/w purity) as beige solid. $^1$H NMR (600 MHz, DMSO) δ 12.16 (s, 1H), 11.61 (s, 1H), 9.03-8.27 (m, 4H), 4.27-4.16 (m, 1H), 1.40 (d, J=6.4 Hz, 3H). LRMS (m/z) calculated, 350.022; found, 351.4 (M+H)$^+$.

Step VI, Synthesis of N-(5-chloro-4-(trifluoromethyl)pyridin-2-yl)-2-(1-(5-chloro-6-(prop-2-yn-1-ylamino)pyrimidine-4-carboxamido)ethyl)thiazole-5-carboxamide To a stirred solution of 2-(1-aminoethyl)-N-(5-chloro-4-(trifluoromethyl)pyridin-2-yl)thiazole-5-carboxamide (207 mg, 0.413 mmol, about 70% w/w purity) in DMF (2.5 mL) were added 5-chloro-6-(prop-2-yn-1-ylamino)pyrimidine-4-carboxylic acid (96.2 mg, 0.454 mmol), HATU (188 mg, 0.496 mmol) and DIPEA (356 uL, 2.07 mmol). The reaction mixture was stirred at rt for 2 h, diluted with EtOAc and water. The phases were separated and the aqueous layer was extracted three times with EtOAc. The combined extracts were dried over sodium sulfate, filtered and concentrated. The residue was purified by flash chromatography on silica gel using a gradient of EtOAc in (0-100%) to afford the compound (100 mg, 45%) as a solid. $^1$H NMR (600 MHz, CDCl$_3$) δ 8.65 (s, 1H), 8.63-8.59 (m, 2H), 8.50 (s, 1H), 8.38 (s, 1H), 8.29 (s, 1H), 6.12 (t, J=5.0 Hz, 1H), 5.58-5.49 (m, 1H), 4.39-4.30 (m, 2H), 2.29 (t, J=2.2 Hz, 1H), 1.76 (d, J=7.0 Hz, 3H). LRMS (m/z) calculated, 543.026; found, 545.8 (M+H)$^+$.

Step VII, Synthesis of N-(5-chloro-4-(trifluoromethyl)pyridin-2-yl)-2-(1-(5-chloro-6-(((1-(6-((2-(2,6-dioxopiperidin-3-yl)-1,3-dioxoisoindolin-4-yl)amino)-6-oxohexyl)-1H-1,2,3-triazol-4-yl)methyl)amino)pyrimidine-4-carboxamido)ethyl)thiazole-5-carboxamide To a stirred mixture of N-(5-chloro-4-(trifluoromethyl)pyridin-2-yl)-2-(1-(5-chloro-6-(prop-2-yn-1-ylamino)pyrimidine-4-carboxamido)ethyl)thiazole-5-carboxamide (100 mg, 0.184 mmol) in THF (2.0 mL) and water (200 uL) was added 6-azido-N-(2-(2,6-dioxopiperidin-3-yl)-1,3-dioxoisoindolin-4-yl)hexanamide (76.9 mg, 0.186 mmol), sodium ascorbate (7.28 mg, 36.7 umol) and copper(II) sulfate pentahydrate (9.17 mg, 36.7 umol) under Argon atmosphere. The resultant mixture was sonicated for about three min and the mixture was vigorously stirred at rt for 2 h (completion observed by TLC), diluted with EtOAc. The reaction mixture was cooled to 0-5° C. and filtered off under reduced pressure. The resultant filtrate was concentrated, dissolved in DCM-MeOH, absorbed on the Celite® and purified by flash chromatography on silica gel cartridge using a gradient of MeOH in DCM to afford the desired product along with an unidentified impurity by $^1$H NMR. The product is further purified on silica gel cartridge (Isco gold) using a gradient of methanol in EtOAc (0 to 20%), followed by lyophilization to afford the title compound (85 mg, 48%) as a white solid. $^1$H NMR (600 MHz, CDCl$_3$) δ 9.38 (d, J=4.6 Hz, 1H), 9.25 (d, J=15.3 Hz, 1H), 8.88 (d, J=17.9 Hz, 1H), 8.78 (d, J=8.3 Hz, 1H), 8.66 (s, 1H), 8.57 (t, J=8.5 Hz, 1H), 8.49 (s, 1H), 8.45 (s, 1H), 8.31 (d, J=7.2 Hz, 1H), 7.72 (t, J=7.6 Hz, 1H), 7.59-7.51 (m, 2H), 6.57 (s, 1H), 5.56-5.46 (m, 1H), 5.01-4.93 (m, 1H), 4.89 (dd, J=15.2, 3.2 Hz, 1H), 4.76 (dd, J=15.0, 2.7 Hz, 1H), 4.41-4.30 (m, 2H), 2.93 (d, J=13.5 Hz, 1H), 2.85-2.71 (m, 2H), 2.49-2.39 (m, 2H), 2.18 (s, 1H), 2.02-1.89 (m, 2H), 1.82-1.69 (m, 5H), 1.44-1.36 (m, 2H). LRMS (m/z) calculated, 955.175; found, 979.527 (M+Na)$^+$. HPLC, $t_R$=11.0 min (purity: 97%).

Example 95 to Example 97 describes the synthesis of Compounds 2.045 to 2.047, each of these conjugates link PF-04880594 and VHL Ligand.

Example 95—Synthesis of (2S,4R)-1-((R)-2-(tert-butyl)-21-(4-(2-((2-cyanoethyl)amino)pyrimidin-4-yl)-3-(1H-pyrrolo[2,3-b]pyridin-5-yl)-H-pyrazol-1-yl)-4-oxo-6,9,12,15-tetraoxa-3-azahenicosan-1-oyl)-4-hydroxy-N—((S)-1-(4-(4-methylthiazol-5-yl)phenyl)ethyl)pyrrolidine-2-carboxamide (Compound 2.045)
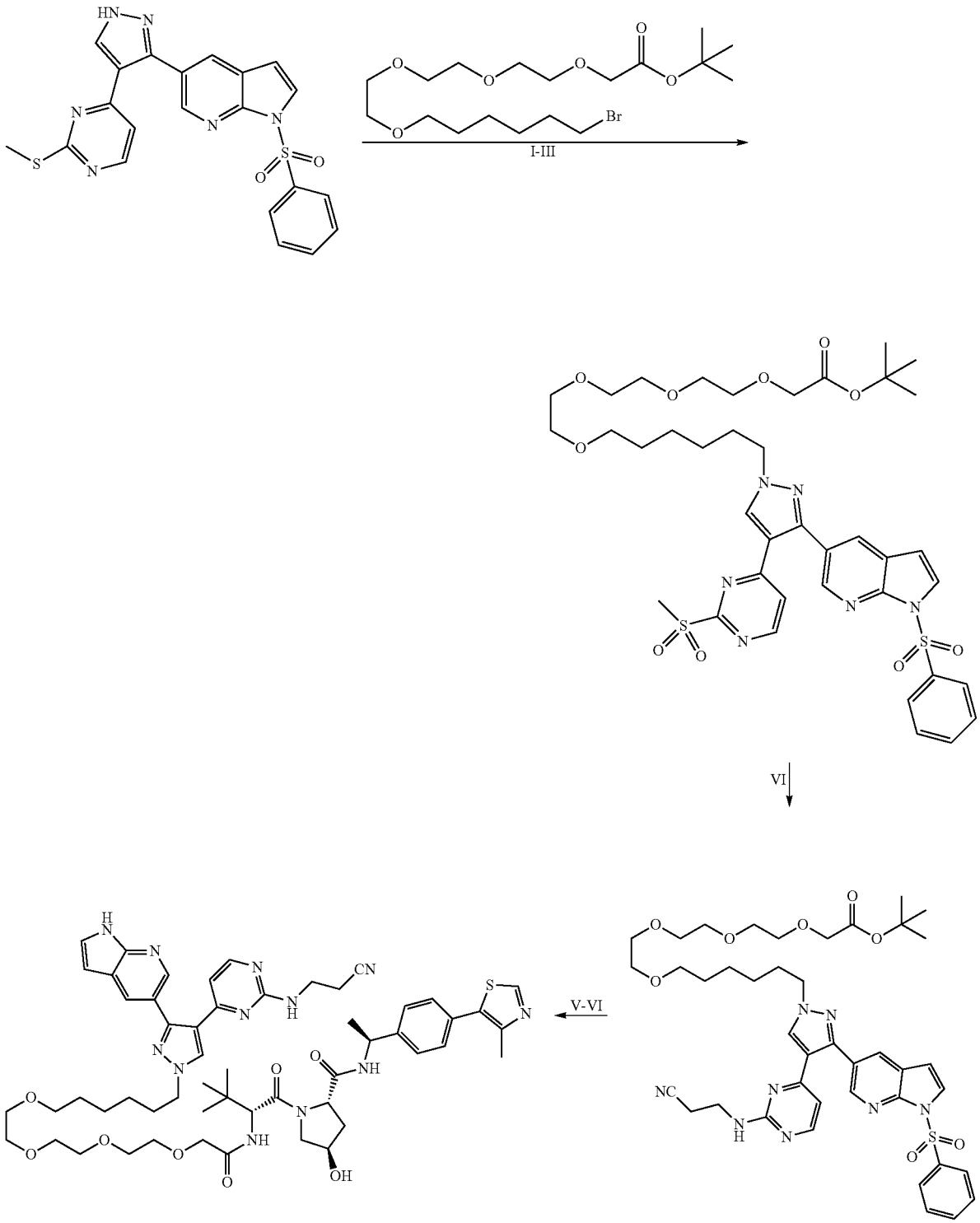

Step I, tert-butyl 18-iodo-3,6,9,12-tetraoxaoctadecan-1-oate

To a solution of the tert-butyl 18-bromo-3,6,9,12-tetraoxaoctadecan-1-oate (360 mg, 0.842 mmol) in acetone (3.0 mL, stored over molecular sieves) was added sodium iodide (253 mg, 1.68 mmol), heated in a sealed vial at 70° C. for 1 h, cooled to rt, filtered through a pad of Celite®, washed with acetone, filtrate was concentrated, dried. The residue was suspended in DCM and ether, filtered through a 0.45μ filter, filtrate was concentrated to afford the title compound (400 mg, quant.) as yellow oil. This material was used as such in the next step. $^1$H NMR (400 MHz, CDCl$_3$) δ 4.11 (s, 2H), 3.78-3.62 (m, 14H), 3.19 (dd, J=8.8, 5.0 Hz, 2H), 1.88-1.77 (m, 2H), 1.74-1.65 (m, 4H), 1.49 (s, 9H), 1.47-1.29 (m, 4H).

Step II, tert-butyl 18-(4-(2-(methylthio)pyrimidin-4-yl)-3-(1-(phenylsulfonyl)-1H-pyrrolo[2,3-b]pyridin-5-yl)-1H-pyrazol-1-yl)-3,6,9,12-tetraoxaoctadecan-1-oate To an ice-cold stirred solution of 5-(4-(2-(methylthio)pyrimidin-4-yl)-1H-pyrazol-5-yl)-1-(phenylsulfonyl)-1H-pyrrolo[2,3-b]pyridine (200 mg, 0.446 mmol) (prepared according to the similar procedures described in WO2009/16460) in DMF was added sodium hydride (30.3 mg, 0.758 mmol, 60% in oil) in one portion, stirred at the same temperature for 35 min, a solution of the tert-butyl 18-iodo-3,6,9,12-tetraoxaoctadecan-1-oate (254 mg, 0.535 mmol) in DMF (0.5 mL) was added, slowly warmed up to rt during 6 h, it was quenched with aq NH$_4$Cl solution, extracted with ethyl acetate (3×15 mL), combined extracts were washed with brine, concentrated. The residue was dissolved in methylene chloride, absorbed on the Celite®, purified on 40 g SiO$_2$ cartridge using a gradient of methanol in methylene chloride (0 to 15%) to afford the title compound (110 mg, 31%) and 67 mg of slightly impure compound which was repurified to afford an additional product (26 mg, 7.6%) as light yellow oil. $^1$H NMR (400 MHz, CDCl$_3$) δ 8.56 (d, J=1.9 Hz, 1H), 8.26 (d, J=5.3 Hz, 1H), 8.19 (d, J=8.1 Hz, 2H), 8.06 (s, 1H), 8.01 (d, J=2.0 Hz, 1H), 7.77 (d, J=4.0 Hz, 1H), 7.58 (t, J=7.5 Hz, 1H), 7.48 (t, J=7.7 Hz, 2H), 6.71 (d, J=5.3 Hz, 1H), 6.62 (d, J=4.0 Hz, 1H), 4.17 (t, J=7.2 Hz, 2H), 4.01 (s, 2H), 3.74-3.54 (m, 12H), 3.44 (t, J=6.5 Hz, 2H), 2.26 (s, 3H), 1.99-1.90 (m, 2H), 1.70-1.54 (m, 2H), 1.47 (s, 9H), 1.42-1.36 (m, 4H). Rf=0.25 (EtOAc). LRMS (m/z) calculated, 794.99; found, 817.36 (M+Na)$^+$.

Step III, tert-butyl 18-(4-(2-(methylsulfonyl)pyrimidin-4-yl)-3-(1-(phenylsulfonyl)-1H-pyrrolo[2,3-b]pyridin-5-yl)-1H-pyrazol-1-yl)-3,6,9,12-tetraoxaoctadecan-1-oate To a stirred solution of tert-butyl 18-(4-(2-(methylthio)pyrimidin-4-yl)-3-(1-(phenylsulfonyl)-1H-pyrrolo[2,3-b]pyridin-5-yl)-1H-pyrazol-1-yl)-3,6,9,12-tetraoxaoctadecan-1-oate (110 mg, 0.138 mmol) in THF-Water (1:1, 400 uL) was added oxone (128 mg, 3 eq) in one portion, stirred at rt for 16 h, TLC and mass showed the presence of mono and disulfoxide, additional amount of oxone (42 mg), THF/Water (1:1, 1 mL) was added, stirred for 6 h, the solvent was removed on rotavap, diluted with water, extracted with methylene chloride (3×10 mL), combined extracts were passed through a phase separator, concentrated, absorbed on the Celite®, purified on 25 g SiO$_2$ column using a gradient of methanol in methylene chloride (0 to 20%) to afford the title compound (74 mg, 64.7%) as gum. $^1$H NMR (400 MHz, CDCl$_3$) δ 8.59-8.53 (m, 2H), 8.26 (s, 1H), 8.22-8.17 (m, 2H), 8.07 (d, J=2.0 Hz, 1H), 7.81 (d, J=4.0 Hz, 1H), 7.61 (t, J=7.5 Hz, 1H), 7.50 (t, J=7.8 Hz, 2H), 7.22 (d, J=5.4 Hz, 1H), 6.66 (d, J=4.0 Hz, 1H), 4.20 (t, J=7.2 Hz, 2H), 4.02 (s, 2H), 3.74-3.53 (m, 14H), 3.45 (t, J=6.5 Hz, 2H), 3.10 (s, 3H), 2.01-1.91 (m, 2H), 1.64-1.55 (m, 2H), 1.47 (s, 9H), 1.44-1.33 (m, 4H). LRMS (m/z) calculated, 826.98; found, 849.36 (M+Na)$^+$.

Step IV, tert-butyl 18-(4-(2-((2-cyanoethyl)amino)pyrimidin-4-yl)-3-(1-(phenylsulfonyl)-1H-pyrrolo[2,3-b]pyridin-5-yl)-1H-pyrazol-1-yl)-3,6,9,12-tetraoxaoctadecan-1-oate A solution of tert-butyl 18-(4-(2-(methylsulfonyl)pyrimidin-4-yl)-3-(1-(phenylsulfonyl)-1H-pyrrolo[2,3-b]pyridin-5-yl)-1H-pyrazol-1-yl)-3,6,9,12-tetraoxaoctadecan-1-oate (74 mg, 0.0895 mmol) in 3-aminopropionitrile (1.57 mL) was heated at 80° C. in a sealed tube for 23 h. The resultant dark yellow solid was cooled to rt, dissolved in water and ethyl acetate, aqueous solution was extracted with ethyl acetate (3×20 mL), combined extracts were washed with water, brine, dried over Na$_2$SO$_4$, and concentrated. The residue was purified on 25 g SiO$_2$ cartridge using a gradient of methanol in methylene chloride (0 to 30%, 20 CV) as eluant to afford the title compound (35 mg, 48%) as an oil. $^1$H NMR (400 MHz, CDCl3) δ 8.59 (d, J=2.0 Hz, 1H), 8.21-8.16 (m, 2H), 8.10 (d, J=5.2 Hz, 1H), 8.02 (d, J=2.0 Hz, 1H), 7.96 (s, 1H), 7.77 (d, J=4.0 Hz, 1H), 7.59 (t, J=7.5 Hz, 1H), 7.48 (t, J=7.7 Hz, 2H), 6.63 (d, J=4.0 Hz, 1H), 6.47 (d, J=5.2 Hz, 1H), 5.41 (t, J=6.4 Hz, 1H), 4.17 (t, J=7.2 Hz, 2H), 4.02 (s, 2H), 3.76-3.40 (m, 18H), 2.01-1.89 (m, 2H), 1.64-1.54 (m, 3H), 1.47 (s, 9H), 1.43-1.35 (m, 4H). Rf=0.15 (5% MeOH in DCM). LRMS (m/z) calculated, 816.98; found, 839.36 (M+Na)$^+$.

Step V, 18-(4-(2-((2-cyanoethyl)amino)pyrimidin-4-yl)-3-(1H-pyrrolo[2,3-b]pyridin-5-yl)-1H-pyrazol-1-yl)-3,6,9,12-tetraoxaoctadecan-1-oic Acid A solution of NaOH in methanol (1.66 mg in 166 μL; Conc. 10 mg/mL) was added to cold (0° C.) tert-butyl 18-(4-(2-((2-cyanoethyl)amino)pyrimidin-4-yl)-3-(1-(phenylsulfonyl)-1H-pyrrolo[2,3-b]pyridin-5-yl)-1Hpyrazol-1-yl)-3,6,9,12-tetraoxaoctadecan-1-oate (17 mg, 0.021 mmol), cooling bath was removed after 15 min, stirred for 2 h (TLC revealed the formation of the slightly more polar compound and the baseline compound), aq. 1M NaOH solution (0.2 mL) was added, stirred for an additional 1.5 h, TLC revealed formation of the more polar compound (baseline), acidified with aq 1 N HCl (0.25 mL), and concentrated. The residue was dissolved in ~10% MeOH in DCM, filtered off solids (NaCl), concentrated to afford the title compound (18 mg, >quant.) as a white solid which contains phenylsulfonic acid. This material was used as such in the next step without further purification. Rf=0.35 (30% MeOH in DCM). LRMS (m/z) calculated, 620.26; found, 621.26 (M+H)+; 643.32 (M+Na)$^+$.

Step VI, (2S,4R)-1-((R)-2-(tert-butyl)-21-(4-(2-((2-cyanoethyl)amino)pyrimidin-4-yl)-3-(1H-pyrrolo[2,3-b]pyridin-5-yl)-1H-pyrazol-1-yl)-4-oxo-6,9,12,15-tetraoxa-3-azaheni-cosan-1-oyl)-4-hydroxy-N—((S)-1-(4-(4-methylthiazol-5-yl)phenyl)ethyl)pyrrolidine-2-carboxamide To a mixture of the crude 18-(4-(2-((2-cyanoethyl)amino)pyrimidin-4-yl)-3-(1H-pyrrolo[2,3-b]pyridin-5-yl)-1H- pyrazol-1-yl)-3,6,9,12-tetraoxaoctadecan-1-oic acid (25.8 mg, 0.0416 mmol) and (2S,4R)-1-((R)-2-amino-3,3-dimethylbutanoyl)-4-hydroxy-N—((S)-1-(4-(4-methylthiazol-5-yl)phenyl)ethyl)pyrrolidine-2-carboxamide (18.5 mg, 0.0416 mmol) and (1-Cyano-2-ethoxy-2-oxoethylidenaminooxy)dimethylaminomorpholino-carbenium hexafluorophosphate (COMU) (53.4 mg, 0.125 mmol) in DMF (1 mL) was added DIPEA (40 µL, 0.229 mmol), reaction mixture was stirred at rt for 7 h, quenched with water (3 mL), extracted with ethyl acetate (5×5 mL), combined extracts were dried, and concentrated. The residue was dissolved in methanol-methylene chloride, absorbed on the Celite®, purified on 25 g SiO$_2$ cartridge using a gradient of methanol in methylene chloride (0 to 50%) as eluant to afford the recovered 18-(4-(2-((2-cyanoethyl)amino)pyrimidin-4-yl)-3-(1H-pyrrolo[2,3-b]pyridin-5-yl)-1H-pyrazol-1-yl)-3,6,9,12-tetraoxaoctadecan-1-oic acid (11.4 mg). Rf=0.35 (10% MeOH in DCM). $^1$H NMR (400 MHz, CD$_3$OD) δ 8.35-8.29 (m, 2H), 8.12 (d, J=2.0 Hz, 1H), 8.08 (d, J=5.3 Hz, 1H), 7.45 (d, J=3.5 Hz, 1H), 6.64 (s, 1H), 6.55 (d, J=3.5 Hz, 1H), 4.25 (t, J=7.0 Hz, 2H), 4.13 (s, 2H), 3.72-3.52 (m, 14H), 3.48 (t, J=6.6 Hz, 2H), 2.42-2.20 (m, 2H), 2.03-1.90 (m, 2H), 1.67-1.55 (m, 2H), 1.51-1.35 (m, 4H). HPLC purity (93%), and the title compound (5.7 mg, 13.1%) as solid. Rf=0.2 (10% MeOH in DCM). $^1$H NMR (400 MHz, CD$_3$OD) δ 8.86 (s, 1H), 8.35-8.28 (m, 2H), 8.12 (d, J=1.8 Hz, 1H), 8.07 (d, J=5.2 Hz, 1H), 7.46-7.34 (m, 5H), 6.63 (s, 1H), 6.54 (d, J=3.5 Hz, 1H), 5.04-4.93 (m, J=7.0 Hz, 1H), 4.67 (s, 1H), 4.60-4.50 (m, 1H), 4.42 (s, 1H), 4.25 (t, J=6.9 Hz, 2H), 4.04 (s, 2H), 3.83 (d, J=11.3 Hz, 1H), 3.73 (dd, J=11.0, 3.6 Hz, 1H), 3.69-3.53 (m, 12H), 3.48 (t, J=6.5 Hz, 2H), 2.47 (d, J=4.9 Hz, 3H), 2.38-2.15 (m, 4H), 1.99-1.93 (m, 2H), 1.65-1.57 (m, 2H), 1.49 (d, J=7.0 Hz, 3H), 1.36 (d, J=49.4 Hz, 6H), 1.02 (s, 9H).

LRMS (m/z) calculated, 1046.61; found, 1047.61 (M+H)+; 1069.68 (M+Na)$^+$. HPLC, t$_R$=10.3 min (purity: 96%).

Example 96—Synthesis of (2S,4R)-1-((R)-2-(tert-butyl)-15-((4-(1-(2,2-difluoroethyl)-3-(1H-pyrrolo[2,3-b]pyridin-5-yl)-1H-pyrazol-4-yl)pyrimidin-2-yl)amino)-4,13-dioxo-6,9-dioxa-3,12-diazapentadecan-1-oyl)-4-hydroxy-N—((S)-1-(4-(4-methylthiazol-5-yl)phenyl)ethyl)pyrrolidine-2-carboxamide (Compound 2.046)

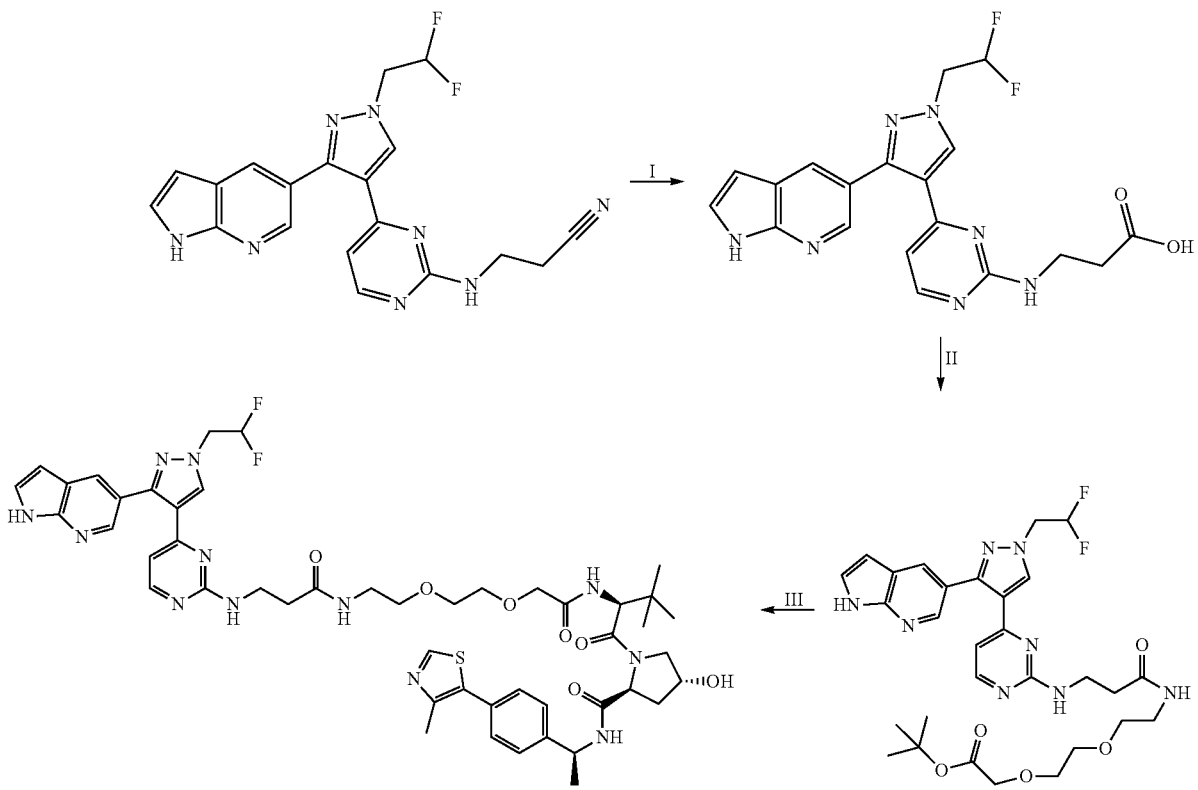

Step I, Synthesis of 3-((4-(1-(2,2-difluoroethyl)-3-(1H-pyrrolo[2,3-b]pyridin-5-yl)-1H-pyrazol-4-yl)pyrimidin-2-yl)amino)propanoic Acid To a solution of commercial 3-((4-(1-(2,2-difluoroethyl)-3-(1H-pyrrolo[2,3-b]pyridin-5-yl)-1H-pyrazol-4-yl)pyrimidin-2-yl)amino)propanenitrile (60.0 mg, 0.152 mmol) in THF (2.0 mL) was added a freshly prepared 5N NaOH aqueous solution (2.0 mL, 10 mmol) at rt. The mixture was heated at 65° C. for 16 h, cooled to 0° C. before being carefully neutralized with aq. 1N HCl, filtered off the solids, washed twice with 1 mL of cold water, dried under reduced pressure to afford the title compound (60 mg, 95%) as a beige solid. LRMS (m/z) calculated, 413.141; found, 414.2 (M+H)$^+$.

Step II, Synthesis of tert-butyl 2-(2-(2-(3-((4-(1-(2,2-difluoroethyl)-3-(1H-pyrrolo[2,3-b]pyridin-5-yl)-1H-pyrazol-4-yl)pyrimidin-2-yl)amino)propanamido)ethoxy)ethoxy)-acetate To a stirred solution of 3-((4-(1-(2,2-difluoroethyl)-3-(1H-pyrrolo[2,3-b]pyridin-5-yl)-1H-pyrazol-4-yl)pyrimidin-2-yl)amino)propanoic acid (60.0 mg, 0.145 mmol) in DMF (2.5 mL) was added [2-(2-amino-ethoxy)-ethoxy]-acetic acid tert-butyl ester (82.7 mg, 0.377 mmol) followed by HATU (75.0 mg, 0.197 mmol) and N-methylmorpholine (100 uL, 0.910 mmol). The mixture was stirred at rt for 20 h, poured into water. The phases were separated. The aqueous layer was extracted twice with EtOAc. The combined organic layers were washed with water, brine, dried over Na$_2$SO$_4$, filtered and concentrated. The residue was purified by flash chromatography on silica gel using a gradient of MeOH in DCM (0-20%) to afford the title compound (60 mg, 67%) which contains an unidentified impurity. This material was used as such in the next step without further purification.

Step III, Synthesis of (2S,4R)-1-((R)-2-(tert-butyl)-15-((4-(1-(2,2-difluoroethyl)-3-(1H-pyrrolo[2,3-b]pyridin-5-yl)-1H-pyrazol-4-yl)pyrimidin-2-yl)amino)-4,13-dioxo-6,9-dioxa-3,12-diazapentadecan-1-oyl)-4-hydroxy-N—((S)-1-(4-(4-methylthiazol-5-yl)phenyl)ethyl)pyrrolidine-2-carboxamide TFA (200 uL, 2.69 mmol) was added dropwise to a stirred solution of tert-butyl 2-(2-(2-(3-((4-(1-(2,2-difluoroethyl)-3-(1H-pyrrolo[2,3-b]pyridin-5-yl)-1H-pyrazol-4-yl)pyrimidin-2-yl)amino)propanamido)ethoxy)ethoxy)acetate (60 mg, 0.098 mmol) in DCM (1.0 mL) at 0° C. The mixture was stirred for 5 min at 0° C. and the ice-bath was removed. The mixture was warmed up to rt, stirred for 2 h, and concentrated under reduced pressure. Traces of the TFA was removed azeotropically few cycles using toluene and dried under high vacuum pump overnight to afford the 2-(2-(2-(3-((4-(1-(2,2-difluoroethyl)-3-(1H-pyrrolo[2,3-b]pyridin-5-yl)-1H-pyrazol-4-yl)pyrimidin-2-yl)amino)propanamido)ethoxy)-ethoxy)acetic acid (60 mg, 88% yield), which was used as such in the next step. To a stirred solution of 2-(2-(2-(3-((4-(1-(2,2-difluoroethyl)-3-(1H-pyrrolo[2,3-b]pyridin-5-yl)-1H-pyrazol-4-yl)pyrimidin-2-yl)amino)propanamido)-ethoxy)ethoxy)acetic acid (37 mg, 0.039 mmol) in DMF (1.0 mL) were added (2S,4R)-1-((R)-2-amino-3,3-dimethylbutanoyl)-4-hydroxy-N—((S)-1-(4-(4-methylthiazol-5-yl)phenyl)ethyl)pyrrolidine-2-carboxamide (25 mg, 0.056 mmol), HATU (60 mg, 0.158 mmol) and DIPEA (100 uL, 0.583 mmol) at rt as described in Compound. 2.045 to afford 4:1 ratio of the title compound (19 mg, 30% yield, 80-90% estimated purity) as a white solid along with a diastereomeric impurity. $^1$H NMR (600 MHz, CDCl3) δ 10.35 (s, 1H), 8.64 (s, 1H), 8.38 (s, 1H), 8.27 (s, 1H), 8.17 (s, 1H), 8.10-8.03 (m, 1H), 8.03-7.87 (m, 2H), 7.76 (d, J=10.2 Hz, 1H), 7.66-7.57 (m, 1H), 7.37-7.28 (m, 5H), 7.18 (t, J=10.1 Hz, 1H), 6.66 (d, J=6.8 Hz, 1H), 6.61-6.32 (m, 2H), 6.18 (t, J=55.4 Hz, 1H), 5.97-5.78 (m, 1H), 5.13 (s, 1H), 4.75 (d, J=9.3 Hz, 1H), 4.64 (s, 1H), 4.55-4.46 (m, 2H), 4.07-3.92 (m, 3H), 3.73-3.45 (m, 10H), 3.25 (s, 1H), 2.45 (s, 3H), 2.23 (s, J=34.9 Hz, 2H), 2.13-2.01 (m, 1H), 1.43 (d, J=4.8 Hz, 3H), 1.06 (s, 9H). LRMS (m/z) calculated, 984.424; found, 991.4 (M+H)$^+$.

Example 97—(2S,4R)-1-((R)-2-(2-(2-(2-((4-(1-(2,2-difluoroethyl)-3-(1H-pyrrolo[2,3-b]pyridin-5-yl)-1H-pyrazol-4-yl)pyrimidin-2-yl)oxy)ethoxy)ethoxy)acetamido)-3,3-dimethylbutanoyl)-4-hydroxy-N—((S)-1-(4-(4-methylthiazol-5-yl)phenyl)ethyl)pyrrolidine-2-carboxamide (Compound 2.047)

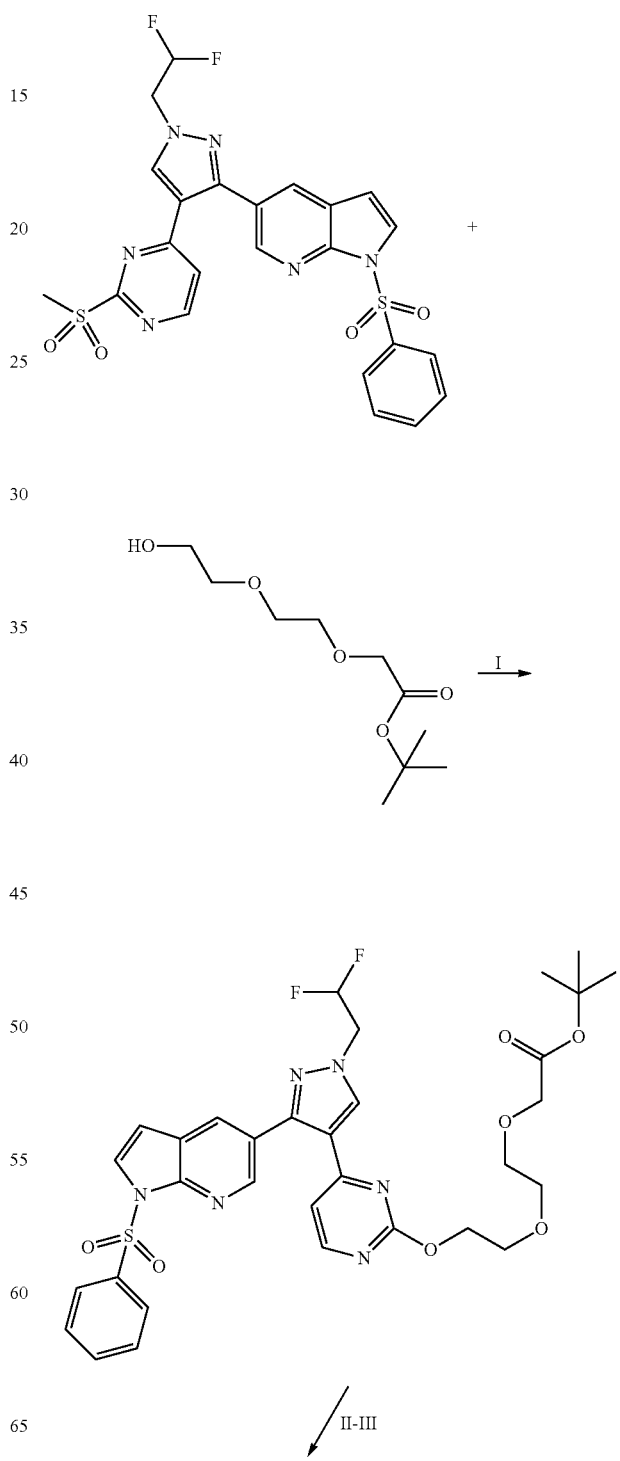

-continued

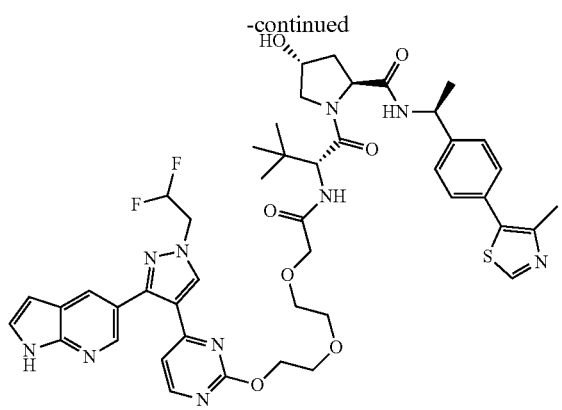

Step I, tert-butyl 2-(2-(2-((4-(1-(2,2-difluoroethyl)-3-(1-(phenylsulfonyl)-1H-pyrrolo[2,3-b]pyridin-5-yl)-1H-pyrazol-4-yl)pyrimidin-2-yl)oxy)ethoxy)ethoxy)acetate In a microwave vial, to a solution of 5-(1-(2,2-difluoroethyl)-4-(2-(methylsulfonyl)pyrimidin-4-yl)-1Hpyrazol-3-yl)-1-(phenylsulfonyl)-1H-pyrrolo[2,3-b]pyridine (20 mg, 0.0367 mmol) (prepared according to the similar procedures described in WO2009/16460) and tert-butyl 2-(2-(2-hydroxyethoxy)ethoxy)acetate (10.1 mg, 0.046 mmol) in DMF (0.3 mL) was added potassium carbonate (5.1 mg, 0.0367 mmol) in one portion, reaction mixture was placed on pre-heated oil bath at 90° C., stirred for 1.5 h (TLC showed ~40% conversion into less polar spot), heated for another 3 h, $^1$H NMR of the aliquot showed ~60% conversion, reaction mixture was diluted with ethyl acetate (5 mL), filtered through 0.4 µmicron filter, and concentrated. The residue was purified on 12 g SiO$_2$ using a gradient of methanol in DCM (0 to 20%) as eluant to afford the title compound (11 mg, 43.7%) as oil. $^1$H NMR (400 MHz, CDCl$_3$) δ 8.57 (d, J=2.0 Hz, 1H), 8.26 (d, J=5.2 Hz, 1H), 8.21-8.17 (m, 3H), 8.02 (d, J=2.0 Hz, 1H), 7.79 (d, J=4.0 Hz, 1H), 7.59 (t, J=7.5 Hz, 1H), 7.49 (t, J=7.7 Hz, 2H), 6.65 (dd, J=9.3, 4.6 Hz, 2H), 6.34-6.00 (m, 1H), 4.53 (td, J=13.4, 4.2 Hz, 2H), 4.44-4.36 (m, 2H), 4.02 (s, 2H), 3.84-3.79 (m, 2H), 3.76-3.70 (m, 4H), 1.47 (s, 9H). LRMS (m/z) calculated, 684.22; found, 685.2 (M+H)$^+$; 707.26 (M+Na)$^+$.

Step II, 2-(2-(2-((4-(1-(2,2-difluoroethyl)-3-(1H-pyrrolo[2,3-b]pyridin-5-yl)-1H-pyrazol-4-yl)pyrimidin-2-yl)oxy)ethoxy)ethoxy)acetic Acid The title compound was prepared as described in Step V of Compound. 2.045, Yield (50%). LRMS (m/z) calculated, 488.16; found, 489.06 (M+H)$^+$.

Step III, (2S,4R)-1-((R)-2-(2-(2-(2-((4-(1-(2,2-difluoroethyl)-3-(1H-pyrrolo[2,3-b]pyridin-5-yl)-1H-pyrazol-4-yl)pyrimidin-2-yl)oxy)ethoxy)ethoxy)acetamido)-3,3-dimethylbutanoyl)-4-hydroxy-N—((S)-1-(4-(4-methylthiazol-5-yl)phenyl)ethyl)pyrrolidine-2-carboxamide The title compound was prepared as described in Step VI of Compound. 2.045, Yield (26.7%). Rf=0.25 (10% MeOH-DCM). LRMS (m/z) calculated, 914.37; found, 915.53 (M+H)$^+$, 937.52 (M+Na)$^+$.

Example 98 and Example 99 describe the synthesis of Compounds 2.048 and 2.049, each of these conjugates are embraced by the following Formula

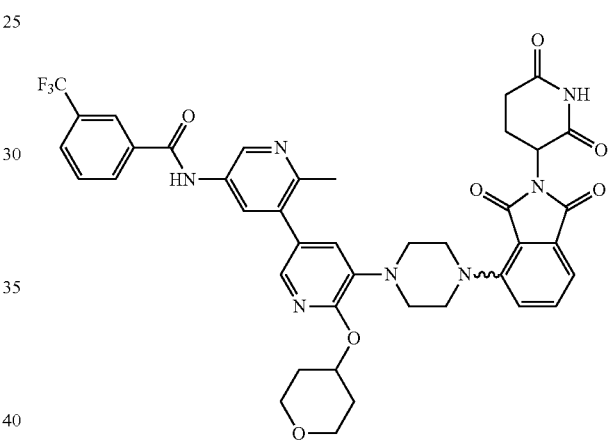

Example 98—Synthesis of N-(5'-(4-(4-(1-(6-((2-(2,6-dioxopiperidin-3-yl)-1,3-dioxoisoindolin-4-yl)amino)-6-oxohexyl)-1H-1,2,3-triazol-4-yl)butyl)piperazin-1-yl)-2-methyl-6'-((tetrahydro-2H-pyran-4-yl)oxy)-[3,3'-bipyridin]-5-yl)-3-(trifluoromethyl)benzamide (Compound 2.048)

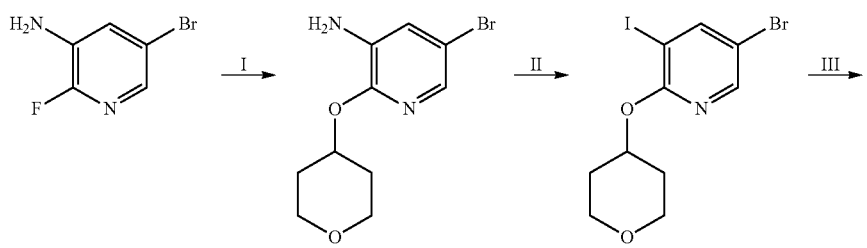

-continued

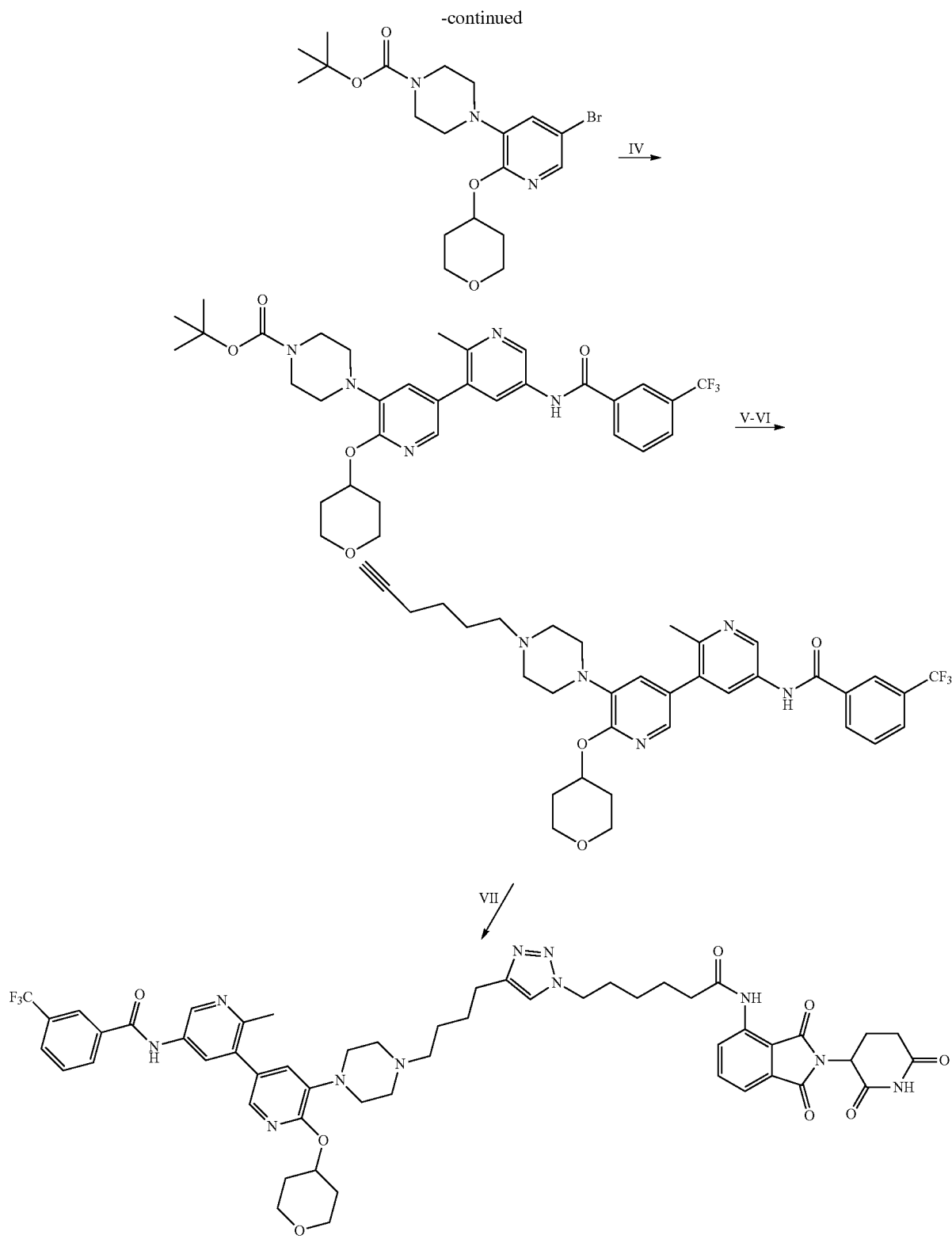

Step I, Synthesis of 5-bromo-2-((tetrahydro-2H-pyran-4-yl)oxy)pyridin-3-amine

Sodium hydride (99.3 mg, 2.48 mmol, 60% w/w in mineral oil) was slurried in DMF (1.5 mL). The slurry was cooled using an ice-water bath and the commercial tetrahydro-4-pyranol (300 uL, 3.14 mmol) was added. After the mixture was stirred for 10 min, the ice bath was removed and 3-amino-5-bromo-2-fluoropyridine (300 mg, 1.57 mmol) was added. The mixture was heated up to 90° C. and was stirred for 2 h. Then, the mixture was cooled down to rt and was poured into water. EtOAc was added and the phases were separated. The aqueous layer was extracted three times with EtOAc and the combined extracts were washed with brine, dried over Na$_2$SO$_4$, filtered and concentrated. The residue was purified by flash chromatography on silica gel using a gradient of EtOAc in hexanes (0-100%) as eluant to afford the title compound (278 mg, 65%) as a dark red residue. $^1$H NMR (600 MHz, CDCl$_3$) δ 7.53 (d, J=2.1 Hz, 1H), 6.98 (d, J=2.1 Hz, 1H), 5.22 (tt, J=8.5, 4.1 Hz, 1H), 3.97 (dt, J=9.4, 4.5 Hz, 2H), 3.81 (s, 2H), 3.64-3.58 (m, 2H), 2.13-2.01 (m, 2H), 1.83-1.74 (m, 2H). LRMS (m/z) calculated, 272.016; found, 274.9 (M+H)$^+$.

Step II, Synthesis of 5-bromo-3-iodo-2-((tetrahydro-2H-pyran-4-yl)oxy)pyridine

To a cold (0° C.) mixture of mixture of conc. HCl (1.3 mL, 42.8 mmol, 37% w/w) and water (1.7 mL) was added to 5-bromo-2-((tetrahydro-2H-pyran-4-yl)oxy)pyridin-3-amine (57 mg, 0.21 mmol). To this was added sodium nitrite (16 mg, 0.23 mmol) in portionwise, after stirred for 30 min, a solution of KI (104 mg, 0.63 mmol) in water (3.0 mL) was added slowly. The mixture was allowed to reach rt and was stirred for 30 min. Then, the mixture was diluted with EtOAc and water was added. The phases were separated and the aqueous layer was extracted twice with EtOAc. The combined organics were washed once with sodium thiosulfate aq. sat., NaHCO$_3$, dried (Na$_2$SO$_4$), and concentrated. The obtained residue was taken up in DCM and purified by flash chromatography on silica gel using a gradient of EtOAc in DCM (0-10%) as eluant to afford the title compound (51 mg, 64%). $^1$H NMR (600 MHz, CDCl$_3$) δ 8.12 (s, 1H), 8.10 (s, 1H), 5.28-5.20 (m, 1H), 4.05-3.95 (m, 2H), 3.72-3.61 (m, 2H), 2.06-2.00 (m, 2H), 1.86-1.78 (m, 2H). LRMS (m/z) calculated, 382.90; found, 384.4 (M+H)$^+$.

Step III, Synthesis of tert-butyl 4-(5-bromo-2-((tetrahydro-2H-pyran-4-yl)oxy)pyridin-3-yl)piperazine-1-carboxylate To a solution of 5-bromo-3-iodo-2-((tetrahydro-2H-pyran-4-yl)oxy)pyridine (780 mg, 2.03 mmol) in toluene (15 mL) was added N-Boc piperazine (416 mg, 2.23 mmol), NaO$^t$Bu (586 mg, 6.09 mmol) and Xantphos (118 mg, 0.203 mmol) and the mixture was degassed with Argon (g) for 2 min. Then, Pd(dba)$_2$ (60.0 mg, 0.104 mmol) was added and the mixture was degassed again with Argon (g) and heated at 90° C. for 50 min (completion observed by TLC). The mixture was cooled to rt and was treated with water and then a saturated aqueous solution of ammonium chloride. EtOAc was added and the phases were separated. The aqueous layer was extracted twice with EtOAc and the combined organic extracts were washed with brine, dried over sodium sulfate, filtered and concentrated. The crude product was purified by flash chromatography on silica gel using a gradient of EtOAc in hexanes (0-100%) as eluant to afford the title compound (852 mg, 95%) as a dark red residue. $^1$H NMR (600 MHz, CDCl$_3$) δ 7.78 (s, 1H), 7.12 (s, 1H), 5.31-5.28 (m, 1H), 3.98-3.89 (m, 2H), 3.69-3.60 (m, 2H), 3.58 (s, 4H), 3.03 (s, 4H), 2.12-2.06 (m, 2H), 1.86-1.76 (m, 2H), 1.49 (s, 9H). LRMS (m/z) calculated, 441.126; found, 443.0 (M+H)$^+$.

Step IV, Synthesis of tert-butyl 4-(2'-methyl-6-((tetrahydro-2H-pyran-4-yl)oxy)-5'-(3-(trifluoromethyl)benzamido)-[3,3'-bipyridin]-5-yl)piperazine-1-carboxylate To a solution of tert-butyl 4-(5-bromo-2-((tetrahydro-2H-pyran-4-yl)oxy)pyridin-3-yl)piperazine-1-carboxylate (200 mg, 0.452 mmol) and N-(6-methyl-5-(4,4,5,5-tetramethyl-1,3,2-dioxaborolan-2-yl)pyridin-3-yl)-3-(trifluoromethyl)benzamide (202 mg, 0.497 mmol) in DME (4.0 mL) was added PdCl$_2$(dppf).CH$_2$Cl$_2$ (20.0 mg, 24.5 umol) and 2M aqueous solution of sodium carbonate (701 μL, 1.40 mmol, 2M). The mixture was degassed with argon for 2 min and was then heated at 90° C. for 90 min before being cooled down to rt. The mixture was diluted with EtOAc and water, followed by a saturated aqueous solution of ammonium chloride. The phases were separated and the aqueous layer was extracted twice with EtOAc. The organic combined extracts were washed with brine, dried (Na$_2$SO$_4$), and concentrated. The residue was purified by flash chromatography on silica gel using a gradient of EtOAc in DCM (0-100%) as eluant to afford the title compound (258 mg, 89%) along with a bit of DMF and EtOAc. $^1$H NMR (600 MHz, CDCl$_3$) δ 8.60 (s, 1H), 8.15 (s, 2H), 8.09 (d, J=7.9 Hz, 1H), 7.90 (s, 1H), 7.85 (d, J=7.6 Hz, 1H), 7.76 (s, 1H), 7.67 (t, J=7.8 Hz, 1H), 7.05 (s, 1H), 5.41 (s, 1H), 4.03-3.94 (m, 2H), 3.70 (t, J=9.5 Hz, 2H), 3.61 (s, 4H), 3.09 (s, 4H), 2.52 (s, J=10.1 Hz, 3H), 2.16 (d, J=10.6 Hz, 2H), 1.92-1.85 (m, 2H), 1.49 (s, 9H). LRMS (m/z) calculated, 641.282; found, 644.8 (M+H)$^+$.

Step V, Synthesis of N-(2-methyl-5'-(piperazin-1-yl)-6'-((tetrahydro-2H-pyran-4-yl)oxy)-[3,3'-bipyridin]-5-yl)-3-(trifluoromethyl)benzamide Trifluoroacetic acid (500 uL, 6.73 mmol) was added to a stirred solution of tert-butyl 4-(2'-methyl-6-((tetrahydro-2H-pyran-4-yl)oxy)-5'-(3-(trifluoromethyl)benzamido)-[3,3'-bipyridin]-5-yl)piperazine-1-carboxylate (258 mg, 0.402 mmol) in DCM (5.0 mL) at rt under argon atmosphere. The mixture was stirred for 3 h before being cooled down to 0° C. The mixture was slowly treated with a saturated aqueous solution of sodium bicarbonate. The ice-bath was removed and the mixture was stirred for 20 min and the phases were separated. The aqueous layer was extracted twice with DCM. The combined organic extracts were washed with brine, dried (Na$_2$SO$_4$), and concentrated to afford the title compound (167 mg, 77%) as a beige solid. $^1$H NMR (600 MHz, CDCl$_3$) δ 8.62 (s, 1H), 8.15 (s, 1H), 8.12 (s, 1H), 8.09 (d, J=7.7 Hz, 1H), 7.89 (s, 1H), 7.85 (d, J=7.5 Hz, 1H), 7.74 (s, 1H), 7.67 (t, J=7.8 Hz, 1H), 7.05 (s, 1H), 5.41 (s, 1H), 4.03-3.96 (m, 2H), 3.70 (t, J=9.4 Hz, 2H), 3.14 (s, 4H), 3.09 (s, 4H), 2.52 (s, 3H), 2.19-2.12 (m, 2H), 1.92-1.86 (m, 2H). LRMS (m/z) calculated, 541.230; found, 544.1 (M+H)$^+$.

Step VI, Synthesis of N-(5'-(4-(hex-5-yn-1-yl)piperazin-1-yl)-2-methyl-6'-((tetrahydro-2H-pyran-4-yl)oxy)-[3,3'-bipyridin]-5-yl)-3-(trifluoromethyl)benzamide To a stirred solution of N-(2-methyl-5'-(piperazin-1-yl)-6'-((tetrahydro-2H-pyran-4-yl)oxy)-[3,3'-bipyridin]-5-yl)-3-(trifluoromethyl)benzamide (22 mg, 0.041 mmol) in DMF (0.5 mL) was added potassium carbonate (8.4 mg, 0.061 mmol) and the mixture was stirred at rt for 10 min. Then, 6-Iodo-1-hexyne (7.5 uL, 0.057 mmol) was added. The mixture was stirred at rt for 65 h, diluted with water and saturated aqueous solution of ammonium chloride. After being stirred for 5 min, the mixture was diluted with EtOAc. The phases were separated and the aqueous layer was extracted twice with EtOAc. The combined organics were washed with brine, dried over sodium sulfate, and concentrated. The residue was purified by flash chromatography on silica gel using a gradient of methanol in DCM (0-15%) to afford the title compound (16 mg, 63%) as a white solid. $^1$H NMR (600 MHz, CDCl$_3$) δ 8.63 (d, J=2.0 Hz, 1H), 8.35 (s, 1H), 8.16 (s, 1H), 8.12-8.07 (m, 2H), 7.82 (d, J=7.7 Hz, 1H), 7.71 (d, J=1.4 Hz, 1H), 7.64 (t, J=7.8 Hz, 1H), 7.03 (d, J=1.3 Hz, 1H), 5.44-5.36 (m, 1H), 4.03-3.92 (m, 2H), 3.75-3.63 (m, 2H), 3.19 (s, 4H), 2.66 (s, 4H), 2.49 (s, 3H), 2.47-2.41 (m, 2H), 2.27-2.21 (m, 2H), 2.18-2.11 (m, 2H), 1.93-1.83 (m, 3H), 1.72-1.63 (m, 2H), 1.61-1.54 (m, 2H). LRMS (m/z) calculated, 621.292; found, 624.8 (M+H)$^+$.

Step VII, Synthesis of N-(5'-(4-(4-(1-(6-((2-(2,6-dioxopiperidin-3-yl)-1,3-dioxoisoindolin-4-yl)amino)-6-oxohexyl)-1H-1,2,3-triazol-4-yl)butyl)piperazin-1-yl)-2-methyl-6'-((tetrahydro-2H-pyran-4-yl)oxy)-[3,3'-bipyridin]-5-yl)-3-(trifluoromethyl)benzamide Under argon atmosphere, THF (800 uL) and water (80 uL) were added to N-(5'-(4-(hex-5-yn-1-yl)piperazin-1-yl)-2-methyl-6'-((tetrahydro-2H-pyran-4-yl)oxy)-[3,3'-bipyridin]-5-yl)-3-(trifluoromethyl)benzamide (16 mg, 0.026 mmol). Then, 6-azido-N-(2-(2,6-dioxopiperidin-3-yl)-1,3-dioxoisoindolin-4-yl)hexanamide (11 mg, 0.027 mmol) was added, followed by sodium ascorbate (1.0 mg, 5.1 umol) and copper(II) sulfate pentahydrate (1.3 mg, 5.1 μmol). The resultant mixture was sonicated for ~15 seconds and the mixture was stirred at rt for 2 h (completion observed by TLC). Then, EtOAc and water were added. The phases were separated and the aqueous layer was extracted twice with EtOAc. The combined organics were washed with brine, dried over sodium sulfate, and concentrated. The residue was purified by flash chromatography on silica gel using a gradient of EtOAc in DCM (0-100%) and Methanol in DCM (0-20%) to afford the title compound (24 mg, 88% yield) as a white solid. $^1$H NMR (600 MHz, CDCl$_3$) δ 9.39 (s, 1H), 8.96 (brs, 1H), 8.78 (d, J=8.5 Hz, 1H), 8.68 (s, 1H), 8.16 (s, 1H), 8.13-8.05 (m, 3H), 7.83 (d, J=7.8 Hz, 1H), 7.75 (s, 1H), 7.70 (t, J=7.9 Hz, 1H), 7.65 (t, J=7.8 Hz, 1H), 7.53 (d, J=7.3 Hz, 1H), 7.32 (s, 1H), 7.07-7.03 (m, 1H), 5.44-5.37 (m, 1H), 4.98-4.91 (m, 1H), 4.34 (t, J=7.0 Hz, 2H), 4.02-3.96 (m, 2H), 3.72-3.66 (m, 2H), 3.26 (brs, 4H), 2.96-2.68 (m, 9H), 2.51 (s, 3H), 2.45 (t, J=7.2 Hz, 2H), 2.18-2.12 (m, 3H), 1.99-1.94 (m, 2H), 1.89-1.84 (m, 2H), 1.81-1.77 (m, 3H), 1.42 (dt, J=15.3, 7.8 Hz, 2H), 1.30-1.23 (m, 5H). LRMS (m/z) calculated, 1033.442; found, 1035.704 (M+H)$^+$. HPLC, $t_R$=8.5 min (purity: 98%).

Example 99—Synthesis of N-(5'-(4-(4-(1-(6-((2-(2,6-dioxopiperidin-3-yl)-1,3-dioxoisoindolin-4-yl)amino)-6-oxohexyl)-1H-1,2,3-triazol-4-yl)butanoyl)piperazin-1-yl)-2-methyl-6'-((tetrahydro-2H-pyran-4-yl)oxy)-[3,3'-bipyridin]-5-yl)-3-(trifluoromethyl)benzamide (Compound 2.049)

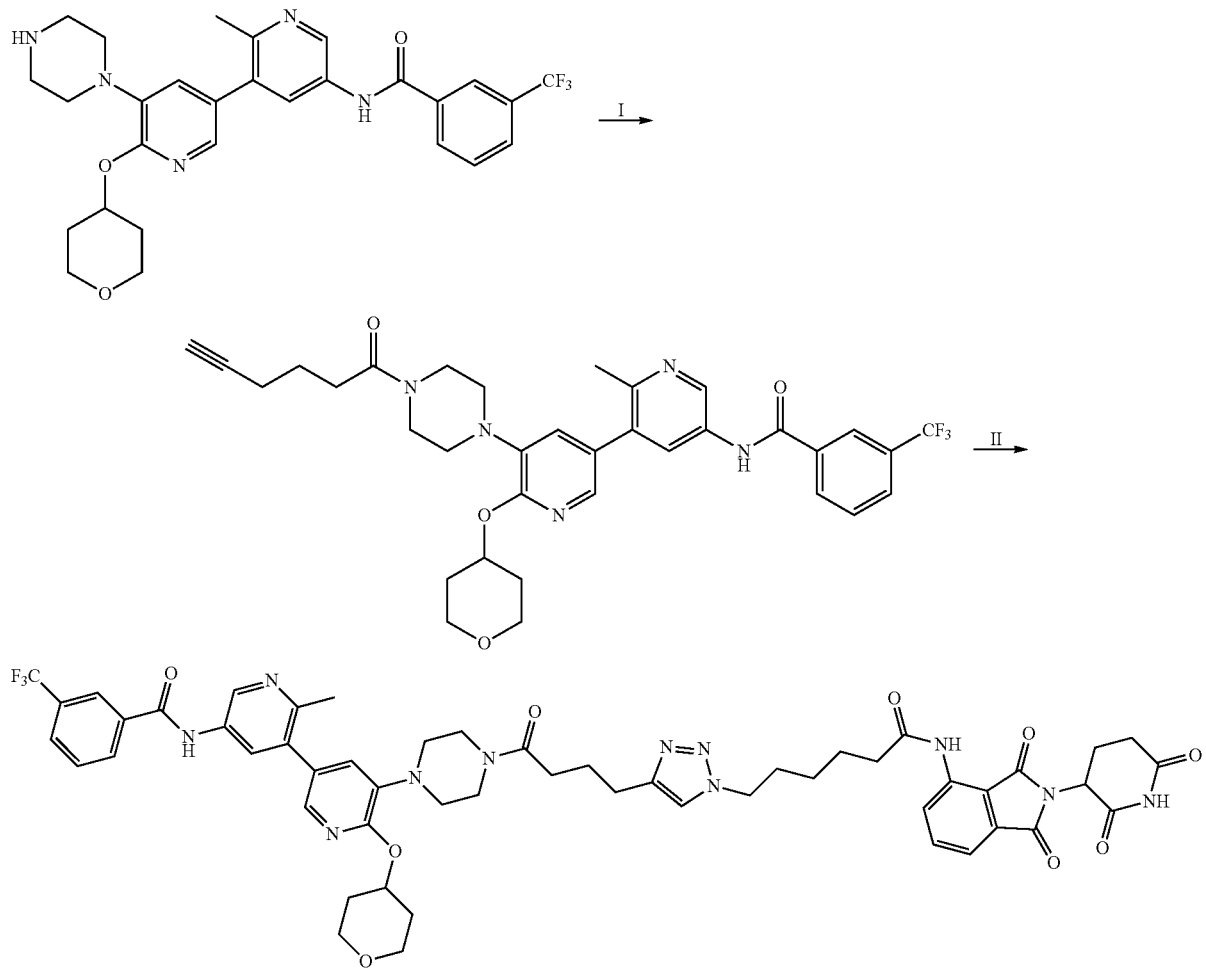

Step I, Synthesis of N-(5'-(4-(hex-5-ynoyl)piperazin-1-yl)-2-methyl-6'-((tetrahydro-2H-pyran-4-yl)oxy)-[3,3'-bipyridin]-5-yl)-3-(trifluoromethyl)benzamide (MAB-00248)

To a stirred solution of N-(2-methyl-5'-(piperazin-1-yl)-6'-((tetrahydro-2H-pyran-4-yl)oxy)-[3,3'-bipyridin]-5-yl)-3-(trifluoromethyl)benzamide (78 mg, 0.144 mmol) in DMF

Example 100—Synthesis of (2R,4S)-1-((R)-3,3-dimethyl-2-(6-(4-((2-(2-(2-((2'-methyl-5-morpholino-5'-(3-(trifluoromethyl)benzamido)-[3,3'-bipyridin]-6-yl)oxy)ethoxy)ethoxy)ethoxy)methyl)-1H-1,2,3-triazol-1-yl)hexanamido)butanoyl)-4-hydroxy-N—((S)-1-(4-(4-methylthiazol-5-yl)phenyl)ethyl)pyrrolidine-2-carboxamide (Compound 2.010)

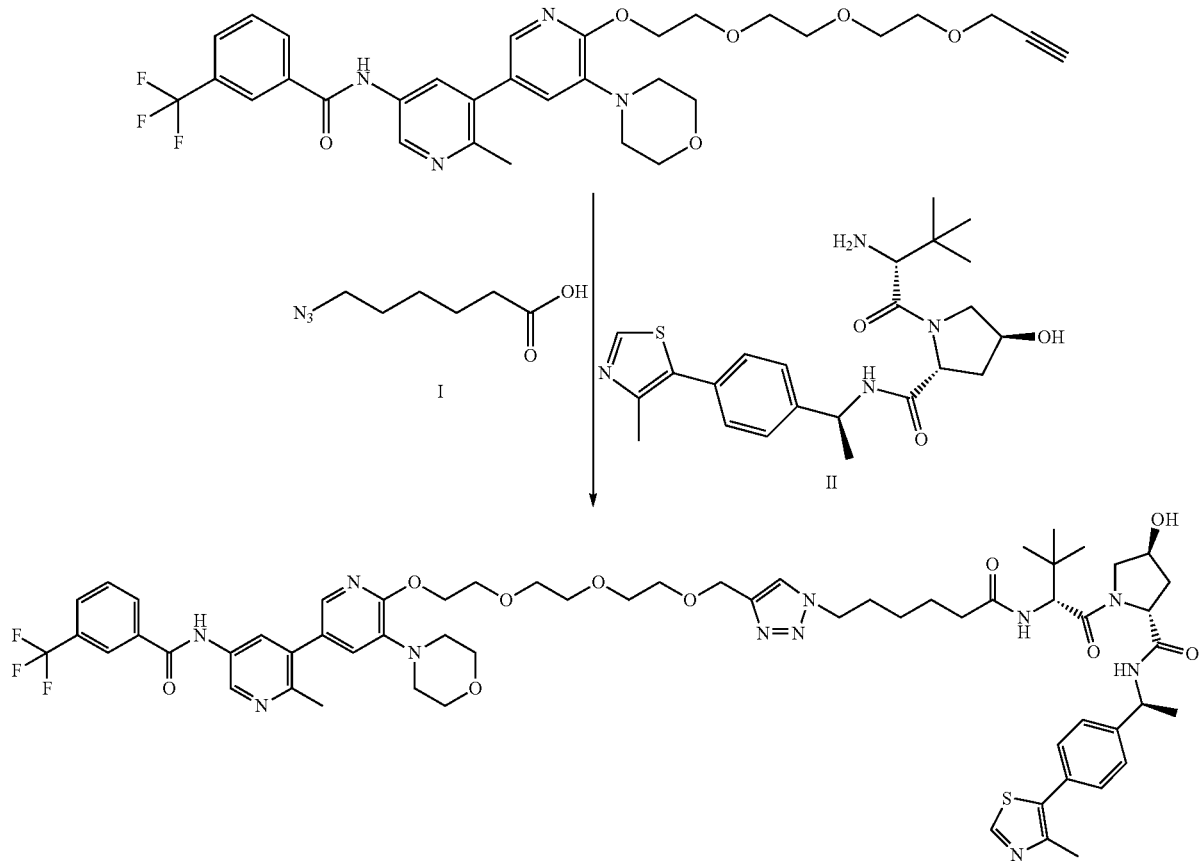

(1.0 mL) were added 5-hexynoic acid (19 uL, 0.172 mmol), HATU (71.2 mg, 0.187 mmol) and DIPEA (124 uL, 0.720 mmol). The reaction mixture was stirred at rt for 20 min. The mixture was diluted with EtOAc and water, followed by 1.0 mL of a saturated $NH_4Cl$ aqueous solution. The phases were separated and the aqueous layer was extracted twice with EtOAc. The organic extracts were combined, washed with brine, dried over sodium sulfate, and concentrated. The residue was purified by flash chromatography on silica gel using a gradient of methanol in DCM (0-20%) to afford the title compound (76 mg, 83%) as a yellow residue. $^1$H NMR (600 MHz, $CDCl_3$) δ 9.77-9.37 (m, 1H), 8.66 (s, 1H), 8.24 (s, 2H), 8.16 (d, J=7.7 Hz, 1H), 7.80-7.72 (m, 2H), 7.63-7.54 (m, 1H), 7.02 (s, 1H), 5.39 (s, 1H), 3.97 (d, J=5.6 Hz, 2H), 3.76 (s, 2H), 3.66 (s, 4H), 3.13 (s, 2H), 3.06 (s, 2H), 2.77-2.74 (m, 5H), 2.50-2.45 (m, 4H), 2.27 (d, J=5.9 Hz, 2H), 2.12 (s, 2H), 1.96 (s, 1H). LRMS (m/z) calculated, 635.272; found, 638.9 (M+H)$^+$.

Example 100 describes the synthesis of a conjugate containing points of inverted stereochemistry for the VHL Ligand

Step I, 6-(4-((2-(2-(2-((2'-methyl-5-morpholino-5'-(3-(trifluoromethyl)benzamido)-[3,3'-bipyridin]-6-yl)oxy)ethoxy)ethoxy)ethoxy)methyl)-1H-1,2,3-triazol-1-yl)hexanoic Acid Title compound (48.2 mg, 77.1%) was prepared as a white solid from N-(2-methyl-5'-morpholino-6'-(2-(2-(2-(prop-2-yn-1-yloxy)ethoxy)ethoxy)ethoxy)-[3,3'-bipyridin]-5-yl)-3-(trifluoromethyl)benzamide and 6-azidohexanoic acid (15.2 mg, 0.0967 mmol) as described in Example 22. Rf=0.34 (10% MeOH in DCM). $^1$H NMR (400 MHz, $CDCl_3$) δ 9.31 (s, 1H), 8.82 (s, 1H), 8.22 (s, 1H), 8.15 (d, J=7.9 Hz, 1H), 8.06 (d, J=1.9 Hz, 1H), 7.79 (d, J=7.7 Hz, 1H), 7.71 (d, J=1.9 Hz, 1H), 7.63 (s, 1H), 7.60 (t, J=7.8 Hz, 1H), 7.03 (d, J=1.9 Hz, 1H), 4.59 (s, 2H), 4.57-4.52 (m, 2H), 4.32 (t, J=6.9 Hz, 2H), 3.91-3.83 (m, 6H), 3.72-3.70 (m Hz, 2H), 3.66-3.57 (m, 6H), 3.13 (bs, 4H), 2.36 (s, 3H), 2.33 (t, J=7.1 Hz, 2H), 1.94-1.85 (m, 2H), 1.71-1.61 (m, 2H), 1.37-1.30 (m, 2H) ppm. $^{19}$F NMR (376 MHz, $CDCl_3$) δ −63.07 (s) ppm. LRMS (ESI) m/z: calculated for $C_{38}H_{46}F_3N_7O_8$, 785.34; found 785.93 (M+H)$^+$; found 808.07 (M+Na)$^+$; found 824.07 (M+K)$^+$; found 784.14 (M−H)$^−$.

Step II: (2R,4S)-1-((R)-3,3-dimethyl-2-(6-(4-((2-(2-(2-((2'-methyl-5-morpholino-5'-(3-(trifluoromethyl)benzamido)-[3,3'-bipyridin]-6-yl)oxy)ethoxy)ethoxy)ethoxy)methyl)-1H-1,2,3-triazol-1-yl)hexanamido)butanoyl)-4-hydroxy-N—((S)-1-(4-(4-methylthiazol-5-yl)phenyl)ethyl)pyrrolidine-2-carboxamide Title compound (12.5 mg, 16.8%) as a white solid from 6-(4-((2-(2-(2-((2'-methyl-5-morpholino-5'-(3-(trifluoromethyl)benzamido)-[3,3'-bipyridin]-6-yl)oxy)ethoxy)ethoxy)-ethoxy)methyl)-1H-1,2,3-triazol-1-yl)hexanoic acid (48.2 mg, 0.0613 mmol) DMF (1.3 mL) using HATU (45.2 mg, 0.119 mmol) and DIPEA (33 μL, 0.0625 mmol) using (2R,4S)-1-((R)-2-amino-3,3-dimethylbutanoyl)-4-hydroxy-N—((S)-1-(4-(4-methylthiazol-5-yl)phenyl) ethyl) pyrrolidine-2-carboxamide (31.5 mg, 0.656 mmol) as described in Example 36. Rf=0.18 (10% MeOH in DCM). $^1$H NMR (400 MHz, CDCl$_3$) δ 9.19 (s, 1H), 8.81 (d, J=2.2 Hz, 1H), 8.65 (s, 1H), 8.26 (s, 1H), 8.17 (d, J=8.0 Hz, 1H), 7.91 (d, J=2.1 Hz, 1H), 7.79 (d, J=7.5 Hz, 1H), 7.66 (d, J=1.7 Hz, 1H), 7.61 (t, J=7.8 Hz, 1H), 7.53 (s, 1H), 7.32 (d, J=7.8 Hz, 1H), 7.27 (s, 4H), 6.97 (d, J=1.7 Hz, 1H), 6.21 (d, J=7.1 Hz, 1H), 4.97-4.89 (m, 1H), 4.66-4.59 (m, 3H), 4.56-4.55 (m, 2H), 4.52-4.47 (m, 1H), 4.32 (d, J=7.0 Hz, 1H), 4.22 (t, J=7.0 Hz, 2H), 4.06 (dd, J=10.4, 6.3 Hz, 1H), 3.92-3.82 (m, 6H), 3.71-3.69 (d, J=4.8 Hz, 2H), 3.64-3.62 (m, 6H), 3.56 (dd, J=10.4, 5.5 Hz, 1H), 3.11-3.10 (m, 4H), 2.61 (s, 1H), 2.46 (s, 3H), 2.45 (s, 3H), 2.43-2.36 (m, 1H), 2.12 (t, J=7.2 Hz, 1H), 2.07-2.02 (m, 1H), 1.82-1.74 (m, 2H), 1.62-1.51 (m, 2H), 1.34 (d, J=7.0 Hz, 3H), 1.27-1.18 (m, 2H), 1.05 (s, 9H) ppm. $^{19}$F NMR (376 MHz, CDCl$_3$) δ −63.03 (s) ppm. LRMS, m/z, calculated for $C_{61}H_{76}F_3N_{11}O_{10}S$, 1211.5449; found 1212.22 (M+H)$^+$; found 1234.07 (M+Na)$^+$. HPLC purity (>99% @ 254 nm; >99% @ 234 nm; 9.10 min) HPLC Method: Column, Agilent, Zorbax-SB-CN, 3.5 μm, 4.6×150 mm, mobile phase, acetonitrile in water (0-100%) contains ammonium acetate buffer; flow rate, 0.1 mL/min, run time, 20 min.

Biochemical & Biological Data

Example 101—Dimerization Assay

The Alpha Screen buffer (50 mM sodium phosphate pH 7.5, 150 mM sodium chloride, 0.1% v/v Tween20, 2% v/v DMSO) was used to make all dilutions for the assay. A stock of GST-Braf was prepared by incubating 680 nM of purified GST-Braf kinase domain with 100 μg/mL AlphaLisa glutathione acceptor beads (Perkin Elmer) for 30 minutes at 4° C. A stock of E3 substrate adapter was prepared by incubating 680 nM of purified biotinylated E3 substrate adapter (VHL/EloB/EloC complex or CRBN$^{318\text{-}425}$) with 100 μg/mL AlphaLisa streptavidin donor beads (Perkin Elmer) for 30 minutes at 4° C. After 30 minutes, unbound streptavidin beads were blocked with 200 μM biocytin and incubate for another 30 minutes at 4° C. The GST-Braf and E3 substrate adapter stocks were combined in a 1:1 ratio. Compounds were prepared by 4 fold serial dilutions from 20 μM. 10 μL of AlphaLisa mixture was added to 12 μL of compound and incubated at room temperature for 30 minutes. Readout the assay in white 96 well Optiplates (Perkin Elmer) using the Alpha Screen method on the Enspire plate reader (Perkin Elmer).

Results

Figure 2:
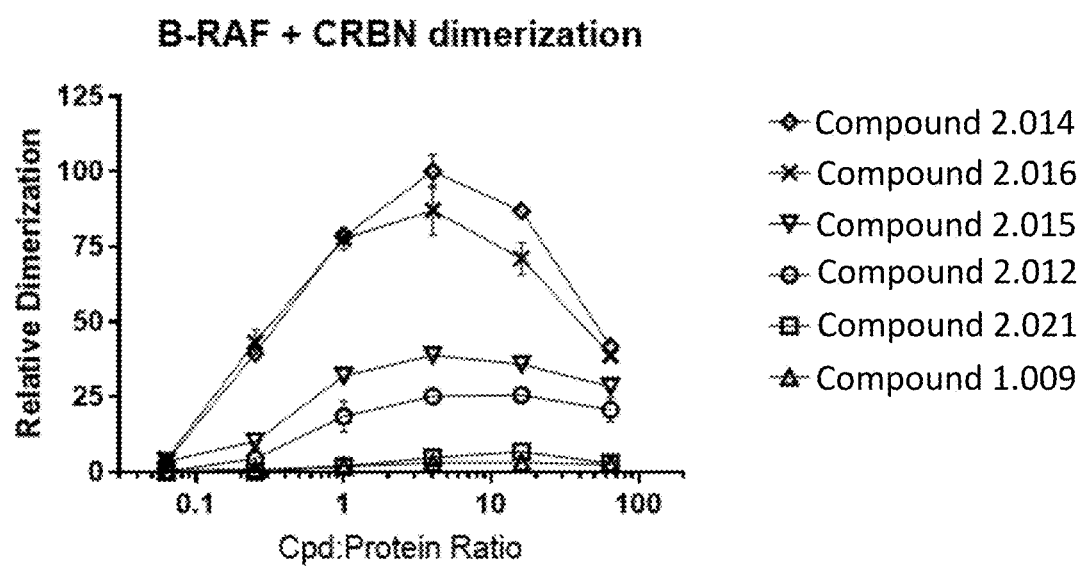
FIG. 2 shows the relative BRAF+CRBN dimerization measured for Compound 2.014 (open diamonds), Compound 2.016 ("x"), Compound 2.015 (open inverted triangles), Compound 2.012 (open circles), Compound 2.021 (open squares), and Compound 1.009 (open triangles) at varying compound to protein ratios.
Figure 3:
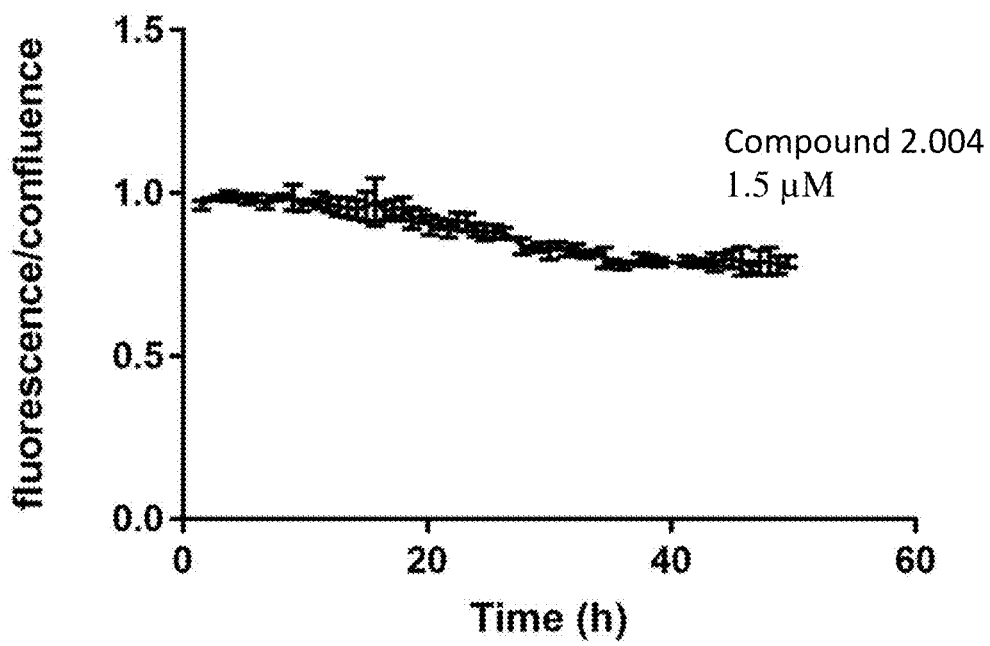
FIG. 3 shows CRAF degradation in Calu6 cells over time after addition of 1.5 µM of Compound 2.004. The values of the y-axis are displayed as a measure of fluorescence/confluence. See, Example 102 for further information on data analysis.
Figure 4:
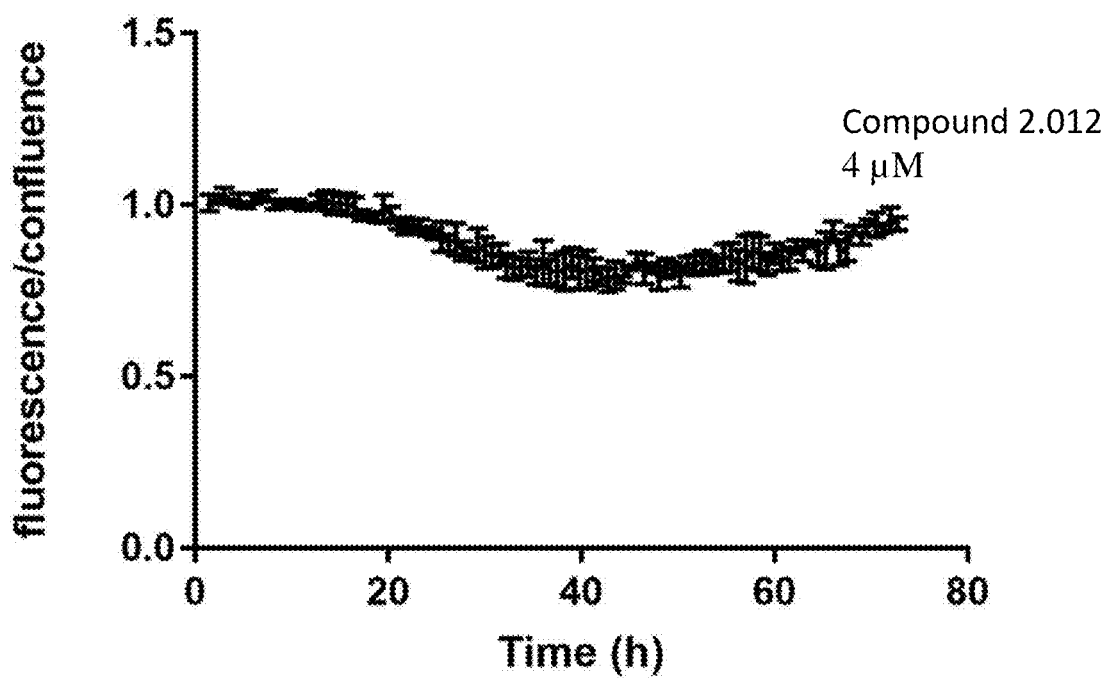
FIG. 4 shows CRAF degradation in Calu6 cells over time after addition of 3 µM of Compound 2.012. The values of the y-axis are displayed as a measure of fluorescence/confluence. See, Example 102 for further information on data analysis.
Figure 5:
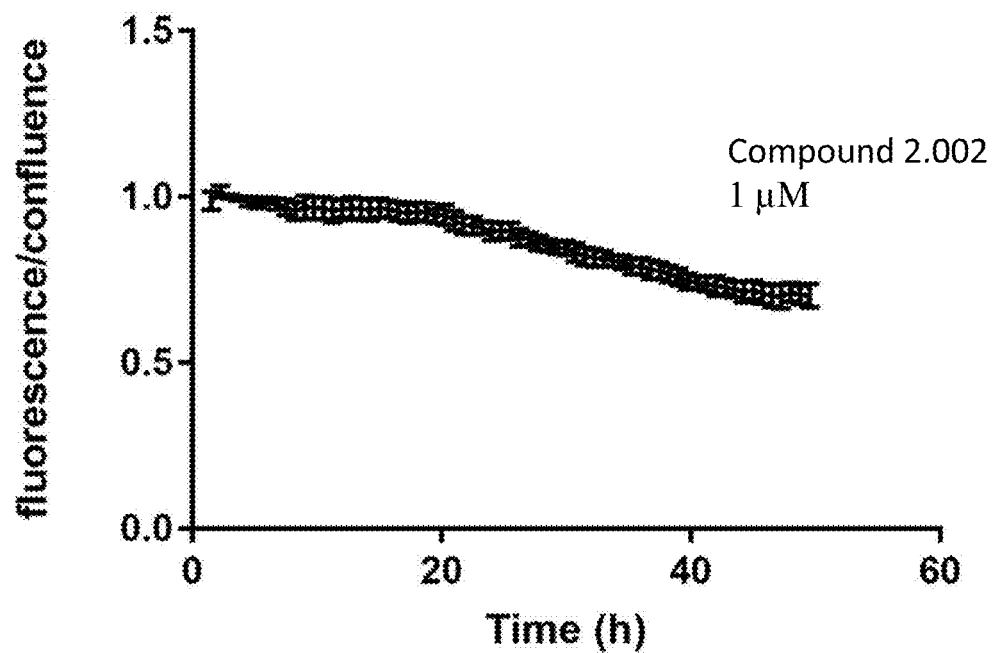
FIG. 5 shows CRAF degradation in Calu6 cells over time after addition of 1 µM of Compound 2.002. The values of the y-axis are displayed as a measure of fluorescence/confluence. See, Example 102 for further information on data analysis.
Figure 6:
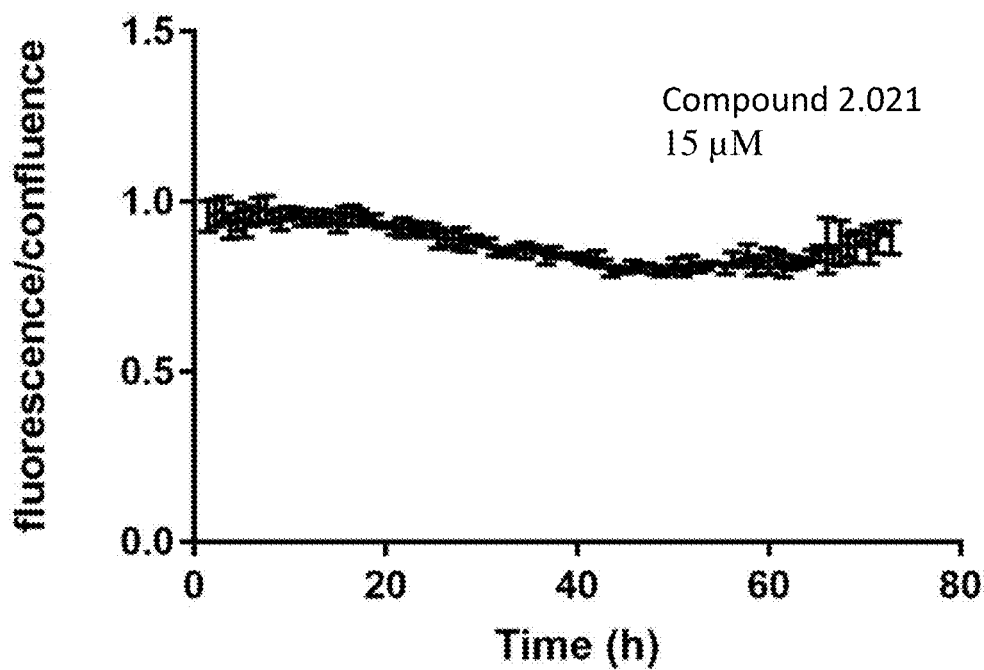
FIG. 6 shows CRAF degradation in Calu6 cells over time after addition of 15 µM of Compound 2.021. The values of the y-axis are displayed as a measure of fluorescence/confluence. See, Example 102 for further information on data analysis.
Figure 7:
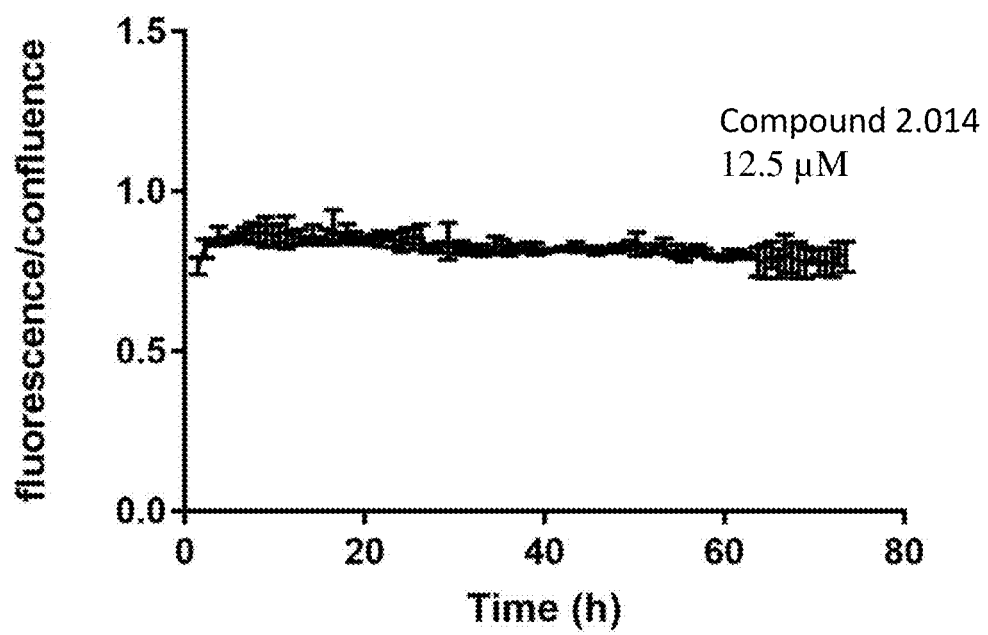
FIG. 7 shows CRAF degradation in Calu6 cells over time after addition of 12.5 µM of Compound 2.014. The values of the y-axis are displayed as a measure of fluorescence/confluence. See, Example 102 for further information on data analysis.
Figure 8:
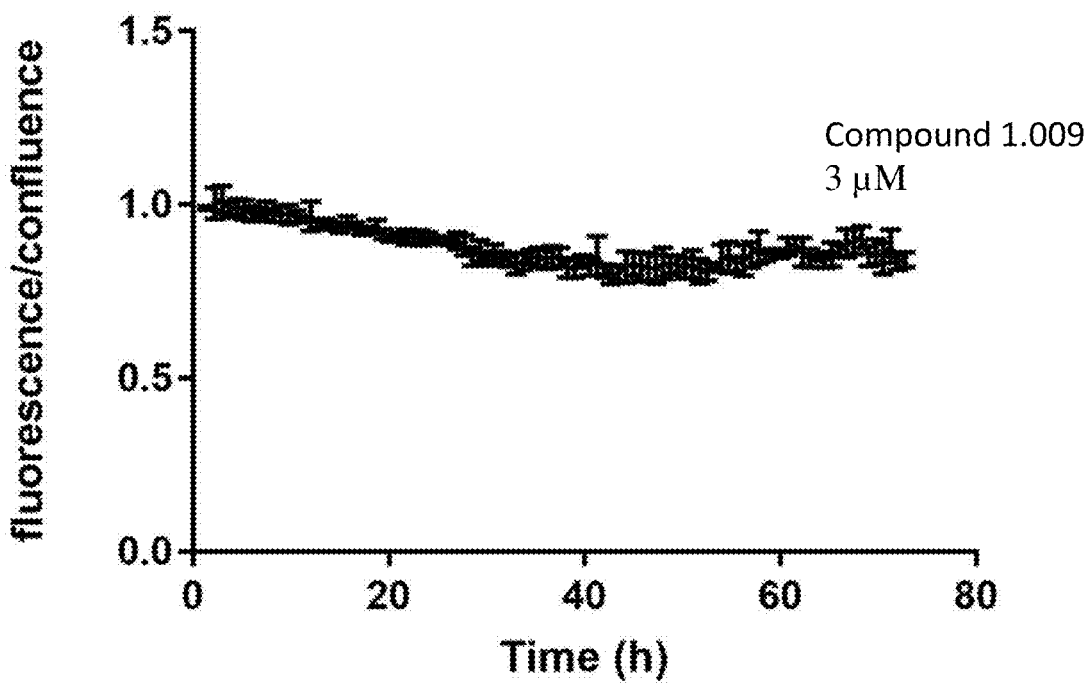
FIG. 8 shows CRAF degradation in Calu6 cells over time after addition of 3 µM of Compound 1.009. The values of the y-axis are displayed as a measure of fluorescence/confluence. See, Example 102 for further information on data analysis.
Figure 9:
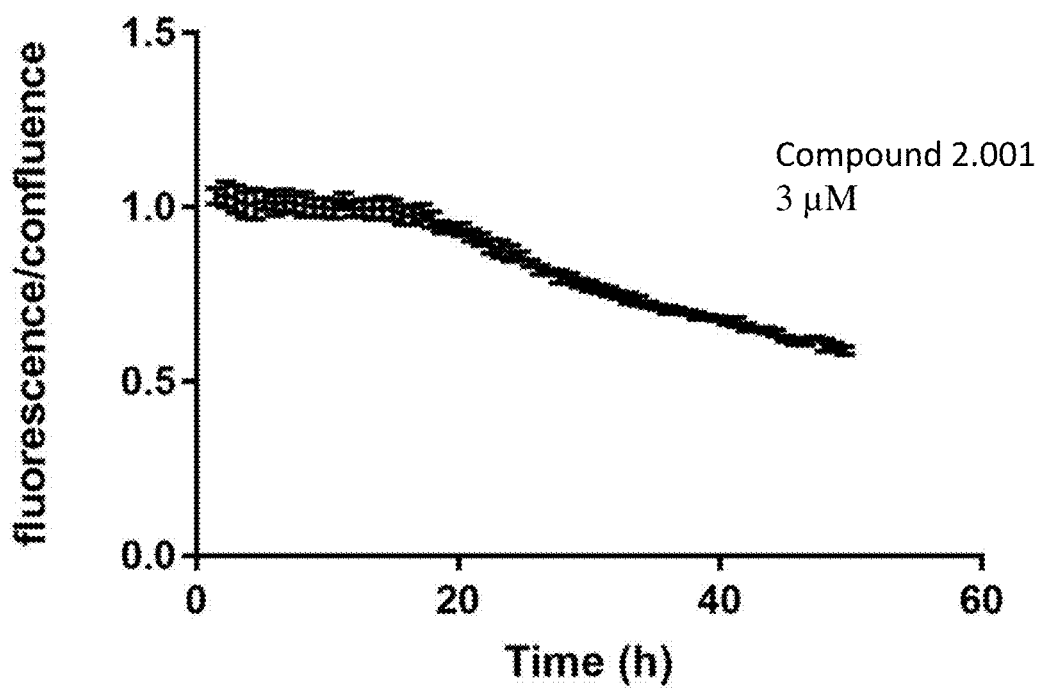
FIG. 9 shows CRAF degradation in Calu6 cells over time after addition of 3 µM of Compound 2.001. The values of the y-axis are displayed as a measure of fluorescence/confluence. See, Example 102 for further information on data analysis.
Figure 10:
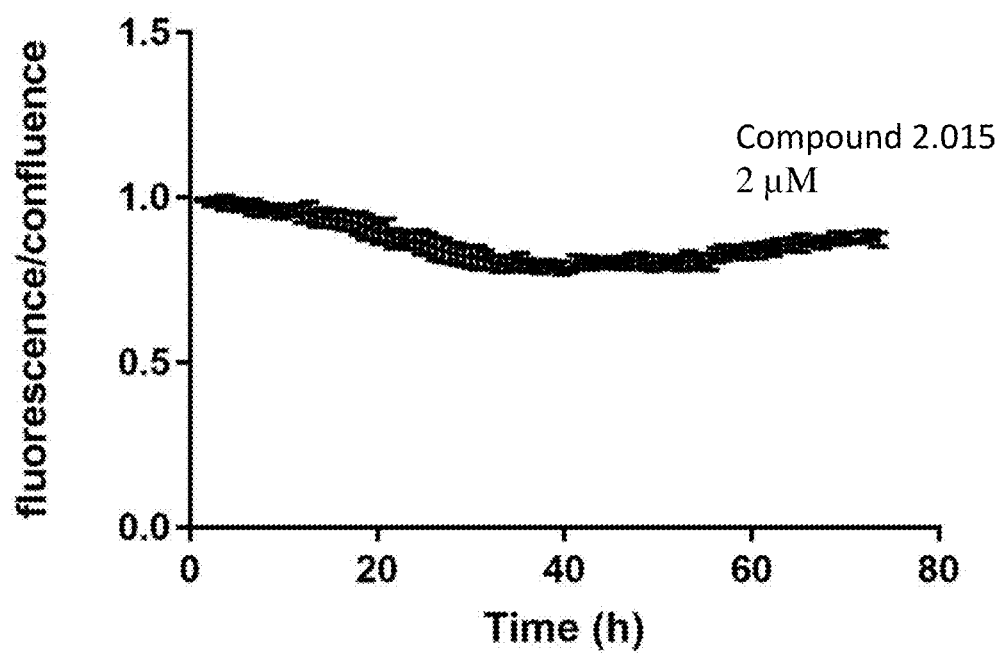
FIG. 10 shows CRAF degradation in Calu6 cells over time after addition of 2 µM of Compound 2.015. The values of the y-axis are displayed as a measure of fluorescence/confluence. See, Example 102 for further information on data analysis.
Figure 11:
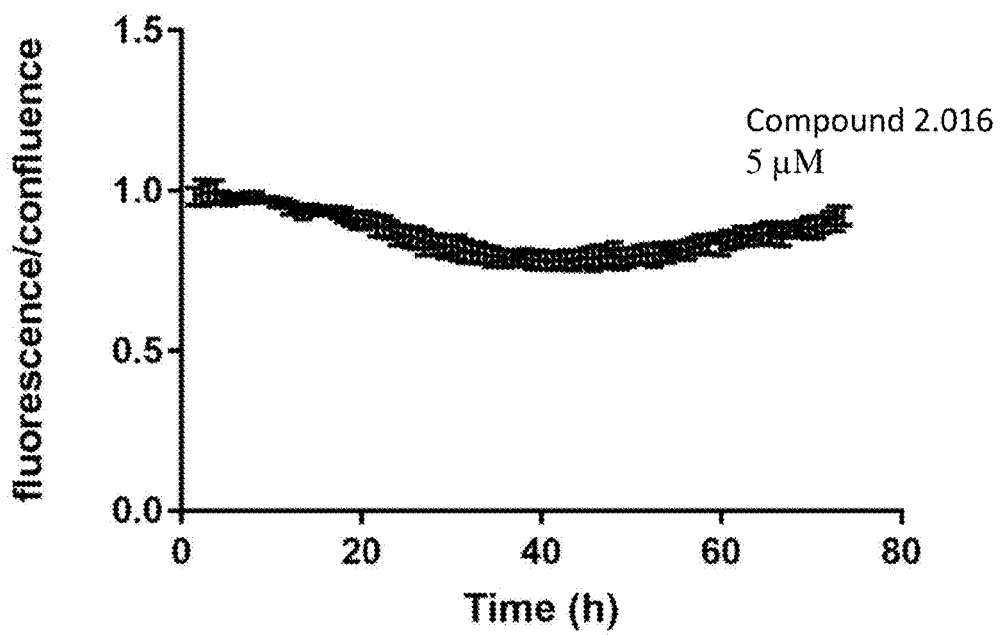
FIG. 11 shows CRAF degradation in Calu6 cells over time after addition of 5 µM of Compound 2.016. The values of the y-axis are displayed as a measure of fluorescence/confluence. See, Example 102 for further information on data analysis.

FIG. 1 and FIG. 2 show the relative dimerization measured for particular compounds at varying compound to protein rations. Table 15, Table 16, and Table 17 below, summarize the dimerization data for particular compounds.

TABLE 15

Relative Degradation of Particular RAF-Degrading Conjugate Compounds

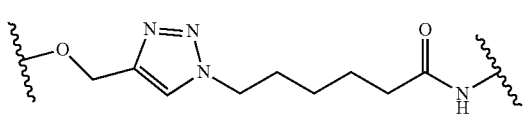 [SMILES: *NC(=O)CCCCCn1cc(CO*)nn1]

| Name | Linker | RAF/E3 dimerization |
|---|---|---|
| 1.001 | | ++ |

TABLE 15-continued

Relative Degradation of Particular RAF-Degrading Conjugate Compounds

| Name | Linker | RAF/E3 dimerization |
|---|---|---|
| 1.002 | —O–CH$_2$CH$_2$–(triazole)–(CH$_2$)$_5$–C(O)NH— | + |
| 1.003 | —O–(CH$_2$)$_3$–(triazole)–(CH$_2$)$_5$–C(O)NH— | + + |
| 1.004 | —O–(CH$_2$)$_4$–(triazole)–(CH$_2$)$_5$–C(O)NH— | + |
| 1.005 | —O–(CH$_2$)$_5$–(triazole)–(CH$_2$)$_5$–C(O)NH— | + |
| 1.006 | —O–(CH$_2$)$_6$–(triazole)–(CH$_2$)$_5$–C(O)NH— | + |
| 1.007 | —O–CH$_2$CH$_2$–O–CH$_2$CH$_2$–O–CH$_2$CH$_2$–O–CH$_2$–(triazole)–(CH$_2$)$_5$–C(O)NH— | + + + |

TABLE 15-continued

Relative Degradation of Particular RAF-Degrading Conjugate Compounds

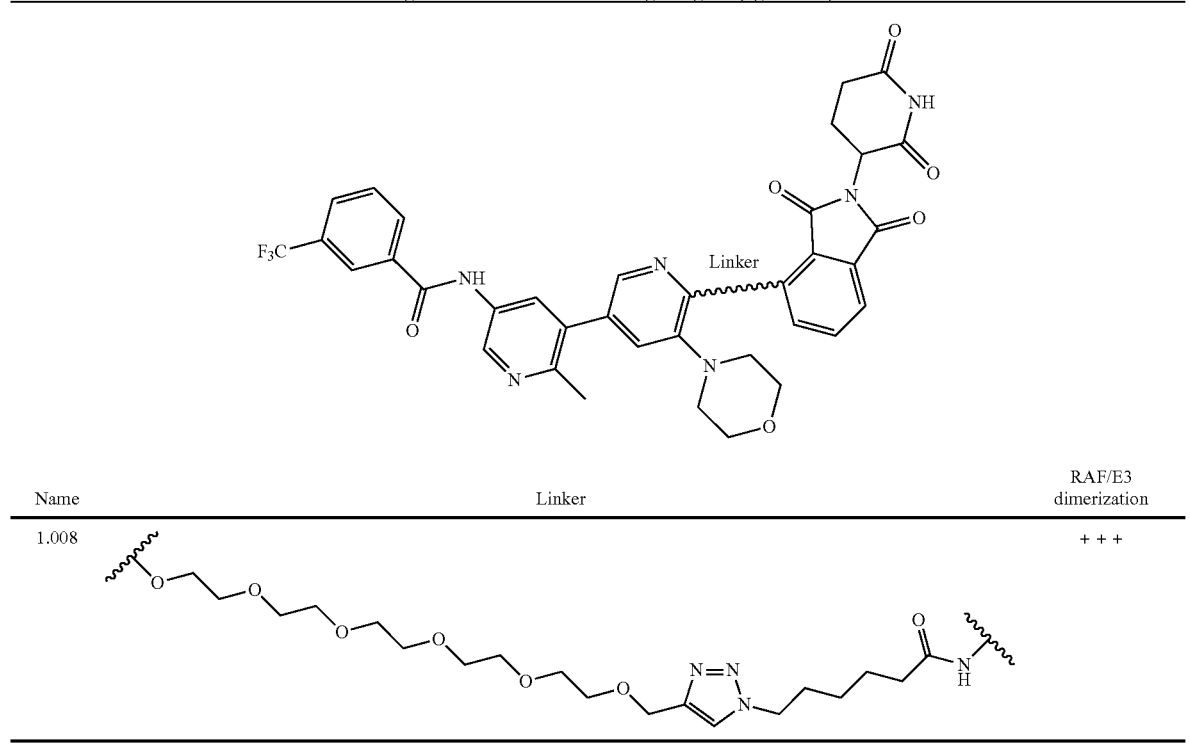

| Name | Linker | RAF/E3 dimerization |
|---|---|---|
| 1.008 | | +++ |

TABLE 16

Relative Degradation of Particular RAF-Degrading Conjugate Compounds

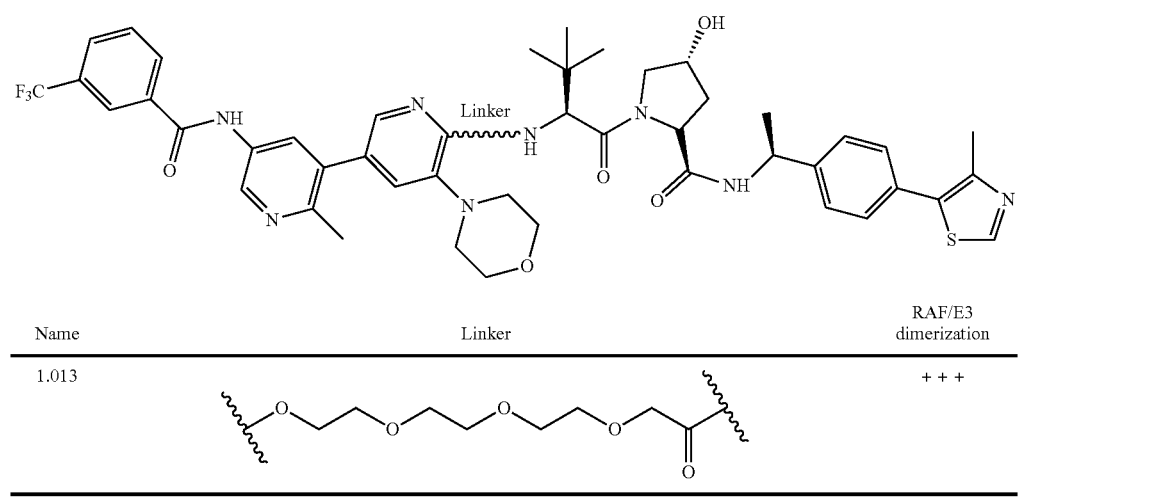

| Name | Linker | RAF/E3 dimerization |
|---|---|---|
| 1.013 | | +++ |

TABLE 17

Relative Degradation of Particular RAF-Degrading Conjugate Compounds

| Compound | RAF/E3 Dimerization |
|---|---|
| 1.009 | + |
| 1.010 | + |
| 1.011 | + |

TABLE 17-continued

Relative Degradation of Particular RAF-Degrading Conjugate Compounds

| Compound | RAF/E3 Dimerization |
|---|---|
| 1.012 | + |
| 1.014 | + |
| 1.015 | + |

TABLE 17-continued

Relative Degradation of Particular RAF-Degrading Conjugate Compounds

| Compound | RAF/E3 Dimerization |
|---|---|
| 1.016 | + |
| 2.001 | +++++ |
| 2.002 | ++++ |
| 2.003 | +++++ |
| 2.004 | +++ |
| 2.005 | ++++ |
| 2.006 | + |
| 2.007 | ++ |
| 2.008 | +++ |
| 2.009 | +++ |
| 2.011 | +++++ |
| 2.012 | +++ |
| 2.013 | ++ |
| 2.014 | +++++ |
| 2.015 | +++ |
| 2.016 | +++++ |
| 2.017 | ++++ |
| 2.018 | ++++ |
| 2.019 | +++ |
| 2.020 | +++ |
| 2.021 | ++ |
| 2.022 | ++ |
| 2.023 | + |
| 2.024 | ++ |
| 2.025 | ++ |
| 2.026 | + |
| 2.027 | ++ |
| 2.028 | ++ |
| 2.029 | + |
| 2.030 | ++ |
| 2.031 | + |
| 2.032 | + |
| 2.033 | ++ |
| 2.034 | ++ |
| 2.036 | ++ |
| 2.037 | ++++ |
| 2.038 | +++ |
| 2.039 | +++++ |
| 2.040 | + |
| 2.041 | + |
| 2.042 | + |
| 2.043 | ++ |
| 2.044 | + |
| 2.045 | +++++ |
| 2.046 | +++ |
| 2.048 | ++ |
| 2.049 | + |

Relative values reported in Table 15, Table 16, and Table 17 are as follows:

| | |
|---|---|
| "+++++" | RAF/E3 Dimerization ≥75%; |
| "++++" | 75% > RAF/E3 Dimerization ≥ 50%; |
| "+++" | 50% > RAF/E3 Dimerization ≥ 25; |
| "++" | 25% > RAF/E3 Dimerization ≥ 5%; |
| "+" | 5% > RAF/E3 Dimerization. |

Example 102—Degradation Assay

Calu-6 cells were stably transfected with a CRAF fusion protein with a fluorescent protein attached to the C-terminus of CRAF in order to monitor protein levels via fluorescence. Cells were seeded into a 96-well plate and allowed to adhere overnight. The next day cells are treated with compounds at the doses indicated in the table below and analyzed over time. Data was collected by monitoring Fluorescent CRAF protein levels an IncuCyte S3 Live Cell Analysis System (Essen BioScience). The fluorescent CRAF fusion protein was excited at 440-480 nm and the emission was measured at 504-544 nm.

Calu6_CRAF fusion protein cells are imaged and analyzed using an Incucyte S3 live-cell analysis system (Essen Biosciences). Fluorescence signal is due to expression of the fluorescent protein covalently fused to the C-terminus of CRAF and degradation is assessed by measuring fluorescence/confluence (~cell number) after treatment with compounds of the present disclosure.

Phase contrast images are analyzed using Incucyte S3 software. Percent confluence is calculated using a phase contrast mask to quantify the area of the image occupied by the Calu6_CRAF fusion protein cells.

Fluorescent images are analyzed using Incucyte S3 software. Green Corrected Units (GCU) is calculated using a fluorescence mask to quantify the area of the image occupied by green fluorescent signal and the intensity of the signal.

FIG. 3 to FIG. 11 show CRAF degradation over time after addition of the indicated compound. As discussed above, degradation is measured as a function of fluorescence/confluence. Table 18 below shows the maximal relative CRAF degradation measured at the indicated concentration for the listed compounds.

TABLE 18

Relative Degradation of Particular RAF-Degrading Conjugate Compounds

| Compound | Concentration, μM | Time (h) | Max CRAF degradation |
|---|---|---|---|
| Geldanamycin | 0.1 | 10.5 | +++ |
| RAF307 | 0.2 | 72 | +++ |
| 1.001 | 1 | 66 | +++ |
| 1.002 | 1.5 | 69 | + |
| 1.003 | 1.5 | 66 | + |
| 1.004 | 1 | 33.75 | ++ |
| 1.005 | 1 | 27 | + |
| 1.006 | 1 | 69.75 | +++ |
| 1.007 | 3 | 47.25 | ++ |
| 1.008 | 3 | 66.75 | + |
| 1.009 | 3 | 41.25 | ++ |
| 1.01 | 6 | 31.5 | + |
| 1.012 | 6 | 47.25 | ++ |
| 1.013 | 3 | 43.5 | +++ |
| 2.001 | 3 | 48 | +++ |
| 2.002 | 1 | 47.25 | +++ |
| 2.003 | 0.6 | 47.25 | +++ |
| 2.004 | 1.5 | 47.25 | ++ |
| 2.008 | 3.12 | 0 | ++ |
| 2.009 | 3.12 | 32.25 | ++ |
| 2.012 | 3 | 41.25 | ++ |
| 2.013 | 3 | 39.75 | ++ |

TABLE 18-continued

Relative Degradation of Particular RAF-Degrading Conjugate Compounds

| Compound | Concentration, μM | Time (h) | Max CRAF degradation |
|---|---|---|---|
| 2.014 | 12.5 | 0 | +++ |
| 2.015 | 2 | 39 | ++ |
| 2.016 | 5 | 39.75 | ++ |
| 2.017 | 12.5 | 60.75 | ++ |
| 2.018 | 1 | 41.25 | ++ |
| 2.019 | 3 | 39 | ++ |
| 2.02 | 3 | 0 | ++ |
| 2.021 | 15 | 47.25 | ++ |
| 2.022 | 4 | 41.25 | +++ |
| 2.028 | 0.12 | 21.75 | + |
| 2.029 | 3 | 0 | + |
| 2.03 | 0.02 | 51 | + |
| 2.032 | 6 | 4.5 | + |
| 2.033 | 0.6 | 12 | + |
| 2.034 | 0.12 | 51 | + |
| 2.037 | 3.12 | 47.25 | + |
| 2.038 | 0.01 | 0.75 | + |
| 2.039 | 0.78 | 0 | + |
| 2.04 | 0.2 | 46.5 | + |
| 2.043 | 5 | 47.25 | +++ |
| 2.045 | 5 | 0 | + |
| 2.049 | 1.5 | 0.75 | + |

Relative values reported in Table 18 are as follows:

| | |
|---|---|
| "+++" | Max % CRAF degradation ≥22.5%; |
| "++" | 22.5% > Max % CRAF degradation ≥ 10%; |
| "+" | 10% > Max % CRAF degradation. |

Example 103—Dual Target Binding Confers Activity

VHL Ligand requires a hydroxyproline residue for VHL binding. Changing two points of stereochemistry on this ligand is known to eliminate VHL binding activity.

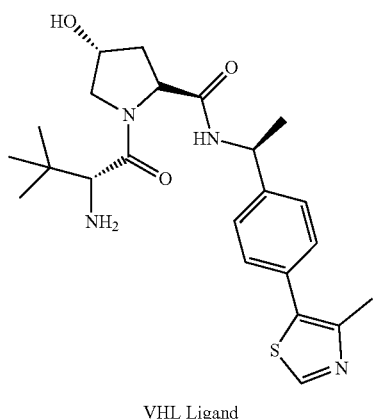

VHL Ligand

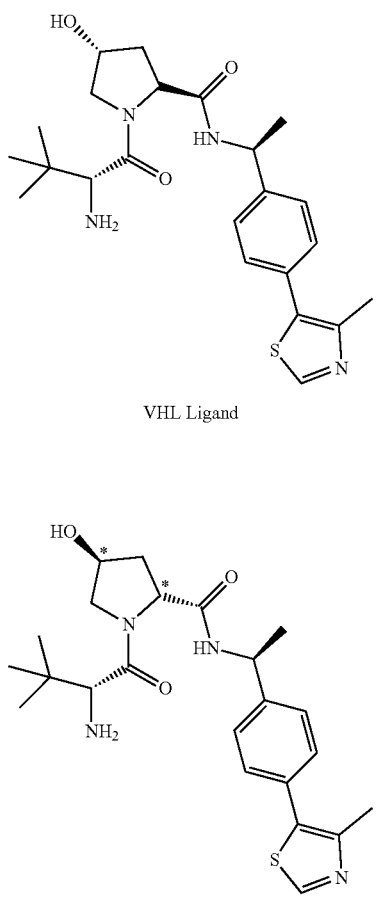

Inactive Isomer of VHL Ligand

A pair of a RAF-Degrading Conjugate Compounds, one with VHL Ligand (Compound 2.003), the other with the inactive isomer of VHL Ligand (Compound 2.010), were tested for activity in the dimerization assay and degradation assay discussed above.

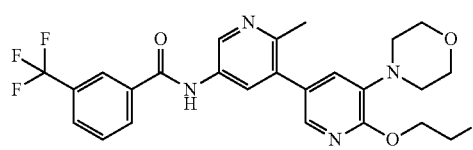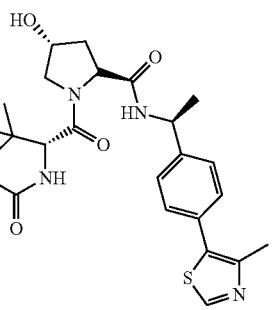

Compound 2.003

(Active Compound)

Compound 2.010

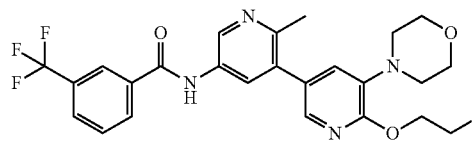

(Inactive Stereoisomer)

Figure 12:
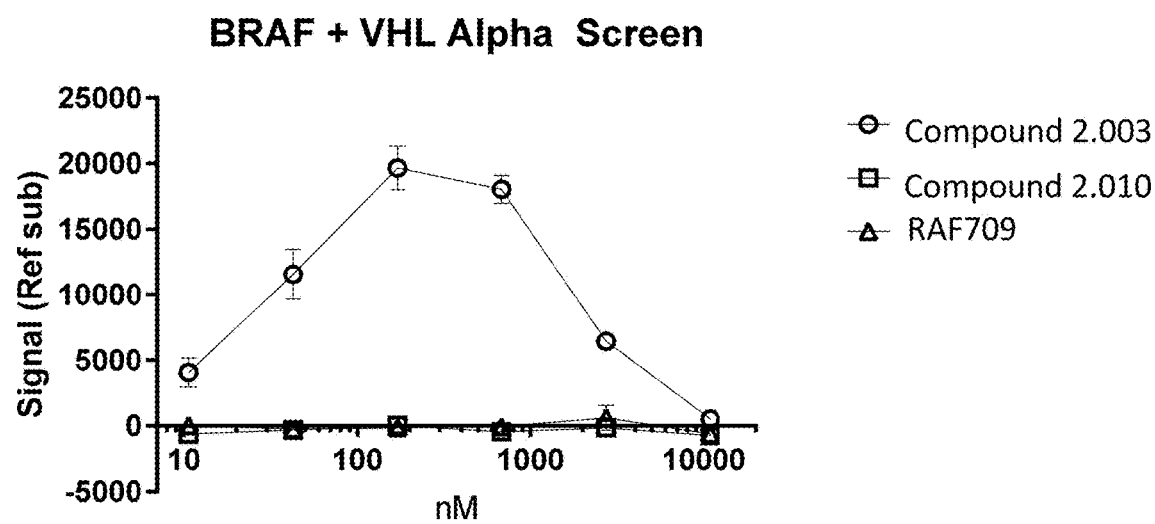
FIG. 12 shows the relative BRAF+VHL dimerization measured for Compound 2.003 (open circles), Compound 2.010 (open squares), and RAF709 (open triangles) at various concentrations. Compound 2.010 is a diastereomer of Compound 2.003; the altered stereochemistry inactivates the VHL ligand such that in longer binds to VHL. This data demonstrates that removal of VHL binding activity eliminates dimerization.

The dimerization assay shows that introduction of Compound 2.003 (active compound) successfully causes BRAF/VHL dimerization, whereas introduction of Compound 2.010 (inactive stereoisomer) does not (FIG. 12). Dimerization data for RAF709 is also included in this figure to show that the RAF inhibitor alone does not cause dimerization.

Figure 13:
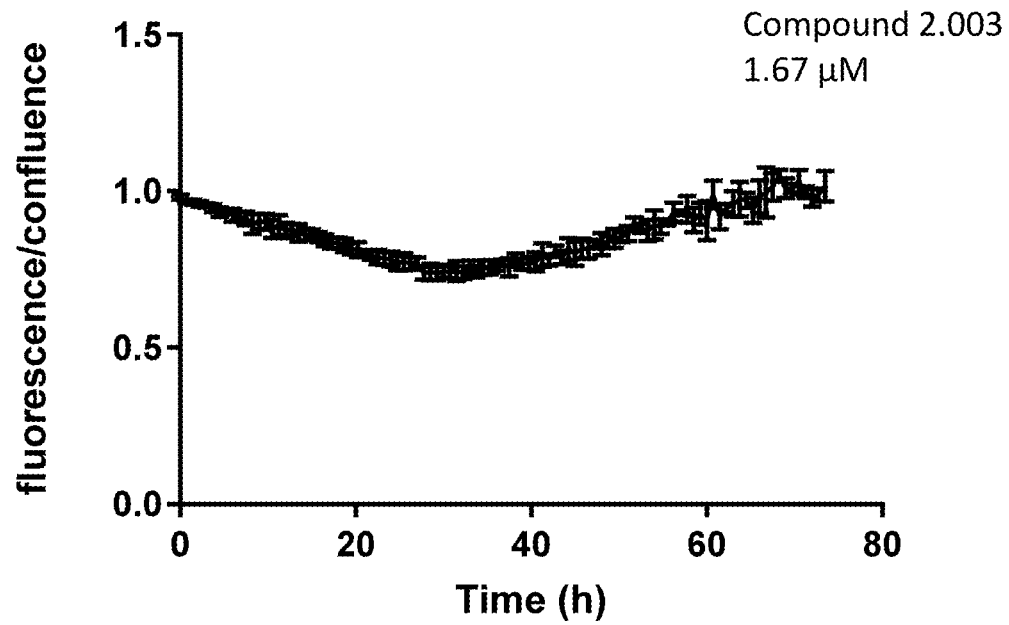
FIG. 13 shows CRAF degradation in Calu6 cells over time after addition of 1.67 µM of Compound 2.003. The values of the y-axis are displayed as a measure of fluorescence/confluence. See, Example 102 for further information on data analysis.
Figure 14:
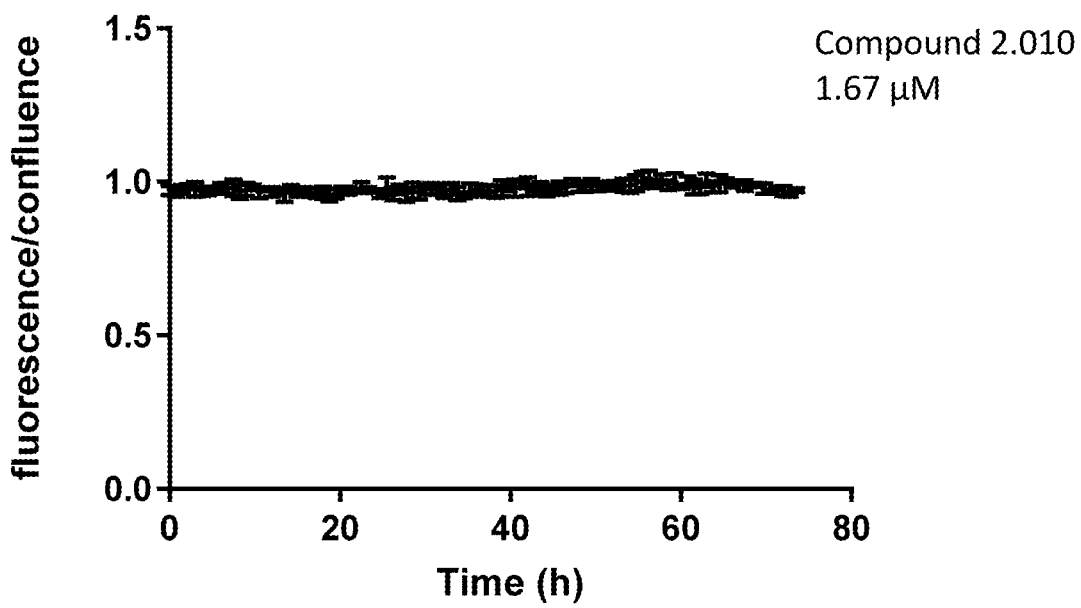
FIG. 14 shows no CRAF degradation in Calu6 cells over time after addition of 1.67 µM of Compound 2.010. Compound 2.010 is a diastereomer of Compound 2.003; the altered stereochemistry inactivates the VHL ligand such that in longer binds to VHL. The values of the y-axis are displayed as a measure of fluorescence/confluence. See, Example 102 for further information on data analysis.

Similarly, the degradation assay shows that Compound 2.003 (active compound) successfully causes CRAF degradation at 1.67 µM (FIG. 13), while the same concentration of Compound 2.010 (inactive stereoisomer) does not significantly reduce the relative amount of CRAF (fluorescence is maintained) (FIG. 14).

Although the foregoing invention has been described in some detail by way of illustration and example for purposes of clarity of understanding, one of skill in the art will appreciate that certain changes and modifications may be practiced within the scope of the appended claims. In addition, each reference provided herein is incorporated by reference in its entirety to the same extent as if each reference was individually incorporated by reference.

What is claimed is:

1. A RAF-Degrading Conjugate Compound consisting of a Ligand for RAF covalently attached via a Linker Component to a Degradation Signaling Agent, wherein
   the Ligand for RAF is selected from the group consisting of sorafenib and RAF709; and
   the Degradation Signaling Agent is selected from the group consisting of a pomalidomide and a small molecule VHL ligand.

2. A RAF-Degrading Conjugate Compound of claim 1, wherein the Ligand for RAF is sorafenib.

3. A RAF-Degrading Conjugate Compound of claim 1, wherein the Ligand for RAF is RAF709.

4. A RAF-Degrading Conjugate Compound of claim 1, wherein the Degradation Signaling Agent is a pomalidomide.

5. A RAF-Degrading Conjugate Compound of claim 1, wherein the Degradation Signaling Agent is a small molecule VHL ligand.

6. A RAF-Degrading Conjugate Compound of claim 1, wherein the Linker Component comprises polyethylene glycol.

7. A RAF-Degrading Conjugate Compound of claim 1, wherein the Linker Component has a formula selected from the group consisting of:

(a)
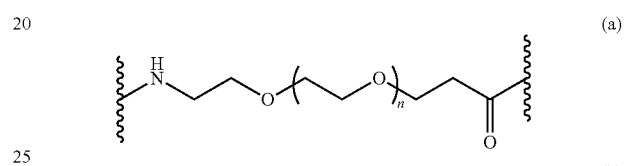

(b)
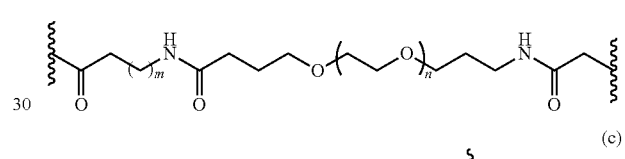

(c)
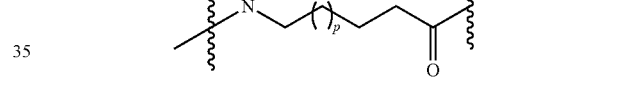

(d)
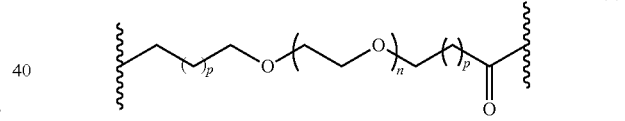

(e)
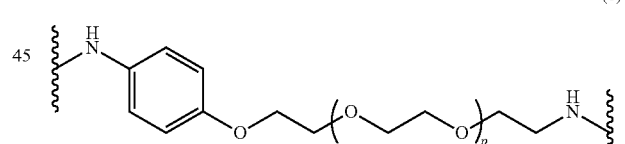

(f)
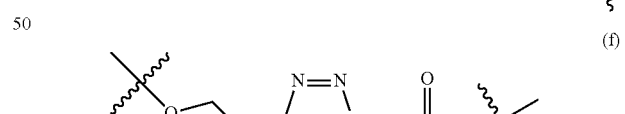

(g)
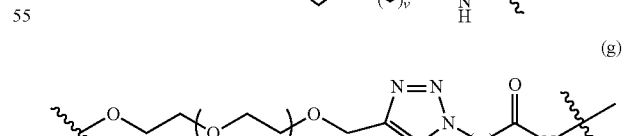

(h)
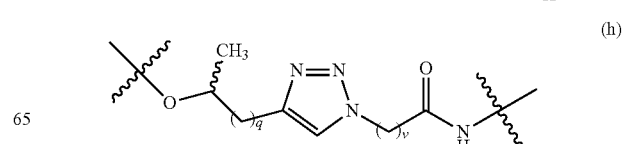

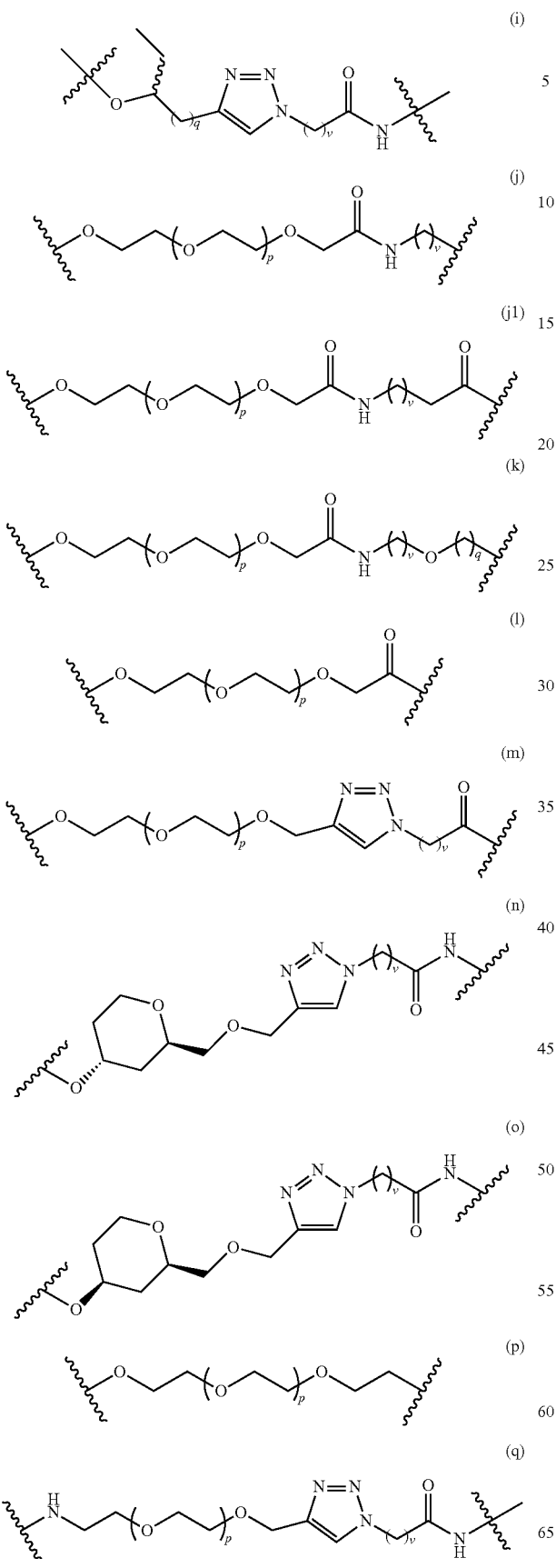
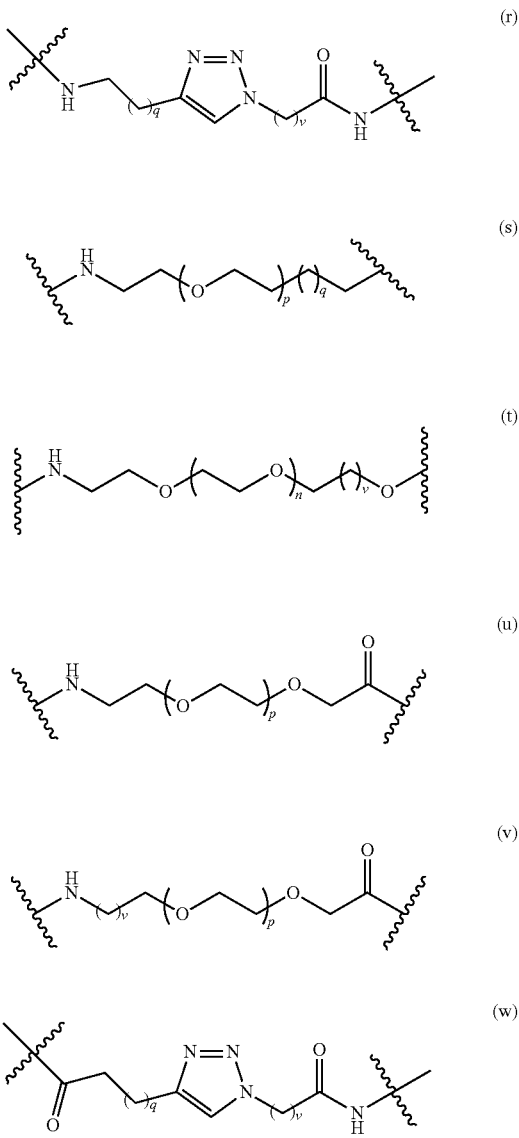

wherein the subscript m is an integer from 1 to 24, the subscript n is an integer from 1 to 14, each subscript p is independently an integer from 0 to 6, the subscript q is an integer from 0 to 8, and subscript v is an integer from 1 to 10 and the wavy lines indicate sites of attachment of the Ligand for RAF and the Degradation Signaling Agent.

8. A RAF-Degrading Conjugate Compound of claim 1, wherein the Ligand for RAF is RAF709, and the Degradation Signaling Agent is a pomalidomide.

9. A RAF-Degrading Conjugate Compound of claim 1, wherein the Ligand for RAF is RAF709, and the Degradation Signaling Agent is a small molecule VHL Ligand.

10. A RAF-Degrading Conjugate Compound of claim 1, wherein the Ligand for RAF is sorafenib, and the Degradation Signaling Agent is a pomalidomide.

11. A RAF-Degrading Conjugate Compound of claim 1, wherein the Ligand for RAF is sorafenib, and the Degradation Signaling Agent is a small molecule VHL Ligand.

12. A RAF-Degrading Conjugate Compound consisting of a Ligand for RAF covalently attached via a Linker Component to a Degradation Signaling Agent, wherein the Ligand for RAF has the structure

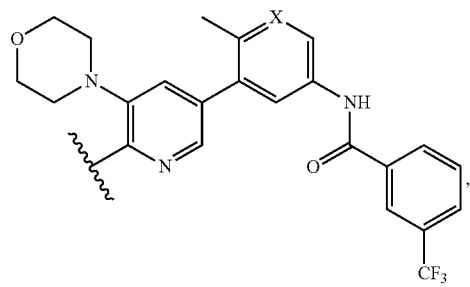

wherein X is N or CH and the wavy line indicates the site of attachment of the Linker Component;

the Degradation Signaling Agent is selected from the group consisting of

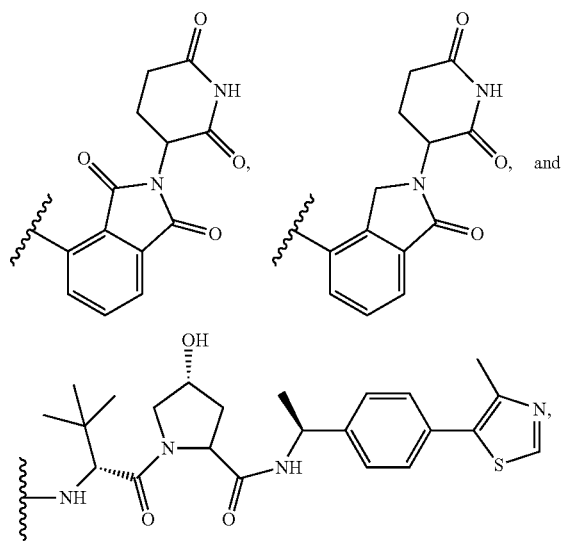

wherein the wavy line indicates the site of attachment of the Linker Component; and the Linker Component is selected from the group consisting of

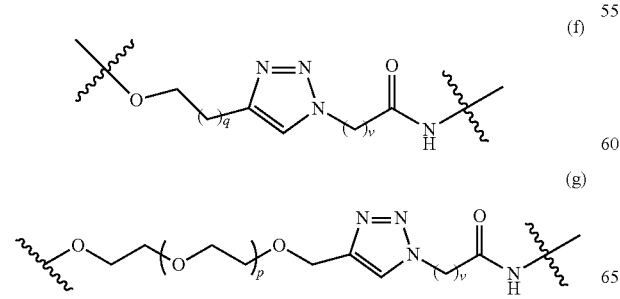

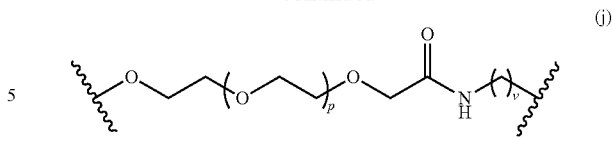

(j)

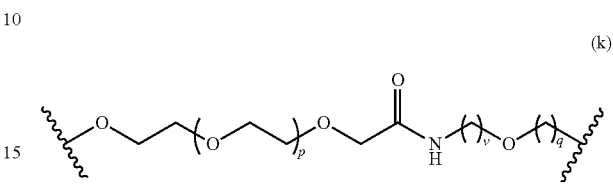

(k)

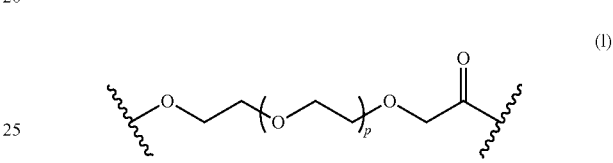

(l)

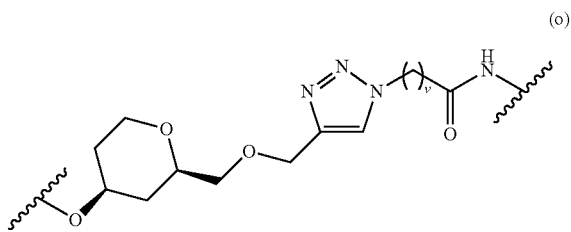

(o)

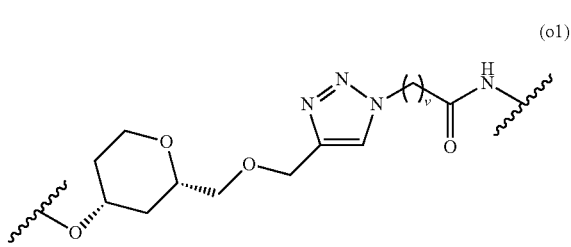

(o1)

and a mixture of (o) and (o1), wherein each subscript p is independently an integer from 0 to 6, the subscript q is an integer from 0 to 8, and subscript v is an integer from 1 to 10 and the wavy line on the left indicates the site of attachment to the Ligand for RAF and the wavy line on the right of the structure indicates the site of attachment to the Degradation Signaling Agent.

13. The RAF-Degrading Conjugate Compound of claim 1, selected from the group consisting of
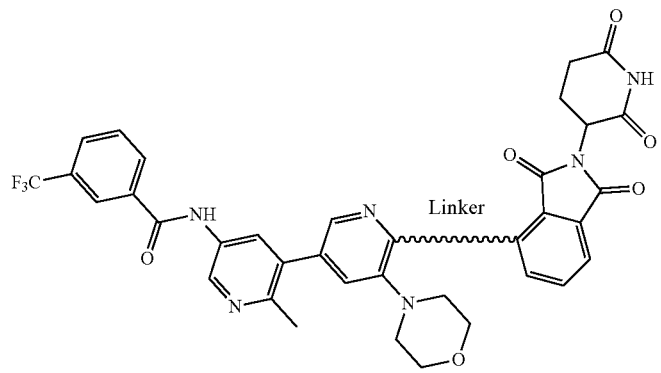
Linker
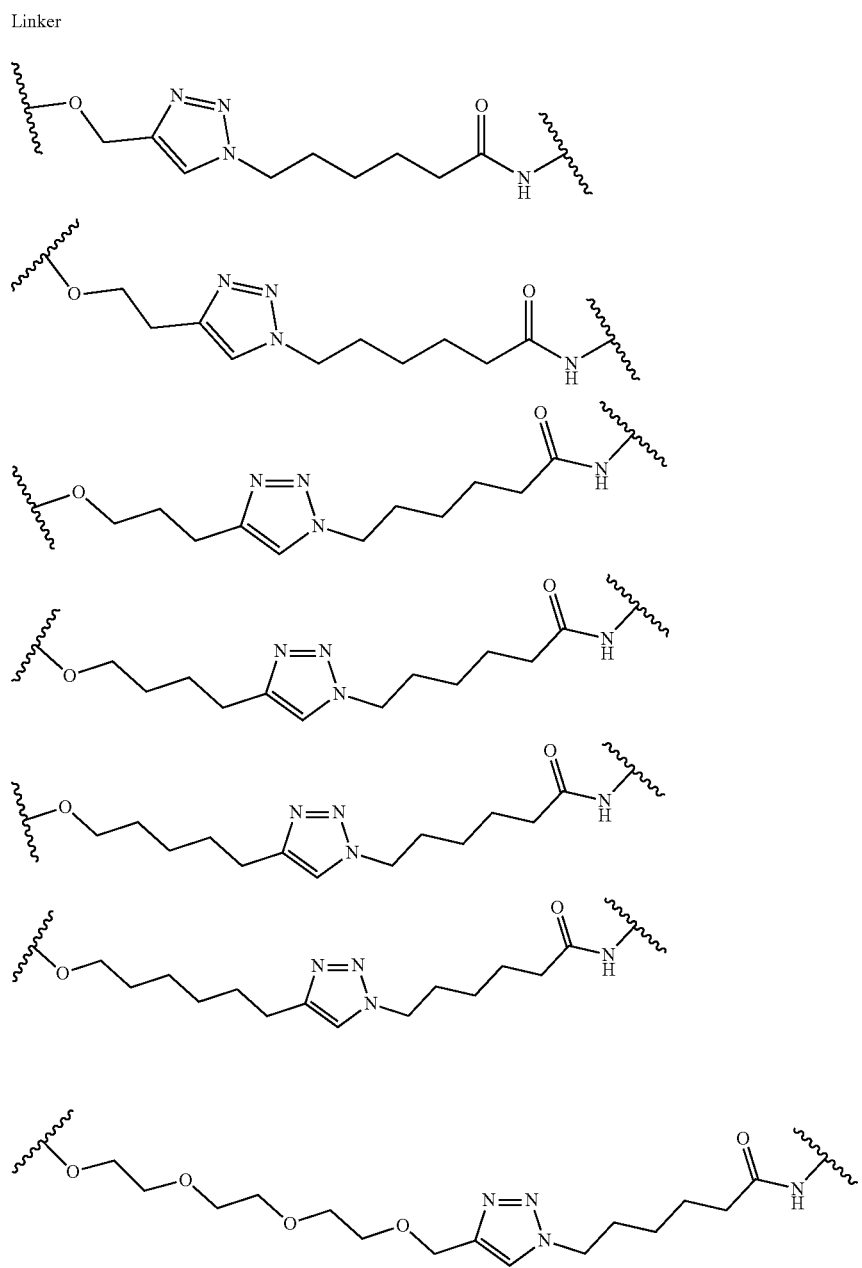

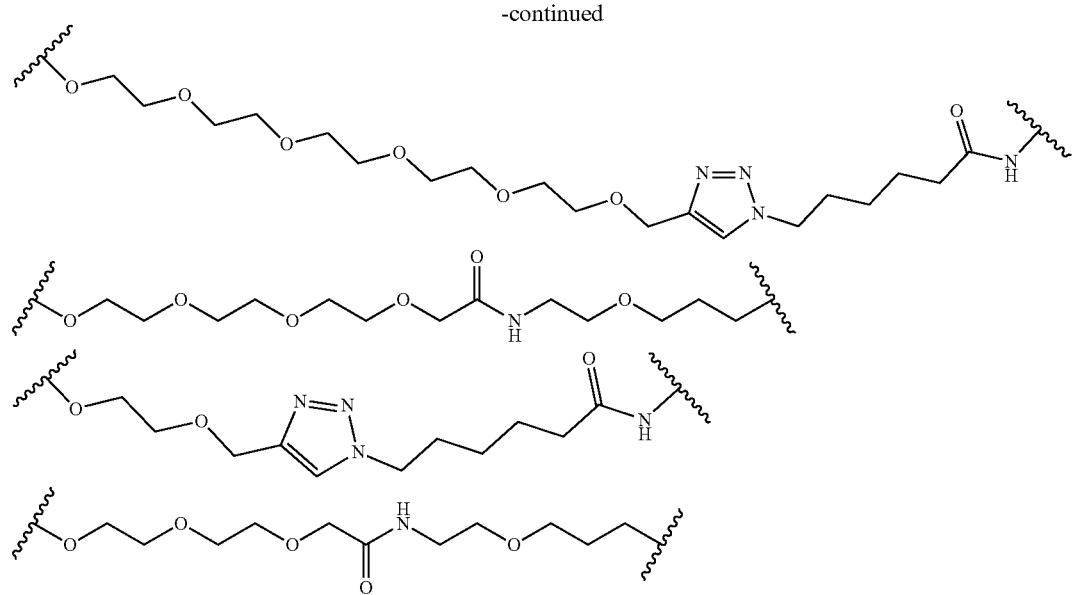
14. A pharmaceutical composition comprising the compound of claim 1 and a pharmaceutically acceptable excipient or carrier.
15. The RAF-Degrading Conjugate Compound of claim 1, selected from the group consisting of
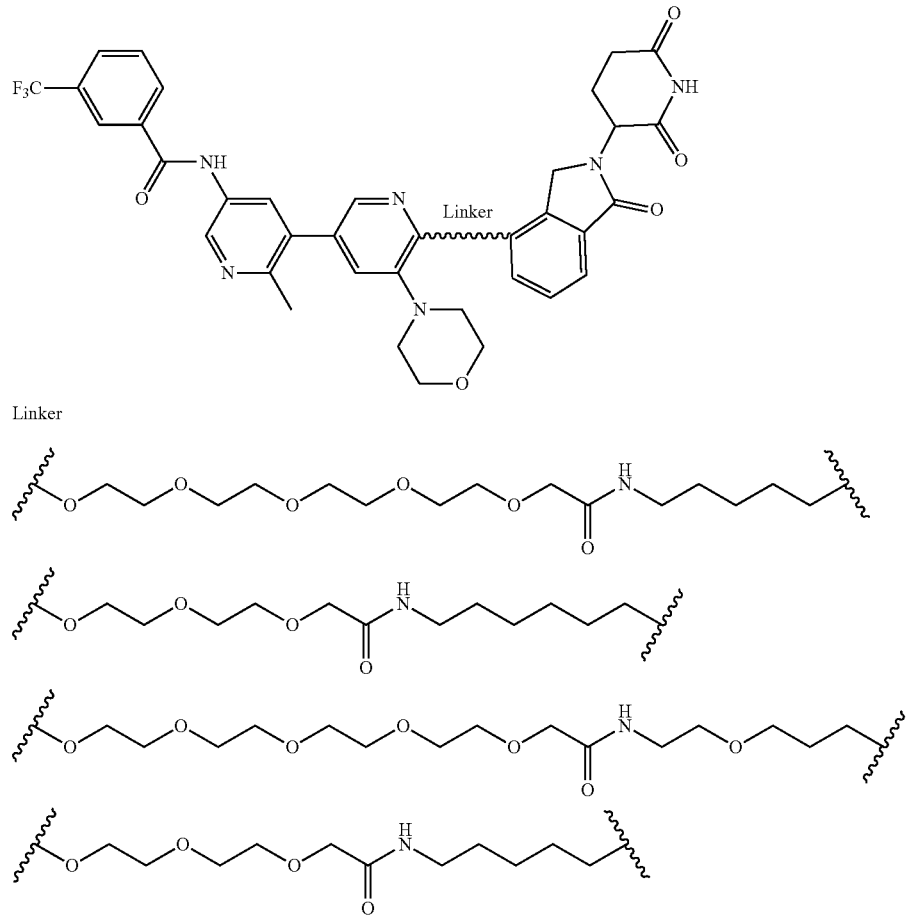

-continued
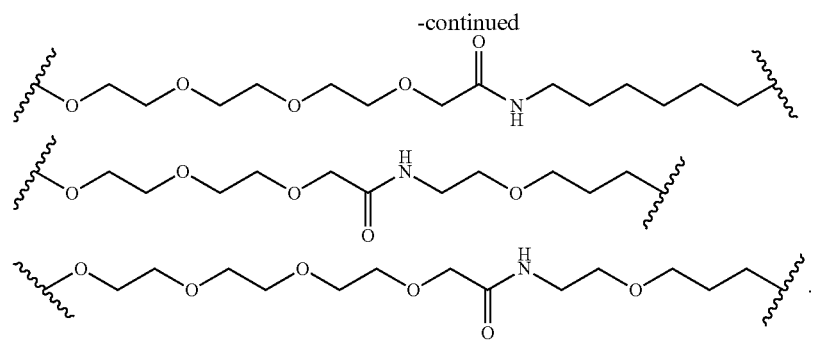
16. The RAF-Degrading Conjugate Compound of claim 1, selected from the group consisting of
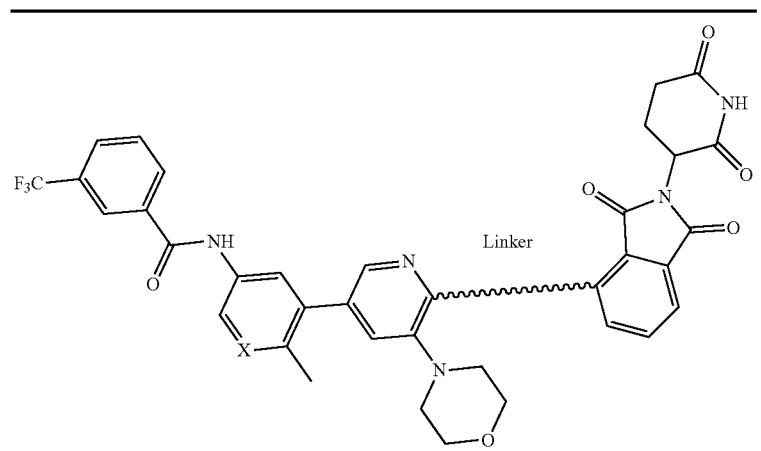
| Linker | X |
|---|---|
| 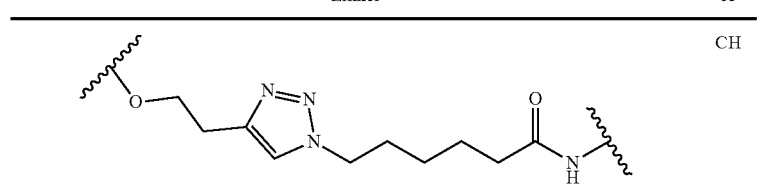 | CH |
| 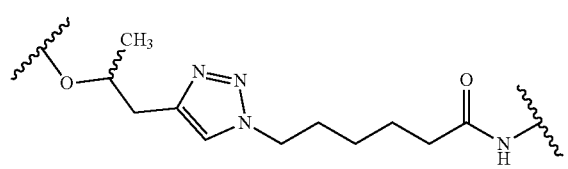 [SMILES: *NC(=O)CCCCCn1cc(CC(C)O*)nn1] | N |
| 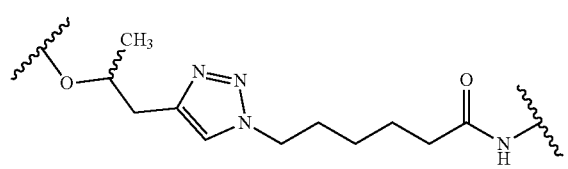 [SMILES: *NC(=O)CCCCCn1cc(CC(C)O*)nn1] | CH |
| 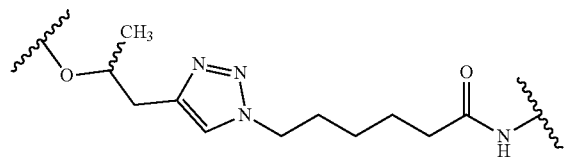 | N |

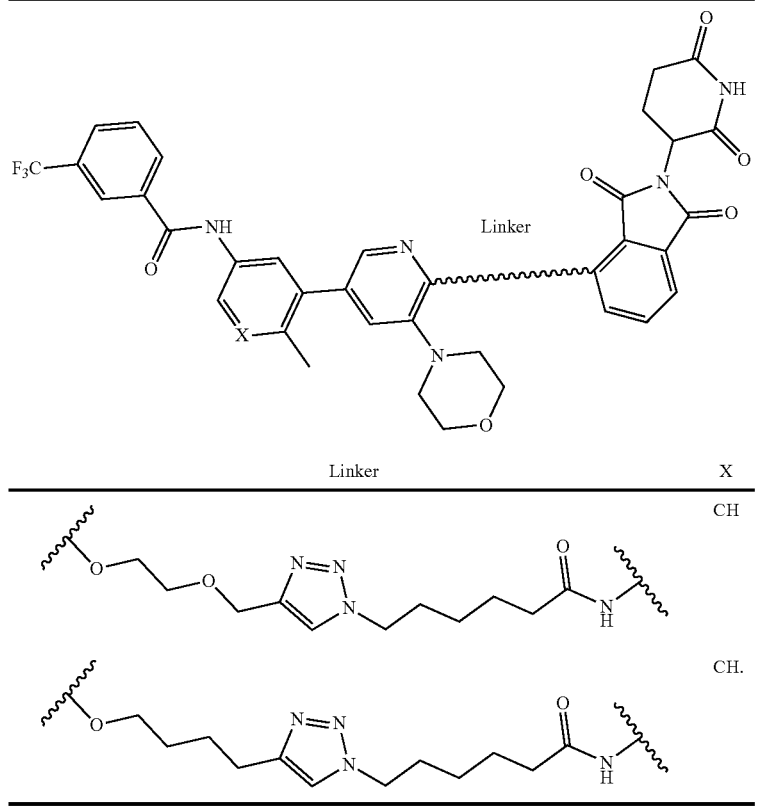
17. The RAF-Degrading Conjugate Compound of claim 1, selected from the group consisting of
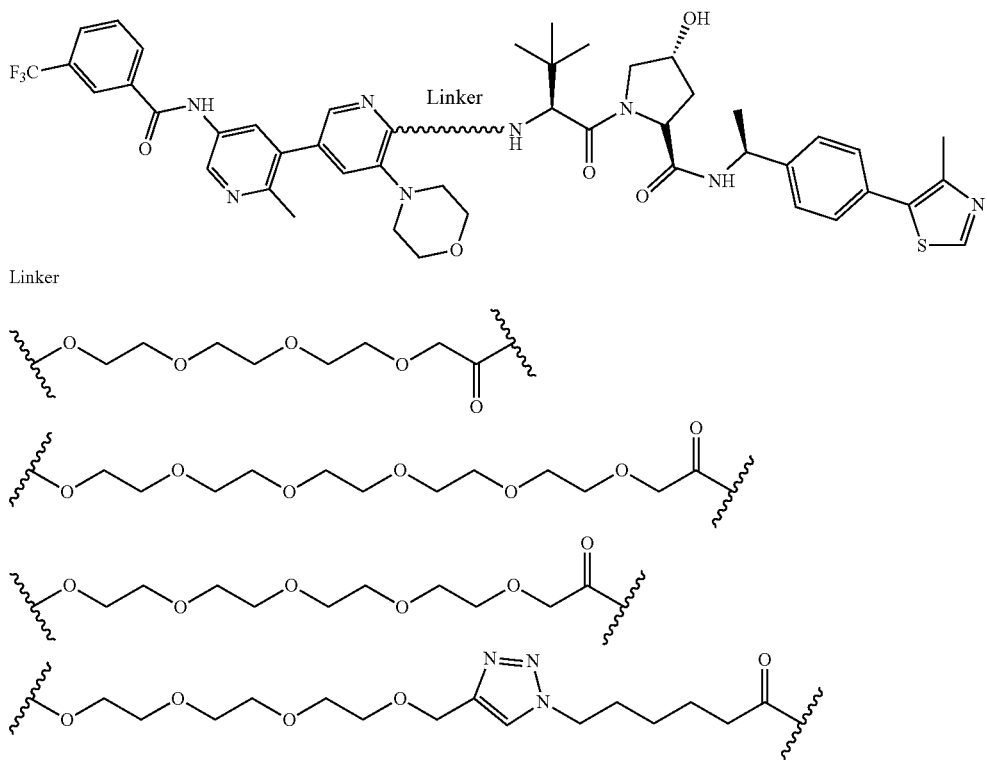

-continued
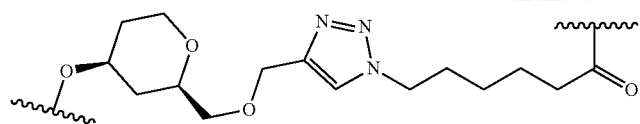
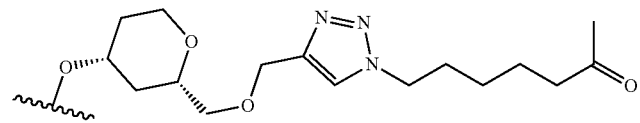
* A mixture of the two disasteromers are present
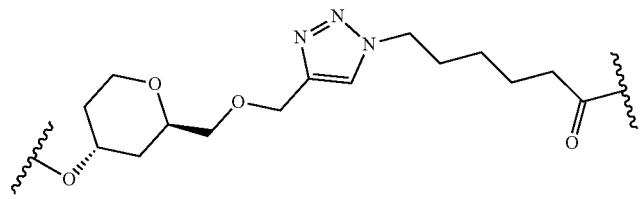
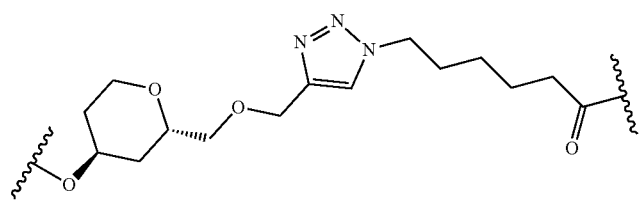
** A mixture of the two disasteromers are present
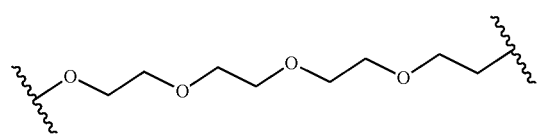
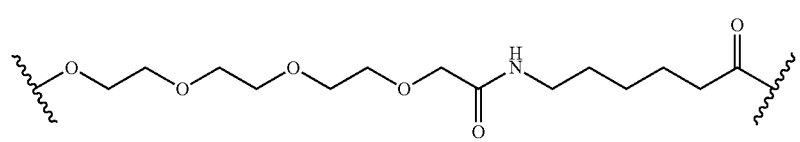
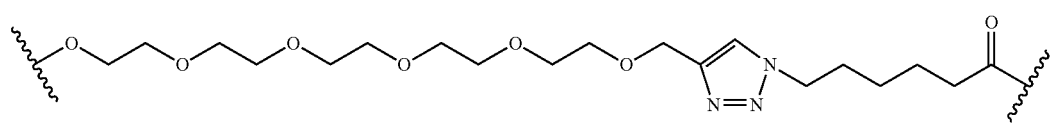
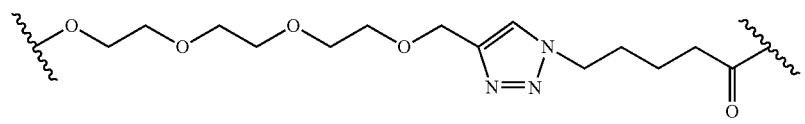

18. The RAF-Degrading Conjugate Compound of claim 1, selected from the group consisting of
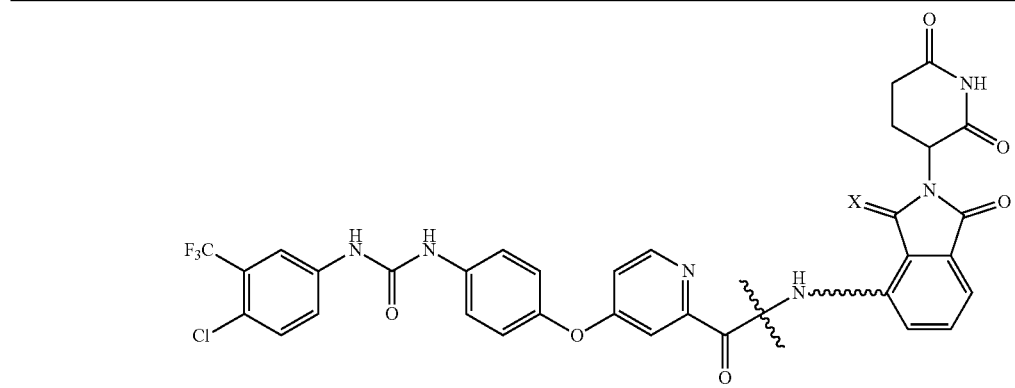
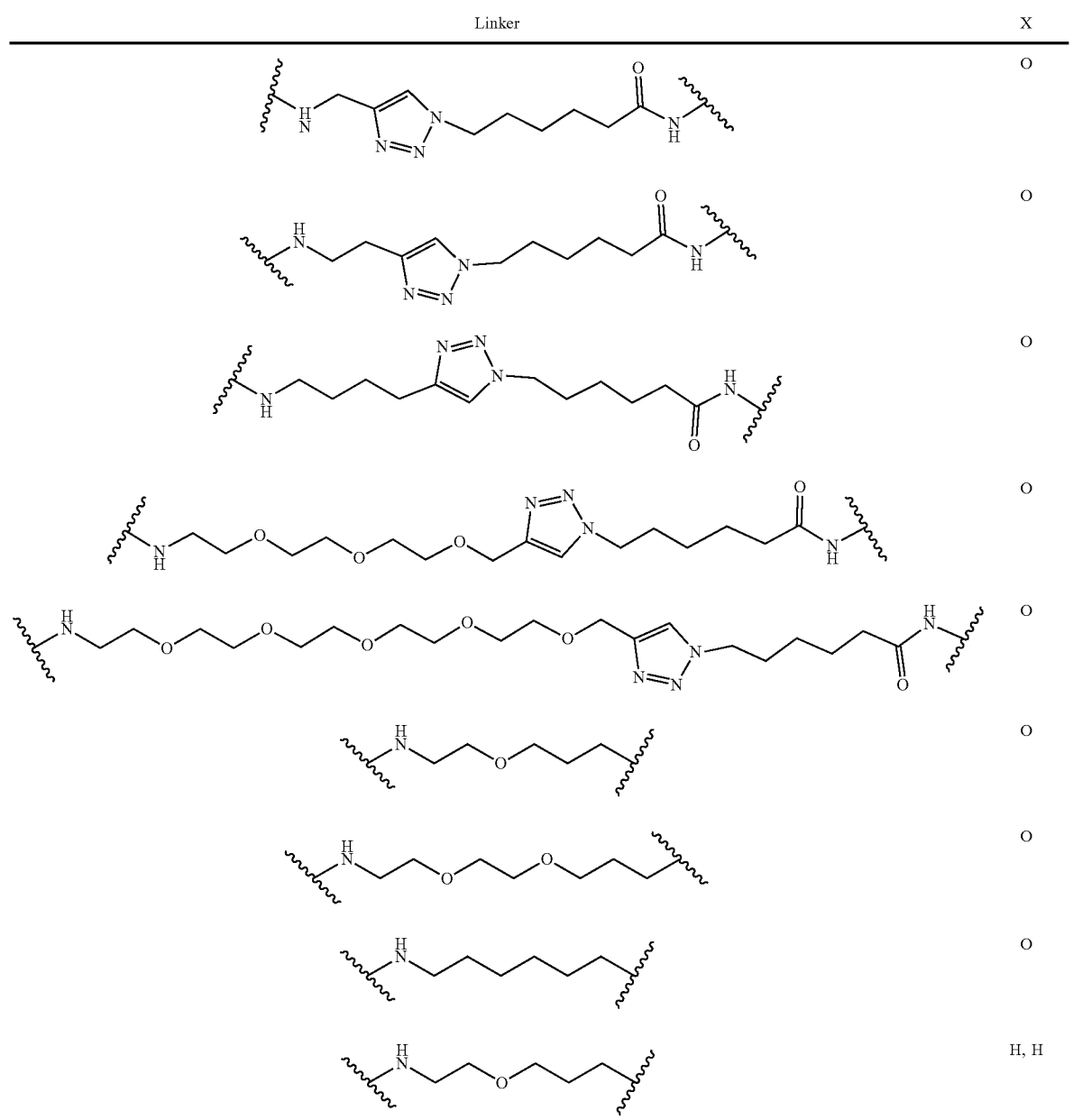

-continued
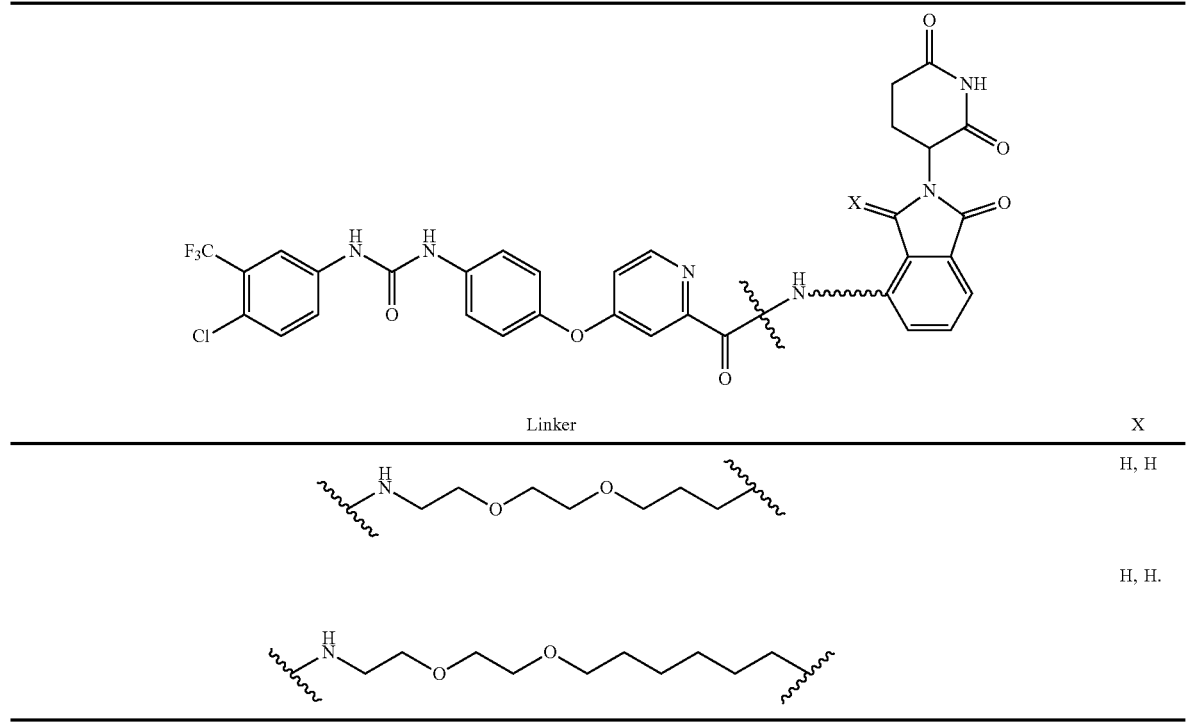
19. The RAF-Degrading Conjugate Compound of claim 1, selected from the group consisting of
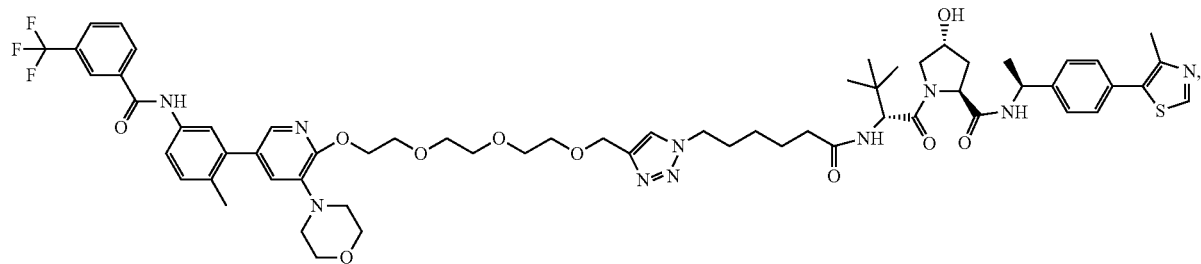
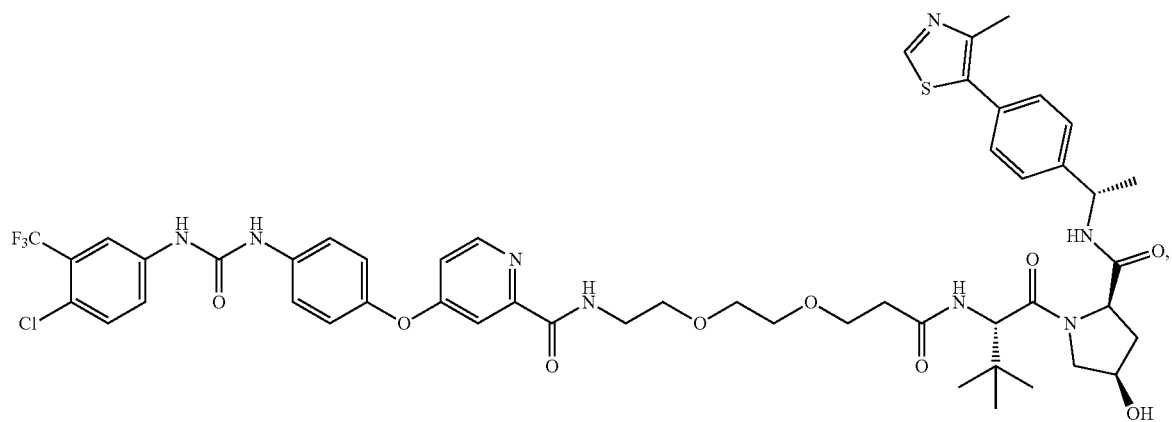

-continued

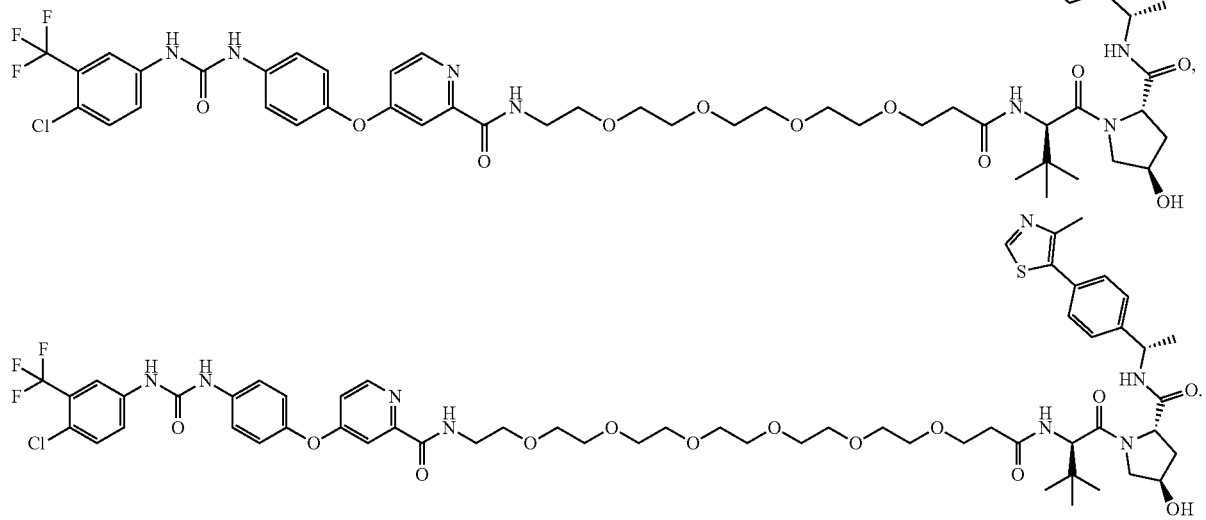

20. The RAF-Degrading Conjugate Compound of claim 8, wherein RAF709 has a structure selected from the group consisting of

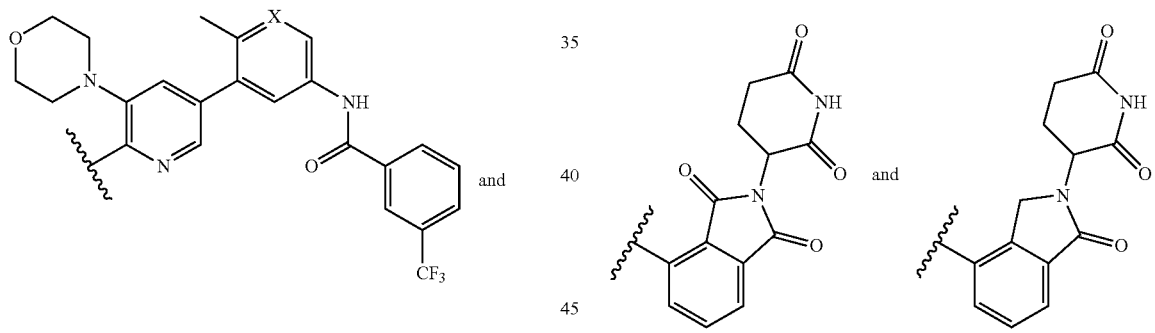

where each X is N or CH and the wavy line indicates the site of attachment of the Linker Component.

21. The RAF-Degrading Conjugate Compound of claim 8, wherein the pomalidomide has a structure selected from the group consisting of

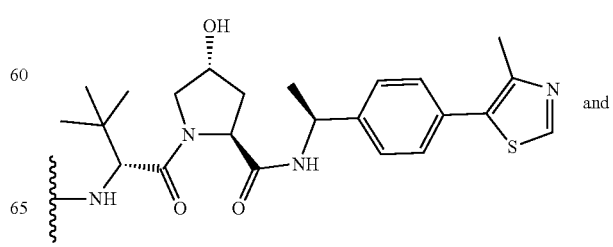

wherein the wavy line indicates the site of attachment of the Linker Component.

22. The RAF-Degrading Conjugate Compound of claim 9, wherein the small molecule VEIL Ligand has a structure selected from the group consisting of

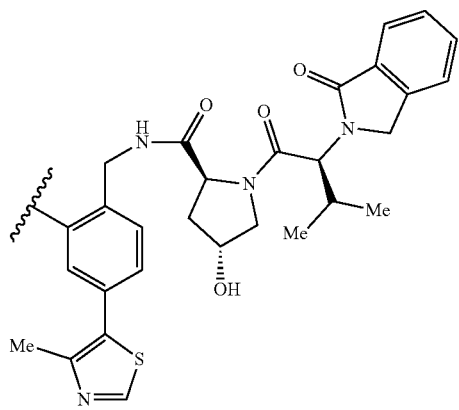

wherein the wavy line indicates the site of attachment of the Linker Component.

23. The RAF-Degrading Conjugate Compound of claim 9, wherein the Linker Component has a formula selected from the group consisting of

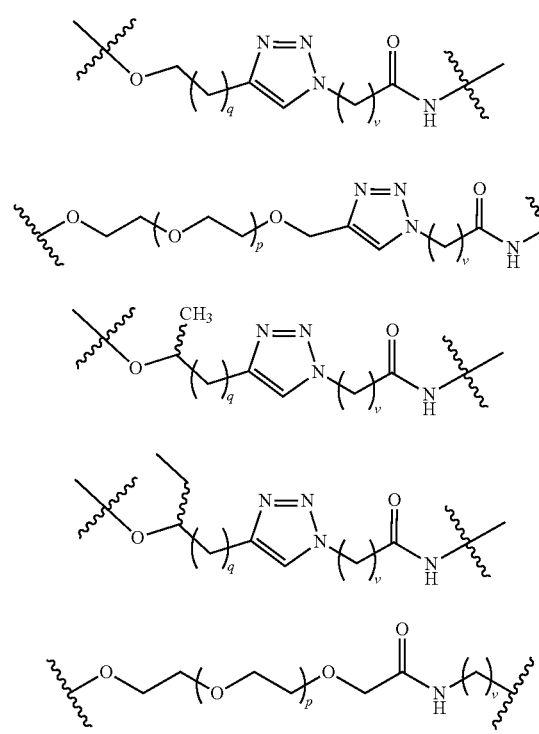

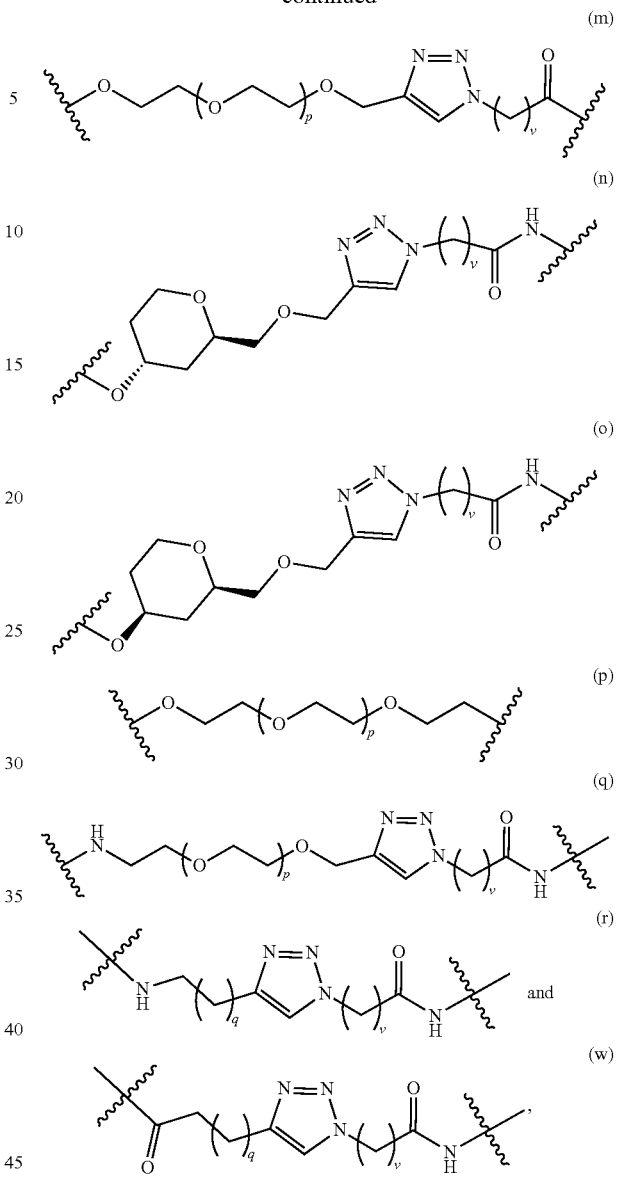

wherein the subscript p is 0 to 4; the subscript q is 0 to 6; and the subscript v is 1 to 6 and the wavy line on the left indicates the site of attachment to the Ligand for RAF and the wavy line on the right of the structure indicates the site of attachment to the Degradation Signaling Agent.

24. The RAF-Degrading Conjugate Compound of claim 10, wherein sorafenib has a structure

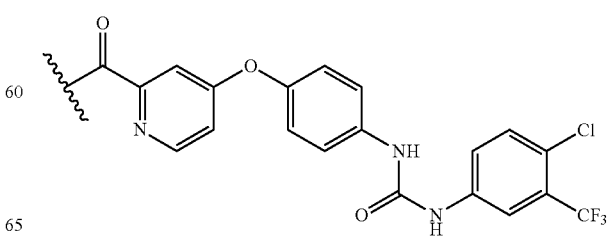

wherein the wavy line indicates the site of attachment of the Linker Component.

25. The RAF-Degrading Conjugate Compound of claim 10, wherein the pomalidomide has a structure selected from the group consisting of

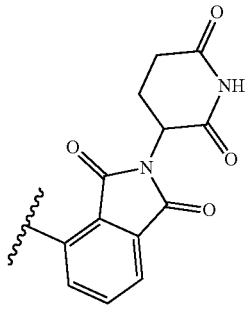
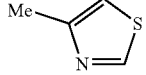
and

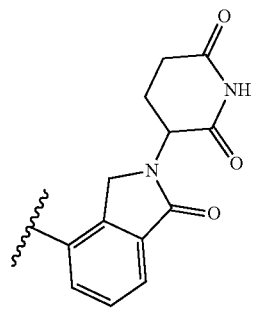

wherein the wavy line indicates the site of attachment of the Linker Component.

26. The RAF-Degrading Conjugate Compound of claim 11, wherein the small molecule VHL Ligand has a structure selected from the group consisting of

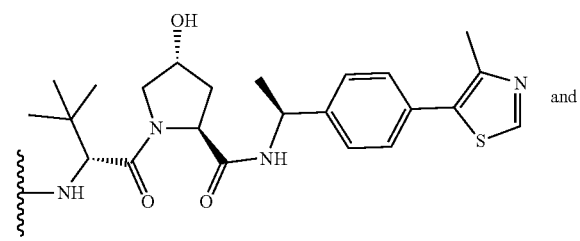
and

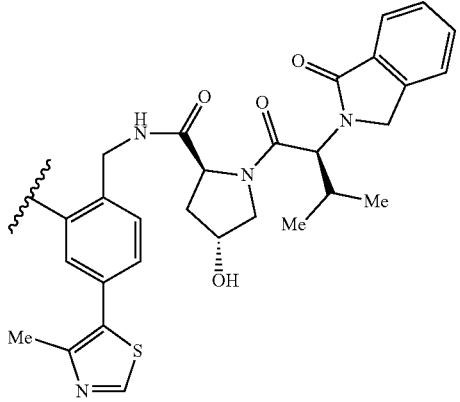

wherein the wavy line indicates the site of attachment of the Linker Component.

27. The RAF-Degrading Conjugate Compound of claim 10, wherein the Linker Component has a formula selected from the group consisting of

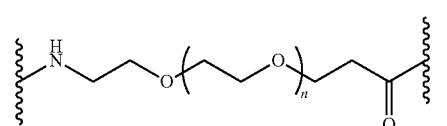
(a)

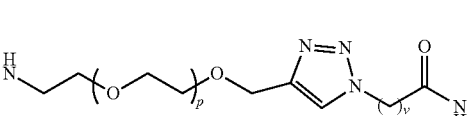
(q)

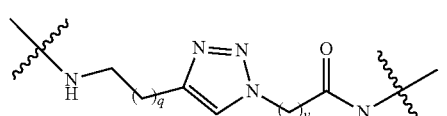
(r)

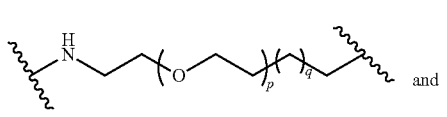
(s)

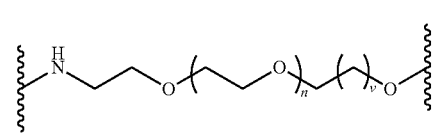
and
(t)

wherein the subscript p is 0 to 4; the subscript q is 0 to 6; and the subscript v is 1 to 6 and the wavy line on the left indicates the site of attachment to the Ligand for RAF and the wavy line on the right of the structure indicates the site of attachment to the Degradation Signaling Agent.

* * * * *